US011007183B2

(12) United States Patent
Saha et al.

(10) Patent No.: US 11,007,183 B2
(45) **Date of Patent: *May 18, 2021**

(54) CANCER TREATMENTS USING COMBINATIONS OF PI3K/AKT PATHWAY AND ERK INHIBITORS

(71) Applicant: BIOMED VALLEY DISCOVERIES, INC., Kansas City, MO (US)

(72) Inventors: Saurabh Saha, Wellesley Hills, MA (US); Dean Welsch, Parkville, MO (US); Gary DeCrescenzo, Parkville, MO (US); Jeffrey James Roix, Boston, MA (US)

(73) Assignee: BIOMED VALLEY DISCOVERIES, INC., Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/105,839

(22) PCT Filed: Dec. 19, 2014

(86) PCT No.: PCT/US2014/071728

§ 371 (c)(1),
(2) Date: Jun. 17, 2016

(87) PCT Pub. No.: WO2015/095829

PCT Pub. Date: Jun. 25, 2015

(65) Prior Publication Data

US 2016/0317517 A1 Nov. 3, 2016

Related U.S. Application Data

(60) Provisional application No. 61/919,638, filed on Dec. 20, 2013.

(51) Int. Cl.

| | |
|---|---|
| ***A61K 31/4439*** | (2006.01) |
| ***A61K 31/506*** | (2006.01) |
| ***A61K 31/5377*** | (2006.01) |
| ***A61K 31/4433*** | (2006.01) |
| ***A61K 31/444*** | (2006.01) |
| ***A61K 45/06*** | (2006.01) |
| ***C12Q 1/00*** | (2006.01) |
| ***G01N 33/50*** | (2006.01) |
| ***C12Q 1/6886*** | (2018.01) |

(52) U.S. Cl.

CPC ........ *A61K 31/4439* (2013.01); *A61K 31/506* (2013.01); *A61K 31/5377* (2013.01); *A61K 45/06* (2013.01); *C12Q 1/00* (2013.01); *C12Q 1/6886* (2013.01); *G01N 33/50* (2013.01); *C12Q 2600/106* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 5,622,824 A | 4/1997 | Koster et al. | |
| 6,140,053 A | 10/2000 | Koster et al. | |
| 7,354,939 B2 * | 4/2008 | Martinez-Botella | C07F 9/65583 514/343 |
| 8,288,520 B2 | 10/2012 | Eder et al. | |
| 8,389,219 B2 | 3/2013 | Anthony et al. | |
| 2011/0152230 A1 | 6/2011 | Mascharak | |
| 2012/0202822 A1 * | 8/2012 | Bachman | A61K 31/51 514/252.04 |
| 2012/0264632 A1 | 10/2012 | Leaman et al. | |
| 2013/0203632 A1 | 8/2013 | Nazarenko et al. | |

FOREIGN PATENT DOCUMENTS

| | | | |
|---|---|---|---|
| WO | 2005021786 A1 | 3/2005 | |
| WO | 2005113541 A1 | 12/2005 | |
| WO | 2012046981 A2 | 4/2012 | |
| WO | WO-2012068562 A2 * | 5/2012 | C12Q 1/6886 |
| WO | 2012125848 A2 | 9/2012 | |
| WO | 2013152165 A1 | 10/2013 | |

OTHER PUBLICATIONS

Serra, Violeta, et al. "PI3K inhibition results in enhanced HER signaling and acquired ERK dependency in HER2-overexpressing breast cancer."Oncogene 30.22 (2011): 2547-2557.*

Hoeflich, Klaus P., et al. "In vivo antitumor activity of MEK and phosphatidylinositol 3-kinase inhibitors in basal-like breast cancer models."Clinical Cancer Research 15.14 (2009): 4649-4664.*

Yadav, Bhagwan, et al. "Searching for drug synergy in complex dose-response landscapes using an interaction potency model." Computational and structural biotechnology journal 13 (2015): 504-513.*

Partial CAS Registry Number file for RN# 53123-88-9 showing chemical names and structure, accessed Jan. 30, 2020 (Year: 2020).*

Atefi, M., et al., Reversing melanoma cross-resistance to BRAF and MEK inhibitors by co-targeting the AKT/mTOR pathway, PioS one 6.12, (2011): e28973.

(Continued)

*Primary Examiner* — Nissa M Westerberg

(74) *Attorney, Agent, or Firm* — Bryan Cave Leighton Paisner LLP

(57) ABSTRACT

The present invention provides, inter alia, methods, kits, and compositions for treating or ameliorating the effects of a cancer in a subject in need thereof. This method includes administering to the subject an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof. Also provided are methods of treating or ameliorating the effects of a subject with cancer in which the subject has a somatic KRAS and a somatic PIK3CA mutation or in which the cancer is refractory to a therapy selected from RAF inhibitor therapy, MEK inhibitor therapy, and RAF and MEK inhibitor therapy.

22 Claims, 99 Drawing Sheets

Specification includes a Sequence Listing.

(56) References Cited

OTHER PUBLICATIONS

Halilovic E., et al., PIK3CAA mutation uncouples tumor growth and cyclin D1 regulation from MEK/ERK and mutant KRAS signaling, Cancer research 70.17 (2010): 6804-6814.
Hoeflich, K. P., et al., In vivo antitumor activity of MEK and phosphatidylinositol 3-kinase inhibitors in basal-like breast cancer models, Clinical Cancer Research 15.14 (2009): 4649-4664.
Karakas, B., et al., Mutation of the PIK3CA oncogene in human cancers, British Journal of Cancer 94.4 (2006): 455-459.
Li, H. F., et al., Recent advances in the research and development of B-Raf inhibitors, Current Medicinal Chemistry 17.16 (201)0: 1618-1634.
Mittal, R. et al., The Acetyltransferase Activity of the Backterial Toxin YopJ of Yersinia is Activated by Eukaryotic Host Cell Inositol Hexakisphosphate, Journal of Biological Chemistry 285.26 (2010): 19927-19934.
Wee, S., et al., PI3K pathway activitation mediates resistance to MEK inhibitors in KRAS mutant cancers, Cancer Research 69.10 (2009): 4286-4293.
Morris, E. J., et al., Discovery of a Novel ERK Inhibitor with Activity in Models of Acquired Resistance to BRAF and MEK inhibitors, Published OnlineFirst Apr. 24, 2013, ODI: 10.1158/2159-8290. CD-13/0070.
Metzker, M. L., et al., Emerging technologies in DNA sequencing, Human Genome Sequencing Center and Dept. of Molecular and Human Genetics, Cold Spring Harbor Lab. Press,15: 1767-1776 (2005).
Ota, M., et al., Single nucleotide polymorphism detection by polymerase chain reaction-restriction fragment length plymorphism, Nature Protocols, vol. 2 No. 11: 2857-2864 (2007).
Absalan, F., et al., Molecular Inversion Probe Assay, Methods in Molecular Biology, vol. 396: Comparative Genomics, vol. 2, pp. 315-330 (2008).
Nilsson, M., et al., Padlock Probes: Circularizing Oligonucleotides for Localized DNA Detection, Science, vol. 265, Sep. 30, 1994.
Hardenbol, P., et al., Multiplexed genotyping with sequence-tagged molecular inversion probes, Nature Publishing Group, vol. 21, No. 6, Jun. 2003.
Maurer, T., Small-molecule ligands bind to a distinct pocket in Ras and inhibit SOS-mediated nucleotide excange activity, PNAS 109(14): 5299-304 (2012).
Shima, F., et al., In silico discovery of small-molecule Ras inhibitors that display antitumor activity by blocking the Ras-effector interaction, Proc Natl Aced Sci U S A, 110(20):8182-7 (2013).
Patgiri, A., et al., An Orthosteric inhibitor of the Ras-Sos interaction, Na. Chem. Biol. 7:585-587 (2011).
Liu, D., et al., BRAF V600E Maintains Proliferation, Tranformation, and Tumorigencity of BRAF-Mutant Papillary Thyroid Cancer Cells, NIH Public Access Author Manuscript, J. Clin. Endocrinol Metab. Jun. 2007, 92(6); 2264-2271.
Serra, V. et al., P13K inhibition results in enhanced HER signaling and acquired ERK dependencey in HER2-overexpressing breast cancer, Ongogene 30.22 (2011): 2547-2557.
Bao et al., Systematic screen with kinases Inhibitors reveals kinases play distinct roles in growth of osteoprogenitor cells, Int. J. Clin Exp. Pathol., Sep. 15, 2013, vol. 6, No. 10, pp. 2082-2091.
International Search Report and Written Opinion issued by the International Search Authority, dated Apr. 20, 2015.
Hoeflich, K. P. et al., Intermittent Administration of MEK Inhibitor GDC-0973 plus PI3K Inhibitor GDC-0941 Triggers Robust Apoptosis and Tumor Growth Inhibition. Cancer Research, vol. 72, No. 1 (2011): 210-219.
Britten C. D, PI3K and MEK inhibitor combinations: examining the evidence in selected tumor types. Cancer Chemotherapy and Pharmacology, vol. 71, No. 6 (2013): 1395-1409.
Sheppard K. E. et al., Synergistic inhibition of ovarian cancer cell growth by combining selective PI3K/mTOR and RAS/ERK pathway inhibitors. European Journal of Cancer, vol. 49, No. 18 (2013): 3936-3944.
Hatzivassiliou, et al. "ERK Inhibition Overcomes Acquired Resistance to MEK Inhibitors," Mol Cancer Ther 2012; 11:1143-1154.
Flaherty. "BRAF Inhibitors and Melanoma." Cancer J. Nov.-Dec. 2011;17(6):505-11.
Jing et al. "Comprehensive Predictive Biomarker Analysis for MEK Inhibitor GSK1120212." Mol Cancer Ther. Mar. 2012;11(3):720-9.
Kwong et al. "Oncogenic NRAS signaling differentially regulates survival and proliferation in melanoma." Nat Med. Oct. 2012;18(10):1503-10.
Sherr and McCormick. "The RB and p53 pathways in cancer." Cancer Cell. Aug. 2002;2(2):103-12.
Tang et al. "Attenuation of the Retinoblastoma Pathway in Pancreatic Neuroendocrine Tumors Due to Increased Cdk4/Cdk6." Clin Cancer Res. Sep. 1, 2012;18(17):4612-20.

* cited by examiner

FIG. 2
Mean Tumor Growth and Kaplan-Meier Plot for the in vivo Study
A
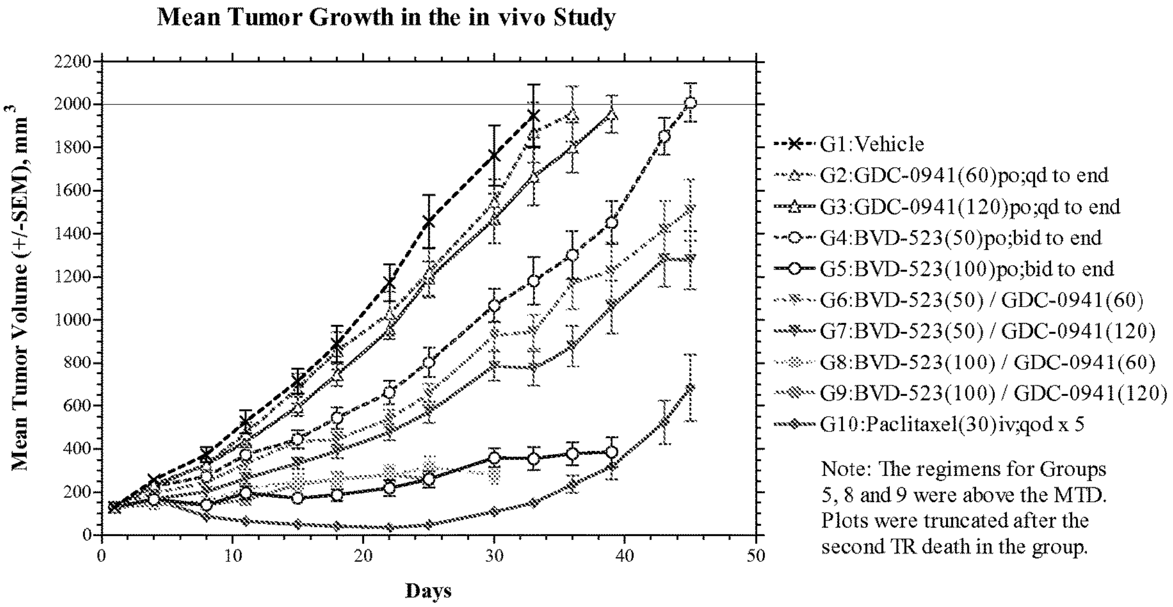
B
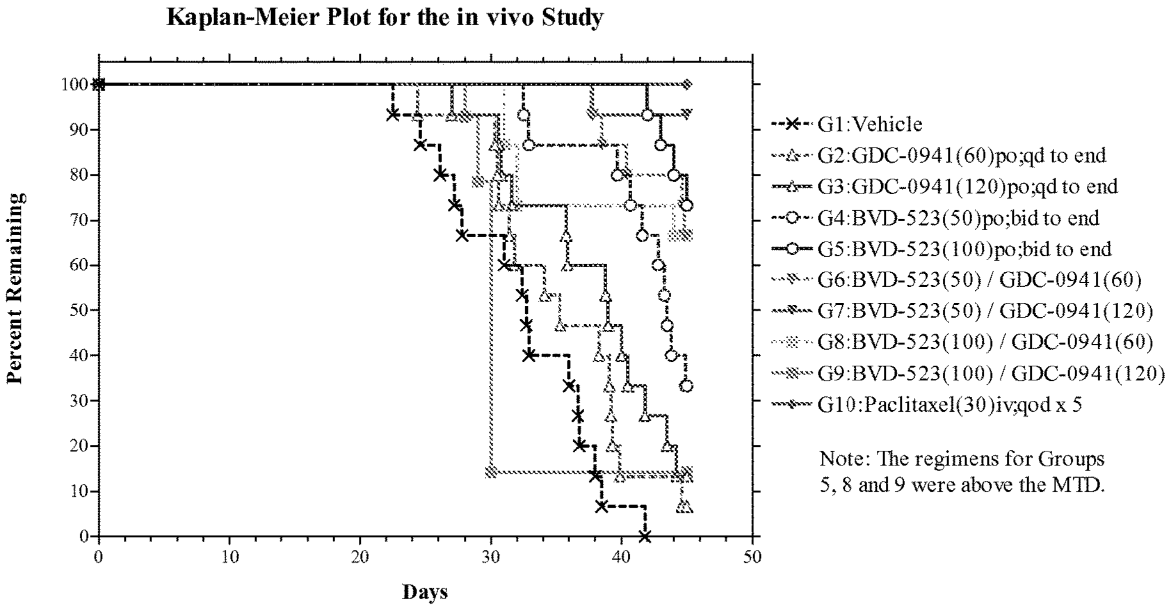

Percent Mean Body Weight Changes from Day 1 in the in vivo Study

FIG. 6, Continued
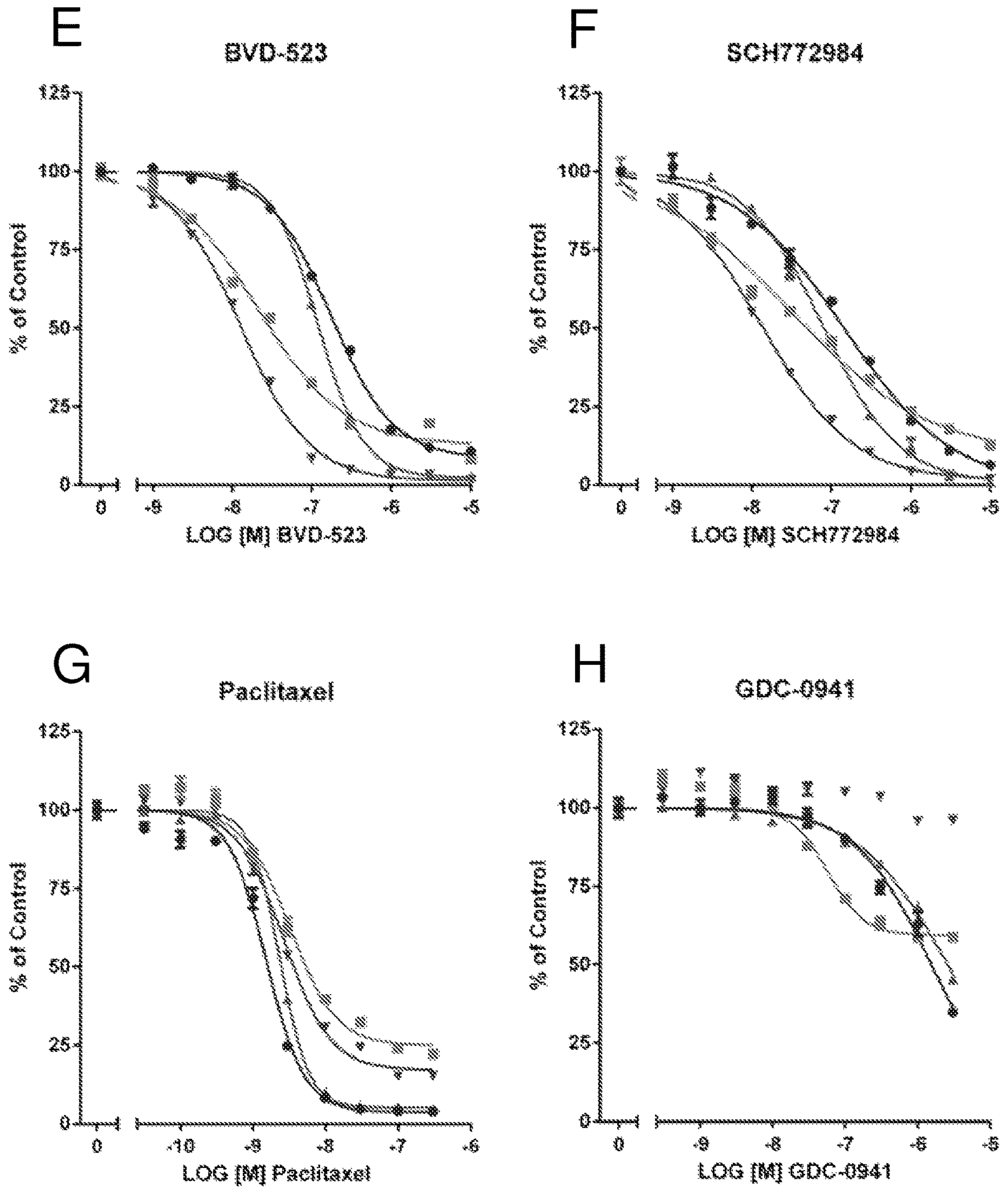

A

FIG. 7, Continued
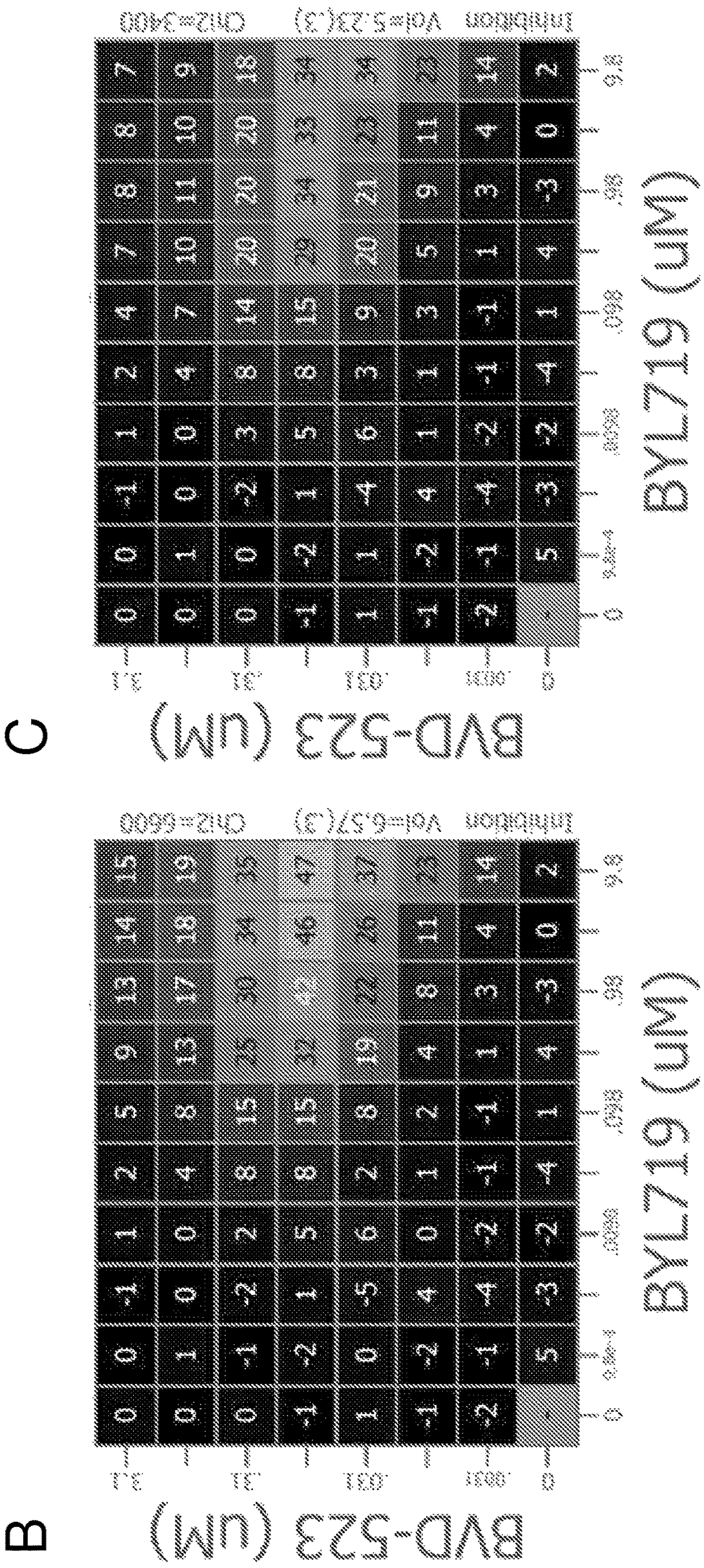

FIG. 7, Continued
D
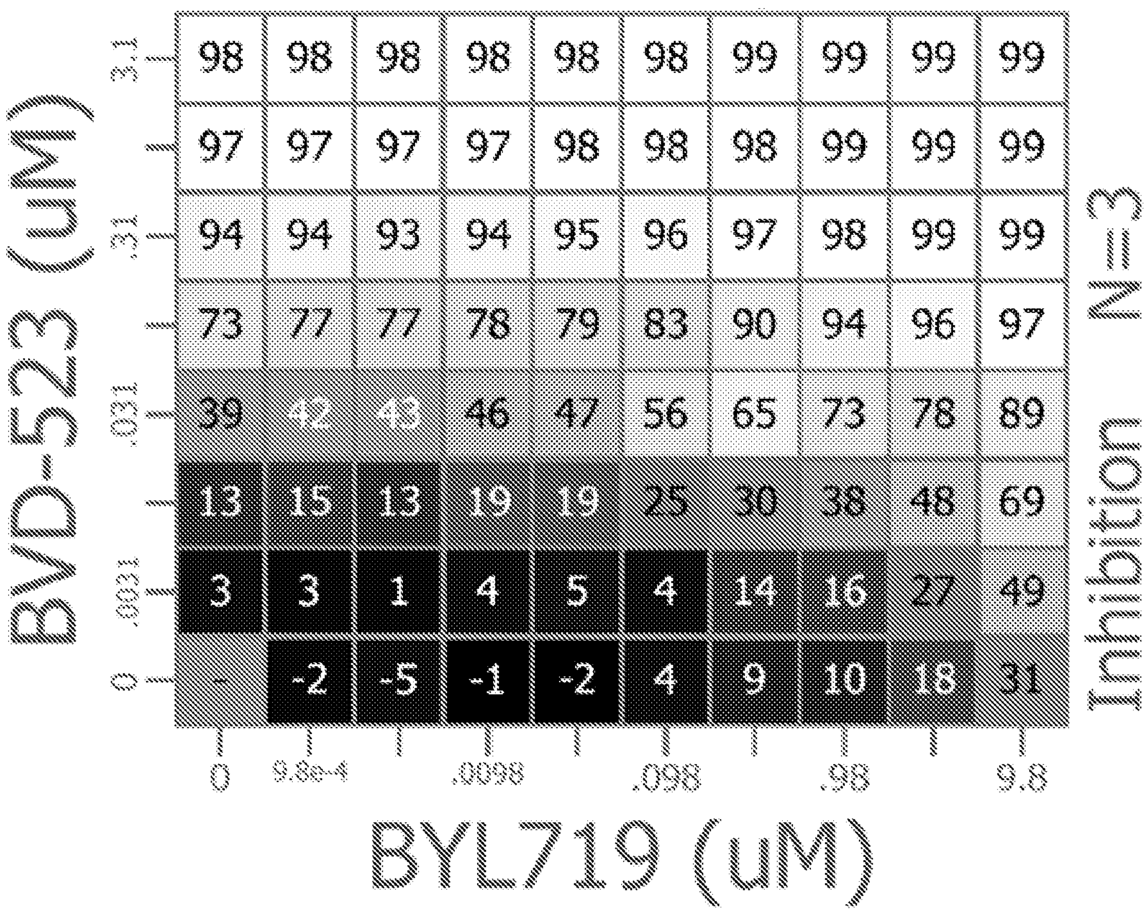

FIG. 7, Continued
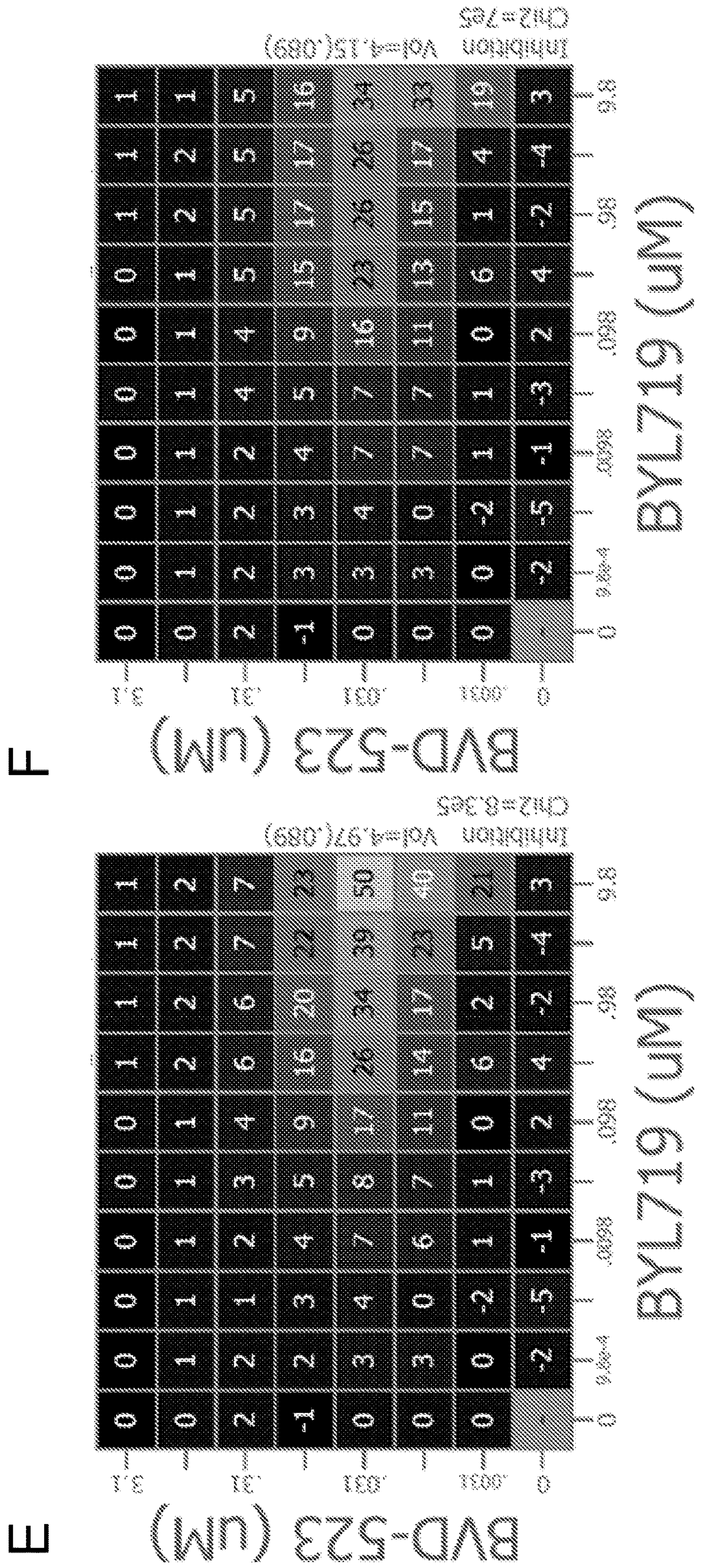

FIG. 7, Continued
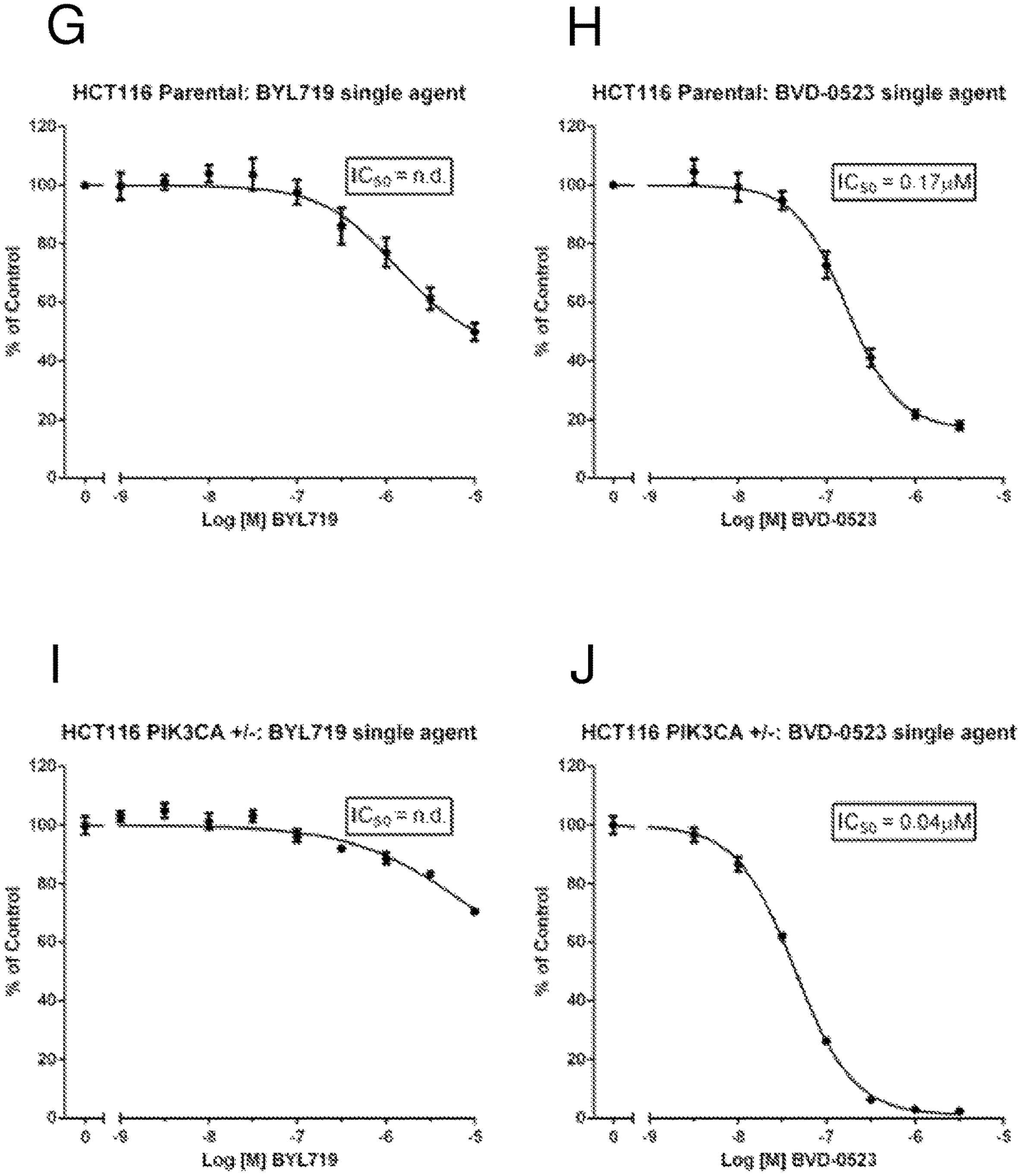

A

FIG. 8, Continued
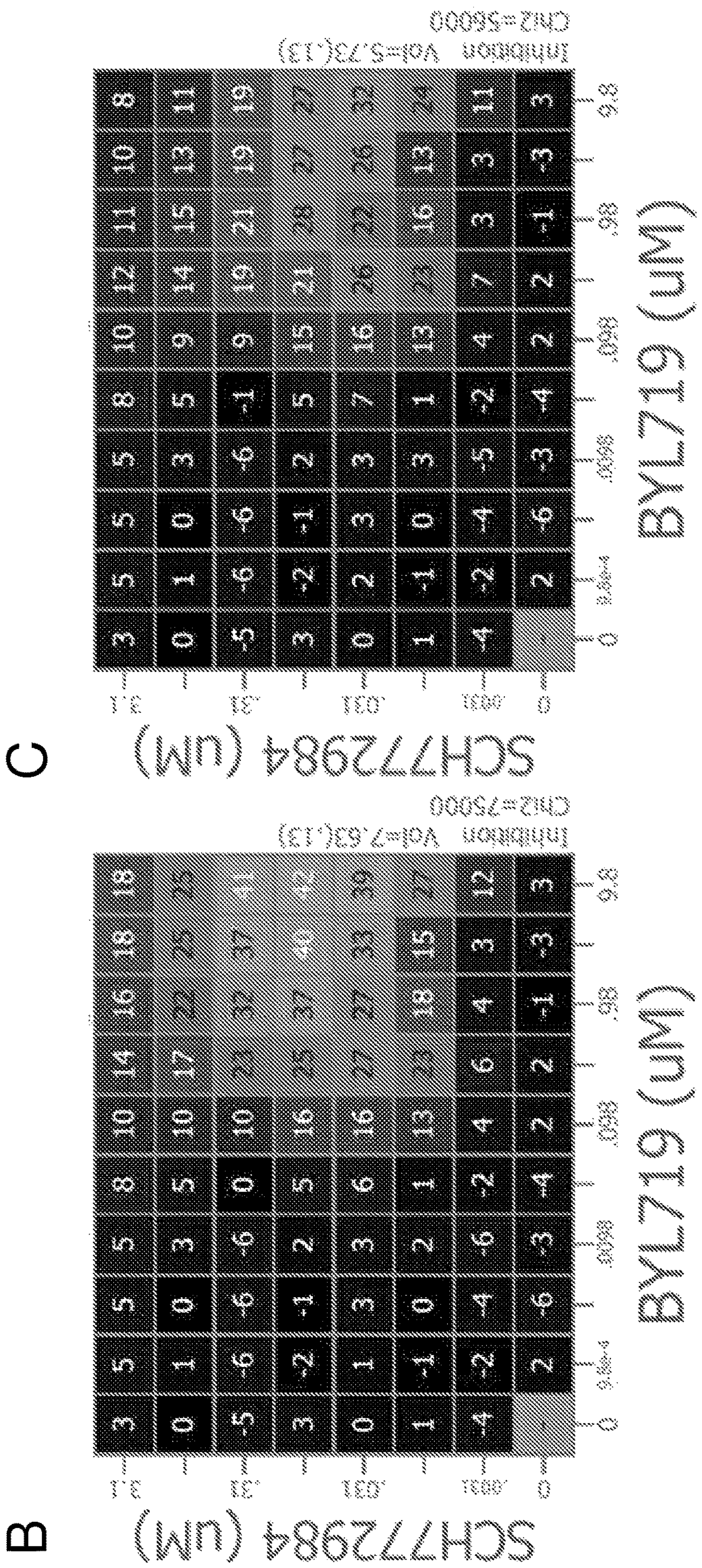

FIG. 8, Continued
D
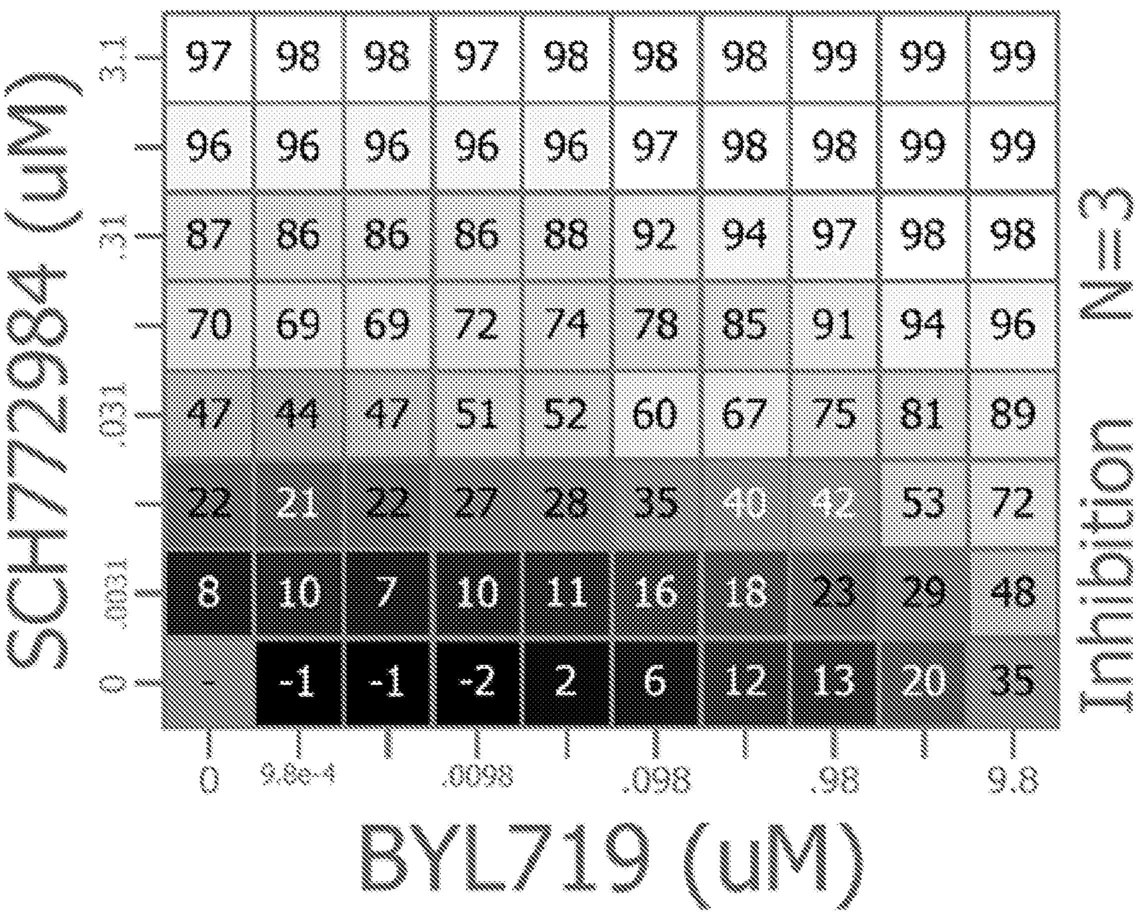

FIG. 8, Continued
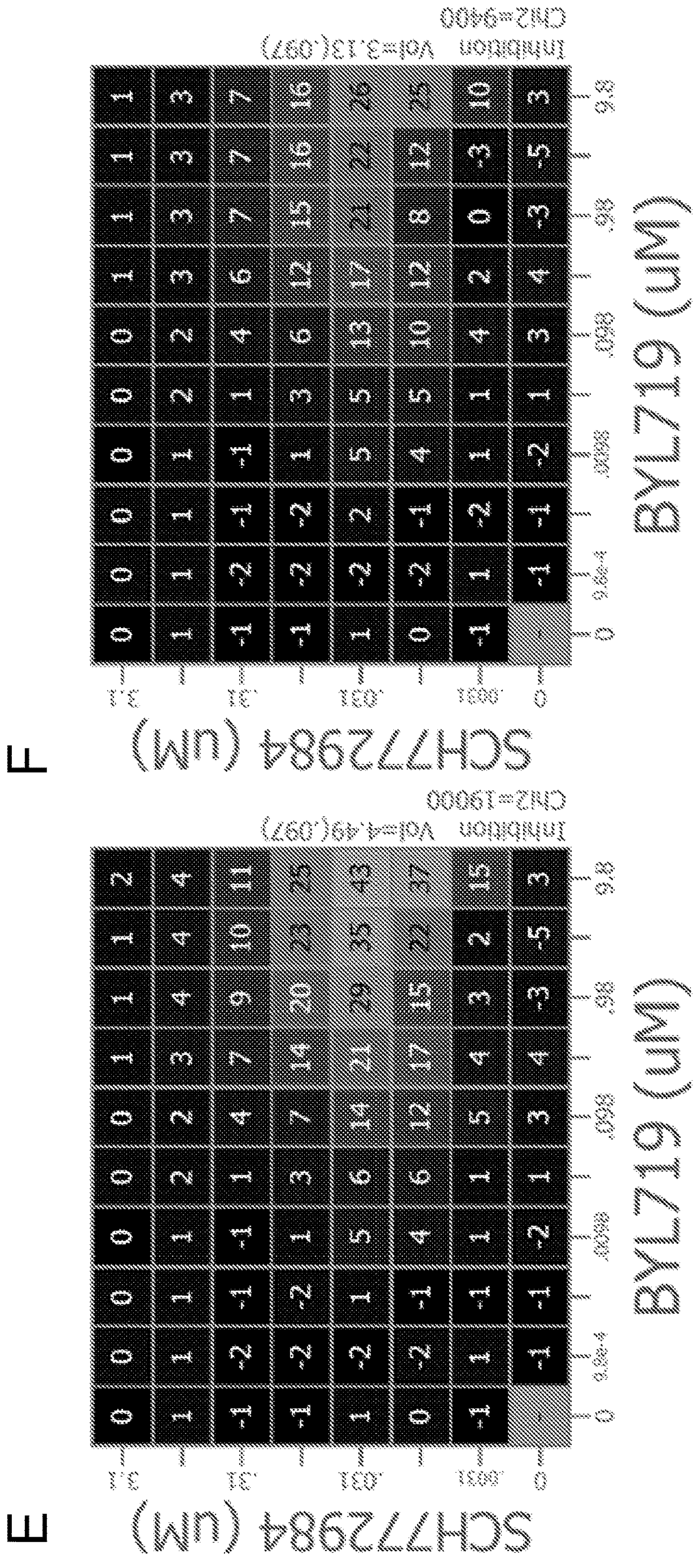

FIG. 8, Continued
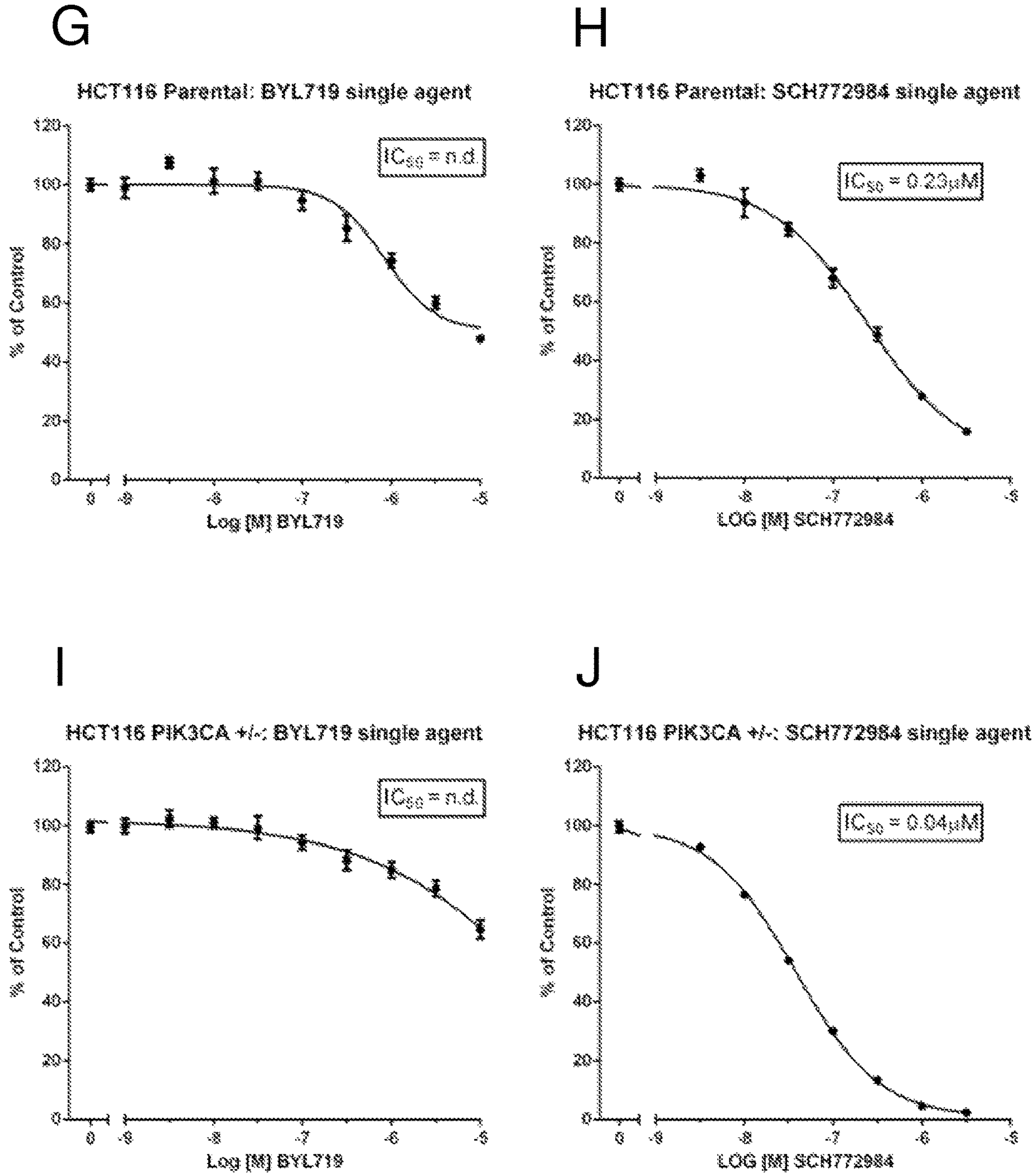

A

FIG. 9, Continued
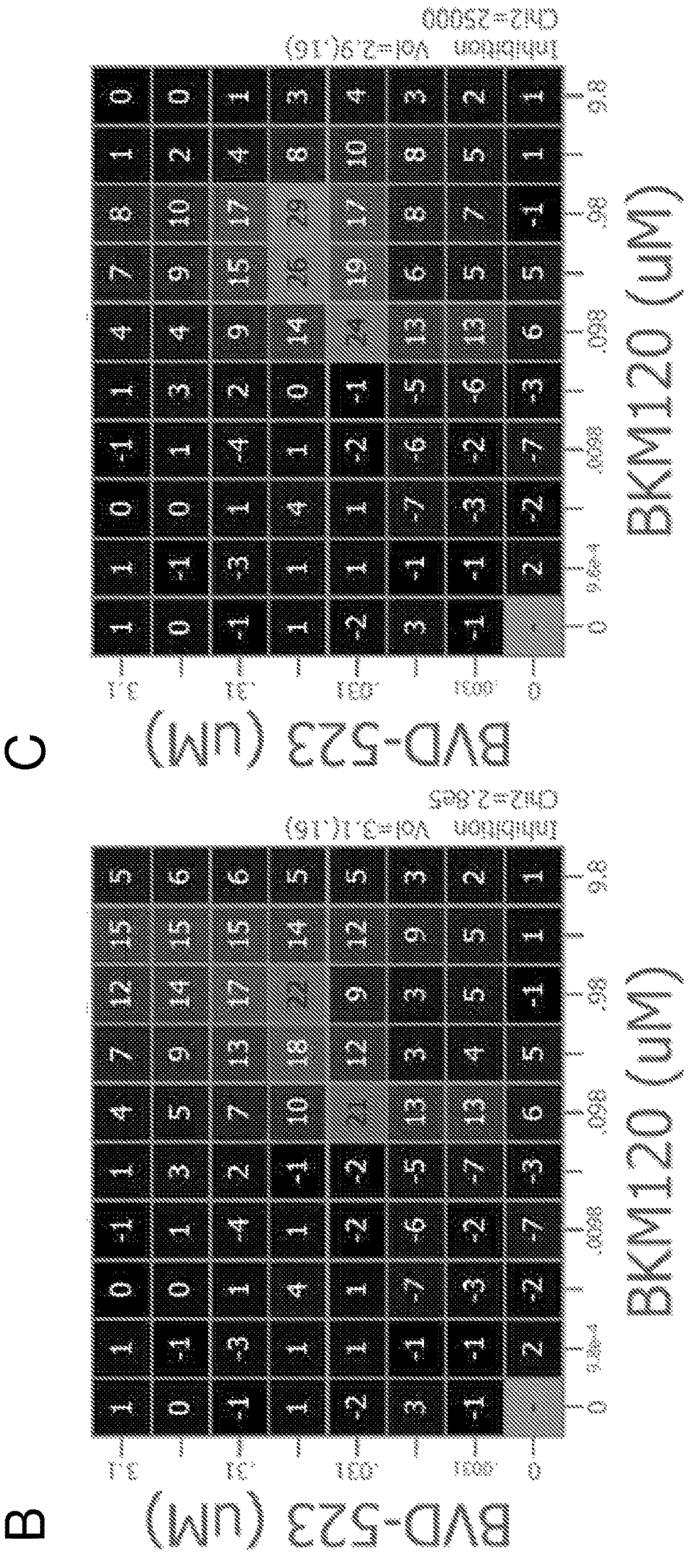

FIG. 9, Continued
D
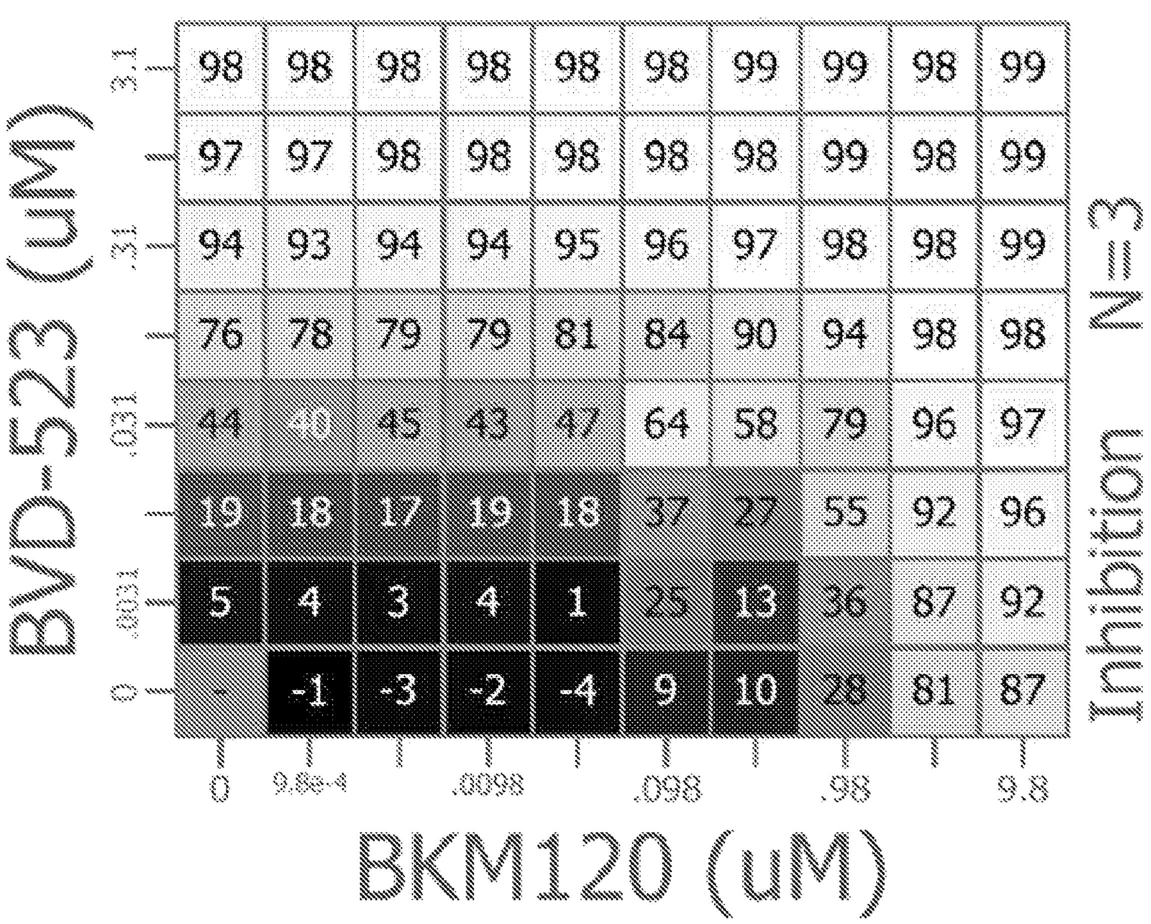

FIG. 9, Continued
E
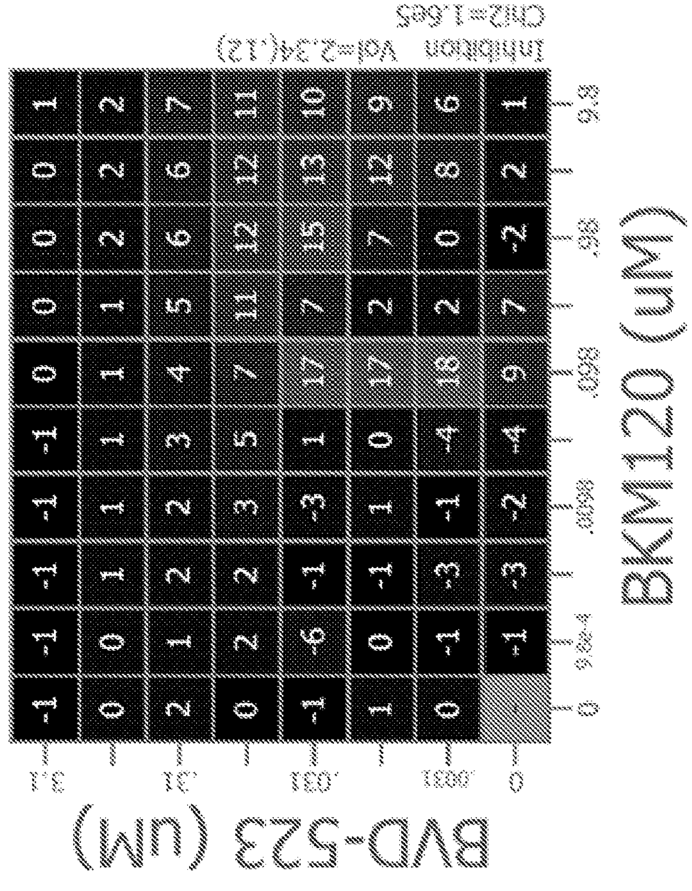
F
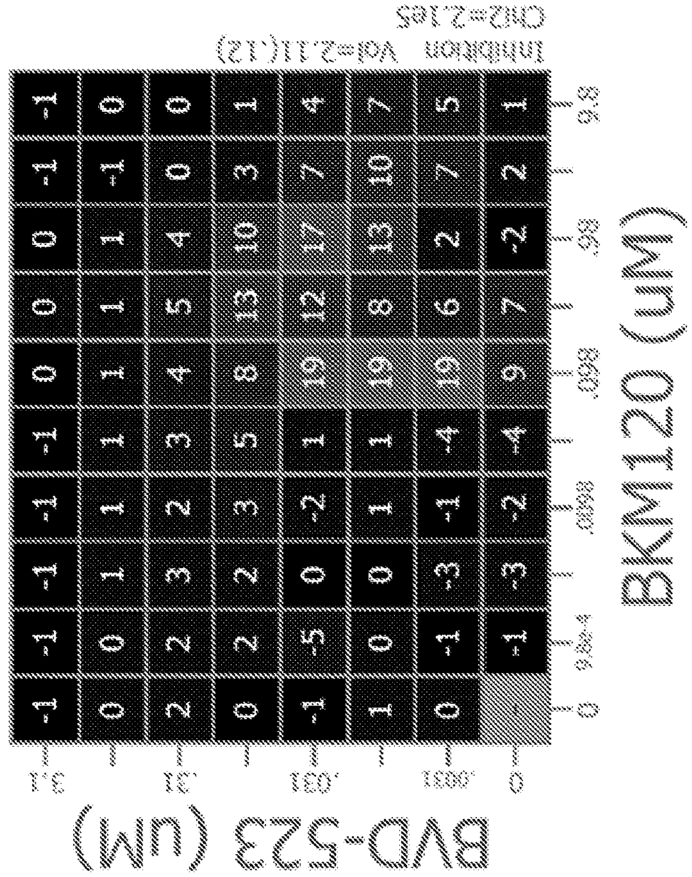

FIG. 9, Continued
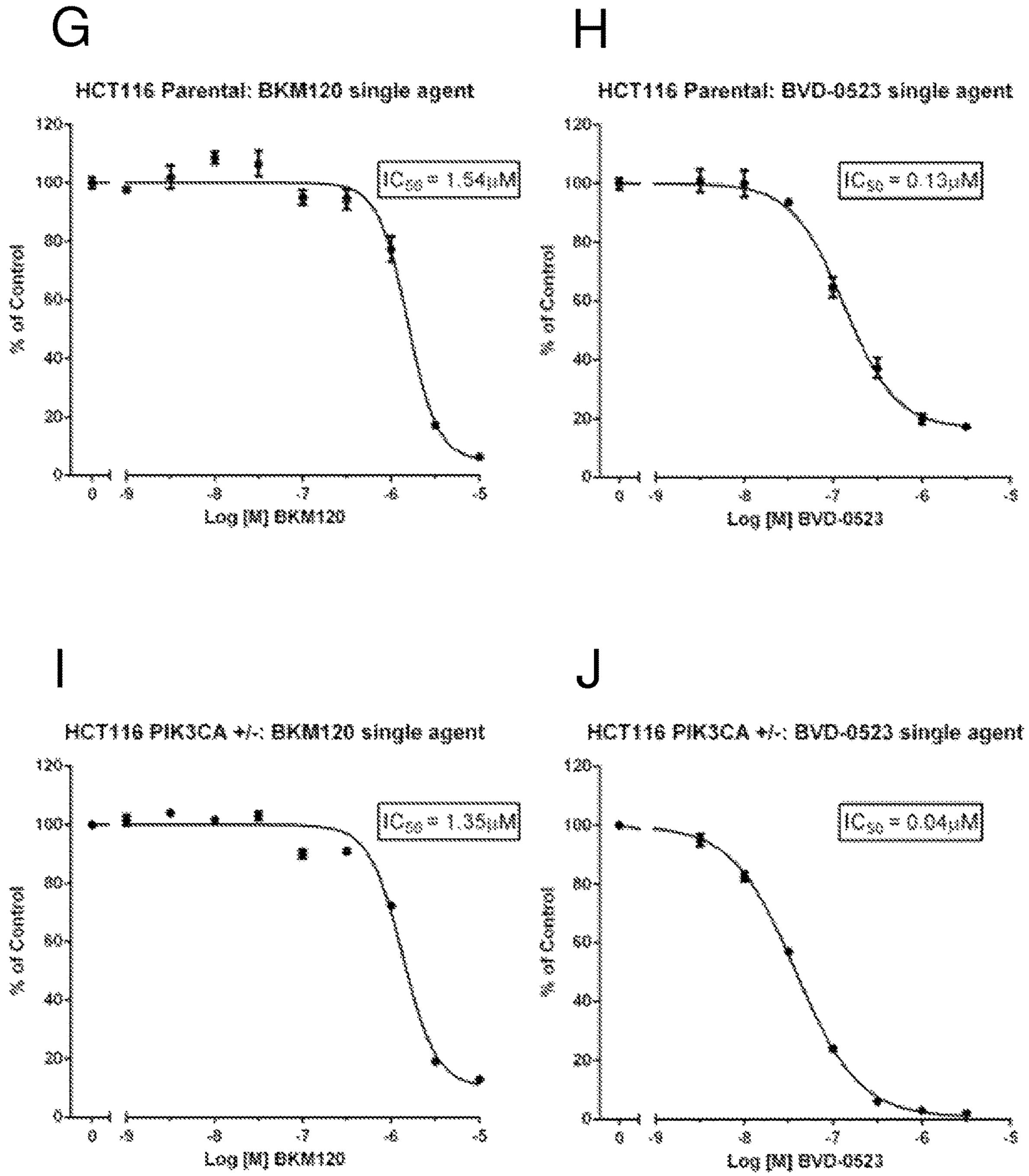

A

FIG. 10, Continued
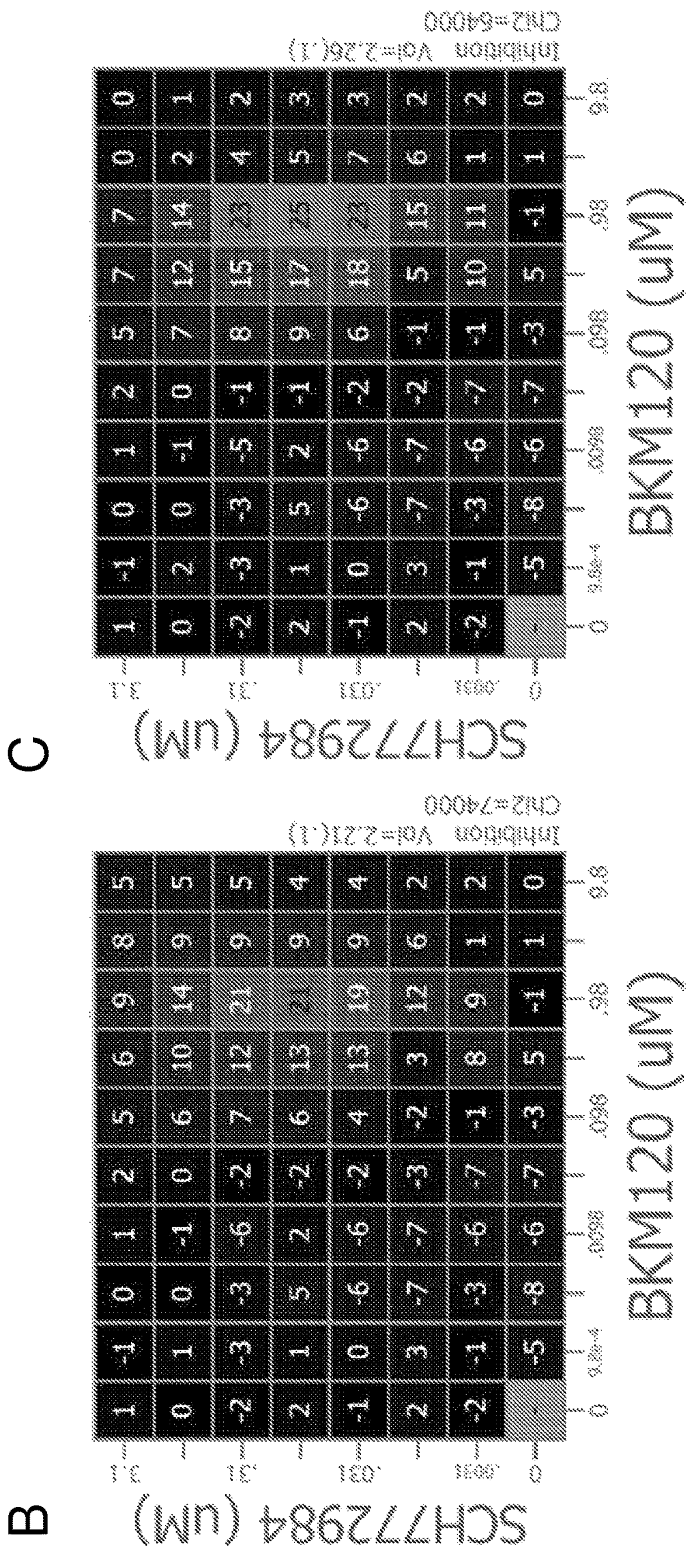

FIG. 10, Continued
D
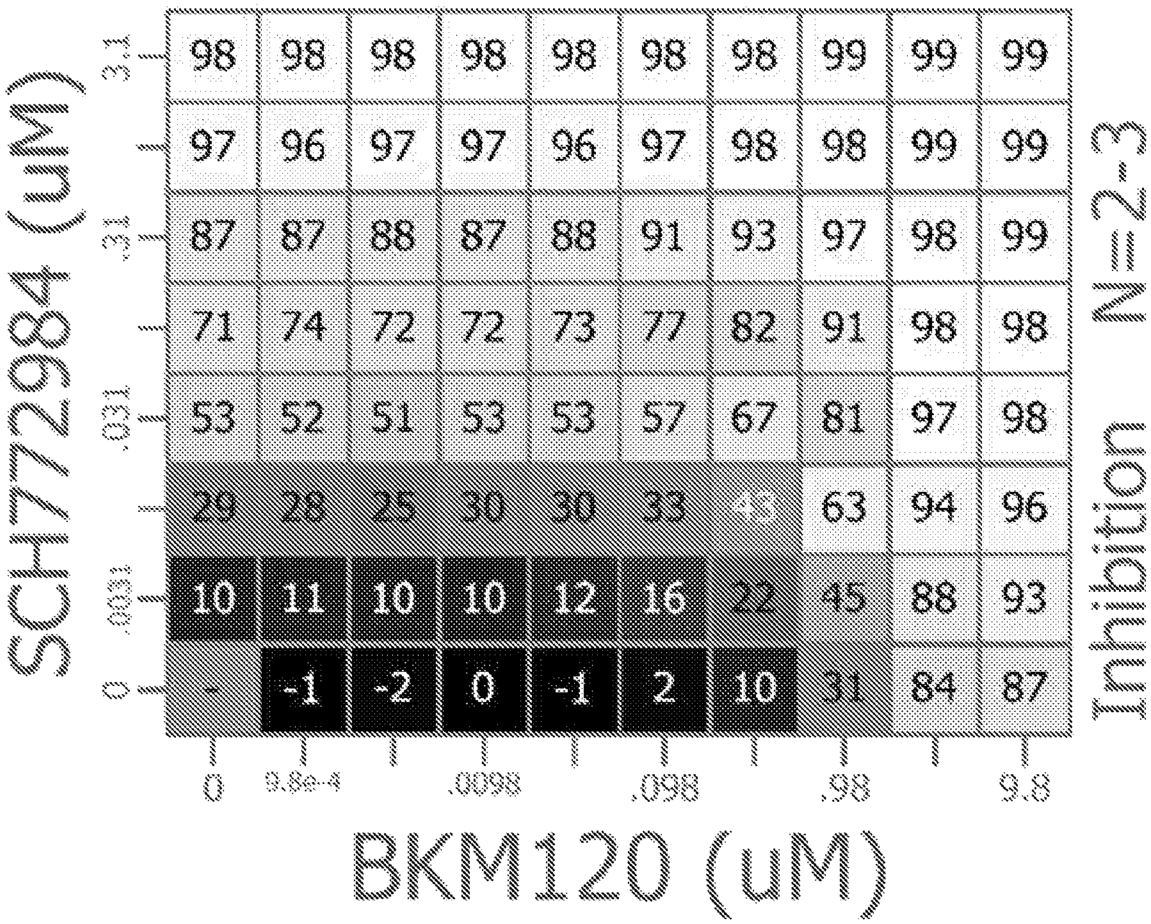

FIG. 10, Continued
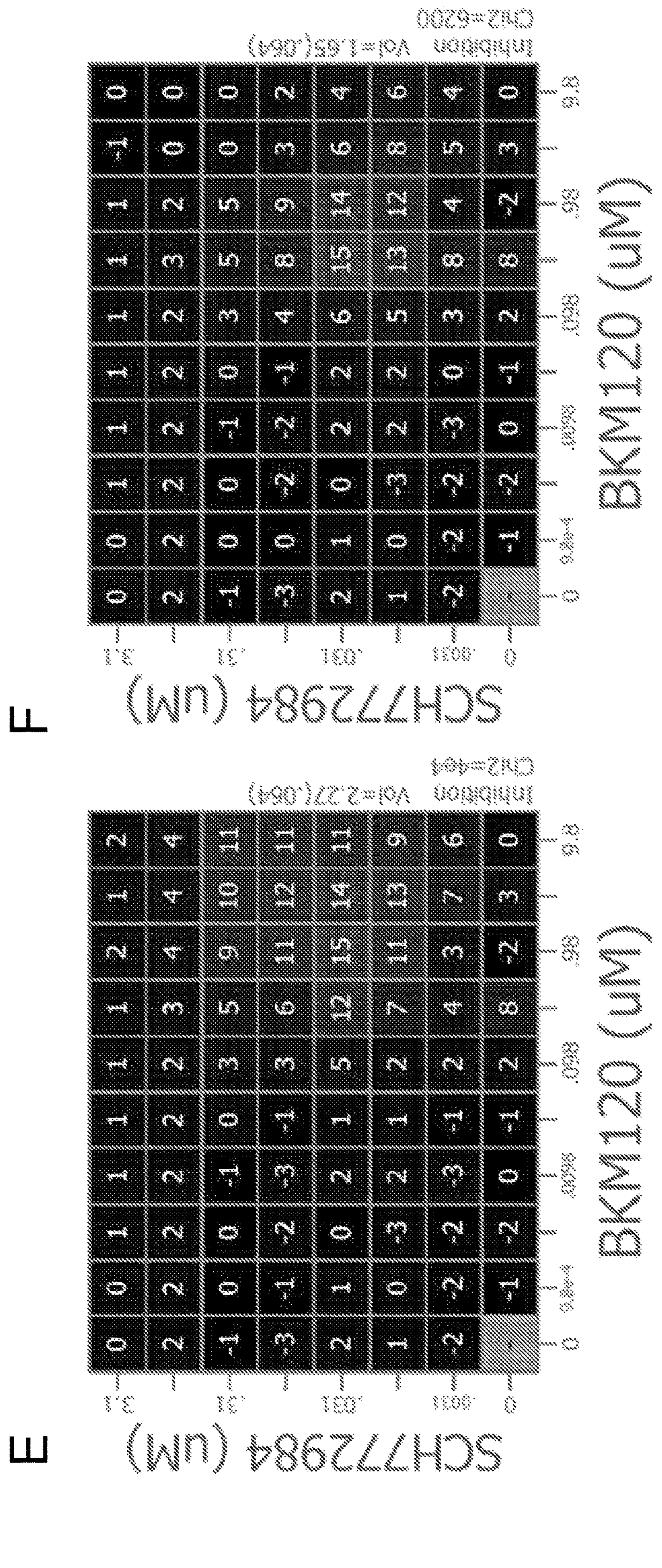

FIG. 10, Continued
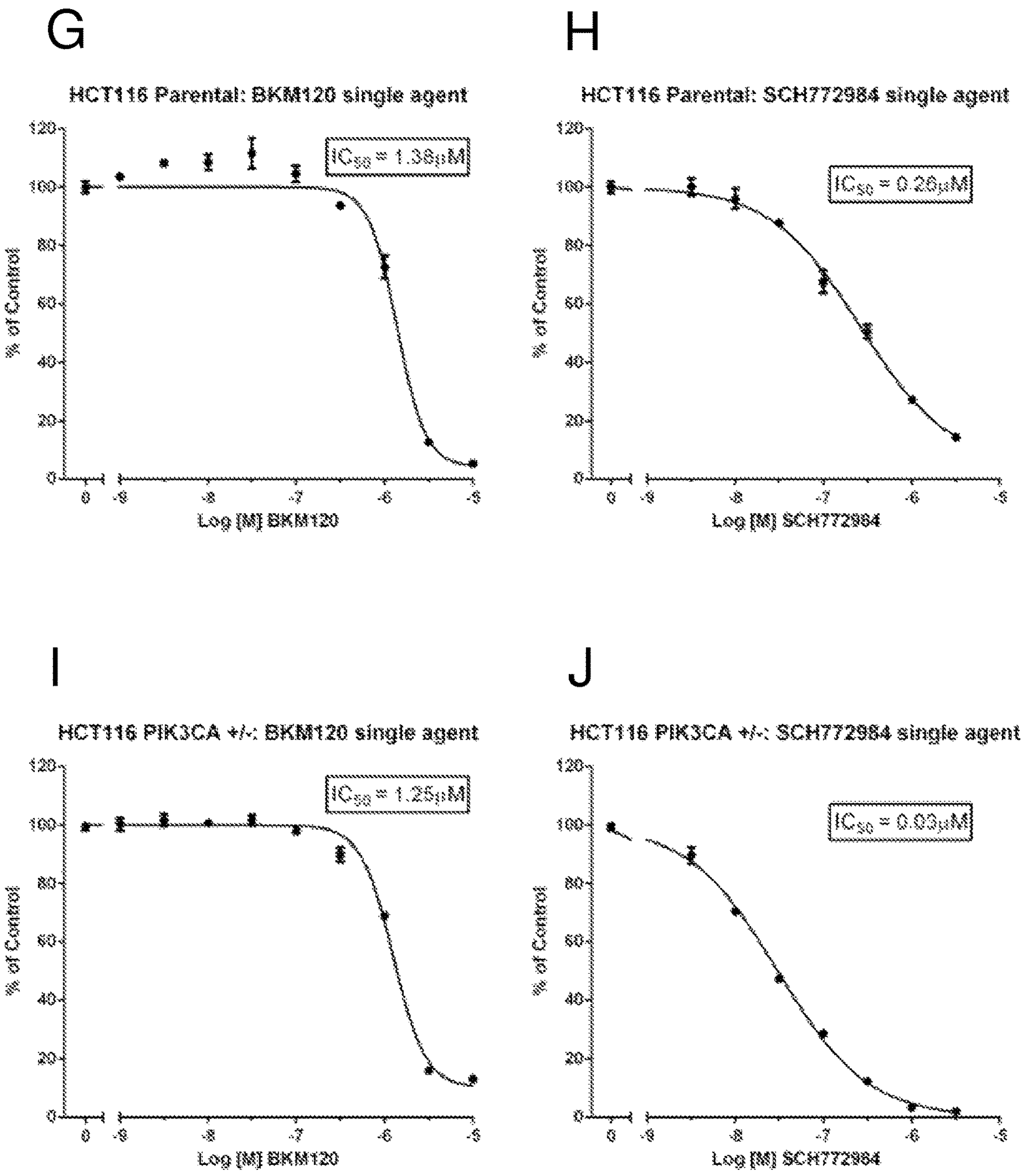

A

FIG. 11, Continued
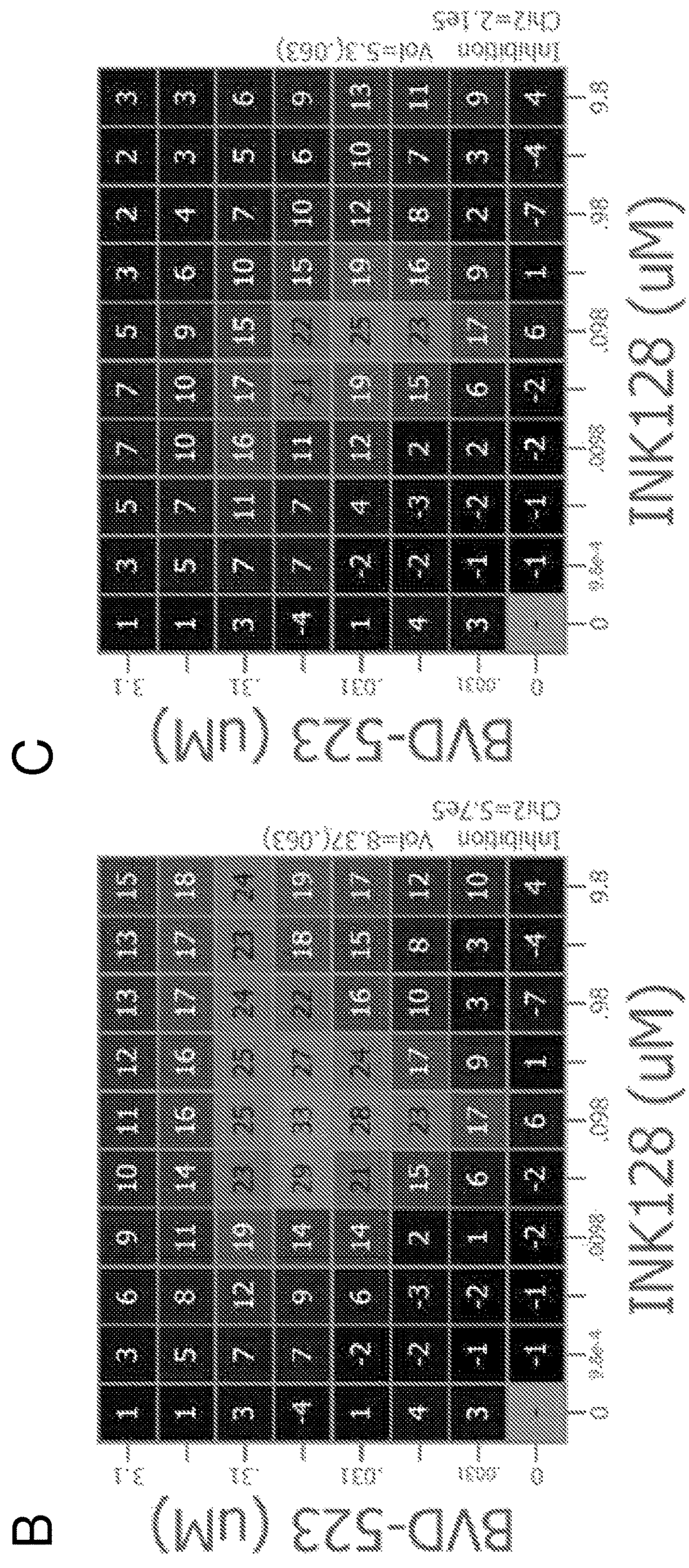

FIG. 11, Continued
D
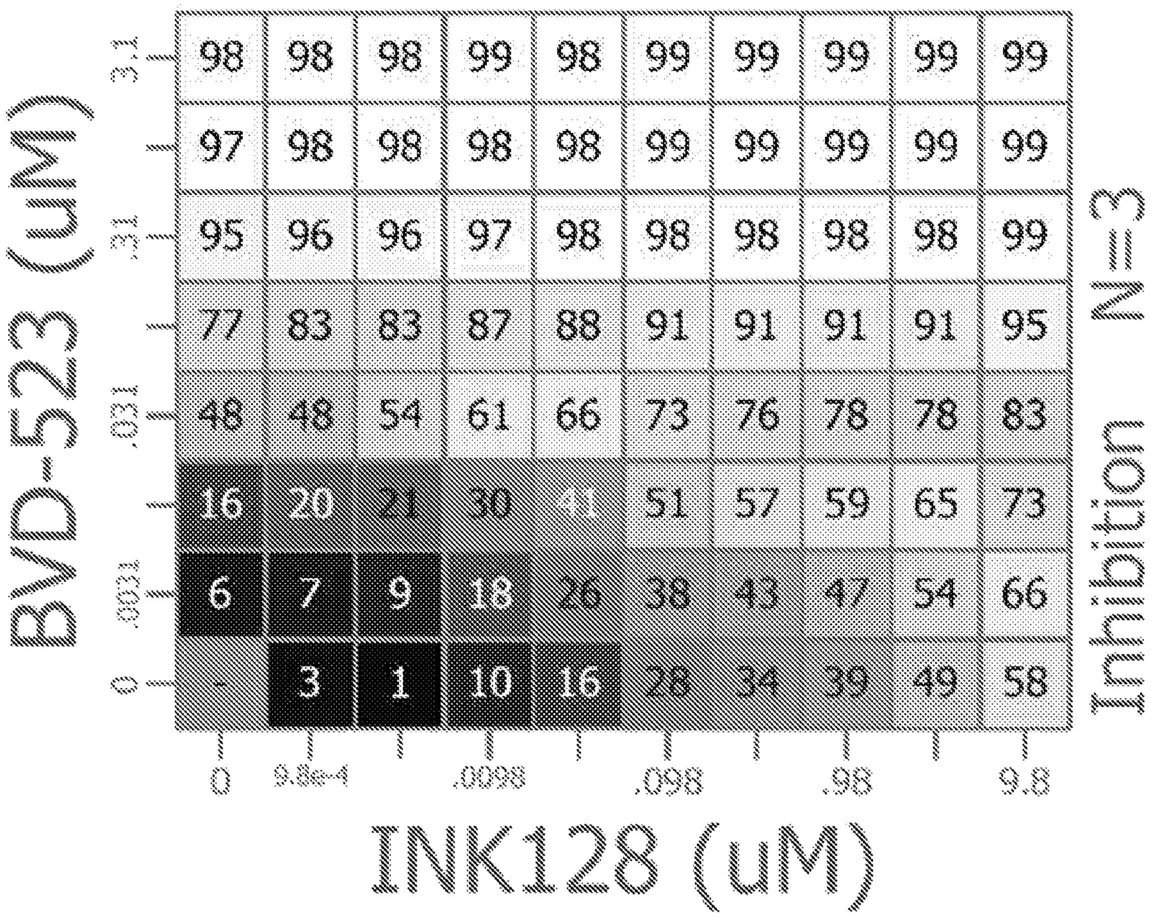

FIG. 11, Continued
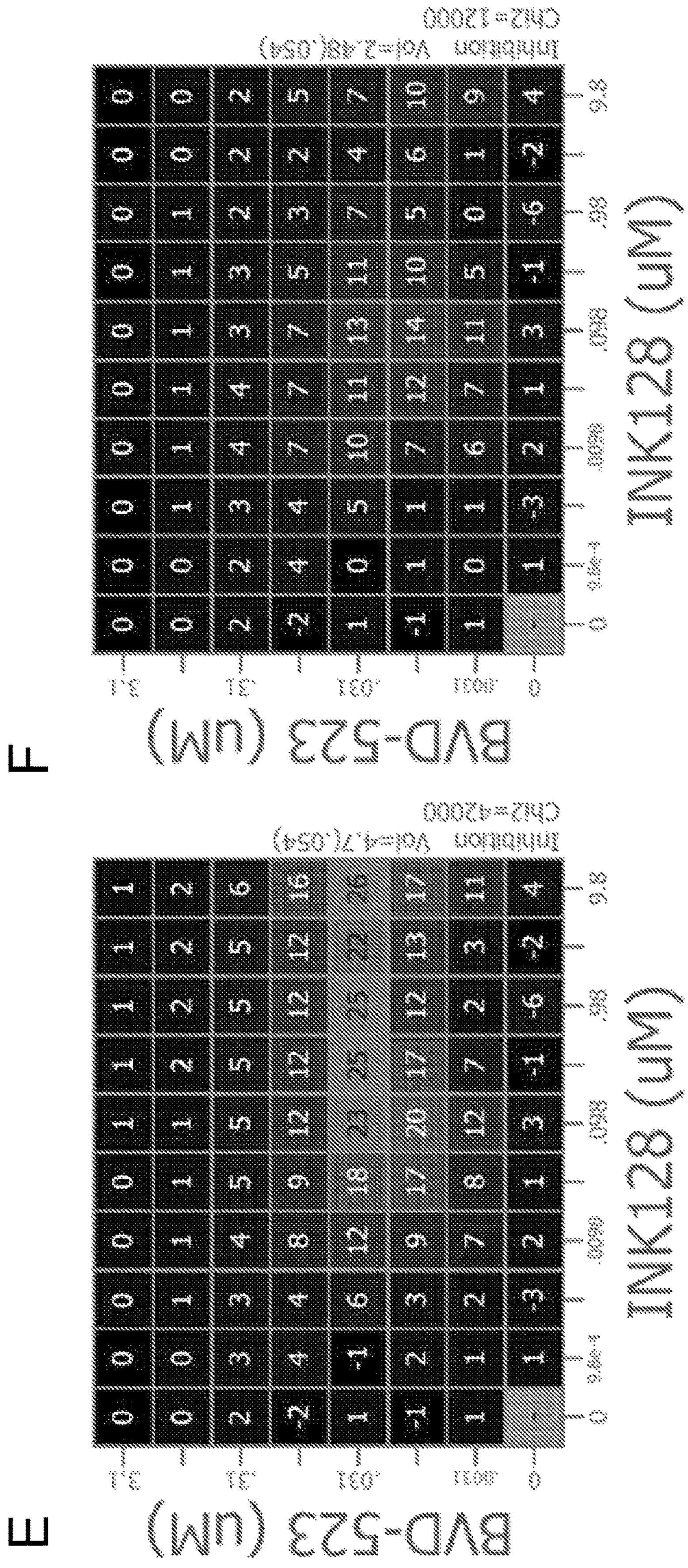

FIG. 11, Continued
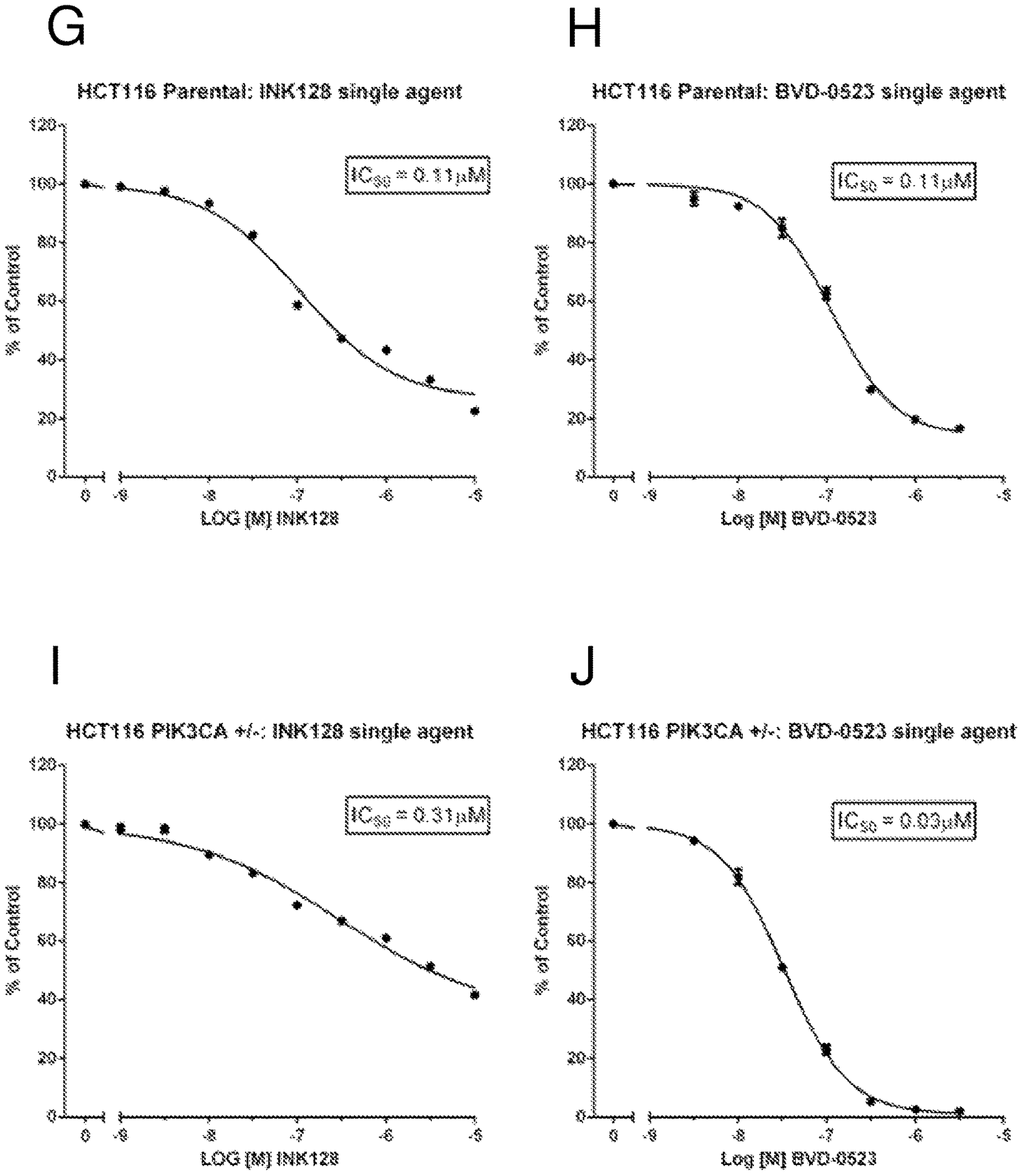

A

FIG. 12, Continued
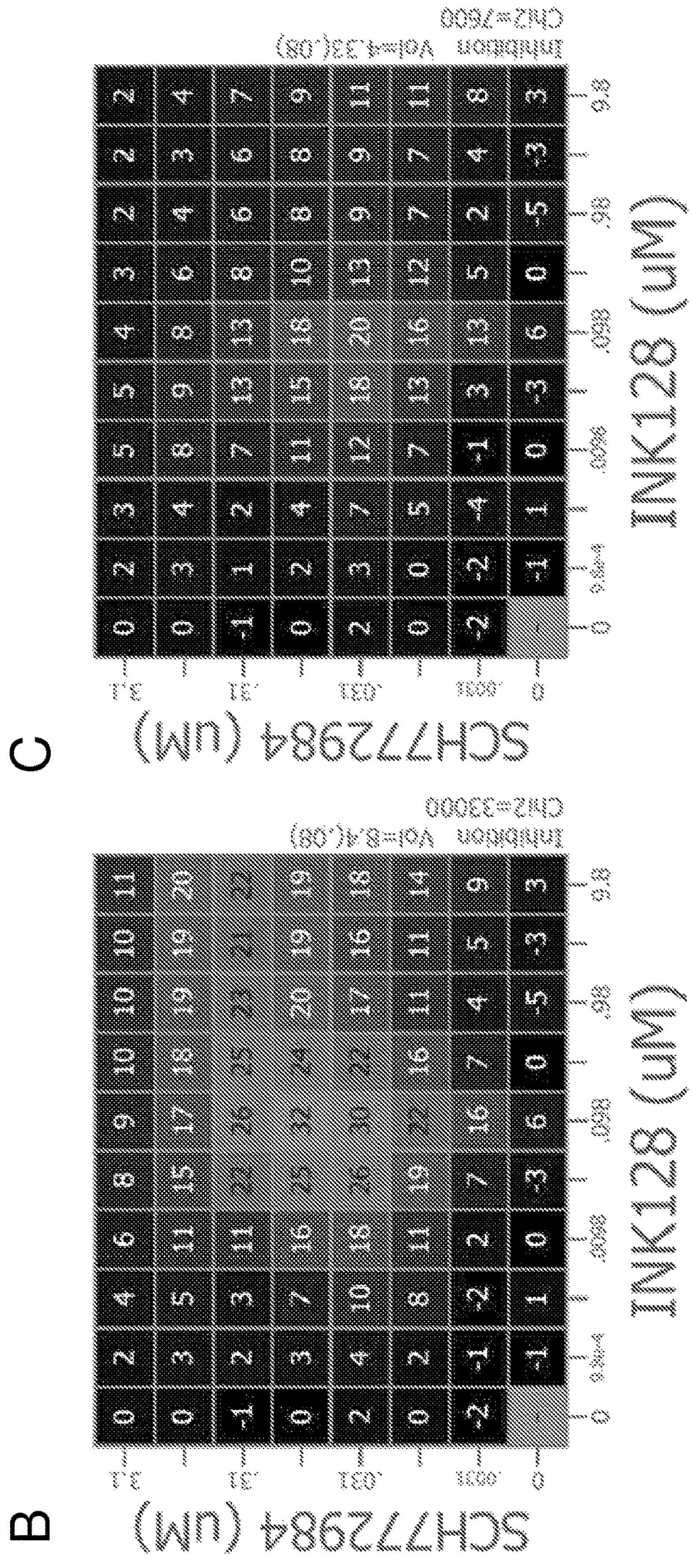

FIG. 12, Continued
D
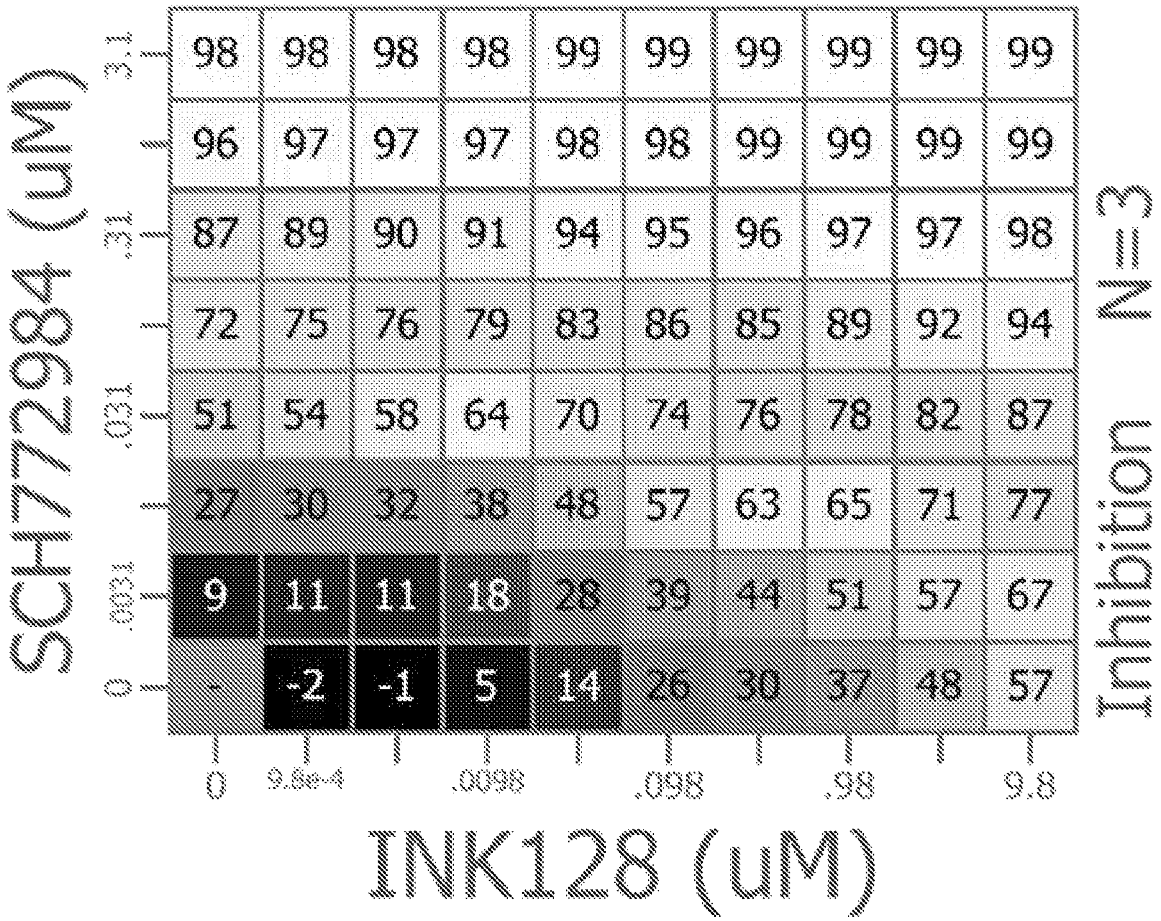

FIG. 12, Continued
E
F
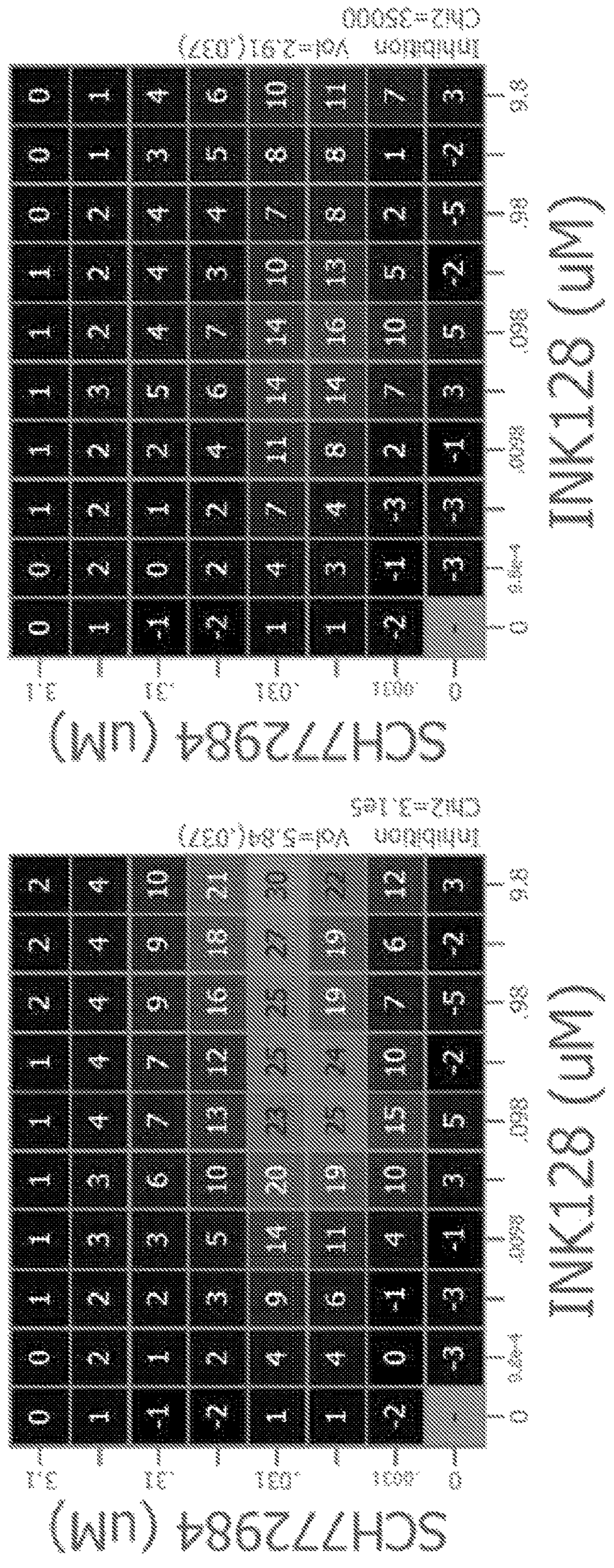

FIG. 12, Continued
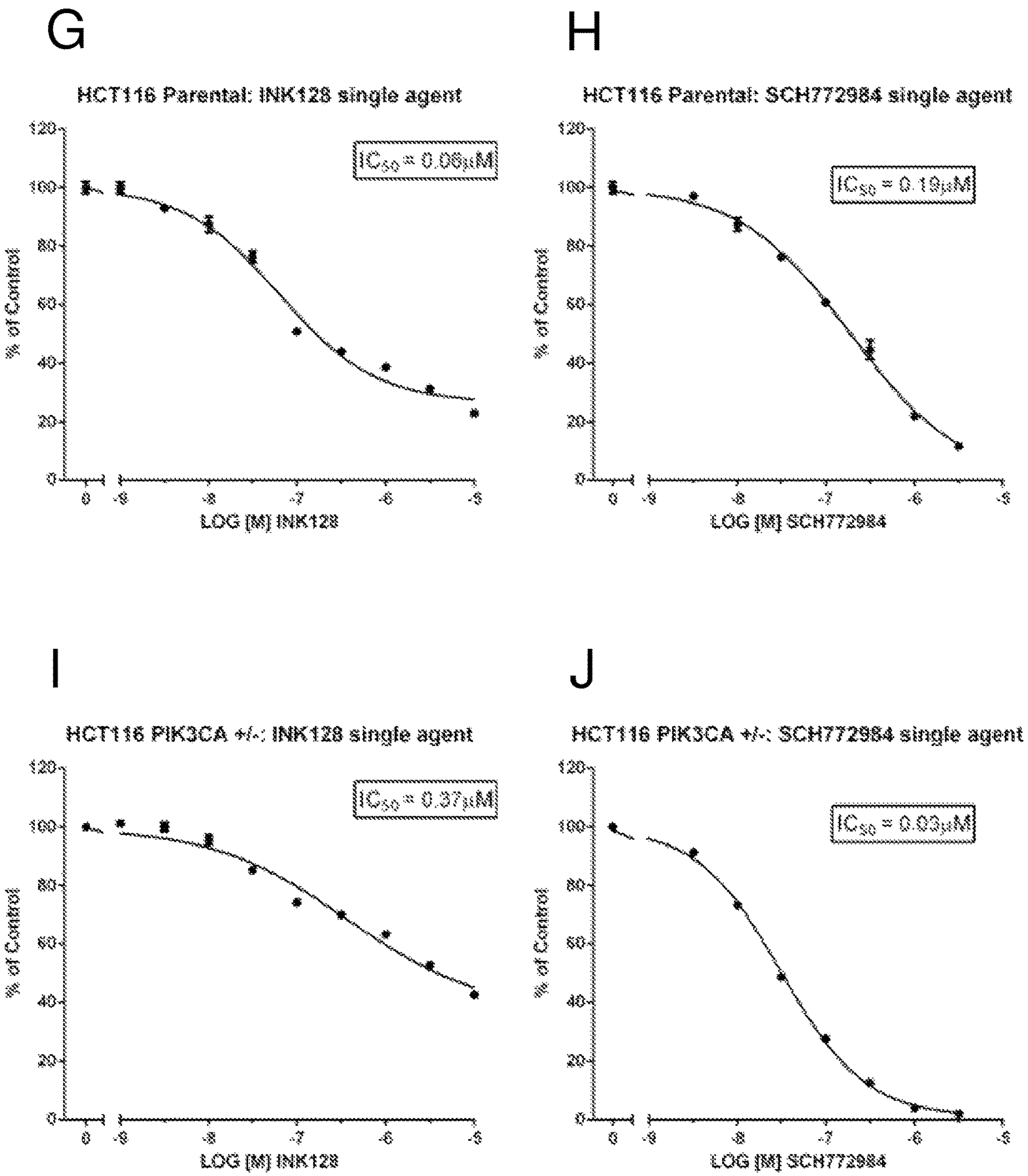

A

FIG. 13, Continued
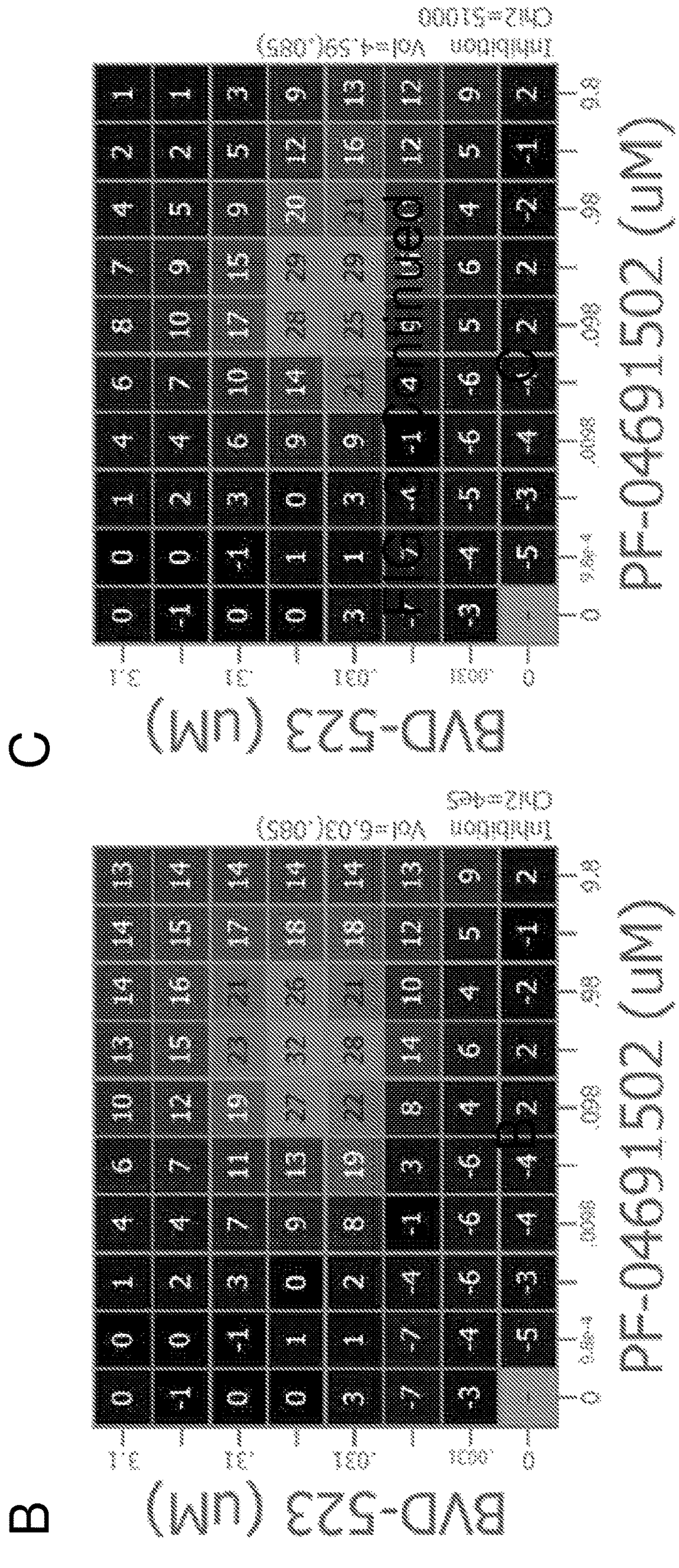

FIG. 13, Continued
D
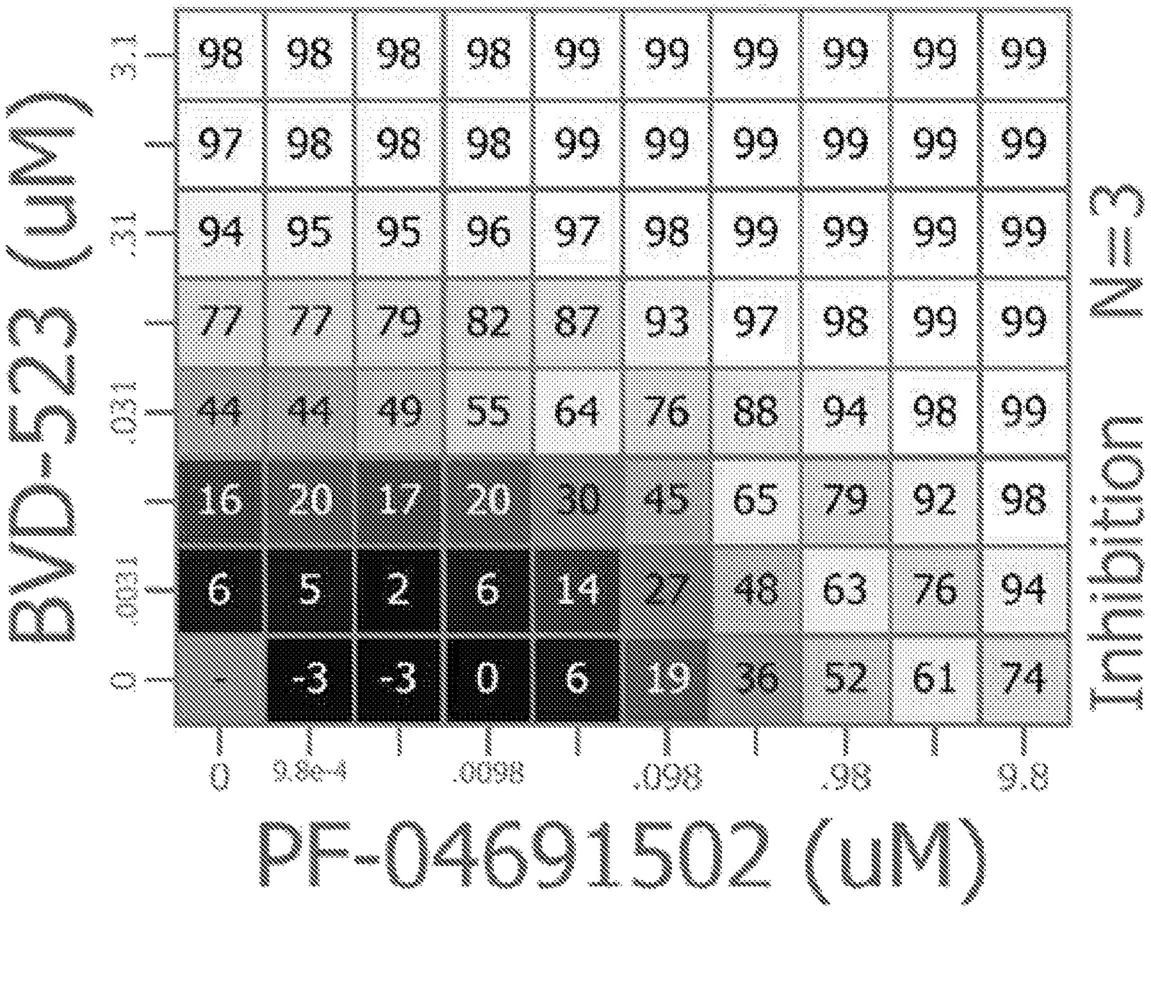

FIG. 13, Continued
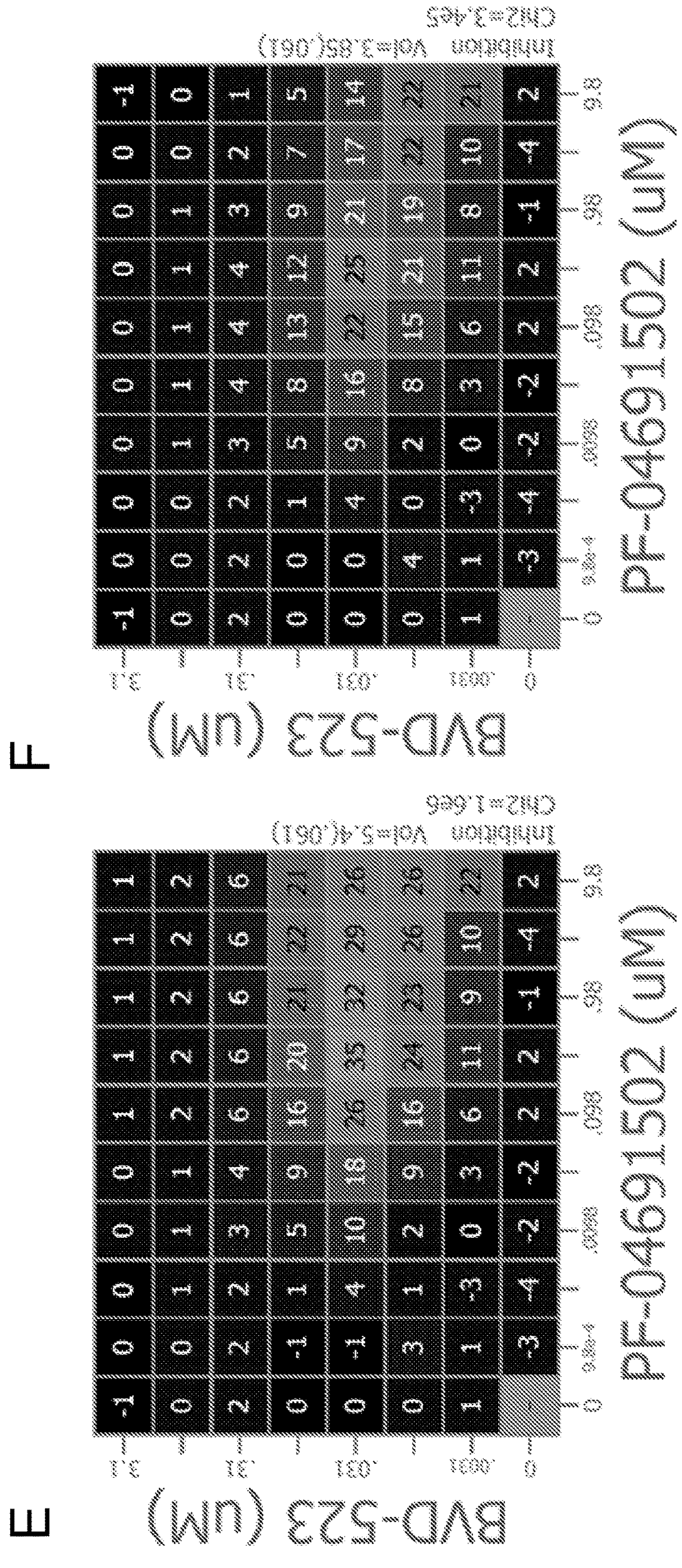

FIG. 13, Continued
G
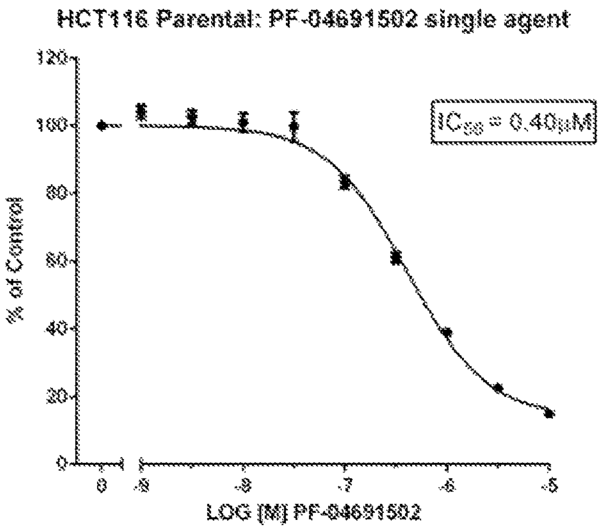
H
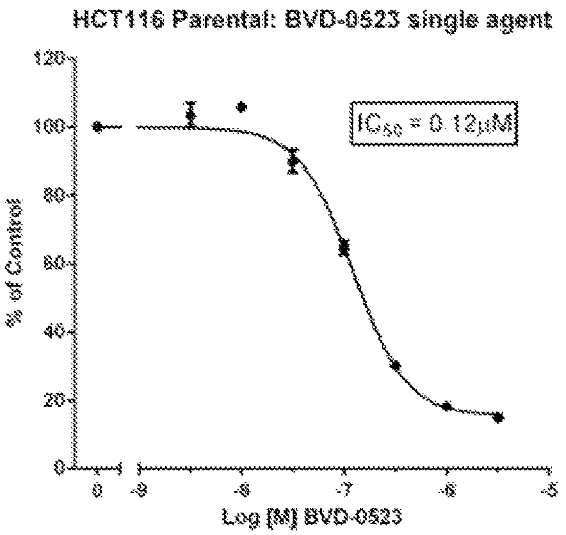
I
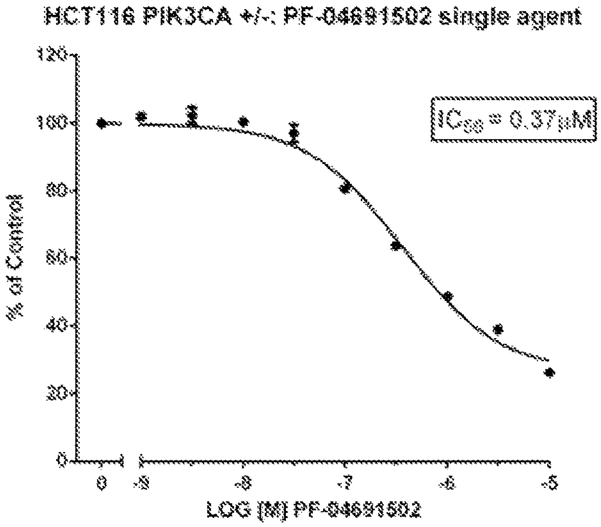
J
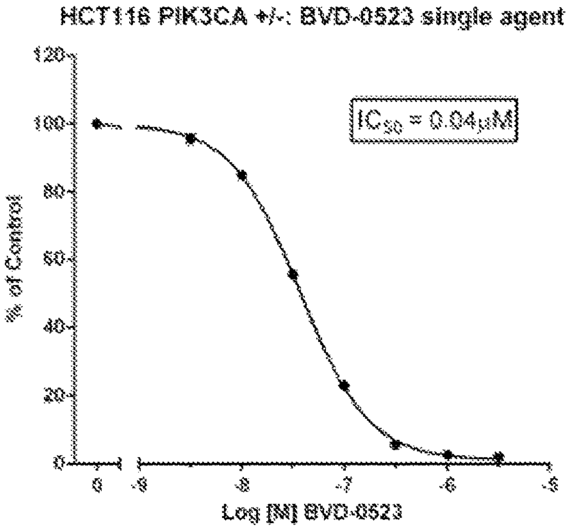

A

FIG. 14, Continued
B
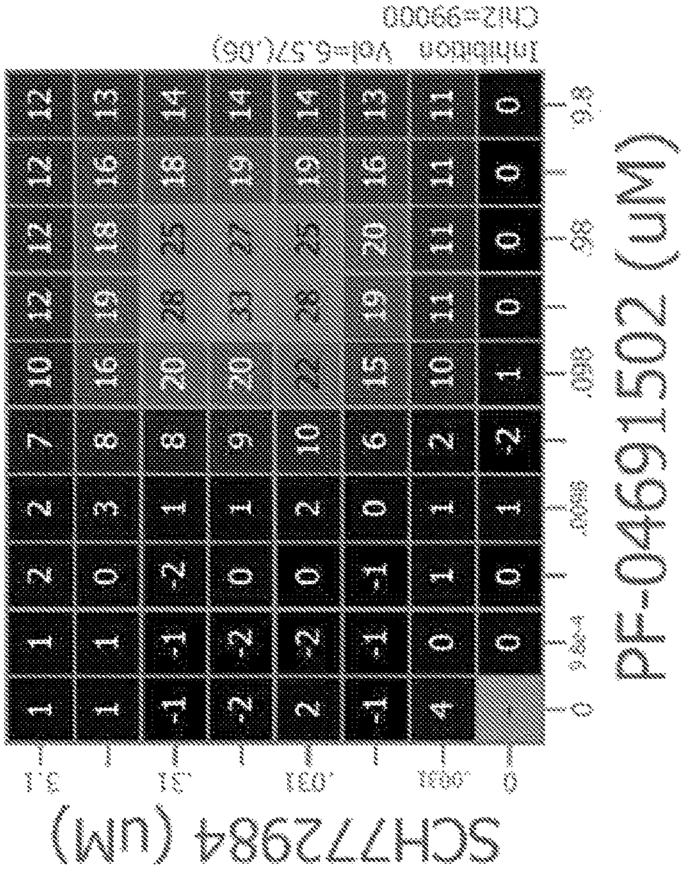
C
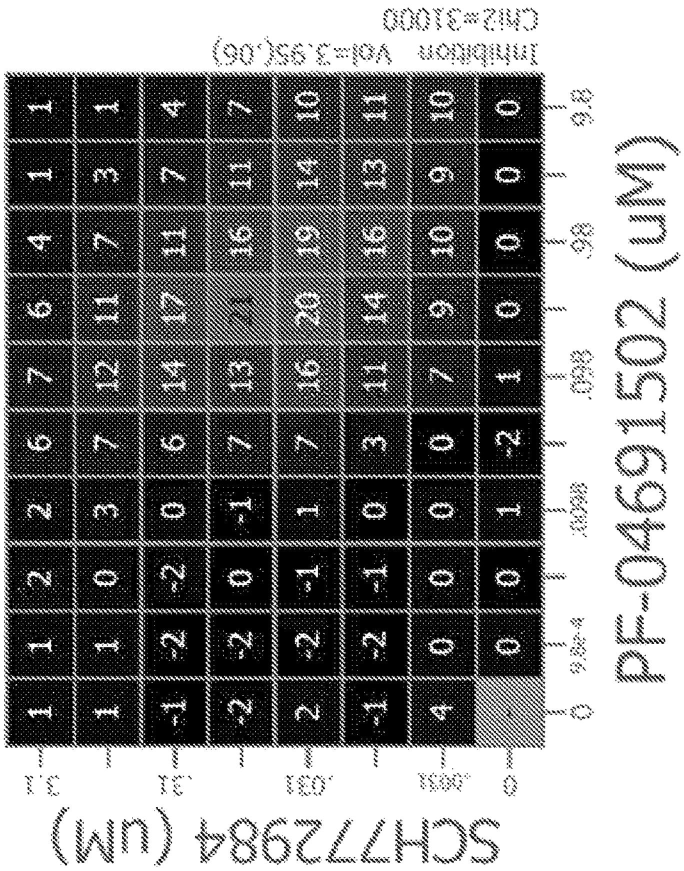

FIG. 14, Continued
D
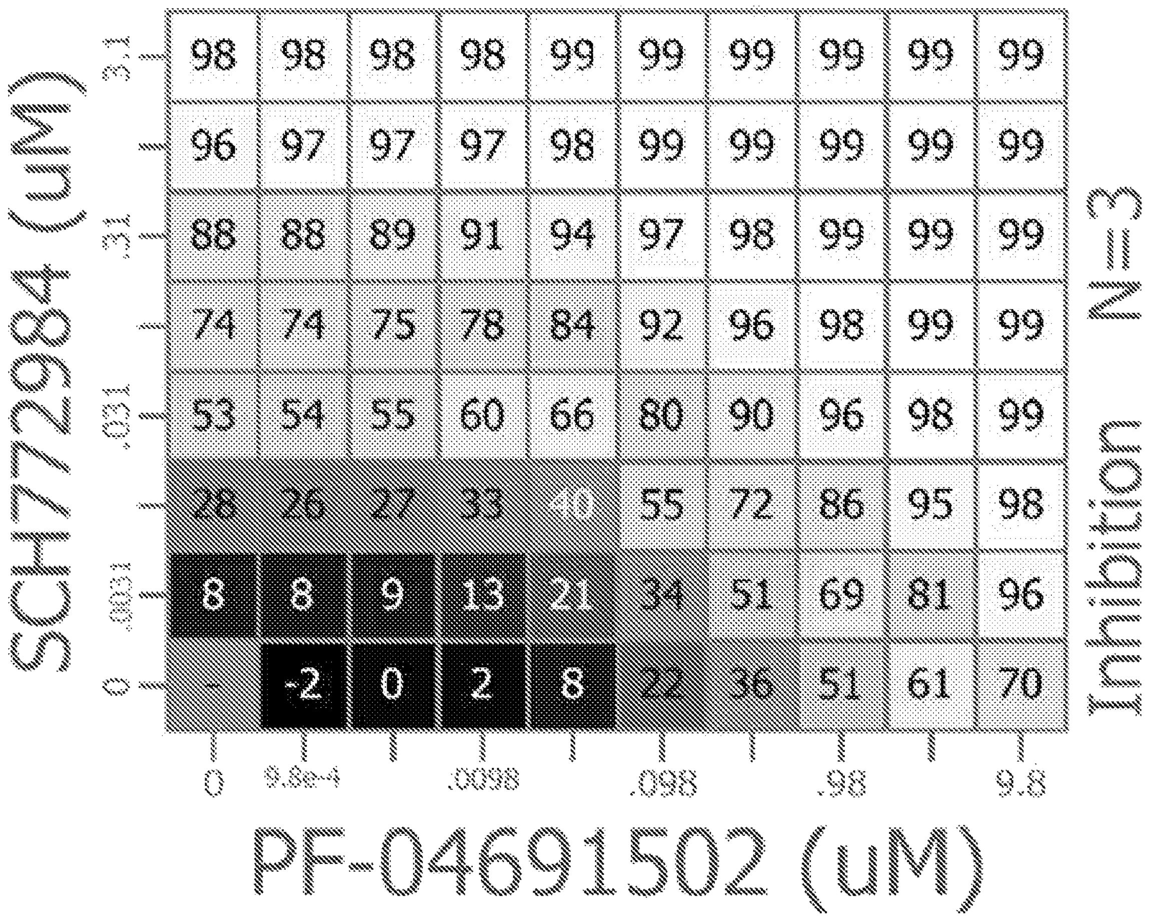

FIG. 14, Continued
F
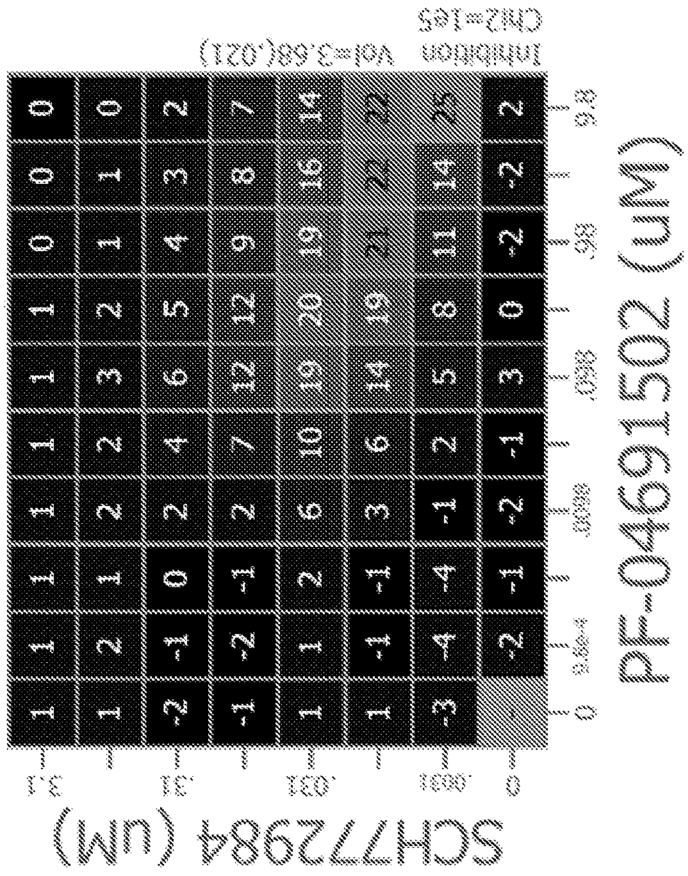
E
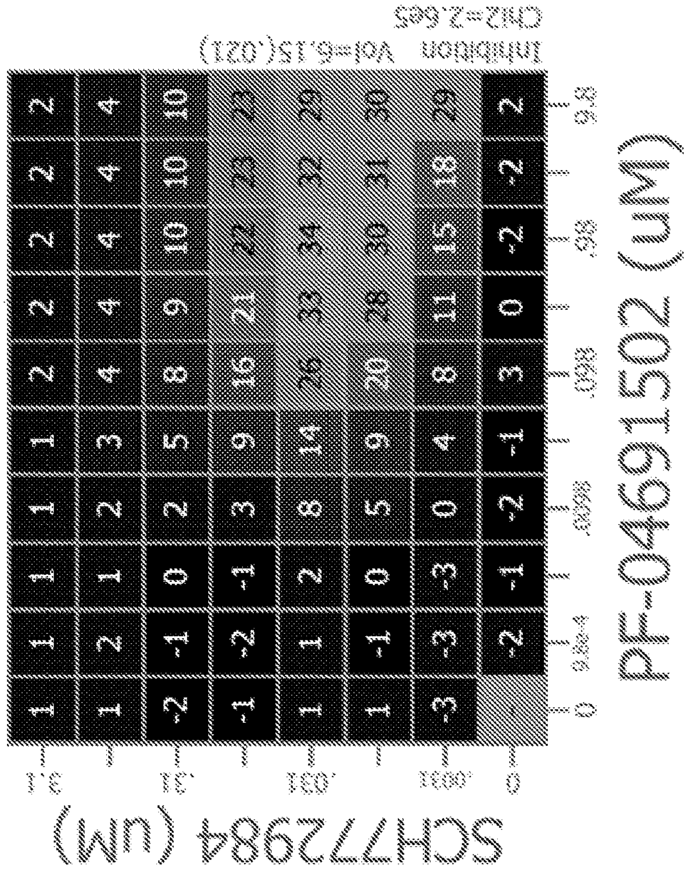

FIG. 14, Continued
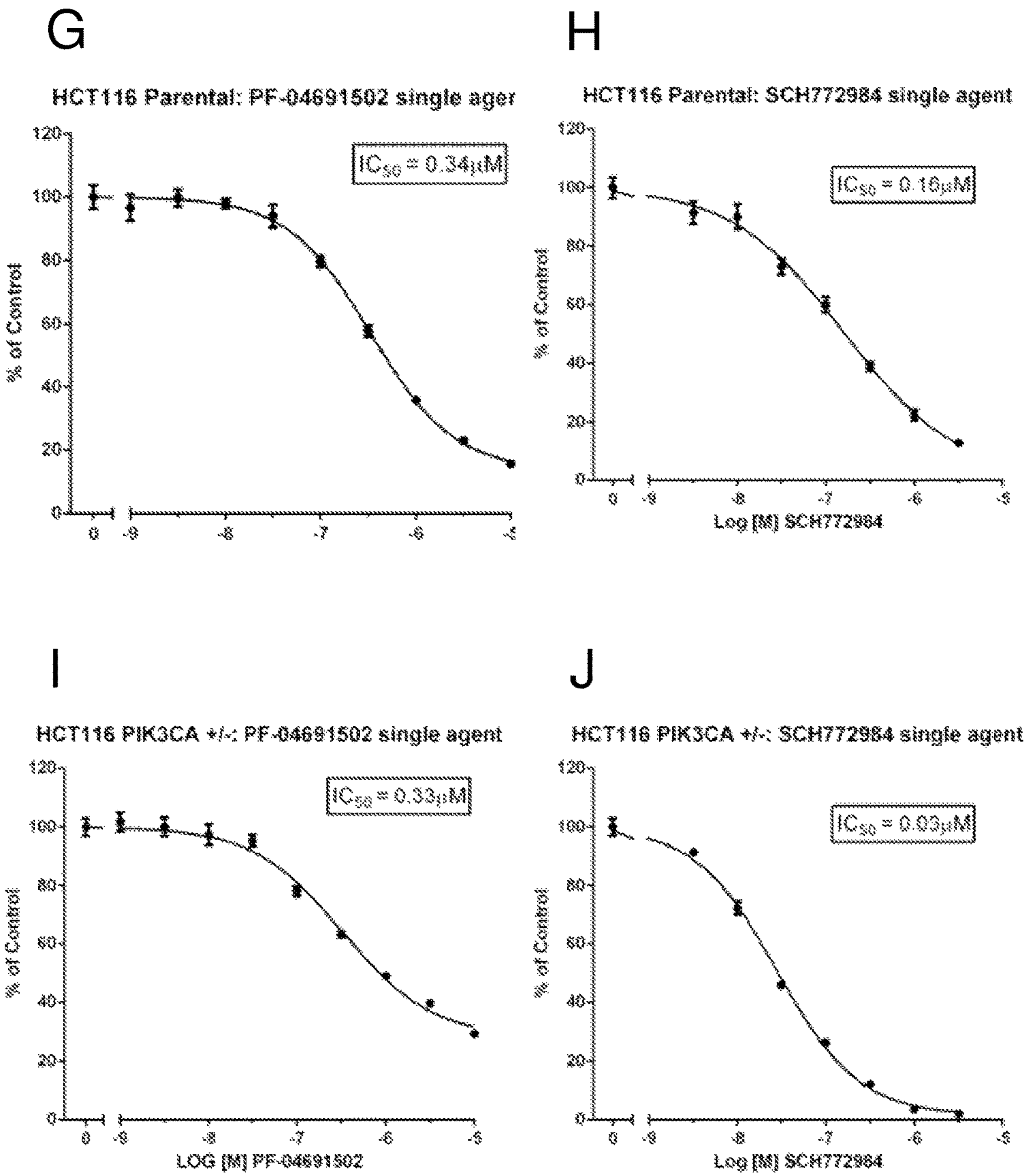

FIG. 15, Continued
E
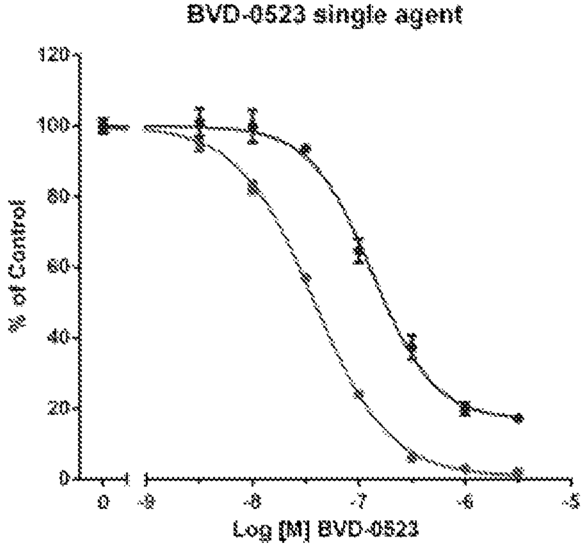
F
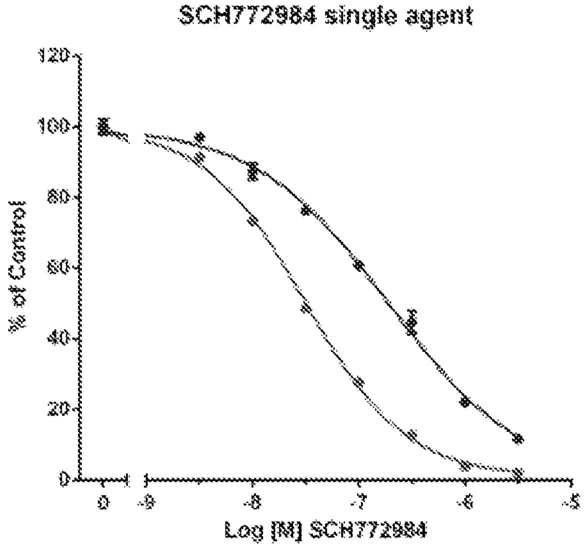

A

FIG. 16, Continued
B
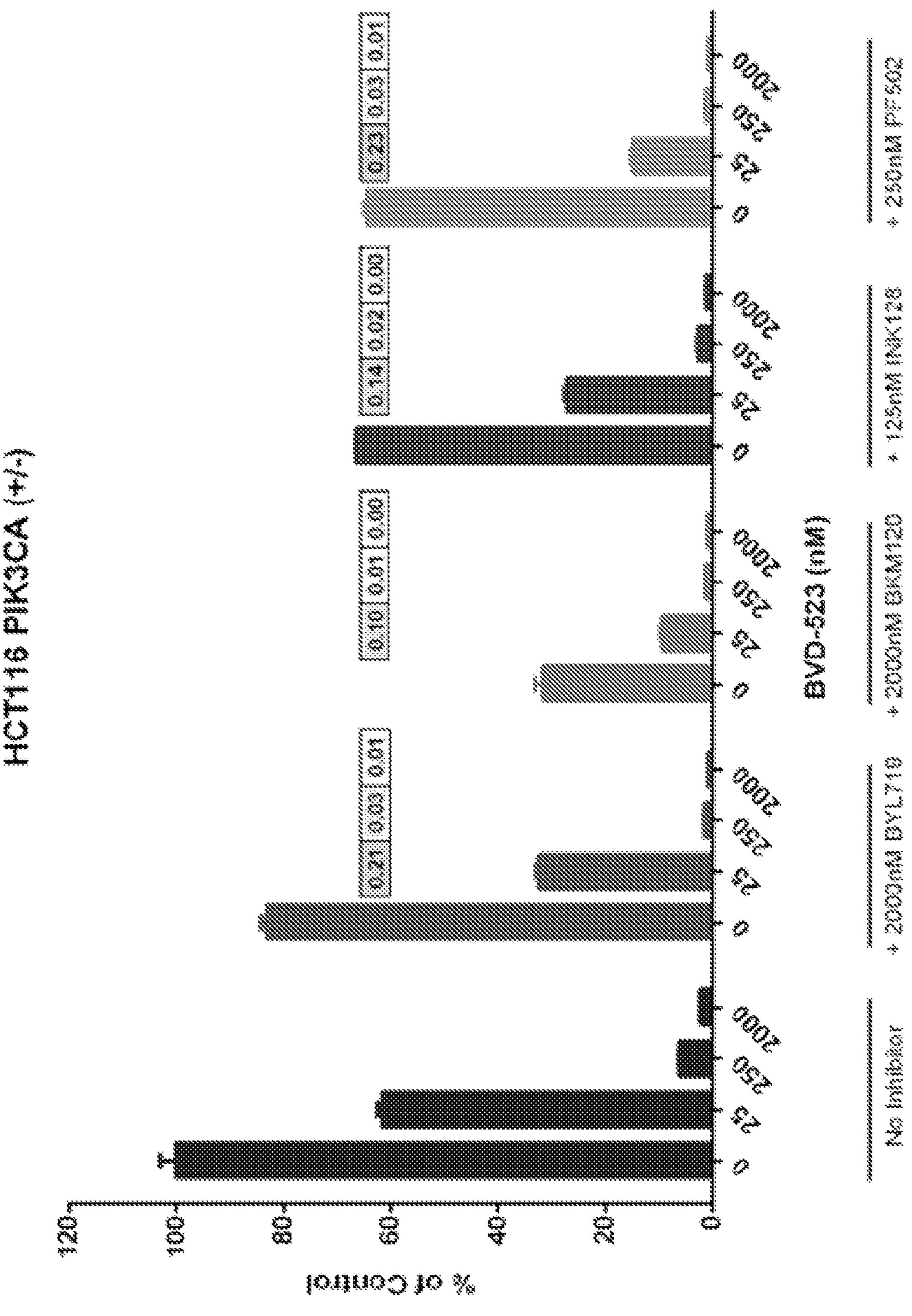

FIG. 16, Continued
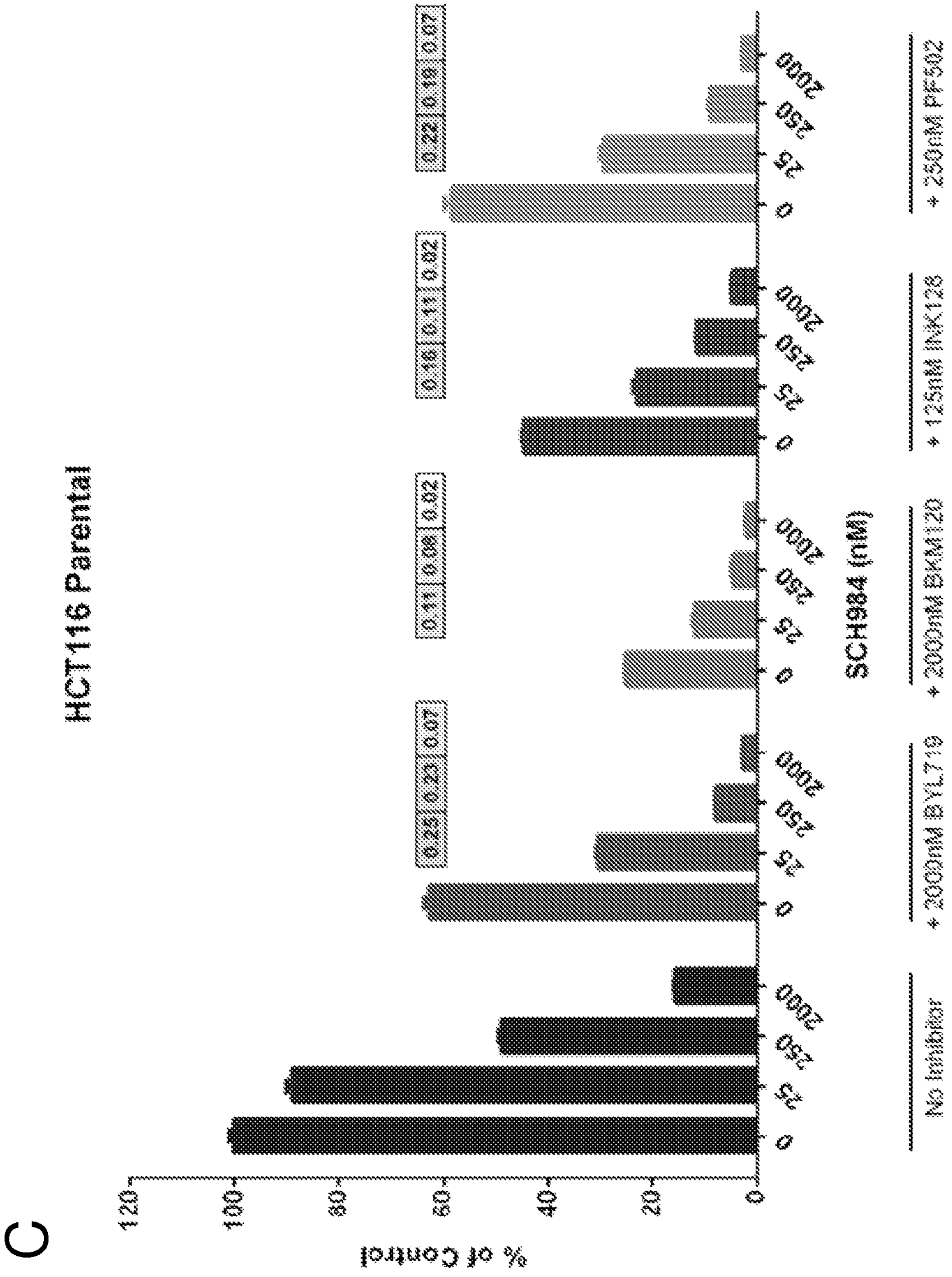

FIG. 16, Continued
D
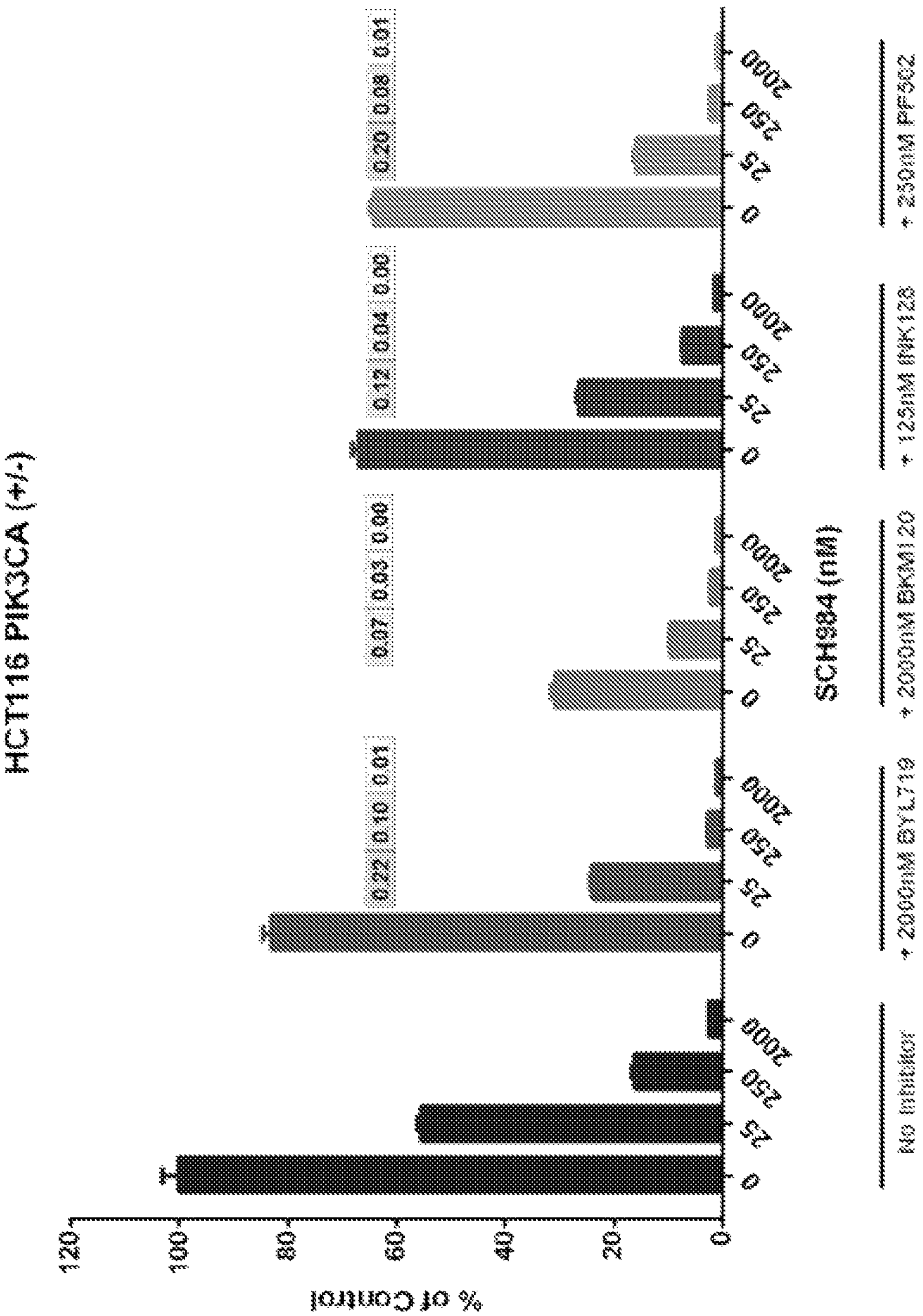

A

FIG. 17, Continued
C
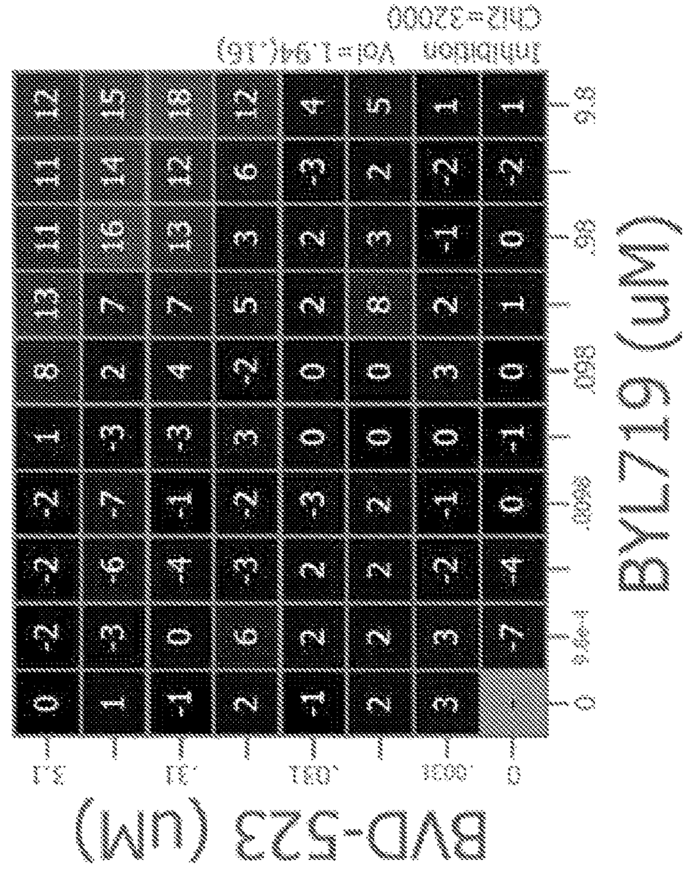
B
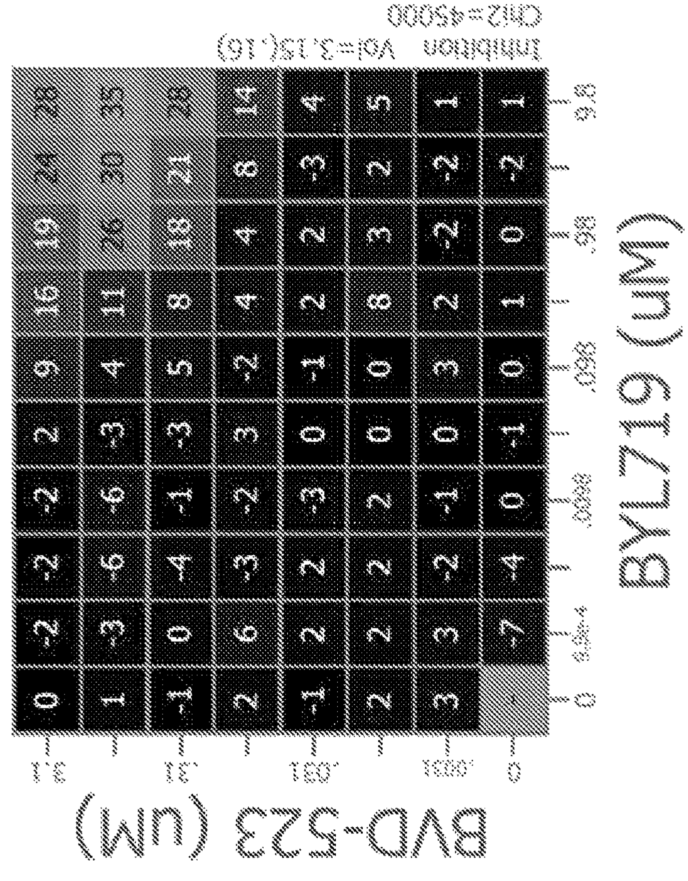

FIG. 17, Continued
D
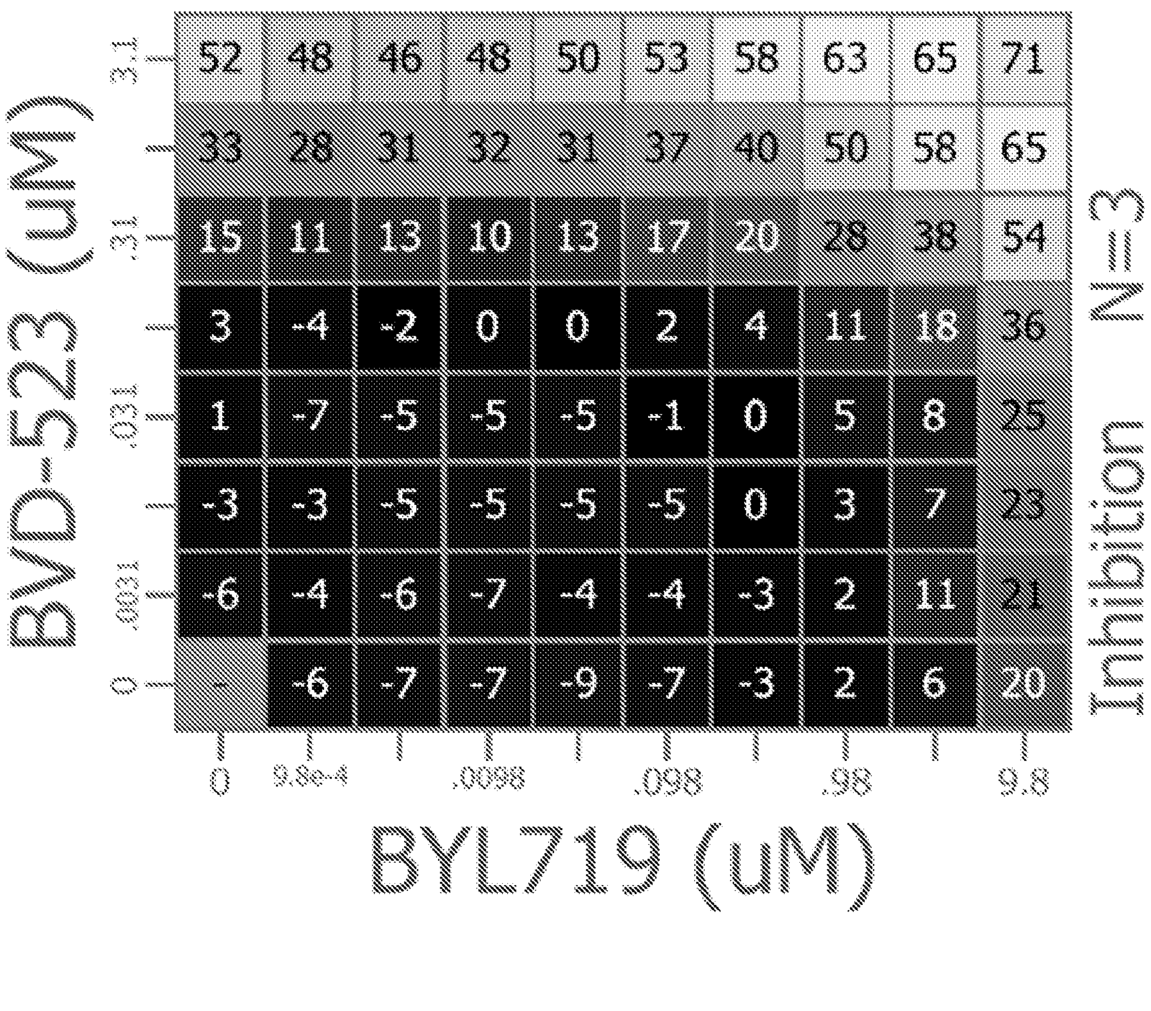

FIG. 17, Continued
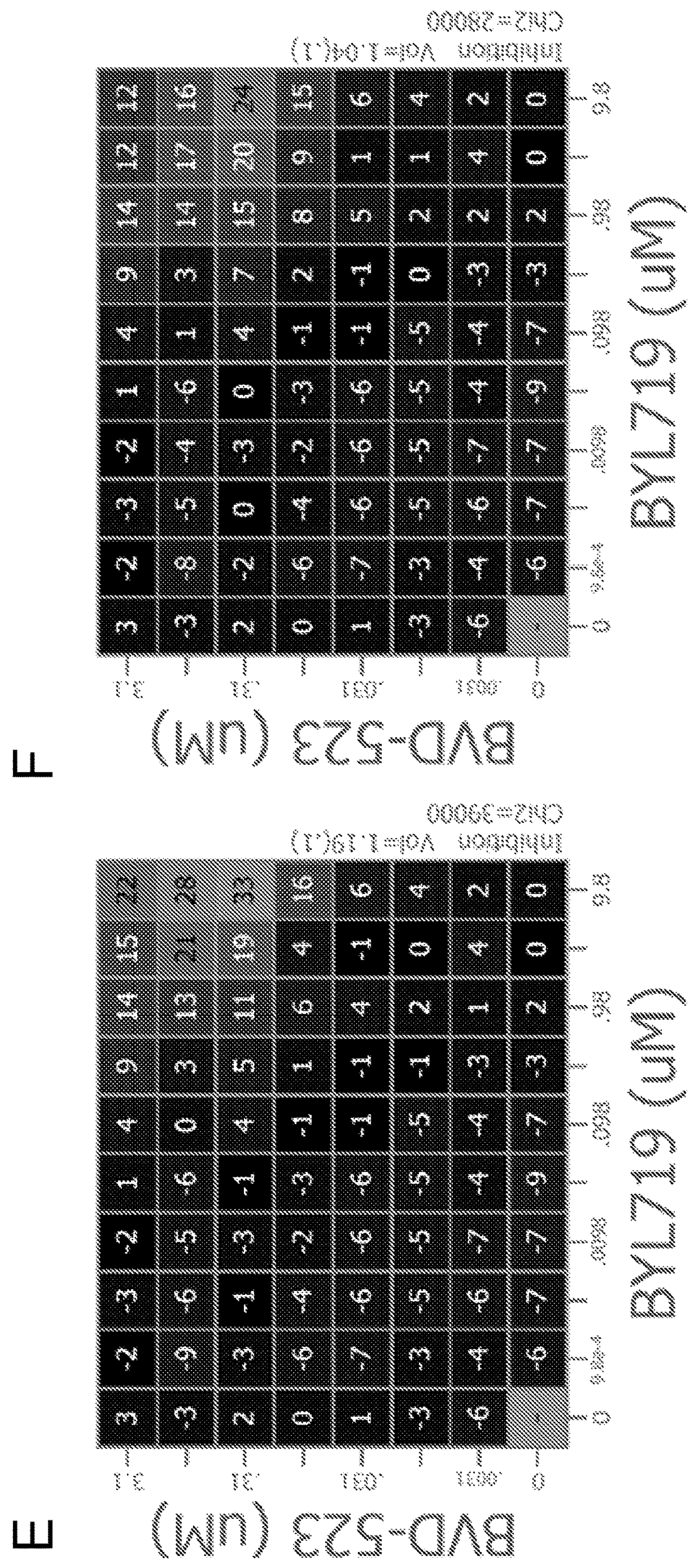

FIG. 17, Continued
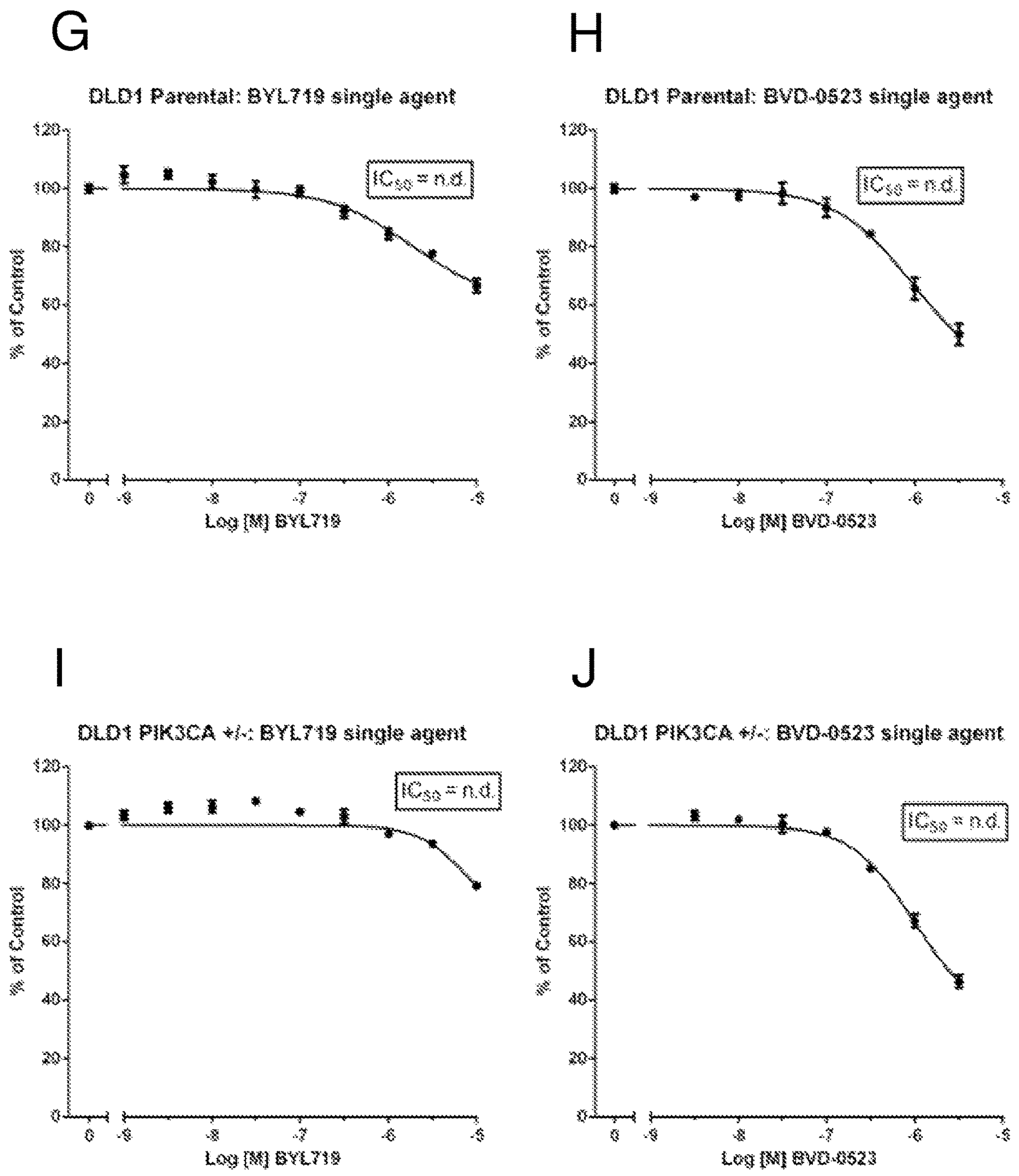

A

FIG. 18, Continued
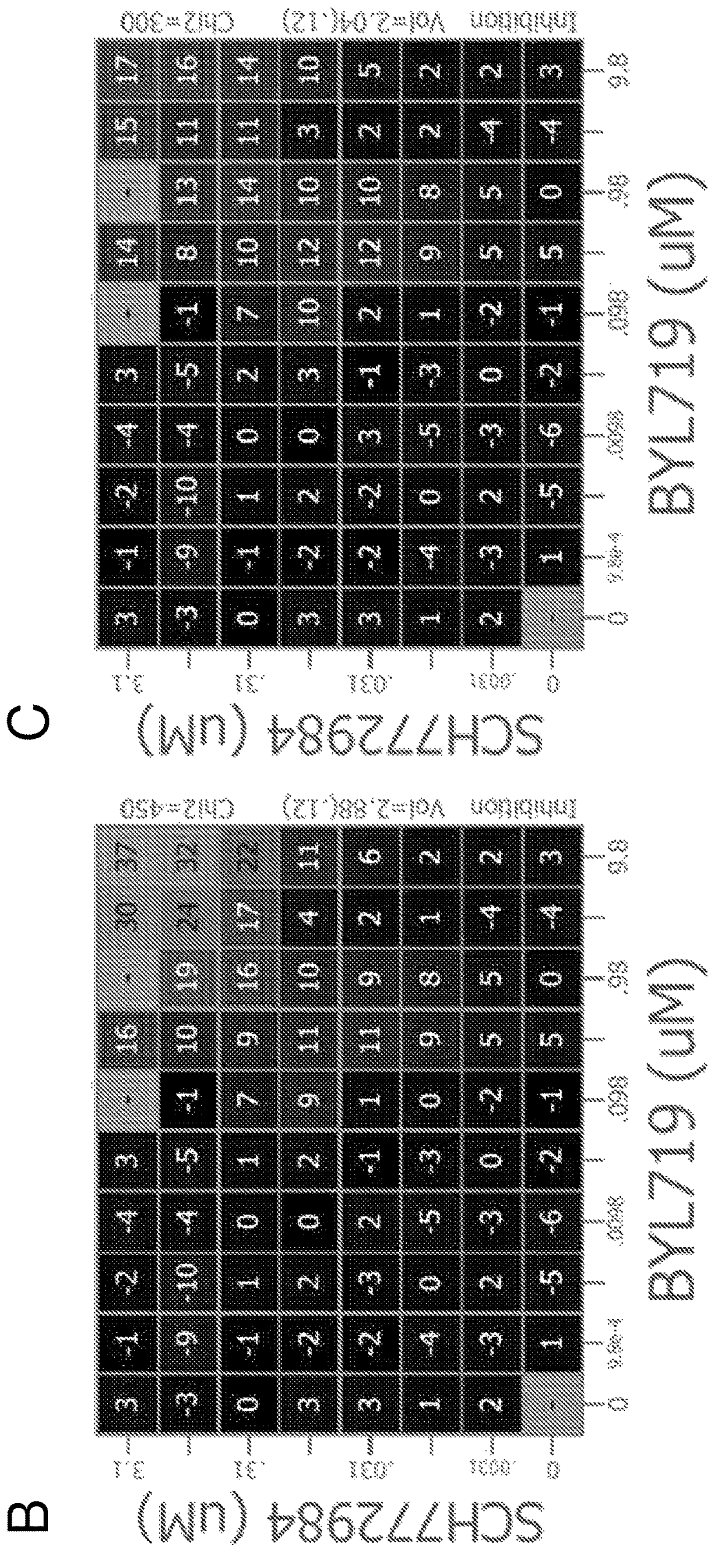

FIG. 18, Continued
D
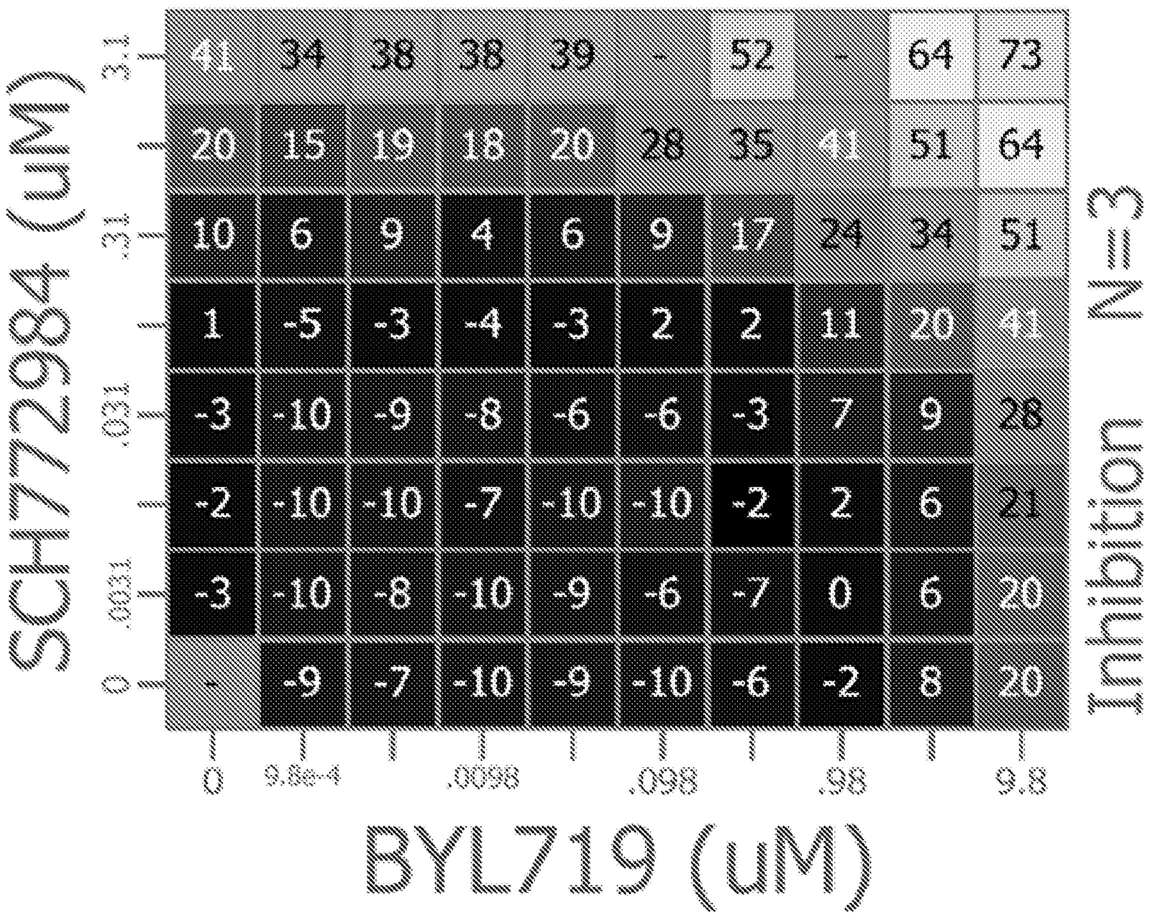

FIG. 18, Continued
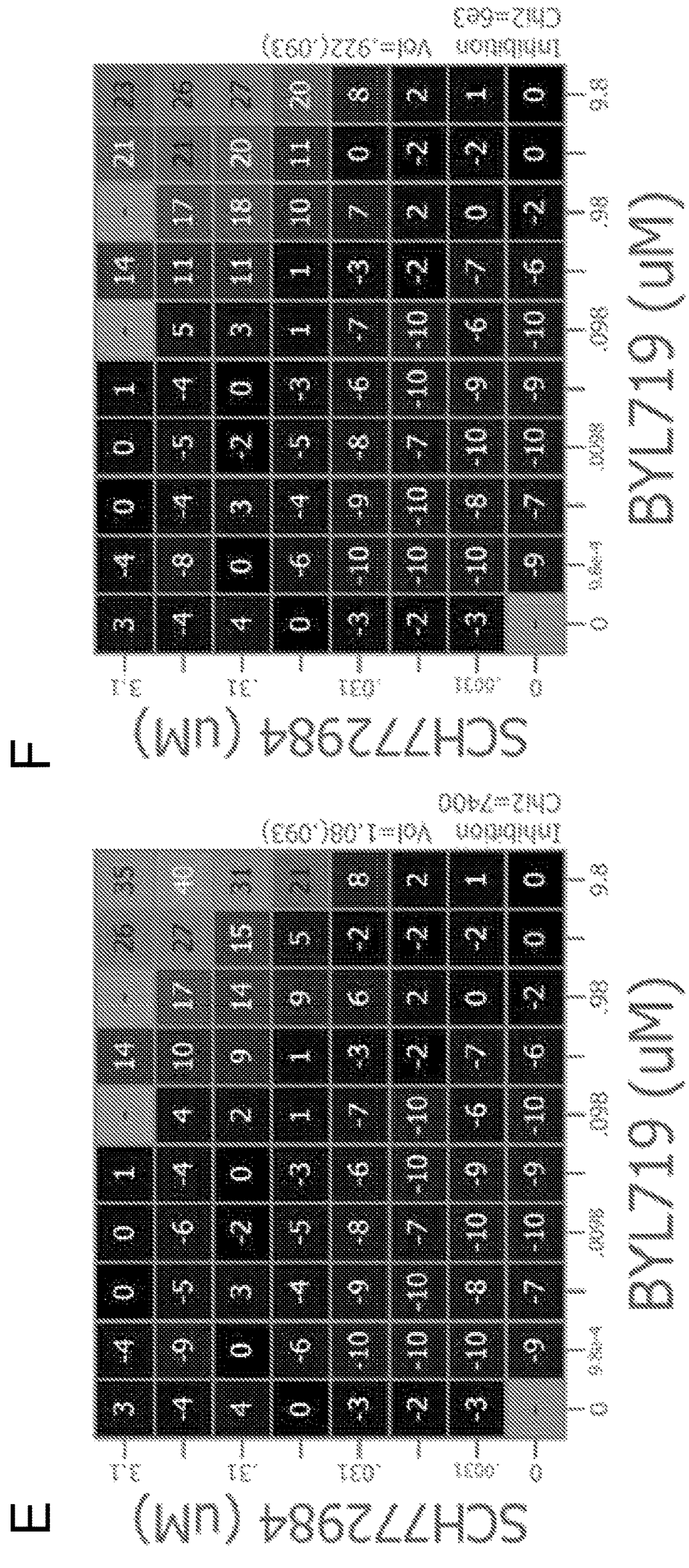

FIG. 18, Continued
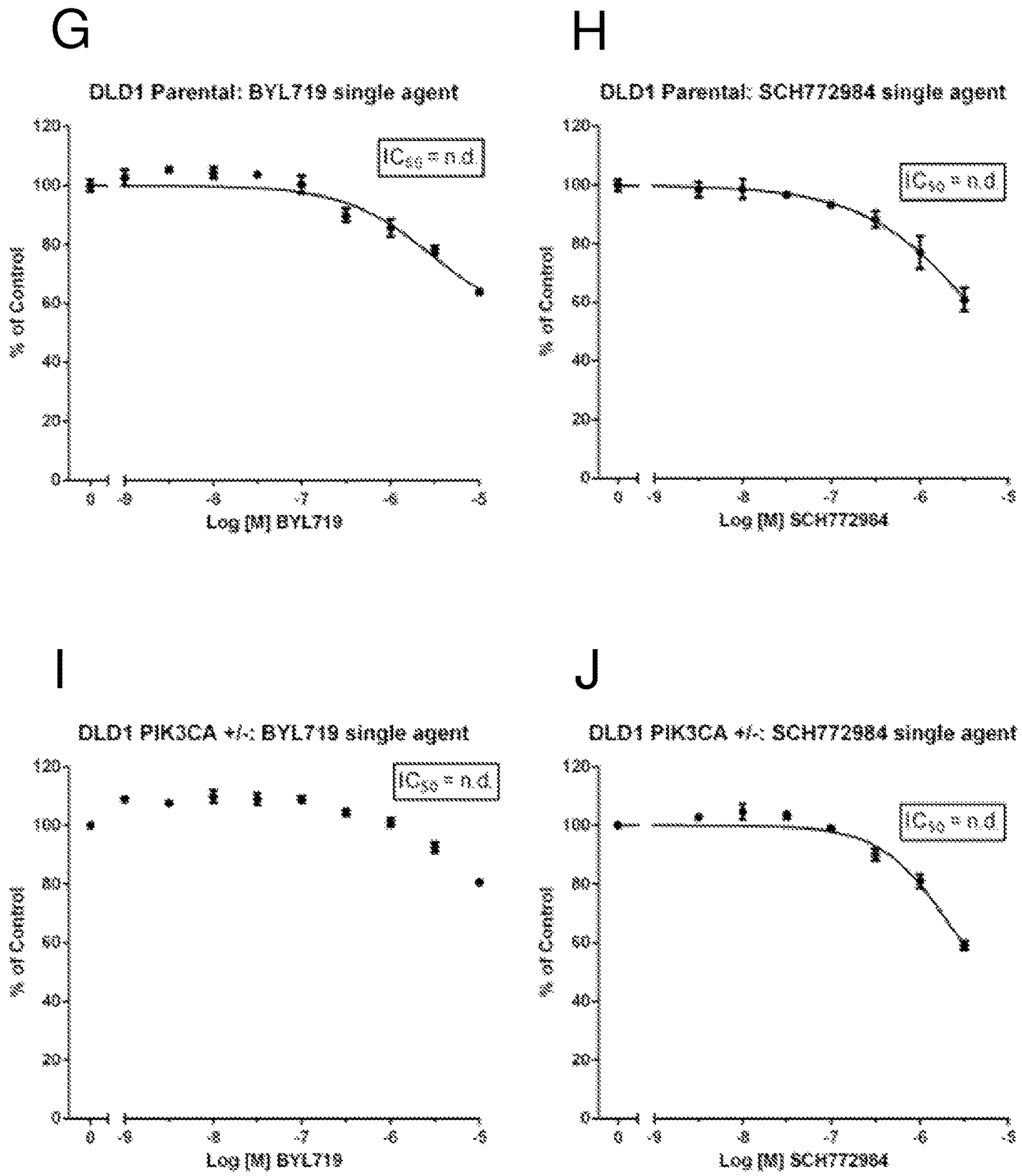

A

FIG. 19, Continued
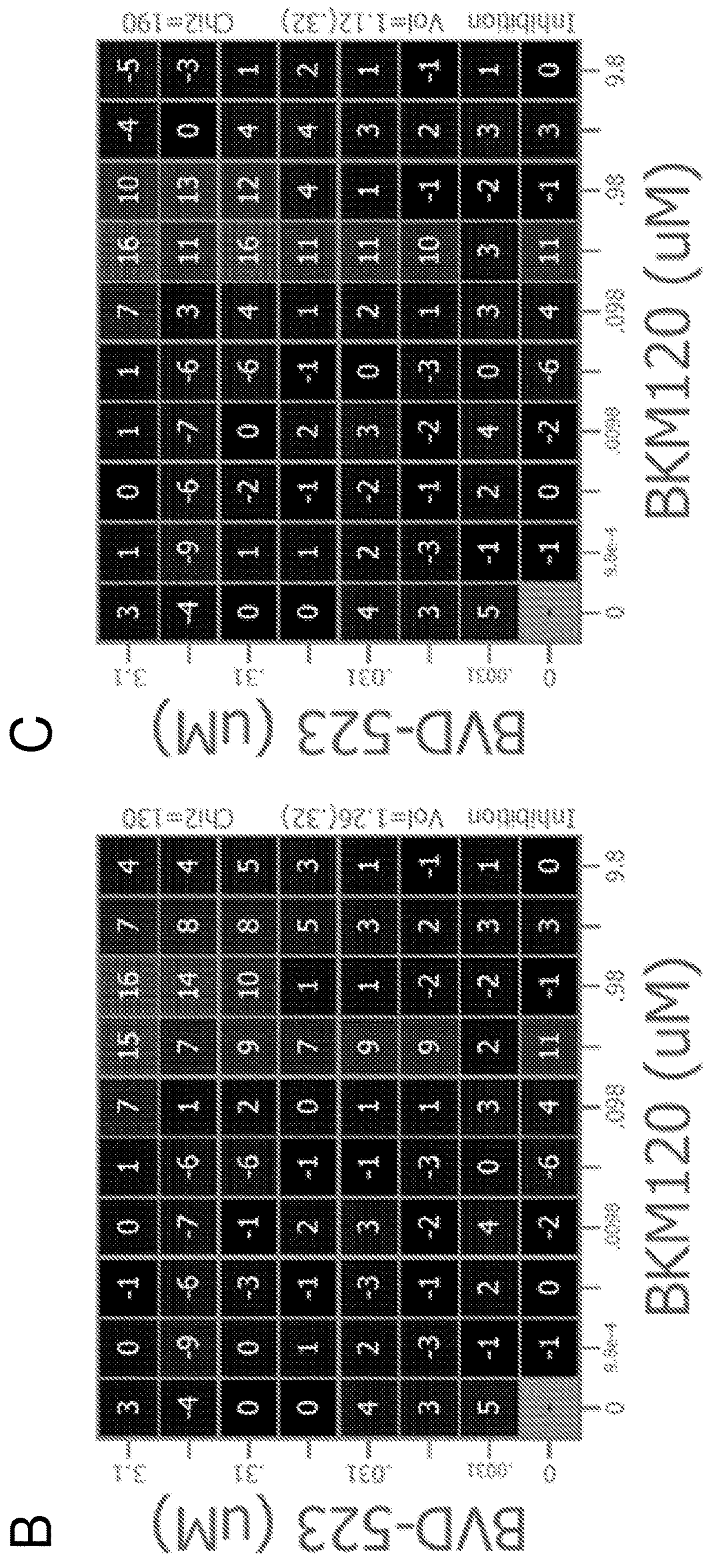

FIG. 19, Continued
D
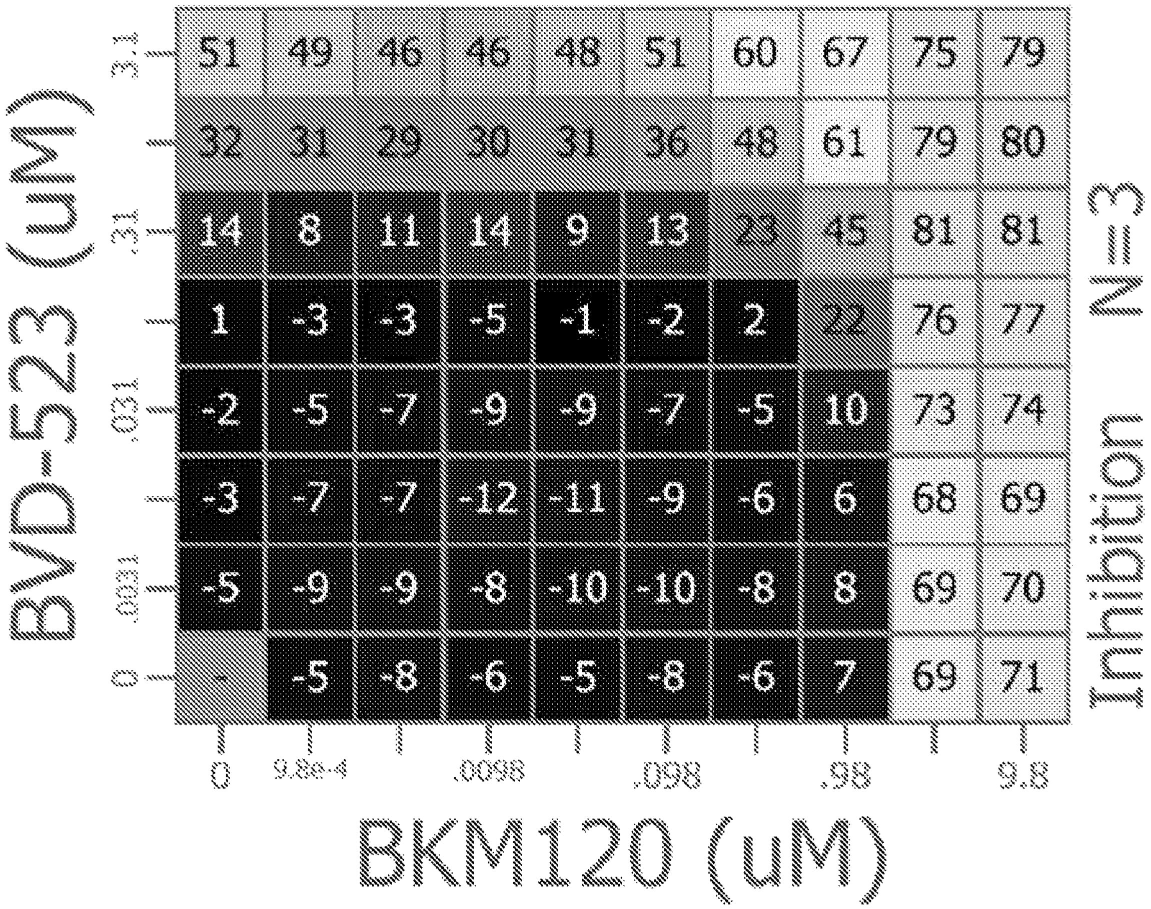

FIG. 19, Continued
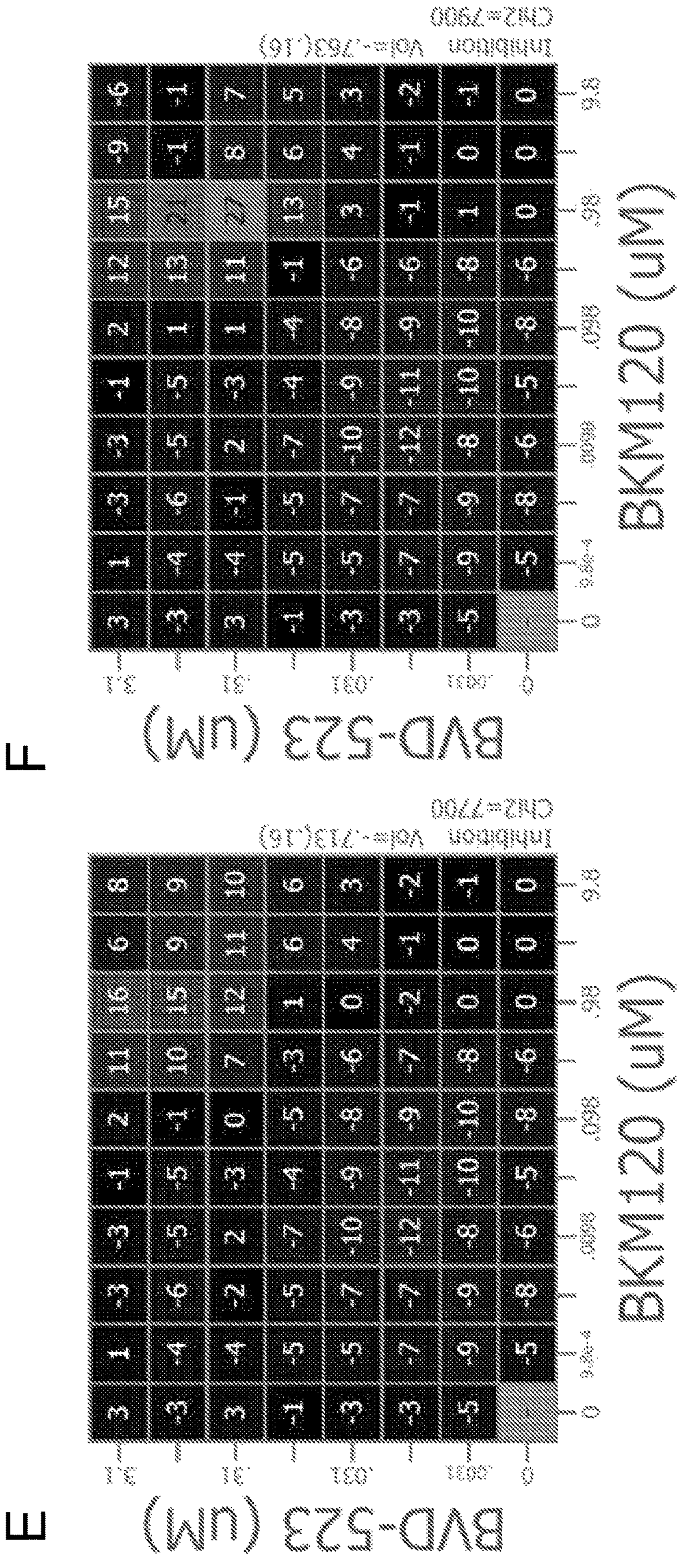

FIG. 19, Continued
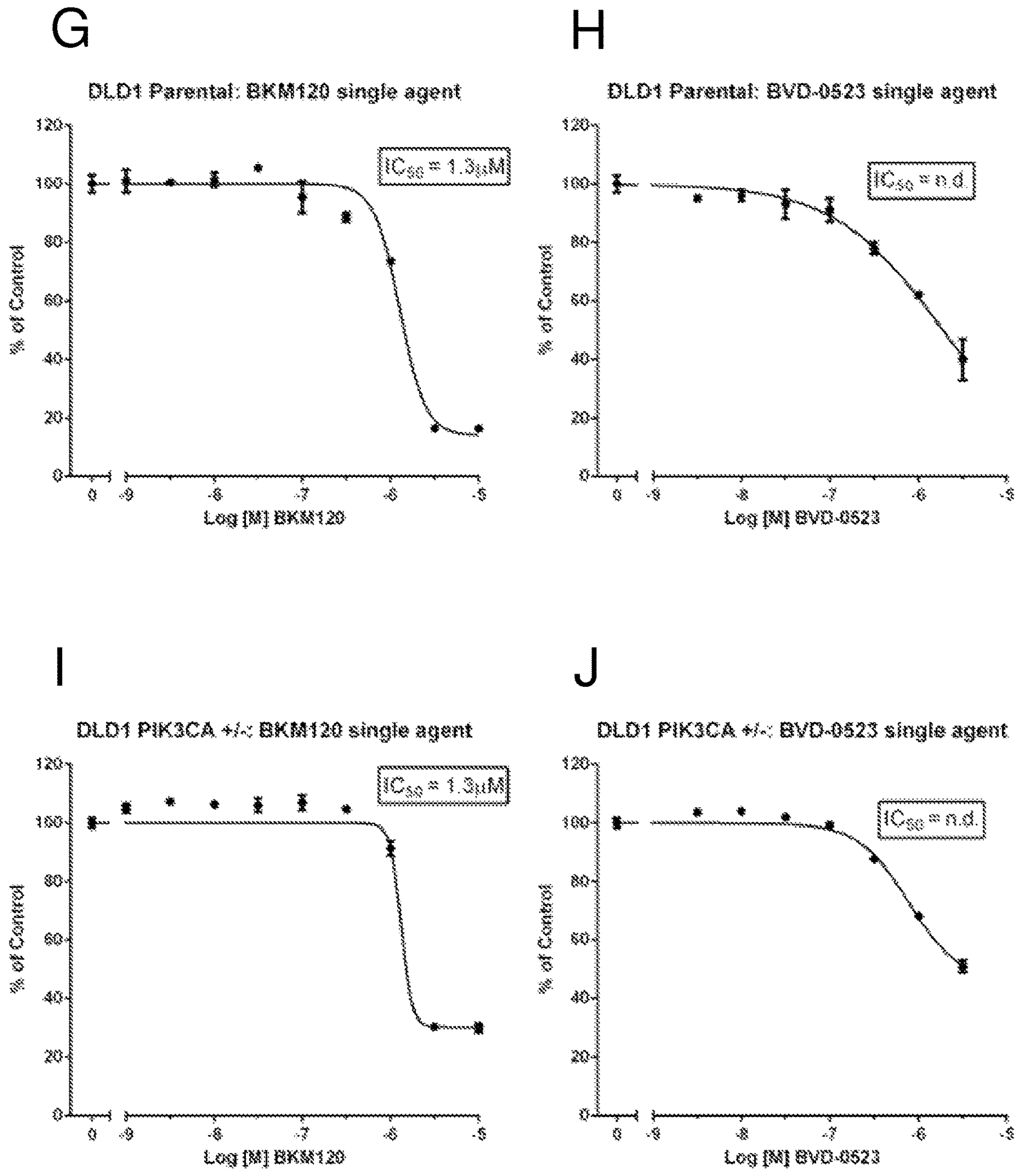

A

FIG. 20, Continued
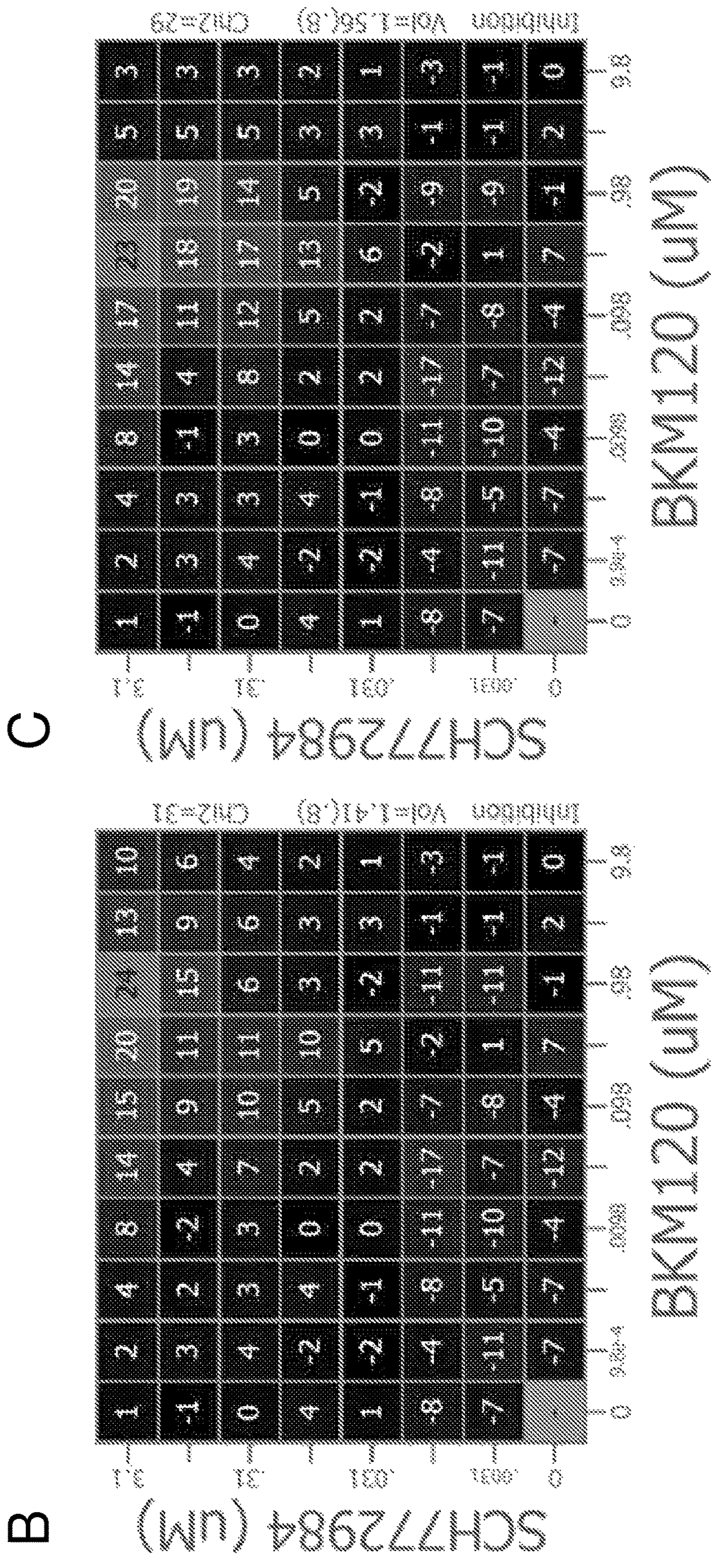

FIG. 20, Continued
D
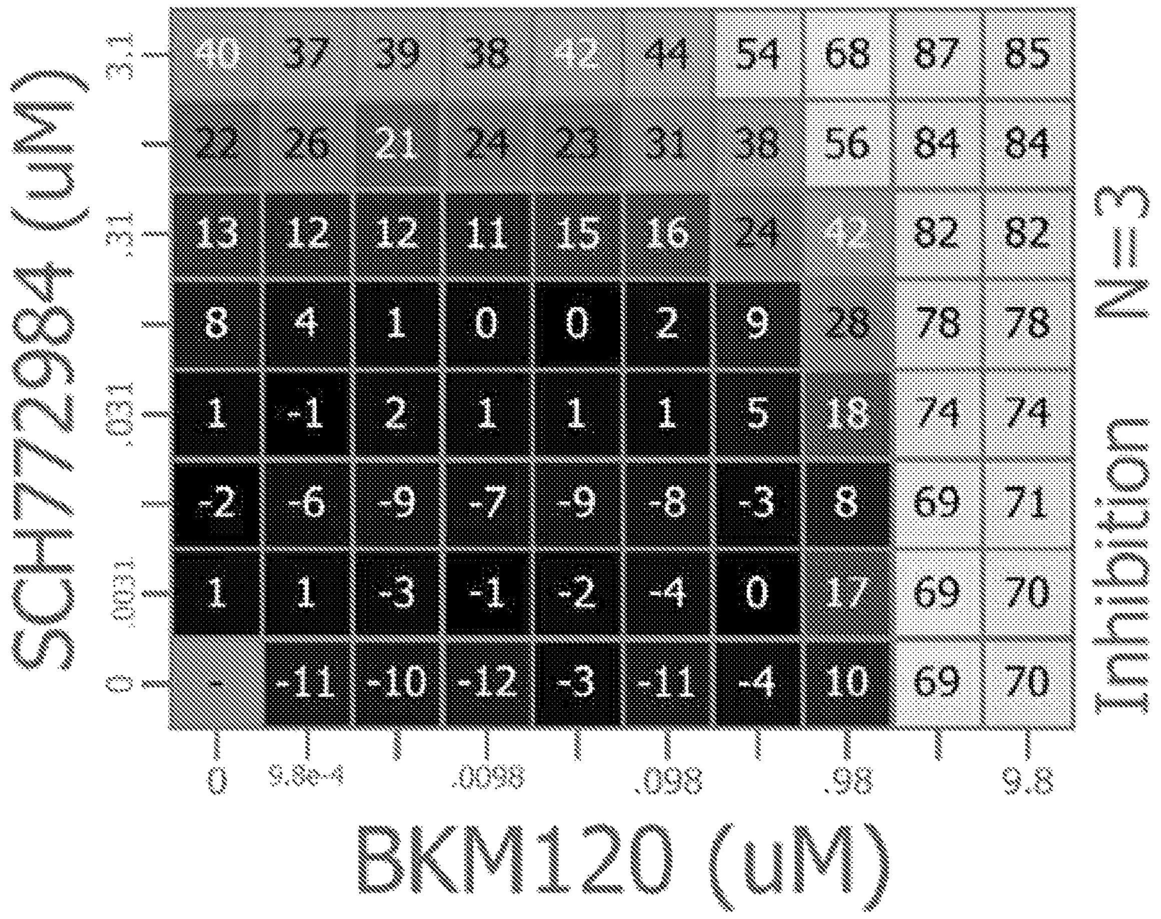

FIG. 20, Continued
F
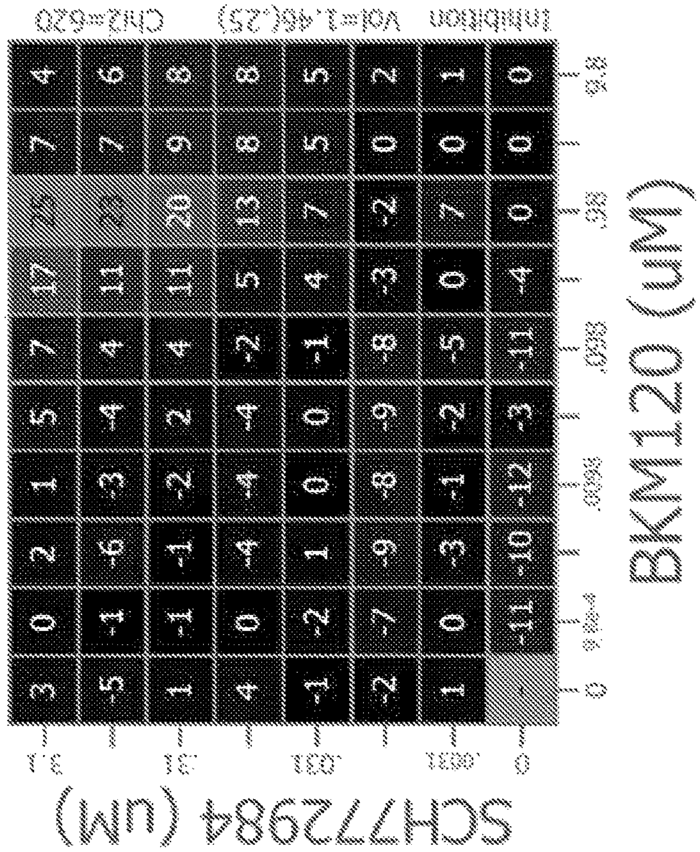
E
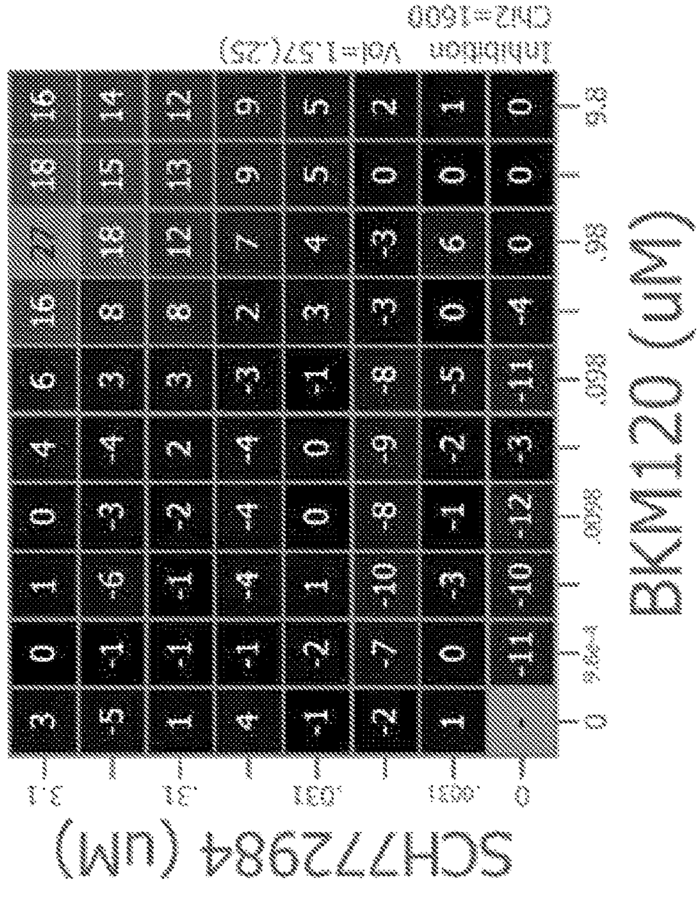

FIG. 20, Continued
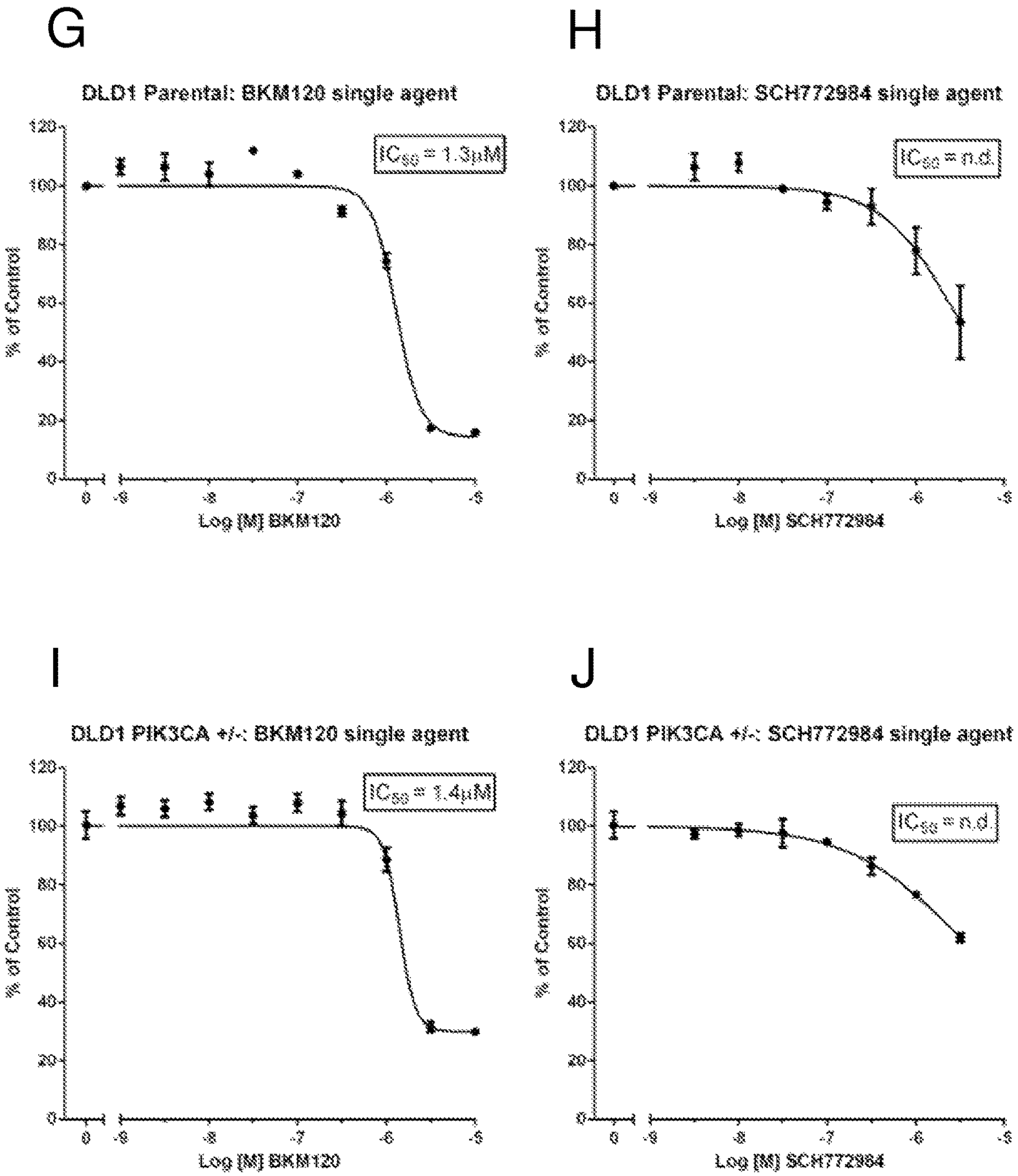

A

FIG. 21, Continued
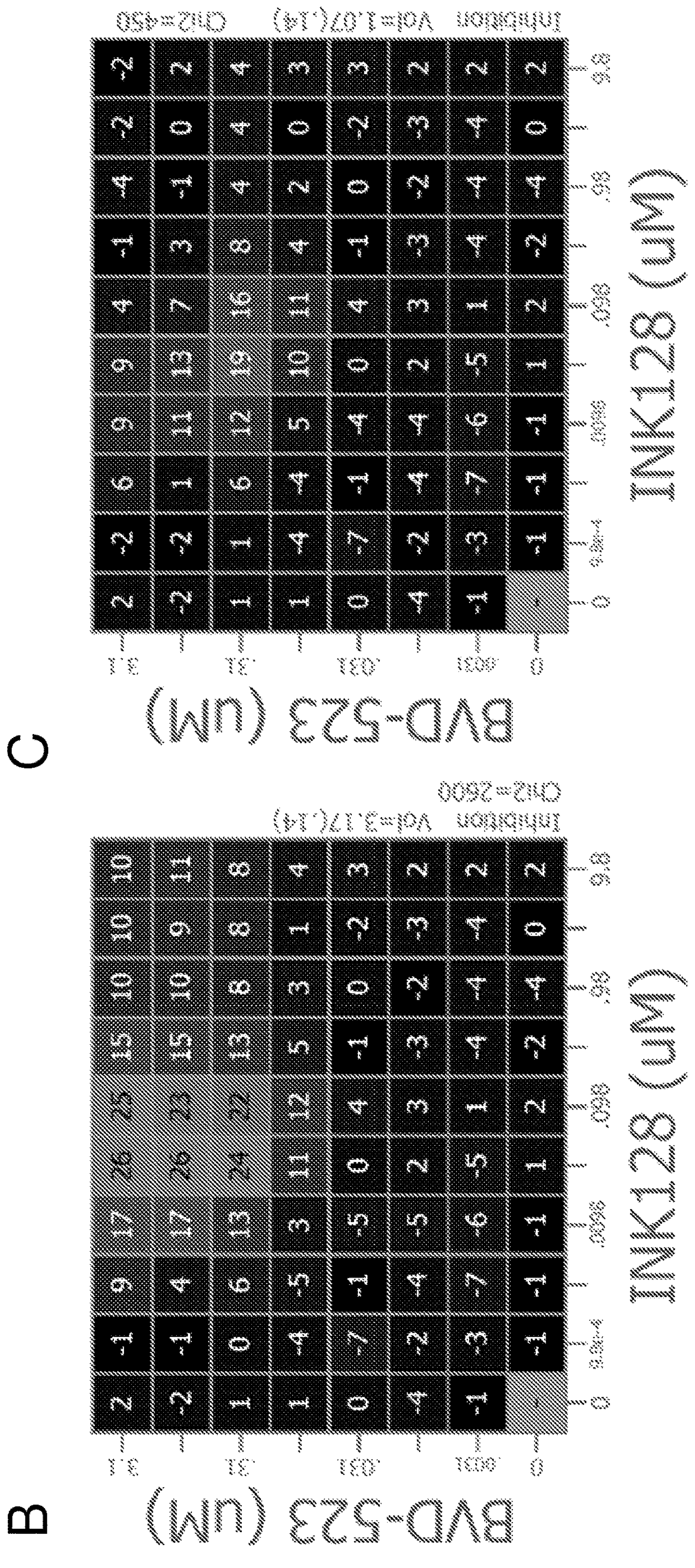

FIG. 21, Continued
D
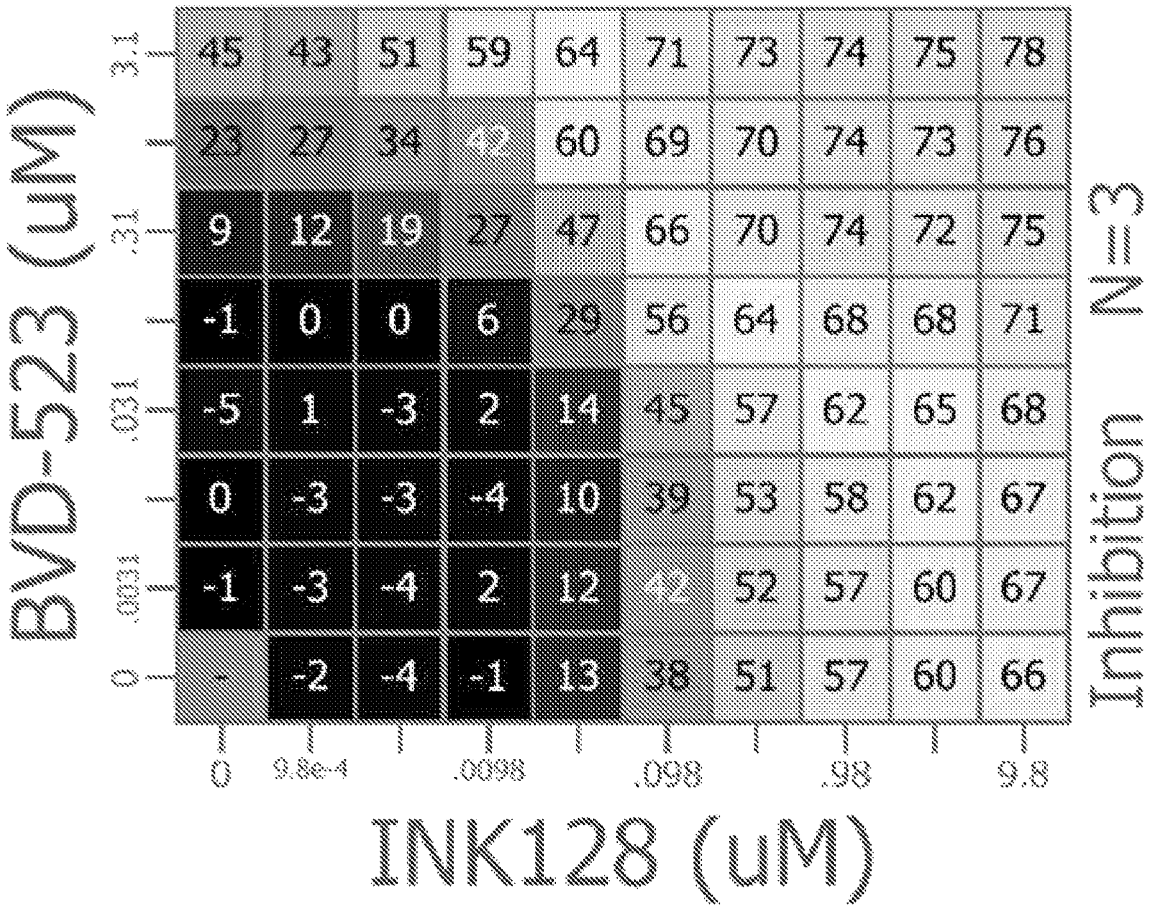

FIG. 21, Continued
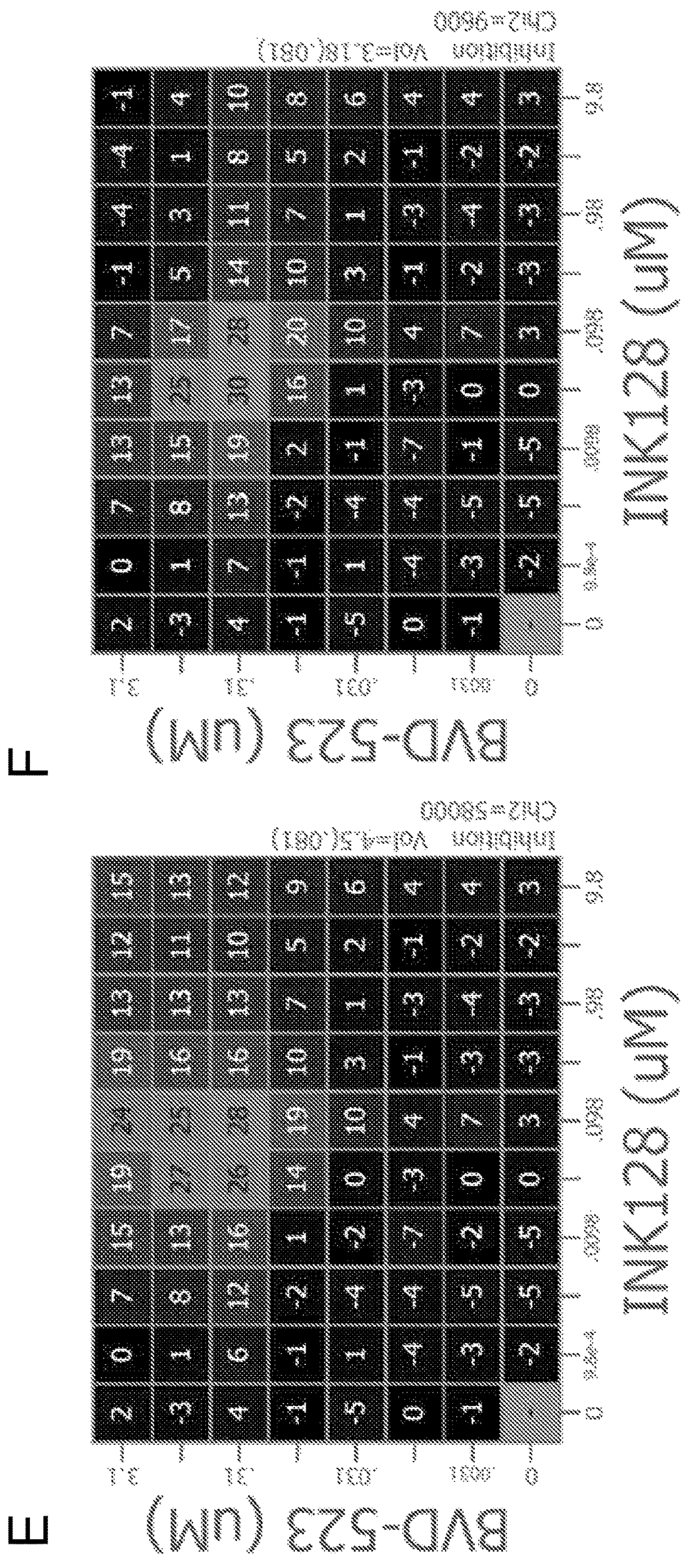

FIG. 21, Continued
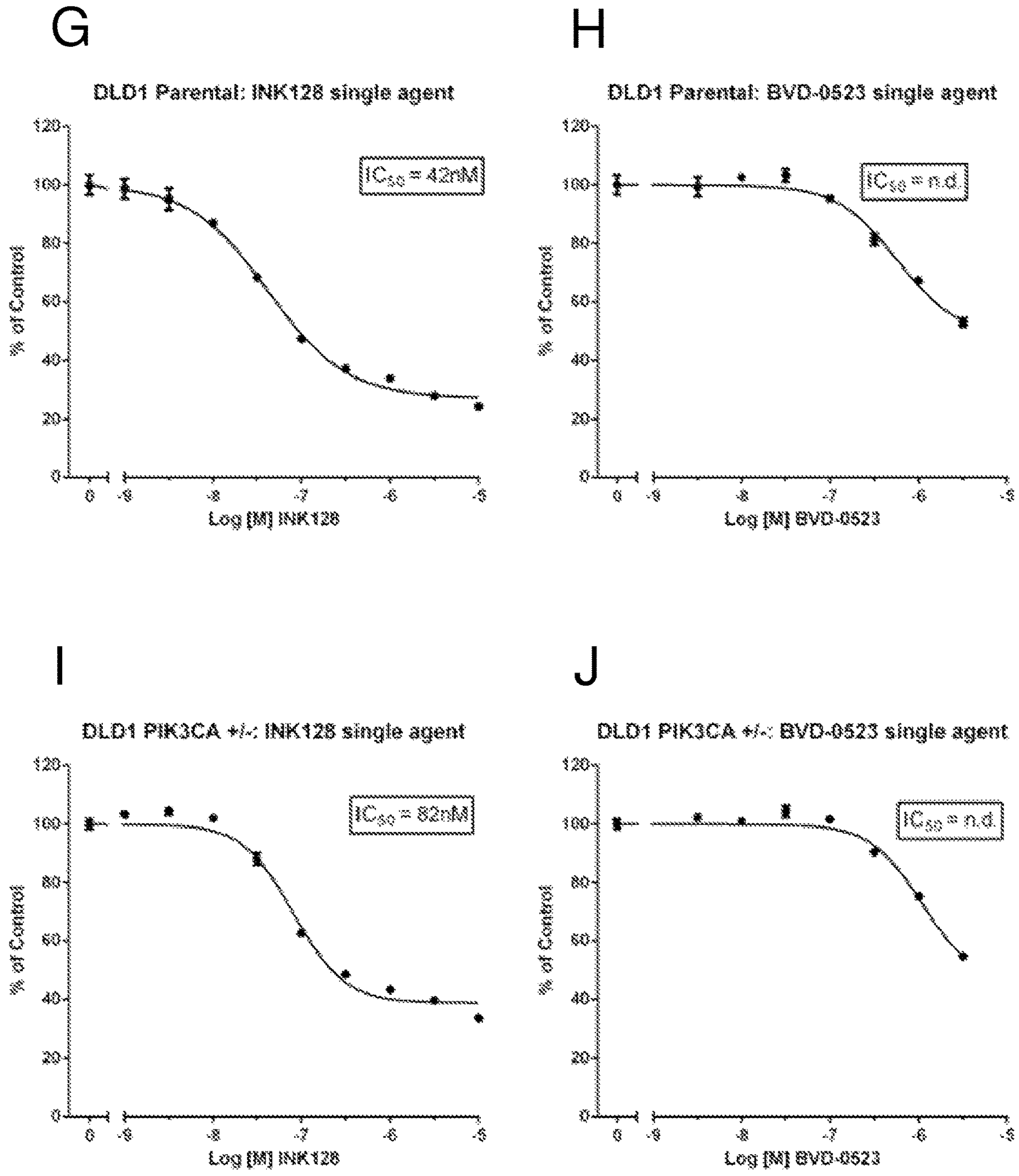

A

FIG. 22, Continued
B
C
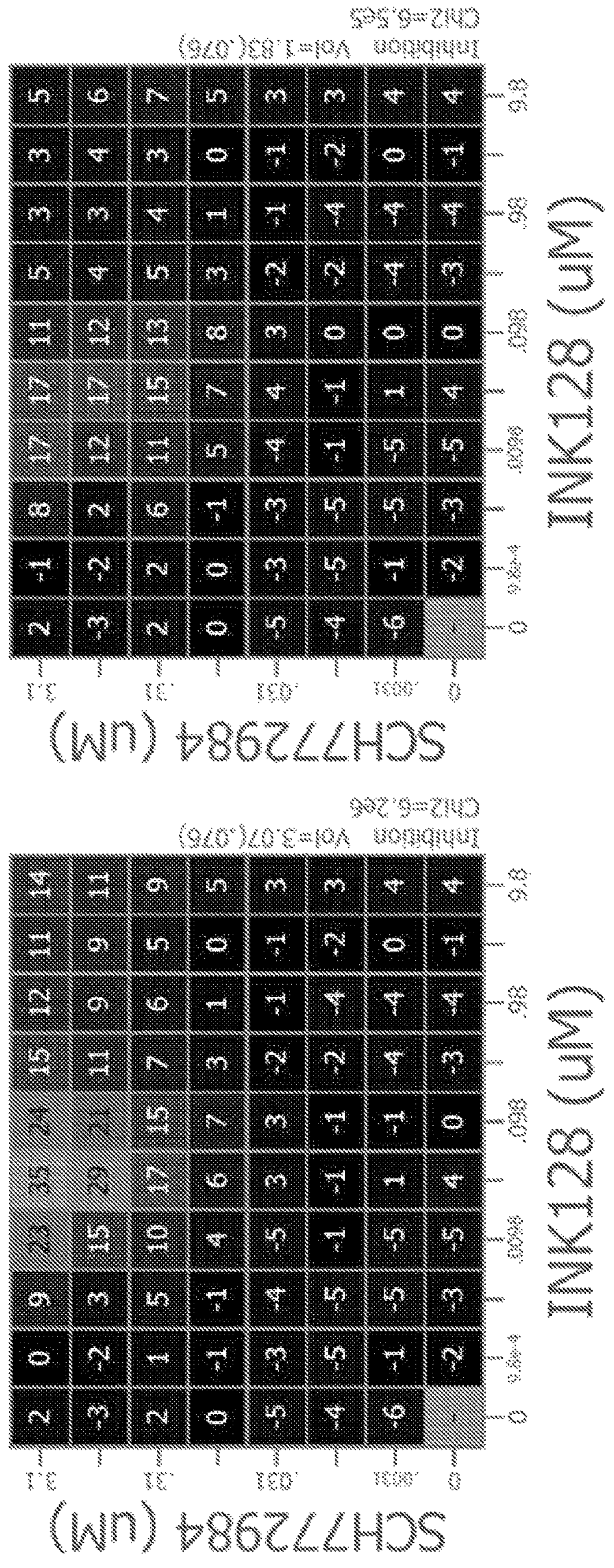

FIG. 22, Continued
D
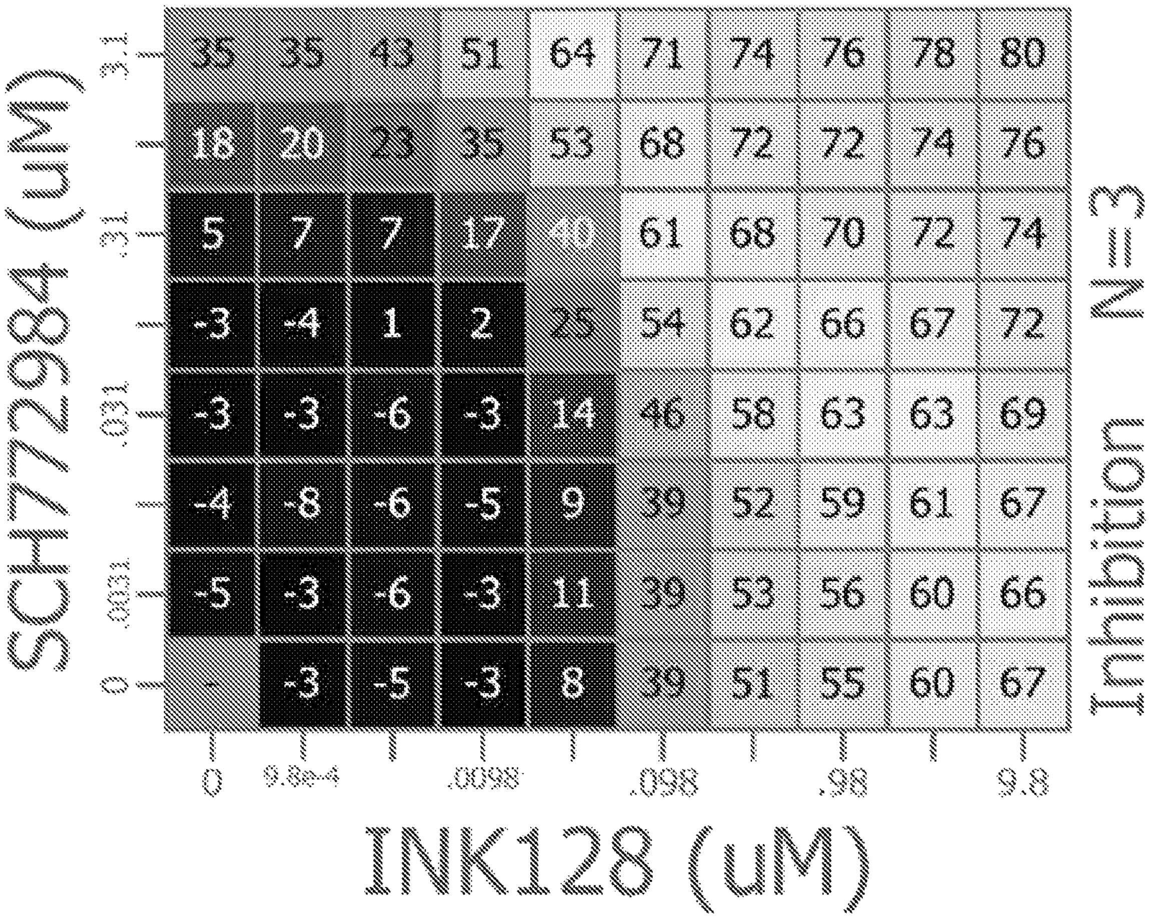

FIG. 22, Continued
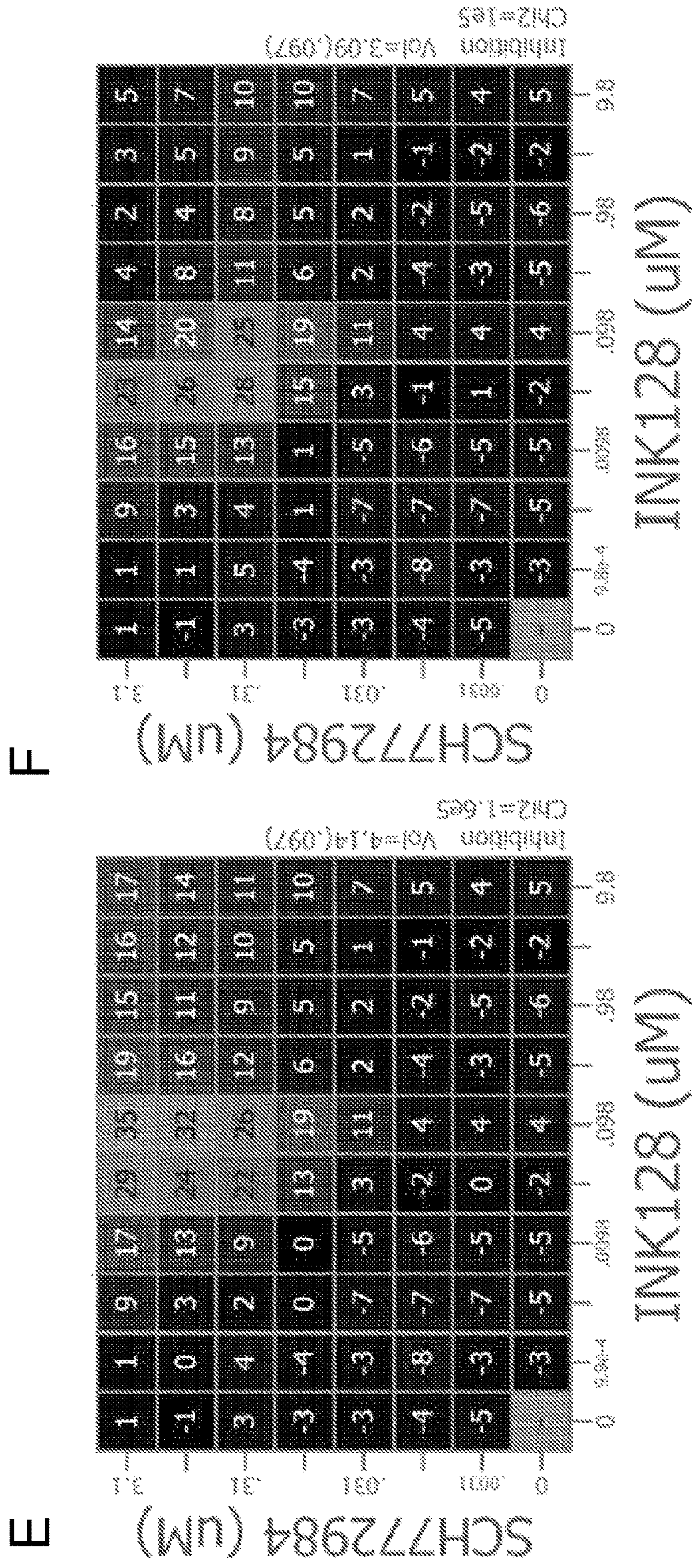

FIG. 22, Continued
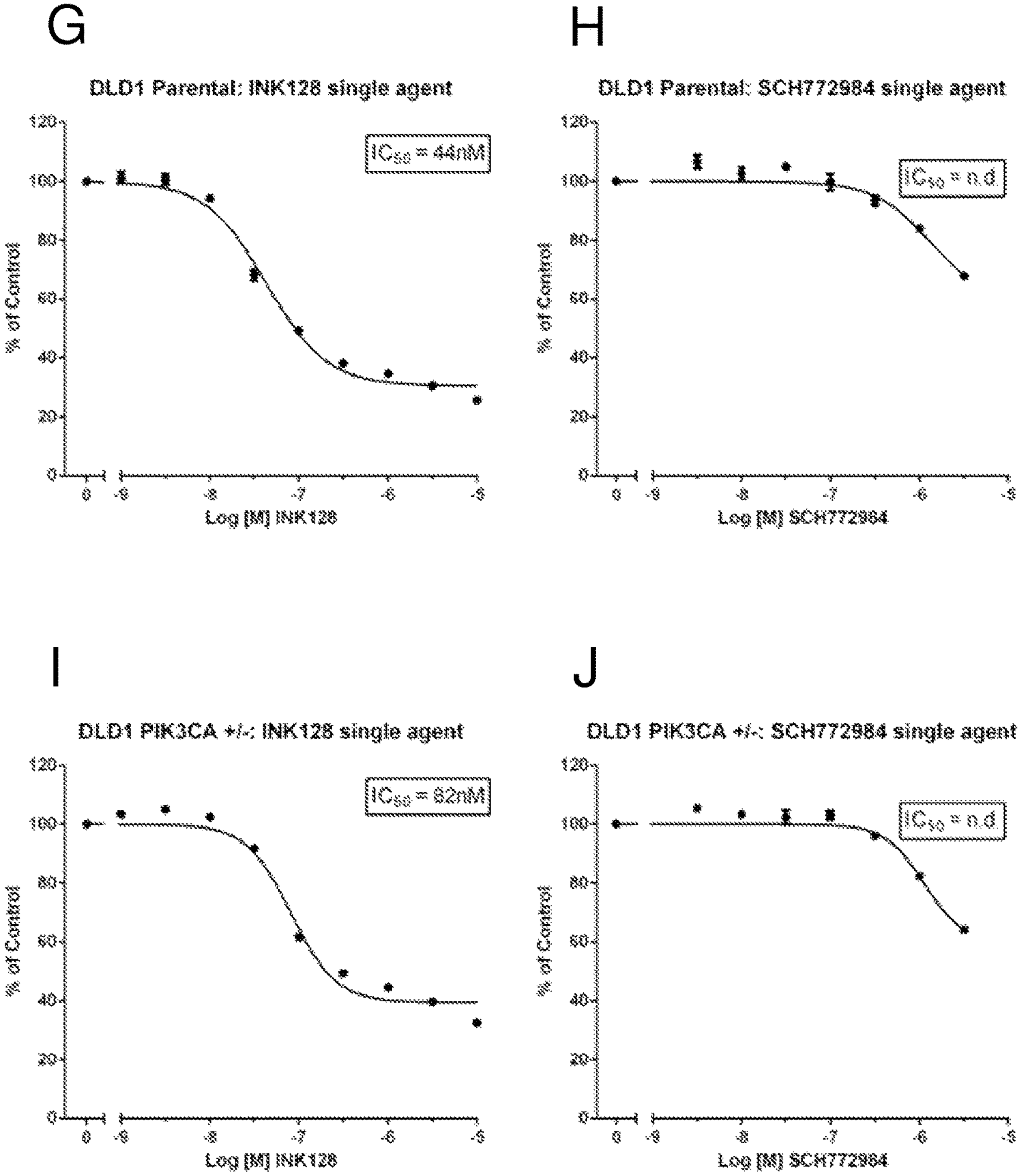

A

FIG. 23, Continued
C
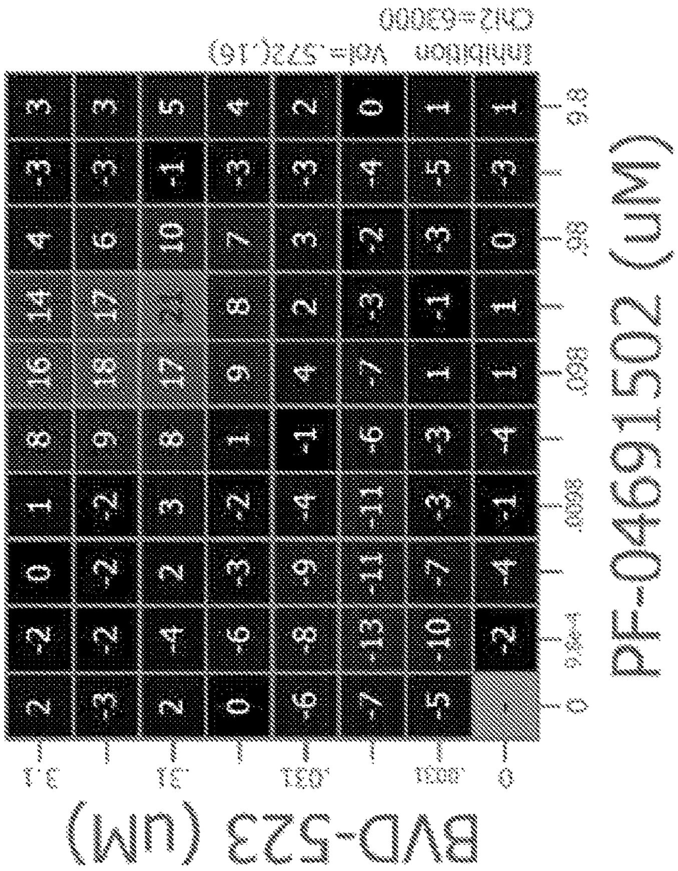
B
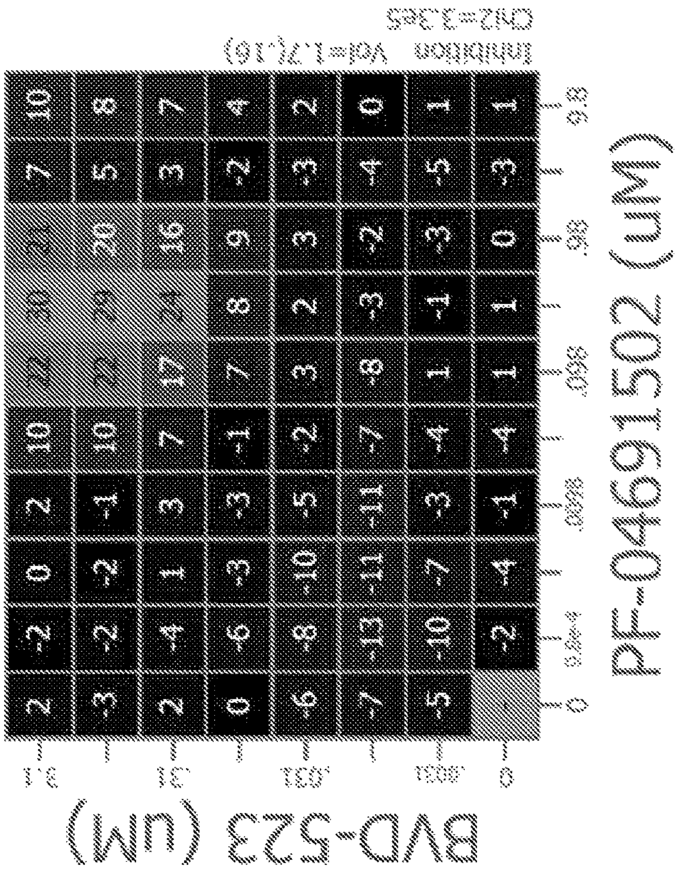

FIG. 23, Continued
D
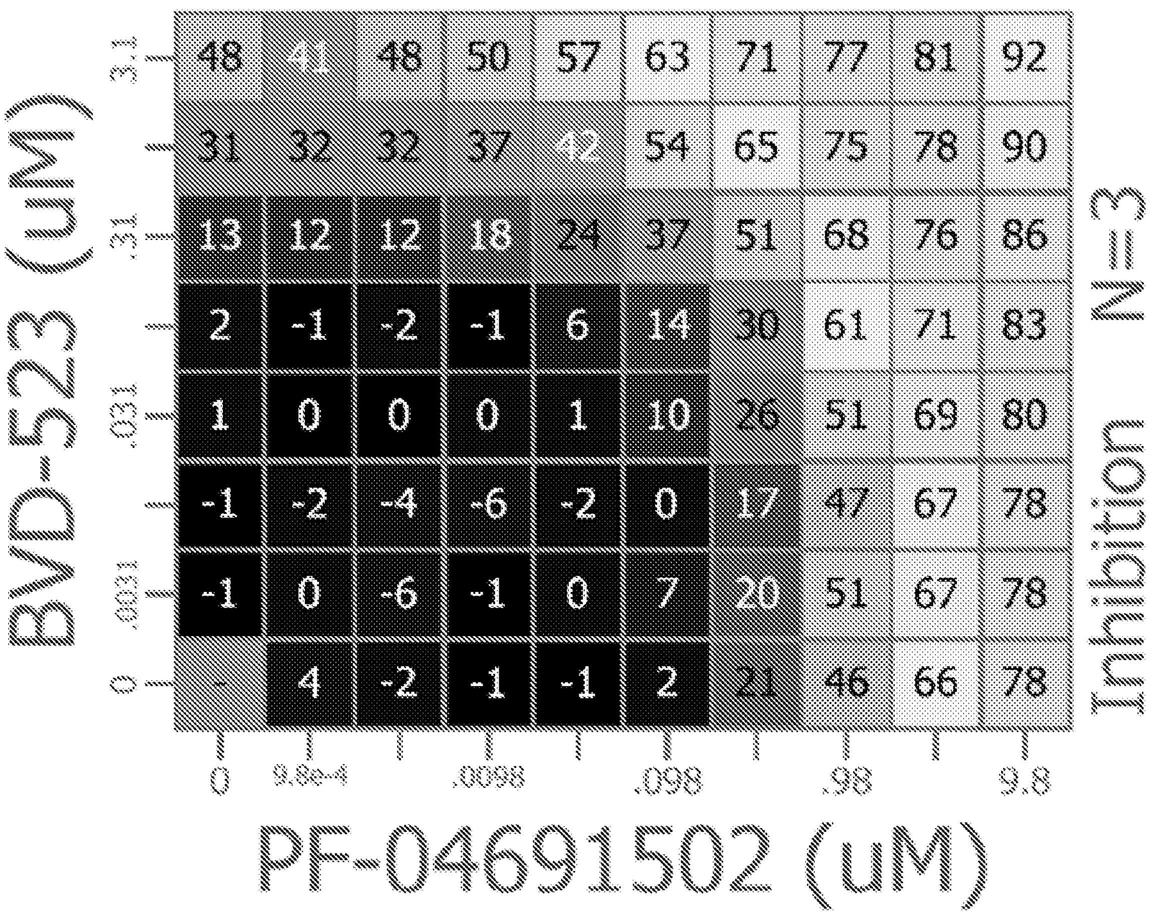

FIG. 23, Continued
F
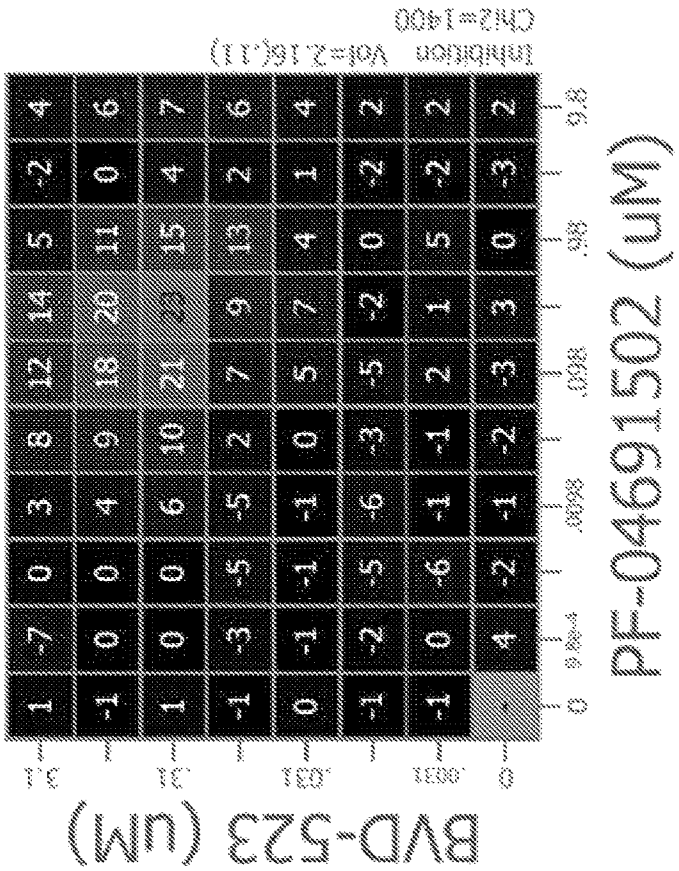
E
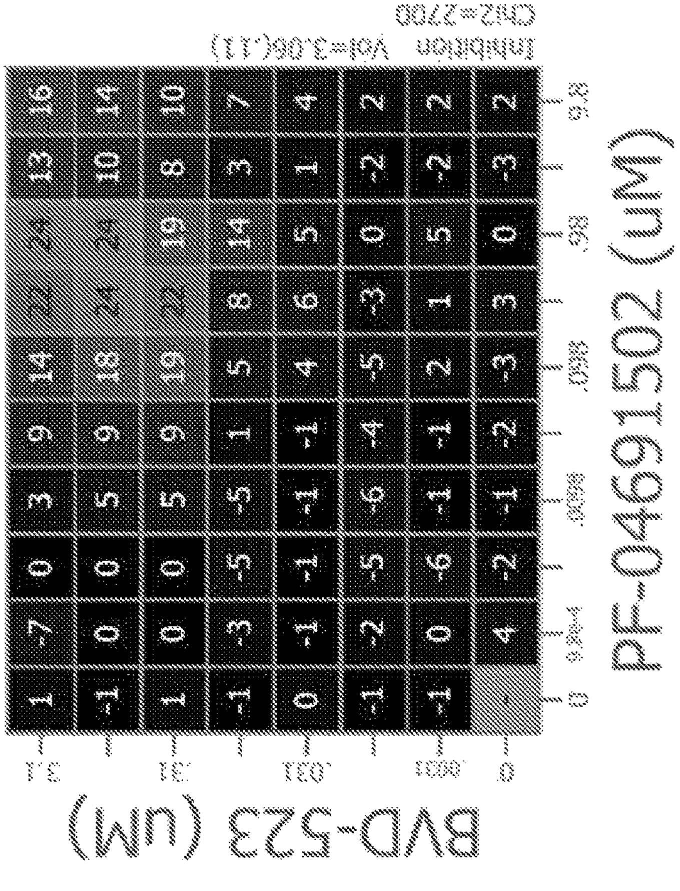

FIG. 23, Continued
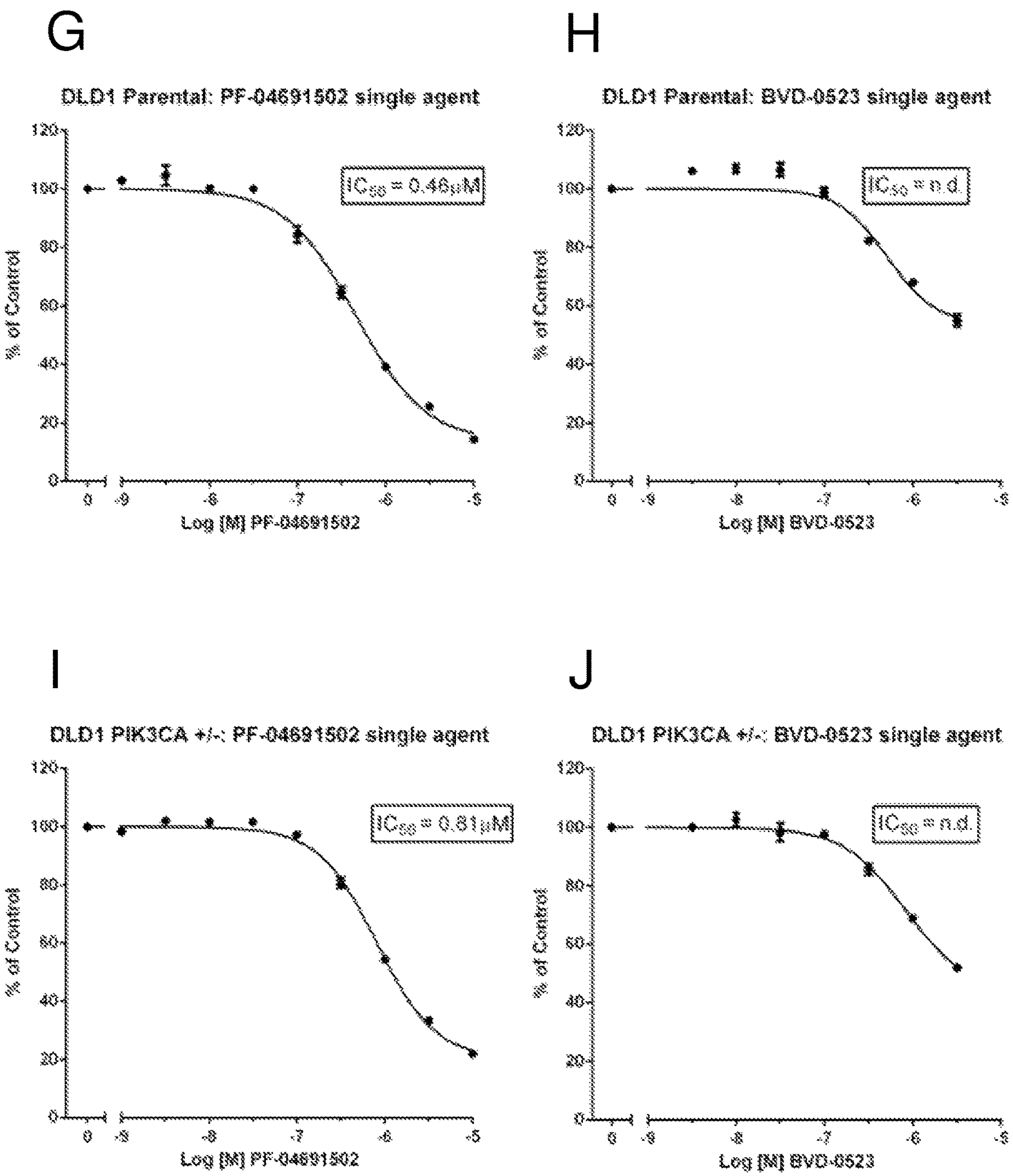

FIG. 24, Continued
B C
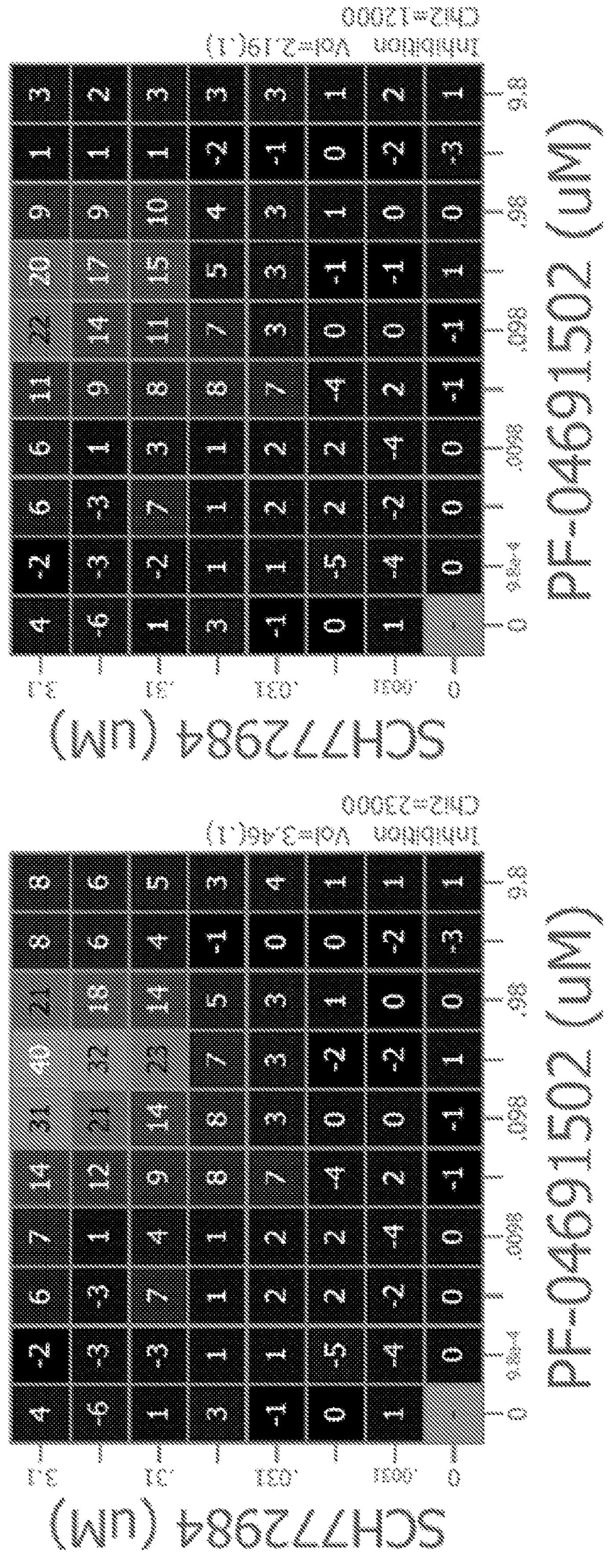

FIG. 24, Continued
D
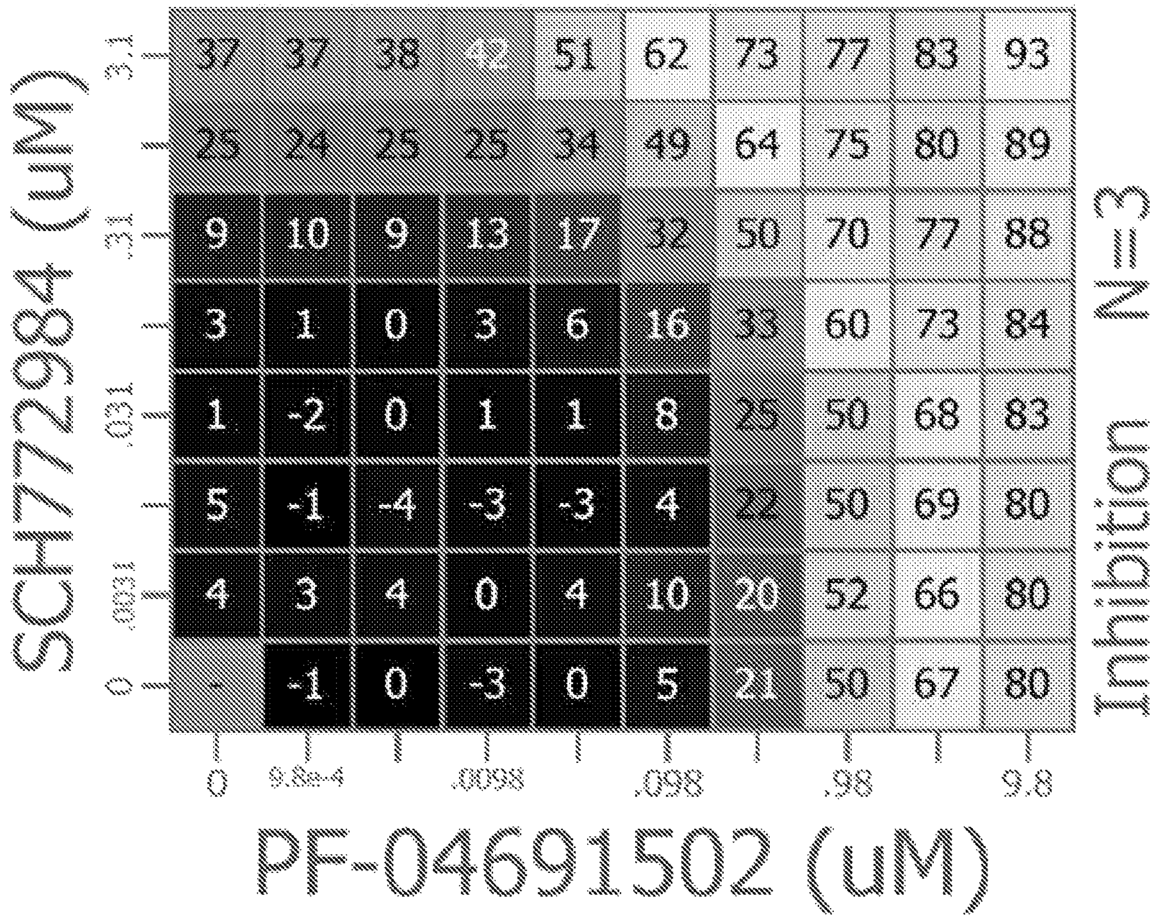

FIG. 24, Continued
F
E
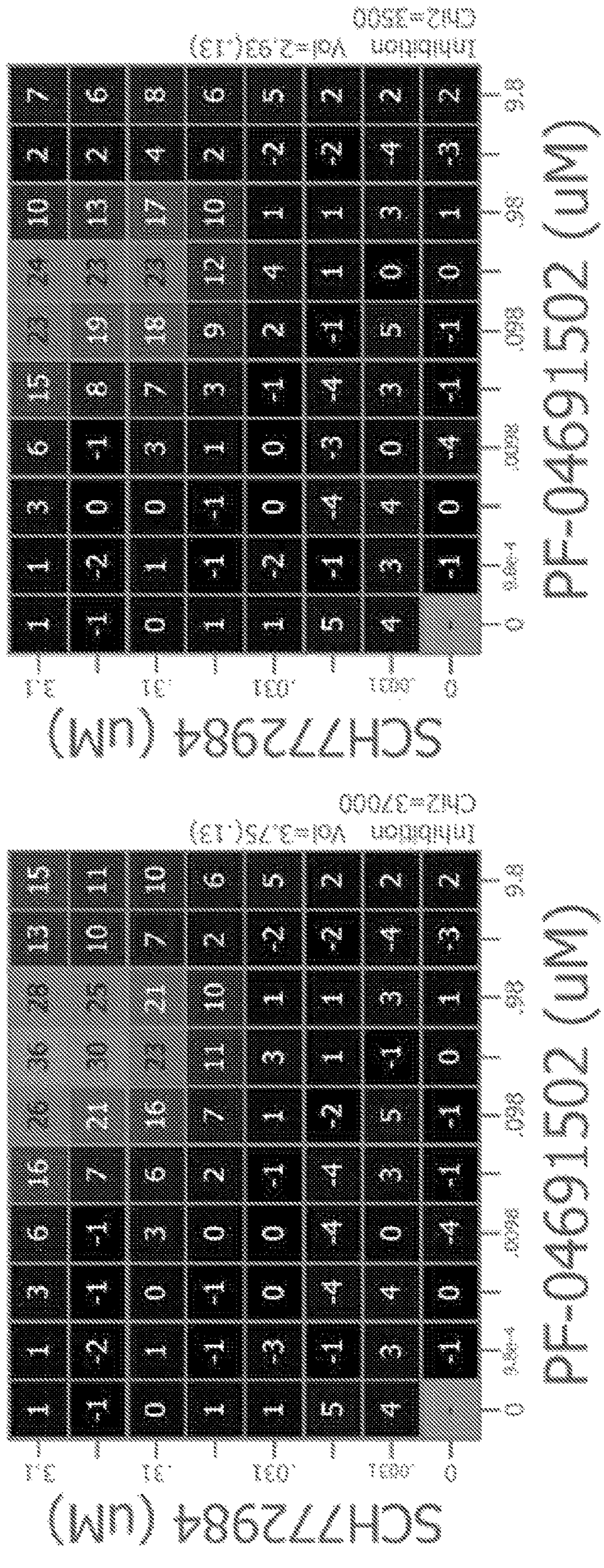

FIG. 24, Continued
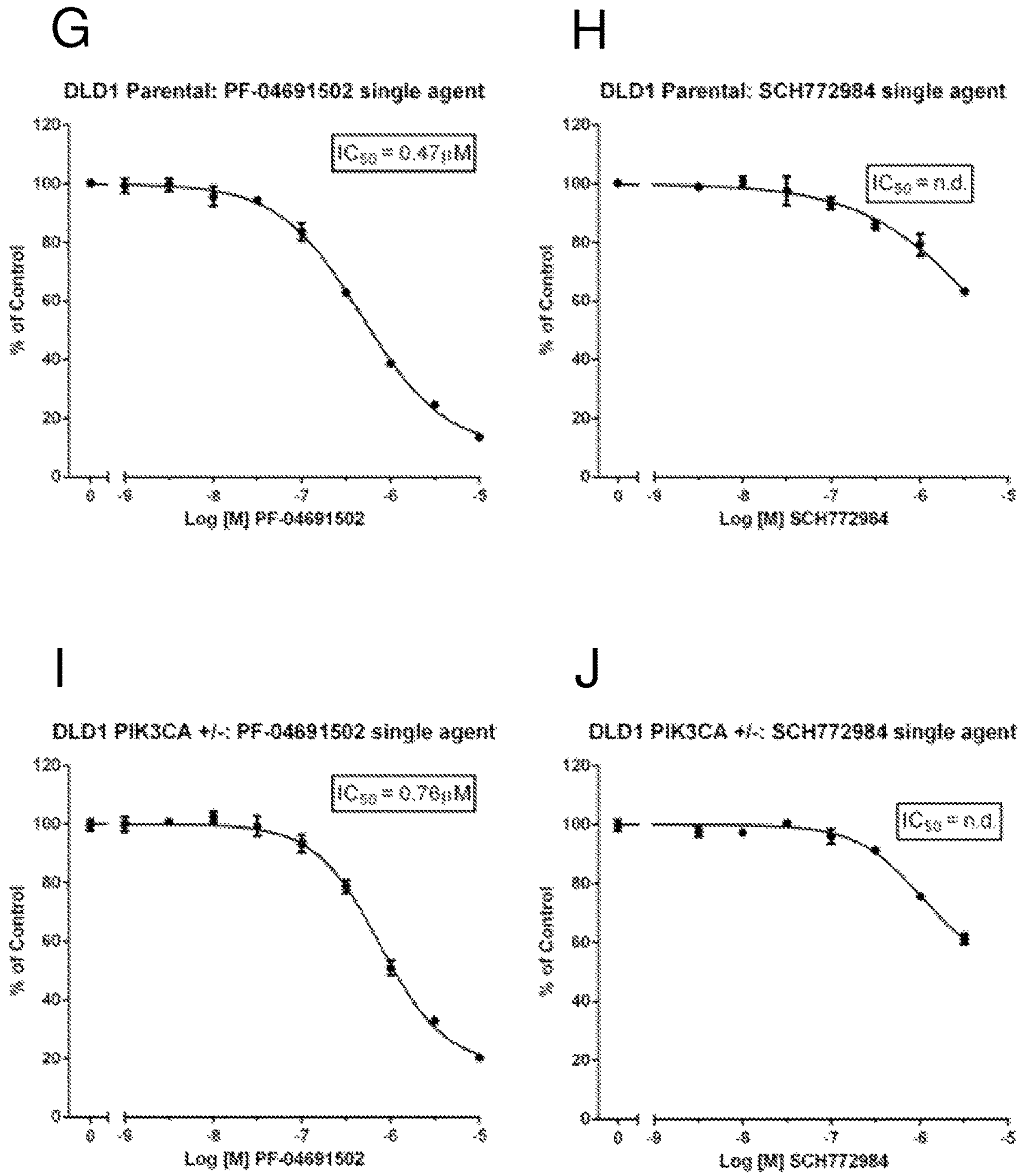

FIG. 25, Continued
E
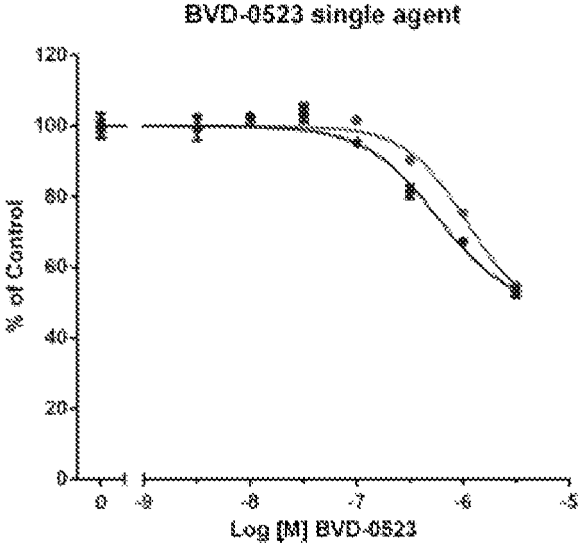
F
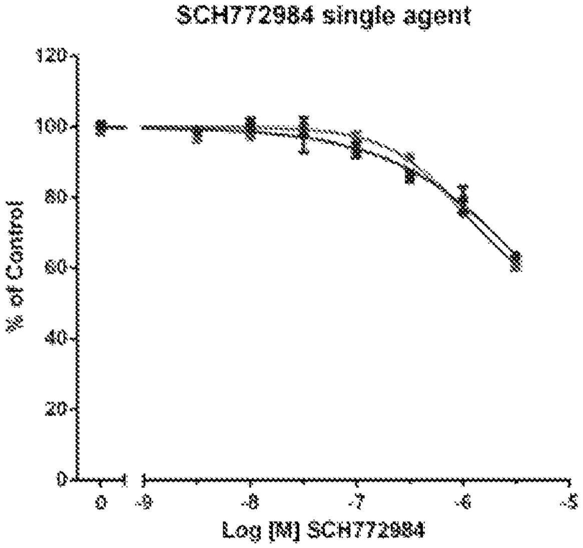

| | DLD1 Parental | DLD1 PIK3CA +/- | HCT116 Parental | HCT116 PIK3CA +/- |
|---|---|---|---|---|
| BKM120 x BVD-523 | 1.26 | [illegible] | 3.1 | 2.34 |
| BKM120 x SCH772984 | 1.41 | 1.57 | 2.21 | 2.27 |
| BVD-523 x BYL719 | [illegible] | 1.19 | [illegible] | [illegible] |
| BVD-523 x INK128 | [illegible] | 4.5 | [illegible] | 4.7 |
| BVD-523 x PF-04691502 | 1.7 | [illegible] | [illegible] | 5.4 |
| BYL719 x SCH772984 | [illegible] | 1.08 | [illegible] | [illegible] |
| INK128 x SCH772984 | [illegible] | [illegible] | [illegible] | [illegible] |
| PF-04691502 x SCH772984 | [illegible] | [illegible] | [illegible] | [illegible] |

B

| | DLD1 Parental | DLD1 PIK3CA +/- | HCT116 Parental | HCT116 PIK3CA +/- |
|---|---|---|---|---|
| BKM120 x BVD-523 | 1.12 | [illegible] | 2.9 | 2.11 |
| BKM120 x SCH772984 | 1.56 | 1.46 | [illegible] | 1.63 |
| BVD-523 x BYL719 | [illegible] | 1.04 | [illegible] | [illegible] |
| BVD-523 x INK128 | 1.07 | [illegible] | [illegible] | [illegible] |
| BVD-523 x PF-04691502 | .572 | [illegible] | [illegible] | [illegible] |
| BYL719 x SCH772984 | [illegible] | .922 | [illegible] | [illegible] |
| INK128 x SCH772984 | [illegible] | [illegible] | [illegible] | [illegible] |
| PF-04691502 x SCH772984 | [illegible] | [illegible] | [illegible] | [illegible] |

Figure 26:
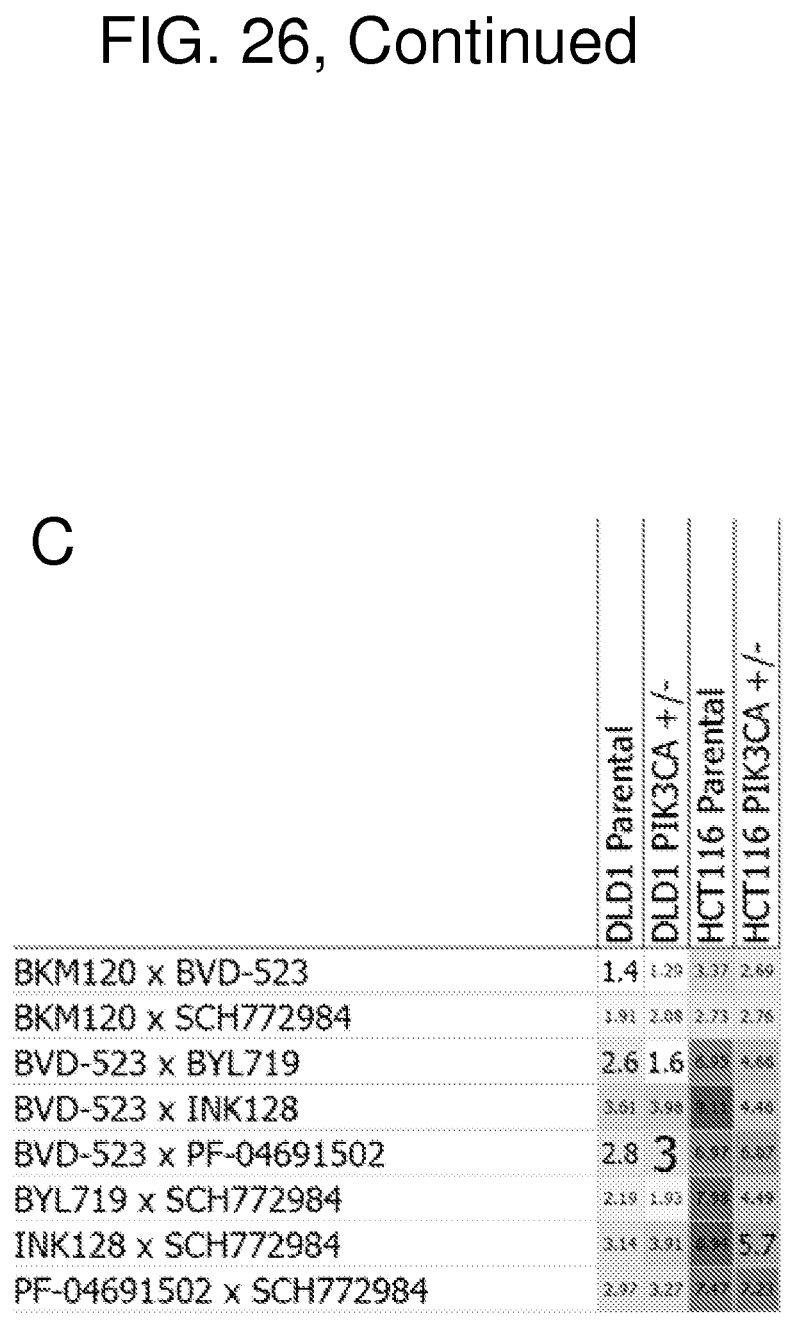

| | DLD1 Parental | DLD1 PIK3CA +/- | HCT116 Parental | HCT116 PIK3CA +/- |
|---|---|---|---|---|
| BKM120 x BVD-523 | 1.4 | 1.29 | 3.37 | 2.69 |
| BKM120 x SCH772984 | 3.81 | 2.08 | 2.73 | 2.76 |
| BVD-523 x BYL719 | 2.6 | 1.6 | [illegible] | 4.68 |
| BVD-523 x INK128 | 3.01 | 3.98 | [illegible] | 4.46 |
| BVD-523 x PF-04691502 | 2.8 | 3 | [illegible] | [illegible] |
| BYL719 x SCH772984 | 2.19 | 1.93 | [illegible] | 4.49 |
| INK128 x SCH772984 | 3.14 | 3.31 | [illegible] | 5.7 |
| PF-04691502 x SCH772984 | 2.87 | 3.27 | [illegible] | [illegible] |

FIG. 27, Continued
D
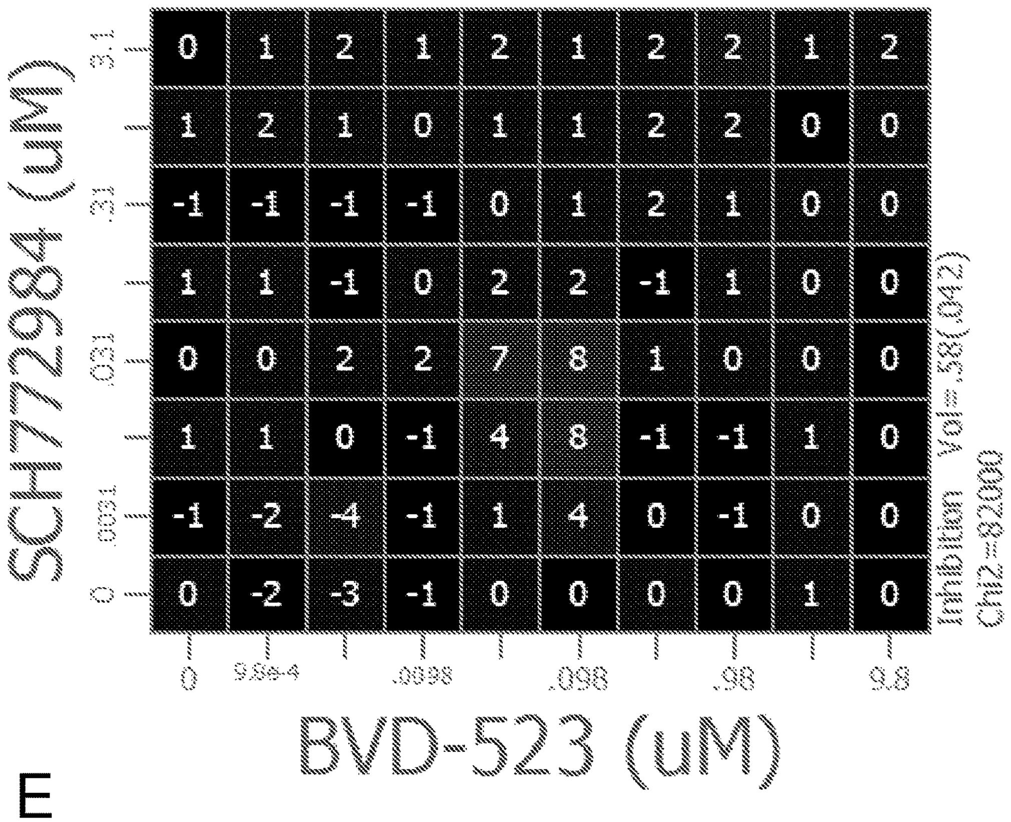
E
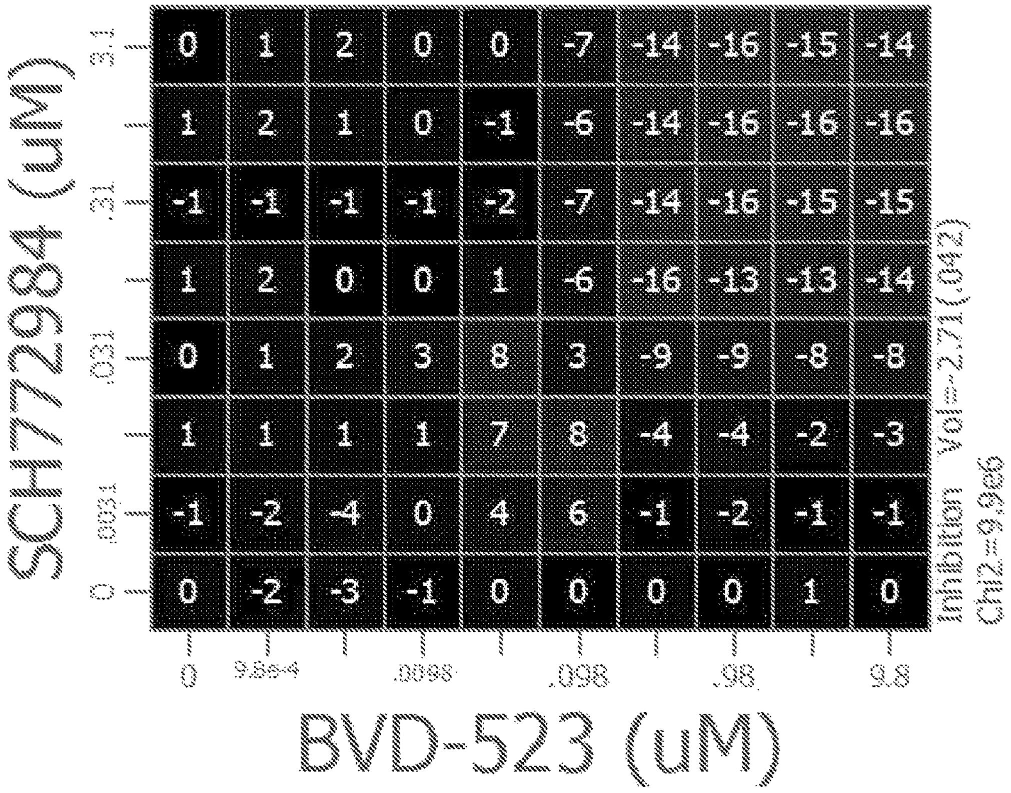

CANCER TREATMENTS USING COMBINATIONS OF PI3K/AKT PATHWAY AND ERK INHIBITORS

CROSS REFERENCE TO RELATED APPLICATIONS

The present application is the National Stage of International Application No. PCT/US2014/071728, filed on Dec. 19, 2014, which claims benefit to U.S. Provisional Application Ser. No. 61/919,638, filed Dec. 20, 2013. The entire contents of the above applications are incorporated by reference as if recited in full herein.

FIELD OF INVENTION

The present invention provides, inter alia, methods, kits and pharmaceutical compositions for treating or ameliorating the effects of a cancer in a subject using a first anti-cancer agent, which is BVD-523 or a pharmaceutically acceptable salt thereof and a second anti-cancer agent, which is an inhibitor of the PI3K/Akt pathway or a pharmaceutically acceptable salt thereof.

INCORPORATION BY REFERENCE OF SEQUENCE LISTING

This application contains references to amino acids and/or nucleic acid sequences that have been filed concurrently herewith as sequence listing text file "0375601.txt", file size of 447 KB, created on Dec. 19, 2014. The aforementioned sequence listing is hereby incorporated by reference in its entirety pursuant to 37 C.F.R. § 1.52(e)(5).

BACKGROUND OF THE INVENTION

Mutations affecting the MAPK and PI3K/Akt signaling pathways are observed at high frequencies in a variety of cancers. Drug inhibitors that target components of the MAPK signaling pathway show clinical efficacy in a many cancers, particularly those bearing mutations in the BRAF protein kinase. Both RAF and MEK kinase inhibitors are approved for single-agent use in advanced metastatic BRAF mutant melanoma, and the combination of dabrafenib and trametinib is currently undergoing Food and Drug Administration (FDA) review for this indication.

As with other targeted therapies, patterns of disease response to MAPK pathway and PI3K/Akt inhibitors appear to be influenced by the intrinsic genetic heterogeneity present in the cancers where the drugs are used. For instance, certain genetic alterations, including PTEN and other changes that activate the PI3K cell growth signaling pathway, may predict a poor initial response, and/or relatively rapid progression, in BRAF mutant melanoma treated with the RAF inhibitor vemurafenib. Likewise, direct mutations in MEK gene loci appear to emerge in tumors that have progressed following either BRAF, MEK, or combined drug treatment. Several additional examples, from RAS and RAF gene amplification and splicing mutations, suggest that acquired drug resistance is produced when oncogenic pleiotropy encounters the selective pressure of targeted drug treatment.

In particular, a number of treated cancers bearing mutations affecting the MAPK signaling pathway develop additional, nascent lesions that affect the PI3K pathway. For example, PIK3CA-activating mutations are a frequent source of acquired resistance in these cancers. In this case, mechanistically distinct inhibitors targeting only the MAPK pathway are not sufficient for effective therapy.

In view of the foregoing limitations, novel targeted agents and therapies are needed to treat such cancers. The present invention is directed to meeting these and other needs.

SUMMARY OF THE INVENTION

One embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof, to treat or ameliorate the effects of the cancer.

Another embodiment of the present invention is a method of treating or ameliorating the effects of a cancer in a subject in need thereof. The method comprises administering to the subject an effective amount of (i) BVD-523 or a pharmaceutically acceptable salt thereof and (ii) pictilisib (GDC-0941) or a pharmaceutically acceptable salt thereof, to treat or ameliorate the effects of the cancer.

An additional embodiment of the present invention is a kit for treating or ameliorating the effects of a cancer in a subject in need thereof. The kit comprises an effective amount of (i) a first anti-cancer agent, which is BVD-523 or a pharmaceutically acceptable salt thereof and (ii) a second anti-cancer agent, which is a PI3K/Akt inhibitor or a pharmaceutically acceptable salt thereof, packaged together with instructions for their use.

Another embodiment of the present invention is a method for treating or ameliorating the effects of a subject with cancer. The method comprises:

(a) identifying a subject with cancer that has a somatic KRAS mutation and a somatic PIK3CA mutation; and (b) administering to the subject with somatic KRAS and PIK3CA mutations an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof, to treat or ameliorate the effects of the cancer.

An additional embodiment of the present invention is a method for treating or ameliorating the effects of a subject with cancer. The method comprises:

(a) identifying a subject with cancer that is refractory to a therapy selected from the group consisting of RAF inhibitor therapy, MEK inhibitor therapy, and RAF and MEK inhibitor therapy; and (b) administering to the subject identified in step (a) an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof, to treat or ameliorate the effects of the cancer.

Another embodiment of the present invention is a pharmaceutical composition for treating or ameliorating the effects of a cancer in a subject in need thereof. The pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof, wherein administration of the first and second anti-cancer agents provides a synergistic effect compared to administration of either anti-cancer agent alone.

A further embodiment of the present invention is a method of effecting cancer cell death. The method comprises contacting the cancer cell with an effective amount of (i) a first anti-cancer agent, which is BVD-523 or a pharmaceutically acceptable salt thereof and (ii) a second anti-cancer agent, which is a an inhibitor of the PI3K/Akt pathway or a pharmaceutically acceptable salt thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A is a line graph showing mean tumor growth in mice treated with various doses of GDC-0941, BVD-523, or a combination of the two in the in vivo study. FIG. 2B is a Kaplan-Meier plot for the in vivo study. The number in the parenthesis indicate the dose in mg/kg.

FIG. 7A shows a dose matrix showing inhibition (%) for the combination in parental HCT116 cells. FIG. 7B shows Loewe excess for the combination in 7A and FIG. 7C shows Bliss excess for the combination in 7A. FIG. 7D shows a dose matrix showing inhibition (%) for the combination in HCT116 PIK3CA (+/−) cells. FIG. 7E shows Loewe excess for the combination in 7D and FIG. 7F shows Bliss excess for the combination in 7D. FIG. 7G-FIG. 7H show the results of single agent proliferation assays for the combination in 7A. FIG. 7I-FIG. 7J show the results of single agent proliferation assays for the combination in 7D.

FIG. 8A shows a dose matrix showing inhibition (%) for the combination in parental HCT116 cells. FIG. 8B shows Loewe excess for the combination in 8A and FIG. 8C shows Bliss excess for the combination in 8A. FIG. 8D shows a dose matrix showing inhibition (%) for the combination in HCT116 PIK3CA (+/−) cells. FIG. 8E shows Loewe excess for the combination in 8D and FIG. 8F shows Bliss excess for the combination in 8D. FIG. 8G-FIG. 8H show the results of single agent proliferation assays for the combination in 8A. FIG. 8I-FIG. 8J show the results of single agent proliferation assays for the combination in 8D.

FIG. 9A shows a dose matrix showing inhibition (%) for the combination in parental HCT116 cells. FIG. 9B shows Loewe excess for the combination in 9A and FIG. 9C shows Bliss excess for the combination in 9A. FIG. 9D shows a dose matrix showing inhibition (%) for the combination in HCT116 PIK3CA (+/−) cells. FIG. 9E shows Loewe excess for the combination in 9D and FIG. 9F shows Bliss excess for the combination in 9D. FIG. 9G-FIG. 9H show the results of single agent proliferation assays for the combination in 9A. FIG. 9I-FIG. 9J show the results of single agent proliferation assays for the combination in 9D.

FIG. 10A shows a dose matrix showing inhibition (%) for the combination in parental HCT116 cells. FIG. 10B shows Loewe excess for the combination in 10A and FIG. 10C shows Bliss excess for the combination in 10A. FIG. 10D shows a dose matrix showing inhibition (%) for the combination in HCT116 PIK3CA (+/−) cells. FIG. 10E shows Loewe excess for the combination in 10D and FIG. 10F shows Bliss excess for the combination in 10D. FIG. 10G-FIG. 10H show the results of single agent proliferation assays for the combination in 10A. FIG. 10I-FIG. 10J show the results of single agent proliferation assays for the combination in 10D.

FIG. 11A shows a dose matrix showing inhibition (%) for the combination in parental HCT116 cells. FIG. 11B shows Loewe excess for the combination in 11A and FIG. 11C shows Bliss excess for the combination in 11A. FIG. 11D shows a dose matrix showing inhibition (%) for the combination in HCT116 PIK3CA (+/−) cells. FIG. 11E shows Loewe excess for the combination in 11D and FIG. 11F shows Bliss excess for the combination in 11D. FIG. 11G-FIG. 11H show the results of single agent proliferation assays for the combination in 11A. FIG. 11I-FIG. 11J show the results of single agent proliferation assays for the combination in 11D.

FIG. 12A shows a dose matrix showing inhibition (%) for the combination in parental HCT116 cells. FIG. 12B shows Loewe excess for the combination in 12A and FIG. 12C shows Bliss excess for the combination in 12A. FIG. 12D shows a dose matrix showing inhibition (%) for the combination in HCT116 PIK3CA (+/−) cells. FIG. 12E shows Loewe excess for the combination in 12D and FIG. 12F shows Bliss excess for the combination in 12D. FIG. 12G-FIG. 12H show the results of single agent proliferation assays for the combination in 12A. FIG. 12I-FIG. 12J show the results of single agent proliferation assays for the combination in 12D.

FIG. 13A shows a dose matrix showing inhibition (%) for the combination in parental HCT116 cells. FIG. 13B shows Loewe excess for the combination in 13A and FIG. 13C shows Bliss excess for the combination in 13A. FIG. 13D shows a dose matrix showing inhibition (%) for the combination in HCT116 PIK3CA (+/−) cells. FIG. 13E shows Loewe excess for the combination in 13D and FIG. 13F shows Bliss excess for the combination in 13D. FIG. 13G-FIG. 13H show the results of single agent proliferation assays for the combination in 13A. FIG. 13I-FIG. 13J show the results of single agent proliferation assays for the combination in 13D.

FIG. 14A shows a dose matrix showing inhibition (%) for the combination in parental HCT116 cells. FIG. 14B shows Loewe excess for the combination in 14A and FIG. 14C shows Bliss excess for the combination in 14A. FIG. 14D shows a dose matrix showing inhibition (%) for the combination in HCT116 PIK3CA (+/−) cells. FIG. 14E shows Loewe excess for the combination in 14D and FIG. 14F shows Bliss excess for the combination in 14D. FIG. 14G-FIG. 14H show the results of single agent proliferation assays for the combination in 14A. FIG. 14I-FIG. 14J show the results of single agent proliferation assays for the combination in 14D.

FIG. 16A shows viability and Bliss scores for combinations with BVD-523 in parental HCT116 cells. FIG. 16B shows viability and Bliss scores for combinations with BVD-523 in HCT116 PIK3CA (+/−) cells. FIG. 16C shows viability and Bliss scores for combinations with SCH772984 in parental HCT116 cells. FIG. 16D shows viability and Bliss scores for combinations with SCH772984 in HCT116 PIK3CA (+/−) cells.

FIG. 17A shows a dose matrix showing inhibition (%) for the combination in parental DLD-1 cells. FIG. 17B shows Loewe excess for the combination in 17A and FIG. 17C shows Bliss excess for the combination in 17A. FIG. 17D shows a dose matrix showing inhibition (%) for the combination in DLD-1 PIK3CA (+/−) cells. FIG. 17E shows Loewe excess for the combination in 17D and FIG. 17F shows Bliss excess for the combination in 17D. FIG. 17G-FIG. 17H show the results of single agent proliferation assays for the combination in 17A. FIG. 17I-FIG. 17J show the results of single agent proliferation assays for the combination in 17D.

FIG. 18A shows a dose matrix showing inhibition (%) for the combination in parental DLD-1 cells. FIG. 18B shows Loewe excess for the combination in 18A and FIG. 18C shows Bliss excess for the combination in 18A. FIG. 18D shows a dose matrix showing inhibition (%) for the combination in DLD-1 PIK3CA (+/−) cells. FIG. 18E shows Loewe excess for the combination in 18D and FIG. 18F shows Bliss excess for the combination in 18D. FIG. 18G-FIG. 18H show the results of single agent proliferation assays for the combination in 18A. FIG. 18I-FIG. 18J show the results of single agent proliferation assays for the combination in 18D.

FIG. 19A shows a dose matrix showing inhibition (%) for the combination in parental DLD-1 cells. FIG. 19B shows Loewe excess for the combination in 19A and FIG. 19C shows Bliss excess for the combination in 19A. FIG. 19D shows a dose matrix showing inhibition (%) for the combination in DLD-1 PIK3CA (+/−) cells. FIG. 19E shows Loewe excess for the combination in 19D and FIG. 19F shows Bliss excess for the combination in 19D. FIG. 19G-FIG. 19H show the results of single agent proliferation assays for the combination in 19A. FIG. 19I-FIG. 19J show the results of single agent proliferation assays for the combination in 19D.

FIG. 20A shows a dose matrix showing inhibition (%) for the combination in parental DLD-1 cells. FIG. 20B shows Loewe excess for the combination in 20A and FIG. 20C shows Bliss excess for the combination in 20A. FIG. 20D shows a dose matrix showing inhibition (%) for the combination in DLD-1 PIK3CA (+/−) cells. FIG. 20E shows Loewe excess for the combination in 20D and FIG. 20F shows Bliss excess for the combination in 20D. FIG. 20G-FIG. 20H show the results of single agent proliferation assays for the combination in 20A. FIG. 20I-FIG. 20J show the results of single agent proliferation assays for the combination in 20D.

FIG. 21A shows a dose matrix showing inhibition (%) for the combination in parental DLD-1 cells. FIG. 21B shows Loewe excess for the combination in 21A and FIG. 21C shows Bliss excess for the combination in 21A. FIG. 21D shows a dose matrix showing inhibition (%) for the combination in DLD-1 PIK3CA (+/−) cells. FIG. 21E shows Loewe excess for the combination in 21D and FIG. 21F shows Bliss excess for the combination in 21D. FIG. 21G-FIG. 21H show the results of single agent proliferation assays for the combination in 21A. FIG. 21I-FIG. 21J show the results of single agent proliferation assays for the combination in 21D.

FIG. 22A shows a dose matrix showing inhibition (%) for the combination in parental DLD-1 cells. FIG. 22B shows Loewe excess for the combination in 22A and FIG. 22C shows Bliss excess for the combination in 22A. FIG. 22D shows a dose matrix showing inhibition (%) for the combination in DLD-1 PIK3CA (+/−) cells. FIG. 22E shows Loewe excess for the combination in 22D and FIG. 22F shows Bliss excess for the combination in 22D. FIG. 22G-FIG. 22H show the results of single agent proliferation assays for the combination in 22A. FIG. 22I-FIG. 22J show the results of single agent proliferation assays for the combination in 22D.

FIG. 23A shows a dose matrix showing inhibition (%) for the combination in parental DLD-1 cells. FIG. 23B shows Loewe excess for the combination in 23A and FIG. 23C shows Bliss excess for the combination in 23A. FIG. 23D shows a dose matrix showing inhibition (%) for the combination in DLD-1 PIK3CA (+/−) cells. FIG. 23E shows Loewe excess for the combination in 23D and FIG. 23F shows Bliss excess for the combination in 23D. FIG. 23G-FIG. 23H show the results of single agent proliferation assays for the combination in 23A. FIG. 23I-FIG. 23J show the results of single agent proliferation assays for the combination in 23D.

FIG. 24A shows a dose matrix showing inhibition (%) for the combination in parental DLD-1 cells. FIG. 24B shows Loewe excess for the combination in 24A and FIG. 24C shows Bliss excess for the combination in 24A. FIG. 24D shows a dose matrix showing inhibition (%) for the combination in DLD-1 PIK3CA (+/−) cells. FIG. 24E shows Loewe excess for the combination in 24D and FIG. 24F shows Bliss excess for the combination in 24D. FIG. 24G-FIG. 24H show the results of single agent proliferation assays for the combination in 24A. FIG. 24I-FIG. 24J show the results of single agent proliferation assays for the combination in 24D.

FIG. 26A shows Lowe Volumes for the combinations tested. FIG. 26B shows Bliss Volumes for the combinations tested. FIG. 26C shows Synergy Scores for the combinations tested.

FIG. 27A shows a dose matrix showing inhibition (%) for the combination in A375 cells. FIG. 27B-FIG. 27C show the results of single agent proliferation assays for the combination in 27A. FIG. 27D shows Loewe excess for the combination in 27A and FIG. 27E shows Bliss excess for the combination in 27A.

DETAILED DESCRIPTION OF THE INVENTION

Figure 1:
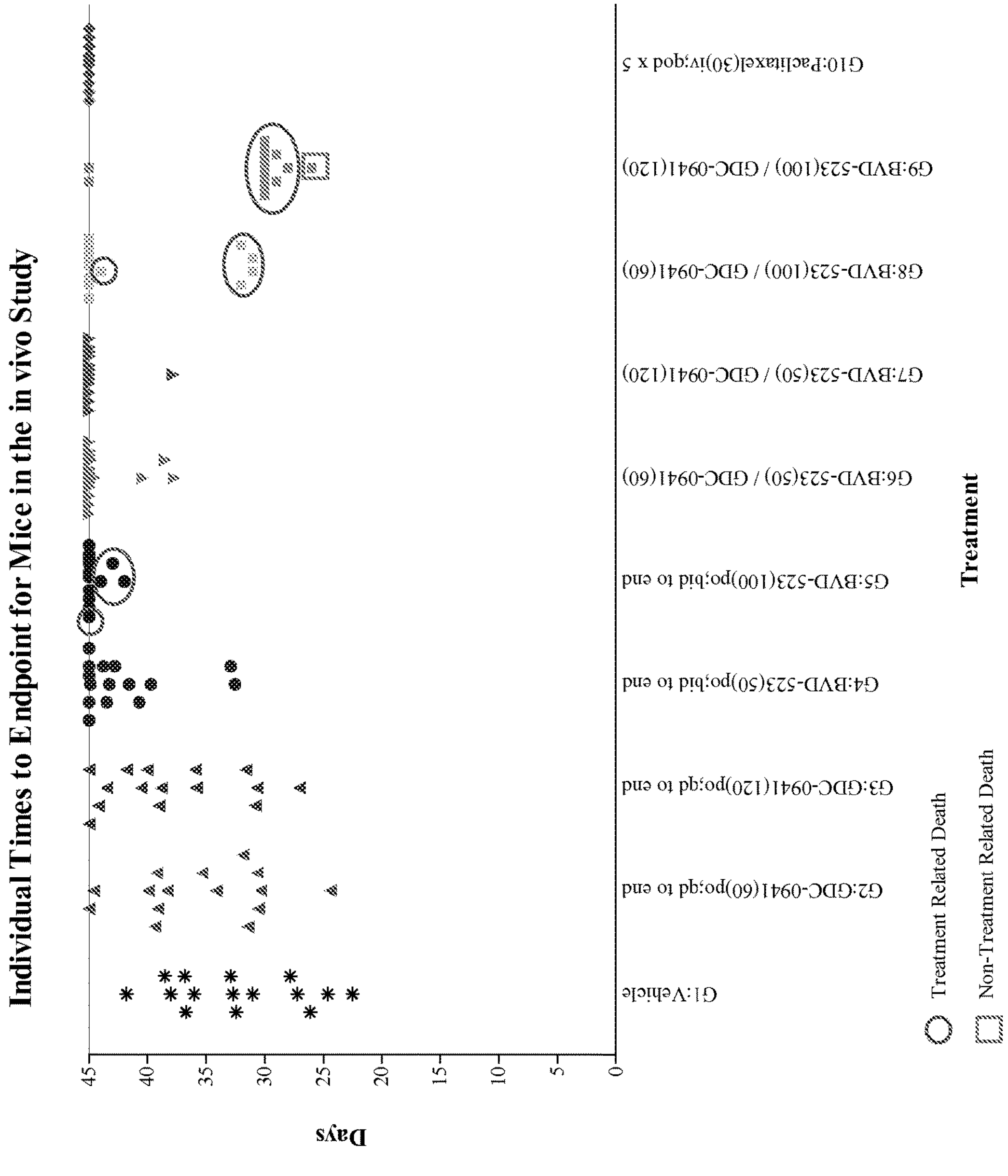
FIG. 1 is a plot showing individual times to endpoint for mice treated with various doses of a PI3K inhibitor (GDC-0941), an ERK inhibitor (BVD-523), or a combination of the two in the in vivo study. The number in the parenthesis indicate the dose in mg/kg.

One embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof, to treat or ameliorate the effects of the cancer.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population, may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, which is a preferred mammal in the present invention, other categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

In the present invention, cancers include both solid and hemotologic cancers. Non-limiting examples of solid cancers include adrenocortical carcinoma, anal cancer, bladder cancer, bone cancer (such as osteosarcoma), brain cancer, breast cancer, carcinoid cancer, carcinoma, cervical cancer, colon cancer, endometrial cancer, esophageal cancer, extra-hepatic bile duct cancer, Ewing family of cancers, extracranial germ cell cancer, eye cancer, gallbladder cancer, gastric cancer, germ cell tumor, gestational trophoblastic tumor, head and neck cancer, hypopharyngeal cancer, islet cell carcinoma, kidney cancer, large intestine cancer, laryngeal cancer, leukemia, lip and oral cavity cancer, liver cancer, lung cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell cancer, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancers (such as cutaneous t-cell lymphoma, Kaposi's sarcoma, mast cell tumor, and melanoma), small intestine cancer, soft tissue sarcoma, stomach cancer, testicular cancer, thymoma, thyroid cancer, urethral cancer, uterine cancer, vaginal cancer, vulvar cancer, and Wilms' tumor.

Examples of hematologic tumors/cancers include, but are not limited to, leukemias, such as adult/childhood acute lymphoblastic leukemia, adult/childhood acute myeloid leukemia, chronic lymphocytic leukemia, chronic myelogenous leukemia, and hairy cell leukemia, lymphomas, such as AIDS-related lymphoma, cutaneous T-cell lymphoma, adult/childhood Hodgkin lymphoma, mycosis fungoides, adult/childhood non-Hodgkin lymphoma, primary central nervous system lymphoma, Sezary syndrome, cutaneous T-cell lymphoma, and Waldenstrom macroglobulinemia, as well as other proliferative disorders such as chronic myeloproliferative disorders, Langerhans cell histiocytosis, multiple myeloma/plasma cell neoplasm, myelodysplastic syndromes, and myelodysplastic/myeloproliferative neoplasms.

Preferably, the cancer is selected from the group consisting of a cancer of the large intestine, breast cancer, liver cancer, colon cancer, pancreatic cancer, endometrial cancers, stomach cancer, lung cancer, and leukemia. More preferably, the cancer is colon cancer.

In the present invention, BVD-523 corresponds to a compound according to formula (I):

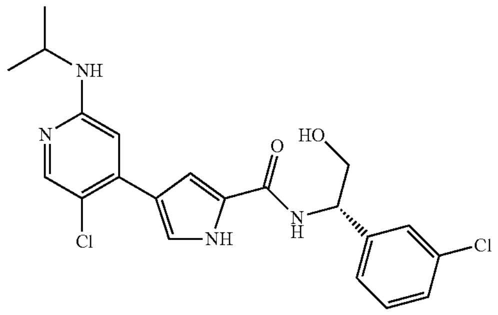 [SMILES: CC(C)Nc1cc(-c2c[nH]c(C(=O)N[C@H](CO)c3cccc(Cl)c3)c2)c(Cl)cn1]

and pharmaceutically acceptable salts thereof. BVD-523 may be synthesized according to the methods disclosed, e.g., in U.S. Pat. No. 7,354,939. Enantiomers and racemic mixtures of both enantiomers of BVD-523 are also contemplated within the scope of the present invention. BVD-523 is an ERK1/2 inhibitor with a mechanism of action that is believed to be, e.g., unique and distinct from certain other ERK1/2 inhibitors, such as SCH772984. For example, other ERK1/2 inhibitors, such as SCH772984, inhibit autophosphorylation of ERK (Morris et al., 2013), whereas BVD-523 allows for the autophosphorylation of ERK while still inhibiting ERK. (See, e.g., FIG. 4).

As used herein, an "inhibitor" of the PI3K/Akt pathway is any substance that decreases the expression or the activity of phosphatidylinositol-3 kinases (PI3Ks) or downstream proteins, such as Akt. PI3Ks, when activated, phosphorylate the inositol ring 3'-OH group in inositol phospholipids to generate the second messenger phosphatidylinositol-3,4,5-trisphosphate (PI-3,4,5-P(3)). Akt interacts with these phospholipids, causing it to translocate to the inner membrane, where it is phosphorylated and activated. Activated Akt modulates the function of numerous substrates involved in the regulation of cell survival, cell cycle progression and cellular growth.

Non-limiting examples of inhibitors of the PI3K/Akt pathway according to the present invention include A-674563 (CAS #552325-73-2), AGL 2263, AMG-319 (Amgen, Thousand Oaks, Calif.), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, Calif.), BML-257 (CAS #32387-96-5), CAL-120 (Gilead Sciences, Foster City, Calif.), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, 1087114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, Mass.), perifosine, PHT-427 (CAS #1191951-57-1), PI3 kinase delta inhibitor, Merck KGaA (Merck & Co., Whitehouse Station, N.J.), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, Calif.), PI3-delta inhibitors, Cellzome (Cellzome AG, Heidelberg, Germany), PI3-delta inhibitors, Intellikine (Intellikine Inc., La Jolla, Calif.), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (GDC-0941) (Roche Holdings Inc.), PIK-90 (CAS #677338-12-4), SC-103980 (Pfizer, New York, N.Y.), SF-1126 (Semafore Pharmaceuticals, Indianapolis, Ind.), SH-5, SH-6, Tetrahydro Curcumin, TG100-115 (Targegen Inc., San Diego, Calif.), Triciribine, X-339 (Xcovery, West Palm Beach, Fla.), XL-499 (Evotech, Hamburg, Germany), pharmaceutically acceptable salts thereof, and combinations thereof. Preferably, the inhibitor of the PI3K/Akt pathway is pictilisib (GDC-0941) or a pharmaceutically acceptable salt thereof.

In one aspect of this embodiment, the subject with cancer has a somatic KRAS mutation or is refractory to MAPK pathway inhibitor treatment. In another aspect of this embodiment, the subject with cancer has a somatic KRAS mutation and a somatic PIK3CA mutation.

As used herein, "somatic mutation" means a change occurring in any cell that is not destined to become a germ cell. The mutation may be a substitution, deletion, insertion, or a fusion. Methods for identifying mutations in nucleic acids, such as the above-listed RAS genes, are known in the art. Non-limiting examples include PCR, sequencing, hybrid capture, in-solution capture, molecular inversion probes, fluorescent in situ hybridization (FISH) assays, and combinations thereof.

Various sequencing methods are known in the art. These include, but are not limited to, Sanger sequencing (also referred to as dideoxy sequencing) and various sequencing-by-synthesis (SBS) methods as disclosed in, e.g., Metzker 2005, sequencing by hybridization, by ligation (for example, WO 2005021786), by degradation (for example, U.S. Pat. Nos. 5,622,824 and 6,140,053) and nanopore sequencing (which is commercially available from Oxford Nanopore Technologies, UK). In deep sequencing techniques, a given nucleotide in the sequence is read more than once during the sequencing process. Deep sequencing techniques are disclosed in e.g., U.S. Patent Publication No. 20120264632 and International Patent Publication No. WO2012125848.

PCR-based methods for detecting mutations are known in the art and employ PCR amplification, where each target sequence in the sample has a corresponding pair of unique, sequence-specific primers. For example, the polymerase chain reaction-restriction fragment length polymorphism (PCR-RFLP) method allows for rapid detection of mutations after the genomic sequences are amplified by PCR. The mutation is discriminated by digestion with specific restriction endonucleases and is identified by electrophoresis. See, e.g., Ota et al., 2007. Mutations may also be detected using real time PCR. See, e.g., International Application publication No. WO2012046981.

Hybrid capture methods are known in the art and are disclosed in e.g., U.S. Patent Publication No. 20130203632 and U.S. Pat. Nos. 8,389,219 and 8,288,520. These methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g. biotin) which can subsequently be immobilized to a solid surface, such as a bead (in-solution capture).

Molecular Inversion Probe (MIP) techniques are known in the art and are disclosed in e.g., Absalan et al., 2008. This method uses MIP molecules, which are special "padlock" probes (Nilsson et al., 1994) for genotyping. A MIP molecule is a linear oligonucleotide that contains specific regions, universal sequences, restriction sites and a Tag (index) sequence (16-22 bp). A MIP hybridizes directly around the genetic marker/SNP of interest. The MIP method may also use a number of "padlock" probe sets that hybridize to genomic DNA in parallel (Hardenbol et al., 2003). In case of a perfect match, genomic homology regions are ligated by undergoing an inversion in configuration (as suggested by the name of the technique) and creating a circular molecule. After the first restriction, all molecules are amplified with universal primers. Amplicons are restricted again to ensure short fragments for hybridization on a microarray. Generated short fragments are labeled and, through a Tag sequence, hybridized to a cTag (complementary strand for index) on an array. After the formation of Tag-cTag duplex, a signal is detected.

The following Tables 1 and 2 show the SEQ ID Nos. of representative nucleic acid and amino acid sequences of wild type K-RAS and PIK3CA from various animal sources, respectively, in the sequence listing. These sequences may be used in methods for identifying subjects with a mutant K-RAS and/or PIK3CA genotype (such as in the methods set forth below).

TABLE 1

K-RAS sequences

| SEQ ID No. | polypeptide or nucleic acid sequence | Organism | Other Information |
|---|---|---|---|
| 1 | nucleic acid | human | isoform a |
| 2 | polypeptide | human | isoform a |
| 3 | nucleic acid | human | isoform b |
| 4 | polypeptide | human | isoform b |
| 5 | nucleic acid | rat (*Rattus norvegicus*) | |
| 6 | polypeptide | rat (*Rattus norvegicus*) | |
| 7 | nucleic acid | mouse, *Mus musculus* | |
| 8 | polypeptide | mouse, *Mus musculus* | |
| 9 | nucleic acid | rabbit, *Oryctolagus cuniculus* | |
| 10 | polypeptide | rabbit, *Oryctolagus cuniculus* | |
| 11 | nucleic acid | guinea pig, *Cavia porcellus* | variant 1 |
| 12 | polypeptide | guinea pig, *Cavia porcellus* | variant 1 |
| 13 | nucleic acid | guinea pig, *Cavia porcellus* | variant 2 |
| 14 | polypeptide | guinea pig, *Cavia porcellus* | variant 2 |
| 15 | nucleic acid | dog, *Canis lupus familiaris* | variant 1 |
| 16 | polypeptide | dog, *Canis lupus familiaris* | variant 1 |
| 17 | nucleic acid | dog, *Canis lupus familiaris* | variant 2 |
| 18 | polypeptide | dog, *Canis lupus familiaris* | variant 2 |
| 19 | nucleic acid | cat, *Felis catus* | variant 1 |
| 20 | polypeptide | cat, *Felis catus* | variant 1 |
| 21 | nucleic acid | cat, *Felis catus* | variant 2 |
| 22 | polypeptide | cat, *Felis catus* | variant 2 |
| 23 | nucleic acid | cow, *Bos taurus* | |
| 24 | polypeptide | cow, *Bos taurus* | |
| 25 | nucleic acid | cow, *Bos taurus* | variant X2 |
| 26 | polypeptide | cow, *Bos taurus* | variant X2 |
| 27 | nucleic acid | cow, *Bos taurus* | variant X3 |
| 28 | polypeptide | cow, *Bos taurus* | variant X3 |
| 29 | nucleic acid | chicken, *Gallus gallus* | |
| 30 | polypeptide | chicken, *Gallus gallus* | |

TABLE 2

PIK3CA sequences

| SEQ ID No. | polypeptide or nucleic acid sequence | Organism |
|---|---|---|
| 31 | nucleic acid | human |
| 32 | polypeptide | human |
| 33 | nucleic acid | rat (*Rattus norvegicus*) |
| 34 | polypeptide | rat (*Rattus norvegicus*) |
| 35 | nucleic acid | mouse, *Mus musculus* |
| 36 | polypeptide | mouse, *Mus musculus* |
| 37 | nucleic acid | rabbit, *Oryctolagus cuniculus* |
| 38 | nucleic acid | guinea pig, *Cavia porcellus* |
| 39 | polypeptide | guinea pig, *Cavia porcellus* |
| 40 | nucleic acid | dog, *Canis lupus familiaris* |
| 41 | polypeptide | dog, *Canis lupus familiaris* |
| 42 | nucleic acid | cat, *Felis catus* |
| 43 | polypeptide | cat, *Felis catus* |
| 44 | nucleic acid | cow, *Bos taurus* |
| 45 | polypeptide | cow, *Bos taurus* |
| 46 | nucleic acid | chicken, *Gallus gallus* |
| 47 | polypeptide | chicken, *Gallus gallus* |

As used herein, being "refractory" to a MAPK pathway inhibitor treatment means that the MAPK pathway inhibitor has reduced efficacy in treating cancer.

As used herein, "mitogen-activated protein kinase (MAPK) pathway inhibitor" means any substance that reduces the activity, expression or phosphorylation of proteins in the MAPK pathway that result in a reduction of cell growth or an increase in cell death.

Figure 5:
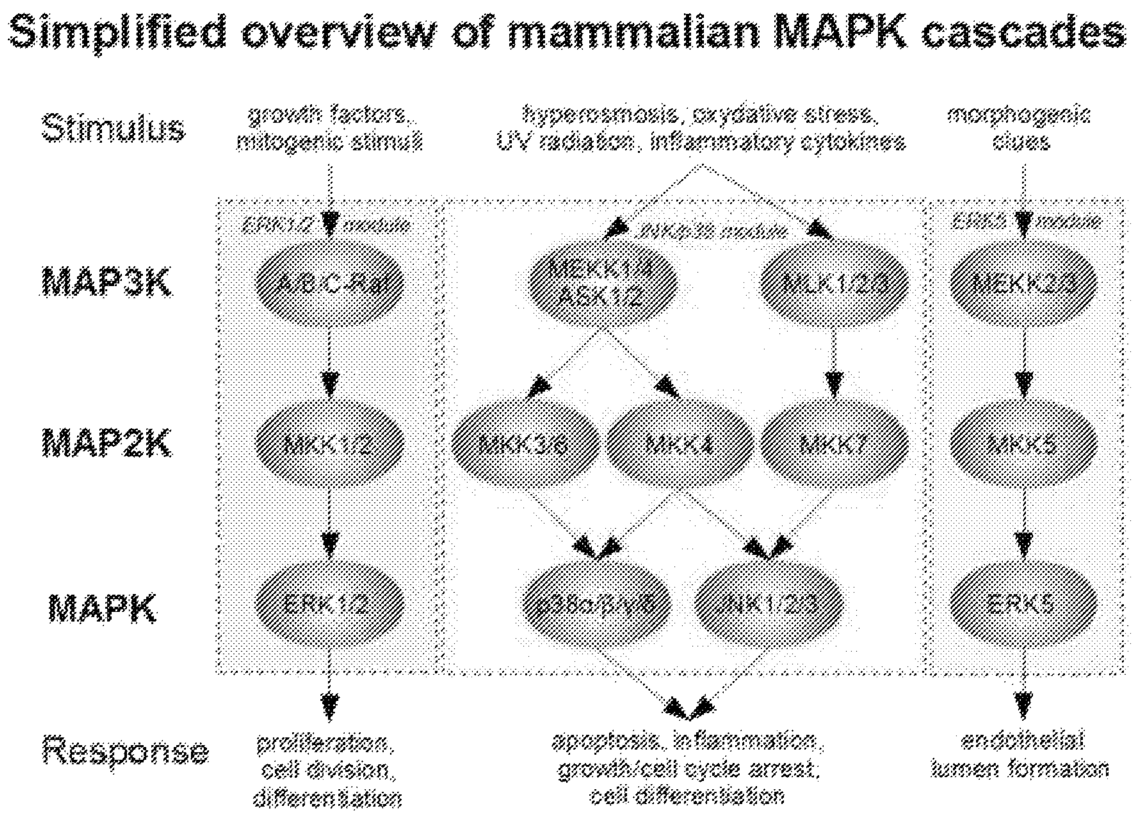
FIG. 5 shows a schematic of the mitogen-activated protein kinase (MAPK) pathway.

An overview of the mammalian MAPK cascades is shown in FIG. 5. The details of the MAPK pathways are reviewed in e.g., Akinleye et al., 2013. Briefly, with respect to the ERK1/2 module in FIG. 5 (light purple box), the MAPK 1/2 signaling cascade is activated by ligand binding to receptor tyrosine kinases (RTK). The activated receptors recruit and phosphorylate adaptor proteins Grb2 and SOS, which then interact with membrane-bound GTPase Ras and cause its activation. In its activated GTP-bound form, Ras recruits and activates Raf kinases (A-Raf, B-Raf, and C-Raf/RaF-1). The activated Raf kinases activate MAPK 1/2 (MKK1/2), which in turn catalyzes the phosphorylation of threonine and tyrosine residues in the activation sequence Thr-Glu-Tyr of ERK1/2. With respect to the JNK/p38 module (yellow box in FIG. 5), upstream kinases, MAP3Ks, such as MEKK1/4, ASK1/2, and MLK1/2/3, activate MAP2K3/6 (MKK3/6), MAP2K4 (MKK4), and MAP2K7 (MKK7). These MAP2K's then activate JNK protein kinases, including JNK1, JNK2, and JNK3, as well as p38 α/β/γ/δ. To execute their functions, JNKs activate several transcription factors, including c-Jun, ATF-2, NF-ATc1, HSF-1 and STAT3. With respect to the ERK5 module (blue box in FIG. 5), the kinases upstream of MAP2K5 (MKK5) are MEKK2 and MEKK3. The best characterized downstream target of MEK5 is ERK5, also known as big MAP kinase 1 (BMK1) because it is twice the size of other MAPKs.

Non-limiting examples of MAPK pathway inhibitors according to the present invention include RAS inhibitors, RAF inhibitors, MEK inhibitors, ERK1/2 inhibitors, pharmaceutically acceptable salts thereof, and combinations thereof.

As used herein, a "RAS inhibitor" means those substances that (i) directly interact with RAS, e.g., by binding to RAS and (ii) decrease the expression or the activity of RAS. Non-limiting examples of RAS inhibitors according to the present invention include, but are not limited to, farnesyl transferase inhibitors (such as, e.g., tipifarnib and lonafarnib), farnesyl group-containing small molecules (such as, e.g., salirasib and TLN-4601), DCAI, as described by Maurer (Maurer, et al., 2012), Kobe0065 and Kobe2602, as described by Shima (Shima, et al., 2013), and HBS 3 (Patgiri, et al., 2011), and AIK-4 (Allinky).

As used herein, a "RAF inhibitor" means those substances that (i) directly interacts with RAF, e.g., by binding to RAF and (ii) decrease the expression or the activity of RAF, such as, e.g., A-RAF, B-RAF, and C-RAF (Raf-1). Non-limiting exemplary RAF inhibitors include:

Compound 7

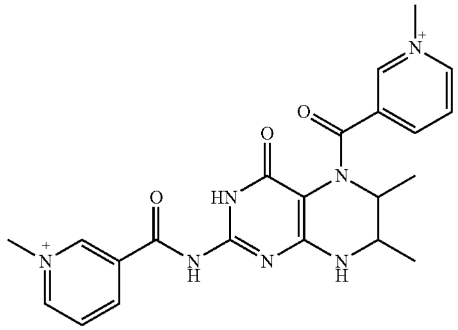

, (Li et al., 2010)

Compound 9

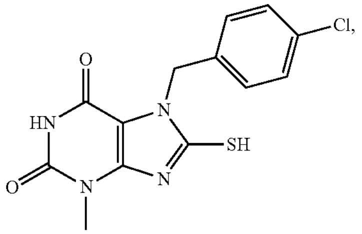

(Id.)

-continued

Compound 10

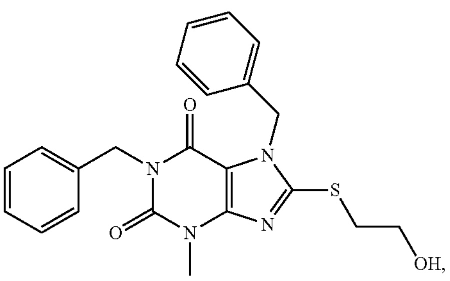

(Id.)

Compound 13

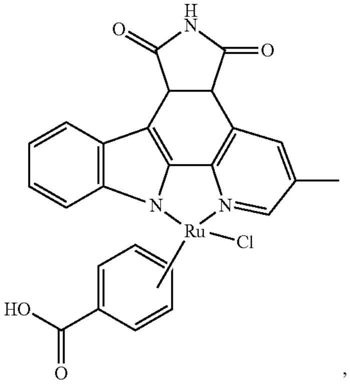

, (Id.)

Compound 14

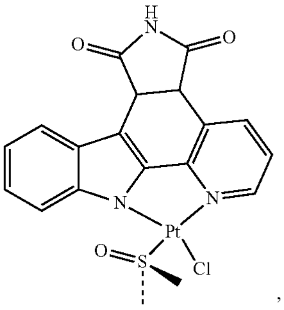

, (Id.)

Compound 15

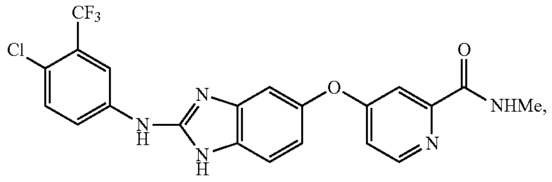

(Id.)

Compound 16

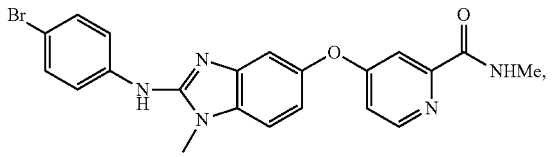

(Id.)

-continued
Compound 18
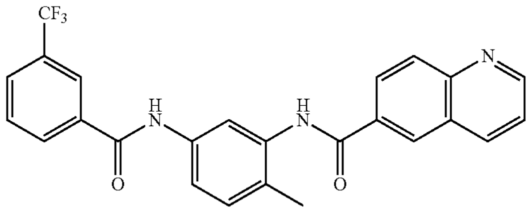
,
(Id.)
Compound 19
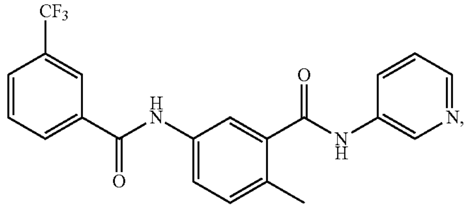
(Id.)
Compound 20
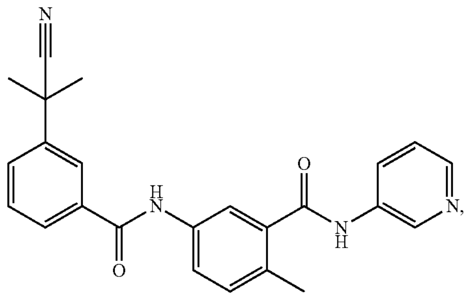
(Id.)
Compound 21
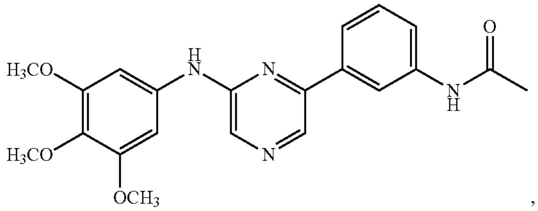
,
(Id.)
Compound 22
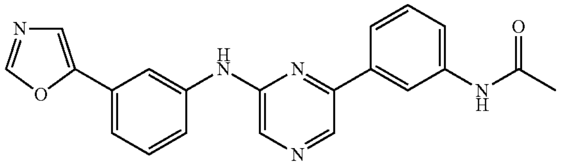
,
(Id.)
Compound 23
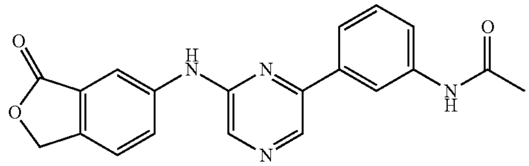
,
(Id.)
-continued
Compound 24
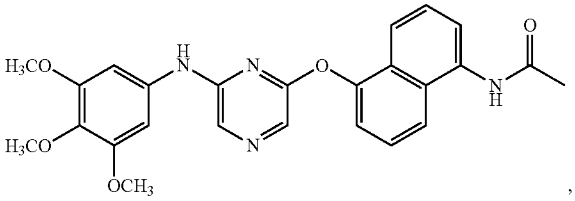
,
(Id.)
Compound 25
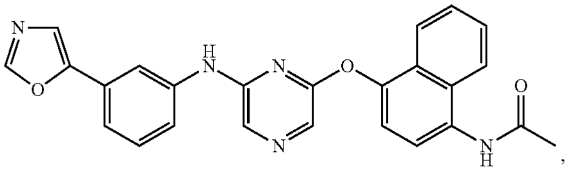
,
(Id.)
Compound 26
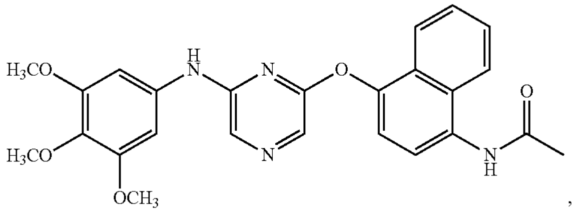
,
(Id.)
Compound 27
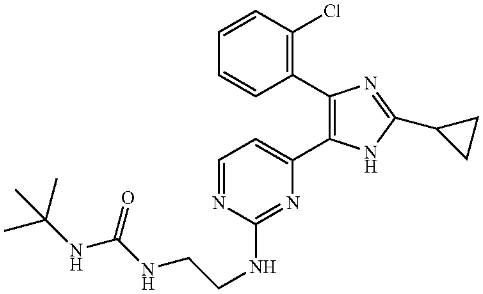
,
(Id.)
Compound 28
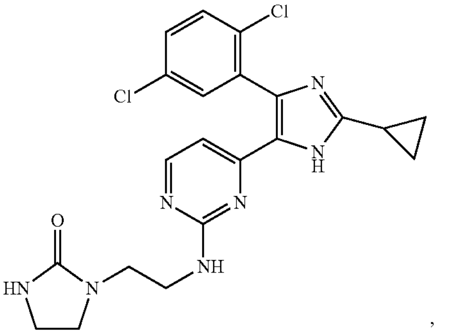
,
(Id.)

-continued
Compound 30
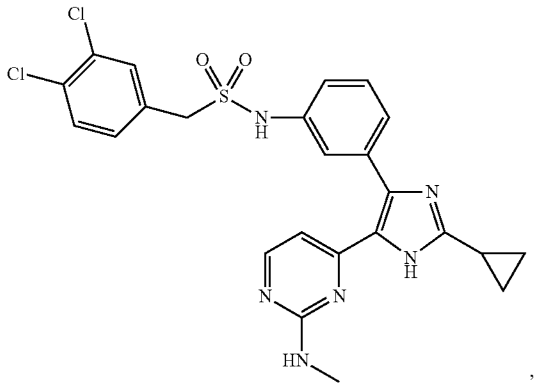
,
(Id.)
Compound 31
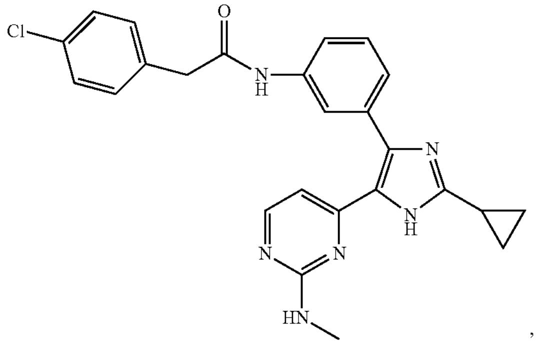
,
(Id.)
Compound 32
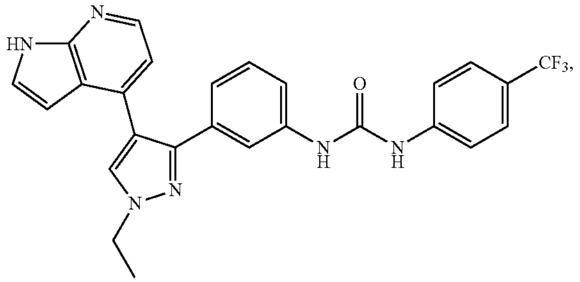
(Id.)
Compound 33
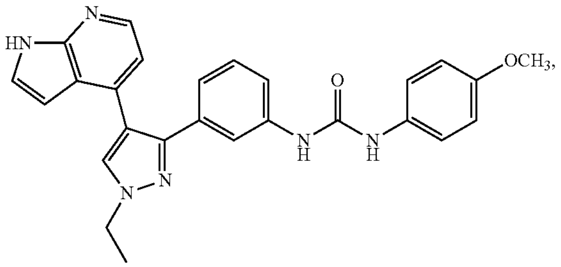
(Id.)
-continued
Compound 34
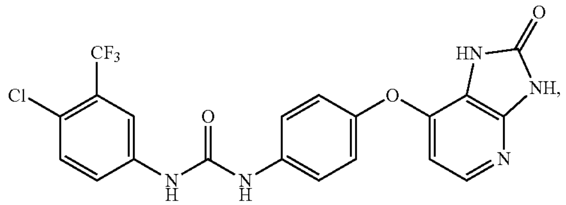
(Id.)
Compound 35
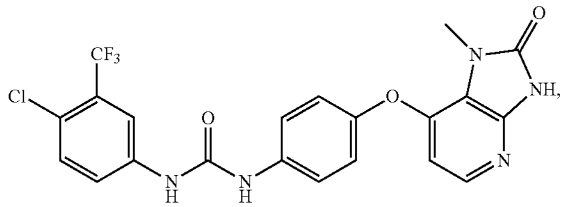
(Id.)
Compound 36
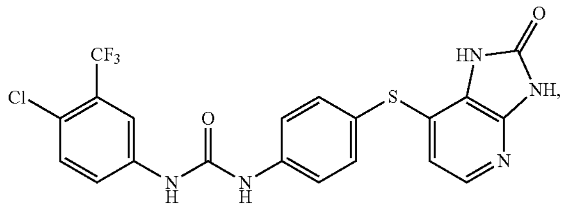
(Id.)
Compound 37
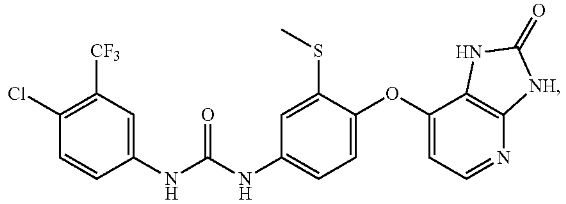
(Id.)
Compound 38
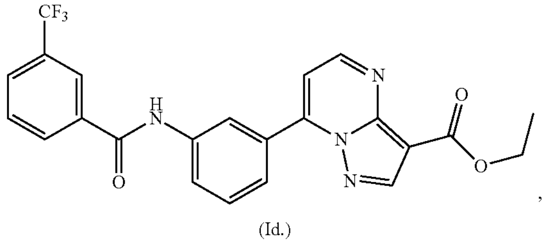
,
(Id.)
Compound 39
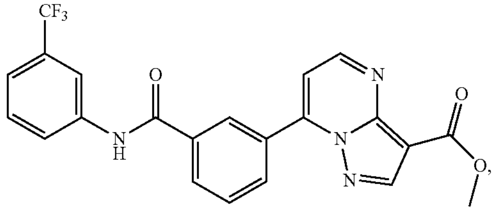
(Id.)

-continued

Compound 40

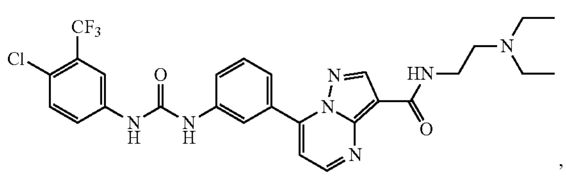

, (Id.)

AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 523 (cctatcgttagagtcttcctg) (Liu et al., 2007), CTT239065 (Institute of Cancer Research), dabrafenib (GSK2118436), DP-4978 (Deciphera Pharmaceuticals), HM-95573 (Hanmi), GDC-0879 (Genentech), GW-5074 (Sigma Aldrich), ISIS 5132 (Novartis), L779450 (Merck), LBT613 (Novartis), LErafAON (NeoPharm, Inc.), LGX-818 (Novartis), pazopanib (GlaxoSmithKline), PLX3202 (Plexxikon), PLX4720 (Plexxikon), PLX5568 (Plexxikon), RAF-265 (Novartis), RAF-365 (Novartis), regorafenib (Bayer Healthcare Pharmaceuticals, Inc.), RO 5126766 (Hoffmann-La Roche), SB-590885 (GlaxoSmithKline), SB699393 (GlaxoSmithKline), sorafenib (Onyx Pharmaceuticals), TAK 632 (Takeda), TL-241 (Teligene), vemurafenib (RG7204 or PLX4032) (Daiichi Sankyo), XL-281 (Exelixis), ZM-336372 (AstraZeneca), pharmaceutically acceptable salts thereof, and combinations thereof.

As used herein, a "MEK inhibitor" means those substances that (i) directly interact with MEK, e.g., by binding to MEK and (ii) decrease the expression or the activity of MEK. Therefore, inhibitors that act upstream of MEK, such as RAS inhibitors and RAF inhibitors, are not MEK inhibitors according to the present invention. Non-limiting examples of MEK inhibitors according to the present invention include anthrax toxin, antroquinonol (Golden Biotechnology), ARRY-142886 (6-(4-bromo-2-chloro-phenylamino)-7-fluoro-3-methyl-3H-benzoimidazole-5-carboxylic acid (2-hydroxy-ethoxy)-amide) (Array BioPharma), ARRY-438162 (Array BioPharma), AS-1940477 (Astellas), AS-703988 (Merck KGaA), bentamapimod (Merck KGaA), BI-847325 (Boehringer Ingelheim), E-6201 (Eisai), GDC-0623 (Hoffmann-La Roche), GDC-0973 (cobimetinib) (Hoffmann-La Roche), L783277 (Merck), lethal factor portion of anthrax toxin, MEK162 (Array BioPharma), PD 098059 (2-(2'-amino-3'-methoxyphenyl)-oxanaphthalen-4-one) (Pfizer), PD 184352 (CI-1040) (Pfizer), PD-0325901 (Pfizer), pimasertib (Santhera Pharmaceuticals), RDEA119 (Ardea Biosciences/Bayer), refametinib (AstraZeneca), RG422 (Chugai Pharmaceutical Co.), RO092210 (Roche), RO4987655 (Hoffmann-La Roche), RO5126766 (Hoffmann-La Roche), selumetinib (AZD6244) (AstraZeneca), SL327 (Sigma), TAK-733 (Takeda), trametinib (Japan Tobacco), U0126 (1,4-diamino-2,3-dicyano-1,4-bis(2-aminophenylthio)butadiene) (Sigma), WX-554 (Wilex), YopJ polypeptide (Mittal et al., 2010), pharmaceutically acceptable salts thereof, and combinations thereof.

As used herein, an "ERK1/2 inhibitor" means those substances that (i) directly interact with ERK1 and/or ERK2, e.g., by binding to ERK1/2 and (ii) decrease the expression or the activity of ERK1 and/or ERK2 protein kinases. Therefore, inhibitors that act upstream of ERK1/2, such as MEK inhibitors and RAF inhibitors, are not ERK1/2 inhibitors according to the present invention. Non-limiting examples of ERK1/2 inhibitors according to the present invention include AEZS-131 (Aeterna Zentaris), AEZS-136 (Aeterna Zentaris), BVD-523 (BioMed Valley Discoveries, Inc.), SCH-722984 (Merck & Co.), SCH-772984 (Merck & Co.), SCH-900353 (MK-8353) (Merck & Co.), pharmaceutically acceptable salts thereof, and combinations thereof.

In an additional aspect of this embodiment, the method further comprises administering at least one additional therapeutic agent selected from the group consisting of an antibody or fragment thereof, a cytotoxic agent, a drug, a toxin, a radionuclide, an immunomodulator, a photoactive therapeutic agent, a radiosensitizing agent, a hormone, an anti-angiogenesis agent, and combinations thereof.

As used herein, an "antibody" encompasses naturally occurring immunoglobulins as well as non-naturally occurring immunoglobulins, including, for example, single chain antibodies, chimeric antibodies (e.g., humanized murine antibodies), heteroconjugate antibodies (e.g., bispecific antibodies). Fragments of antibodies include those that bind antigen, (e.g., Fab', $F(ab')_2$, Fab, Fv, and rIgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

Examples of therapeutic antibodies that may be used in the present invention include rituximab (Rituxan), Cetuximab (Erbitux), bevacizumab (Avastin), and Ibritumomab (Zevalin).

Cytotoxic agents according to the present invention include DNA damaging agents, antimetabolites, anti-microtubule agents, antibiotic agents, etc. DNA damaging agents include alkylating agents, platinum-based agents, intercalating agents, and inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, pharmaceutically acceptable salts thereof, prodrugs, and combinations thereof. Non-limiting examples of platinum-based agents include cisplatin, carboplatin, oxaliplatin, nedaplatin, satraplatin, triplatin tetranitrate, pharmaceutically acceptable salts thereof, prodrugs, and combinations thereof. Non-limiting examples of intercalating agents include doxorubicin, daunorubicin, idarubicin, mitoxantrone, pharmaceutically acceptable salts thereof, prodrugs, and combinations thereof. Non-limiting examples of inhibitors of DNA replication include irinotecan, topotecan, amsacrine, etoposide, etoposide phosphate, teniposide, pharmaceutically acceptable salts thereof, prodrugs, and combinations thereof. Antimetabolites include folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, decitabine, pharmaceutically acceptable salts thereof, prodrugs, and combinations thereof. Anti-microtubule agents include without limitation vinca alkaloids, paclitaxel (Taxol®), docetaxel (Taxotere®), and ixabepilone (Ixempra®). Antibiotic agents include without limitation actinomycin, anthracyclines, valrubicin, epirubicin, bleomycin, plicamycin, mitomycin, pharmaceutically acceptable salts thereof, prodrugs, and combinations thereof.

Cytotoxic agents according to the present invention also include inhibitors of the mTOR pathway. Non-limiting examples of such inhibitors include zotarolimus (AbbVie), umirolimus (Biosensors), temsirolimus (Pfizer), sirolimus (Pfizer), sirolimus NanoCrystal (Elan Pharmaceutical Technologies), sirolimus TransDerm (TransDerm), sirolimus-PNP (Samyang), everolimus (Novartis), biolimus A9 (Biosensors), ridaforolimus (Ariad), rapamycin, TCD-10023 (Terumo), DE-109 (MacuSight), MS-R001 (MacuSight), MS-R002 (MacuSight), MS-R003 (MacuSight), Perceiva (MacuSight), XL-765 (Exelixis), quinacrine (Cleveland BioLabs), PKI-587 (Pfizer), PF-04691502 (Pfizer), GDC-0980 (Genentech and Piramed), dactolisib (Novartis), CC-223 (Celgene), PWT-33597 (Pathway Therapeutics), P-7170 (Piramal Life Sciences), LY-3023414 (Eli Lilly), INK-128 (Takeda), GDC-0084 (Genentech), DS-7423 (Daiichi Sankyo), DS-3078 (Daiichi Sankyo), CC-115 (Celgene), CBLC-137 (Cleveland BioLabs), AZD-2014 (AstraZeneca), X-480 (Xcovery), X-414 (Xcovery), EC-0371 (Endocyte), VS-5584 (Verastem), PQR-401 (Piqur), PQR-316 (Piqur), PQR-311 (Piqur), PQR-309 (Piqur), PF-06465603 (Pfizer), NV-128 (Novogen), nPT-MTOR (Biotica Technology), BC-210 (Biotica Technology), WAY-600 (Biotica Technology), WYE-354 (Biotica Technology), WYE-687 (Biotica Technology), LOR-220 (Lorus Therapeutics), HMPL-518 (Hutchison China MediTech), GNE-317 (Genentech), EC-0565 (Endocyte), CC-214 (Celgene), ABTL-0812 (Ability Pharmaceuticals), and pharmaceutically acceptable salts thereof, and combinations thereof.

In the present invention, the term "toxin" means an antigenic poison or venom of plant or animal origin. An example is diphtheria toxin or portions thereof.

In the present invention, the term "radionuclide" means a radioactive substance administered to the patient, e.g., intravenously or orally, after which it penetrates via the patient's normal metabolism into the target organ or tissue, where it delivers local radiation for a short time. Examples of radionuclides include, but are not limited to, I-125, At-211, Lu-177, Cu-67, I-131, Sm-153, Re-186, P-32, Re-188, In-114m, and Y-90.

In the present invention, the term "immunomodulator" means a substance that alters the immune response by augmenting or reducing the ability of the immune system to produce antibodies or sensitized cells that recognize and react with the antigen that initiated their production. Immunomodulators may be recombinant, synthetic, or natural preparations and include cytokines, corticosteroids, cytotoxic agents, thymosin, and immunoglobulins. Some immunomodulators are naturally present in the body, and certain of these are available in pharmacologic preparations. Examples of immunomodulators include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

In the present invention, "photoactive therapeutic agent" means compounds and compositions that become active upon exposure to light. Certain examples of photoactive therapeutic agents are described in U.S. Patent Application Serial No. 2011/0152230 A1, "Photoactive Metal Nitrosyls For Blood Pressure Regulation And Cancer Therapy."

In the present invention, "radiosensitizing agent" means a compound that makes tumor cells more sensitive to radiation therapy. Examples of radiosensitizing agents include misonidazole, metronidazole, tirapazamine, and trans sodium crocetinate.

In the present invention, the term "hormone" means a substance released by cells in one part of a body that affects cells in another part of the body. Examples of hormones include, but are not limited to, prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. These hormone-interfering compounds include, but are not limited to, tamoxifen (Nolvadex®), anastrozole (Arimidex®), letrozole (Femara®), and fulvestrant (Faslodex®). Such compounds are also within the meaning of hormone in the present invention.

As used herein, an "anti-angiogenesis" agent means a substance that reduces or inhibits the growth of new blood vessels, such as, e.g., an inhibitor of vascular endothelial growth factor (VEGF) and an inhibitor of endothelial cell migration. Anti-angiogenesis agents include without limitation 2-methoxyestradiol, angiostatin, bevacizumab, cartilage-derived angiogenesis inhibitory factor, endostatin, IFN-$\alpha$, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

In another aspect of this embodiment, administration of the first and second anti-cancer agents provides a synergistic effect compared to administration of either anti-cancer agent alone. As used herein, "synergistic" means more than additive. Synergistic effects may be measured by various assays known in the art, including but not limited to those disclosed herein, such as the excess over bliss assay.

Another embodiment of the present invention is a method of treating or ameliorating the effects of a cancer in a subject in need thereof. The method comprises administering to the subject an effective amount of (i) BVD-523 or a pharmaceutically acceptable salt thereof and (ii) pictilisib (GDC-0941) or a pharmaceutically acceptable salt thereof, to treat or ameliorate the effects of the cancer.

Suitable and preferred subjects are as disclosed herein. In this embodiment, the methods may be used to treat the cancers disclosed above, including those cancers with the mutational backgrounds identified above. Methods of identifying such mutations are also as set forth above.

In one aspect of this embodiment, the BVD-523 or a pharmaceutically acceptable salt thereof is administered in the form of a pharmaceutical composition further comprising a pharmaceutically acceptable carrier or diluent.

In an additional aspect of this embodiment, the pictilisib (GDC-0941) or a pharmaceutically acceptable salt thereof is administered in the form of a pharmaceutical composition further comprising a pharmaceutically acceptable carrier or diluent.

In another aspect of this embodiment, the method further comprises administering at least one additional therapeutic agent, preferably an inhibitor of the mTOR pathway, as disclosed herein.

In a further aspect of this embodiment, administration of the first and second anti-cancer agents provides a synergistic effect compared to administration of either anti-cancer agent alone.

An additional embodiment of the present invention is a kit for treating or ameliorating the effects of a cancer in a subject in need thereof. The kit comprises an effective amount of (i) a first anti-cancer agent, which is BVD-523 or a pharmaceutically acceptable salt thereof and (ii) a second anti-cancer agent, which is a PI3K/Akt inhibitor or a pharmaceutically acceptable salt thereof, packaged together with instructions for their use.

The kits may include suitable storage containers, e.g., ampules, vials, tubes, etc., for each anti-cancer agent of the present invention (which may e.g., may be in the form of pharmaceutical compositions) and other reagents, e.g., buffers, balanced salt solutions, etc., for use in administering the anti-cancer agents to subjects. The anti-cancer agents of the invention and other reagents may be present in the kits in any convenient form, such as, e.g., in a solution or in a powder form. The kits may further include a packaging container, optionally having one or more partitions for housing the anti-cancer agents or pharmaceutical compositions containing same and other optional reagents.

Suitable and preferred PI3K/Akt inhibitors and subjects are as set forth above. In this embodiment, the kit may be used to treat the cancers disclosed above, including those cancers with the mutational backgrounds identified herein. Methods of identifying such mutations are as set forth above.

In an additional aspect of this embodiment, the kit further comprises at least one additional therapeutic agent, preferably an inhibitor of the mTOR pathway, as disclosed herein.

In another aspect of this embodiment, administration of the first and second anti-cancer agents provides a synergistic effect compared to administration of either anti-cancer agent alone.

An additional embodiment of the present invention is a method for treating or ameliorating the effects of a subject with cancer comprising:

(a) identifying a subject with cancer that has a somatic KRAS mutation and a somatic PIK3CA mutation; and (b) administering to the subject with somatic KRAS and PIK3CA mutations an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof, to treat or ameliorate the effects of the cancer.

Suitable and preferred PI3K/Akt inhibitors and subjects are as set forth above. In this embodiment, the methods may be used to treat the cancers disclosed above, including those cancers with the mutational backgrounds identified above. Methods of identifying such mutations are also as set forth above.

In one aspect of this embodiment, identifying a subject with cancer that has somatic KRAS and PIK3CA mutations comprises:

(a) obtaining a biological sample from the subject; and (b) screening the sample to determine whether the subject has a somatic KRAS and PIK3CA mutations.

In the present invention, biological samples include, but are not limited to, blood, plasma, urine, skin, saliva, and biopsies. Biological samples are obtained from a subject by routine procedures and methods which are known in the art.

In this embodiment, the screening comprises detection of at least one of the KRAS and PIK3CA mutations using a method as disclosed herein. Preferably the screening method is selectee from PCR, sequencing, hybrid capture, in-solution capture, MIP, and combinations thereof. Other preferred methods include FISH, Sanger sequencing, deep sequencing, and combinations thereof.

In another aspect of this embodiment, the method further comprises administering at least one additional therapeutic agent, preferably an inhibitor of the mTOR pathway, as disclosed herein.

In a further aspect of this embodiment, administration of the first and second anti-cancer agents provides a synergistic effect compared to administration of either anti-cancer agent alone.

An additional embodiment of the present invention is a method for treating or ameliorating the effects of a subject with cancer. The method comprises:

(a) identifying a subject with cancer that is refractory to a therapy selected from the group consisting of RAF inhibitor therapy, MEK inhibitor therapy, and RAF and MEK inhibitor therapy; and (b) administering to the subject identified in step (a) an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof, to treat or ameliorate the effects of the cancer.

RAF inhibitors and MEK inhibitors are as disclosed herein. Suitable and preferred PI3K/Akt inhibitors and subjects are also as set forth above. In this embodiment, the methods may be used to treat the cancers disclosed above, including those cancers with the mutational backgrounds identified above. Methods of identifying such mutations are also as set forth above.

In one aspect of this embodiment, identifying a subject with cancer that is refractory to a therapy selected from the group consisting of RAF inhibitor therapy, MEK inhibitor therapy, and RAF and MEK inhibitor therapy comprises:

(a) obtaining a biological sample from the subject; and (b) screening the sample to determine whether the subject has a somatic BRAF mutation.

In this embodiment, the screening comprises detection of a somatic BRAF mutation using a method as disclosed herein. Preferably, the screening method is selected from PCR, sequencing, hybrid capture, in-solution capture, MIP, and combinations thereof. Other preferred screening methods include FISH, Sanger sequencing, deep sequencing, and combinations thereof. The following Table 3 shows the SEQ ID Nos. of representative nucleic acid and amino acid sequences of wild type BRAF from various animal sources the sequence listing. These sequences may be used in methods for identifying subjects with a mutant BRAF genotype (such as in the methods disclosed herein).

TABLE 3

B-RAF sequences

| SEQ ID No. | polypeptide or nucleic acid sequence | Organism | Other Information |
|---|---|---|---|
| 48 | nucleic acid | human | |
| 49 | polypeptide | human | |
| 50 | nucleic acid | rat (*Rattus norvegicus*) | |
| 51 | polypeptide | rat (*Rattus norvegicus*) | |
| 52 | nucleic acid | mouse, *Mus musculus* | |
| 53 | polypeptide | mouse, *Mus musculus* | |
| 54 | nucleic acid | rabbit, *Oryctolagus cuniculus* | |
| 55 | polypeptide | rabbit, *Oryctolagus cuniculus* | |
| 56 | nucleic acid | guinea pig, *Cavia porcellus* | |
| 57 | polypeptide | guinea pig, *Cavia porcellus* | |
| 58 | nucleic acid | dog, *Canis lupus familiaris* | variant x1 |
| 59 | polypeptide | dog, *Canis lupus familiaris* | variant x1 |
| 60 | nucleic acid | dog, *Canis lupus familiaris* | variant x2 |
| 61 | polypeptide | dog, *Canis lupus familiaris* | variant x2 |
| 62 | nucleic acid | cat, *Felis catus* | |
| 63 | polypeptide | cat, *Felis catus* | |
| 64 | nucleic acid | cow, *Bos taurus* | variant X1 |
| 65 | polypeptide | cow, *Bos taurus* | variant X1 |
| 66 | nucleic acid | cow, *Bos taurus* | variant X2 |
| 67 | polypeptide | cow, *Bos taurus* | variant X2 |
| 68 | nucleic acid | cow, *Bos taurus* | variant X3 |
| 69 | polypeptide | cow, *Bos taurus* | variant X3 |
| 70 | nucleic acid | cow, *Bos taurus* | variant X4 |
| 71 | polypeptide | cow, *Bos taurus* | variant X4 |
| 72 | nucleic acid | cow, *Bos taurus* | variant X5 |
| 73 | polypeptide | cow, *Bos taurus* | variant X5 |
| 74 | nucleic acid | cow, *Bos taurus* | variant X6 |
| 75 | polypeptide | cow, *Bos taurus* | variant X6 |
| 76 | nucleic acid | cow, *Bos taurus* | variant X7 |
| 77 | polypeptide | cow, *Bos taurus* | variant X7 |
| 78 | nucleic acid | cow, *Bos taurus* | variant X8 |
| 79 | polypeptide | cow, *Bos taurus* | variant X8 |
| 80 | nucleic acid | cow, *Bos taurus* | variant X9 |
| 81 | polypeptide | cow, *Bos taurus* | variant X9 |
| 82 | nucleic acid | cow, *Bos taurus* | variant X10 |
| 83 | polypeptide | cow, *Bos taurus* | variant X10 |
| 84 | nucleic acid | cow, *Bos taurus* | variant X11 |
| 85 | polypeptide | cow, *Bos taurus* | variant X11 |
| 86 | nucleic acid | cow, *Bos taurus* | variant 2 |
| 87 | polypeptide | cow, *Bos taurus* | variant 2 |
| 88 | nucleic acid | horse, *Equus caballus* | |
| 89 | polypeptide | horse, *Equus caballus* | |
| 90 | nucleic acid | chicken, *Gallus gallus* | |
| 91 | polypeptide | chicken, *Gallus gallus* | |

In another aspect of this embodiment, the method further comprises administering at least one additional therapeutic agent, preferably an inhibitor of the mTOR pathway, as disclosed herein.

In another aspect of this embodiment, administration of the first and second anti-cancer agents provides a synergistic effect compared to administration of either anti-cancer agent alone.

Another embodiment of the present invention is a pharmaceutical composition for treating or ameliorating the effects of a cancer in a subject in need thereof. The pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof, wherein administration of the first and second anti-cancer agents provides a synergistic effect compared to administration of either anti-cancer agent alone.

Suitable and preferred PI3K/Akt inhibitors and subjects are also as set forth above. The pharmaceutical compositions of the invention may be used to treat the cancers disclosed above, including those cancers with the mutational backgrounds identified herein. Methods of identifying such mutations are also as set forth above.

In one aspect of this embodiment, the pharmaceutical composition further comprises at least one additional therapeutic agent, preferably an inhibitor of the mTOR pathway, as disclosed herein.

The pharmaceutical compositions according to the present invention may be in a unit dosage form comprising both anti-cancer agents. In another aspect of this embodiment, the first anti-cancer agent is in a first unit dosage form and the second anti-cancer agent is in a second unit dosage form, separate from the first.

The first and second anti-cancer agents may be co-administered to the subject, either simultaneously or at different times, as deemed most appropriate by a physician. If the first and second anti-cancer agents are administered at different times, for example, by serial administration, the first anti-cancer agent may be administered to the subject before the second anti-cancer agent. Alternatively, the second anti-cancer agent may be administered to the subject before the first anti-cancer agent.

A further embodiment of the present invention is a method of effecting cancer cell death. The method comprises contacting the cancer cell with an effective amount of (i) a first anti-cancer agent, which is BVD-523 or a pharmaceutically acceptable salt thereof and (ii) a second anti-cancer agent, which is a an inhibitor of the PI3K/Akt pathway or a pharmaceutically acceptable salt thereof. In this embodiment, "contacting" means bringing BVD-523, an inhibitor of the PI3K/Akt pathway, and optionally one or more additional therapeutic agents into close proximity to the cancer cells. This may be accomplished using conventional techniques of drug delivery to mammals or in the in vitro situation by, e.g., providing BVD-523, an inhibitor of the PI3K/Akt pathway, and optionally other therapeutic agents to a culture media in which the cancer cells are located.

Suitable and preferred PI3K/Akt inhibitors are also as set forth above. In this embodiment, effecting cancer cell death may be accomplished in cancer cells having various mutational backgrounds and/or that are characterized as disclosed above. Methods of identifying such mutations are also as set forth above.

The methods of this embodiment, which may be carried out in vitro or in vivo, may be used to effect cancer cell death, by e.g., killing cancer cells, in cells of the types of cancer disclosed herein.

In one aspect of this embodiment, the cancer cell is a mammalian cancer cell. Preferably, the mammalian cancer cell is obtained from a mammal selected from the group consisting of humans, primates, farm animals, and domestic animals. More preferably, the mammalian cancer cell is a human cancer cell.

In another aspect of this embodiment, the method further comprises contacting the cancer cell with at least one additional therapeutic agent, preferably an inhibitor of the mTOR pathway, as disclosed herein.

In a further aspect of this embodiment, contacting the cancer cell with the first and second anti-cancer agents provides a synergistic effect compared to contacting with either anti-cancer agent alone.

In the present invention, an "effective amount" or a "therapeutically effective amount" of an anti-cancer agent of the invention including pharmaceutical compositions containing same that are disclosed herein is an amount of such agent or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of an agent or composition according to the invention will be that amount of the agent or composition, which is the lowest dose effective to produce the desired effect. The effective dose of an agent or composition of the present invention may be administered as two, three, four, five, six or more sub-doses, administered separately at appropriate intervals throughout the day.

A suitable, non-limiting example of a dosage of BVD-523, a PI3K/Akt pathway inhibitor, or another anti-cancer agent disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of BVD-523, a PI3K/Akt pathway inhibitor, or another anti-cancer agent disclosed herein may be administered as two, three, four, five, six or more sub-doses, administered separately at appropriate intervals throughout the day.

BVD-523, PI3K/Akt pathway inhibitors, other anti-cancer agents, or pharmaceutical compositions containing same of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, BVD-523, PI3K/Akt pathway inhibitors, other anti-cancer agents, or pharmaceutical compositions containing same of the present invention may be administered in conjunction with other treatments. BVD-523, PI3K/Akt pathway inhibitors, other anti-cancer agents, or the pharmaceutical compositions containing the same of the present invention may be encapsulated or otherwise protected against gastric or other secretions, if desired.

The pharmaceutical compositions of the invention comprise one or more active ingredients, e.g. anti-cancer agents, in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21$^{st}$ Edition, Lippincott Williams and Wilkins, Philadelphia, Pa.).

Pharmaceutically acceptable diluents or carriers are well known in the art (see, e.g., Remington, The Science and Practice of Pharmacy (21$^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluents or carriers used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The present invention provides combinations shown to enhance the effects of ERK inhibitors. Herein, applicants have also shown that the combination of different ERK inhibitors is likewise synergistic. Therefore, it is contemplated that the effects of the combinations described herein can be further improved by the use of one or more additional ERK inhibitors. Accordingly, some embodiments of the present invention include one or more additional ERK inhibitors.

The following examples are provided to further illustrate the methods of the present invention. These examples are illustrative only and are not intended to limit the scope of the invention in any way.

EXAMPLES

Example 1

Materials and Methods for the In Vivo Study

Mice

Female athymic nude mice (Crl:NU(Ncr)-Foxn1$^{nu}$, Charles River) were eight weeks old with a body weight (BW) range of 14.6 to 25.7 grams on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fiber. The mice were housed on irradiated Enrich-O'Cobs™ Laboratory Animal Bedding in static microisolators on a 12-hour light cycle at 20-22° C. (68-72° F.) and 40-60% humidity.

Tumor Cell Culture

HCT116 human colon carcinoma cells were cultured in RPMI-1640 medium supplemented with 10% fetal bovine serum, 2 mM glutamine, 100 units/mL penicillin G sodium, 100 μg/mL streptomycin sulfate, and 25 μg/mL gentamicin. The tumor cells were grown in tissue culture flasks in a humidified incubator at 37° C., in an atmosphere of 5% $CO_2$ and 95% air.

In Vivo Implantation and Tumor Growth

The HCT116 cells used for implantation were harvested during exponential growth and resuspended in 50% Matrigel (BD Biosciences): 50% phosphate buffered saline at a concentration of $2.5\times10^7$ cells/mL. On the day of tumor implant, each test mouse was injected subcutaneously in the right flank with $5\times10^6$ cells (0.2 mL cell suspension), and tumor growth was monitored as the average size approached the target range of 100 to 150 mm$^3$. Tumors were measured in two dimensions using calipers, and volume was calculated using the formula:

$$\text{Tumor Volume (mm}^3\text{)}=(w^2\times l)/2$$

where w=width and l=length, in mm, of the tumor. Tumor weight may be estimated with the assumption that 1 mg is equivalent to 1 mm$^3$ of tumor volume.

Ten days after tumor implantation, designated as Day 1 of the study, the animals were sorted into nine groups (Groups 1-9) each consisting of fifteen mice and one group (Group 10) consisting of ten mice. Individual tumor volumes ranged from 88 to 172 mm$^3$ and group mean tumor volumes were 130 or 131 mm$^3$.

Therapeutic Agents

BVD-523 and GDC-0941 were supplied as dry powders and were stored at room temperature.

BVD-523 doses were prepared by suspending the required amount of BVD-523 powder in 1% carboxymethyl cellulose (CMC) in deionized water ("Vehicle"). A 10 mg/mL BVD-523 stock was prepared, and was used to dose the 100 mg/kg BVD-523 group. Aliquots of the stock were diluted with the vehicle to a concentration of 5.0 mg/mL, which provided a 50 mg/kg BVD-523 dosage in a dosing volume of 10 mL/kg. The BVD-523 doses were stored at 4° C. for up to one week. The 1% CMC vehicle was used to dose the control group.

GDC-0941 doses were formulated in 0.5% methylcellulose: 0.2% Tween 80 in deionized water. A 12 mg/mL GDC-0941 stock was prepared, and was used to dose the 120 mg/kg GDC-0941 group. Aliquots of the stock were diluted with the vehicle to a concentration of 6.0 mg/mL to provide the 60 mg/kg GDC-0941 dosage in a dosing volume of 10 mL/kg. The GDC-0941 doses were stored at 4° C. for up to one week.

Paclitaxel (Lot CP2N10007) was purchased as a dry powder from Phyton Biotech, LLC (Fort Worth, Tex.). A paclitaxel stock solution (30 mg/mL) in 50% ethanol: 50% Cremophor EL was prepared and stored at room temperature protected from light during the dosing period. On each day of dosing, an aliquot of the paclitaxel stock was diluted with 5% dextrose in water (D5W) to yield a 3.0 mg/mL paclitaxel dosing solution in a vehicle consisting of 5% ethanol: 5% Cremophor EL: 90% D5W.

Treatment

On Day 1 of the study, mice were sorted into nine groups (Group 1-9) each consisting of fifteen mice and one group (Group 10) consisting of ten mice, and dosing was initiated according to the treatment plan summarized in Table 4 below. All doses were given by oral gavage (p.o.) except paclitaxel, which was given i.v. For each agent, the dosing volume of 10 mL/kg (0.2 mL per 20 grams of BW) was scaled to the BW of the individual animal. The GDC-0941 doses were to be given once daily (qd) until study end (qd to end), whereas the vehicle and BVD-523 doses were to be given twice daily (bid) until study end (bid to end). For bid dosing, dosing was initiated in the afternoon of Day 1, so that one dose was given on the first day ("first day 1 dose"). Due to toxicity, dosing in the 100 mg/kg BVD-523 combination groups was modified during the study, as described below.

Controls

Group 1 received 1% CMC vehicle p.o. bid to end, and served as the control group for calculation of % TGD. Group 10 received paclitaxel i.v. at 30 mg/kg once every other day (qod) for five doses (qodx5), and served as the positive control for the model.

Monotherapy Treatments

Groups 2 and 3 received 60 and 120 mg/kg GDC-0941, respectively, p.o. qd to end. Groups 4 and 5 received 50 and 100 mg/kg BVD-523, respectively, p.o. bid to end.

Combination Treatments

Groups 6 and 7 received the combinations of 50 mg/kg BVD-523 with 60 or 120 mg/kg GDC-0941, respectively. Groups 8 and 9 were scheduled to receive the combinations of 100 mg/kg BVD-523 with 60 or 120 mg/kg GDC-0941, respectively. However, due to emerging toxicity, dosing in Group 9 was ended on Day 29 and a dosing holiday was given on Days 31 and 32 in Group 8. The final dosing schedules are shown in Table 5.

Endpoint and Tumor Growth Delay (TGD) Analysis

Tumors were measured using calipers twice per week, and each animal was euthanized when its tumor reached the pre-determined tumor volume endpoint of 2000 mm$^3$ or on the final day, whichever came first. Animals that exited the study for tumor volume endpoint were documented as euthanized for tumor progression (TP), with the date of euthanasia. The time to endpoint (TTE) for analysis was calculated for each mouse by the following equation:

$$TTE=[\log_{10}(\text{endpoint volume})-b]/m$$

where TTE is expressed in days, endpoint volume is expressed in $mm^3$, b is the intercept, and m is the slope of the line obtained by linear regression of a log-transformed tumor growth data set. The data set consists of the first observation that exceeded the endpoint volume used in analysis and the three consecutive observations that immediately preceded the attainment of this endpoint volume. The calculated TTE is usually less than the TP date, the day on which the animal was euthanized for tumor size. Animals with tumors that did not reach the endpoint volume were assigned a TTE value equal to the last day of the study. Any animal classified as having died from NTR (non-treatment-related) causes due to accident (NTRa) or due to unknown etiology (NTRu) were excluded from TTE calculations (and all further analyses). Animals classified as TR (treatment-related) deaths or NTRm (non-treatment-related death due to metastasis) were assigned a TTE value equal to the day of death.

Treatment outcome was evaluated from TGD, defined as the increase in the median TTE in a treatment group compared to the control group:

$$TGD=T-C,$$

expressed in days, or as a percentage of the median TTE of the control group:

$$\%\ TGD=[(T-C)/C]\times 100$$

where:

T=median TTE for a treatment group, and

C=median TTE for the designated control group.

Criteria for Regression Responses

Treatment efficacy may be determined from the incidence and magnitude of regression responses observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 $mm^3$ for one or more of these three measurements. In a CR response, the tumor volume was less than 13.5 $mm^3$ for three consecutive measurements during the course of the study. An animal with a CR response at the termination of the study was additionally classified as a tumor-free survivor (TFS). Animals were monitored for regression responses.

Toxicity

Animals were weighed daily on Days 1-5, then twice per week until completion of the study. The mice were observed frequently for overt signs of any adverse, TR side effects, and clinical signs were recorded when observed. Individual BW loss was monitored as per protocol, and any animal whose weight exceeded the limits for acceptable BW loss was euthanized. Group mean BW loss also was monitored as per protocol. Dosing was to be suspended in any group that exceeded the limits for acceptable mean BW loss. If mean BW recovered, then dosing was to be resumed in that group, but at a lower dosage or less frequent dosing schedule. Acceptable toxicity for the maximum tolerated dose (MTD) was defined as a group mean BW loss of less than 20% during the study and not more than 10% TR deaths. A death was classified as TR if attributable to treatment side effects as evidenced by clinical signs and/or necropsy, or may also be classified as TR if due to unknown causes during the dosing period or within 14 days of the last dose. A death was classified as NTR if there was no evidence that death was related to treatment side effects. NTR deaths may be further characterized based on cause of death. A death was classified as NTRa if it resulted from an accident or human error. A death was classified as NTRm if necropsy indicated that it may have resulted from tumor dissemination by invasion and/or metastasis. A death was classified as NTRu if the cause of death was unknown and there was no available evidence of death related to treatment side effects, metastasis, accident or human error, although death due to treatment side effects cannot be excluded.

Sampling

When available, five mice per group were euthanized by terminal cardiac puncture under carbon dioxide anesthesia at 3, 6, and 12 hours post-final dose, and the full blood volumes were collected. For each sample, the serum was separated and stored frozen at −80° C. until shipment. In addition, the tumors of these mice were harvested and divided into two parts. One part was snap-frozen and stored at −80° C. The other part was fixed for 16 to 24 hours in 10% neutral buffered formalin, and then transferred to 70% ethanol.

Statistical and Graphical Analyses

Prism (GraphPad) for Windows 3.03 was used for graphical presentations and statistical analyses.

The logrank test, which evaluates overall survival experience, was used to analyze the significance of the differences between the TTE values of two groups. Logrank analysis includes the data for all animals in a group except those assessed as NTR deaths. Two-tailed statistical analyses were conducted at significance level P=0.05. The statistical tests were not adjusted for multiple comparisons. Prism summarizes test results as not significant (ns) at $P>0.05$, significant (symbolized by "*") at $0.01<P<0.05$, very significant ("") at $0.001<P\leq 0.01$, and extremely significant ("*") at $P\leq 0.001$. Because tests of statistical significance do not provide an estimate of the magnitude of the difference between groups, all levels of significance were described as either significant or not significant within the text of this example. Groups with regimens above the MTD were not evaluated statistically.

A scatter plot was constructed to show TTE values for individual mice, by group. Group mean tumor volumes were plotted as a function of time. When an animal exited the study due to tumor size, the final tumor volume recorded for the animal was included with the data used to calculate the mean volume at subsequent time points. Error bars (when present) indicate one standard error of the mean (SEM). Tumor growth plots excluded the data for NTR deaths, and were truncated after 50% of the assessable animals in a group had exited the study or after the second TR death in a group, whichever came first. Kaplan-Meir plots show the percentage of animals in each group remaining in the study versus time. The Kaplan-Meier plot and logrank test share the same TTE data sets. Percent mean BW changes from Day 1 were calculated for each group for each day of BW measurement, and were plotted as a function of time. BW plots excluded the data for NTR deaths, and were truncated after 50% of the assessable animals in a group had exited the study.

Example 2

Results of the In Vivo Study

Groups in the in vivo study were treated in accordance with the modified protocol as set forth in Table 4. The experiment was terminated on Day 45. Table 5 presents a summary of the treatment responses for each group.

TABLE 4

Protocol Design for the HCT116-e399 Study.

| | | Treatment Regimen 1 | | | | Treatment Regimen 2 | | | |
|---|---|---|---|---|---|---|---|---|---|
| Group | n | Agent | mg/kg | Route | Schedule | Agent | mg/kg | Route | Schedule |
| 1 | 15 | Vehicle | — | po | bid to end first day 1 dose | — | — | — | — |
| 2 | 15 | GDC-0941 | 60 | po | qd to end | — | — | — | — |
| 3 | 15 | GDC-0941 | 120 | po | qd to end | — | — | — | — |
| 4 | 15 | BVD-523 | 50 | po | bid to end first day 1 dose | — | — | — | — |
| 5 | 15 | BVD-523 | 100 | po | bid to end first day 1 dose | — | — | — | — |
| 6 | 15 | BVD-523 | 50 | po | bid to end first day 1 dose | GDC-0941 | 60 | po | qd to end |
| 7 | 15 | BVD-523 | 50 | po | bid to end first day 1 dose | GDC-0941 | 120 | po | qd to end |
| 8 | 15 | BVD-523 | 100 | po | bid to end first day 1 dose[a] | GDC-0941 | 60 | po | qd to end[a] |
| 9 | 15 | BVD-523 | 100 | po | bid to end first day 1 dose[b] | GDC-0941 | 120 | po | qd to end[b] |
| 10 | 10 | Paclitaxel | 30 | iv | qod x 5 | — | — | — | — |

Vehicle = 1% CMC in deionized water

Note:

All bid doses were started on the afternoon of the first day of dosing, so a single dose was given on the first and last days ("bid first 1 day dose").

[a]Group 8 dosing holiday on Days 31-32. Final BVD-523 schedule = bid x 30 first day 1 dose/2/bid to end first day 1 dose, and GDC-0941 schedule = 31/1/qd to end.

[b]Group 9 dosing ended on Day 29. Final BVD-523 schedule = bid x28 first day 1 dose, and GDC-0941 schedule = qd x 29

TABLE 5

Response Summary in the HCT116-e399 Study

| | | Treatment Regimen | | | | Median | | | Statistical Significance | | | | MTV (n) | Regressions | | | Mean BW | Deaths | |
|---|---|---|---|---|---|---|---|---|---|---|---|---|---|---|---|---|---|---|---|
| Group | n | Agent | mg/kg | Route | Schedule | TTE | T − C | % TGD | vsG1 | vsG2 | vsG3 | vsG4 | D 45 | PR | CR | TFS | Nadir | TR | NTR |
| 1 | 15 | Vehicle | — | po | bid to end | 32.7 | — | — | — | — | — | — | — | 0 | 0 | 0 | — | 0 | 0 |
| 2 | 15 | GDC-0941 | 60 | po | qd to end | 35.3 | 2.6 | 8 | ns | — | — | — | 1568 (1) | 0 | 0 | 0 | — | 0 | 0 |
| 3 | 15 | GDC-0941 | 120 | po | qd to end | 39.0 | 6.3 | 19 | ** | — | — | — | 1857 (2) | 0 | 0 | 0 | — | 0 | 0 |
| 4 | 15 | BVD-523 | 50 | po | bid to end | 43.5 | 10.8 | 33 | *** | — | — | — | 1666 (5) | 0 | 0 | 0 | — | 0 | 0 |
| 5 | 15 | BVD-523 | 100 | po | bid to end | 45.0 | 12.3 | 38 | ne | — | — | — | 405 (11) | 0 | 0 | 0 | — | 4 | 0 |
| 6 | 15 | BVD-523 | 50 | po | bid to end | 45.0 | 12.3 | 38 | *** | *** | — | ns | 1226 (10) | 0 | 0 | 0 | — | 0 | 0 |
| | | GDC-0941 | 60 | po | qd to end | | | | | | | | | | | | | | |
| 7 | 15 | BVD-523 | 50 | po | bid to end | 45.0 | 12.3 | 38 | *** | — | *** | *** | 1268 (14) | 0 | 0 | 0 | — | 0 | 0 |
| | | GDC-0941 | 120 | po | qd to end | | | | | | | | | | | | | | |
| 8 | 15 | BVD-523 | 100 | po | bid x 30/2/bid to end | 45.0 | 12.3 | 38 | ne | — | — | — | 363 (10) | 0 | 0 | 0 | −6.7% Day 45 | 5 | 0 |
| | | GDC-0941 | 60 | po | 31/1/qd to end | | | | | | | | | | | | | | |

TABLE 5-continued

Response Summary in the HCT116-e399 Study

| | | Treatment Regimen | | | | Median | | | Statistical Significance | | | | MTV (n) | Regressions | | | Mean BW | Deaths | |
|---|---|---|---|---|---|---|---|---|---|---|---|---|---|---|---|---|---|---|---|
| Group | n | Agent | mg/kg | Route | Schedule | TTE | T − C | % TGD | vsG1 | vsG2 | vsG3 | vsG4 | D 45 | PR | CR | TFS | Nadir | TR | NTR |
| 9 | 14 | BVD-523 | 100 | po | bid x 28 | 30.0 | — | — | ne | — | — | — | 1492 (2) | 0 | 0 | 0 | | 12 | 1 |
| | | GDC-0941 | 120 | po | qd x 29 | | | | | | | | | | | | | | |
| 10 | 10 | Paclitaxel | 30 | iv | qod x 5 | 45.0 | 12.3 | 38 | *** | — | — | — | 688 (10) | 8 | 0 | 0 | −8.7% Day 11 | 0 | 0 |

Figure 3:
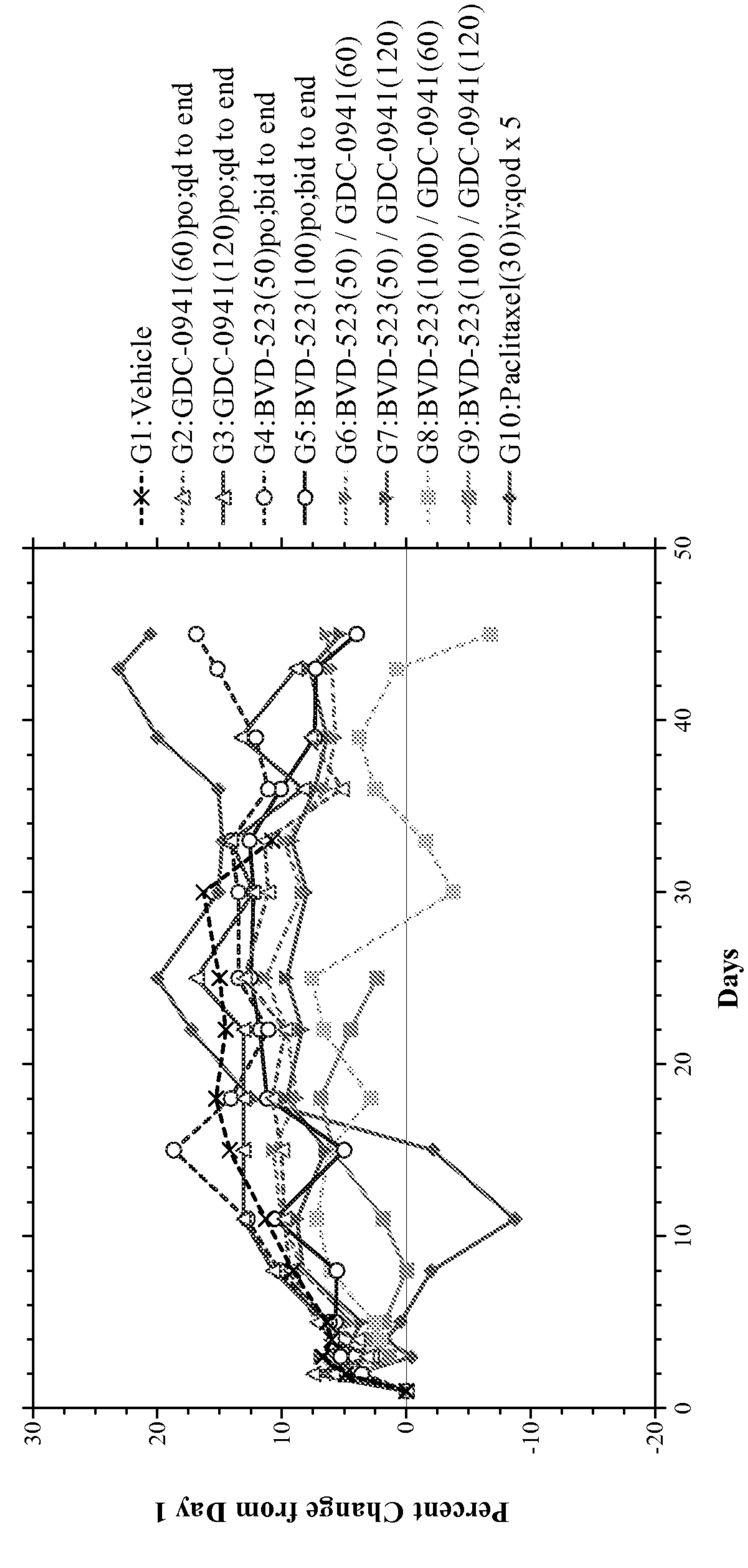
FIG. 3 is a line graph showing percent mean body weight (BW) changes from day 1 in the in vivo study.

Study Endpoint = 2000 $mm^3$; Study Duration = 45 Days.
n = number of animals in a group not dead from accidental or unknown causes (NTR deaths excluded from TGD calculations).
Vehicle = 1% CMC in deionized water.
Note:
All bid doses were started on the afternoon of the first day of dosing, so a single dose was given on the first and last days. Group 8 received a dosing holiday on Days 31-32 due to toxicity. Group 9 dosing was ended on Day 29 due to toxicity.
TTE = time to endpoint, T − C = difference between median TTE (days) of treated versus control group, % TGD = [(T − C)/C] × 100. The maximum T − C in this study is 12.3 days (38%), compared to Group 1.
Statistical Significance (Logrank test):
ne = not evaluated (above MTD),
ns = not significant,
* = P ≤ 0.05,
** = P ≤ 0.01,
*** = P ≤ 0.001, compared to group indicated.
MTV (n) = median tumor volume ($mm^3$) for the number of animals on the day of TGD analysis (excludes animals attaining tumor volume endpoint).
PR = partial regressions; CR = total number complete regressions; TFS = tumor free survivors, i.e. CRs at end of study.
Mean BW Nadir = lowest group mean body weight, as % change from Day 1;
"—" indicates no decrease in mean body weight was observed.
TR = treatment-related death;
NTR = non-treatment-related death FIG. 1 is a scatter plot showing the individual TTEs for each group. FIG. 2 presents plots of mean tumor growth (2A) and Kaplan-Meier survival (2B) for each group in the study. FIG. 3 presents plots of percent mean BW changes from Day 1 for each group. Table 6 below shows the clinical observations and study events recorded during the study.

TABLE 6

HCT116-e399 Clinical Observations & Study Events

| Group | Animals | Date | Day | Clinical Observations & Study Events |
|---|---|---|---|---|
| 2 | 6, 8 | Jun. 3, 2013 | 36 | Tumor ulcerated/cannibalized. (LR) |
| 3 | 5 | May 28, 2013 | 30 | Found on cage top; dehydrated, but active. (JCH) |
| 3 | 10, 11, 3, 4, 9 | Jun. 3, 2013 | 36 | Tumore ulcerated/cannibalized. (LR) |
| 4 | 13 | Apr. 30, 2013 | 2 | Day 2 body weight carried over from Day 1 |
| 4 | 11, 3, 5 | Jun. 3, 2013 | 36 | Tumor ulcerated. (LR) |
| 4 | 7, 8 | Jun. 10, 2013 | 43 | Tumor ulcerated. (LR) |
| 5 | 6 | Jun. 3, 2013 | 36 | Tumor ulcerated. (LR) |
| 5 | 5 | Jun. 9, 2013 | 42 | Found dead; beyond necropsy; TR by definition. (AR) |
| 5 | 6 | Jun. 10, 2013 | 43 | Found dead; beyond necropsy; TR. (LP) |
| 5 | 14 | Jun. 10, 2013 | 43 | Tumor ulcerated (LR) |
| 5 | 3, 4 | Jun. 10, 2013 | 43 | Cool to the touch; slightly dehydrated. (KAS) |
| 5 | 3 | Jun. 11, 2013 | 44 | Found dead; necropsy: impacted stomach, no evidence of gavage error; TR by definition (ER) |
| 5 | 4 | Jun. 12, 2013 | 45 | Found dead; TR by definition (LR) |
| 6 | 7 | Jun. 3, 2013 | 36 | Tumor ulcerated. (LR) |
| 7 | 13, 6 | Jun. 3, 2013 | 36 | Tumor ulcerated. (LR) |
| 8 | 14, 15 | May 29, 2013 | 31 | Found dead; beyond necropsy; TR by definition. (LR) |
| 8 | All | May 29, 2013 | 31 | Stop dosing per PM. (AHR) EDC dosing stopped (AHR) |
| 8 | 10, 3 | May 30, 2013 | 32 | Found dead; beyond necropsy; TR by definition. (LR) |
| 8 | All | May 31, 2013 | 33 | Resume dosing per PM. (LR) EDC dosing resumed (LR). |

TABLE 6-continued

| HCT116-e399 Clinical Observations & Study Events | | | | |
|---|---|---|---|---|
| Group | Animals | Date | Day | Clinical Observations & Study Events |
| 8 | 9 | Jun. 3, 2013 | 36 | Cool to the touch. (LR) |
| 8 | 7 | Jun. 11, 2013 | 44 | Cold to the touch; lethargic. (CS) Found dead; necropsy: impacted large stomach, autolyzed intestines, no evidence of gavage error; TR by definition. (ER) |
| 9 | 10 | May 24, 2013 | 26 | Found dead; beyond necropsy; unable to check for gavage error; NTRu (non-treatment-related (death) of unknown causes or etiology). (LR) |
| 9 | 12 | May 26, 2013 | 28 | Found dead; beyond necropsy; unable to check for gavage error; TR by definition. (AJW) |
| 9 | 4 | May 27, 2013 | 29 | Found dead; negative for gavage error; all other organs appear normal; TR. (KST) |

The clinical observations included occasional notes of tumor ulceration, known to occur in the absence of treatment. The ulcerated tumors were deemed not to impact overall interpretation of activity, and therefore, all mice with ulcerated tumors were included in the data set for analysis. The detailed results of statistical analyses are located in Tables 7 and 8.

TABLE 7

| Statistical Analysis | | | | | | | |
|---|---|---|---|---|---|---|---|
| | Groups Compared | | | | | | |
| | Vehicle(—) (po)bid to end Group 1 vs 2 MR228(60) (po)qd to end | Vehicle(—) (po)bid to end Group 1 vs 3 MR228(120) (po)qd to end | Vehicle(—) (po)bid to end Group 1 vs 4 MR216(50) (po)bid to end | Vehicle(—) (po)bid to end Group 1 vs 5 MR216(100) (po)bid to end | Vehicle(—) (po)bid to end Group 1 vs 6 MR216(50) (po)bid to end/ MR228(60) (po)qd to end | Vehicle(—) (po)bid to end Group 1 vs 7 MR216(50) (po)bid to end/ MR228(120) (po)qd to end | Vehicle(—) (po)bid to end Group 1 vs 8 MR216(100) (po)bid x 30/2/bid to end/ MR228(60) (po)31/1/qd to end |
| Logrank test | | | | | | | |
| Chi square | 2.635 | 7.162 | 21.86 | Not Evaluated (Above MTD) | 28.49 | 31.3 | Not Evaluated (Above MTD) |
| Df | 1 | 1 | 1 | | 1 | 1 | |
| P value | 0.1045 | 0.0074 | P < 0.0001 | | P < 0.0001 | P < 0.0001 | |
| P value summary | ns | ** | *** | | *** | *** | |
| Are survival curves diff.? | No | Yes | Yes | | Yes | Yes | |
| Median survival | | | | | | | |
| Column A | 32.7 | 32.7 | 32.7 | | 32.7 | 32.7 | |
| Column B | 35.3 | 39 | 43.5 | | Undefined | Undefined | |
| Ratio | 0.9263 | 0.8385 | 0.7517 | | | | |
| 95% CI of ratio | 0.4436 to 1.409 | 0.3626 to 1.314 | 0.3025 to 1.201 | | | | |
| Hazard Ratio | | | | | | | |
| Ratio | 1.775 | 2.507 | 4.813 | | 8.443 | 32.65 | |
| 95% CI of ratio | 0.8748 to 4.154 | 1.364 to 7.456 | 4.060 to 30.70 | | 6.347 to 54.19 | 7.700 to 69.58 | |

TABLE 8

| Statistical Analysis | | | | | | |
|---|---|---|---|---|---|---|
| | Groups Compared | | | | | |
| | Vehicle(—) (po)bid to end Group 1 vs 9 MR216(100) (po)bid x28/ MR228(120) (po)qd x29 | Vehicle(—) (po)bid to end Group 1 vs 10 Paclitaxel(30) (iv)qod x 5 | MR228(60) (po)qd to end Group 2 vs 6 MR216(50) (po)bid to end/ MR228(60) (po)qd to end | MR228(120) (po)qd to end Group 3 vs 7 MR216(50) (po)bid to end/ MR228(120) (po)qd to end | MR216(50) (po)bid to end Group 4 vs 6 MR216(50) (po)bid to end/ MR228(60) (po)qd to end | MR216(50) (po)bid to end Group 4 vs 7 MR216(50) (po)bid to end/ MR228(120) (po)qd to end |
| Logrank Test | | | | | | |
| Chi square | Not Evaluated (Above MTD) | 24.03 | 17.43 | 19.75 | 3.17 | 10.91 |
| Df | | 1 | 1 | 1 | 1 | 1 |
| P value | | P < 0.0001 | P < 0.0001 | P < 0.0001 | 0.075 | 0.001 |
| P value summary | | *** | *** | *** | ns | *** |
| Are survival curves diff.? | | Yes | Yes | Yes | No | Yes |
| Median survival | | | | | | |
| Column A | | 32.7 | 35.3 | 39 | 43.5 | 43.5 |
| Column B | | Undefined | Undefined | Undefined | Undefined | Undefined |
| Ratio | | | | | | |
| 95% CI of ratio | | | | | | |
| Hazard Ratio | | | | | | |
| Ratio | | Undefined | 6.205 | 22.41 | 2.546 | 13.73 |
| 95% CI of ratio | | | 3.136 to 23.70 | 4.075 to 37.39 | 0.9103 to 7.088 | 2.287 to 25.55 |

Efficacy

Growth of HCT116 Human Colorectal Carcinomas in Control Mice (Group 1)

Group 1 mice received 1% CMC vehicle p.o. bid to end and served as the control group for analysis of efficacy. All control tumors attained the 2000 $mm^3$ endpoint with a median TTE of 32.7 days, establishing a maximum possible TGD of 12.3 days (38%) for the 45-day study (Table 5). The scatter plot shows a relatively broad but uniform distribution of Group 1 TTEs (FIG. 1). Mean tumor growth for controls was progressive (FIG. 2A).

Response to GDC-0941 as Monotherapy (Groups 2 and 3)

Groups 2 and 3 received GDC-0941 as monotherapy at 60 and 120 mg/kg, respectively, p.o. qd to end. The median TTEs for Groups 2 and 3 were 35.3 and 39.0 days, respectively, corresponding to TGDs of 2.6 days (8%) and 6.3 days (19%), with a significant survival difference only for the 120 mg/kg GDC-0941 group compared to controls (Group 1 vs. 2, P>0.05; Group 1 vs. 3, P<0.01). No regressions were recorded (Table 5). Group 2 had one 45-day survivor, whereas Group 3 had two 45-day survivors, and all other tumors in these groups attained the 2000 $mm^3$ endpoint volume (Table 5). The mean tumor growth plots for Groups 2 and 3 indicated negligible dose-related delays consistent with the TGDs (FIG. 2A).

Response to BVD-523 as Monotherapy (Groups 4 and 5)

Groups 4 and 5 received BVD-523 as monotherapy at 50 and 100 mg/kg, respectively, p.o. bid to end. The median TTEs for Groups 4 and 5 were 43.5 and 45.0 days, respectively, which corresponded to TGD of 10.8 days (33%) for the 50 mg/kg BVD-523 group and the maximum TGD (12.3 days, 38%) for the 100 mg/kg BVD-523 group (Table 5). However, Group 5 had four TR deaths during the final days of the study (Days 42-45), and therefore this regimen was above the MTD and was not evaluated statistically (FIG. 1 and Table 5). Logrank analysis detected a significant survival benefit for the 50 mg/kg BVD-523 treatment (Group 1 vs. 4, P<0.001). No regressions were recorded in either group (Table 5). Group 4 had five 45-day survivors, and all other tumors in this group attained the 2000 $mm^3$ endpoint volume, whereas the eleven Group 5 mice that did not die due to treatment were 45-day survivors (Table 5). The mean tumor growth plots for the 50 and 100 mg/kg BVD-523 groups illustrated dose-related delays (FIG. 2A).

Response to Treatment with BVD-523 Combined with GDC-0941 (Groups 6-9)

Groups 6 and 7 received 50 mg/kg BVD-523 with 60 or 120 mg/kg GDC-0941, respectively, on the planned schedules (Table 5). The median TTEs for Groups 6 and 7 were each 45.0 days, corresponding to the maximum TGD (12.3 days, 38%), with a significant overall survival benefit compared to controls (Group 1 vs. 6 or 7, P<0.001). No regression responses were recorded in either group (Table 5). Group 6 had five tumors that attained the 2000 $mm^3$ endpoint and ten 45-day survivors, whereas fourteen Group 7 mice were 45-day survivors (Table 5). Both combinations produced superior survival to the corresponding GDC-0941 treatment (Group 2 vs. 6 or 3 vs. 7, P<0.001). The Group 7 combination was also superior to the corresponding BVD-523 regimen (Group 4 vs. 6, P>0.05; Group 4 vs. 7, P<0.001). Mean tumor growth for Group 6 was similar to that for the 50 mg/kg BVD-523 monotherapy (Group 4), while mean tumor growth for Group 7 showed greater delay compared to both Groups 3 and 4 (FIG. 2A).

Groups 8 and 9 received 100 mg/kg BVD-523 with 60 or 120 mg/kg GDC-0941, respectively, on schedules modified due to toxicity (Table 5). As indicated in Table 5, Group 8 received a 2-day dosing holiday on Days 31-32, while Group 9 dosing was terminated on Day 29 (Table 5). The median TTE for Group 8 was 45.0 days, corresponding to the maximum TGD (12.3 days, 38%). However, 5/15 TR deaths were recorded (four on Days 31-32 and one on Day 44), and this regimen was above the MTD and was not evaluated statistically (FIG. 1 and Table 5). The other ten Group 8 mice were 45-day survivors. Group 9 had one NTRu death on Day 26 and twelve TR deaths from Days 28-30, and this regimen was also above the MTD and was not evaluated statistically (FIG. 1 and Table 5). The two remaining Group 9 mice were 45-day survivors. The mean tumor growth plots for Groups 8 and 9 were comparable to the plot for Group 5, the 100 mg/kg BVD-523 monotherapy (FIG. 2A).

Response to Paclitaxel Treatment (Group 10)

The paclitaxel treatment resulted in a median TTE of 45.0 days, which corresponded to the maximum TGD (12.3 days, 38%), and a significant overall survival benefit compared to controls (Group 1 vs. 10, P<0.001). Group 10 had 8/10 PR responses, which were the only regressions recorded in the study (Table 5). The mean tumor growth plot for this group indicated noteworthy activity (FIG. 2A).

Side Effects

Table 5 provides a summary of maximum mean BW losses, TR and NTR deaths. FIG. 3 presents plots of percent mean BW changes from Day 1 for each group.

The 60 and 120 mg/kg GDC-0941 groups (Groups 2 and 3) and the 50 mg/kg BVD-523 group (Group 4) had no TR or NTR deaths, no mean BW losses, and no noteworthy adverse clinical signs. Likewise, the two-drug combinations of these regimens (Groups 6 and 7) had no TR or NTR deaths, no mean BW losses, and no noteworthy adverse clinical signs.

The 100 mg/kg BVD-523 group (Group 5) had no mean BW loss, but four Group 5 mice were found dead near study end on Days 42, 43, 44 and 45, respectively. Group 5 had no reported adverse clinical signs until Day 43, when two mice were noted to be dehydrated and cool to the touch (Table 6). The combinations of 100 mg/kg BVD-523 with 60 or 120 mg/kg GDC-0941 (Groups 8 and 9) resulted in five and twelve TR deaths, respectively (Table 5). Group 8 had two TR deaths on Day 31, and a dosing holiday was initiated. Two additional TR deaths were recorded on Day 32. Dosing was resumed on Day 33, with no adverse effects noted until Day 44, when one additional TR death was recorded (Table 6). Group 8 had a mean BW nadir of −6.7% on Day 45 (Table 5). Group 9 had one death due to unknown etiology (NTRu) on Day 26, followed by one TR death on Day 28 and two TR deaths on Day 29, when dosing was ended. Nine additional Group 9 animals were found dead on Day 30, and these deaths were also assessed as TR. Thus, the 100 mg/kg BVD-523 mono- and combination therapies were above the MTD.

The present study also evaluated combinations of BVD-523 with GDC-0941 for efficacy in the HCT116 human colorectal carcinoma xenograft model. BVD-523 was administered p.o. at 50 or 100 mg/kg on a bid schedule and GDC-0941 was given p.o. at 60 or 120 mg/kg on a daily schedule, alone and in combination.

BVD-523 at 100 mg/kg p.o. bid to end, either alone or combined with GDC-0941, was above the MTD. The 100 mg/kg BVD-523 monotherapy was acceptably tolerated until Day 42, when the first of four TR deaths occurred. The 100 mg/kg BVD-523/60 mg/kg GDC-0941 combination had the first death on Day 31, and a total of five TR deaths; whereas the 100 mg/kg BVD-523/120 mg/kg GDC-0941 combination had the first death on Day 26, and a total of twelve TR deaths. Thus, the addition of GDC-0941 shortened the onset of toxicity and increased the extent of toxicity in a dose-related manner. All other regimens in the study were well tolerated, and could be evaluated for efficacy.

The median TTE for controls was 32.7 days, establishing a maximum possible TGD of 12.3 days (38%) for the 45-day study. The paclitaxel positive control treatment resulted in the maximum TGD and eight PRs, consistent with expected activity in this tumor model (DRS-NC internal data).

The 50 mg/kg BVD-523 monotherapy resulted in marginal TGD of 10.8 days (33%), but a significant survival difference versus controls (P<0.001). The 60 and 120 mg/kg GDC-0941 monotherapies produced small dose-related TGDs of 2.6 days (8%) and 6.3 days (19%), and significance versus controls for the higher GDC-0941 dosage (P<0.01). However, GDC-0941 showed negligible delay on the tumor growth plot (FIG. 2A).

The 50 mg/kg BVD-523/60 or 120 mg/kg GDC-0941 combinations each produced the maximum TGD, although they were distinct in the numbers of 45-day survivors (10/15 vs. 14/15). Both regimens were statistically superior to the corresponding GDC-0941 monotherapy, and the 50 mg/kg BVD-523/120 mg/kg GDC-0941 combination was also statistically superior to the 50 mg/kg BVD-523 monotherapy.

In summary, BVD-523 at 50 mg/kg p.o. bid to end was active. GDC-0941 was inactive at 60 mg/kg p.o. qd to end, and negligibly active at 120 mg/kg. BVD-523 at 100 mg/kg p.o. bid to end, alone or combined, was above the maximum tolerated dose (MTD). The combination of 50 mg/kg BVD-523/120 mg/kg GDC-0941 was statistically superior to either monotherapy alone.

Example 3

BVD-523 Altered Markers of MAPK Kinase Activity and Effector Function

For Western blot studies, HCT116 cells ($5\times10^6$) were seeded into 10 cm dishes in McCoy's 5A plus 10% FBS. A375 cells ($2.5\times10^6$) were seeded into 10 cm dishes in DMEM plus 10% FBS. Cells were allowed to adhere overnight prior to addition of the indicated amount of test compound (BVD-523) or vehicle control. Cells were treated for either 4 or 24 hours before isolation of whole-cell protein lysates, as specified below. Cells were harvested by trypsinisation, pelleted and snap frozen. Lysates were prepared with RIPA (Radio-Immunoprecipitation Assay) buffer, clarified by centrifugation and quantitated by bicinchoninic acid assay (BCA) assay. 20-50 μg of protein was resolved by SDS-PAGE electrophoresis, blotted onto PVDF membrane and probed using the antibodies detailed in Table 9 (for the 4-hour treatment) and Table 10 (for the 24-hour treatment) below.

TABLE 9

| Antibody Details | | | | | | |
|---|---|---|---|---|---|---|
| Antigen | Size (kDa) | Supplier | Cat No | Dilution | Incubation/ Block Conditions | Secondary |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| pMEK1/2 | 45 | Cell Signaling | 9154 | 1:1000 | o/n 4° C. 5% BSA | anti-rabbit |
| Total MEK | 45 | Cell Signaling | 9126 | 1:1000 | o/n 4° C. 5% BSA | anti-rabbit |
| pS6-pS235 | 32 | Cell Signaling | 2211S | 1:3000 | o/n 4° C. 5% milk | anti-rabbit |
| Total S6 | 32 | Cell Signaling | 2217 | 1:2000 | o/n 4° C. 5% milk | anti-rabbit |
| DUSP6 | 48 | Cell Signaling | 3058S | 1:1000 | o/n 4° C. 5% BSA | anti-rabbit |
| Total CRAF | 73 | BD Bio-sciences | 610152 | 1:2000 | o/n 4° C. 5% milk | anti-mouse |
| pCRAF-Ser338 | 73 | Cell Signaling | 9427 | 1:1000 | o/n 4° C. 5% BSA | anti-rabbit |
| pRB (Ser780) | 105 | Cell Signaling | 9307 | 1:2000 | o/n 4° C. 5% BSA | anti-rabbit |
| β-Actin | 42 | Sigma | A5441 | 1:500,000 | o/n 4° C. 5% milk | anti-mouse |

TABLE 10

| Antibody details | | | | | | |
|---|---|---|---|---|---|---|
| Antigen | Size (kDa) | Supplier | Cat No | Dilution | Incubation/ Block Conditions | Secondary |
| pRB (Ser780) | 105 | Cell Signaling | 9307 | 1:2000 | o/n 4° C. 5% BSA | anti-rabbit |
| CCND1 | 34 | Abcam | ab6152 | 1:500 | o/n 4° C. 5% milk | anti-mouse |
| Bim-EL | 23 | Millipore | AB17003 | 1:1000 | o/n 4° C. 5% BSA | anti-rabbit |
| Bim-EL | 23 | Cell Signaling | 2933 | 1:1000 | o/n 4° C. 5% BSA | anti-rabbit |
| BCL-xL | 30 | Cell Signaling | 2762 | 1:2000 | o/n 4° C. 5% BSA | anti-rabbit |
| PARP | 116/89 | Cell Signaling | 9542 | 1:1000 | o/n 4° C. 5% milk | anti-rabbit |
| Cleaved Caspase 3 | 17, 19 | Cell Signaling | 9664X | 1:1000 | o/n 4° C. 5% milk | anti-rabbit |
| DUSP6 | 48 | Cell Signaling | 3058S | 1:1000 | o/n 4° C. 5% BSA | anti-rabbit |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| β-Actin | 42 | Sigma | A5441 | 1:500,000 | o/n 4° C. 5% milk | anti-mouse |

Figure 4:
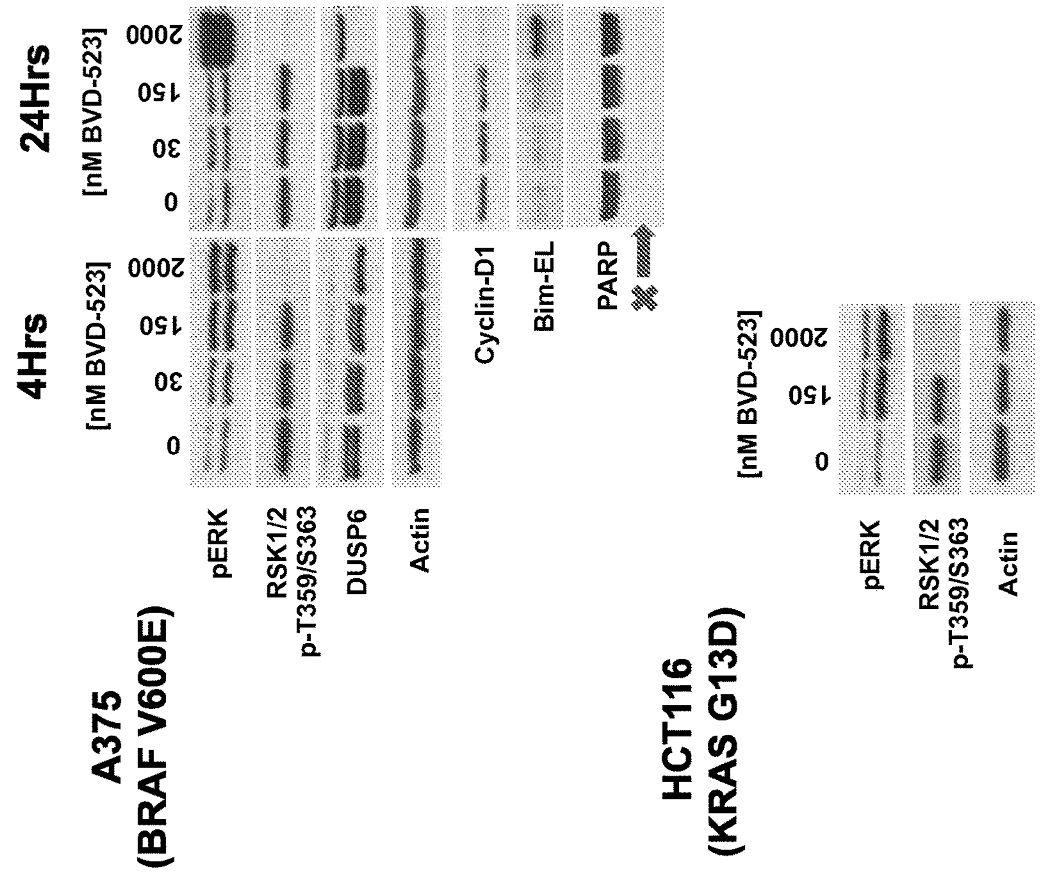
FIG. 4 shows that both direct ERK substrate phosphorylation and known effector pathways are modulated following acute and prolonged treatment with BVD-523 in vitro. Western blots were performed using a variety of antibodies to detect changes in whole-cell lysates of cancer lines exposed to BVD-523. In the A375 BRAF mutant cell line (a human melanoma cell line) and in the HCT116 KRAS mutant cell line (a human colorectal carcinoma cell line), phosphorylation of ERK-dependent residues (T359/S363) in RSK 1 and 2 proteins was reduced after 4 hours of treatment with BVD-523 at micromolar concentrations. Following 24 hours of treatment, direct substrate inhibition was maintained in BRAF mutant cell lines, and the MAPK feedback phosphatase DUSP6 was greatly reduced, suggesting durable and nearly complete MAPK pathway inhibition. Lastly, consistent with cytostatic effects of BVD-523 across multiple cell line backgrounds, the MAPK effector and G1/S-cell-cycle determinant gene cyclin-D1 was greatly reduced after 24 hours of treatment. In the A375 cell line, while the apoptosis effector and ERK substrate Bim-EL was increased following prolonged treatment, increased apoptosis was not observed, consistent with a lack of PARP cleavage, as well as other observations (not shown) that additional factors influence the capacity for BVD-523 to induce cell death.

FIG. 4 shows Western blot analyses of cells treated with BVD-523 at various concentrations for the following: 1) MAPK signaling components in A375 cells after 4 hours; 2) cell cycle and apoptosis signaling in A375 24 hours treatment with various amounts of BVD-523; and 3) MAPK signaling in HCT-116 cells treated for 4 hours. The results show that acute and prolonged treatment with BVD-523 in RAF and RAS mutant cancer cells in-vitro affects both substrate phosphorylation and effector targets of ERK kinases. The concentrations of BVD-523 required to induce these changes is typically in the low micromolar range.

Changes in several specific activity markers are noteworthy. First, the abundance of slowly migrating isoforms of ERK kinase increase following BVD-523 treatment; modest changes can be observed acutely, and increase following prolonged treatment. While this could indicate an increase in enzymatically active, phosphorylated forms of ERK, it remains noteworthy that multiple proteins subject to both direct and indirect regulation by ERK remain "off" following BVD-523 treatment. First, RSK1/2 proteins exhibit reduced phosphorylation at residues that are strictly dependent on ERK for protein modification (T359/S363). Second, BVD-523 treatment induces complex changes in the MAPK feedback phosphatase, DUSP6: slowly migrating protein isoforms are reduced following acute treatment, while total protein levels are greatly reduced following prolonged BVD-523 treatment. Both of these findings are consistent with reduced activity of ERK kinases, which control DUSP6 function through both post-translational and transcriptional mechanisms. Overall, despite increases in cellular forms of ERK that are typically thought to be active, it appears likely that cellular ERK enzyme activity is fully inhibited following either acute or prolonged treatment with BVD-523.

Consistent with these observations, effector genes that require MAPK pathway signaling are altered following treatment with BVD-523. The G1/S cell-cycle apparatus is regulated at both post-translational and transcriptional levels by MAPK signaling, and cyclin-D1 protein levels are greatly reduced following prolonged BVD-523 treatment. Similarly, gene expression and protein abundance of apoptosis effectors often require intact MAPK signaling, and total levels of Bim-EL increase following prolonged BVD-523 treatment. As noted above, however, PARP protein cleavage and increased apoptosis were not noted in the A375 cell background; this suggests that additional factors may influence whether changes in BVD-523/ERK-dependent effector signaling are translated into definitive events such as cell death and cell cycle arrest.

Consistent with the cellular activity of BVD-523, marker analysis suggests that ERK inhibition alters a variety of molecular signaling events in cancer cells, making them susceptible to both decreased cell proliferation and survival.

In sum, FIG. 4 shows that BVD-523 inhibits the MAPK signaling pathway and may be more favorable compared to RAF or MEK inhibition in this setting.

Finally, properties of BVD-523 may make this a preferred agent for use as an ERK inhibitor, compared to other agents with a similar activity. It is known that kinase inhibitor drugs display unique and specific interactions with their enzyme targets, and that drug efficacy is strongly influenced by both the mode of direct inhibition, as well as susceptibility to adaptive changes that occur following treatment. For example, inhibitors of ABL, KIT, EGFR and ALK kinases are effective only when their cognate target is found in active or inactive configurations. Likewise, certain of these inhibitors are uniquely sensitive to either secondary genetic mutation, or post-translational adaptive changes, of the protein target. Finally, RAF inhibitors show differential potency to RAF kinases present in certain protein complexes and/or subcellular localizations. In summary, as ERK kinases are similarly known to exist in diverse, variable, and complex biochemical states, it appears likely that BVD-523 may interact with and inhibit these targets in a fashion that is distinct and highly preferable to other agents.

Example 4

Cell Culture Studies of PI3K-MTOR and ERK Inhibitors

Single Agent Proliferation Assay

Cells were seeded in 96-well plates at the densities and media conditions indicated in Table 11 in McCoy's 5A containing either 10% FBS or 1% charcoal-stripped FBS (CS-FBS), and allowed to adhere overnight prior to addition of compound or vehicle control. Compounds were prepared from DMSO stocks to give the desired final concentrations. The final DMSO concentration was constant at 0.1%. Test compounds were incubated with the cells for 72 h at 37° C., 5% $CO_2$ in a humidified atmosphere. CellTiter-Glo® reagent (Promega, Madison, Wis.) was added according to manufacturer's instructions and luminescence detected using the BMG FLUOstar plate reader (BMG Labtech, Ortenberg, Germany). The average media only background value was deducted and the data analysed using a 4-parameter logistic equation in GraphPad Prism (GraphPad Software, La Jolla, Calif.).

Combination Proliferation Assay

Cells were seeded into triplicate 96-well plates at the densities indicated in Table 11 in McCoy's 5A media containing 2.5% FBS and allowed to adhere overnight prior to addition of test compound or vehicle control. Combinations were tested using either a 10×8 or for the follow-up HCT116 study a 3×1 dose matrix.

Test compounds were incubated with the cells for 72 h at 37° C., 5% $CO_2$ in a humidified atmosphere. CellTiter-Glo® reagent (Promega, Madison, Wis.) was added according to manufacturer's instructions and luminescence detected using the BMG FLUOstar plate reader (BMG Labtech, Ortenberg, Germany). The average media only background value was deducted and the data analysed.

For the 10×8 combination assays the combination interactions across the dose matrix were determined by the Loewe Additivity and Bliss independence models using Chalice™ Combination Analysis Software (Horizon Discovery Group, Cambridge, Mass.) as outlined in the user manual (available at chalice.horizondiscovery.com/chalice-portal/documentation/analyzer/home.jsp). Synergy is determined by comparing the experimentally observed level of inhibition at each combination point with the value expected for additivity, which is derived from the single-agent responses along the edges of the matrix. Potential synergistic interactions were identified by displaying the calculated excess inhibition over that predicted as being additive across the dose matrix as a heat map, and by reporting a quantitative 'Synergy Score' based on the Loewe model. The single agent data derived from the combination assay plates were presented as dose-response curves generated in GraphPad Prism (GraphPad Software, La Jolla, Calif.) (plotted using percentage viability relative to DMSO only treated controls).

The 3×1 combination assay follow-up experiment was analysed using the Bliss additivity model in Microsoft Excel as follows: first, predicted fractional inhibition values for combined inhibition were calculated using the equation $C_{bliss}$=A+B−(A×B) where A and B are the fractional inhibitions obtained by drug A alone or drug B alone at specific concentrations. ($C_{bliss}$ is the fractional inhibition that would be expected if the combination of the two drugs were exactly additive). $C_{bliss}$ values were then subtracted from the experimentally observed fractional inhibition values to give an 'excess over Bliss' value which were plotted as heat maps±SD. Excess of Bliss values greater than 0 indicate synergy, whereas values less than 0 indicate antagonism.

TABLE 11

Cell Line Seeding Density and Growth Media

| Cell Line | Seeding Density in 10% FBS (cells/well) | Seeding Density in 1% CS-FBS (cells/well) | Seeding Density in 2.5% FBS (cells/well) |
|---|---|---|---|
| HCT116 Parental | 1000 | 3000 | 2000 |
| HCT116 PIK3CA (+/−) | 3000 | 4500 | 7500 |
| DLD-1 Parental | — | — | 2000 |
| DLD-1 PIK3CA (+/−) | — | — | 3000 |

The aim of this study was to assess the effects on cell viability of combining ERK inhibitors with a panel of PI3K-MTOR inhibitors (Table 12) in HCT116 and DLD1 cell line pairs that are isogenic for the presence or absence of PIK3CA activating mutations. (Table 13).

TABLE 12

Description of PI3K-MTOR Inhibitors Studied

| Inhibitor | Selectivity |
|---|---|
| BYL719 | PI3K α-slective inhibitor |
| BKM120 | Pan-PI3K (α/β/δ/γ) inhibitor |
| INK128 | mTOR inhibitor |
| PF-04691502 | PI3K/mTOR dual inhibitor |

TABLE 13

Description of Cell Lines Studied

| Cell Line | Description |
|---|---|
| HCT116 Parental | Heterozygous parental cells containing one mutant PIK3CA allele (H1047R) and one wild type allele |
| HCT116 PIK3CA (+/−) | Knock out of mutant KRAS allele in heterozygous parental cells Knock-out of PIK3CA mutant allele (H1047R) in heterozygous parental cells |
| DLD-1 Parental | Heterozygous parental cells containing one mutant PIK3CA allele (E545K) and one wild type allele |
| DLD-1 PIK3CA (+/−) | Knock-out of PIK3CA mutant allele (E545K) in heterozygous parental cells |

Figure 6:
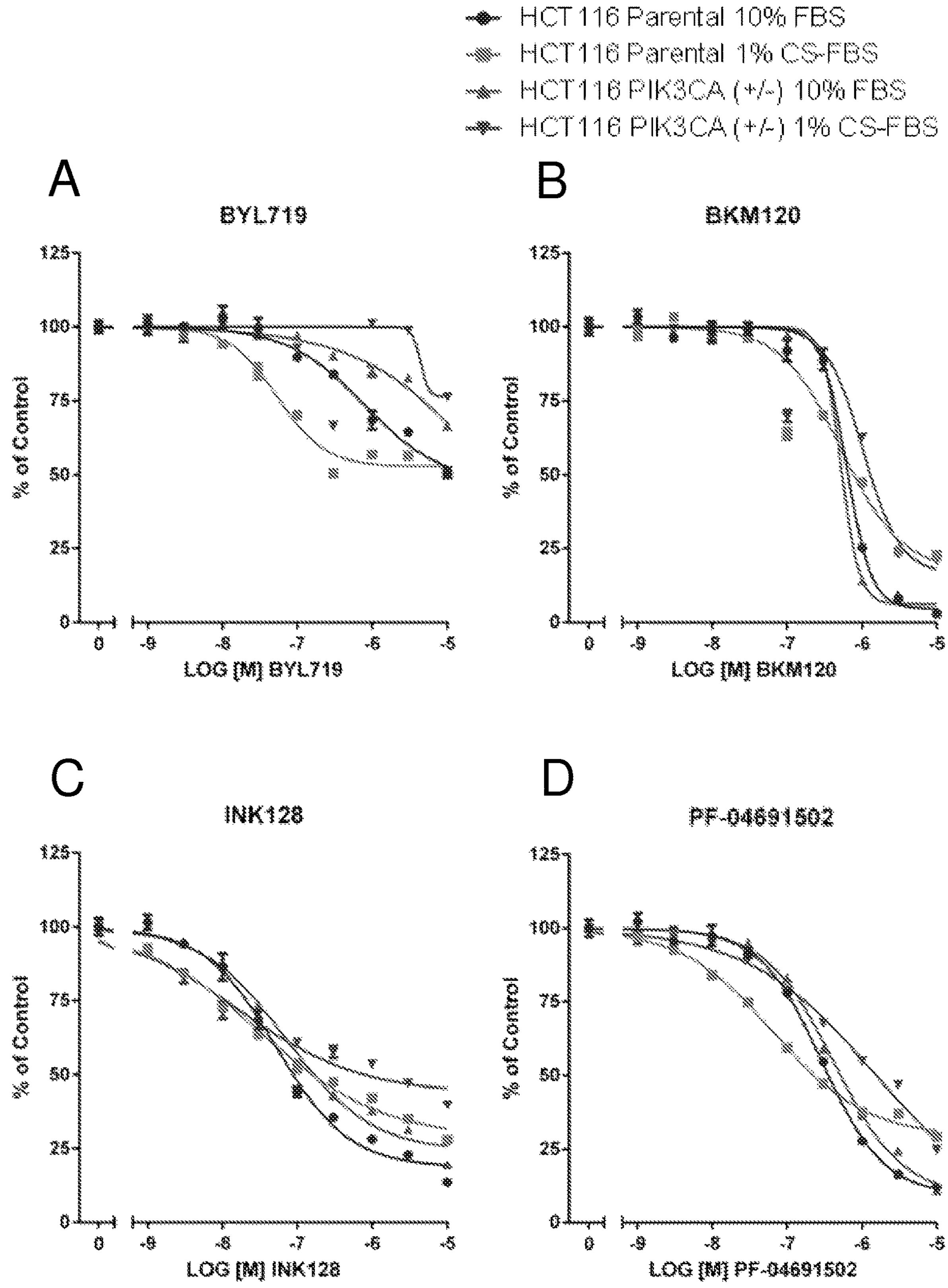
FIG. 6 shows the results of single agent proliferation assays in HCT116 isogenic cells in McCoy's 5A containing either 10% FBS or 1% charcoal-stripped FBS (CS-FBS). Proliferation results are shown for treatment with BYL719 (FIG. 6A), BKM120 (FIG. 6B), INK128 (FIG. 6C), PF-004691502 (FIG. 6D), BVD-523 (FIG. 6E), SCH772984 (FIG. 6F), Paclitaxel (FIG. 6G), and GDC-0941 (FIG. 6H).
Figure 7:
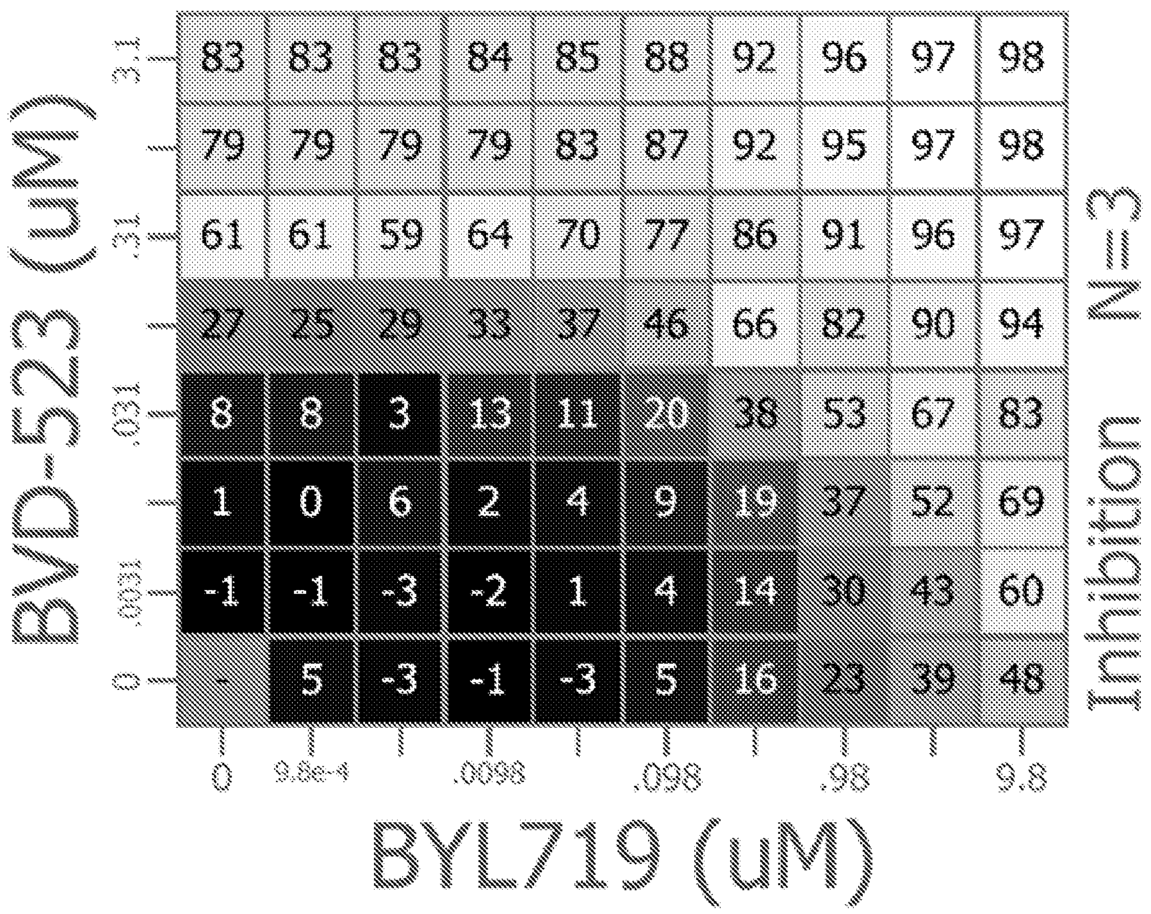
FIG. 7 shows the results of the combination of BVD-523 and BYL719 in parental HCT116 and HCT116 PIK3CA (+/−) cells.
Figure 8:
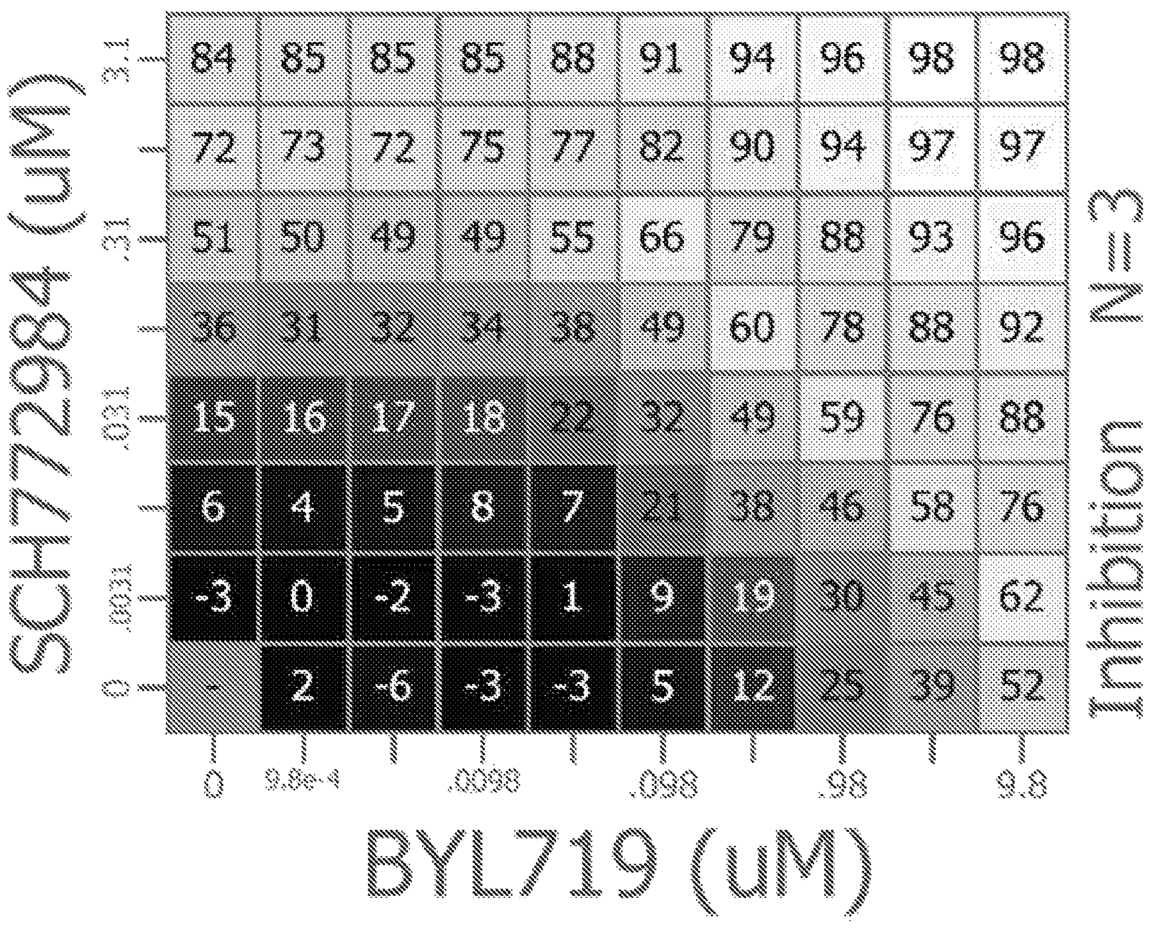
FIG. 8 shows the results of the combination of SCH772984 and BYL719 in parental HCT116 and HCT116 PIK3CA (+/−) cells.
Figure 9:
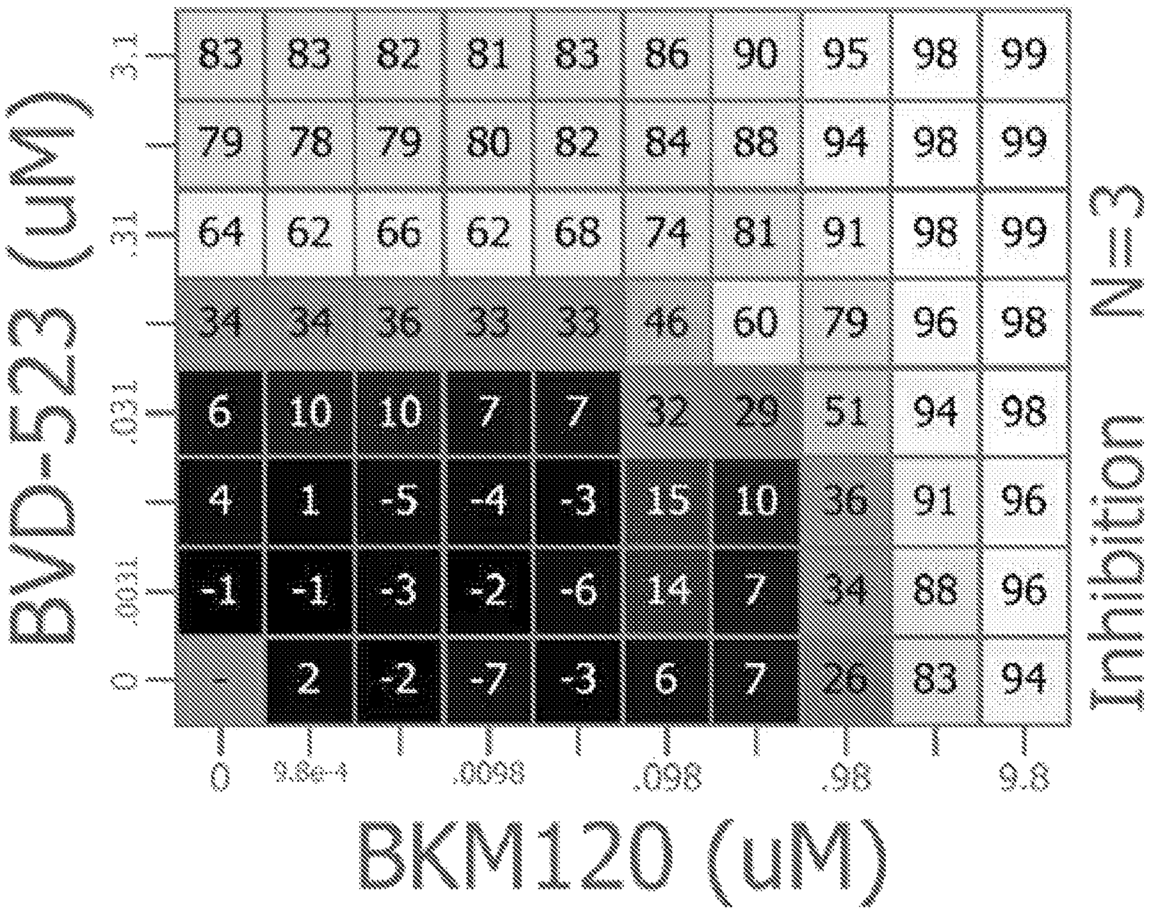
FIG. 9 shows the results of the combination of BVD-523 and BKM120 in parental HCT116 and HCT116 PIK3CA (+/−) cells.
Figure 10:
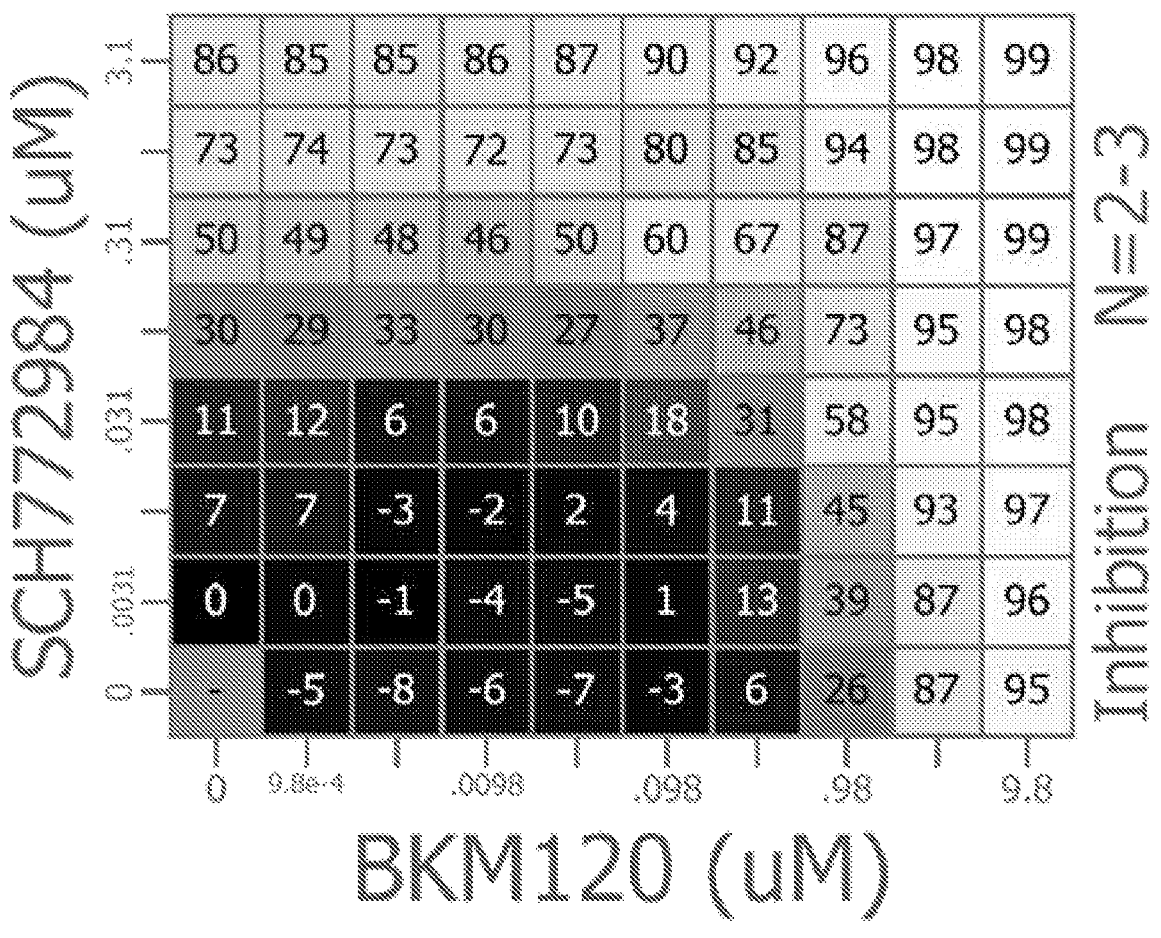
FIG. 10 shows the results of the combination of SCH772984 and BKM120 in parental HCT116 and HCT116 PIK3CA (+/−) cells.
Figure 11:
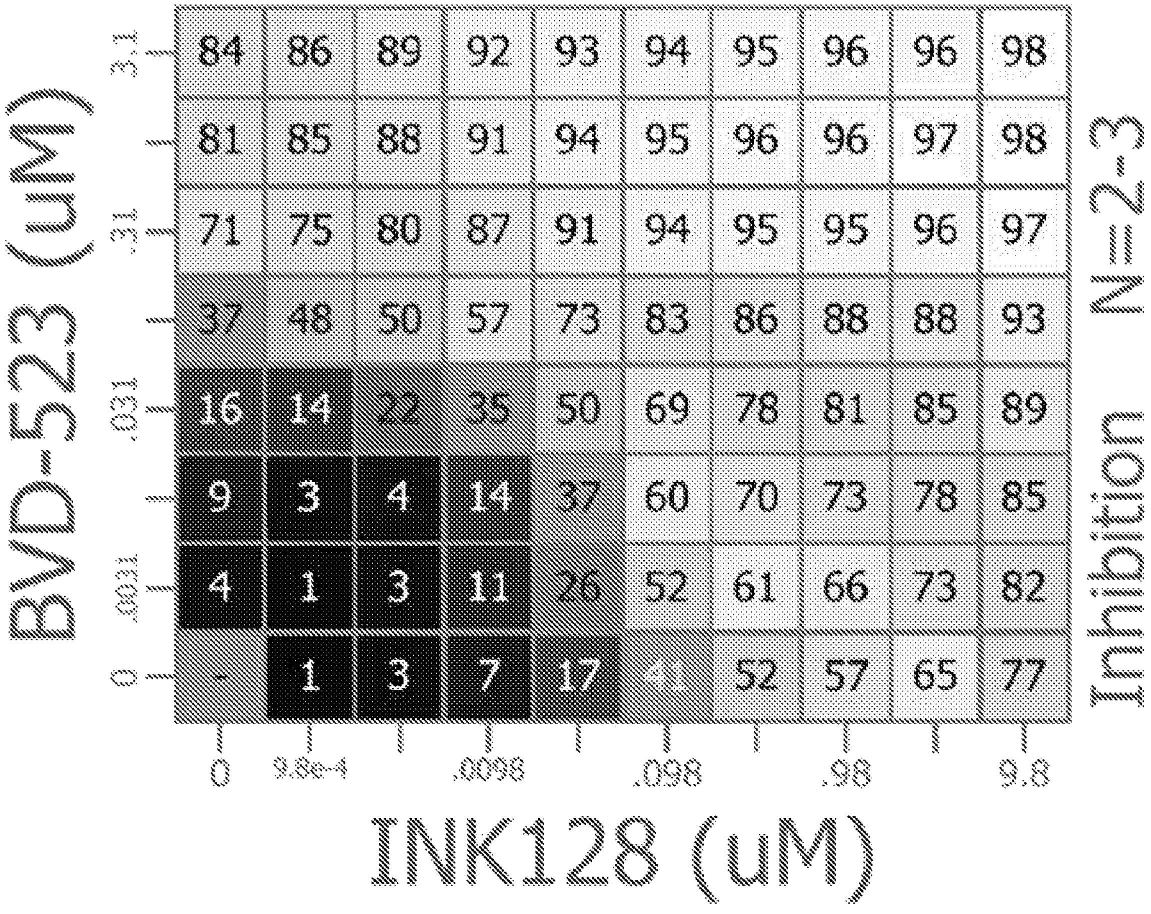
FIG. 11 shows the results of the combination of BVD-523 and INK128 in parental HCT116 and HCT116 PIK3CA (+/−) cells.
Figure 12:
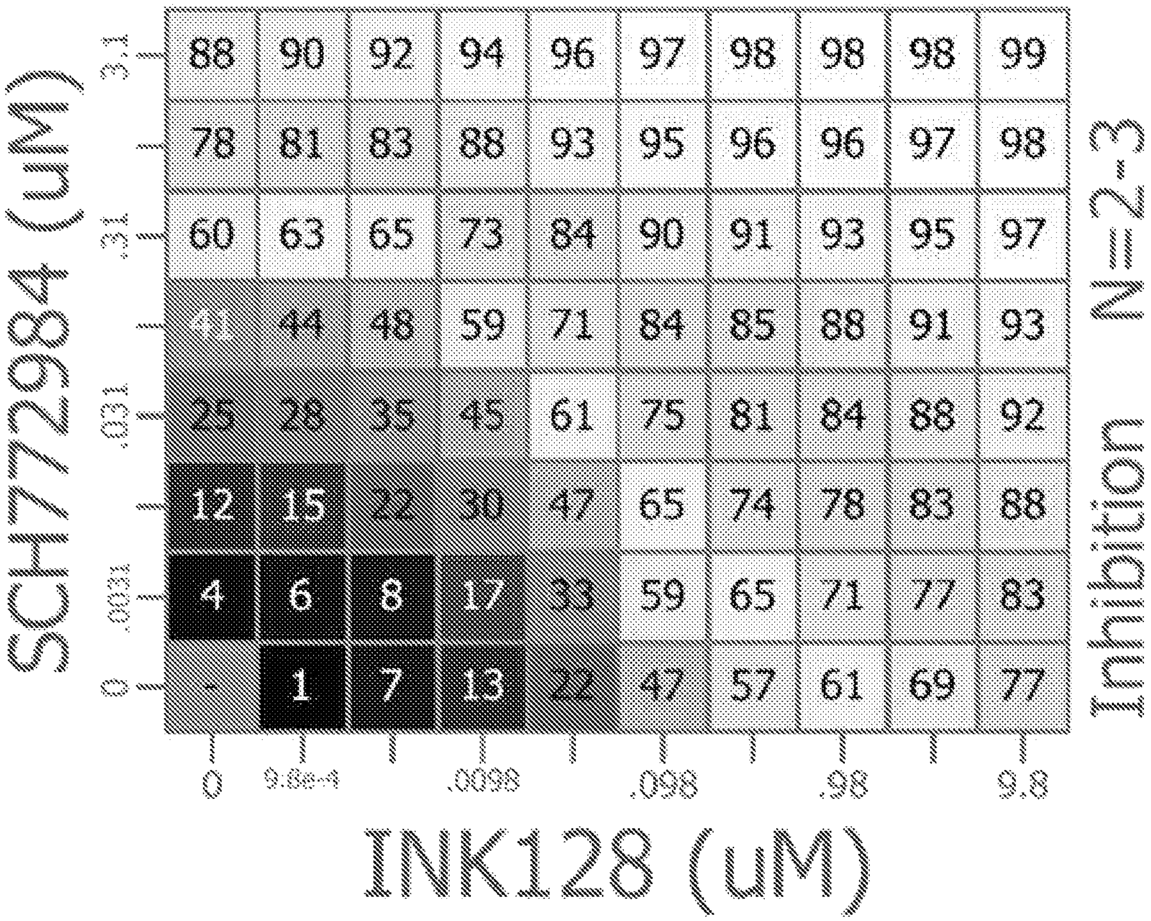
FIG. 12 shows the results of the combination of SCH772984 and INK128 in parental HCT116 and HCT116 PIK3CA (+/−) cells.
Figure 13:
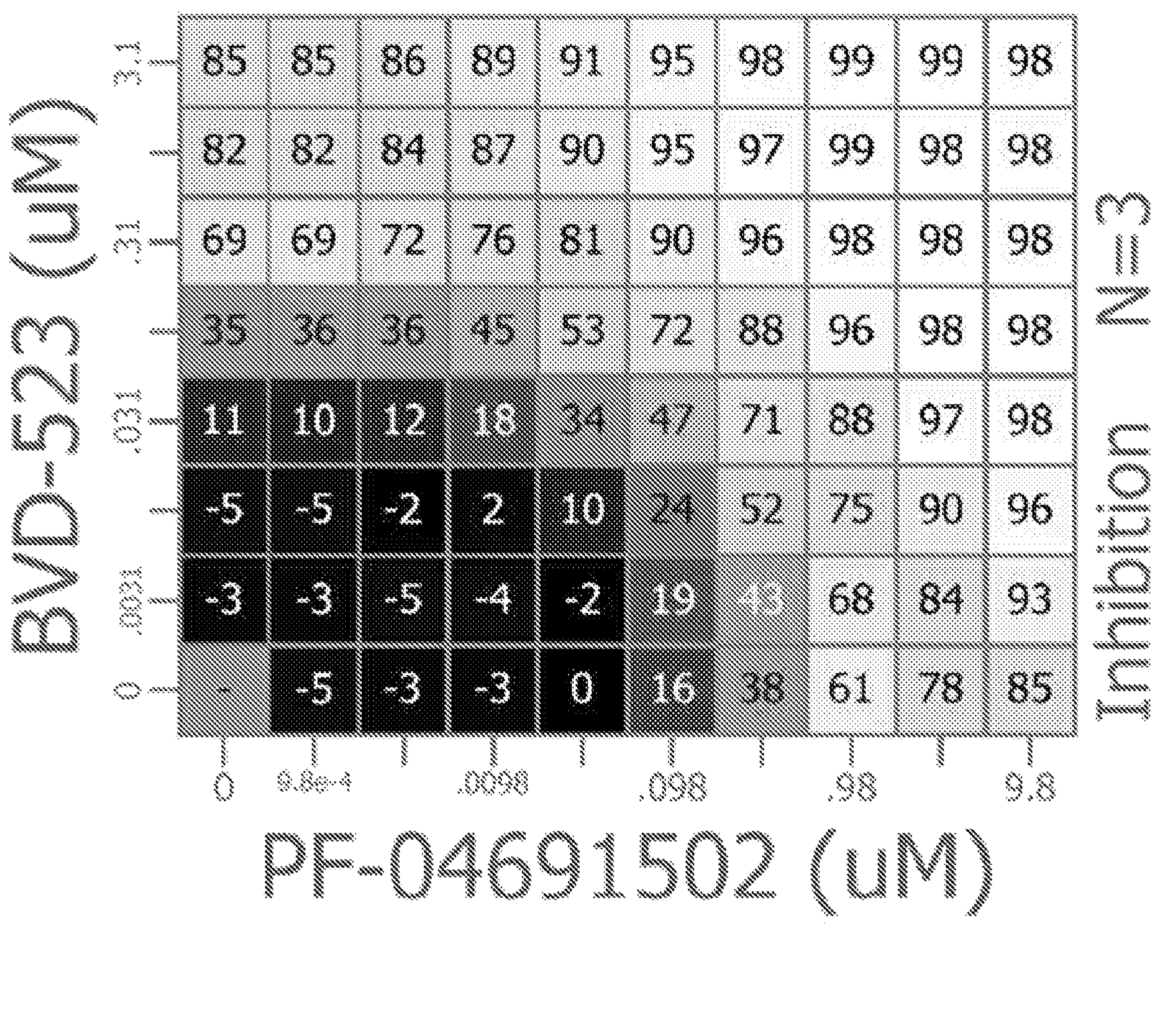
FIG. 13 shows the results of the combination of BVD-523 and PF-004691502 in parental HCT116 and HCT116 PIK3CA (+/−) cells.
Figure 14:
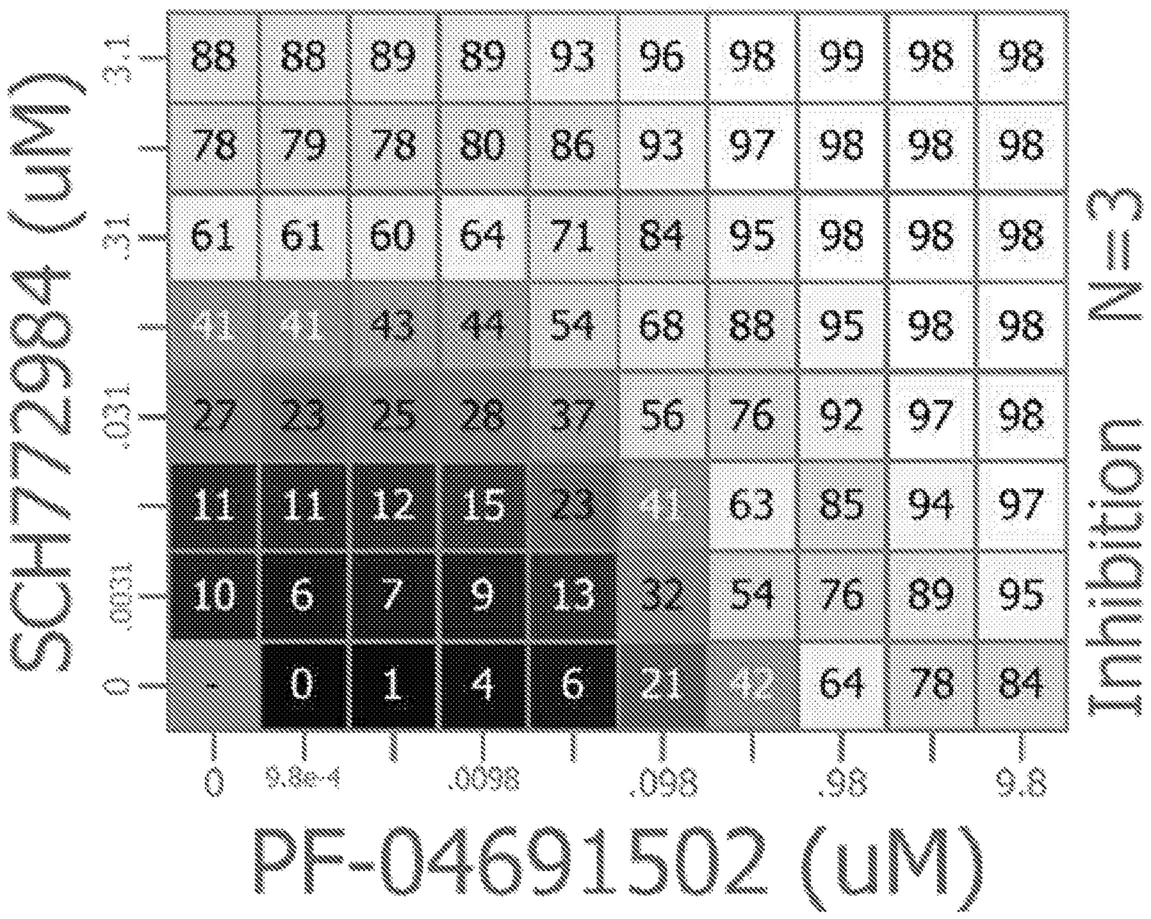
FIG. 14 shows the results of the combination of SCH772984 and PF-004691502 in parental HCT116 and HCT116 PIK3CA (+/−) cells.
Figure 15:
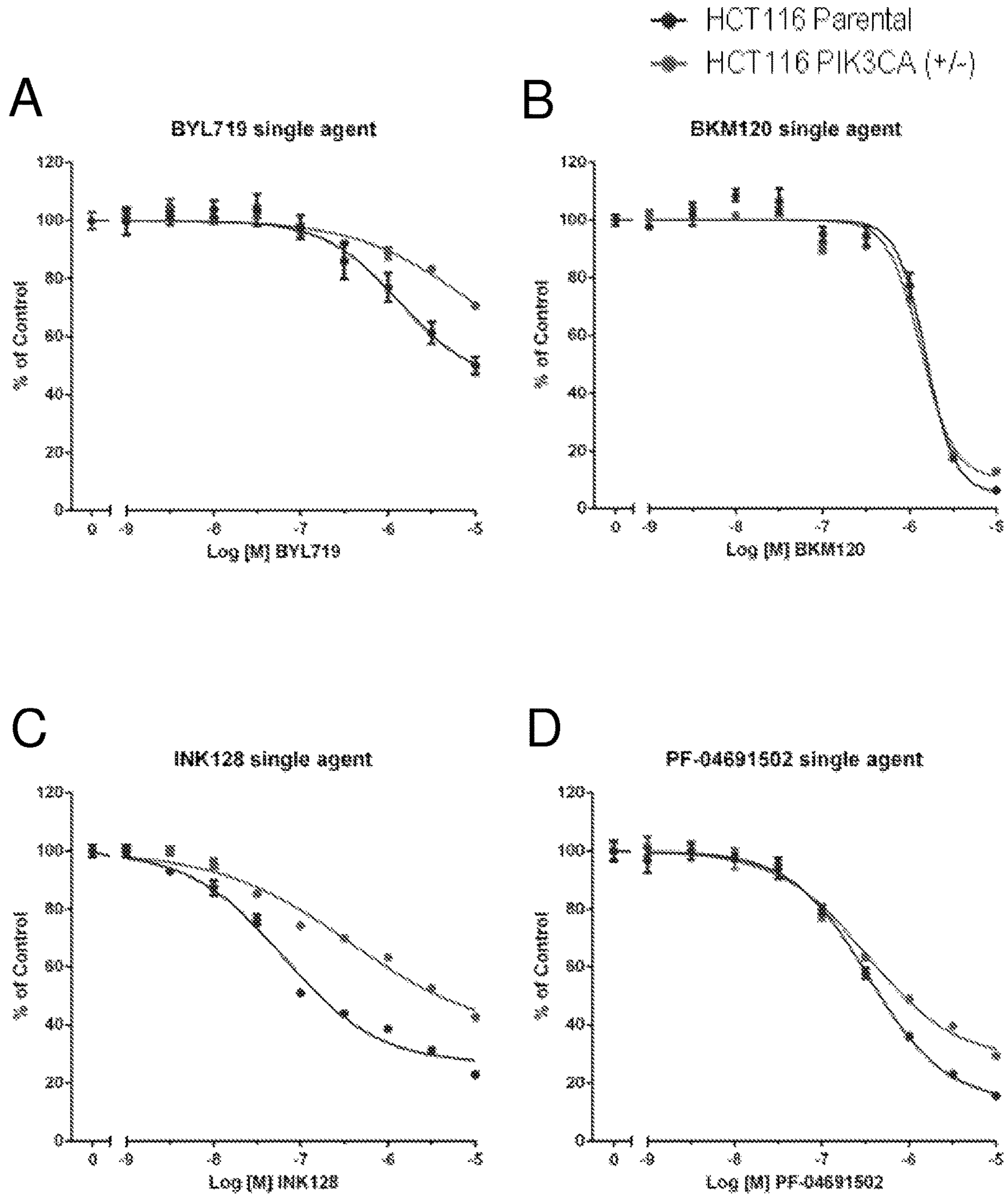
FIG. 15 shows a comparison of single agent proliferation responses in parental HCT116 and HCT116 PIK3CA (+/−). Proliferation results are shown for treatment with BYL719 (FIG. 15A), BKM120 (FIG. 15B), INK128 (FIG. 15C), PF-004691502 (FIG. 15D), BVD-523 (FIG. 15E), and SCH772984 (FIG. 15F).

Initial single agent assays were performed in the HCT116 isogenic cells in order to select appropriate concentration ranges to use in the combination assays (FIG. 6, Table 14). As high levels of serum can potentially mask interactions between targeted agents and specific mutant genotypes, due to an excess of growth factors, these assays were performed under both standard (10% FBS) and reduced serum conditions (1% charcoal-stripped FBS).

TABLE 14

Single agent IC50 values (μM) for each compound in the HCT116 PIK3CA (+/−) isogenic cell line pair

| Compound | HCT116 Parental 10% FBS | HCT116 Parental 1% CS-FBS | HCT116 PIK3CA (+/−) 10% FBS | HCT116 PIK3CA (+/−) 1% CS-FBS |
|---|---|---|---|---|
| BYL719 | n.d. | n.d. | n.d. | n.d. |
| BKM120 | 0.62 | 0.53 | 0.52 | 1.03 |
| INK128 | 0.05 | 0.03 | 0.07 | 0.02 |
| PF-04691502 | 0.29 | 0.07 | 0.42 | 1.54 |
| BVD-523 | 0.17 | 0.02 | 0.12 | 0.01 |
| SCH772984 | 0.14 | 0.03 | 0.08 | 0.01 |
| Paclitaxel | 0.002 | 0.003 | 0.002 | 0.003 |
| GDC-0941 | 1.53 | 0.06 | n.d. | n.d. |

Although, there were apparent differences in the calculated $IC_{50}$ values between the two serum conditions, a reliable interpretation of these differences was confounded by the poor levels of cell growth and compromised cell health (microscopic observations) under the reduced serum conditions. As an intermediate to these conditions, all the combination assays were therefore performed in medium containing 2.5% serum.

Combination interactions between two compounds were assessed across a matrix of concentrations using the Loewe Additivity and Bliss Independence Models with Chalice™ Bioinformatics Software (Horizon Discovery Group, Cambridge, Mass.). Chalice™ enables potential synergistic interactions to be identified by displaying the calculated excess inhibition over that predicted as being additive across the dose matrix as a heat map, and by reporting a quantitative 'Synergy Score' based on the Loewe model.

BVD-523 showed strong synergistic interactions with BYL719, BKM120 and PF04691502, and modestly synergistic with BKM120, in the parental HCT116 cell line, which carries the PIK3CA mutation. Potential synergies were also observed in the HCT116 isogenic cell line lacking the PIK3CA mutation, however, the strength and/or windows of synergy tended to be smaller relative to the parental line.

A similar pattern of results was seen with a second benchmark ERK inhibitor SCH772984 in this HCT116 isogenic pair supporting the notion that these synergies are specifically related to inhibition of ERK and not due to an off-target effect. (FIG. 7-FIG. 15)

Figure 16:
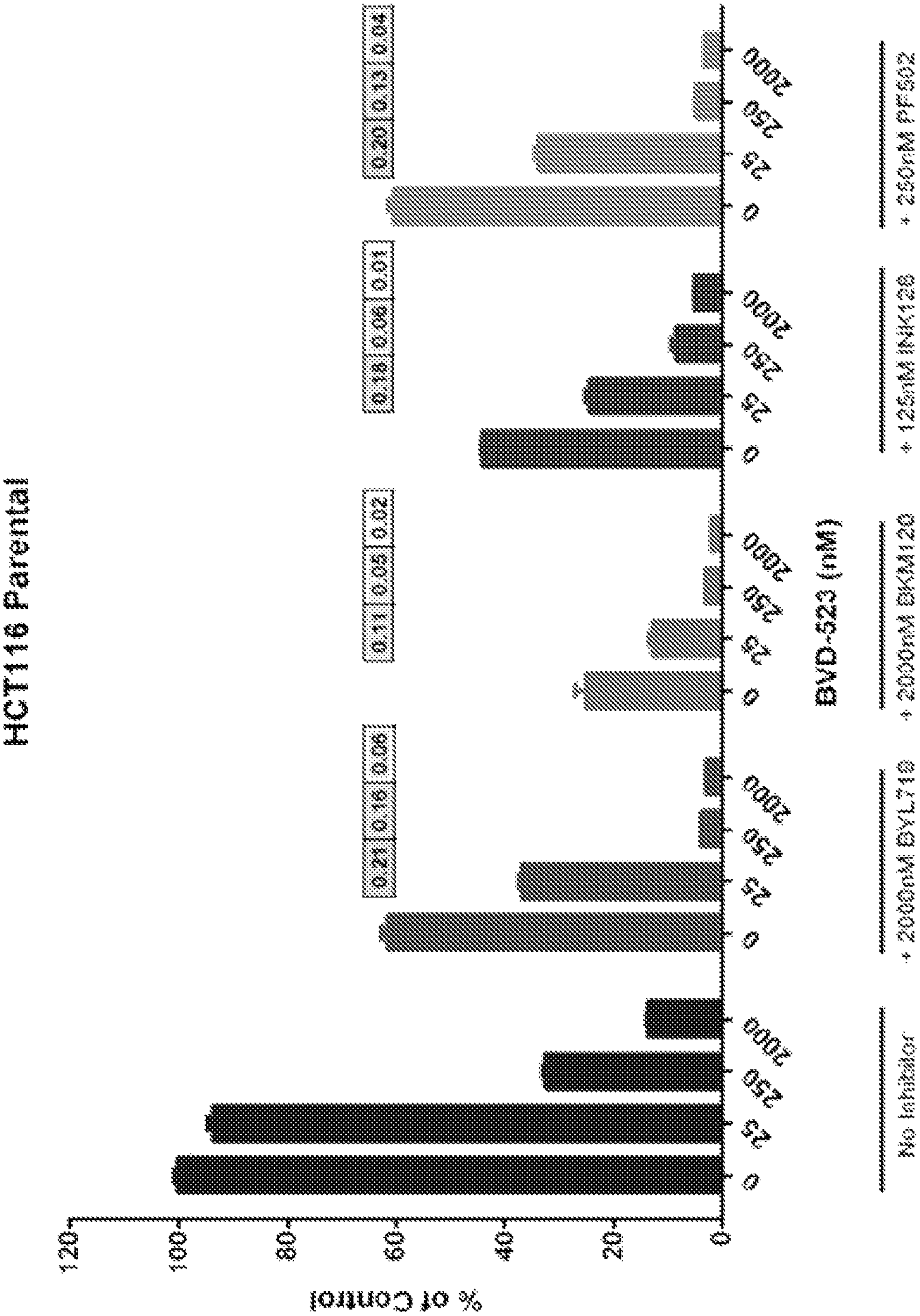
FIG. 16 shows results of focused concentration combination assays in the HCT116 PIK3CA (+/−) isogenic cell line pair.
Figure 17:
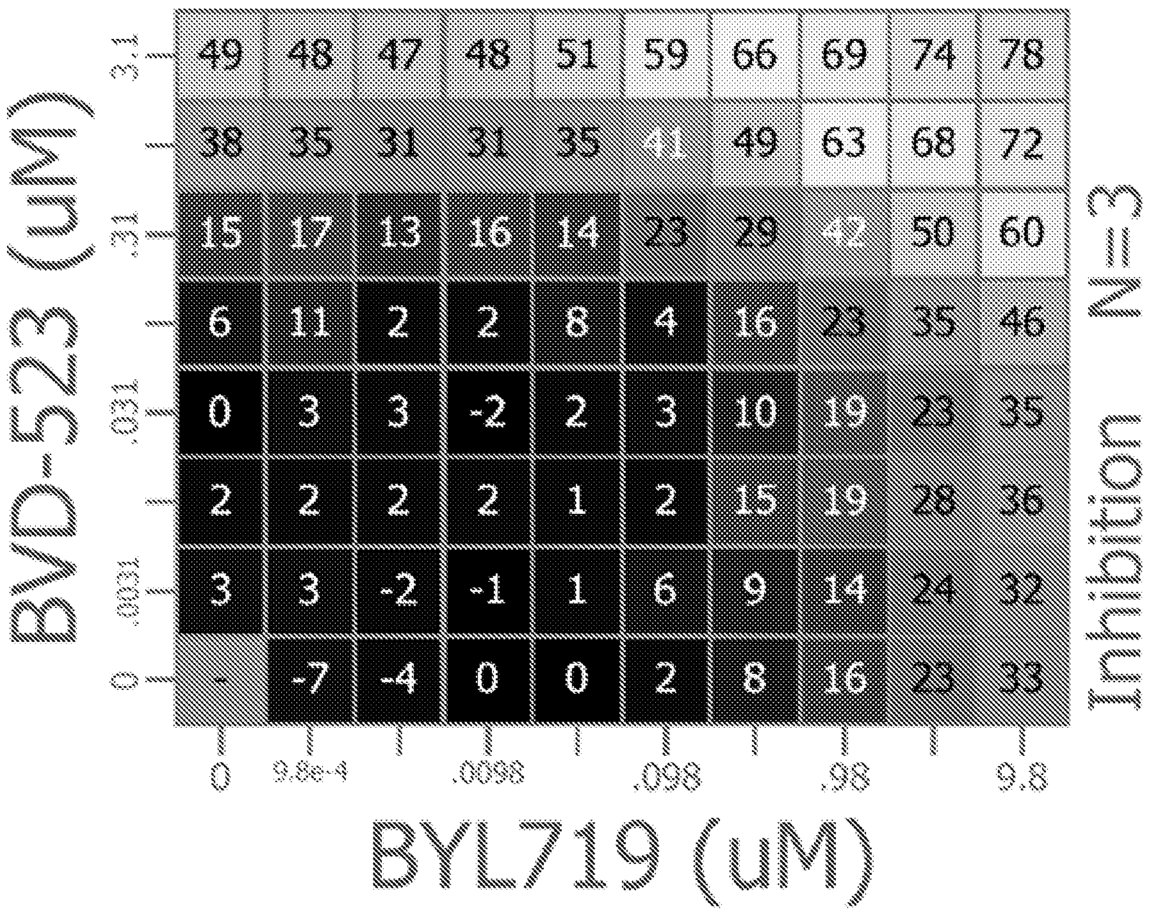
FIG. 17 shows the results of the combination of BVD-523 and BYL719 in parental DLD-1 and DLD-1 PIK3CA (+/−) cells.
Figure 18:
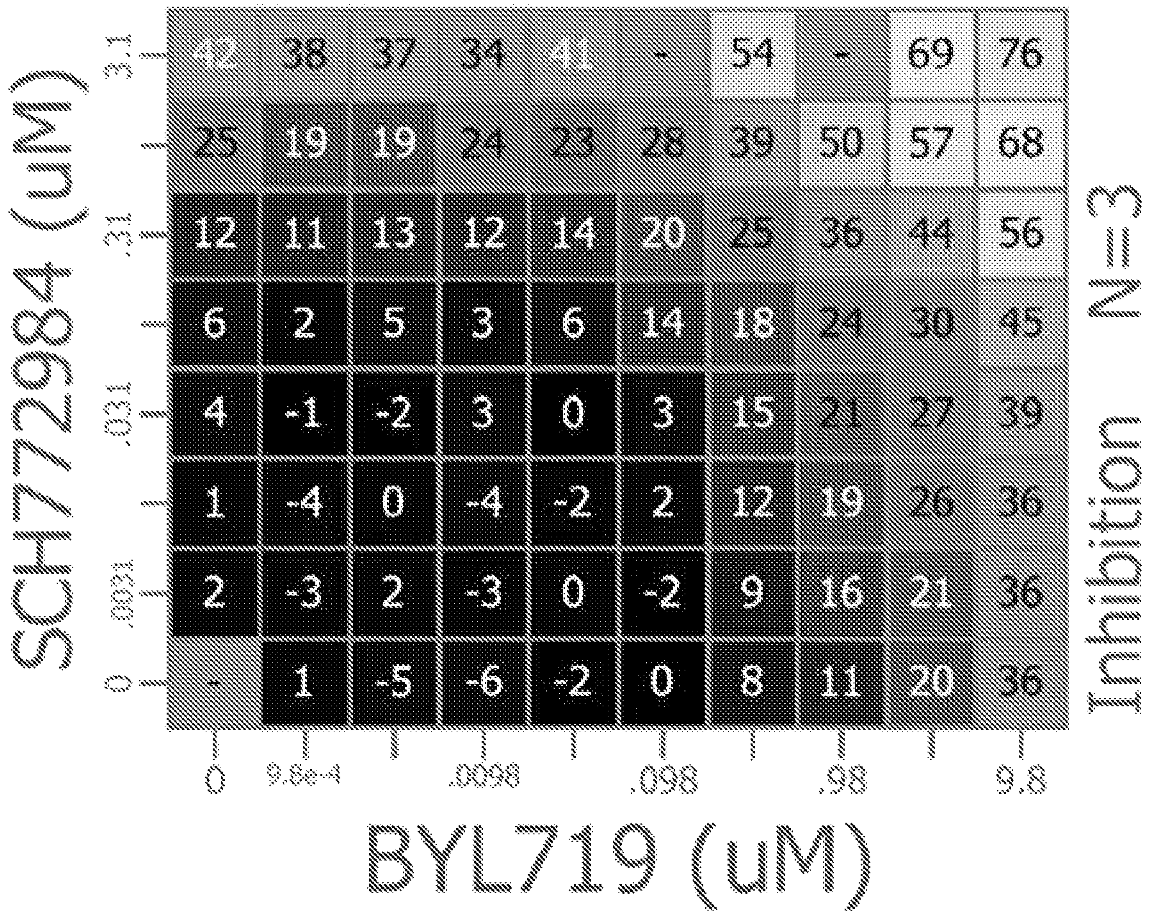
FIG. 18 shows the results of the combination of SCH772984 and BYL719 in parental DLD-1 and DLD-1 PIK3CA (+/−) cells.
Figure 19:
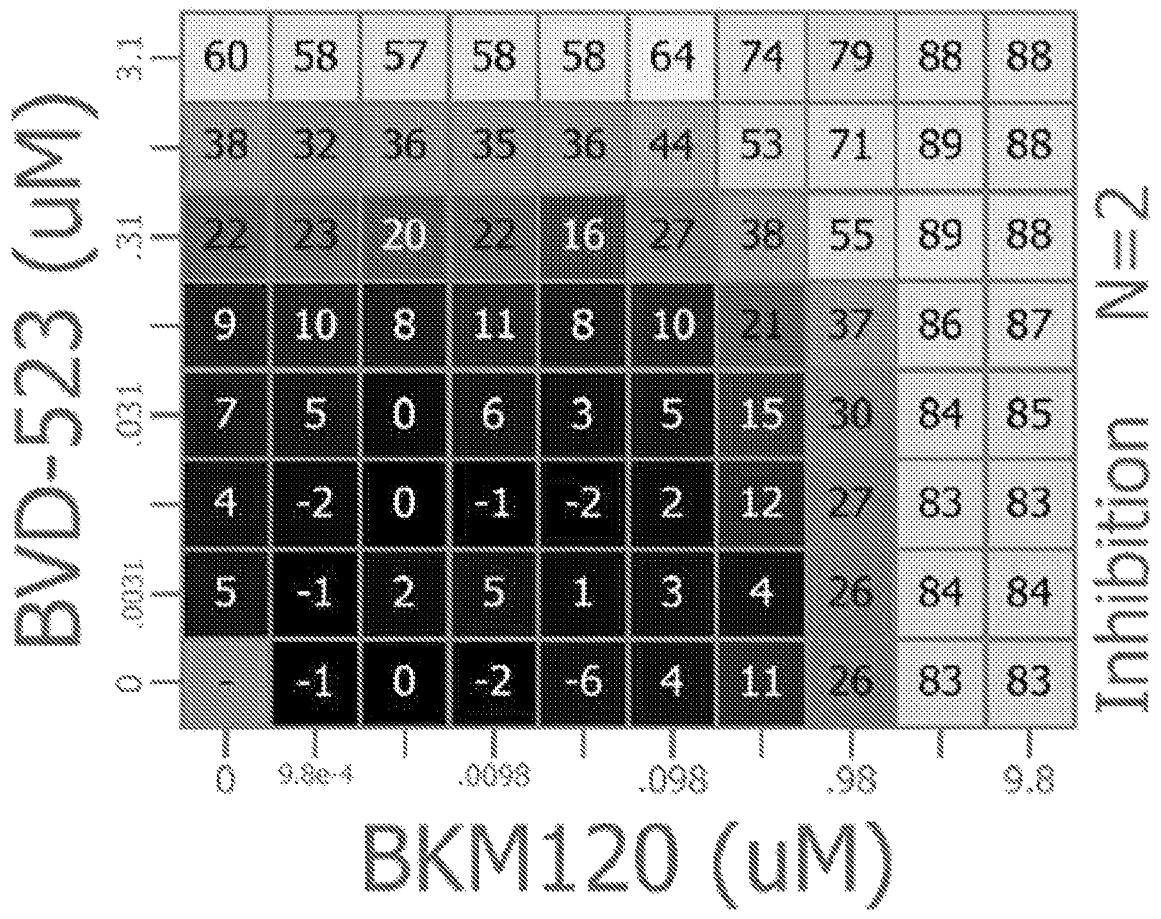
FIG. 19 shows the results of the combination of BVD-523 and BKM120 in parental DLD-1 and DLD-1 PIK3CA (+/−) cells.
Figure 20:
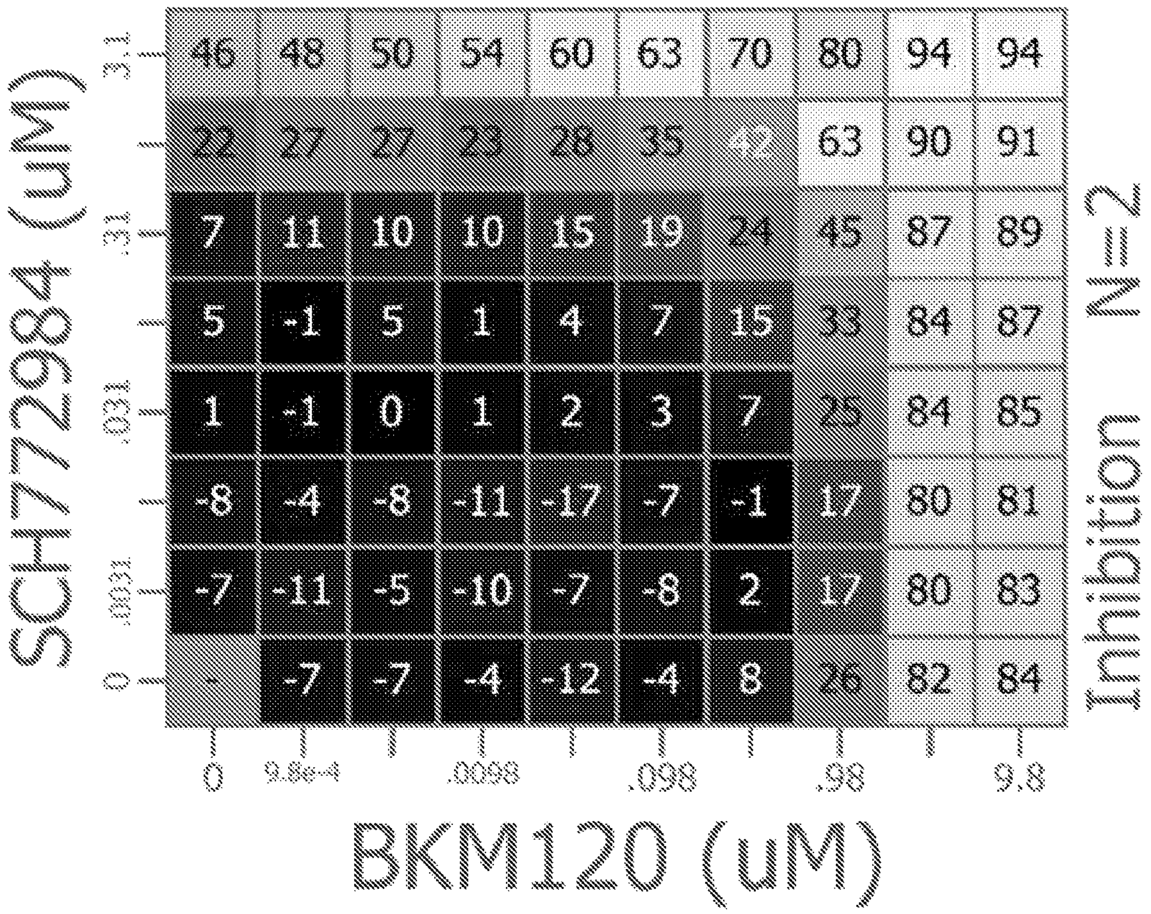
FIG. 20 shows the results of the combination of SCH772984 and BKM120 in parental DLD-1 and DLD-1 PIK3CA (+/−) cells.
Figure 21:
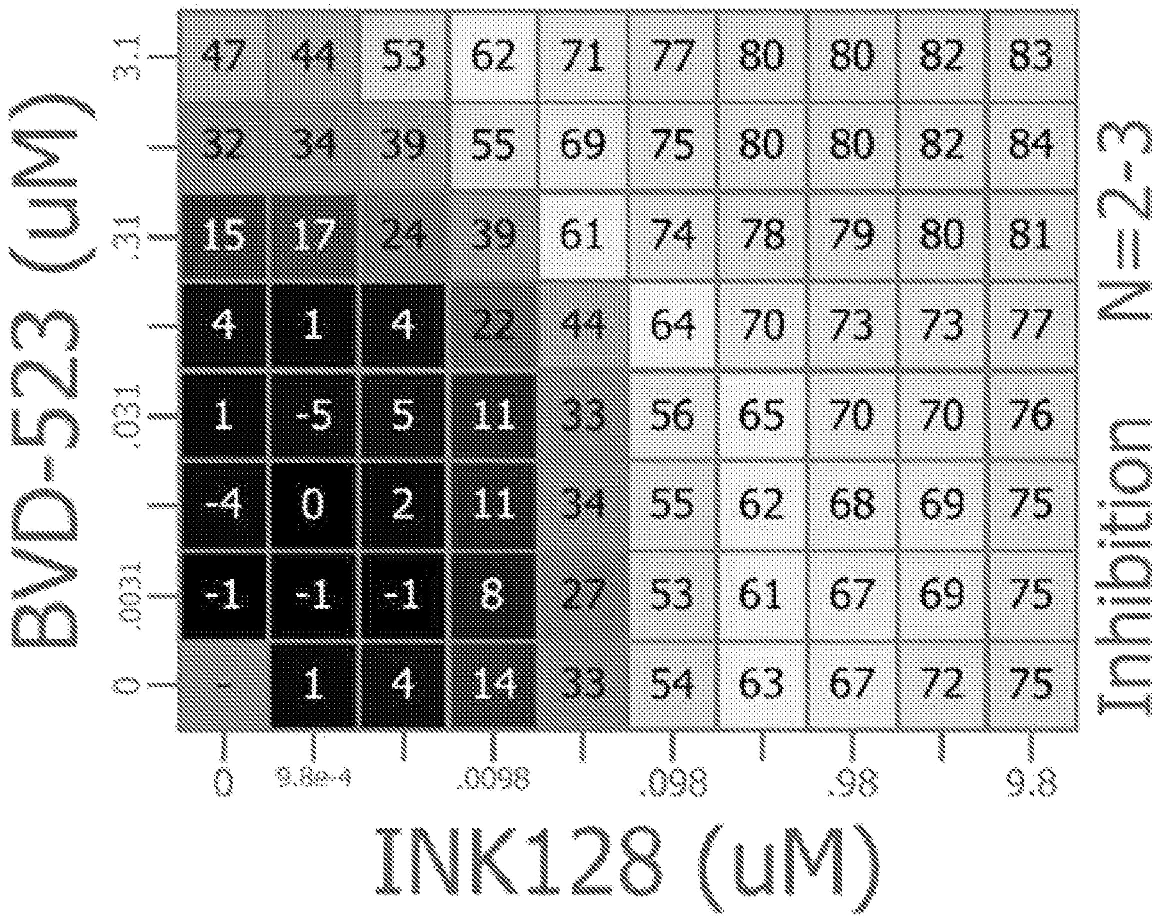
FIG. 21 shows the results of the combination of BVD-523 and INK128 in parental DLD-1 and DLD-1 PIK3CA (+/−) cells.
Figure 22:
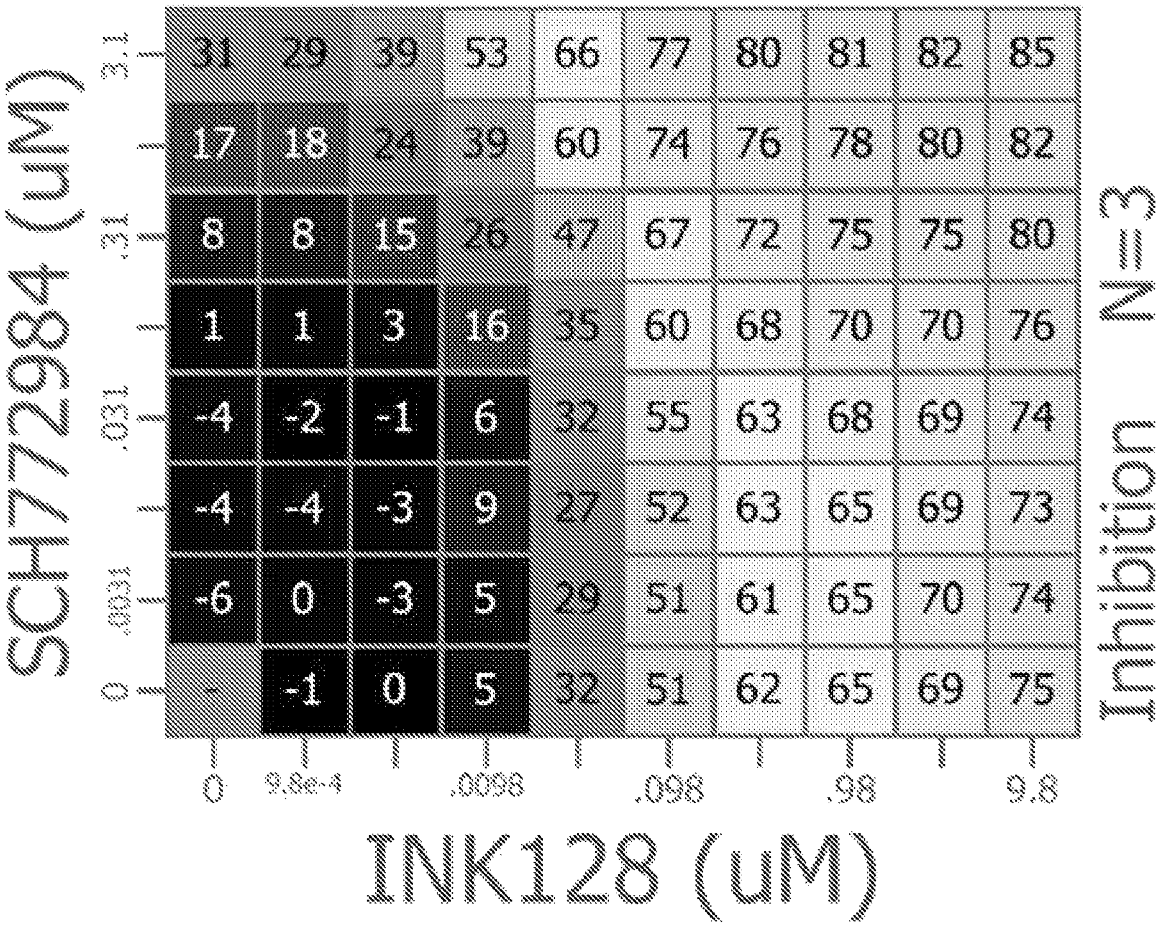
FIG. 22 shows the results of the combination of SCH772984 and INK128 in parental DLD-1 and DLD-1 PIK3CA (+/−) cells.
Figure 23:
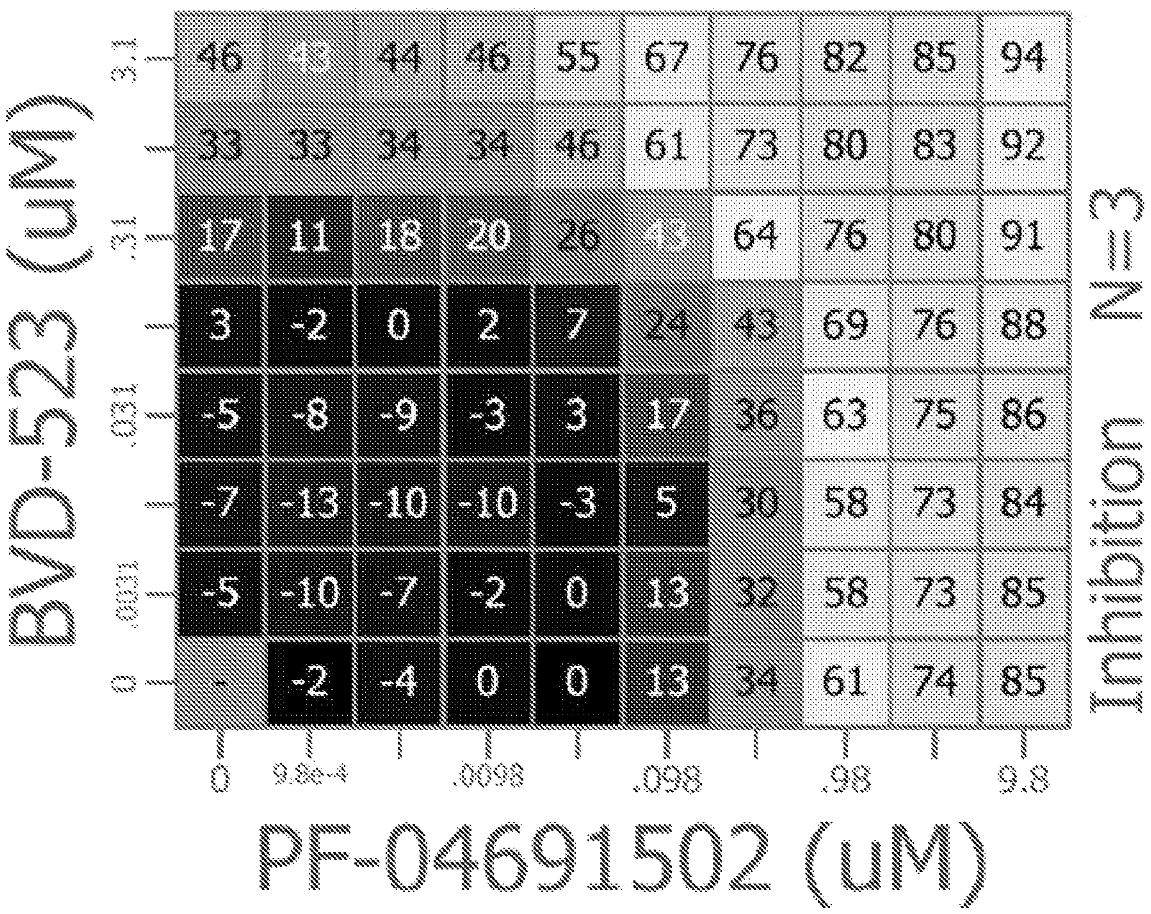
FIG. 23 shows the results of the combination of BVD-523 and PF-004691502 in parental DLD-1 and DLD-1 PIK3CA (+/−) cells.
Figure 24:
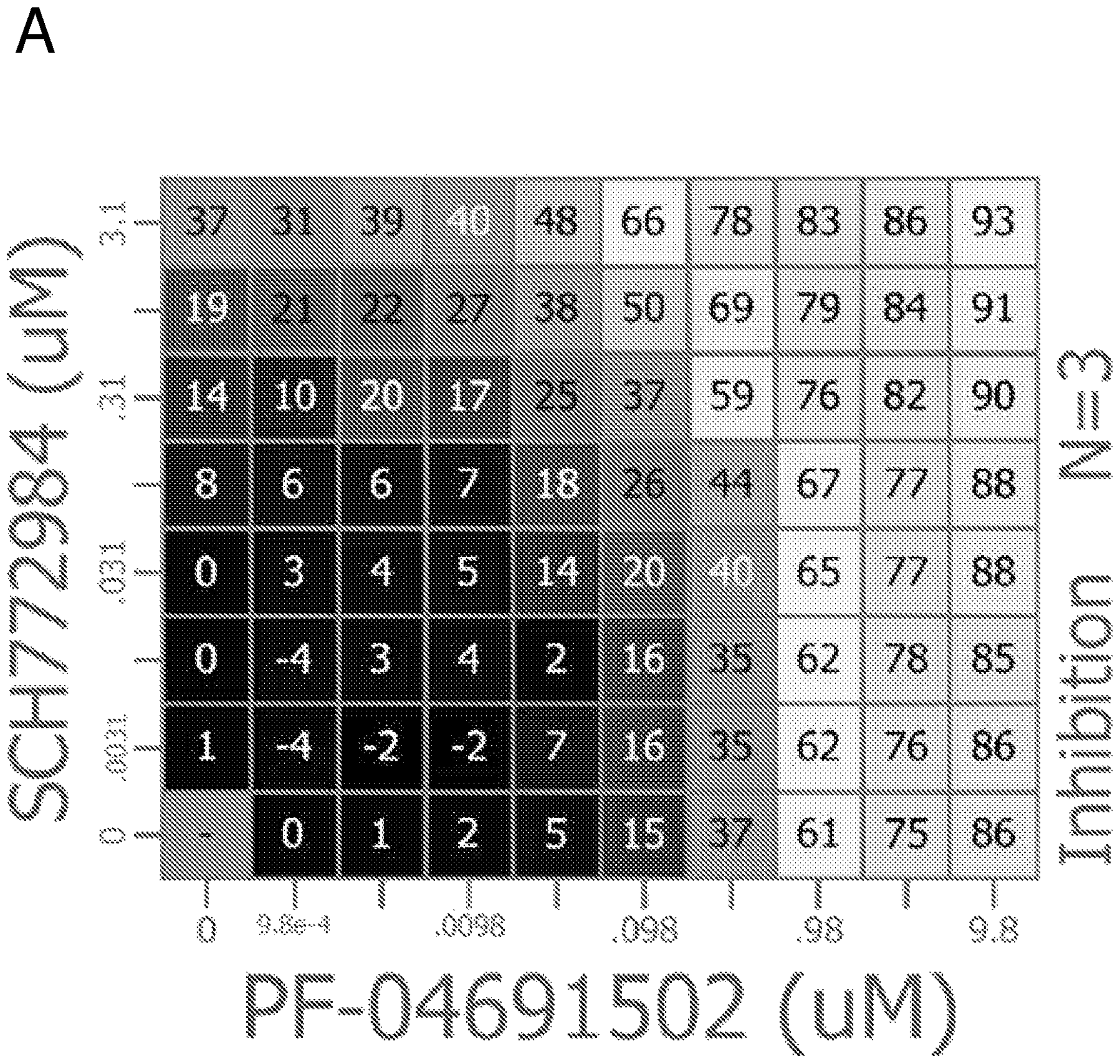
FIG. 24 shows the results of the combination of SCH772984 and PF-004691502 in parental DLD-1 and DLD-1 PIK3CA (+/−) cells.
Figure 25:
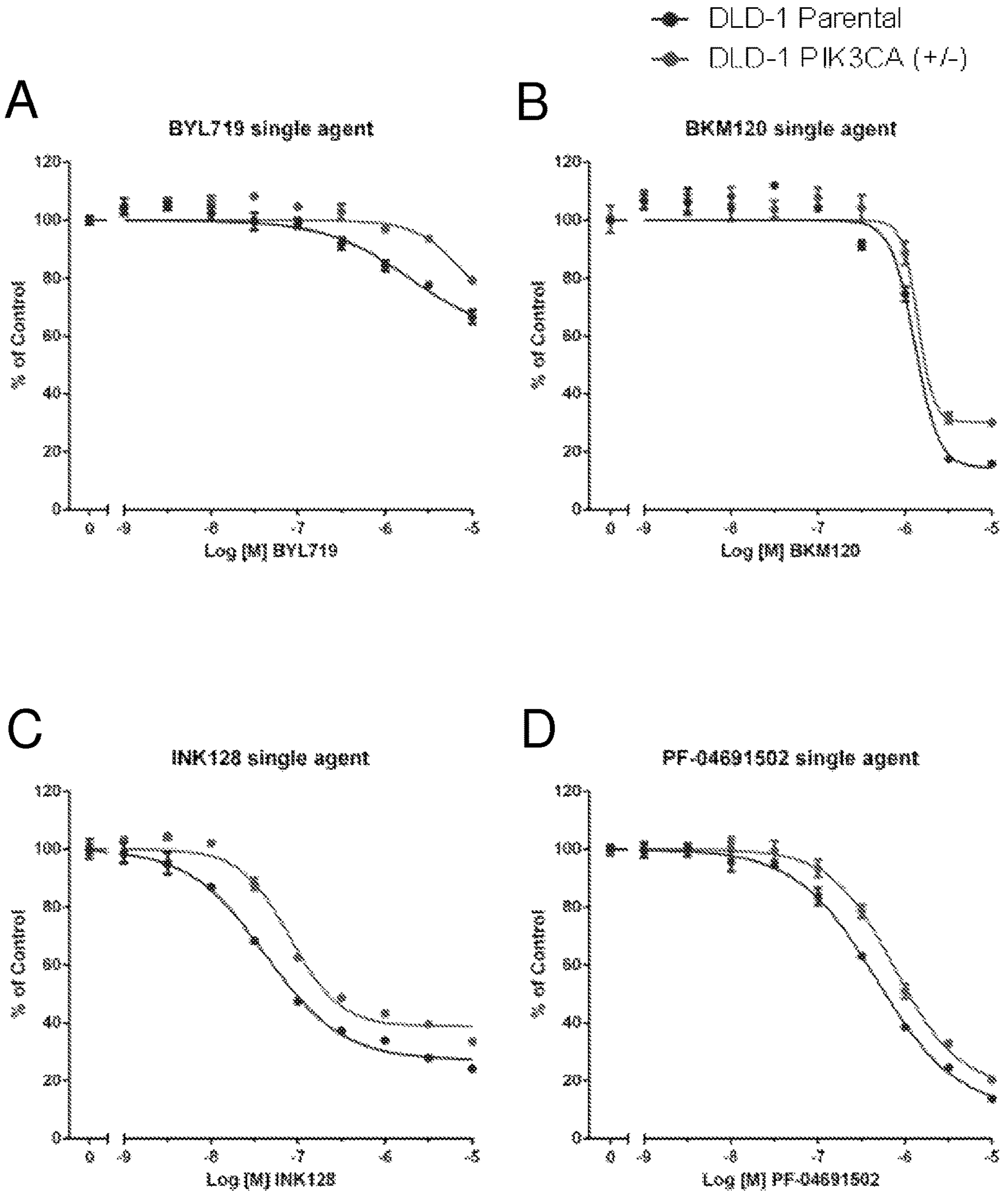
FIG. 25 shows a comparison of single agent proliferation responses in parental DLD-1 and DLD-1 PIK3CA (+/−). Proliferation results are shown for treatment with BYL719 (FIG. 25A), BKM120 (FIG. 25B), INK128 (FIG. 25C), PF-004691502 (FIG. 25D), BVD-523 (FIG. 25E), and SCH772984 (FIG. 25F).

These results were confirmed in the HCT116 isogenics in a repeat experiment using a narrower range of inhibitor concentrations. (FIG. 16) BVD-523 and SCH772984 also showed a similar pattern of potentially synergistic interactions in the DLD-1 isogenic cells. (FIG. 17-FIG. 25) However, in contrast to the HCT116 cells, synergies were weaker and there was little difference in the magnitude of synergy between the cell line lacking the PIK3CA mutation relative to the parental line. (FIG. 26)

In summary, these results suggest synergistic interactions between BVD-523 and PI3K-MTOR pathway inhibitors in cancer cell lines that are either wild type or mutated for PIK3CA.

Single agent dose-response curves in 2.5% serum were derived from the combination assay plates. $IC_{50}$ values are a mean derived from n=4 separate combinations. A comparison of the single agent dose responses derived from the combination assay data in the HCT116 isogenics showed that the cell line lacking the PIK3CA mutation was more sensitive to BVD-523 relative to the parental line that contained the mutation. A similar result was seen with SCH772984. This may indicate that PIK3CA mutation status is a potential biomarker for predicting response to single agent BVD-523 treatment. (Table 15)

TABLE 15

| Differential sensitivity to ERK inhibition in HCT116 isogenics | | |
|---|---|---|
| | $IC_{50}$ (μM) | |
| | HCT116 Parental | HCT116 PIK3CA (+/−) |
| BVD-523 | 0.13 | 0.04 |
| SCH772984 | 0.21 | 0.03 |

Example 5

Combination Interactions Between ERK Inhibitors

RAF mutant melanoma cell line A375 cells were cultured in DMEM with 10% FBS and seeded into triplicate 96-well plates at an initial density of 2000 cells per well. Combination interactions between ERK inhibitors BVD-523 and SCH772984 were analized after 72 hours as described above in Example 4. Viability was determined using CellTiter-Glo® reagent (Promega, Madison, Wis.) according to manufacturer's instructions and luminescence was detected using the BMG FLUOstar plate reader (BMG Labtech, Ortenberg, Germany).

Figure 27:
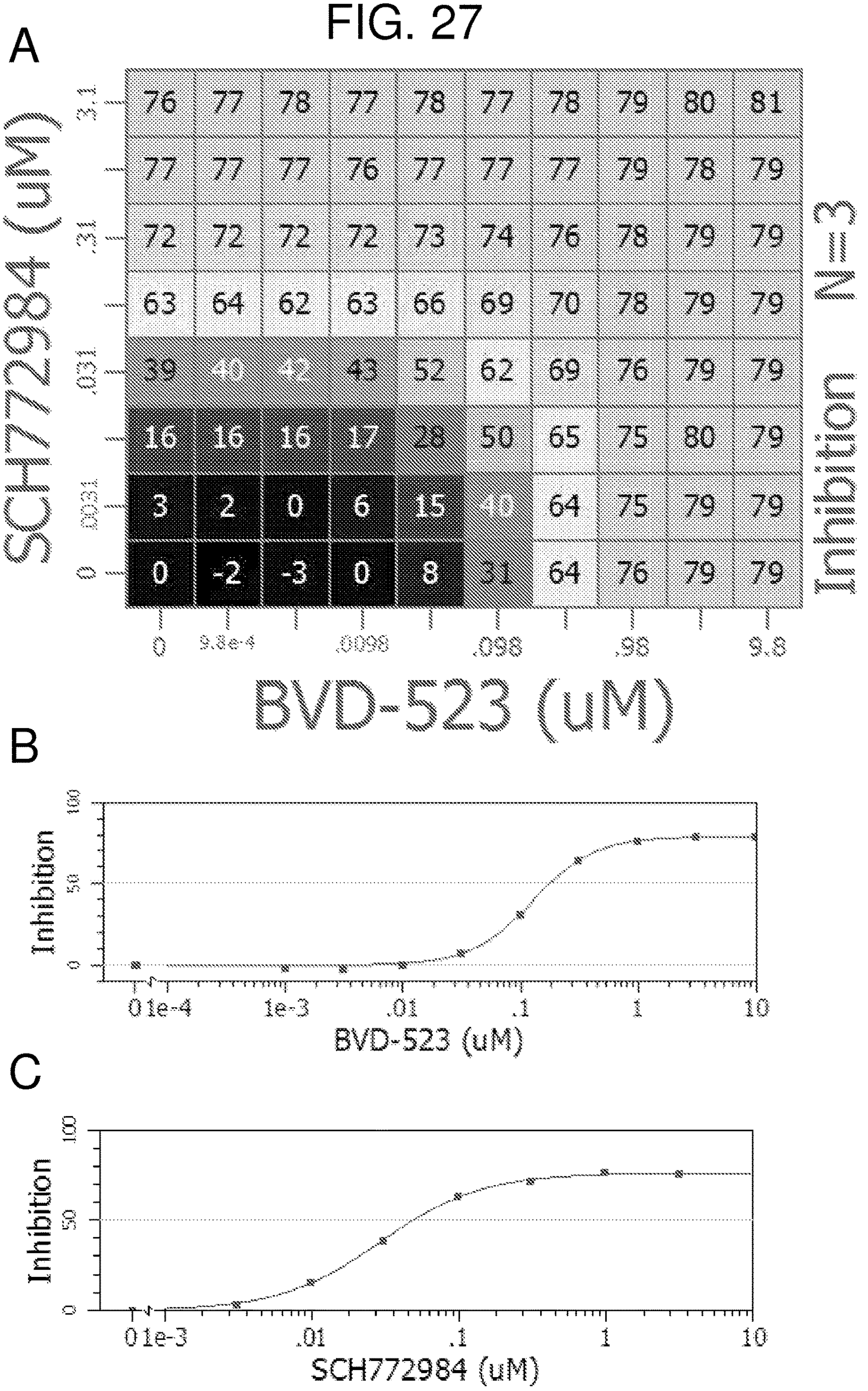
FIG. 27 shows the results of the combination of BVD-523 and SCH772984.

Visualization of the Loewe and Bliss 'excess inhibition' heat maps suggested that the combination of BVD-523 and SCH772984 was mainly additive with windows of potential synergy in mid-range doses (FIG. 27).

In summary, these results suggest that interactions between BVD-523 and SCH772984 are at least additive, and in some cases synergistic.

DOCUMENTS

ATEFI, Mohammad et al. "Reversing melanoma cross-resistance to BRAF and MEK inhibitors by co-targeting the AKT/mTOR pathway." PloS one 6.12 (2011): e28973.

HALILOVIC, Ensar et al. "PIK3CA mutation uncouples tumor growth and cyclin D1 regulation from MEK/ERK and mutant KRAS signaling." Cancer research 70.17 (2010): 6804-6814.

HOEFLICH, Klaus P. et al. "In vivo antitumor activity of MEK and phosphatidylinositol 3-kinase inhibitors in basal-like breast cancer models." Clinical Cancer Research 15.14 (2009): 4649-4664.

KARAKAS, B., K. E. Bachman, and B. H. Park. "Mutation of the PIK3CA oncogene in human cancers." British journal of cancer 94.4 (2006): 455-459.

LI, Hui-Fang, et al. "Recent advances in the research and development of B-Raf inhibitors." Current medicinal chemistry 17.16 (2010): 1618-1634.

MITTAL, Rohit et al. "The acetyltransferase activity of the bacterial toxin YopJ of *Yersinia* is activated by eukaryotic host cell inositol hexakisphosphate." Journal of Biological Chemistry 285.26 (2010): 19927-19934

WEE, Susan et al. "PI3K pathway activation mediates resistance to MEK inhibitors in KRAS mutant cancers." Cancer Research 69.10 (2009): 4286-4293.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method of treating or ameliorating the effects of a cancer in a subject in need thereof comprising administering to the subject an effective amount of (i) a first anti-cancer agent, which is BVD-523 or a pharmaceutically acceptable salt thereof and (ii) a second anti-cancer agent, which is an inhibitor of the PI3K/Akt pathway or a pharmaceutically acceptable salt thereof, to treat or ameliorate the effects of the cancer, wherein the inhibitor of the PI3K/Akt pathway is selected from the group consisting of BYL719, BKM120, PF-04691502, pharmaceutically acceptable salts thereof, and combinations thereof, and wherein administration of the first and second anti-cancer agents provides a synergistic effect compared to administration of either anti-cancer agent alone.

2. The method according to claim 1, wherein the subject is a mammal.

3. The method according to claim 2, wherein the mammal is selected from the group consisting of humans, primates, farm animals, and domestic animals.

4. The method according to claim 2, wherein the mammal is a human.

5. The method according to claim 1, wherein the subject with cancer has a somatic KRAS mutation or is refractory to MAPK pathway inhibitor treatment.

6. The method according to claim 5, wherein the subject with cancer has a somatic KRAS mutation and a somatic PIK3CA mutation.

7. The method according to claim 5, wherein the cancer is selected from the group consisting of a cancer of the large intestine, breast cancer, liver cancer, colon cancer, pancreatic cancer, endometrial cancers, stomach cancer, lung cancer, and leukemia.

8. The method according to claim 5, wherein the cancer is colon cancer.

9. The method according to claim 1 further comprising administering at least one additional therapeutic agent selected from the group consisting of an antibody or fragment thereof, a cytotoxic agent, a drug, a toxin, a radionuclide, an immunomodulator, a photoactive therapeutic agent, a radiosensitizing agent, a hormone, an anti-angiogenesis agent, and combinations thereof.

10. The method according to claim 9, wherein the additional therapeutic agent is an inhibitor of the mTOR pathway.

11. The method according to claim 10, wherein the inhibitor of the mTOR pathway is selected from the group consisting of zotarolimus, umirolimus, temsirolimus, sirolimus, sirolimus NanoCrystal, everolimus, biolimus A9, ridaforolimus, rapamycin, TCD-10023, DE-109, MS R001, MS R002, MS-R003, (−)-rapamycin, XL-765, quinacrine, PKI-587, PF-04691502, GDC-0980, dactolisib, CC-223, PWT-33597, P-7170, LY-3023414, INK-128, GDC-0084, DS-7423, DS-3078, CC-115, CBLC-137, AZD-2014, X-480, X-414, EC-0371, VS-5584, PQR-401, PQR-316, PQR-311, PQR-309, PF-06465603, NV-128, nPT-MTOR, BC-210, WAY-600, WYE-354, WYE-687, LOR-220, HMPL-518, GNE-317, EC-0565, CC-214, ABTL-0812, and pharmaceutically acceptable salts thereof, and combinations thereof.

12. A method of effecting cancer cell death comprising contacting the cancer cell with an effective amount of (i) a first anti-cancer agent, which is BVD-523 or a pharmaceutically acceptable salt thereof and (ii) a second anti-cancer agent, which is a an inhibitor of the PI3K/Akt pathway or a pharmaceutically acceptable salt thereof, wherein the inhibitor of the PI3K/Akt pathway is selected from the group consisting of BYL719, BKM120, PF-04691502, pharmaceutically acceptable salts thereof, and combinations thereof, and wherein administration of the first and second anti-cancer agents provides a synergistic effect compared to administration of either anti-cancer agent alone.

13. The method according to claim 12, wherein the cancer cell is mammalian cancer cell.

14. The method according to claim 13, wherein the mammalian cancer cell is obtained from a mammal selected from the group consisting of humans, primates, farm animals, and domestic animals.

15. The method according to claim 13, wherein the mammalian cancer cell is a human cancer cell.

16. The method according to claim 12, wherein the subject with cancer has a somatic KRAS mutation or is refractory to MAPK pathway inhibitor treatment.

17. The method according to claim 16, wherein the subject with cancer has a somatic KRAS mutation and a somatic PIK3CA mutation.

18. The method according to claim 16, wherein the cancer is selected from the group consisting of a cancer of the large intestine, breast cancer, liver cancer, colon cancer, pancreatic cancer, endometrial cancers, stomach cancer, lung cancer, and leukemia.

19. The method according to claim 16, wherein the cancer is colon cancer.

20. The method according to claim 12 further comprising contacting the cancer cell with at least one additional therapeutic agent selected from the group consisting of an antibody or fragment thereof, a cytotoxic agent, a drug, a toxin, a radionuclide, an immunomodulator, a photoactive therapeutic agent, a radiosensitizing agent, a hormone, an anti-angiogenesis agent, and combinations thereof.

21. The method according to claim 20, wherein the additional therapeutic agent is an inhibitor of the mTOR pathway.

22. The method according to claim 21, wherein the inhibitor of the mTOR pathway is selected from the group consisting of zotarolimus, umirolimus, temsirolimus, sirolimus, sirolimus NanoCrystal, everolimus, biolimus A9, ridaforolimus, rapamycin, TCD-10023, DE-109, MS-R001, MS-R002, MS-R003, (−)-rapamycin, XL-765, quinacrine, PKI-587, PF-04691502, GDC-0980, datolisib, CC-223, PWT-33597, P-7170, LY-3023414, INK-128, GDC 0084, DS-7423, DS-3078, CC-115, CBLC-137, AZD-2014, X-480, X-414, EC-0371, VS-5584, PQR-401, PQR-316, PQR-311, PQR-309, PF-06465603, NV-128, nPT MTOR, BC-210, WAY-600, WYE-354, WYE-687, LOR-220, HMPL-518, GNE-317, EC-0565, CC-214, ABTL-0812, and pharmaceutically acceptable salts thereof, and combinations thereof.

* * * * *

SEQUENCE LISTING

```
<160> NUMBER OF SEQ ID NOS: 91

<210> SEQ ID NO 1
<211> LENGTH: 5436
<212> TYPE: DNA
<213> ORGANISM: Homo sapiens

<400> SEQUENCE: 1

ggccgcggcg gcggaggcag cagcggcggc ggcagtggcg gcggcgaagg tggcggcggc      60

tcggccagta ctcccggccc ccgccatttc ggactgggag cgagcgcggc gcaggcactg     120

aaggcggcgg cggggccaga ggctcagcgg ctcccaggtg cgggagagag gcctgctgaa     180

aatgactgaa tataaacttg tggtagttgg agctggtggc gtaggcaaga gtgccttgac     240

gatacagcta attcagaatc attttgtgga cgaatatgat ccaacaatag aggattccta     300

caggaagcaa gtagtaattg atggagaaac ctgtctcttg gatattctcg acacagcagg     360

tcaagaggag tacagtgcaa tgagggacca gtacatgagg actggggagg gctttctttg     420

tgtatttgcc ataaataata ctaaatcatt tgaagatatt caccattata gagaacaaat     480

taaaagagtt aaggactctg aagatgtacc tatggtccta gtaggaaata aatgtgattt     540

gccttctaga acagtagaca caaaacaggc tcaggactta gcaagaagtt atggaattcc     600

ttttattgaa acatcagcaa agacaagaca gagagtggag gatgcttttt atacattggt     660
```

-continued

```
gagggagatc cgacaataca gattgaaaaa aatcagcaaa gaagaaaaga ctcctggctg     720
tgtgaaaatt aaaaaatgca ttataatgta atctgggtgt tgatgatgcc ttctatacat     780
tagttcgaga aattcgaaaa cataaagaaa agatgagcaa agatggtaaa aagaagaaaa     840
agaagtcaaa gacaaagtgt gtaattatgt aaatacaatt tgtacttttt tcttaaggca     900
tactagtaca agtggtaatt tttgtacatt acactaaatt attagcattt gttttagcat     960
tacctaattt ttttcctgct ccatgcagac tgttagcttt taccttaaat gcttatttta    1020
aaatgacagt ggaagttttt ttttcctcta agtgccagta ttcccagagt tttggttttt    1080
gaactagcaa tgcctgtgaa aaagaaactg aatacctaag atttctgtct tggggttttt    1140
ggtgcatgca gttgattact tcttattttt cttaccaatt gtgaatgttg gtgtgaaaca    1200
aattaatgaa gcttttgaat catccctatt ctgtgtttta tctagtcaca taaatggatt    1260
aattactaat ttcagttgag accttctaat tggtttttac tgaaacattg agggaacaca    1320
aatttatggg cttcctgatg atgattcttc taggcatcat gtcctatagt ttgtcatccc    1380
tgatgaatgt aaagttacac tgttcacaaa ggttttgtct cctttccact gctattagtc    1440
atggtcactc tccccaaaat attatatttt ttctataaaa agaaaaaaat ggaaaaaaat    1500
tacaaggcaa tggaaactat tataaggcca tttccttttc acattagata aattactata    1560
aagactccta atagcttttc ctgttaaggc agacccagta tgaaatgggg attattatag    1620
caaccatttt ggggctatat ttacatgcta ctaaattttt ataataattg aaaagatttt    1680
aacaagtata aaaaattctc ataggaatta aatgtagtct ccctgtgtca gactgctctt    1740
tcatagtata actttaaatc ttttcttcaa cttgagtctt tgaagatagt tttaattctg    1800
cttgtgacat taaaagatta tttgggccag ttatagctta ttaggtgttg aagagaccaa    1860
ggttgcaagg ccaggccctg tgtgaacctt tgagctttca tagagagttt cacagcatgg    1920
actgtgtccc cacggtcatc cagtgttgtc atgcattggt tagtcaaaat ggggagggac    1980
tagggcagtt tggatagctc aacaagatac aatctcactc tgtggtggtc ctgctgacaa    2040
atcaagagca ttgcttttgt ttcttaagaa aacaaactct tttttaaaaa ttacttttaa    2100
atattaactc aaaagttgag attttggggt ggtggtgtgc caagacatta attttttttt    2160
taaacaatga agtgaaaaag ttttacaatc tctaggtttg gctagttctc ttaacactgg    2220
ttaaattaac attgcataaa cacttttcaa gtctgatcca tatttaataa tgctttaaaa    2280
taaaaataaa aacaatcctt ttgataaatt taaaatgtta cttattttaa aataaatgaa    2340
gtgagatggc atggtgaggt gaaagtatca ctggactagg aagaaggtga cttaggttct    2400
agataggtgt cttttaggac tctgattttg aggacatcac ttactatcca tttcttcatg    2460
ttaaaagaag tcatctcaaa ctcttagttt ttttttttta caactatgta atttatattc    2520
catttacata aggatacact tatttgtcaa gctcagcaca atctgtaaat ttttaaccta    2580
tgttacacca tcttcagtgc cagtcttggg caaaattgtg caagaggtga agtttatatt    2640
tgaatatcca ttctcgtttt aggactcttc ttccatatta gtgtcatctt gcctccctac    2700
cttccacatg ccccatgact tgatgcagtt ttaatacttg taattcccct aaccataaga    2760
tttactgctg ctgtggatat ctccatgaag ttttcccact gagtcacatc agaaatgccc    2820
tacatcttat ttcctcaggg ctcaagagaa tctgacagat accataaagg gatttgacct    2880
aatcactaat tttcaggtgg tggctgatgc tttgaacatc tctttgctgc ccaatccatt    2940
agcgacagta ggatttttca aacctggtat gaatagacag aaccctatcc agtggaagga    3000
gaatttaata aagatagtgc tgaaagaatt ccttaggtaa tctataacta ggactactcc    3060
```

-continued

```
tggtaacagt aatacattcc attgttttag taaccagaaa tcttcatgca atgaaaaata   3120
ctttaattca tgaagcttac tttttttttt tggtgtcaga gtctcgctct tgtcacccag   3180
gctggaatgc agtggcgcca tctcagctca ctgcaacctc catctcccag gttcaagcga   3240
ttctcgtgcc tcggcctcct gagtagctgg gattacaggc gtgtgccact acactcaact   3300
aatttttgta tttttaggag agacggggtt tcaccctgtt ggccaggctg gtctcgaact   3360
cctgacctca agtgattcac ccaccttggc ctcataaacc tgttttgcag aactcattta   3420
ttcagcaaat atttattgag tgcctaccag atgccagtca ccgcacaagg cactgggtat   3480
atggtatccc caaacaagag acataatccc ggtccttagg tagtgctagt gtggtctgta   3540
atatcttact aaggcctttg gtatacgacc cagagataac acgatgcgta ttttagtttt   3600
gcaaagaagg ggtttggtct ctgtgccagc tctataattg ttttgctacg attccactga   3660
aactcttcga tcaagctact ttatgtaaat cacttcattg ttttaaagga ataaacttga   3720
ttatattgtt tttttatttg gcataactgt gattctttta ggacaattac tgtacacatt   3780
aaggtgtatg tcagatattc atattgaccc aaatgtgtaa tattccagtt ttctctgcat   3840
aagtaattaa aatatactta aaaattaata gttttatctg ggtacaaata aacaggtgcc   3900
tgaactagtt cacagacaag gaaacttcta tgtaaaaatc actatgattt ctgaattgct   3960
atgtgaaact acagatcttt ggaacactgt ttaggtaggg tgttaagact tacacagtac   4020
ctcgtttcta cacagagaaa gaaatggcca tacttcagga actgcagtgc ttatgagggg   4080
atatttaggc ctcttgaatt tttgatgtag atgggcattt ttttaaggta gtggttaatt   4140
acctttatgt gaactttgaa tggtttaaca aaagatttgt ttttgtagag attttaaagg   4200
gggagaattc tagaaataaa tgttacctaa ttattacagc cttaaagaca aaaatccttg   4260
ttgaagtttt tttaaaaaaa gctaaattac atagacttag gcattaacat gtttgtggaa   4320
gaatatagca gacgtatatt gtatcatttg agtgaatgtt cccaagtagg cattctaggc   4380
tctatttaac tgagtcacac tgcataggaa tttagaacct aacttttata ggttatcaaa   4440
actgttgtca ccattgcaca attttgtcct aatatataca tagaaacttt gtggggcatg   4500
ttaagttaca gtttgcacaa gttcatctca tttgtattcc attgattttt tttttcttct   4560
aaacattttt tcttcaaaca gtatataact ttttttaggg gatttttttt tagacagcaa   4620
aaactatctg aagatttcca tttgtcaaaa agtaatgatt tcttgataat tgtgtagtaa   4680
tgttttttag aacccagcag ttaccttaaa gctgaattta tatttagtaa cttctgtgtt   4740
aatactggat agcatgaatt ctgcattgag aaactgaata gctgtcataa aatgaaactt   4800
tctttctaaa gaaagatact cacatgagtt cttgaagaat agtcataact agattaagat   4860
ctgtgtttta gtttaatagt ttgaagtgcc tgtttgggat aatgataggt aatttagatg   4920
aatttagggg aaaaaaaagt tatctgcaga tatgttgagg gcccatctct ccccccacac   4980
ccccacagag ctaactgggt tacagtgttt tatccgaaag tttccaattc cactgtcttg   5040
tgttttcatg ttgaaaatac ttttgcattt ttcctttgag tgccaatttc ttactagtac   5100
tatttcttaa tgtaacatgt ttacctggaa tgtattttaa ctatttttgt atagtgtaaa   5160
ctgaaacatg cacattttgt acattgtgct ttcttttgtg ggacatatgc agtgtgatcc   5220
agttgttttc catcatttgg ttgcgctgac ctaggaatgt tggtcatatc aaacattaaa   5280
aatgaccact cttttaattg aaattaactt ttaaatgttt ataggagtat gtgctgtgaa   5340
gtgatctaaa atttgtaata tttttgtcat gaactgtact actcctaatt attgtaatgt   5400
```

aataaaaata gttacagtga caaaaaaaaa aaaaaa 5436

<210> SEQ ID NO 2
<211> LENGTH: 189
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

Gln Ala Gln Asp Leu Ala Arg Ser Tyr Gly Ile Pro Phe Ile Glu Thr
130 135 140

Ser Ala Lys Thr Arg Gln Arg Val Glu Asp Ala Phe Tyr Thr Leu Val
145 150 155 160

Arg Glu Ile Arg Gln Tyr Arg Leu Lys Lys Ile Ser Lys Glu Glu Lys
165 170 175

Thr Pro Gly Cys Val Lys Ile Lys Lys Cys Ile Ile Met
180 185

<210> SEQ ID NO 3
<211> LENGTH: 5312
<212> TYPE: DNA
<213> ORGANISM: Homo sapiens

<400> SEQUENCE: 3
ggccgcggcg gcggaggcag cagcggcggc ggcagtggcg gcggcgaagg tggcggcggc 60
tcggccagta ctcccggccc ccgccatttc ggactgggag cgagcgcggc gcaggcactg 120
aaggcggcgg cggggccaga ggctcagcgg ctcccaggtg cgggagagag gcctgctgaa 180
aatgactgaa tataaacttg tggtagttgg agctggtggc gtaggcaaga gtgccttgac 240
gatacagcta attcagaatc attttgtgga cgaatatgat ccaacaatag aggattccta 300
caggaagcaa gtagtaattg atggagaaac ctgtctcttg gatattctcg acacagcagg 360
tcaagaggag tacagtgcaa tgagggacca gtacatgagg actggggagg gctttctttg 420
tgtatttgcc ataaataata ctaaatcatt tgaagatatt caccattata gagaacaaat 480
taaaagagtt aaggactctg aagatgtacc tatggtccta gtaggaaata aatgtgattt 540
gccttctaga acagtagaca caaaacaggc tcaggactta gcaagaagtt atggaattcc 600
ttttattgaa acatcagcaa agacaagaca gggtgttgat gatgccttct atacattagt 660
tcgagaaatt cgaaaacata aagaaaagat gagcaaagat ggtaaaaaga agaaaaagaa 720
gtcaaagaca aagtgtgtaa ttatgtaaat acaatttgta ctttttttctt aaggcatact 780

-continued

```
agtacaagtg gtaatttttg tacattacac taaattatta gcatttgttt tagcattacc    840
taattttttt cctgctccat gcagactgtt agcttttacc ttaaatgctt attttaaaat    900
gacagtggaa gttttttttt cctctaagtg ccagtattcc cagagttttg gtttttgaac    960
tagcaatgcc tgtgaaaaag aaactgaata cctaagattt ctgtcttggg gtttttggtg   1020
catgcagttg attacttctt atttttctta ccaattgtga atgttggtgt gaaacaaatt   1080
aatgaagctt ttgaatcatc cctattctgt gttttatcta gtcacataaa tggattaatt   1140
actaatttca gttgagacct tctaattggt ttttactgaa acattgaggg aacacaaatt   1200
tatgggcttc ctgatgatga ttcttctagg catcatgtcc tatagtttgt catccctgat   1260
gaatgtaaag ttacactgtt cacaaaggtt ttgtctcctt tccactgcta ttagtcatgg   1320
tcactctccc caaaatatta tatttttttct ataaaaagaa aaaaatggaa aaaaattaca   1380
aggcaatgga aactattata aggccatttc cttttcacat tagataaatt actataaaga   1440
ctcctaatag cttttcctgt taaggcagac ccagtatgaa atggggatta ttatagcaac   1500
cattttgggg ctatatttac atgctactaa atttttataa taattgaaaa gattttaaca   1560
agtataaaaa attctcatag gaattaaatg tagtctccct gtgtcagact gctctttcat   1620
agtataactt taaatctttt cttcaacttg agtctttgaa gatagtttta attctgcttg   1680
tgacattaaa agattatttg ggccagttat agcttattag gtgttgaaga gaccaaggtt   1740
gcaaggccag gccctgtgtg aacctttgag ctttcataga gagtttcaca gcatggactg   1800
tgtccccacg gtcatccagt gttgtcatgc attggttagt caaaatgggg agggactagg   1860
gcagtttgga tagctcaaca agatacaatc tcactctgtg gtggtcctgc tgacaaatca   1920
agagcattgc ttttgtttct taagaaaaca aactcttttt taaaaattac ttttaaatat   1980
taactcaaaa gttgagattt tggggtggtg gtgtgccaag acattaattt tttttttaaa   2040
caatgaagtg aaaaagtttt acaatctcta ggtttggcta gttctcttaa cactggttaa   2100
attaacattg cataaacact tttcaagtct gatccatatt taataatgct ttaaaataaa   2160
aataaaaaca atccttttga taaatttaaa atgttactta ttttaaaata aatgaagtga   2220
gatggcatgg tgaggtgaaa gtatcactgg actaggaaga aggtgactta ggttctagat   2280
aggtgtcttt taggactctg attttgagga catcacttac tatccatttc ttcatgttaa   2340
aagaagtcat ctcaaactct tagttttttt tttttacaac tatgtaattt atattccatt   2400
tacataagga tacacttatt tgtcaagctc agcacaatct gtaaattttt aacctatgtt   2460
acaccatctt cagtgccagt cttgggcaaa attgtgcaag aggtgaagtt tatatttgaa   2520
tatccattct cgttttagga ctcttcttcc atattagtgt catcttgcct ccctaccttc   2580
cacatgcccc atgacttgat gcagttttaa tacttgtaat tcccctaacc ataagattta   2640
ctgctgctgt ggatatctcc atgaagtttt cccactgagt cacatcagaa atgccctaca   2700
tcttatttcc tcagggctca agagaatctg acagatacca taaagggatt tgacctaatc   2760
actaattttc aggtggtggc tgatgctttg aacatctctt tgctgcccaa tccattagcg   2820
acagtaggat ttttcaaacc tggtatgaat agacagaacc ctatccagtg gaaggagaat   2880
ttaataaaga tagtgctgaa agaattcctt aggtaatcta taactaggac tactcctggt   2940
aacagtaata cattccattg ttttagtaac cagaaatctt catgcaatga aaaatacttt   3000
aattcatgaa gcttactttt tttttttggt gtcagagtct cgctcttgtc acccaggctg   3060
gaatgcagtg gcgccatctc agctcactgc aacctccatc tcccaggttc aagcgattct   3120
```

-continued

```
cgtgcctcgg cctcctgagt agctgggatt acaggcgtgt gccactacac tcaactaatt   3180

tttgtatttt taggagagac ggggtttcac cctgttggcc aggctggtct cgaactcctg   3240

acctcaagtg attcacccac cttggcctca taaacctgtt ttgcagaact catttattca   3300

gcaaatattt attgagtgcc taccagatgc cagtcaccgc acaaggcact gggtatatgg   3360

tatccccaaa caagagacat aatcccggtc cttaggtagt gctagtgtgg tctgtaatat   3420

cttactaagg cctttggtat acgacccaga gataacacga tgcgtatttt agttttgcaa   3480

agaaggggtt tggtctctgt gccagctcta taattgtttt gctacgattc cactgaaact   3540

cttcgatcaa gctactttat gtaaatcact tcattgtttt aaaggaataa acttgattat   3600

attgtttttt tatttggcat aactgtgatt cttttaggac aattactgta cacattaagg   3660

tgtatgtcag atattcatat tgacccaaat gtgtaatatt ccagttttct ctgcataagt   3720

aattaaaata tacttaaaaa ttaatagttt tatctgggta caaataaaca ggtgcctgaa   3780

ctagttcaca gacaaggaaa cttctatgta aaaatcacta tgatttctga attgctatgt   3840

gaaactacag atctttggaa cactgtttag gtagggtgtt aagacttaca cagtacctcg   3900

tttctacaca gagaaagaaa tggccatact tcaggaactg cagtgcttat gaggggatat   3960

ttaggcctct tgaatttttg atgtagatgg gcattttttt aaggtagtgg ttaattacct   4020

ttatgtgaac tttgaatggt ttaacaaaag atttgttttt gtagagattt taaaggggga   4080

gaattctaga aataaatgtt acctaattat tacagcctta aagacaaaaa tccttgttga   4140

agttttttta aaaaaagcta aattacatag acttaggcat taacatgttt gtggaagaat   4200

atagcagacg tatattgtat catttgagtg aatgttccca agtaggcatt ctaggctcta   4260

tttaactgag tcacactgca taggaattta gaacctaact tttataggtt atcaaaactg   4320

ttgtcaccat tgcacaattt tgtcctaata tatacataga aactttgtgg ggcatgttaa   4380

gttacagttt gcacaagttc atctcatttg tattccattg attttttttt tcttctaaac   4440

atttttcttt caaacagtat ataacttttt ttaggggatt ttttttaga cagcaaaaac    4500

tatctgaaga tttccatttg tcaaaaagta atgatttctt gataattgtg tagtaatgtt   4560

ttttagaacc cagcagttac cttaaagctg aatttatatt tagtaacttc tgtgttaata   4620

ctggatagca tgaattctgc attgagaaac tgaatagctg tcataaaatg aaactttctt   4680

tctaaagaaa gatactcaca tgagttcttg aagaatagtc ataactagat taagatctgt   4740

gttttagttt aatagtttga agtgcctgtt tgggataatg ataggtaatt tagatgaatt   4800

taggggaaaa aaaagttatc tgcagatatg ttgagggccc atctctcccc ccacaccccc   4860

acagagctaa ctgggttaca gtgttttatc cgaaagtttc caattccact gtcttgtgtt   4920

ttcatgttga aaatactttt gcatttttcc tttgagtgcc aatttcttac tagtactatt   4980

tcttaatgta acatgtttac ctggaatgta ttttaactat ttttgtatag tgtaaactga   5040

aacatgcaca ttttgtacat tgtgctttct tttgtgggac atatgcagtg tgatccagtt   5100

gttttccatc atttggttgc gctgacctag gaatgttggt catatcaaac attaaaaatg   5160

accactcttt taattgaaat taacttttaa atgtttatag gagtatgtgc tgtgaagtga   5220

tctaaaattt gtaatatttt tgtcatgaac tgtactactc ctaattattg taatgtaata   5280

aaaatagtta cagtgacaaa aaaaaaaaaa aa                                   5312
```

```
<210> SEQ ID NO 4
<211> LENGTH: 188
<212> TYPE: PRT
<213> ORGANISM: Homo sapiens
```

-continued

<400> SEQUENCE: 4

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 5
<211> LENGTH: 661
<212> TYPE: DNA
<213> ORGANISM: Rattus norvegicus

<400> SEQUENCE: 5

```
atgactgagt ataaacttgt ggtagttgga gctggtggcg taggcaagag tgccttgacg     60

atacagctaa ttcagaatca ctttgtggat gaatatgatc ctacgataga ggactcctac    120

aggaaacaag tagtaattga tggagaaacc tgtctcttgg atattctcga cacagcaggt    180

caagaggagt acagtgcaat gagggaccag tacatgagaa ctggggaggg ctttctttgt    240

gtatttgcca taaataatac taaatcattt gaagatattc accattatag agaacaaatt    300

aaaagagtaa aggactctga agatgtgcct atggtcctag tagggaataa gtgtgacttg    360

ccttctagaa cagtagacac gaaacaggct caggagttag caaggagtta tgggattcca    420

ttcattgaga cctcagcgaa gacaagacag ggtgttgacg atgccttcta tacattagtc    480

cgagaaattc gaaaacataa agaaaagatg agcaaagatg ggaaaaagaa gaagaagaag    540

tcaaggacaa ggtgtatagt catgtgaata gtttgtactc tttcttaagg cacacttaag    600

taaagtgtga tttttgtaca ttacactaaa ttattagcat ttgttttagc attacctaat    660

c                                                                    661
```

<210> SEQ ID NO 6
<211> LENGTH: 188
<212> TYPE: PRT
<213> ORGANISM: Rattus norvegicus

<400> SEQUENCE: 6

-continued

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Glu Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Arg Thr Arg Cys Ile Val Met
            180                 185
```

<210> SEQ ID NO 7
<211> LENGTH: 4670
<212> TYPE: DNA
<213> ORGANISM: Mus musculus

<400> SEQUENCE: 7

```
aggcggcggc cgcggcggct gaggcggcag cgctgtggcg gcggctgaga cggcagggga     60

aggcggcggc ggctcggccc ggagtcccgc tcccgcgcca tttcggaccc ggagcgagcg    120

cggcgcgggc ctgaaggcgg cggcgggagc ctgaggcgcg gcggctccgc ggcgcggaga    180

gaggcctgct gaaaatgact gagtataaac ttgtggtggt tggagctggt ggcgtaggca    240

agagcgcctt gacgatacag ctaattcaga atcactttgt ggatgagtat gaccctacga    300

tagaggactc ctacaggaaa caagtagtaa ttgatggaga aacctgtctc ttggatattc    360

tcgacacagc aggtcaagag gagtacagtg caatgaggga ccagtacatg agaactgggg    420

agggctttct ttgtgtattt gccataaata atactaaatc atttgaagat attcaccatt    480

atagagaaca aattaaaaga gtaaaggact ctgaagatgt gcctatggtc ctggtaggga    540

ataagtgtga tttgccttct agaacagtag acacgaaaca ggctcaggag ttagcaagga    600

gttacgggat tccgttcatt gagacctcag caaagacaag acagggtgtt gacgatgcct    660

tctatacatt agtccgagaa attcgaaaac ataaagaaaa gatgagcaaa gatgggaaga    720

agaagaagaa gaagtcaagg acaaggtgta cagttatgtg aatactttgt actctttctt    780

aaggcacact taagtaaaag tgtgattttt gtacattaca ctaaattatt agcatttgtt    840

ttagcattac ctaatctttt tttttcttct gttcgtgcaa actgtcagct tttatctcaa    900

atgcttattt taaaagaaca gtggaaacct tctttttttct aagtgccagt attccctggg    960

ttttggactt aaactagcaa tgcctgtgga agagactaaa gacctgagac tctgtcttgg   1020

gatttggtgc atgcagttga ttccttgcta gttctcttac caactgtgaa cactgatggg   1080
```

-continued

```
aagcaggata atgaagcttc cggaccatcc ctgctctgtg tccatctact catccaatgg   1140
agtcattagc agtcaatcgc cgcttcactg gacactgagg ggtcacagac ttaggctccc   1200
tttgagtcgc gtccagcgtg tcctagactt tatcatcttt cagaggcgta ggcagactgt   1260
tcacaaaggc tttctgtagc tttccactgc aattaatctt ggtcactccc tcaaatagta   1320
tattttttct agaaaagggg aaaaatggaa aaaaaaaggc aatggaaaat gttgaaatcc   1380
attcagtttc catgttagct aaattactgt aagattccta taatagcttt tcctggtaag   1440
gcagacccag tatgaaatag taataaccat ttgggctata tttacatgct actaaatttt   1500
tgtaataatt caaacaactt tagcatatat aaaaagttct cataagaatt aagtacaatt   1560
ccccttttgtc agattgttct tatcctaact ttcaagtctt ttttgaattt ctgttgttga   1620
aagtagtttt aatggttgtg aagctgaaga tgatctgaga cagttatagc ttggcaggtg   1680
ttgaggagac cagagttgca gggttgggcc ttacgtgaac ctgtgacgaa cgctactggg   1740
ttttgcagca ctgctgcatt caatgttggc gacgcattgt ttggtcaaca taggggataa   1800
ggagactttg atggcttagt ataatgcatt ctcaccatgt aacagtccta ctgacaaatc   1860
aagaaatttg tttataataa taaaaaattt ttaaaaattt cgatgttcgc ttcaaggttg   1920
agattttggg gtaggaggct acaacaagag taaatcttaa agcaaggttt taagaaggtt   1980
tgaaaatgca ggtttgacta gtctctcaac tctagctaaa caaacattcc caagtacttc   2040
ccaaatctga taggtattta aaattatcta atgctttaag aatagttaac aggaaaaaaa   2100
tctcctcagt gcacttaaag caacccttca catcatttga aatgagatgg aaatatcact   2160
ggactatgag gactggatgt ctgtctgatt ttaagcaaat cactgtctgc ttggttttga   2220
atcatctcaa agacattaac ctcccagccg tgtaacatag tttacatgtt gacacaccta   2280
gttatcaagc tcagcacaat ctgtaactgt tttacatgga ttaacatctt cactgccagt   2340
cttgggcaaa ttgtgcaaga ggtaaaattt atatttcagt atccattctc ccatttcagg   2400
actcccctcc aacattatgc tggctttcag cctgtctctc acctgcccat cacttagtgt   2460
agttttaata atttccccca cttcaaactt tgtttccact atggacaact tcatgaactt   2520
tgcccactaa ggtaggtaca tcaaagctgc cctatggctt tcttccccgg gactgaaaat   2580
aacagacacc atagtgggat ttaaactaat agatggtttt cagggccact acaacaattc   2640
aatctcaatc ctttggactt cattcctgct gcccaggcca ctggtgcctc agtaggaatt   2700
ttcaaaatta gtgtgaacag acagagcaca gtccagtgga aggtgagctt aatcttcatc   2760
tagccatcat catggtaagt gatagattct attgttttaa taaatacagt ctaacaatga   2820
aaaacacttc gaagtttcaa tcataaagct gtctttttaa aaattttatt tactcaacat   2880
ttattcagtg cttgtcatat tctgggaatt acactaggca ctcagggtgc ggtgtcctca   2940
atccttggcc agtggtatgt agcatgatct gtaataccac taaataaggc atatagcata   3000
tgacttagac ataatgaaat acatgatttg agttttgcag agaggagttt gggtttgtac   3060
attcccttcc cccccagttt agcaagaatt gtttgctgtg aatccaatgc aacttttaaa   3120
tcaaactact ttatataatt atttcatttt tctaaaggaa cagaagtacc ctaaactatt   3180
tttttgaaat gttctaaact gtacatattc atagaacatt ctttgggtga attttaagtc   3240
ttaaaatgca attagtaata cttctcattt ctattcagag gaacaggtgt acttcaaaag   3300
ctgcagtgta taatcagata tttttaatgg acaatgtgtt aaagaagtgg taattaccac   3360
tatgtaaatt tgaattgtgt tacactttgg ttaacaaaag gggaaagaat cctagaaaca   3420
```

-continued

```
aatatgttat ctagttactg cagccttaaa gtccttgttg aagttaaaaa gcaatgctaa   3480

gttacagtca taggcattaa catgtttatg ggaaggatat agtaggcaaa tacaatttga   3540

gtaaatattt tcagtaggga attttaggct ctactgactg agtcacactg cataggaatt   3600

tagatcttaa cttttatagg ttatcgacct ttgccaccat tgcacaattt tgtcctaaca   3660

taaatacaag ttctgtgagg catgtcaaaa gttacagttt gcataaattc atctcatttt   3720

gtattccact gattttacat tttcctcaaa catacataca tacatacata caacacacac   3780

acactcacac atgaagggtt tttttttgt aggcaataaa aatttaacta atttccattt   3840

gttaaaaagt agtgatttat tgagaattat gcagtcattt tttaaaccca aaagttattt   3900

aaaggtgaat ttatactcaa taacttctgt gtaatactgg gtagcatgaa ttctgcattg   3960

aaaaattgaa cagataatac caatagctgt aaattctgtc aaaacatgaa aattatttct   4020

aaagaagtac attagttttc aaagaacagt tattagaatc agatctgtgg tttagttcaa   4080

taatttgaag tgcctgtttg ggatggtggt aggcatttta gatgaatttg ggaaaaataa   4140

agttctgcag aaatgccagt ttcagacccc gctaacccgc tgagtgggct gtgtgctgtg   4200

ttagctccag tgccccaatc ccgtttcatg tcttcatgtt gaaacacttc tgcattttta   4260

tttgagtgcc aatttcttac tagtgctatt tcttagtgta acatgtttac ctgggatgta   4320

ttttaactat ttttgtatag tgtaaactga aacatgcaca ttttgtacat tgtgctttcc   4380

ttctttccat tccttttctt tctgttttgt ttgtttgttt gtttgtttgt ttgttatggg   4440

acatatgcag tgtgatccag ttgttttcca tcctttggtt gcgctgacct agggaatgtt   4500

ggtcatatca aacattaaat ttaaaagtga ccactcttaa ttaaaattaa cttttaaatg   4560

tttataggag tacgtgctgt gaagtgatct gaaatttgta atatttttgt catgaaccgt   4620

actgctccta atcattgtaa tgtaataaaa atagttatgg tgactatgaa              4670
```

<210> SEQ ID NO 8
<211> LENGTH: 188
<212> TYPE: PRT
<213> ORGANISM: Mus musculus

<400> SEQUENCE: 8

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Glu Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160
```

```
Arg Glu Ile Arg Lys His Lys Glu Lys Met Ser Lys Asp Gly Lys Lys
                165                 170                 175

Lys Lys Lys Lys Ser Arg Thr Arg Cys Thr Val Met
            180                 185


<210> SEQ ID NO 9
<211> LENGTH: 2068
<212> TYPE: DNA
<213> ORGANISM: Oryctolagus cuniculus

<400> SEQUENCE: 9

acacacgcgc ccacccagcc acccggccac cagccgccat gggcaaggac aggcagcccc     60

gcgggcagca gaggcagggg gacgccgccg ggcccgacga cccggggccg aagaaaggcg    120

ccgggacccg cgagcagcgc ggggaggagg aggcccagac gtgctgcggc tgccgcttcc    180

cgctgctgct cgcgctgctg cagctggccc tgggcgtcgc cgtgaccgtg gtgggcttcc    240

tcatggcgag cgtcagctcc tccctgctag tcagagccac tccatattgg gctgggatca    300

ttgtctgcgt ggtggcctat cttggcttgt ttatgctttg tgtctcgtac caagttgatg    360

aacggacgtg tatccagttt tctatgaaac tgctgtactt cgtgctgagc gccctggggc    420

tggtggtgtg cgtgctggcc gtggccttcg ccgcccacca ctactcgctg ctcacgcacc    480

tgacctgtga gaacgccccc gactcctgcc agtgcaagct gccgtcctcg gagccgctga    540

gccggacctt cgtgtaccgg gatgtgactg actgtaccag catcacgggc accttccagg    600

tgttcctgct cgtccagatg gttctgaact tggtctgtgg ccttgtgtgc ttggtggcct    660

gctttgtgat gtggaaacac aggtatcagg tcttttatgt gggggtcagg atgtgccccc    720

tgtcggcttc cgaaggccag cagcagaagg tgtaggaatc ttgctcagaa ttgggagaga    780

aaatggcaca ctggctagct gaggttaaaa agaaaaatta tttttaagga gaaagagaga    840

aaacttttgc caatatttac tgctctaaat gaatattttt tatatttttc aagaaacaaa    900

agagcatttc ttcaggtttc tattgtattt ttaaacattc gtataggttc aacaagatac    960

acattgattt gcgggatatt caaagtcaaa agcacaccaa actgggaagc aatggcacag   1020

aactgtcctc acagtctggg gtttactctt catgctcact ttcgccacca ctgacgtacg   1080

gctttctggt taatacggtc taaggtttgt agtggctgcc ccaggtcctt cccgcctcct   1140

accacaatcc cccactgcgt cttagagaaa ggcaaggtgt ggagaagtca ctgggcaacc   1200

aggtggaatc tcttcatttc ccctactgcg gatgttgtca aggcccaaaa catgagcgaa   1260

cttcaaaaac ctcatgggaa gtggagttcg aagtttattt tgctgccaaa aaattaagat   1320

ccacacatat atagggatct tcagaaagtt cacagaaaat gcataatatg ggaaaaaaaa   1380

agattcacgg atttcagaat tttgtttgga ccaaactaaa gttatctttt aatgccattt   1440

ctgaagtgcc ctcatagctt ggaaagccaa gcagaaaaga ggctttgcaa aaatacaagt   1500

aattataaac acctgggcca gggcggctgt ctcagctgcc ttcgcttggc tctgtacgta   1560

gatcactcgc gcggggcttg gcagggctct ctgcttctca ataattgaaa tatggtggta   1620

gttgtattct taatgatgta gaaggtttaa aaataattac attacgcttc cattctatca   1680

tctacaacaa atcattcaac ctaatttcta gctaattgtt aattataatt atgctcagaa   1740

gtctatttaa tgagctctgg ctgtacttag gcagctctgc cagtgtaaag agaaattatt   1800

ctcgtaagag aagaggccta aagattcttt cttctgaaag tcaagcgtta taagggaaaa   1860

ctttttttta attaatagct caggataaaa acaccaattt aaacaaaaac aagagcattt   1920
```

-continued

```
ataataggaa gtacttgtac aaatagcacg tttgtggcac attgcagagt gtctctcttt   1980

gcagctaaat agctttgaag aaggctggcg agtgcagatg tattctgtgc acaaaactgt   2040

atttggctca taaccctatt attgattc                                      2068


<210> SEQ ID NO 10
<211> LENGTH: 238
<212> TYPE: PRT
<213> ORGANISM: Oryctolagus cuniculus

<400> SEQUENCE: 10

Met Gly Lys Asp Arg Gln Pro Arg Gly Gln Gln Arg Gln Gly Asp Ala
1               5                   10                  15

Ala Gly Pro Asp Asp Pro Gly Pro Lys Lys Gly Ala Gly Thr Arg Glu
            20                  25                  30

Gln Arg Gly Glu Glu Glu Ala Gln Thr Cys Cys Gly Cys Arg Phe Pro
        35                  40                  45

Leu Leu Leu Ala Leu Leu Gln Leu Ala Leu Gly Val Ala Val Thr Val
    50                  55                  60

Val Gly Phe Leu Met Ala Ser Val Ser Ser Ser Leu Leu Val Arg Ala
65                  70                  75                  80

Thr Pro Tyr Trp Ala Gly Ile Ile Val Cys Val Val Ala Tyr Leu Gly
                85                  90                  95

Leu Phe Met Leu Cys Val Ser Tyr Gln Val Asp Glu Arg Thr Cys Ile
            100                 105                 110

Gln Phe Ser Met Lys Leu Leu Tyr Phe Val Leu Ser Ala Leu Gly Leu
        115                 120                 125

Val Val Cys Val Leu Ala Val Ala Phe Ala Ala His His Tyr Ser Leu
    130                 135                 140

Leu Thr His Leu Thr Cys Glu Asn Ala Pro Asp Ser Cys Gln Cys Lys
145                 150                 155                 160

Leu Pro Ser Ser Glu Pro Leu Ser Arg Thr Phe Val Tyr Arg Asp Val
                165                 170                 175

Thr Asp Cys Thr Ser Ile Thr Gly Thr Phe Gln Val Phe Leu Leu Val
            180                 185                 190

Gln Met Val Leu Asn Leu Val Cys Gly Leu Val Cys Leu Val Ala Cys
        195                 200                 205

Phe Val Met Trp Lys His Arg Tyr Gln Val Phe Tyr Val Gly Val Arg
    210                 215                 220

Met Cys Pro Leu Ser Ala Ser Glu Gly Gln Gln Gln Lys Val
225                 230                 235


<210> SEQ ID NO 11
<211> LENGTH: 1039
<212> TYPE: DNA
<213> ORGANISM: Cavia porcellus

<400> SEQUENCE: 11

ggtggcttct cggccagacc tcccggcccc cgccatttcg gaccgggagc cagcgcgacg     60

cgggcactga gggcggcggc gggggccaca ggctcggcgg ctcccaggtg cgggagagag    120

gcctgctgaa aatgactgaa tataaacttg tggtagttgg agctggtggc gtaggcaaga    180

gtgccttgac gatacagcta attcagaatc actttgtgga tgaatatgat cctacaatag    240

aggattccta caggaaacaa gtagtaattg atggagaaac ctgtctcttg gatattctcg    300

acacagcagg tcaagaggag tacagtgcaa tgagggacca gtacatgagg actggggagg    360
```

-continued

```
gctttctttg tgtatttgcc ataaataata ctaaatcttt tgaagatatt caccattata    420

gagaacaaat taaaagagtt aaagactctg aagatgtacc tatggtccta gtaggaaata    480

aatgtgattt gccttctaga acagtagaca caaaacaagc tcaggactta gcaagaagtt    540

atggaattcc ttttattgaa acatcagcaa agacaagaca gagagtggag gatgcttttt    600

atacattggt gagagagatt cgacaataca gattgaaaaa aatcagcaaa gaagaaaaga    660

ctcctggctg tgtgaaaatt aaaaaatgca ttataatggg tgttgatgat gccttctata    720

cgttagttcg agaaattcga aaacataaag aaaagatgag caaagatggt aaaaagaaga    780

aaaagaagtc gaagacaaag tgtataatta tgtaaataca atttgtactt ttttcttaag    840

gcatacttaa gtaaaagtgg taatttttgt acattacact aaattattag cttttgtttt    900

agcattactt aattcttttc ctatttcatg caaactgtta gcttttatct taaatgctca    960

ttttaaaatg acagtggaaa ccttttattt cctcttaagt gccagtattc cctgcatttt   1020

ggtttttgaa ctagcaatg                                                1039


<210> SEQ ID NO 12
<211> LENGTH: 227
<212> TYPE: PRT
<213> ORGANISM: Cavia porcellus

<400> SEQUENCE: 12

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met Gly Val Asp
            180                 185                 190

Asp Ala Phe Tyr Thr Leu Val Arg Glu Ile Arg Lys His Lys Glu Lys
        195                 200                 205

Met Ser Lys Asp Gly Lys Lys Lys Lys Lys Lys Ser Lys Thr Lys Cys
    210                 215                 220

Ile Ile Met
225


<210> SEQ ID NO 13
```

<211> LENGTH: 835
<212> TYPE: DNA
<213> ORGANISM: Cavia porcellus

<400> SEQUENCE: 13
acaggctcgg cggctcccag gtgcgggaga gaggcctgct gaaaatgact gaatataaac 60
ttgtggtagt tggagctggt ggcgtaggca agagtgcctt gacgatacag ctaattcaga 120
atcactttgt ggatgaatat gatcctacaa tagaggattc ctacaggaaa caagtagtaa 180
ttgatggaga aacctgtctc ttggatattc tcgacacagc aggtcaagag gagtacagtg 240
caatgaggga ccagtacatg aggactgggg agggctttct ttgtgtattt gccataaata 300
atactaaatc ttttgaagat attcaccatt atagagaaca aattaaaaga gttaaagact 360
ctgaagatgt acctatggtc ctagtaggaa ataaatgtga tttgccttct agaacagtag 420
acacaaaaca agctcaggac ttagcaagaa gttatggaat tccttttatt gaaacatcag 480
caaagacaag acagggtgtt gatgatgcct tctatacgtt agttcgagaa attcgaaaac 540
ataaagaaaa gatgagcaaa gatggtaaaa agaagaaaaa gaagtcgaag acaaagtgta 600
taattatgta aatacaattt gtactttttt cttaaggcat acttaagtaa aagtggtaat 660
ttttgtacat tacactaaat tattagcttt tgttttagca ttacttaatt cttttcctat 720
ttcatgcaaa ctgttagctt ttatcttaaa tgctcatttt aaaatgacag tggaaacctt 780
ttatttcctc ttaagtgcca gtattccctg cattttggtt tttgaactag caatg 835

<210> SEQ ID NO 14
<211> LENGTH: 188
<212> TYPE: PRT
<213> ORGANISM: Cavia porcellus

<400> SEQUENCE: 14

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Ile Ile Met
            180                 185
```

<210> SEQ ID NO 15
<211> LENGTH: 4993
<212> TYPE: DNA
<213> ORGANISM: Canis lupus familiaris

<400> SEQUENCE: 15
gctgaaaatg actgaatata aacttgtggt agttggagct ggtggcgtag gcaagagtgc 60
cttgacgata cagctaattc agaatcactt tgtggatgaa tatgatccta caatagagga 120
ttcctacagg aaacaagtag taattgatgg agaaacctgt ctcttggata ttctcgacac 180
agcaggtcaa gaggagtaca gtgcaatgag ggaccagtac atgaggactg gggagggctt 240
tctttgtgta tttgccataa ataatactaa atcatttgaa gatattcacc attatagaga 300
acaaattaaa agagttaaag actctgaaga tgtacctatg gtcctagtag gaaataaatg 360
tgatttgcct tctagaacag tagacacaaa acaggctcag gacttagcaa gaagttatgg 420
aattcctttt attgaaacat cagcaaagac aagacagaga gtggaggatg ctttttatac 480
attggtgaga gagatccgac aatacagatt gaaaaaaatc aacaaagaag aaaagactcc 540
tggctgtgtg aaaattaaaa aatgcattgt aatgggtgtt gacgatgcct tctatacatt 600
agttcgagaa attcgaaaac ataaagaaaa gatgagcaaa gatggtaaaa agaagaaaaa 660
gaagtcaaag acaaagtgta taattatgta aatacaattt gtactttttt cttaaggcat 720
acttaagtaa aagtggtaat ttttgtacat tacactaaat tattagcatt tgttttagca 780
ttacctaatt ttctgctcca tccaaactgt tagcttttat cttgaatgct tattttaaaa 840
tgacagtgga aactttttcc tctaagtgcc agtattccct gagttttggt tttgaactag 900
caatgcctgt gaaaaagaaa ctgaatacct gagatttctg tcttggggtt tttggtgcat 960
gcagttgatt acttcctatt tttcttacca attgtgaact ttggtgtgaa acaaattaat 1020
gaagctttcg aatcatccct attctgtgtt ttacctagtc acatacatgg attaattact 1080
aattataact tcagttgata tttcatgatt ggttttactg aaacattgag ggaacatgaa 1140
tttatgggct gcttcttata ggtataatgt cctatagttt cagtcaccct taatgaatgt 1200
aaagctacac tgttcacaaa ggttttctcc atcttttcac tgctatttgt catagccacg 1260
ctcccaaaaa tattatattt tttctataaa aaagggaaaa aatagaaaaa aatacaaggc 1320
aatggaaaat attaaaaggc atttactttc catattagat aaattcctat aatactctga 1380
atagcttttc ctgttaaggc agacccagta tgtaatgagg attatagcaa ccattttggg 1440
gctatattta catgctacta aatttttgta ttaattgaaa aagttttaac atgtataaaa 1500
aattcccata ggaattaaat atagtctccc tgtgtcagat tgctctttct tagcataact 1560
ttaaatcttt tcttgatctt caatcttaga aaatagtttt aattcttgta gtgatgttaa 1620
agattatttg ggccagttag tttttaatag atgttaaaga gaccacagtt ccaaggccag 1680
gccttgtgtg aacctttaag cttcattaag agtttcatag tacagactgc atccctgtgg 1740
tctcccaggg tcatcatgca ttgattgggt ggtcaaaagt ggggacaaag agtgtttaga 1800
taagatgcat cctcactgta tggtggtcct gctgacagat caggaccatc acttttgttt 1860
tttaaaaaac caacagagct ttttaaaaac attatttaaa atgagatttt tgggggcagg 1920
gggtggcaag acttgaattt tttttaaaca atgaagtaaa aaggtttcaa aatctctagt 1980
gttggctagt tctcaacatt ggctaaagta acatttcata aacactttac aagtattggt 2040
ccatatttaa gaatatctaa tgcttaaata atagattaat aacaattctt tcagtgcatt 2100
taaaatgtat ttttaaatat ctgaagtgag atggtgtgtt gaggtgaaaa tatcactgga 2160

-continued

```
ctaggaggaa ggtgacttag attctagtta cgtgtctttt acaacttcag ttttgggcaa   2220
atcactcact atccatttct tcatgttaag tcatctcaaa ggctatatct agcatcaact   2280
atgtgattta cattcagttt acataaggat atacctattt gtcaatctca gcacaatctg   2340
taacttttta cctatgttct cttcagcgcc agtcttaggc aaagttgtgc aagaggtgag   2400
gtttattttt gagaatctga tctccggtag caggtactcc tctcccatgt tagtgtcatc   2460
ttgcctgcct accttctaca tgccccatga cttgatgctt tctaattccc cgaacctcaa   2520
gatgtagtgc tgctttggat atctccatga ggtaataagt cacattagtc aggctcaaca   2580
taatctgaca gatactgtag tgggatttga tctaatagct aattttcagg tggtaactgt   2640
atcaatttaa ttttgatctt ttgaacatca tctctgctac ctggtccatt agtgactaag   2700
taggaaaagt aggaattttc atatctgtga tgtgtagaca gaccctatcc agtagaagaa   2760
tttaataaat ttaattaata aatactgaaa gatttcctta gataatccaa aactaggact   2820
agccctggta acggtgatac attccattat tttaataagt aaaatcttct tacaatgaaa   2880
aatactttaa aatttaattc ataaagctta ctttttagca gaattcattt attcaacaaa   2940
tacttgagtg cctgctagat gccaggttct acacaaggca ccggggatat tatggtattc   3000
ccaacaaggg acataatccc tatccttaag tagtactgtt attttagagt ggtctgtagt   3060
atattagtga ggcatttggc acatgaccca gagataatat aatgcatatt ttagttttgc   3120
acagaaggga tatggtctct aaggtttttt ccagctctaa aataattgtt cgctctgatt   3180
ccaataaact gtttaatcaa gctactttat ataaatcact ttacttcatt attttaaaga   3240
agtaaacttg actatattgt tttttatttg ggataattat gtgattctgt tgggatactt   3300
atatagtaca cattaaattg tatgtcagat gataacatta aaattcccaa gtgtaatatt   3360
ctacttggtc tctgtgtatc ataattaaaa tagatttaaa tattgagttc aaaaatagtt   3420
ttatttatct gggtgtgaat aaacagatgc ctgaactaat tcacagaaaa ggaaacttct   3480
gtgtaaaaag tcagtccaat ttctgaaatg ctatgctaaa ctacaggttt atggaacatt   3540
agatagggtg ttaagacttt atatagtact tcctcttgtt tctatacaag agaaagaaat   3600
ggccatactt caggaattgc agtgcataac tgagggattt ttaggactct tgaatttttg   3660
atgtagccgg gcaacttttt ttaggcagtg gtaattatcc tttattatgt gaattttgaa   3720
tggtttgaca aaacgtttgt ttttgtagag attttaaaag gggagcgcta atcctagaaa   3780
taaatattat gtaattatta cggccttaaa gataaaaatc cttgttgaaa gttgaaaaaa   3840
attgctaaat tacatagtct tagacattaa catgtttgtg gaagaatgta gcagaggtat   3900
gtagtataat ttgagtgaat attcccaatt aggaattcta ggctctagtt taactgagtc   3960
acactgcata ggaatttaga acctaacttc taggttatca aaatctttgc caccattgca   4020
caattttgtc ctaatatata gagaaacttt gtgaggcatg ttcagttgcg gtttgcacaa   4080
gttcatctca tttgtattcc agtgattttt tttcttctaa ccattttttt aaacaacatg   4140
tacacattgt tttttttggt aggcaatgaa aactgtcatt tccattgtca aacagtaatt   4200
cctcgataac tgtattaatg gtttttaaaa aaccatcagt tactttaaaa ctgaatttat   4260
atttaataac ttctgtatta gtattgggta gcatgaaatc tctattgaga aattgaacag   4320
catacaacta gtagctgtaa attccttcag aaagtgaaaa ttatttcttc ctaaagatat   4380
cttgacatca gtgcttgaag aatagtcata actagattaa taattgtttt agttaaacag   4440
ttttaagtgc ctgtttcaga tgatgatagg caatttagat gaatttagga aaatcaaag    4500
tttttacttg cagaaatgtc cattataggg ggcccccctc ctcatagagc tgaatgggtt   4560
```

atgtaatgtt ttatccaaaa gtttccaatt ccactgtctt gtgttttcat gttgaaaata 4620
cttttgcatt tttcctttga gtgccaattt cttactagta ctatttctta atgtaacatg 4680
tttacctgga atgtatttta actatttttg tatagtgtaa actgaaacat gcacattttg 4740
tacattgtgc tttttttgt gggacatatg cagtgtgatc cagttgtttt ccatcatttg 4800
gttgcgctga cctaggaatg ttggtcatat caaacattaa atttaaaaat gaccactctt 4860
ttaattaaaa ttaactttta aatgtttata ggagtatgtg ctgtgaagtg atctgaaatt 4920
tgtaatattt ttgtcatgaa ctgtactgct cctaattatt gtaatgtaat aaaaatagtt 4980
atggtgacta tga 4993

<210> SEQ ID NO 16
<211> LENGTH: 227
<212> TYPE: PRT
<213> ORGANISM: Canis lupus familiaris

<400> SEQUENCE: 16

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

Gln Ala Gln Asp Leu Ala Arg Ser Tyr Gly Ile Pro Phe Ile Glu Thr
130 135 140

Ser Ala Lys Thr Arg Gln Arg Val Glu Asp Ala Phe Tyr Thr Leu Val
145 150 155 160

Arg Glu Ile Arg Gln Tyr Arg Leu Lys Lys Ile Asn Lys Glu Glu Lys
165 170 175

Thr Pro Gly Cys Val Lys Ile Lys Lys Cys Ile Val Met Gly Val Asp
180 185 190

Asp Ala Phe Tyr Thr Leu Val Arg Glu Ile Arg Lys His Lys Glu Lys
195 200 205

Met Ser Lys Asp Gly Lys Lys Lys Lys Lys Lys Ser Lys Thr Lys Cys
210 215 220

Ile Ile Met
225

<210> SEQ ID NO 17
<211> LENGTH: 4876
<212> TYPE: DNA
<213> ORGANISM: Canis lupus familiaris

<400> SEQUENCE: 17
gctgaaaatg actgaatata aacttgtggt agttggagct ggtggcgtag gcaagagtgc 60

-continued

```
cttgacgata cagctaattc agaatcactt tgtggatgaa tatgatccta caatagagga   120
ttcctacagg aaacaagtag taattgatgg agaaacctgt ctcttggata ttctcgacac   180
agcaggtcaa gaggagtaca gtgcaatgag ggaccagtac atgaggactg ggagggcctt   240
tctttgtgta tttgccataa ataatactaa atcatttgaa gatattcacc attatagaga   300
acaaattaaa agagttaaag actctgaaga tgtacctatg gtcctagtag gaaataaatg   360
tgatttgcct tctagaacag tagacacaaa acaggctcag gacttagcaa gaagttatgg   420
aattcctttt attgaaacat cagcaaagac aagacagggt gttgacgatg ccttctatac   480
attagttcga gaaattcgaa aacataaaga aaagatgagc aaagatggta aaaagaagaa   540
aaagaagtca aagacaaagt gtataattat gtaaatacaa tttgtacttt tttcttaagg   600
catacttaag taaaagtggt aatttttgta cattacacta aattattagc atttgtttta   660
gcattaccta attttctgct ccatccaaac tgttagcttt tatcttgaat gcttatttta   720
aaatgacagt ggaaactttt tcctctaagt gccagtattc cctgagtttt ggttttgaac   780
tagcaatgcc tgtgaaaaag aaactgaata cctgagattt ctgtcttggg gtttttggtg   840
catgcagttg attacttcct atttttctta ccaattgtga actttggtgt gaaacaaatt   900
aatgaagctt tcgaatcatc cctattctgt gttttaccta gtcacataca tggattaatt   960
actaattata acttcagttg atatttcatg attggtttta ctgaaacatt gagggaacat  1020
gaatttatgg gctgcttctt ataggtataa tgtcctatag tttcagtcac ccttaatgaa  1080
tgtaaagcta cactgttcac aaaggttttc tccatctttt cactgctatt tgtcatagcc  1140
acgctcccaa aaatattata ttttttctat aaaaaaggga aaaaatagaa aaaaatacaa  1200
ggcaatggaa aatattaaaa ggcatttact ttccatatta gataaattcc tataatactc  1260
tgaatagctt ttcctgttaa ggcagaccca gtatgtaatg aggattatag caaccatttt  1320
ggggctatat ttacatgcta ctaaattttt gtattaattg aaaaagtttt aacatgtata  1380
aaaaattccc ataggaatta aatatagtct ccctgtgtca gattgctctt tcttagcata  1440
actttaaatc ttttcttgat cttcaatctt agaaaatagt tttaattctt gtagtgatgt  1500
taaagattat ttgggccagt tagtttttaa tagatgttaa agagaccaca gttccaaggc  1560
caggccttgt gtgaaccttt aagcttcatt aagagtttca tagtacagac tgcatccctg  1620
tggtctccca gggtcatcat gcattgattg ggtggtcaaa agtggggaca aagagtgttt  1680
agataagatg catcctcact gtatggtggt cctgctgaca gatcaggacc atcacttttg  1740
ttttttaaaa aaccaacaga gctttttaaa aacattattt aaaatgagat tttgggggc  1800
agggggtggc aagacttgaa tttttttaa acaatgaagt aaaaaggttt caaaatctct  1860
agtgttggct agttctcaac attggctaaa gtaacatttc ataaacactt tacaagtatt  1920
ggtccatatt taagaatatc taatgcttaa ataatagatt aataacaatt ctttcagtgc  1980
atttaaaatg tatttttaaa tatctgaagt gagatggtgt gttgaggtga aaatatcact  2040
ggactaggag gaaggtgact tagattctag ttacgtgtct tttacaactt cagttttggg  2100
caaatcactc actatccatt tcttcatgtt aagtcatctc aaaggctata tctagcatca  2160
actatgtgat ttacattcag tttacataag gatataccta tttgtcaatc tcagcacaat  2220
ctgtaacttt ttacctatgt tctcttcagc gccagtctta ggcaaagttg tgcaagaggt  2280
gaggtttatt tttgagaatc tgatctccgg tagcaggtac tcctctccca tgttagtgtc  2340
atcttgcctg cctaccttct acatgcccca tgacttgatg ctttctaatt ccccgaacct  2400
```

-continued

```
caagatgtag tgctgctttg gatatctcca tgaggtaata agtcacatta gtcaggctca   2460
acataatctg acagatactg tagtgggatt tgatctaata gctaattttc aggtggtaac   2520
tgtatcaatt taattttgat cttttgaaca tcatctctgc tacctggtcc attagtgact   2580
aagtaggaaa agtaggaatt ttcatatctg tgatgtgtag acagacccta tccagtagaa   2640
gaatttaata aatttaatta ataaatactg aaagatttcc ttagataatc caaaactagg   2700
actagccctg gtaacggtga tacattccat tattttaata agtaaaatct tcttacaatg   2760
aaaaatactt taaaatttaa ttcataaagc ttacttttta gcagaattca tttattcaac   2820
aaatacttga gtgcctgcta gatgccaggt tctacacaag gcaccgggga tattatggta   2880
ttcccaacaa gggacataat ccctatcctt aagtagtact gttattttag agtggtctgt   2940
agtatattag tgaggcattt ggcacatgac ccagagataa tataatgcat attttagttt   3000
tgcacagaag ggatatggtc tctaaggttt tttccagctc taaaataatt gttcgctctg   3060
attccaataa actgtttaat caagctactt tatataaatc actttacttc attattttaa   3120
agaagtaaac ttgactatat tgttttttat ttgggataat tatgtgattc tgttgggata   3180
cttatatagt acacattaaa ttgtatgtca gatgataaca ttaaaattcc caagtgtaat   3240
attctacttg gtctctgtgt atcataatta aaatagattt aaatattgag ttcaaaaata   3300
gttttattta tctgggtgtg aataaacaga tgcctgaact aattcacaga aaaggaaact   3360
tctgtgtaaa aagtcagtcc aatttctgaa atgctatgct aaactacagg tttatggaac   3420
attagatagg gtgttaagac tttatatagt acttcctctt gtttctatac aagagaaaga   3480
aatggccata cttcaggaat tgcagtgcat aactgaggga tttttaggac tcttgaattt   3540
ttgatgtagc cgggcaactt tttttaggca gtggtaatta tcctttatta tgtgaatttt   3600
gaatggtttg acaaaacgtt tgtttttgta gagattttaa aaggggagcg ctaatcctag   3660
aaataaatat tatgtaatta ttacggcctt aaagataaaa atccttgttg aaagttgaaa   3720
aaaattgcta aattacatag tcttagacat taacatgttt gtggaagaat gtagcagagg   3780
tatgtagtat aatttgagtg aatattccca attaggaatt ctaggctcta gtttaactga   3840
gtcacactgc ataggaattt agaacctaac ttctaggtta tcaaaatctt tgccaccatt   3900
gcacaatttt gtcctaatat atagagaaac tttgtgaggc atgttcagtt gcggtttgca   3960
caagttcatc tcatttgtat tccagtgatt ttttttcttc taaccatttt tttaaacaac   4020
atgtacacat tgtttttttt ggtaggcaat gaaaactgtc atttccattg tcaaacagta   4080
attcctcgat aactgtatta atggttttta aaaaaccatc agttacttta aaactgaatt   4140
tatatttaat aacttctgta ttagtattgg gtagcatgaa atctctattg agaaattgaa   4200
cagcatacaa ctagtagctg taaattcctt cagaaagtga aaattatttc ttcctaaaga   4260
tatcttgaca tcagtgcttg aagaatagtc ataactagat taataattgt tttagttaaa   4320
cagttttaag tgcctgtttc agatgatgat aggcaattta gatgaattta ggaaaaatca   4380
aagtttttac ttgcagaaat gtccattata gggggccccc ctcctcatag agctgaatgg   4440
gttatgtaat gttttatcca aaagtttcca attccactgt cttgtgtttt catgttgaaa   4500
atacttttgc atttttcctt tgagtgccaa tttcttacta gtactatttc ttaatgtaac   4560
atgtttacct ggaatgtatt ttaactattt ttgtatagtg taaactgaaa catgcacatt   4620
ttgtacattg tgcttttttt tgtgggacat atgcagtgtg atccagttgt tttccatcat   4680
ttggttgcgc tgacctagga atgttggtca tatcaaacat taaatttaaa aatgaccact   4740
cttttaatta aaattaactt ttaaatgttt ataggagtat gtgctgtgaa gtgatctgaa   4800
```

atttgtaata tttttgtcat gaactgtact gctcctaatt attgtaatgt aataaaaata 4860
gttatggtga ctatga 4876

<210> SEQ ID NO 18
<211> LENGTH: 188
<212> TYPE: PRT
<213> ORGANISM: Canis lupus familiaris

<400> SEQUENCE: 18

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

Gln Ala Gln Asp Leu Ala Arg Ser Tyr Gly Ile Pro Phe Ile Glu Thr
130 135 140

Ser Ala Lys Thr Arg Gln Gly Val Asp Asp Ala Phe Tyr Thr Leu Val
145 150 155 160

Arg Glu Ile Arg Lys His Lys Glu Lys Met Ser Lys Asp Gly Lys Lys
165 170 175

Lys Lys Lys Lys Ser Lys Thr Lys Cys Ile Ile Met
180 185

<210> SEQ ID NO 19
<211> LENGTH: 1394
<212> TYPE: DNA
<213> ORGANISM: Felis catus

<400> SEQUENCE: 19
gctgaaaatg actgaatata aacttgtggt agttggagct ggtggcgtag gcaagagtgc 60
cttgacgata cagctaattc agaatcactt tgtggatgaa tatgatccta caatagagga 120
ttcctacagg aaacaagtag taattgatgg agaaacctgt ctcttggata ttctcgacac 180
agcaggtcaa gaggagtaca gtgcaatgag ggaccagtac atgaggactg gggagggctt 240
tctttgcgta tttgccataa ataatactaa atcatttgaa gatattcacc actatagaga 300
acaaataaaa agagttaaag actctgaaga tgtacctatg gtcctagtag gaaataaatg 360
tgatttgcct tctagaacag tagatacaaa acaggctcag gacttagcaa gaagttatgg 420
aattcctttt attgaaacat cagcaaagac aagacagggt gttgacgatg ccttctatac 480
attagttcga gaaattcgaa aacataaaga aaagatgagc aaagatggta aaaagaagaa 540
aaagaagtca aagacaaagt gtataattat gtaaatacaa tttgtacttt tttcttaagg 600
catacttaag taaaagtggt aatttttgta cattacacta aattattagc atttgtttta 660

```
gcattaccta attttctgct ccatccaaac tgttagcttt tatcttgaat gcttatttta    720

aatgacagtg gaaacttttt ttcctctaag tgccagtatt ccctgagttt tggtttttga    780

actagcaatg cctgtgaaaa agaaactgaa tacctgagat ttctgtcttg gggtttttgg    840

tgcatgcagt tgattacttc ctatttttct taccaattgt gaactttggt gtgaaacaaa    900

ttaatgaaac tttcgaatca tccctattct gtgtttcatg tagtcacata catggattaa    960

ttactaatta taacttcagt tgagatttca tgattcgttt tactgaaaca ttgagggaac   1020

atgaatttat gggcttcttg tagattcatc ttgtaggtat taatgtccta tagtttcagt   1080

caccccttaat gaatgtaaag ttacactgtt cataaaagtt tctccatctt ttcactgctg  1140

tttgtcatcg tcacgctccc ccaaaatatt atattttttc tataaaaagg gaaaaaagga   1200

aaaaaataca aggcaatgga aaatattaaa aggcatttac tttctgtatt agataaattc   1260

ctataatact ctgaatagct tttcctgtta aggcagaccc agtatgtgat gaggattata   1320

gcaaccattt tggggctata tttacatgct actaaatttt tgtaataatt gaaaaaattt   1380

taacatgtat aaaa                                                     1394
```

<210> SEQ ID NO 20
<211> LENGTH: 188
<212> TYPE: PRT
<213> ORGANISM: Felis catus

<400> SEQUENCE: 20

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Ile Ile Met
            180                 185
```

<210> SEQ ID NO 21
<211> LENGTH: 1512
<212> TYPE: DNA
<213> ORGANISM: Felis catus

<400> SEQUENCE: 21

```
tgctgaaaat gactgaatat aaacttgtgg tagttggagc tggtggcgta ggcaagagtg     60
```

-continued

```
ccttgacgat acagctaatt cagaatcact ttgtggatga atatgatcct acaatagagg    120

attcctacag gaaacaagta gtaattgatg gagaaacctg tctcttggat attctcgaca    180

cagcaggtca agaggagtac agtgcaatga gggaccagta catgaggact ggggagggct    240

ttctttgcgt atttgccata aataatacta aatcatttga agatattcac cactatagag    300

aacaaataaa aagagttaaa gactctgaag atgtacctat ggtcctagta ggaaataaat    360

gtgatttgcc ttctagaaca gtagatacaa aacaggctca ggacttagca agaagttatg    420

gaattccttt tattgaaaca tcagcaaaga caagacagag agtggaggat gctttttata    480

cattggtgag agagatccga cagtacagat tgaaaaaaat caacaaagaa gaaaagactc    540

ctggctgtgt gaaaattaaa aaatgcattg taatgggtgt tgacgatgcc ttctatacat    600

tagttcgaga aattcgaaaa cataaagaaa agatgagcaa agatggtaaa aagaagaaaa    660

agaagtcaaa gacaaagtgt ataattatgt aaatacaatt tgtacttttt tcttaaggca    720

tacttaagta aaagtggtaa tttttgtaca ttacactaaa ttattagcat ttgttttagc    780

attacctaat tttctgctcc atccaaactg ttagctttta tcttgaatgc ttattttaaa    840

tgacagtgga aacttttttt cctctaagtg ccagtattcc ctgagttttg gtttttgaac    900

tagcaatgcc tgtgaaaaag aaactgaata cctgagattt ctgtcttggg gtttttggtg    960

catgcagttg attacttcct atttttctta ccaattgtga actttggtgt gaaacaaatt   1020

aatgaaactt tcgaatcatc cctattctgt gtttcatgta gtcacataca tggattaatt   1080

actaattata acttcagttg agatttcatg attcgtttta ctgaaacatt gagggaacat   1140

gaatttatgg gcttcttgta gattcatctt gtaggtatta atgtcctata gtttcagtca   1200

cccttaatga atgtaaagtt acactgttca taaaagtttc tccatctttt cactgctgtt   1260

tgtcatcgtc acgctccccc aaaatattat atttttttcta taaaaaggga aaaaaggaaa   1320

aaaatacaag gcaatggaaa atattaaaag gcatttactt tctgtattag ataaattcct   1380

ataatactct gaatagcttt tcctgttaag gcagacccag tatgtgatga ggattatagc   1440

aaccattttg gggctatatt tacatgctac taaatttttg taataattga aaaaatttta   1500

acatgtataa aa                                                       1512
```

<210> SEQ ID NO 22
<211> LENGTH: 227
<212> TYPE: PRT
<213> ORGANISM: Felis catus

<400> SEQUENCE: 22

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110
```

```
Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Asn Lys Glu Glu Lys
                165                 170                 175

Thr Pro Gly Cys Val Lys Ile Lys Lys Cys Ile Val Met Gly Val Asp
            180                 185                 190

Asp Ala Phe Tyr Thr Leu Val Arg Glu Ile Arg Lys His Lys Glu Lys
        195                 200                 205

Met Ser Lys Asp Gly Lys Lys Lys Lys Lys Lys Ser Lys Thr Lys Cys
    210                 215                 220

Ile Ile Met
225


<210> SEQ ID NO 23
<211> LENGTH: 2144
<212> TYPE: DNA
<213> ORGANISM: Bos taurus

<400> SEQUENCE: 23

ggcggtggcg gcggcggcgg cggtggcggt ggcggttcgg ccagtactcc cggccccccgc     60

catttctgac tgggagcgag cgcggcgcag gcactgaagg cagcggcggg ggccagaggc    120

tcggcggctc ccaggtgagg gagagaggcc tgctgaaaat gactgaatat aaacttgtgg    180

tagttggagc tggtggcgta ggcaagagtg ccttgacgat acagctaatt cagaatcact    240

ttgtggatga atatgatcct acgatagagg attcctacag gaaacaagta gtaattgatg    300

gagaaacctg tctcttggat attctcgaca cagcaggtca agaggagtac agtgcaatga    360

gggaccagta catgaggact ggggagggct ttctttgtgt atttgccata aataatacta    420

aatcatttga agatattcac cattatagag aacaaataaa aagagttaaa gactctgaag    480

atgtacctat ggttctagta ggaaataaat gtgatttgcc ttctagaaca gtagacacaa    540

aacaggctca ggacttagca agaagttatg gaattccttt tattgaaaca tcagcaaaga    600

caagacaggg tgttgacgat gccttctata cattagttcg agaaattcga aaacataaag    660

aaaagatgag caaagatggt aaaaagaaga aaaagaagtc aaagacaaag tgtataatta    720

tgtaaataca atttgtactt ttttcttaag gcatacttaa gtaaaagtgg taattttgt     780

atattacact aaattattag catttgtttt agcattatct aattttcttt ctgctccatc    840

catactgtta gcttttatct tgaatgctta ttttaaaatg acagtggaaa cttttttcct    900

ctaagtgcca gtattccctg cgttttggtt tttgaactag caatgcctgt gaaaaagaaa    960

ctgaacaccc aagatttttg tcttggggtt tttggtgcat gcagttgatt acttcctatt   1020

tttcttatca attgtgaact ttagtgtgaa acaaattaat gaggctttca aatcatccct   1080

attgtattgt tttatctagt cacacacatg gattaattac taattataac ttcagttgag   1140

atttcatgat tggttttact gaaacatcga gggaacatga atttatgggc ttcctatagt   1200

ttcatcttgt aggtatcatt gtcctatagt ttcagttacc cttaatgaat gtcaggttac   1260

actgttcaca aaggttttct tctttccact gctatttgtc aaatggtcac gttccctaaa   1320

atactatatt ttttctataa aaaaaagaaa aaaatggaaa aaaatacaag gcaatggaaa   1380
```

```
atattaaaag gccacttact ttccacatta ggtaaattcc tataatgctc tgaatagctt   1440

tttatgttaa ggcagaccca gtaggtaatg aggattagaa caagcatttt gggactatat   1500

ttacatgctt taaattttg taataacaaa aaaattttaa catgtataaa gaattctcat   1560

aggaattaaa tacagtctcc ctgtgtcaga ttgctctttc ttagcataaa tctttttctt   1620

gaacttcaat ctttaaaagt agttttaatt ctactgatag tgatgtaaaa gattatttgg   1680

gccagttagc ttggtaggtg ttacagagac cagggtggca tagccgggcc ttgtgtgaac   1740

ctttaagcta catggagagt ttcacagtgt ggactgcatc cctgtggtct tccattgttg   1800

ccatgccttg gttggtcaaa aacaaggact tgcagagaga ttgaatagct cagcaaggta   1860

cattctcatt atgtcgtagt cctactcagg aacatcactt ttttaaaata aaaaacccca   1920

aaaaacagaa cttaaaaaaa aaaacaacat tattttaaat gagattttcg gtggggtgga   1980

aagattttaa ttttttttaa acgatgaaat gaaaaaatgt caaaatcttg agtattggct   2040

agttctcttt aacactggct aaagtaacat ttttgtaaac acttcagtac agtctggtcc   2100

attattaaga atatctaatg cttatacaat aaagtaatgc taac                    2144


<210> SEQ ID NO 24
<211> LENGTH: 188
<212> TYPE: PRT
<213> ORGANISM: Bos taurus

<400> SEQUENCE: 24

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Ile Ile Met
            180                 185


<210> SEQ ID NO 25
<211> LENGTH: 1010
<212> TYPE: DNA
<213> ORGANISM: Bos taurus

<400> SEQUENCE: 25

ggcggtggcg gcggcggcgg cggtggcggt ggcggttcgg ccagtactcc cggccccgc      60
```

```
catttctgac tgggagcgag cgcggcgcag gcactgaagg cagcggcggg ggccagaggc    120

tcggcggctc ccaggtgagg gagagaggcc tgctgaaaat gactgaatat aaacttgtgg    180

tagttggagc tggtggcgta ggcaagagtg ccttgacgat acagctaatt cagaatcact    240

ttgtggatga atatgatcct acgatagagg attcctacag gaaacaagta gtaattgatg    300

gagaaacctg tctcttggat attctcgaca cagcaggtca agaggagtac agtgcaatga    360

gggaccagta catgaggact ggggagggct ttctttgtgt atttgccata aataatacta    420

aatcatttga agatattcac cattatagag aacaaataaa aagagttaaa gactctgaag    480

atgtacctat ggttctagta ggaaataaat gtgatttgcc ttctagaaca gtagacacaa    540

aacaggctca ggacttagca agaagttatg gaattccttt tattgaaaca tcagcaaaga    600

caagacagag agtggaggat gctttttata cattggtgag agagatccga caatacagat    660

tgaaaaaaat cagcaaagaa gaaaagactc ctggctgtgt gaaaattaaa aaatgcattg    720

taatgggtgt tgacgatgcc ttctatacat tagttcgaga aattcgaaaa cataaagaaa    780

agatgagcaa agatggtaaa aagaagaaaa agaagtcaaa gacaaagtgt ataattatgt    840

aaatacaatt tgtacttttt tcttaaggca tacttaagta aaagtggtaa tttttgtata    900

ttacactaaa ttattagcat ttgttttagc attatctaat tttctttctg ctccatccat    960

actgttagct tttatcttga atgcttattt taaaatgaca gtggaaactt              1010
```

<210> SEQ ID NO 26
<211> LENGTH: 227
<212> TYPE: PRT
<213> ORGANISM: Bos taurus

<400> SEQUENCE: 26

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Val Met Gly Val Asp
            180                 185                 190

Asp Ala Phe Tyr Thr Leu Val Arg Glu Ile Arg Lys His Lys Glu Lys
        195                 200                 205
```

```
Met Ser Lys Asp Gly Lys Lys Lys Lys Lys Lys Ser Lys Thr Lys Cys
    210                 215                 220

Ile Ile Met
225


<210> SEQ ID NO 27
<211> LENGTH: 797
<212> TYPE: DNA
<213> ORGANISM: Bos taurus

<400> SEQUENCE: 27

gcggtggcgg cggcggcggc ggtggcggtg gcggttcggc cagtactccc ggcccccgcc      60

atttctgact gggagcgagc gcggcgcagg cactgaaggc agcggcgggg gccagaggct     120

cggcggctcc caggtgaggg agagaggcct gctgaaaatg actgaatata aacttgtggt     180

agttggagct ggtggcgtag gcaagagtgc cttgacgata cagctaattc agaatcactt     240

tgtggatgaa tatgatccta cgatagagga ttcctacagg aaacaagtag taattgatgg     300

agaaacctgt ctcttggata ttctcgacac agcaggtcaa gaggagtaca gtgcaatgag     360

ggaccagtac atgaggactg ggagggcctt tctttgtgta tttgccataa ataatactaa     420

atcatttgaa gatattcacc attatagaga acaaataaaa agagttaaag actctgaaga     480

tgtacctatg gttctagtag gaaataaatg tgatttgcct tctagaacag tagacacaaa     540

acaggctcag gacttagcaa gaagttatgg aattcctttt attgaaacat cagcaaagac     600

aagacagaga gtggaggatg ctttttatac attggtgaga gagatccgac aatacagatt     660

gaaaaaaatc agcaaagaag aaaagactcc tggctgtgtg aaaattaaaa aatgcattgt     720

aatgtaatct gggtgttgac gatgccttct atacattagt tcgagaaatt cgaaaacata     780

aagaaaagat gagcaaa                                                    797


<210> SEQ ID NO 28
<211> LENGTH: 189
<212> TYPE: PRT
<213> ORGANISM: Bos taurus

<400> SEQUENCE: 28

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
```

-continued

```
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Val Met
            180                 185


<210> SEQ ID NO 29
<211> LENGTH: 1112
<212> TYPE: DNA
<213> ORGANISM: Gallus gallus

<400> SEQUENCE: 29

caggtctgct aaaaaatgac agagtataag cttgttgtcg ttggagctgg tggtgtgggc      60

aagagcgcct tgacaataca gctcattcag aaccactttg tggatgagta tgaccctacc     120

atagaggatt cctacagaaa gcaagtagta attgatgggg aaacctgtct cttggatatt     180

cttgatacag caggtcaaga agaatatagt gcaatgaggg accaatatat gagaacagga     240

gaaggctttc tgtgtgtttt tgctataaac aatacaaaat cttttgaaga tattcaccat     300

tatagggaac aaataaagag agttaaagac tctgaagatg tcccaatggt gctagtagga     360

aacaaatgtg atttgccttc cagaacagta gatacaaaac aagctcagga tttagcaaga     420

agttatggaa ttccttttat tgaaacatca gcaaagacaa gacagggtgt tgatgatgcc     480

ttctatacat tagttcgaga aatcagaaaa cacaaagaga agatgagcaa agatggtaaa     540

aagaagaaaa agaagacaaa gacaaagtgt ataattatgt aaatacaatg tatccttatt     600

cttaagacgt actgaagtaa tttttgtaca ttacactaaa ttattagcat ttgtttttag     660

cattacttta ctttctgctt catgatcctg ttagctttac ctgaatgctt gttttaaatg     720

acagtggaaa cttcattcct cttaaagtgc cagtattctt tgagtgttgg ttcttgaact     780

agcaatgcct gtgaagaaaa ataaaaacaa atgaaaaaaa aaaaaacaca caaaaacctg     840

agaactgtct taggactctt tggtgcatgc acagttgcta acttcctatt tttcttactg     900

attgtgaact tctgttccgt gcgtaaacaa aacaatgaaa cgatctacac gttctaacat     960

ccccccttcat ttgtactctc ttattttta catctggttg ggaaaacgga ccagttagtg    1020

acaaagactt tattttcaga cttccttcta atttcgactg actgcaatat agagagacca    1080

gaagccttta tagtcttcct gtagattttg ct                                   1112


<210> SEQ ID NO 30
<211> LENGTH: 188
<212> TYPE: PRT
<213> ORGANISM: Gallus gallus

<400> SEQUENCE: 30

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95
```

-continued

```
Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Thr Lys Thr Lys Cys Ile Ile Met
            180                 185
```

<210> SEQ ID NO 31
<211> LENGTH: 3724
<212> TYPE: DNA
<213> ORGANISM: Homo sapiens

<400> SEQUENCE: 31

```
tctccctcgg cgccgccgcc gccgcccgcg gggctgggac ccgatgcggt tagagccgcg     60
gagcctggaa gagccccgag cgtttctgct ttgggacaac catacatcta attccttaaa    120
gtagttttat atgtaaaact tgcaaagaat cagaacaatg cctccacgac catcatcagg    180
tgaactgtgg ggcatccact tgatgccccc aagaatccta gtagaatgtt tactaccaaa    240
tggaatgata gtgactttag aatgcctccg tgaggctaca ttaataacca taaagcatga    300
actatttaaa gaagcaagaa aatacccct ccatcaactt cttcaagatg aatcttctta    360
cattttcgta agtgttactc aagaagcaga aagggaagaa ttttttgatg aaacaagacg    420
actttgtgac cttcggcttt ttcaaccctt tttaaaagta attgaaccag taggcaaccg    480
tgaagaaaag atcctcaatc gagaaattgg ttttgctatc ggcatgccag tgtgtgaatt    540
tgatatggtt aaagatccag aagtacagga cttccgaaga aatattctga acgtttgtaa    600
agaagctgtg gatcttaggg acctcaattc acctcatagt agagcaatgt atgtctatcc    660
tccaaatgta gaatcttcac cagaattgcc aaagcacata tataataaat tagataaagg    720
gcaaataata gtggtgatct gggtaatagt ttctccaaat aatgacaagc agaagtatac    780
tctgaaaatc aaccatgact gtgtaccaga acaagtaatt gctgaagcaa tcaggaaaaa    840
aactcgaagt atgttgctat cctctgaaca actaaaactc tgtgttttag aatatcaggg    900
caagtatatt ttaaaagtgt gtggatgtga tgaatacttc ctagaaaaat atcctctgag    960
tcagtataag tatataagaa gctgtataat gcttgggagg atgcccaatt tgatgttgat   1020
ggctaaagaa agcctttatt ctcaactgcc aatggactgt tttacaatgc catcttattc   1080
cagacgcatt tccacagcta caccatatat gaatggagaa acatctacaa aatccctttg   1140
ggttataaat agtgcactca gaataaaaat tctttgtgca acctacgtga atgtaaatat   1200
tcgagacatt gataagatct atgttcgaac aggtatctac catggaggag aacccttatg   1260
tgacaatgtg aacactcaaa gagtaccttg ttccaatccc aggtggaatg aatggctgaa   1320
ttatgatata tacattcctg atcttcctcg tgctgctcga ctttgccttt ccatttgctc   1380
tgttaaaggc cgaaagggtg ctaaagagga acactgtcca ttggcatggg gaaatataaa   1440
cttgtttgat tacacagaca ctctagtatc tggaaaaatg gctttgaatc tttggccagt   1500
acctcatgga ttagaagatt tgctgaaccc tattggtgtt actggatcaa atccaaataa   1560
```

-continued

```
agaaactcca tgcttagagt tggagtttga ctggttcagc agtgtggtaa agttcccaga   1620
tatgtcagtg attgaagagc atgccaattg gtctgtatcc cgagaagcag gatttagcta   1680
ttcccacgca ggactgagta acagactagc tagagacaat gaattaaggg aaaatgacaa   1740
agaacagctc aaagcaattt ctacacgaga tcctctctct gaaatcactg agcaggagaa   1800
agattttcta tggagtcaca gacactattg tgtaactatc cccgaaattc tacccaaatt   1860
gcttctgtct gttaaatgga attctagaga tgaagtagcc cagatgtatt gcttggtaaa   1920
agattggcct ccaatcaaac ctgaacaggc tatggaactt ctggactgta attacccaga   1980
tcctatggtt cgaggttttg ctgttcggtg cttggaaaaa tatttaacag atgacaaact   2040
ttctcagtat ttaattcagc tagtacaggt cctaaaatat gaacaatatt tggataactt   2100
gcttgtgaga tttttactga agaaagcatt gactaatcaa aggattgggc actttttctt   2160
ttggcattta aaatctgaga tgcacaataa aacagttagc cagaggtttg gcctgctttt   2220
ggagtcctat tgtcgtgcat gtgggatgta tttgaagcac ctgaataggc aagtcgaggc   2280
aatggaaaag ctcattaact taactgacat tctcaaacag gagaagaagg atgaaacaca   2340
aaaggtacag atgaagtttt tagttgagca aatgaggcga ccagatttca tggatgctct   2400
acagggcttt ctgtctcctc taaaccctgc tcatcaacta ggaaacctca ggcttgaaga   2460
gtgtcgaatt atgtcctctg caaaaaggcc actgtggttg aattgggaga acccagacat   2520
catgtcagag ttactgtttc agaacaatga gatcatcttt aaaaatgggg atgatttacg   2580
gcaagatatg ctaacacttc aaattattcg tattatggaa aatatctggc aaaatcaagg   2640
tcttgatctt cgaatgttac cttatggttg tctgtcaatc ggtgactgtg tgggacttat   2700
tgaggtggtg cgaaattctc acactattat gcaaattcag tgcaaaggcg gcttgaaagg   2760
tgcactgcag ttcaacagcc acacactaca tcagtggctc aaagacaaga acaaaggaga   2820
aatatatgat gcagccattg acctgtttac acgttcatgt gctggatact gtgtagctac   2880
cttcattttg ggaattggag atcgtcacaa tagtaacatc atggtgaaag acgatggaca   2940
actgtttcat atagattttg gacacttttt ggatcacaag aagaaaaaat ttggttataa   3000
acgagaacgt gtgccatttg ttttgacaca ggatttctta atagtgatta gtaaaggagc   3060
ccaagaatgc acaaagacaa gagaatttga gaggtttcag gagatgtgtt acaaggctta   3120
tctagctatt cgacagcatg ccaatctctt cataaatctt ttctcaatga tgcttggctc   3180
tggaatgcca gaactacaat cttttgatga cattgcatac attcgaaaga ccctagcctt   3240
agataaaact gagcaagagg ctttggagta tttcatgaaa caaatgaatg atgcacatca   3300
tggtggctgg acaacaaaaa tggattggat cttccacaca attaaacagc atgcattgaa   3360
ctgaaaagat aactgagaaa atgaaagctc actctggatt ccacactgca ctgttaataa   3420
ctctcagcag gcaaagaccg attgcatagg aattgcacaa tccatgaaca gcattagaat   3480
ttacagcaag aacagaaata aaatactata taatttaaat aatgtaaacg caaacagggt   3540
ttgatagcac ttaaactagt tcatttcaaa attaagcttt agaataatgc gcaatttcat   3600
gttatgcctt aagtccaaaa aggtaaactt tgaagattgt ttgtatcttt ttttaaaaaa   3660
caaaacaaaa caaaaatccc caaaatatat agaaatgatg gagaaggaaa aaaaaaaaaa   3720
aaaa                                                                3724
```

<210> SEQ ID NO 32
<211> LENGTH: 1068
<212> TYPE: PRT
<213> ORGANISM: Homo sapiens

<400> SEQUENCE: 32

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys

```
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830
```

```
Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065
```

<210> SEQ ID NO 33
<211> LENGTH: 6435
<212> TYPE: DNA
<213> ORGANISM: Rattus norvegicus

<400> SEQUENCE: 33

```
atgcctccac gaccatcttc gggtgaactg tggggcatcc acttgatgcc cccacgaatc      60

ctagtggaat gtttactccc aaatggaatg atagtgactt tagaatgcct ccgtgaggcc     120

acactagtca ccatcaagca tgaactgttc aaagaggcca ggaaataccc tctccatcag     180

cttctgcaag atgaatcatc ttacattttc gtaagtgtta cccaagaagc agaaagggaa     240

gaatttttcg atgaaacaag acggctttgt gaccttcggc tttttcaacc ctttttaaaa     300

gtaattgagc cagtaggcaa ccgtgaagaa aagatcctca accgagaaat tggttttgtt     360

attggcatgc cagtgtgtga atttgatatg gttaaagatc cagaagtcca agacttccga     420

aggaacattc tgaatgtttg caaagaagcc gtggacctgc gggatctcaa ctcgcctcat     480

agcagagcaa tgtatgtcta ccctccaaat gtcgagtctt ccccagaact gccaaagcac     540

atctacaaca agttagataa aggacaaatc atagtggtga tttgggtgat agtctctcca     600

aacaacgaca agcagaagta cactctgaag atcaaccatg actgcgtgcc agagcaagtc     660

attgctgagg ccatcaggaa gaagacccgg agcatgttgc tgtcctcgga gcagctgaaa     720

ctctgtgtct tagaatacca gggcaagtac attctcaaag tgtgtggctg tgatgagtac     780
```

-continued

```
ttcctagaga agtaccctct gagtcagtac aagtacataa gaagctgtat aatgctgggg    840
aggatgccca acttgatgct gatggccaag gagagcctgt actctcagct gccgatcgat    900
agcttcacaa tgccatccta ctccaggcgc atttccacag cgacacccta tatgaacggg    960
gagactgcta cgaaatccct ctgggttata aatagcgcgc tcagaataaa aattctgtgt   1020
gcaacctatg taaatgtaaa tattcgagac attgataaga tctatgttcg aacaggtatc   1080
taccatggag gagaaccctt atgtgacaat gtgaatactc aaagagtccc ttgttccaat   1140
cctaggtgga atgaatggct gaattatgat atatacattc ctgatcttcc tcgtgctgcc   1200
cgcctttgcc tttcaatctg ctctgttaaa ggccgaaagg gtgctaagga ggagcactgt   1260
ccgttggcct ggggaaacat aaacttgttt gattatacag acaccctagt gtccgggaaa   1320
atggctttga atctctggcc tgtaccacat gggttggaag atctgctgaa ccctattggt   1380
gttactgggt caaatccaaa taaagaaact ccatgcttag agttggagtt tgattggttc   1440
agcagtgtgg tgaagtttcc agatatgtct gtgatcgaag agcatgccaa ttggtctgtg   1500
tcccgagaag ccggattcag ttactctcat acaggactga gtaacagact agccagagac   1560
aatgagttaa gagaaaatga caaggaacag ctccgagcac tttgtacccg ggacccactg   1620
tctgaaatca ctgaacaaga gaaagacttc ctatggagcc acagacacta ctgtgtaact   1680
attcctgaaa tcctacccaa attgcttctg tctgtcaagt ggaattccag agatgaagtg   1740
gcccagatgt actgcttagt aaaagattgg cctccaatca aaccagagca agccatggag   1800
ctcctggact gtaactaccc agaccccatg gttcggagct ttgctgtccg gtgcttggaa   1860
aaatacttaa cagatgacaa actttctcag tacctcatcc agcttgtaca ggtcttaaaa   1920
tatgaacagt atttggataa cctgcttgtg agatttttac tcaagaaagc actgacaaat   1980
caaaggattg gccatttttt cttttggcat ttaaaatctg agatgcacaa taagactgtc   2040
agtcagaggt tcggcctgct gttggagtcc tactgccgtg cctgtgggat gtatctgaag   2100
cacctgaaca gacaggtaga ggccatggag aagctcatca atctaactga catcctcaag   2160
caggagaaga aggatgagac acagaaggta cagatgaagt tcttggttga acagatgaga   2220
cagccagatt tcatggatgc tttgcagggt tttctgtccc ctctaaatcc tgctcatcaa   2280
ctaggaaacc tcaggcttga agagtgtcga attatgtcct ctgcaaaaag gccactgtgg   2340
ttgaattggg agaacccaga catcatgtca gagctactgt ttcagaacaa tgagatcatc   2400
tttaaaaatg gcgatgactt acggcaagac atgttaaccc ttcagatcat ccgaatcatg   2460
gagaacatct ggcaaaacca aggccttgac cttcgcatgc taccttatgg ctgtctatcc   2520
attggggact gtgtgggtct catcgaggtg gtgagaaact ctcacaccat catgcagatt   2580
cagtgcaaag gaggcctgaa aggggcactg cagttcaaca gccacacgct gcatcagtgg   2640
ctcaaggaca agaacaaggg cgagatatat gacgcagcca ttgacctgtt cactcggtcc   2700
tgcgctgggt actgcgtggc aacctttatc ttgggaattg gagaccggca caacagcaac   2760
atcatggtga aagatgacgg acagctgttt catatagatt ttgggcactt tttggatcac   2820
aagaagaaaa aatttggcta taaacgggaa cgtgtgccgt ttgttttgac gcaggatttc   2880
ttaatagtga ttagtaaagg agcacaagag tacacaaaga ccagagagtt tgagaggttt   2940
caggagatgt gttacaaggc gtacctagca attcggcagc atgccaatct cttcatcaac   3000
cttttctcca tgatgcttgg ctccggaatg ccagaactgc agtctttcga tgatattgca   3060
tatattcgaa agactctagc cttagacaaa actgagcaag aggctctgga gtatttcaca   3120
```

```
aagcaaatga atgacgcaca tcatggtggc tggacaacaa aaatggactg gatcttccac   3180
accatcaagc agcatgcatt gaactgagat ggcagctggg gactgcgagc tggtgcctag   3240
cttctccact gcatggcagt gagtggcagc aggcacacgg tggcatggga tggcacagtc   3300
aggaacaaca tcaggactcg agcaagaaca taaacaacgt gctctataat tgaaacactg   3360
tacacgcaaa cagggtttga tagcactaaa ctagttcatt tcaaaattca gctttagaat   3420
aatgagcaat ttcatgttat gccttaagtc caaaaaaagg taaactttga agattgtttg   3480
tatctttttt aaaaaaacaa aacaaaacaa aaatccccaa aatacataca aatgatggag   3540
acgaaaagag aatgctgttg tttgtctgcc agtgttctgt ccaagatgtg gacacccaag   3600
ctgactgctg taggcccgag taagctgaag cttatattaa gttacatgaa attgaagaag   3660
aatgaaaatt ctgattttcc caatgctgtt cagacttatg attggaagtg ggtattttga   3720
ctccctgctt aatgaggaac aacttttggg gtgaagggat ttgctttttg ctttgaacaa   3780
acaacccttc gatggacttg gggtctcacc tacggttttg aaagcagtca cgaatgatac   3840
ctgcagacag ctgtgttttt gttgggtttt gtttttttgt tgtttttctc tctggacagt   3900
atttacaagg atctgactta tttcctaggg aaattctggg ctcgcgtcaa gtacagcagt   3960
aaccacagag gagaggcagc agggagctcc tgttcctgac ttgtacagta ttcactttaa   4020
gctgattgtt tctccttttg caattgaact gaatactttt ttttcatgca tgttttccag   4080
aaaatagaag tgagtattaa tgttattaaa aagattattt ttttttatta aaggctattt   4140
atattataga aactatcatt aatatatatt ctttatttac ataatctgtc ccatagtcat   4200
gcattgtttt gcaccccaaa tttttttattg ttggtaacag catggttagg ttttctcggt   4260
ctatagatga ggctcaggca ctattccatt tacccagata cccctgtatg actccttaag   4320
gaacagattg acctgcacat gctctccttc ctctgctgtc cgttttttac acgctgccct   4380
cattgcacac ccatctgtag ttgagatggc acaatcctat gagatcagtt actgaaatga   4440
atgcaaagca gactatcatc ctgactccta agtccctctg ctgaggtcag tcatgaatga   4500
ctttttacat tatatatgag agactggaaa ccatgaattt tttaccttca taagctgtgt   4560
atccatatcc aatgataaaa gtaggacatt aacccatttt tactatcatg tcccatttcc   4620
aagtggtgag gtctcactcc gacttcatga tcccgttcag tcacggagtg cgttggtgag   4680
cattctgagg agcgtccatc ctagatgtag ggctgctgtt agtggtcact ctagacttct   4740
actccgtgtt tgaatgattc atgtcctaga aaatagcttt agcagatact cagatgccac   4800
accaaaaaga aaaaaaaaaa aagaaaaaaa aagaaaaaga aaaaaaagtg caataattta   4860
ctgacagttc ctagcttagg cgttattgga gagcatcttc atgaagagcg cacgctgtac   4920
actctagaaa acacaatcct tttaataaag cgctcaccgt gaggtcagac acatatatag   4980
aagttttgaa tagtaaacag gggactctaa taaaaatact cttaatatct gcctatttta   5040
gaacccttaa agggcataat tattgaagat ttaggtactt cactaaagca tgtatatatt   5100
attgccaaca agaaaaacct gaagattagg ggaacttagt tctgtaaact gtcttggaat   5160
agttaagcag aatttaaact ctgttttatg cagaaaacca gatagattct tttgcagata   5220
tagaaaactt cctaacttat ttaaacttgg catttaacac tttgtgttac ttagatatgc   5280
agttgctagg tactaacatc ccattcttct ctatatcagg gattattaca gtcaaactca   5340
gtgacatggt acaaatctac aactttgatg gtggaaactg aggaattaca gagaactgtt   5400
ttcccgagtg ccaaaaaaaa aaaaaaaaaa aaaaaaaaaa agccgcgagc ctccttgcac   5460
aaaattgata ggtgtgtgtg tgtgtgtgtg tgtgtgtgtg tgtgtgtgtg tgtgtttaac   5520
```

-continued

```
attagttcat tagttgccgc agtatcacct cccagggtct ctgcacaatt aaaacacagc   5580

cacatagctt attttgtcac ttactaccac actgatttta tttgaaagaa agtctatatt   5640

ctataaaggg tattagtaaa gaaaggagaa ctggtgtatt caaaaaggca aaagccaaac   5700

ttgaatgaag ctggggtgat caatatctgt ttccagagag caataatgtg ccactcactc   5760

ccaggtgctt cagtaccaga aagtcctgca gacctggtct gtaggtgacc gaccttgtca   5820

ttaaatattg tataaatgac ttgggctcca tagttacact aagtcatgtg gggatgcttc   5880

atcagtgatt tttttctgga aggaaagaaa acaaatctaa agaaagaaac taaatacact   5940

gtagcaagaa gtaactctta aatcatgctt taacttttta ccatattctc agctataaaa   6000

caaaacaact ttagtgtgaa gattttagac tgctgttcat ttgaaatctg ttgtttttac   6060

tggggagttt gatttgtttg tttgtttgct ttttgtttgt ttttaaagat gtttctaatt   6120

agattttcta aaaaaagaag aatggaatct ggttgctatt ttaaggtaga acctgagact   6180

tttgtggttc ttcatgtcct ctgtaaaacg tggtgtcaag agtcatcaac tctgaggttg   6240

tcccttctgt tatgctttat attactgccc atcaggacat gggaacctgg tgaatatatg   6300

atgacctgta aaatatttta aatgtgtaac tttttcaact gtgaaactga ctattggttt   6360

tttgatgaaa acagctgctc ataaagtatt ttgtgtaaag tgtagttctt attaatcaga   6420

aaaaaaaaaa aaaaa                                                    6435


<210> SEQ ID NO 34
<211> LENGTH: 1068
<212> TYPE: PRT
<213> ORGANISM: Rattus norvegicus

<400> SEQUENCE: 34

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205
```

-continued

```
Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Ile Asp Ser Phe Thr Met
    290                 295                 300

Pro Ser Tyr Ser Arg Arg Ile Ser Thr Ala Thr Pro Tyr Met Asn Gly
305                 310                 315                 320

Glu Thr Ala Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Thr Gly
            500                 505                 510

Leu Ser Asn Arg Leu Ala Arg Asp Asn Glu Leu Arg Glu Asn Asp Lys
        515                 520                 525

Glu Gln Leu Arg Ala Leu Cys Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Ser Phe Ala Val Arg Cys Leu Glu Lys Tyr Leu Thr
    610                 615                 620
```

-continued

```
Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Gln Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Tyr Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Thr  Lys Gln Met Asn Asp  Ala His His Gly Gly  Trp Thr Thr
```

-continued 1040 1045 1050

Lys Met Asp Trp Ile Phe His Thr Ile Lys Gln His Ala Leu Asn
1055 1060 1065

<210> SEQ ID NO 35
<211> LENGTH: 8917
<212> TYPE: DNA
<213> ORGANISM: Mus musculus

<400> SEQUENCE: 35
tgattctgac tccataaggc ggttttctat gtaaagtttg cagagggtca gagcaatgcc 60
tccacgacca tcttcgggtg aactgtgggg catccacttg atgcccccac gaatcctagt 120
ggaatgttta ctccccaatg gaatgatagt gactttagaa tgcctccgtg aggccacact 180
cgtcaccatc aaacatgaac tgttcagaga ggccaggaaa taccctctcc atcagcttct 240
gcaagacgaa acttcttaca ttttcgtaag tgtcacccaa gaagcagaaa gggaagaatt 300
ttttgatgaa acaagacgac tttgtgacct tcggcttttt caacccttt taaaagttat 360 tgaaccagta ggcaaccgtg aagaaaagat cctcaatcga gaaattggtt ttgttattgg 420
catgccagtg tgtgaatttg atatggttaa agatccagaa gtccaagact ttcgaaggaa 480
cattctgaat gtttgcaaag aagctgtgga cctgcgggat ctcaactcgc ctcatagcag 540
agcaatgtat gtctaccctc caaatgtcga gtcttcccca gaactgccaa agcacatcta 600
caacaagtta gataaaggac aaatcatagt ggtgatttgg gtaatagtct ctccaaacaa 660
cgacaagcag aagtacactc tgaagatcaa tcatgactgt gtgccagagc aagtcattgc 720
tgaagccatc aggaaaaaga ctcggagcat gttgttgtcc tctgagcagc tgaaactctg 780
tgtcttagaa tatcagggca agtatattct gaaagtgtgt ggctgtgacg aatacttcct 840
ggaaaagtac cctctgagtc agtacaagta cataagaagc tgtataatgc tggggaggat 900
gcccaacttg atgctgatgg ccaaagaaag cctatactct cagctgccga ttgatagctt 960
caccatgccg tcatactcca ggcgcatctc cacagccaca ccctacatga atggagagac 1020
atctacgaaa tccctctggg tcataaatag tgcgctcaga ataaaaattc tttgtgcaac 1080
ctatgtaaat gtaaatattc gagacattga taagatctat gttcgaacag gtatctacca 1140
tggaggagaa cccttatgtg acaatgtgaa cactcaaaga gtaccttgtt ccaatcctag 1200
gtggaatgaa tggctgaatt atgatatata cattcctgat cttcctcgtg ctgcgcgcct 1260 ttgccttca atctgctctg ttaaaggccg aaagggtgct aaggaggagc actgtccgtt 1320
ggcctgggga aacataaact tgtttgatta tacagacacc ctagtgtccg ggaaaatggc 1380
tttgaatctc tggcctgtac cgcatgggtt agaagatctg ctgaacccta ttggtgttac 1440
tgggtcaaat ccaaataaag aaactccatg cttagagttg gagtttgatt ggttcagcag 1500
tgtggtgaag tttccagaca tgtctgtgat cgaagaacat gccaattggt ccgtgtcccg 1560
agaagctgga ttcagttact cccatacagg actgagtaac agactagcca gagacaatga 1620
gttaagagaa aatgacaagg aacagctccg agcactttgc acccgggacc cactatctga 1680
aatcactgaa caagagaaag acttcctatg gagccacaga cactactgcg taactattcc 1740
tgaaatccta cccaaattgc ttctgtctgt caagtggaat tccagagacg aagtggccca 1800
gatgtactgc ttagtaaaag attggcctcc aatcaaacca gagcaagcca tggaactcct 1860
ggactgtaac tatccagatc ctatggttcg gagttttgct gttcggtgct tagaaaaata 1920
tttaacagat gacaaacttt ctcagtacct cattcaactt gtacaggtct taaaatatga 1980
acagtatttg gataacctgc ttgtgagatt tttactcaag aaagcattga caaatcaaag 2040
gattggccat tttttctttt ggcatttaaa atctgagatg cacaataaga ctgtcagtca 2100
gaggtttggc ctgctattgg agtcctactg ccgtgcctgt gggatgtatc tgaagcacct 2160
gaacagacaa gtagaggcca tggagaagct catcaaccta acggacatcc ttaagcagga 2220
gaagaaggat gagacacaaa aggtacagat gaagtttttg gttgaacaga tgagacagcc 2280
agacttcatg gatgctttgc agggttttct gtcccctctg aatcctgctc accaactagg 2340
aaacctcagg cttgaagagt gtcgaattat gtcctctgca aaaaggccac tgtggttgaa 2400
ttgggagaac ccagacatca tgtcagagct actgtttcag aacaatgaga tcatctttaa 2460
aaatggcgac gacttacggc aagatatgtt aacccttcag atcatccgaa tcatggagaa 2520
catctggcaa aaccaaggcc ttgaccttcg catgctacct tatggctgtc tatccattgg 2580
ggactgtgtg ggtctcatcg aggtggtgag aaactctcac accatcatgc aaatccagtg 2640
caaaggaggc ctgaaggggg cgctgcagtt caacagccac acactgcatc aatggctcaa 2700
ggacaagaac aagggcgaga tatatgatgc agccattgac ctgttcactc ggtcctgcgc 2760
tgggtactgc gtggcaacct ttatcttggg aattggagac cggcacaaca gcaacatcat 2820
ggtgaaagat gacggacagc tgtttcatat agattttggg cactttttgg atcacaagaa 2880
gaaaaaattt ggctataagc gggaacgtgt gccatttgtg ttgacacagg atttcttgat 2940
tgtgattagt aagggagcac aagagtacac caagaccaga gagtttgaga ggtttcagga 3000
gatgtgttac aaggcttacc tagcaattcg gcagcatgcc aatctcttca tcaacctttt 3060
ttcaatgatg cttggctctg gaatgccaga actacaatct tttgatgaca ttgcatatat 3120
ccgaaagact ctagccttgg acaaaactga gcaagaagct ttggaatatt tcacaaagca 3180
aatgaatgat gcacatcatg gtggatggac gacaaaaatg gattggatct tccacaccat 3240
caagcagcat gctttgaact gagatgggag ctgggactgc gagctggctc ccggcttctc 3300
cactgcatgg cagtgagtgg cagcaggcag gcagtggcat gggatggcac agtcaggaac 3360
aacattagga cttgagcaag aacataaaca acgtgctcta taattgaaac actgtacacg 3420
caagcagggt ttgatagcac taaactagtt tatttcaaaa tccagcttta gaataacgag 3480
caatttcatg ttatgcctta agtccaaaaa aggtaaactt tgaagattgt ttgtatcttt 3540
ttttaaaaaa acaaaacaaa acaaaaatcc ccaaaataca tacaaatgat ggagacaaaa 3600
ctagaatgct gttgtttgtc tgccagtgtt ctgtctaaca cgtggacacg cccaaggctg 3660
tgactgctat aggtctgagt aagctaaagc ttatattaag ttacatgaat tggagaagaa 3720
ggaaaattct gattttccca ttgctgttca gacttaacga tttgaagtgg ggattttgat 3780
ccctgcttaa tgaggaacaa cacttggggt gaagggactc gctttttgct ttgaacaaac 3840
aacactttga tggacttggg gtctcacctg cggttttgaa agcagtcaca atacttgcag 3900
acagctgcgt tttgttgggg tgttgttttt tgttgttttt ttctctggac agtatttaca 3960
aggatctgac ttatttccta gggaaattct gggctggcat caagtatagc agtaagggca 4020
gaggagaggc cgcagggagc ccctgttcct gacctgtaca gtgttcactt tcagctgatt 4080
gtttctcctt ttgcaattga actgaatact ttttttttcat gcatgttttc cagaaaatag 4140
aagtgagtat taatgttatt aaaaagatta ttttttttta ttaaaggcta tttatattat 4200
agaaactatc attaatatat attctttatt tacataatct gtcccatagt catgcattgt 4260
tttgcacccc aaatttttta tcgttggtaa cagcatggtt agcttttctc tcggtctgta 4320
gatgaggctc aggcactatt ccatttatcc aatacccgtg tatgactcct taaggaacag 4380

```
attgaatcgc acacgctttc ctgccgctgc tggccgtttt ttacacgacg ccctcatcca   4440
ttcctccgta gttgagacag cacaatcaca tgaaacccgt tactaaaatg aatacaaaac   4500
cgactatcat cctgactctt aatccttctg cagaggtcta gtcatgagtg actctttaca   4560
ttatgagaga ctggaaacca tgaatttttt accttcgtaa gctacgtatc cgtacttcaa   4620
tgataaaagt aggacattaa cccattttac tatcatgtcc caattccaag tggtgaggtc   4680
tcactccagt gtcattaaat cccattcagg cacggtgcat tagtgagcat tctgaaatgc   4740
atccatctaa gatgtagggc taatgttagt ggtcgctcta gatttctact cagtgtttga   4800
atgattcatg tcctagaaaa tagctttagc agatactcag atgccacacc aaaaaaagaa   4860
gaaaaaaaga aaaaaaaaag aataaataaa aaggaaaaaa aaaagaaaaa ctgtgcaata   4920
atctcctgac agttcctagc tcaggcgttc ctggggagca tcgttatgaa gagcgcacgc   4980
tgtacacgct agaaaacaga atccctgtaa tacagtgctc accttgaggc cagacaccta   5040
tatagacgtt ttgaatagtg aacaggggac tctaatagaa atactcttaa tatctgccta   5100
tttttagaac ccttaaaggg cataattatt gaagatttag gtacttcact aaagcatgta   5160
tatattattg ccaacaagaa aaataaacct gaagattagg ggaacttggt tctgtaaact   5220
gtcttggaat agttaagcag aatttaagct ctgttttatg cagaaaacca gatagattct   5280
tttgcagata tagaaaactt cctaacttat ttaaacttgg catttaacac tttgtgttac   5340
ttagatatac agttgctagg tactaacatc ccattcttct ctatatcagg gattattaca   5400
gtcaaactca gtgacatggt acaaatctac aactttgatg gtgggaactg aagaattaca   5460
gagaactgtg ttttcccgag tgccaaaaga aacaaaaaca aaacaaaaca aacaaacccc   5520
acaaaaaaaa gaaaaaaaaa aaaaagccgc gagcctcctt gcacaaaatt gataggtttt   5580
tttttgtgtg tatgtgtgtg tttgtgtgtg tgtatgttta acattagtcc atcagttgcc   5640
gtagtatcac ctcccaggtc tctgcacaat taaaacacag ccacatagct tattttgtca   5700
tttacaacca cattgatttt atttgaaaga aagtctatag tctgtgaagg gtataagtaa   5760
agaaaggaga actggttgta ttcaaaaagg caaaagccaa acttgaattg cagctggggt   5820
gatcaatatc tgcttccaga gagcaataat gtgccactta ctcccaggtg cttcagtacc   5880
agaaagtgct gtgggactcg gtcacctctg tagatgaccg tccttgtcag tgaatgacta   5940
ttgtggaaat gacttgggct ccatagtttc actaagtcac ttgaggatgt ctcatcagca   6000
attatttcag gaaggaaaga aagcaaatct aaagaaagaa actaaataca ctgtagcaag   6060
aaataactct tcaatcatgc tttaactttt taccatagtc tcagctatac aaaaaacttt   6120
agtttgaaga ttttacattg ctgttaattt gaaatctgtt gttcttactg tggagtttga   6180
tttgttcgtt tgtttgcttt ctgttggttt tttttttttt ttttaagatg tttctaaata   6240
gattttttaa aaaaaagaaa gaagaagaag aatggaatct ggttgctatt ttaaggtaga   6300
acctgagact ttttgtggtt cttcatgtcc tctgtaaaat ttggtgtcaa gagtcatcaa   6360
ctctgaggtt gtcccttctg ttctgcttta tattactgcc catcaggaaa tgggaacctg   6420
gtgaatatat aatgaattgt aaaatatttt aaatgtgtaa ctttttcaac tgtgaaactg   6480
actattggtt tttttttttt ttgatgaaaa cagctgctca taaagtattt tgtgtaaagt   6540
gtagttctta ttaatcagga aatgattacg tgattagatg tgtgccctct tgacttttat   6600
ctgaaagaga ttggtaatta tcacagagac agagcacgat ccatctgtgt tctctgctcg   6660
tcaggagcca gctgatgtgg cgtcacagaa aagacgaacc tgttttaatg gtacagtaga   6720
```

-continued

```
aacctcacag cacgtggact tcgctgtgtt tcttaacata atttttgtaa gcttgatgtc   6780
catgctttcc agctctttga agaaatttat ttccagcatt atgttaatct tttctgaata   6840
ttacagtttc cactttttttc ctgtttctct ggaaactgca gacctgggct ggaccccccac   6900
actacagaat attaatgaat tacttttgat gtctacaaca ttgctaaaat accaaattca   6960
aaggcatttt gtggcgtcat agattgtggt atgtctgctt cagatgtttg gggagatggg   7020
ggtgtggtgg aagggcctga gcagggagaa gcacaaaggg gcatggaagt tacagggatg   7080
ctgtccacgt actagaaagg aatcagttcc aggttggaat tttgaaggct gaactcagtc   7140
ttgacatcat ctttaattag taactcttga tgacagagga gtccagctga gctgttttaa   7200
acagacaaac aaaagcattt cagttattaa aactgtaaac agatcatgtc gtggcctgga   7260
aagccttttt ttttttcctt ataaaaatat tgtttttact ctctggaaag atgttgggct   7320
ccagctcaaa agaattgcat tcctgatagc cctggtagct gtctccaaag gtttgtaagg   7380
gaaatggcca tgttaccact cagtgctctc acaggacagc aaagagaatc tcattgtagg   7440
ttttcaagtc aagattgggc atgcgctgct gttcatggac caggagacag gatgggtcaa   7500
ggaatggggc taaaatctat tgctccagcc acttgggaaa gctttattgt taaagcaatt   7560
caaggtgcca gttcttgagt gcggcgctca tagcatgctc tcctgtgttg ctttgctagc   7620
actggccaag gctctgtaac gaaaggtgta aacagatacc aaggttctaa aatgcagaaa   7680
ggacttgttg ttaggagtca cccagattgc attggcaatc ctgggtgagt ttttgtggga   7740
ttgtgcacct ccatccattt tattatgcgg tgccttttcc tttgcttggc ttttgggtat   7800
ggtagggtat cagccgtgtg ctaattacag caaagggaat gggaacagag cagttatcac   7860
acttctcagg tgtcacaaag agtgttggtg ggcaggactg aaatgaggct ccatcctgtg   7920
tgctgttggc tgatttttaa ctcactacca gcagtagatg ccatttctcg tggtaataag   7980
taccaaaagg aaaatacttt ataggccacg tggactttat ataacctcat cttgtgtcac   8040
aagcttgtgg cagaaatata catacacata tacatactat atgtatgtat gtgtatatat   8100
atatatattt tttttttttt ttgagacatg gtttctctgt atagccctgt ctgtcctgga   8160
actcactctg tagaccaggc tggcctcaaa ctcagaaatc tgcctgcctc tgcctcccaa   8220
gtaccgggat taaaggcgtg tgccaacacc tgcccggccg gaagtatata tttttaaata   8280
ctgtttttgt tgatcttcta ggttagctga aggaagaacc tttggtgttt ccaattaaag   8340
catgggaatt tgggtcagtt gttagcccaa caaatgtgtg tggagtggag ctctgggctt   8400
gagcccagca catcataaac ggggtctgat gacatatgcc tgtaattccc cacctcagga   8460
ggtagagaac agaagttcag ggccatcctc agcctacatt actaacataa tgtaatgcat   8520
gcttggggta ctctggctcc aaaacatccc cactaaactt gttctagtac aaattcacaa   8580
gtgtaattat ttctgttggt tcataagaaa gaaatactta aatagattta atgtatgttc   8640
ctaagagtag ctaagaaatg tgatttttct ggaaatgttt ttgattatga aacccaaaca   8700
aatttgttgt ggtgatgatg gtggatttct tagggttttg tcattttatt gttggtacaa   8760
ggtctcagtg tagcccaggc tggcctcaaa ttcaagatcc tctggactta gcttcggggt   8820
gctgagttta cagtaccctc actccaggct ccaagaatcc gtgcttcaaa tgcagctgat   8880
ggttctattg tcatttggtc ttagctgaat aaaatct                            8917
```

<210> SEQ ID NO 36
<211> LENGTH: 1068
<212> TYPE: PRT
<213> ORGANISM: Mus musculus -continued

<400> SEQUENCE: 36

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Arg Glu Ala Arg Lys Tyr Pro Leu His Gln Leu Leu Gln Asp
    50                  55                  60

Glu Thr Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Ile Asp Ser Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
```

-continued

```
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Thr Gly
            500                 505                 510

Leu Ser Asn Arg Leu Ala Arg Asp Asn Glu Leu Arg Glu Asn Asp Lys
        515                 520                 525

Glu Gln Leu Arg Ala Leu Cys Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Ser Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Gln Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830
```

```
Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Tyr Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Thr  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065
```

<210> SEQ ID NO 37
<211> LENGTH: 4335
<212> TYPE: DNA
<213> ORGANISM: Oryctolagus cuniculus

<400> SEQUENCE: 37

```
ccgtcgccgc cgccgccgcc gcccgcgcgg tttgggaccc gatgcggttg gagccgcgga     60

tcctggagga gccccgagcg tgtctgcttt ggaacaacaa tatatataat tccttcaagt    120

agttttaaat gtaaaacttg taaaggatca gaacaatgcc tccacgacca tcatcaggtg    180

aactgtgggg catccacttg atgcccccaa gaatcttagt agaatgttta ctgccaaatg    240

gaatgatagt gactttagaa tgcctccgtg aggctacatt aattactata aagcatgaac    300

tatttaaaga agcaagaaaa taccctctcc atcaacttct tcaagatgaa tcttcttaca    360

ttttcgtaag tgttacccaa gaagcagaaa gggaagaatt ttttgatgaa acaaggcgcc    420

tttgtgacct tcggcttttt caacccttt taaaagtaat tgaaccagta ggcaaccgtg    480

aagaaaagat cctgaatcga gaaattggtt ttgttattgg catgccagtg tgtgaatttg    540

atatggttaa agatccagaa gtacaggact tccgaagaaa tattctgaat gtttgtaaag    600

aagctgtgga tcttagagat ctgaattcac ctcatagtag agcaatgtat gtctatcctc    660

caaatgtaga atcttcacca gaactgccaa agcacatata taataaatta gataaagggc    720

aaataatagt ggtgatttgg gtaatagttt ctccaaataa tgataagcag aagtataccc    780
```

```
tgaaaatcaa ccatgactgt gtgccagaac aagtaattgc tgaagcaatc aggaagaaaa    840
cccggagcat gttgctatcc tctgaacaac taaaactatg tgttttagaa tatcagggca    900
agtatatttt aaaagtgtgt ggatgtgatg aatacttctt agaaaaatat cctctgagtc    960
agtataagta tataagaagc tgtataatgc ttgggaggat gcccaatttg atgctgatgg   1020
ctaaagaaag cctttattct caactgccaa tggactgttt tacaatgcca tcttattcca   1080
gacgcatctc cactgctaca ccatatatga atggagaaac atctacaaaa tccctttggg   1140
ttataaatag tgcactcaga ataaaaattc tttgtgctac ctatgtgaat gtaaatattc   1200
gagacattga caagatctat gttcgaacag gtatctacca tggaggagaa cctttatgtg   1260
acaatgtgaa cactcaaaga gtaccttgtt ccaatcccag gtggaatgaa tggctgaatt   1320
atgatatata cattcctgat cttcctcgtg ctgctcgact ttgcctttct atatgctctg   1380
ttaaaggccg aaagggtgct aaggaggaac actgtccact ggcttgggga aatataaact   1440
tgtttgatta cactgacact ctggtatctg gaaaaatggc tctgaatctt tggccagtac   1500
ctcatggatt agaagattta ctgaacccta ttggtgttac tgggtcaaat ccaaataaag   1560
aaactccatg cttagagttg gagtttgact ggtttagcag tgtggtaaag tttccagata   1620
tgtcagtgat tgaggaacat gccaattggt ctgtatccag agaagcagga tttagttatt   1680
cccatgcagg actgagtaac agactagcaa gagacaatga attaagagaa aatgataaag   1740
aacagctccg agcaatctgt acacgcgatc ctctatctga aatcactgag caagagaaag   1800
attttctgtg gagccacaga cattattgtg taactatccc agagattcta cccaaattgc   1860
ttctgtctgt taaatggaat tctagagatg aagttgccca gatgtactgc ttggtaaaag   1920
attggcctcc aataaaacct gagcaggcca tggagctcct ggactgcaac tacccagatc   1980
cgatggttcg agcttttgct gttcgatgct tggaaaaata tttaacagat gacaaacttt   2040
ctcagtatct gattcagcta gtacaggtcc taaaatatga acagtatttg gataaccttc   2100
tcgtgagatt tttactcaag aaagcattga ctaaccaaag gattgggcac tttttctttt   2160
ggcatttaaa atctgagatg cacaataaaa cagttagtca gaggtttggc ctgcttttgg   2220
agtcctactg ccgggcatgt ggaatgtatt tgaagcacct gaataggcaa gttgaggcta   2280
tggaaaagct cattaacttg actgacattc tcaaacagga gaagaaggat gaaacacaaa   2340
aggtacaaat gaagttttta gttgagcaaa tgaggcaacc agatttcatg gatgctctac   2400
agggctttct gtctccttta aaccctgctc atcaactggg aaatctcagg cttgaagagt   2460
gtcgaataat gtcctctgca aaaaggccac tgtggttgaa ttgggagaac ccagacatca   2520
tgtcagagtt actgtttcag aacaatgaga tcatctttaa aaatggggat gatttacggc   2580
aagatatgct aacacttcaa attattcgca ttatggaaaa tatctggcaa aatcaaggtc   2640
ttgatcttcg aatgttacct tatggttgtc tgtcaattgg tgactgtgtg ggacttattg   2700
aggtggtgag aaattctcac actatcatgc agattcagtg caaaggtggc ctgaaaggtg   2760
cactgcagtt caatagccat acactgcatc agtggctcaa agacaagaac aaaggagaaa   2820
tatatgatgc agccattgac ctgttcaccc gttcatgtgc tggctattgc gttgcaactt   2880
tcatcttggg aattggagat cggcacaaca gtaacatcat ggtgaaagat gatggacaac   2940
tgtttcatat agatttcgga cactttttgg accacaagaa gaaaaaattt ggttataagc   3000
gagaacgtgt accatttgtt ctgacacagg atttcttaat agtgattagt aaaggagccc   3060
aagaatgcac aaaaactaga gaatttgaga ggtttcaaga gatgtgttac aaggcttatc   3120
```

tagctattcg gcagcatgcc aatctcttca taaatctttt ctcaatgatg cttggctctg 3180
gaatgccaga actgcaatct tttgatgaca ttgcatatat tcgaaagacc ctagccttag 3240
ataaaactga gcaggaggct ttggaatatt tcatgaaaca aatgaacgat gcacatcatg 3300
gtggctggac aacaaaaatg gattggatct tccacacaat taagcagcat gcattgaact 3360
gaaatgatat ctaagaaact gagagctcaa tatctggatt ctacaccgca ctgttaataa 3420
ctgtcagcag gcaaagactg attgcatagg aattgcacaa tccatgaaca gcattagaat 3480
ttacagcaag aacagaaata aaatagtata taatttaaaa taatgtaaac gcaaacaggg 3540
tttgatagca ctaaactagt tcatttcaaa attaagcttt agaataatgc gcaatttcat 3600
gttatgcctt aagtccaaaa aggtaaactt tgaagattgt ttgtatcttt ttttaaaaac 3660
aaaacaaaac aaaaatcccc taaatatata taaatgatgg agaaggaaaa agaatgatgt 3720
tctatttgtc ttgcaaatgc tctgcgtttc gacatgtgga tacaactata aggctgttat 3780
tgcattagga ctgagtcaac tggagtttat gttgaattac atagaatgga aaaggatgac 3840
agtttcttat ttttccattg ctgttcaatt tatagtttga agtgggtttt ttgactcctt 3900
gtttaatgaa gaaaagtgct tggggtggaa gggactctcg agatttctcc agagactttt 3960
tctttttaat aaatcaaacc ttttgatgat ttgggggtct tatctgcaca attttggaag 4020
cagtcacaaa tgagacctgt aataaggtgg tgtttttggt tttgggtttt ttgctttttg 4080
tttctttttg acagtattct taatacctag ggaaattctg ggctcccaca aagtgaagta 4140
atcatcatag aaacagaatg agcaggagta gttctcattc caggattgta cagtattcac 4200
cttaagttga ttttttttct ccttttgcaa ttgaactgaa cacatttttc atgcatgttt 4260
tccagaaaat agaagtatta atgttattaa aaagattatt ttttttatta aaggctattt 4320
atattataga aacta 4335

<210> SEQ ID NO 38
<211> LENGTH: 3505
<212> TYPE: DNA
<213> ORGANISM: Cavia porcellus
<220> FEATURE:
<221> NAME/KEY: misc_feature
<222> LOCATION: (1224)..(1225)
<223> OTHER INFORMATION: n is a, c, g, or t

<400> SEQUENCE: 38
acagccataa atctagttac ttaaagtagt tttatatgta aaacttgtaa aggatcagaa 60
caatgcctcc acgaccatca tcaggtgaac tgtggggcat ccacttgatg cccccaagaa 120
tcctcgtaga atgtttacta ccaaatggaa tgatcgtgac tttagaatgc ctccgtgagg 180
ctacattaat aaccataaag catgaactgt ttaaggaagc aagaaaatac cctctccatc 240
aacttcttca agacgaatct tcttacattt tcgtaagtgt tactcaagaa gcagaaaggg 300
aagaattttt tgatgaaaca agacgactat gtgaccttcg gcttttccaa cccttttttaa 360 aagtaattga accagttggc aaccgtgagg aaaagatcct caatcgagaa atcggttttg 420
ttatcggcat gccagtgtgt gaatttgata tggttaaaga tccagaagta caggacttca 480
gaagaaatat tttgaatgtt tgtaaagaag ctgtggacct tagggacctc aattcacctc 540
atagtagagc aatgtatgtc tatcctccaa atgtagaatc atcaccagag ctgccaaagc 600
acatatacaa taaattagac aaaggacaaa taattgtggt gatttgggta atagtttctc 660
caaacaatga caagcagaag tatactttga aaatcaacca tgactgtgtg ccagaacaag 720
taattgctga agcaatcagg aaaaaaactc gaagtatgtt gctatcctct gaacaactaa 780
aactctgtgt tttagaatat cagggcaagt atattttaaa agtatgtgga tgtgatgaat 840
acttcctaga aaaatatcct ctgagtcagt ataagtatat aagaagctgt ataatgcttg 900
ggaggatgcc caatttgatg ctgatggcta aagaaagcct ttactctcag ctgccaatgg 960
actgttttac aatgccatcc tattccagac gcatctctac agctacaccg tatatgaatg 1020
gagaaacatc tacaaaatcc ctttgggtta taaatagtgc actcagaata aaaattcttt 1080
gtgcaactta tgtaaatgta aatattcgag acattgataa gatctatgtt cgaacgggta 1140
tctaccatgg aggagaaccc ttatgtgaca atgtgaacac tcagagagta ccttgttcca 1200
atcctaggtg gaatgaatgg ctgnnatacg atatatacat tcccgatctc tcacttttta 1260
gatatgagca ttgtccattg gcctggggaa atataaactt gtttgattac acagacacac 1320
tagtatctgg aaaaatggcc ttgaatcttt ggccagtacc tcatggatta gaagacttgc 1380
tgaatcctat tggtgttact gggtcaaatc caaataaaga aactccatgc ttagaattag 1440
agtttgattg gttcagcagt gtggtaaagt ttccagatat gtcagtgatt gaggagcatg 1500
caaattggtc tgtatcccga gaagcaggat ttagttattc acatgcagga ctgagtaaca 1560
gactagctcg agacaatgaa ttaagagaaa atgacaaaga acagctccga gcaatttgta 1620
cacgagaccc tctgtctgaa atcactgagc aagagaaaga ttttctgtgg agtcacagac 1680
actattgtgt aactatccct gaaattctac ccaaattgct tctgtccgtt aaatggaact 1740
ctagagatga agtagctcag atgtactgct tagtgaaaga ctggcccccca attaaacctg 1800 agcaggcaat ggaacttctg gactgcaact acccagaccc tatggttcga ggttttgctg 1860
ttcgatgctt ggaaaaatac ttgacagatg acaaactttc tcagtacctt atccagctag 1920
tacaggtcct aaaatatgaa caatatttgg ataatcttct tgtgagattt ttactcaaga 1980
aagcattaac aaatcaaagg attggacact tttcttttg gcatttaaaa tctgagatgc 2040
acaataaaac agtgagtcaa agatttggtc tgcttttgga gtcctattgc cgcgcctgtg 2100
ggatgtacct aaagcacctg aacaggcaag ttgaggccat ggaaaagctc atcaacttaa 2160
ctgacatcct caaacaggag aagaaggatg aaacacagaa ggtacagatg aaattcttag 2220
ttgagcaaat gaggcaacca gatttcatgg atgcactaca aggcttttg tctcctctaa 2280 accctgctca tcaactggga aatctcaggc ttgaagagtg tcgaattatg tcttctgcaa 2340
aaaggccact gtggttgaat tgggagaacc cagacatcat gtcagagtta ctgtttcaga 2400
acaatgagat catctttaaa aatggggatg atttacggca agatatgcta acgcttcaga 2460
ttattcgcat aatggaaaat atctggcaaa atcaaggcct tgatcttcga atgctgccgt 2520
atggttgtct ctccattggg gactgtgtag gactgatcga ggtggtgaga aattctcaca 2580
cgatcatgca gattcagtgc aaaggtggcc tgaaaggtgc actgcagttc aatagccaca 2640
cgctgcatca gtggctcaaa gacaagaaca aaggagaaat atacgatgca gccattgacc 2700
tatttacacg gtcgtgtgcc ggatactgcg tagctacctt cattttggga attggtgacc 2760
gtcacaacag taacatcatg gtgaaagatg atggacagct gtttcatata gactttggac 2820
actttttgga tcacaagaag aaaaaatttg gttataaacg agaacgtgta ccatttgttt 2880
tgacacaaga tttcttaata gtgataagca aaggggccca agaatgtaca aagaccagag 2940
aatttgaaag gtttcaggag atgtgttaca aggcgtatct agctattcgg cagcatgcta 3000
atctcttcat aaatcttttc tcaatgatgc ttggctctgg aatgccagaa ctacagtctt 3060
ttgatgacat tgcatatatt cgaaagaccc tagccttaga taaaactgag caagaggctt 3120

```
tggaatattt catgaaacaa atgaatgatg cacatcatgg tggctggaca acaaaaatgg   3180

attggatctt ccacacaatt aagcagcatg cattgaactg aaatgataag tgagaaactg   3240

aaagcccaat gatctggatt ctacactgca ctgttaataa ctgacagcag gcaaagactg   3300

attgcatagg aattgcacaa tccatgaaaa gcattagaac ttacagcaag aaacagaaat   3360

aaaatactat ctaatttaaa taatgtaaat gcaaacaggg tttgatagca ctaaactagt   3420

tcatttcaaa gttaagcttt agaataatgc gcaatttcat gttatgcctt aagtccaaaa   3480

aaaggtaaac tttgaagatt gtttg                                         3505


<210> SEQ ID NO 39
<211> LENGTH: 1052
<212> TYPE: PRT
<213> ORGANISM: Cavia porcellus
<220> FEATURE:
<221> NAME/KEY: misc_feature
<222> LOCATION: (388)..(388)
<223> OTHER INFORMATION: Xaa can be any naturally occurring amino acid

<400> SEQUENCE: 39

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285
```

```
Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Xaa Tyr Asp Ile Tyr Ile Pro Asp Leu Ser Leu Phe Arg
385                 390                 395                 400

Tyr Glu His Cys Pro Leu Ala Trp Gly Asn Ile Asn Leu Phe Asp Tyr
                405                 410                 415

Thr Asp Thr Leu Val Ser Gly Lys Met Ala Leu Asn Leu Trp Pro Val
            420                 425                 430

Pro His Gly Leu Glu Asp Leu Leu Asn Pro Ile Gly Val Thr Gly Ser
        435                 440                 445

Asn Pro Asn Lys Glu Thr Pro Cys Leu Glu Leu Glu Phe Asp Trp Phe
    450                 455                 460

Ser Ser Val Val Lys Phe Pro Asp Met Ser Val Ile Glu Glu His Ala
465                 470                 475                 480

Asn Trp Ser Val Ser Arg Glu Ala Gly Phe Ser Tyr Ser His Ala Gly
                485                 490                 495

Leu Ser Asn Arg Leu Ala Arg Asp Asn Glu Leu Arg Glu Asn Asp Lys
            500                 505                 510

Glu Gln Leu Arg Ala Ile Cys Thr Arg Asp Pro Leu Ser Glu Ile Thr
        515                 520                 525

Glu Gln Glu Lys Asp Phe Leu Trp Ser His Arg His Tyr Cys Val Thr
    530                 535                 540

Ile Pro Glu Ile Leu Pro Lys Leu Leu Leu Ser Val Lys Trp Asn Ser
545                 550                 555                 560

Arg Asp Glu Val Ala Gln Met Tyr Cys Leu Val Lys Asp Trp Pro Pro
                565                 570                 575

Ile Lys Pro Glu Gln Ala Met Glu Leu Leu Asp Cys Asn Tyr Pro Asp
            580                 585                 590

Pro Met Val Arg Gly Phe Ala Val Arg Cys Leu Glu Lys Tyr Leu Thr
        595                 600                 605

Asp Asp Lys Leu Ser Gln Tyr Leu Ile Gln Leu Val Gln Val Leu Lys
    610                 615                 620

Tyr Glu Gln Tyr Leu Asp Asn Leu Leu Val Arg Phe Leu Leu Lys Lys
625                 630                 635                 640

Ala Leu Thr Asn Gln Arg Ile Gly His Phe Phe Phe Trp His Leu Lys
                645                 650                 655

Ser Glu Met His Asn Lys Thr Val Ser Gln Arg Phe Gly Leu Leu Leu
            660                 665                 670

Glu Ser Tyr Cys Arg Ala Cys Gly Met Tyr Leu Lys His Leu Asn Arg
        675                 680                 685

Gln Val Glu Ala Met Glu Lys Leu Ile Asn Leu Thr Asp Ile Leu Lys
    690                 695                 700
```

```
Gln Glu Lys Lys Asp Glu Thr Gln Lys Val Gln Met Lys Phe Leu Val
705                 710                 715                 720

Glu Gln Met Arg Gln Pro Asp Phe Met Asp Ala Leu Gln Gly Phe Leu
                725                 730                 735

Ser Pro Leu Asn Pro Ala His Gln Leu Gly Asn Leu Arg Leu Glu Glu
            740                 745                 750

Cys Arg Ile Met Ser Ser Ala Lys Arg Pro Leu Trp Leu Asn Trp Glu
        755                 760                 765

Asn Pro Asp Ile Met Ser Glu Leu Leu Phe Gln Asn Asn Glu Ile Ile
    770                 775                 780

Phe Lys Asn Gly Asp Asp Leu Arg Gln Asp Met Leu Thr Leu Gln Ile
785                 790                 795                 800

Ile Arg Ile Met Glu Asn Ile Trp Gln Asn Gln Gly Leu Asp Leu Arg
                805                 810                 815

Met Leu Pro Tyr Gly Cys Leu Ser Ile Gly Asp Cys Val Gly Leu Ile
            820                 825                 830

Glu Val Val Arg Asn Ser His Thr Ile Met Gln Ile Gln Cys Lys Gly
        835                 840                 845

Gly Leu Lys Gly Ala Leu Gln Phe Asn Ser His Thr Leu His Gln Trp
    850                 855                 860

Leu Lys Asp Lys Asn Lys Gly Glu Ile Tyr Asp Ala Ala Ile Asp Leu
865                 870                 875                 880

Phe Thr Arg Ser Cys Ala Gly Tyr Cys Val Ala Thr Phe Ile Leu Gly
                885                 890                 895

Ile Gly Asp Arg His Asn Ser Asn Ile Met Val Lys Asp Asp Gly Gln
            900                 905                 910

Leu Phe His Ile Asp Phe Gly His Phe Leu Asp His Lys Lys Lys Lys
        915                 920                 925

Phe Gly Tyr Lys Arg Glu Arg Val Pro Phe Val Leu Thr Gln Asp Phe
    930                 935                 940

Leu Ile Val Ile Ser Lys Gly Ala Gln Glu Cys Thr Lys Thr Arg Glu
945                 950                 955                 960

Phe Glu Arg Phe Gln Glu Met Cys Tyr Lys Ala Tyr Leu Ala Ile Arg
                965                 970                 975

Gln His Ala Asn Leu Phe Ile Asn Leu Phe Ser Met Met Leu Gly Ser
            980                 985                 990

Gly Met Pro Glu Leu Gln Ser Phe  Asp Asp Ile Ala Tyr  Ile Arg Lys
        995                 1000                1005

Thr Leu  Ala Leu Asp Lys Thr  Glu Gln Glu Ala Leu  Glu Tyr Phe
    1010                1015                1020

Met Lys  Gln Met Asn Asp Ala  His His Gly Gly Trp  Thr Thr Lys
    1025                1030                1035

Met Asp  Trp Ile Phe His Thr  Ile Lys Gln His Ala  Leu Asn
    1040                1045                1050


<210> SEQ ID NO 40
<211> LENGTH: 6632
<212> TYPE: DNA
<213> ORGANISM: Canis lupus familiaris

<400> SEQUENCE: 40

gccgccgcaa ggggggctgg gacccgatgt ggttagagcc gcggagcctg gagcagcccc      60

gagcatttct gctttgggac agccacacat ataattcctt aaaatagttt tatatgtaaa     120

acttgtaaag gatcagaaca atgcctccaa gaccatcatc aggtgaactg tggggcatcc     180
```

-continued

```
actttgatgcc cccaagaatc ctagtagaat gtttactacc aaatggaatg atagtgacgt    240
tagaatgcct ccgtgaggct acattaataa ctataaagca tgaattattt aaagaagcaa    300
gaaagtaccc tctccatcaa cttcttcaag atgaatcttc ttacattttc gtaagtgtta    360
cccaagaagc agaaagggaa gaattttttg atgaaacaag acggctttgt gaccttcggc    420
tttttcaacc ctttttaaaa gtaattgagc cagtaggcaa ccgagaagaa aagatcctca    480
atcgagaaat tggttttgct attggcatgc cagtgtgtga atttgatatg gttaaagatc    540
cagaagtaca ggacttccga agaaatattc tgaatgtttg taaagaagct gtggatcttc    600
gggatcttaa ttcacctcat agtagagcaa tgtatgtcta tcctccaaat gtagaatctt    660
caccagaact gccaaagcac atatataata aattagataa agggcaaata atagtggtga    720
tttgggtaat agtttctcca aataatgaca aacagaagta tactctgaaa atcaaccatg    780
actgtgttcc agaacaagta attgctgaag caatcagaaa aaaaactaga agtatgttgc    840
tatcatctga acaactaaaa ctctgtgttt tagaatatca gggcaagtat attttaaaag    900
tatgtggatg tgatgaatac ttccttgaaa aatatcctct aagtcagtat aagtacataa    960
gaagctgtat aatgcttgga aggatgccca atttgatgtt gatggctaaa gaaagccttt   1020
actcccaatt gccaatggac tgtttcacaa tgccatctta ttccagacgc atctccacag   1080
ctacaccata tatgaatgga gaaacatcta caaaatccct ttgggttata aatagcgcac   1140
tcagaataaa aatcctttgt gcaacctatg taaatgtaaa tattcgagac attgacaaga   1200
tttatgttcg aacaggtatc tatcatggag gagaaccctt atgtgataat gttaacactc   1260
aaagagtacc ttgttctaat cccaggtgga atgaatggct aaattacgat atatacattc   1320
ctgatcttcc tcgtgctgct cgactttgcc tttccatttg ttctgttaaa ggccgaaagg   1380
gtgctaaaga ggaacactgt ccattggcct ggggaaatat aaacttgttt gattacacag   1440
atactctagt atctggaaaa atggctctga atctttggcc agtacctcat ggattagaag   1500
atttgctgaa ccctattggt gttactgggt caaatccaaa taaagaaact ccatgcttag   1560
agttggagtt tgactggttc agcagtgtgg taaagttccc agatatgtca gtgattgaag   1620
agcatgccaa ctggtcggtg tctcgggaag caggatttag ttattcccat gcaggactga   1680
gtaacagact ggctagagac aacgaattaa gagaaaatga taaagaacag ctccgagcaa   1740
tttgtacccg agatcctctc tctgaaatca ctgagcaaga gaaagatttt ctgtggagcc   1800
acagacacta ttgtgtaact atccctgaaa ttctacccaa actgcttctg tccgttaaat   1860
ggaattctag agatgaagta gctcagatgt actgcttagt aaaagattgg cctccaatca   1920
aacctgaaca agctatggag cttctggact gtaattaccc agatcctatg gttcgaggtt   1980
ttgctgttcg gtgcttggaa aaatacttaa cagatgacaa gctttctcag tacctaattc   2040
agctagtaca ggtcctaaaa tacgaacaat atttggataa cctgcttgtg agatttttac   2100
tcaagaaagc attgactaat caaaggattg ggcatttttt cttttggcat ttaaaatctg   2160
agatgcacaa taaaacggtt agtcagaggt ttggcctgct tttggagtcc tattgccgtg   2220
cttgtgggat gtatttgaag cacctaaata ggcaagttga ggctatggaa aagctcatta   2280
acttaactga cattctcaaa caagagaaga aggatgaaac acaaaaggta cagatgaagt   2340
ttttagttga gcaaatgcgg cgaccagatt tcatggatgc tctacaaggt tttctatctc   2400
ctctaaatcc tgctcatcaa ctaggaaatc tcaggcttga agagtgtcga attatgtcct   2460
ctgcaaaaag gccactgtgg ttgaattggg agaacccaga catcatgtca gagttactct   2520
```

-continued

```
ttcagaacaa tgagatcatc tttaaaaatg gggatgattt acgacaagat atgctaacac   2580
ttcaaataat tcgcattatg gaaaatatct ggcaaaatca aggtcttgat cttcgaatgt   2640
taccttatgg ttgtctgtca atcggtgact gtgtgggact tattgaggtg gtgcgaaatt   2700
ctcacactat tatgcagatt cagtgcaaag gtggcctgaa aggtgcactg cagttcaaca   2760
gccacacact acaccagtgg ctcaaagaca agaacaaagg agaaatatat gatgcagcca   2820
ttgacctgtt cacacgttca tgtgctggat attgtgttgc taccttcatt ttgggaattg   2880
gagatcgtca caatagtaac atcatggtta aagatgatgg acaactgttt catatagatt   2940
ttggacactt tttggaccat aagaagaaaa aatttggtta taaacgggaa cgtgtgccat   3000
ttgttttgac acaggatttc ttaatagtga ttagtaaagg agcccaggaa tgcacaaaaa   3060
caagagaatt tgagaggttt caggagatgt gttacaaggc ttacctagct attcggcagc   3120
atgccaatct cttcataaat cttttctcaa tgatgcttgg ctctggaatg ccagaactac   3180
aatcttttga tgatattgca tacattcgaa agaccctagc tttagataaa actgaacaag   3240
aggctttgga atatttcatg aaacaaatga atgatgcaca tcatggtggc tggacaacaa   3300
aaatggattg gatcttccac accattaagc agcatgcttt gaactgaaat gataactgag   3360
aaaccgaaag ctcattatct ggattctata ctgcactgtt aataactgtc aacaggcaaa   3420
gactgattgc ataggaattg cacaatccat gaacagcatt agaatttaca caagaacaga   3480
aataaaatac tatataattt aaataatgta aacgcaaaca gggtttgaga gcactaaact   3540
agttcatttc aaaattaagc tttagaataa tgcgcaattt catgttatgc cttaaagtcc   3600
aaaaaggtaa actttgaaga ttgtttgtat cttttttaa aaaagaaaac aaaacaaaaa   3660
aaccccaaaa tatatagaaa ttatggagaa ggaaaaagaa tgatgttctt tttttgtctt   3720
gcaaatgttc tatgttttga aattgtggac acagcgaagt ctattattgc attaggtcca   3780
aggaaactga agtttggtgt taaattacat tgagattaga aaaataatga agatttctta   3840
tttttccatt gctgttcaat ttatagtttg aagtgggttt ttttgactcc ttgtttaatg   3900
aagaaaaatg cttggggtgg aagggactct tgagatttca ccagagactt cctttttaat   3960
aaatcaaacc ttttgatgat ttgaggtctt atctgcaaag ttttggaagc agtcacaaat   4020
gagacctgtt ataagatggt gtttttgggt ttttttttc tggacagtat ttacaagaat   4080
ctgattctta cttcccaggg aaattctggg ctcccacaaa gtaaaataat cattatagag   4140
aaagaatgag caggactagt tcttgctcca gaattgtaca gtattcacct taggttgatt   4200
ttttttctc cttttgcaat tgaattgaat acatttttca tgcatgtttc cagaaaatag   4260
aagtgagtat taatgttatt aaaaagatta tttttttat taaaggctat ttatattata   4320
gaaactatca ttaatatata ttctttattt acatgatctg tcccatagtc atgcattgtt   4380
ttgcacccca aatttttat tgttcgtagc agcatggtca gctttcctct tggtttgtgg   4440
gtgaggctca ggcactatcc catttatacc aatgactagt gtataattgc ataaggaaaa   4500
cagattaaag ttcatcctct ttcttttat ttctttgttt tcatgtaact cccccatttt   4560
ccatctctta tagttgataa tgcctcagtc atgaaaccag ttaccaaaat taacacaata   4620
tagagtatct tcctgattgc ttcaacccct ctgctgaggt atgctcatga ataatacttt   4680
ataatatggg ggaatagaaa ccacaaactt tttacctttt taggctattt atgcaatatc   4740
tggataataa aagtaggatt ttaaaccatt ttaaggtcat gtcccatttc caagcaatta   4800
gggctcactg tccaacttta ttaaattgca tttgagtaca ggatacattc ttaaacactt   4860
tggaaaacat tgacccaagg tgtaggggct aatgctaatc atctctctag actctgatat   4920
```

tttactcagt atttgaaatg aatgattaat gccctaggaa atagctttag caaatgtcca 4980
ggtgccacac cagaaaaagt gcaataattt actgacagtt ttctagatta ggcatattat 5040
tggaatacaa ctttataaaa agtgcacatt atatactcta gtaaaacagc atcactaaaa 5100
caatattcat ttatgaaatc agttacctat aatagaagtc ttgaatagtg aataagggac 5160
tctaatacaa atactcttaa tatttggcta ttttagagcc cttaaagggc ctaattattg 5220
gagacttagg tacttcacta aagcatgtat ataatattgc caacaagaaa aataaatttg 5280
aagattaggg gaacttattt ctgtaaactg tcttggaata gttaagaaga atttaaactc 5340
ccattttaag caggaagcca aatagattct tttgcagata tagatttcat aacttcttaa 5400
agcttcttta acattttgtg ccttttagat atattcagtt aatacatact aacatcccag 5460
ccttttctat atcagggatt aattacagga aaactcaatg aaatggtaca aatctggaac 5520
tctgatggtg gagactgaag acttaacaga gaacagcgtt tttacctgag tgccaaaaaa 5580
gctttgagct tccttgcaca aaatttatat gatctttgca tgtctcacat cagtccagct 5640
agtccccttc ccctgagacc tctctaccat taaaacacaa gccacatagc ttatttcatc 5700
atttacattt attttcaata gttattacaa ccaagtctat tctgttggaa gaagtgtaga 5760
caaattttac aaagaatgat taaacaatct cgctgaaaac aaagtaaatt ttaaacaaat 5820
ccaagcagag tttaagcaaa caacattaaa aataagaaaa aagggtcaag tcgtgctcag 5880
aaggcaaagc caaaaattga actgaatgct acatggggtg actaggatgt caagtcaggg 5940
gtaagctgtt tccaggtact tcggtgtcag accactttca tggattggtc cgttcctgtg 6000
gccaaccatc cttgtcattg aacattgtat aactgattat tgactctacg gtttcatgta 6060
gtcacttgag aaatagttcc ttcaaggtat tttgtagggg gaaaaaacca agcaggttta 6120
aggaaaataa aacctaattt taaacacatt ctagtaagat agactctgaa aatcatgttt 6180
taacttttta atcatattct cagctataca gaatcattta ttttgaagat ttttagactg 6240
ctgttaattt gaaatctgtt aatcatattg tagaatttgg tttttaaaaa aaagatgttt 6300
ctaattggat tttttaaaga agaatggaat ttggtcacta ttttatgata gaacctaagc 6360
tttttgtggt tctcagtgtc ctctgtaaaa ttcagtgtca aagtaatcta ctttgaggtt 6420
ttccctttta atctgcttta tattacaagc cctttaggaa atgggaacgt ggtgaatata 6480
caatgaattg taaaatattt taatgtgtaa ttttttcaac tgtgaaacta tgaatattgg 6540
ttttttgatg aaaacagctg ctgataaagt attttgtgta aagtgtagtt cttattaatc 6600
aggaaaataa tcaatgactt gattagaatg ta 6632

<210> SEQ ID NO 41
<211> LENGTH: 1068
<212> TYPE: PRT
<213> ORGANISM: Canis lupus familiaris

<400> SEQUENCE: 41

Met Pro Pro Arg Pro Ser Ser Gly Glu Leu Trp Gly Ile His Leu Met
1 5 10 15

Pro Pro Arg Ile Leu Val Glu Cys Leu Leu Pro Asn Gly Met Ile Val
20 25 30

Thr Leu Glu Cys Leu Arg Glu Ala Thr Leu Ile Thr Ile Lys His Glu
35 40 45

Leu Phe Lys Glu Ala Arg Lys Tyr Pro Leu His Gln Leu Leu Gln Asp
50 55 60

-continued

```
Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
```

```
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Arg Ala Ile Cys Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910
```

```
Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                 1005

Gly Met  Pro Glu Leu Gln Ser  Phe Asp Asp Ile Ala  Tyr Ile Arg
    1010                 1015                 1020

Lys Thr  Leu Ala Leu Asp Lys  Thr Glu Gln Glu Ala  Leu Glu Tyr
    1025                 1030                 1035

Phe Met  Lys Gln Met Asn Asp  Ala His His Gly Gly  Trp Thr Thr
    1040                 1045                 1050

Lys Met  Asp Trp Ile Phe His  Thr Ile Lys Gln His  Ala Leu Asn
    1055                 1060                 1065
```

<210> SEQ ID NO 42
<211> LENGTH: 3757
<212> TYPE: DNA
<213> ORGANISM: Felis catus

<400> SEQUENCE: 42

```
tttctgcttt gggacagcca cgcatctaat tccttaaaac agttttatat gtaaaacttg     60

taaaggatca gaacaatgcc tccaagacca tcatcaggtg aactgtgggg catccacttg    120

atgcccccaa gaatcctagt agaatgttta ctaccaaatg gaatgatagt gacgttagaa    180

tgcctccgtg aggctacatt aataactata aagcatgaat tatttaaaga agcaagaaaa    240

tatcctctcc atcaacttct tcaagatgaa tcttcttaca ttttcgtaag tgttacccaa    300

gaagcagaaa gggaagaatt ttttgatgaa acaagacgac tttgtgacct gcggcttttt    360

caacccttttt taaaagtaat tgagccagta ggcaaccgtg aagaaaagat cctcaatcga    420

gaaattggtt ttgctattgg catgccagtg tgtgaatttg atatggttaa agatccagaa    480

gtacaggact tccgaagaaa tattctgaat gtttgtaaag aagctgtgga tcttcgggat    540

cttaattcac ctcatagtag agcaatgtat gtctatcctc caaatgtaga atcttcacca    600

gaactgccaa agcacatata taataaacta gataaagggc aaataatagt ggtgatttgg    660

gtaatagttt ctccaaataa tgacaagcag aagtatactc tgaaaatcaa ccatgactgt    720

gtgccagaac aagtaattgc tgaagcaatc aggaaaaaaa ctcgaagtat gttgctatca    780

tctgaacaac taaaactctg tgttttagaa taccagggca agtatatttt aaaagtgtgt    840

ggatgtgatg aatacttcct tgaaaaatat cctctaagtc agtataagta cataagaagc    900

tgtataatgc ttgggaggat gcccaatttg atgctgatgg ctaaagaaag cctttactcc    960

caactgccaa tggactgttt cacaatgcca tcttattcca gacgcatctc cacagctaca   1020

ccatatatga atggagaaac atctacaaag tccctttggg ttataaatag tgcactcaga   1080

ataaaaatcc tttgtgcaac ctatgtgaat gtaaatattc gagacatcga caagatctat   1140

gttcgaacag gtatctatca tggaggagaa ccccttatgtg ataatgtgaa cactcaaaga   1200
```

-continued

```
gtaccttgtt ctaatcccag gtggaatgaa tggctaaact acgatatata cattcctgat   1260
cttcctcgtg ctgctcgact ttgcctttcc atttgttctg ttaaaggccg aaagggtgct   1320
aaagaggaac actgtccatt ggcctgggga aatataaact tgtttgatta cacagatact   1380
ctagtatctg gaaaaatggc tttgaatctt tggccagtac ctcatggatt agaagatttg   1440
ctgaacccta ttggtgttac tgggtcaaat ccaaataaag aaaccccatg cttagagttg   1500
gagtttgact ggttcagcag tgtggtaaag ttcccagata tgtcagtgat tgaagagcat   1560
gccaactggt ctgtgtctcg agaagcagga tttagttatt cccatgcagg actgagtaac   1620
agactagcta gagacaacga attaagagaa aatgataaag aacagctccg agcaatttgt   1680
acccgagatc ctctatctga aatcactgag caagagaaag attttctgtg gagccacaga   1740
cactattgtg taactatccc tgaaattcta cccaaactgc ttctgtctgt taaatggaat   1800
tctagagatg aagtagctca gatgtactgc ttagtaaaag attggcctcc aatcaaacct   1860
gaacaggcaa tggagcttct ggattgtaat tacccagatc ctatggttcg aggttttgct   1920
gttcgatgct tggaaaaata tttaacagat gacaagcttt ctcagtactt aattcagcta   1980
gtacaggtcc taaaatatga acagtatttg gataacctgc ttgtgagatt tttactcaag   2040
aaagcattga ctaatcaaag gattgggcac tttttctttt ggcatttaaa atctgagatg   2100
cacaataaaa cagttagtca gaggtttggc ctgcttttgg agtcgtattg tcgtgcatgt   2160
gggatgtatt tgaagcacct aaataggcaa gttgaagcta tggaaaagct cattaactta   2220
actgacattc tcaaacaaga aaagaaggat gaaacacaaa aggtacagat gaagttttta   2280
gttgagcaaa tgcggagacc agatttcatg gatgctctac agggttttct gtctcctcta   2340
aatcctgctc atcaactagg aaatctcagg cttgaagagt gtcgaattat gtcctctgca   2400
aaaaggccac tgtggttgaa ttgggagaac ccagacatca tgtcagagtt actctttcag   2460
aacaatgaga tcatctttaa aaatggggat gatttacggc aagatatgtt aacactgcag   2520
atcattcgca ttatggaaaa tatctggcaa aatcaaggcc ttgatcttcg aatgttacct   2580
tatggttgtc tgtcaatcgg tgactgtgtg ggacttattg aggtggttag aaattctcac   2640
actattatgc agattcaatg caaaggtggc ctgaaaggcg cactgcagtt caacagccac   2700
actctacacc agtggctcaa agacaagaac aaaggcgaaa tatacgatgc agccattgac   2760
ctgttcacac gttcatgtgc tggatattgt gttgctacct tcatactggg aatcggagat   2820
cgtcacaata gtaacatcat ggttaaagat gatggacaac tatttcatat agattttgga   2880
cactttttgg atcataagaa gaaaaaattt ggttataaac gggaacgtgt gccgtttgtt   2940
ttgacacaag atttcttaat agtgattagt aaaggagccc aagaatgcac aaagacaaga   3000
gaattcgaaa ggtttcagga gatgtgttac aaggcttatc tagctattcg gcagcatgcc   3060
aatctcttca taaatctctt ctcaatgatg cttggctctg gaatgccaga actgcaatct   3120
tttgatgata ttgcatacat tcgaaagacc ctagctttag ataaaactga acaagaggct   3180
ttggaatatt tcatgaaaca aatgaatgat gcacatcatg gtggctggac aacaaaaatg   3240
gattggatct tccacacaat taagcagcat gctttgaact gaaatgataa ctgagaaacc   3300
aaaagctcat tatctggatt ctatactgca ctgttaataa ctgtcaacag gcaaagactg   3360
attgcatagg aattgcacaa tccatgaaca gcattagaat ttacacaaga acagaaataa   3420
aatactatat aatttaaata atgtaaacgc aaacagggtt tgagagcact aaactagttc   3480
atttcaaaat taagctttag aataatgcgc aatttcatgt tatgccttaa gtccaaaaag   3540
gtaaactttg aagattgttt gtatcttttt ttaaaaaaga aacaaaaaca aaaaaacccc   3600
```

aaaatatata gaaatggtgg agaaggaaaa agaatgatgt tcttttttg tcttgcaaat 3660 gttctatgtt ttgaaattgt ggacacaaca aagtctatta ttgcattagg tccaaggaaa 3720
ctgaagtttg atgttaaatt gcattaagat tagaaaa 3757

<210> SEQ ID NO 43
<211> LENGTH: 1068
<212> TYPE: PRT
<213> ORGANISM: Felis catus

<400> SEQUENCE: 43

Met Pro Pro Arg Pro Ser Ser Gly Glu Leu Trp Gly Ile His Leu Met
1 5 10 15

Pro Pro Arg Ile Leu Val Glu Cys Leu Leu Pro Asn Gly Met Ile Val
20 25 30

Thr Leu Glu Cys Leu Arg Glu Ala Thr Leu Ile Thr Ile Lys His Glu
35 40 45

Leu Phe Lys Glu Ala Arg Lys Tyr Pro Leu His Gln Leu Leu Gln Asp
50 55 60

Glu Ser Ser Tyr Ile Phe Val Ser Val Thr Gln Glu Ala Glu Arg Glu
65 70 75 80

Glu Phe Phe Asp Glu Thr Arg Arg Leu Cys Asp Leu Arg Leu Phe Gln
85 90 95

Pro Phe Leu Lys Val Ile Glu Pro Val Gly Asn Arg Glu Glu Lys Ile
100 105 110

Leu Asn Arg Glu Ile Gly Phe Ala Ile Gly Met Pro Val Cys Glu Phe
115 120 125

Asp Met Val Lys Asp Pro Glu Val Gln Asp Phe Arg Arg Asn Ile Leu
130 135 140

Asn Val Cys Lys Glu Ala Val Asp Leu Arg Asp Leu Asn Ser Pro His
145 150 155 160

Ser Arg Ala Met Tyr Val Tyr Pro Pro Asn Val Glu Ser Ser Pro Glu
165 170 175

Leu Pro Lys His Ile Tyr Asn Lys Leu Asp Lys Gly Gln Ile Ile Val
180 185 190

Val Ile Trp Val Ile Val Ser Pro Asn Asn Asp Lys Gln Lys Tyr Thr
195 200 205

Leu Lys Ile Asn His Asp Cys Val Pro Glu Gln Val Ile Ala Glu Ala
210 215 220

Ile Arg Lys Lys Thr Arg Ser Met Leu Leu Ser Ser Glu Gln Leu Lys
225 230 235 240

Leu Cys Val Leu Glu Tyr Gln Gly Lys Tyr Ile Leu Lys Val Cys Gly
245 250 255

Cys Asp Glu Tyr Phe Leu Glu Lys Tyr Pro Leu Ser Gln Tyr Lys Tyr
260 265 270

Ile Arg Ser Cys Ile Met Leu Gly Arg Met Pro Asn Leu Met Leu Met
275 280 285

Ala Lys Glu Ser Leu Tyr Ser Gln Leu Pro Met Asp Cys Phe Thr Met
290 295 300

Pro Ser Tyr Ser Arg Arg Ile Ser Thr Ala Thr Pro Tyr Met Asn Gly
305 310 315 320

Glu Thr Ser Thr Lys Ser Leu Trp Val Ile Asn Ser Ala Leu Arg Ile
325 330 335

Lys Ile Leu Cys Ala Thr Tyr Val Asn Val Asn Ile Arg Asp Ile Asp

-continued

```
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Arg Ala Ile Cys Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765
```

```
Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065


<210> SEQ ID NO 44
<211> LENGTH: 3207
<212> TYPE: DNA
<213> ORGANISM: Bos taurus

<400> SEQUENCE: 44

atgcctccaa gaccatcatc aggtgaactg tggggcatcc acttgatgcc cccaagaatc      60

ctagtagaat gtttactacc aaatgggatg atagtgactt tagaatgcct ccgtgaggct     120

acgttaataa cgataaagca tgaactattt aaagaagcaa gaaaataccc tctccatcaa     180

cttcttcaag atgaatcttc ttacattttc gtaagtgtta cccaagaagc agaaagggaa     240

gaatttttg atgaaacaag acgactttgt gaccttcggc tttttcaacc ctttttaaaa     300

gtaattgaac cagtaggcaa ccgtgaagaa aagatcctca atcgagaaat tggttttgct     360

atcggcatgc cagtgtgtga attcgatatg gttaaagatc cagaagtaca ggacttccga     420
```

```
agaaatattc tcaatgtttg taaagaagct gtggatctta gggatcttaa ttcacctcat    480
agtagagcaa tgtatgttta tcctccaaat gtagaatctt caccagaact gccaaagcac    540
atatataata aattggataa agggcaaata atagtggtga tttgggtaat agtttctcca    600
aataatgaca aacagaagta tactctgaaa atcaaccatg actgtgtgcc agaacaagta    660
attgctgaag caatcaggaa aaaaactcga agtatgttgc tatcatctga acaactaaaa    720
ctctgtgttt tagaatatca gggcaagtat attttaaaag tgtgtggatg tgatgaatac    780
ttcctagaaa aatatcctct gagtcagtat aagtatataa gaagctgtat aatgcttggg    840
aggatgccca atttgatgct gatggctaaa gaaagcctct attctcaact gccaatggac    900
tgttttacaa tgccatcata ttccagacgc atctccacag ctacgccata tatgaatgga    960
gaaacatcta caaaatccct ttgggttata aatagtgcac tcagaataaa aattctttgt   1020
gcaacctatg tgaatgtaaa tattcgagac attgacaaga tttatgttcg aacaggtatc   1080
taccatggag gagaaccctt atgtgataat gtgaacactc aaagagtacc ttgttccaat   1140
cccaggtgga atgaatggct gaattacgat atatacattc ctgatcttcc tcgtgctgct   1200
cgactttgcc tttccatttg ttctgttaaa ggccgaaagg gtgctaaaga ggaacactgt   1260
ccattggcct ggggaaatat aaacttgttt gattacacag atactctagt atctggaaaa   1320
atggctttga atctttggcc agtacctcat ggactagaag atttgctgaa ccctattggt   1380
gttactggat caaatccaaa taaagaaact ccatgtttag agttggagtt tgactggttc   1440
agcagtgtgg taaagtttcc agatatgtca gtgattgaag agcatgccaa ttggtctgta   1500
tcccgtgaag caggatttag ttattcccat gcaggactga gtaacagact agctagagac   1560
aatgaattaa gagaaaatga taaagaacag ctccgagcaa tttgtacacg agatcctcta   1620
tctgaaatca ctgagcaaga gaaagatttt ctgtggagcc acagacacta ttgtgtaact   1680
atccccgaaa ttctacccaa attgcttctg tctgttaaat ggaactctag agatgaagta   1740
gctcagatgt actgcttggt aaaagattgg cctccaatca agcctgaaca ggctatggag   1800
cttctggact gcaattaccc agatcctatg gttcgaggtt ttgctgttcg gtgcttagaa   1860
aaatatttaa cagatgacaa actttctcag tacctaattc agctagtaca ggtactaaaa   1920
tatgaacagt atttggataa cctgcttgtg agatttttac tcaaaaaagc gttaactaat   1980
caaaggatcg gtcacttttt cttttggcat ttaaaatctg agatgcacaa taaaacagtt   2040
agtcagaggt ttggcctgct tttggagtcc tattgccgtg catgtgggat gtatctgaag   2100
caccttaata ggcaagttga ggctatggaa aagctcatta acttgactga cattctcaaa   2160
caagagaaga aggatgaaac acaaaaggta cagatgaagt ttttagttga gcaaatgcgg   2220
cgaccagatt tcatggatgc tctccagggc tttctgtctc ctctaaaccc tgctcatcag   2280
ctgggaaatc tcaggcttga agagtgtcga attatgtctt ctgcaaaaag gccactgtgg   2340
ttgaattggg agaacccaga catcatgtca gaattactct ttcagaacaa tgagatcatc   2400
tttaaaaatg gggatgattt acggcaagat atgctaaccc ttcagattat tcgcattatg   2460
gaaaatatct ggcaaaatca aggtcttgat cttcgaatgt taccttatgg atgtctgtca   2520
atcggtgact gtgtgggact tatcgaggtg gtgagaaatt ctcacactat aatgcagatt   2580
cagtgtaaag gaggcctgaa aggtgcactg cagtttaaca gccacacact ccatcagtgg   2640
ctcaaagaca agaacaaggg ggaaatatat gatgcggcca tcgatttgtt tacacgatca   2700
tgtgctggat attgtgttgc caccttcatt ttgggaattg gagatcgtca caatagtaat   2760
```

```
atcatggtta aagatgatgg acaactgttt catatagatt ttggacactt tttggatcac   2820

aagaagaaaa aatttggtta taaacgagag cgcgtgccgt ttgttttgac acaagatttc   2880

ttaatagtga ttagtaaagg agcccaagaa tgcacaaaga caagagaatt tgagaggttt   2940

caggagatgt gttacaaggc ttatctagct attcggcagc atgccaatct cttcataaat   3000

cttttctcaa tgatgcttgg ctctggaatg ccagaactgc aatcttttga tgatattgca   3060

tacattcgaa agaccctagc tttagataaa actgagcaag aggctttgga gtatttcatg   3120

aaacaaatga atgatgcaca ccatggtggc tggacaacaa aaatggattg gatcttccac   3180

acaattaagc agcatgcttt gaactga                                       3207


<210> SEQ ID NO 45
<211> LENGTH: 1068
<212> TYPE: PRT
<213> ORGANISM: Bos taurus

<400> SEQUENCE: 45

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
```

-continued

```
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Arg Ala Ile Cys Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720
```

```
Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                 1005

Gly Met  Pro Glu Leu Gln Ser  Phe Asp Asp Ile Ala  Tyr Ile Arg
    1010                 1015                 1020

Lys Thr  Leu Ala Leu Asp Lys  Thr Glu Gln Glu Ala  Leu Glu Tyr
    1025                 1030                 1035

Phe Met  Lys Gln Met Asn Asp  Ala His His Gly Gly  Trp Thr Thr
    1040                 1045                 1050

Lys Met  Asp Trp Ile Phe His  Thr Ile Lys Gln His  Ala Leu Asn
    1055                 1060                 1065
```

<210> SEQ ID NO 46
<211> LENGTH: 3452
<212> TYPE: DNA
<213> ORGANISM: Gallus gallus

<400> SEQUENCE: 46

```
cggggctcgc gcgaaagccc ggcggcgcaa tgaaggtgag ggccggcgcg cggtgaggtg      60

ggatcccggg gcggccccca gacttgcatg gtttaactca tacgaatcac tgcttgaaag     120
```

-continued

```
acttcaagta caaaattgaa agactttaaa atgccacccc gaccatcatc tggtgaacta    180
tggggcatcc acttgatgcc cccgaggatc cttgtggagt gtcttctccc aaatggaatg    240
atagtgactc tagaatgcct ccgtgaggcc acactgctaa ctatcaaaca tgaacttttt    300
aaagaagcaa gaaaataccc tctctatcag ctccttcaag atgaatcttc ttacattttt    360
gtaagtgtta cgcaagaagc agaaagagaa gaatttttttg atgaaacacg gagactttgt    420
gacctgcggc tatttcaacc tttcctaaaa gtcattgaac cagtaggtaa cagagaagaa    480
aagatcctta atagagaaat aggttttgct attggcatgc ccatctgtga gtttgacatg    540
gttaaggatc ctgaagtaca agatttcaga agaaacattc ttaatgtttg taaagaagca    600
gtagatcttc gagatgccaa tgctccacat agtagagcat tatatgtctg tcctccaaat    660
gtagaatctt cacctgagct acccaaacac atatacaata aactagataa agggcaaata    720
atagtggtga tatgggtaat agtttcacct aacaacgata agcagaagta caccttaaaa    780
atcaatcatg actgtgtgcc tgagcaagtt attgctgaag caattaggaa gaaaacacga    840
agtatgttgc tgtcatctga acaactgaag ctttgcgtgt tggagtacca gggcaagtat    900
attctgaaag tgtgtggctg tgatgaatac ttgctagaaa aatatccact gagccagtat    960
aagtacataa gaagttgtat aatgcttggt cgcatgccca atctcatgct gatggctaaa   1020
gaaagcctat atacccagct gccgctcgat acctttacaa tgccatctta ctccaggcgt   1080
atctctacag ctacacccta catgaatgga gaagctacag ccaagtccct ctggactata   1140
aacagtgctc tcagaataag aatcctctgt gcaacctatg taaatgtgaa cattagagac   1200
attgacaaaa tctacgttag aacaggtatc taccatggag gagaaccttt atgtgacaat   1260
gtgaatactc agagggtacc ttgttctaat cccagatgga atgaatggct gtcgtatgac   1320
atgtacattc ctgatcttcc acgtgctgct cggctctgcc tctctatctg ttctgttaaa   1380
ggccggaagg gtgctaaaga ggagcactgt ccattggctt ggggaaacat aaacatgttt   1440
gactacacgg acactcttgt atctgggaaa atggctttga atctttgggc agtacccccat   1500
ggactggagg atttgttgaa tcctataggt gttactggat caaatccgaa taaggaaact   1560
ccatgtttag agctggaatt tgattggttt agcaatcctg ttaagtttcc agatatgaca   1620
gtgattgaag aacatgccaa ttggacgatc tcacgtgaac tgggctttaa ctacagctat   1680
gcgggactga gtaacagaat agctagagac aatgaattaa gagaaagtga caaggagcaa   1740
ctgagagcca tatgtacgcg agatcctttg tctgaaatca ctgagcaaga gaaggacttc   1800
ctctggagcc acagacacta ttgtgtaaat acgccagaaa ttctgcccaa attacttctg   1860
tctgttaaat ggaattctag agatgaagtg gctcagatgt actgtttggt aaaagattgg   1920
cctccaatca agccagagca agcaatggag cttttggatt gtaattatcc agatccaatg   1980
gtgcgggctt ttgcagttcg gtgtctagag aagtacttaa cagatgacaa actgtctcag   2040
tacttaatcc agctagtaca ggttctgaaa tatgagcagt acttagataa tcaactcgtg   2100
agatttttac tcaagaaggc actgaccaat caacggatag gacacttctt cttttggcat   2160
ttaaagtctg aaatgcacaa taaaactgta agtcagaggt ttggtttact tctggagtcc   2220
tattgtcgag catgtggaat gtacctaaag catctgagca ggcaggtgga ggctatggag   2280
aagttgatta acctcacaga tattctcaag caggaaaaga aagatgagac ccagaaggtg   2340
cagatgaagt ttcttgttga acaaatgaga cgtccagatt ttatggatgc tttacaaggc   2400
tttatctctc ctcttaatcc tgctcatcaa ctgggaaatc ttcggcttga ggagtgcaga   2460
ataatgtcat ctgcaaaaag gcccctgtgg ttaaactggg aaaacccaga tattatgtct   2520
```

-continued

```
gaattgctat ttcagaacaa tgagataatc tttaaaaatg gagatgactt gcgtcaagac   2580

atgctgacac ttcagataat tagaattatg gaaaacatct ggcaaaacca aggtcttgat   2640

cttcggatgt tgccttacgg ttgtttgtct attggtgact gtgtgggact cattgaggta   2700

gtgagaagtt ctcatacaat catgcagatt cagtgtaaag gaggcttaaa gggagcattg   2760

cagttcaaca gccatacatt gcatcagtgg ctcaaggaca agaacaaagg agaaatgtat   2820

gatgcagcta ttgacttgtt tacacgttct tgtgctggct actgtgtcgc tacctttata   2880

ctgggcattg gtgatcgcca caacagtaac atcatggtga aagatgatgg acaactgttt   2940

catattgact ttggccactt ccttgaccac aagaagaaga aatttggcta caaaagagag   3000

cgtgtgccct ttgtcttaac acaggacttt ttaatagtga ttagtaaagg agcccaagaa   3060

tgtaccaaaa caagggagtt tgaaaggttt caagagatgt gttataaggc atatctagca   3120

attcggcagc atgccaatct gttcataaat ctcttctcca tgatgcttgg ctcaggaatg   3180

ccagaactgc agtcctttga cgatattgca tacattcgaa agacccttgc attggacaaa   3240

actgagcagg aagctcttga gtacttcatg aagcaaatga atgatgctca ccatggtggc   3300

tggacaacaa aaatggactg gatcttccac acaataaagc aacatgcttt gaactgaaat   3360

gaaagtgaag aaaacaacta ataacccgct ttgtgggtac tacactgtta atacctgtta   3420

gcagcaaaga ctggttgcat aggaattgca ca                                 3452
```

<210> SEQ ID NO 47
<211> LENGTH: 1068
<212> TYPE: PRT
<213> ORGANISM: Gallus gallus

<400> SEQUENCE: 47

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Leu Thr Ile Lys His Glu
        35                  40                  45

Leu Phe Lys Glu Ala Arg Lys Tyr Pro Leu Tyr Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Ile Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Ala Asn Ala Pro His
145                 150                 155                 160

Ser Arg Ala Leu Tyr Val Cys Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205
```

-continued

```
Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Leu Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Thr Gln Leu Pro Leu Asp Thr Phe Thr Met
    290                 295                 300

Pro Ser Tyr Ser Arg Arg Ile Ser Thr Ala Thr Pro Tyr Met Asn Gly
305                 310                 315                 320

Glu Ala Thr Ala Lys Ser Leu Trp Thr Ile Asn Ser Ala Leu Arg Ile
                325                 330                 335

Arg Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Ser Tyr Asp Met Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Met Phe Asp Tyr
            420                 425                 430

Thr Asp Thr Leu Val Ser Gly Lys Met Ala Leu Asn Leu Trp Ala Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Asn Pro Val Lys Phe Pro Asp Met Thr Val Ile Glu Glu His Ala
                485                 490                 495

Asn Trp Thr Ile Ser Arg Glu Leu Gly Phe Asn Tyr Ser Tyr Ala Gly
            500                 505                 510

Leu Ser Asn Arg Ile Ala Arg Asp Asn Glu Leu Arg Glu Ser Asp Lys
        515                 520                 525

Glu Gln Leu Arg Ala Ile Cys Thr Arg Asp Pro Leu Ser Glu Ile Thr
    530                 535                 540

Glu Gln Glu Lys Asp Phe Leu Trp Ser His Arg His Tyr Cys Val Asn
545                 550                 555                 560

Thr Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Ala Phe Ala Val Arg Cys Leu Glu Lys Tyr Leu Thr
    610                 615                 620
```

-continued

```
Asp Asp Lys Leu Ser Gln Tyr Leu Ile Gln Leu Val Gln Val Leu Lys
625                 630                 635                 640

Tyr Glu Gln Tyr Leu Asp Asn Gln Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Ser Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Ile
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Ser Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Met Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala His His Gly Gly  Trp Thr Thr
```

1040 1045 1050

Lys Met Asp Trp Ile Phe His Thr Ile Lys Gln His Ala Leu Asn
1055 1060 1065

<210> SEQ ID NO 48
<211> LENGTH: 2949
<212> TYPE: DNA
<213> ORGANISM: Homo sapiens

<400> SEQUENCE: 48
cgcctccctt cccccctcccc gcccgacagc ggccgctcgg gccccggctc tcggttataa 60
gatggcggcg ctgagcggtg gcggtggtgg cggcgcggag ccgggccagg ctctgttcaa 120
cggggacatg gagcccgagg ccggcgccgg cgccggcgcc gcggcctctt cggctgcgga 180
ccctgccatt ccggaggagg tgtggaatat caaacaaatg attaagttga cacaggaaca 240
tatagaggcc ctattggaca aatttggtgg ggagcataat ccaccatcaa tatatctgga 300
ggcctatgaa gaatacacca gcaagctaga tgcactccaa caaagagaac aacagttatt 360
ggaatctctg gggaacggaa ctgatttttc tgtttctagc tctgcatcaa tggataccgt 420
tacatcttct tcctcttcta gcctttcagt gctaccttca tctctttcag tttttcaaaa 480
tcccacagat gtggcacgga gcaaccccaa gtcaccacaa aaacctatcg ttagagtctt 540
cctgcccaac aaacagagga cagtggtacc tgcaaggtgt ggagttacag tccgagacag 600
tctaaagaaa gcactgatga tgagaggtct aatcccagag tgctgtgctg tttacagaat 660
tcaggatgga gagaagaaac caattggttg ggacactgat atttcctggc ttactggaga 720
agaattgcat gtggaagtgt tggagaatgt tccacttaca acacacaact ttgtacgaaa 780
aacgtttttc accttagcat tttgtgactt ttgtcgaaag ctgcttttcc agggtttccg 840
ctgtcaaaca tgtggttata aatttcacca gcgttgtagt acagaagttc cactgatgtg 900
tgttaattat gaccaacttg atttgctgtt tgtctccaag ttctttgaac accacccaat 960
accacaggaa gaggcgtcct tagcagagac tgccctaaca tctggatcat ccccttccgc 1020
acccgcctcg gactctattg ggccccaaat tctcaccagt ccgtctcctt caaaatccat 1080
tccaattcca cagcccttcc gaccagcaga tgaagatcat cgaaatcaat ttgggcaacg 1140
agaccgatcc tcatcagctc ccaatgtgca tataaacaca atagaacctg tcaatattga 1200
tgacttgatt agagaccaag gatttcgtgg tgatggagga tcaaccacag gtttgtctgc 1260
taccccccct gcctcattac ctggctcact aactaacgtg aaagccttac agaaatctcc 1320
aggacctcag cgagaaagga agtcatcttc atcctcagaa gacaggaatc gaatgaaaac 1380
acttggtaga cgggactcga gtgatgattg ggagattcct gatgggcaga ttacagtggg 1440
acaaagaatt ggatctggat catttggaac agtctacaag ggaaagtggc atggtgatgt 1500
ggcagtgaaa atgttgaatg tgacagcacc tacacctcag cagttacaag ccttcaaaaa 1560
tgaagtagga gtactcagga aaacacgaca tgtgaatatc ctactcttca tgggctattc 1620
cacaaagcca caactggcta ttgttaccca gtggtgtgag ggctccagct tgtatcacca 1680
tctccatatc attgagacca aatttgagat gatcaaactt atagatattg cacgacagac 1740
tgcacagggc atggattact tacacgccaa gtcaatcatc cacagagacc tcaagagtaa 1800
taatatattt cttcatgaag acctcacagt aaaaataggt gattttggtc tagctacagt 1860
gaaatctcga tggagtgggt cccatcagtt tgaacagttg tctggatcca ttttgtggat 1920
ggcaccagaa gtcatcagaa tgcaagataa aaatccatac agctttcagt cagatgtata 1980

-continued

```
tgcatttgga attgttctgt atgaattgat gactggacag ttaccttatt caaacatcaa   2040

caacagggac cagataattt ttatggtggg acgaggatac ctgtctccag atctcagtaa   2100

ggtacggagt aactgtccaa aagccatgaa gagattaatg gcagagtgcc tcaaaaagaa   2160

aagagatgag agaccactct ttccccaaat tctcgcctct attgagctgc tggcccgctc   2220

attgccaaaa attcaccgca gtgcatcaga accctccttg aatcgggctg gtttccaaac   2280

agaggatttt agtctatatg cttgtgcttc tccaaaaaca cccatccagg caggggggata   2340

tggtgcgttt cctgtccact gaaacaaatg agtgagagag ttcaggagag tagcaacaaa   2400

aggaaaataa atgaacatat gtttgcttat atgttaaatt gaataaaata ctctcttttt   2460

ttttaaggtg aaccaaagaa cacttgtgtg gttaaagact agatataatt tttccccaaa   2520

ctaaaattta tacttaacat tggattttta acatccaagg gttaaaatac atagacattg   2580

ctaaaaattg gcagagcctc ttctagaggc tttactttct gttccgggtt tgtatcattc   2640

acttggttat tttaagtagt aaacttcagt ttctcatgca acttttgttg ccagctatca   2700

catgtccact agggactcca gaagaagacc ctacctatgc ctgtgtttgc aggtgagaag   2760

ttggcagtcg gttagcctgg gttagataag gcaaactgaa cagatctaat ttaggaagtc   2820

agtagaattt aataattcta ttattattct taataatttt tctataacta tttcttttta   2880

taacaatttg gaaaatgtgg atgtctttta tttccttgaa gcaataaact aagtttcttt   2940

ttataaaaa                                                            2949
```

```
<210> SEQ ID NO 49
<211> LENGTH: 766
<212> TYPE: PRT
<213> ORGANISM: Homo sapiens

<400> SEQUENCE: 49

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
```

-continued

```
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620
```

-continued

```
Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765
```

<210> SEQ ID NO 50
<211> LENGTH: 3906
<212> TYPE: DNA
<213> ORGANISM: Rattus norvegicus

<400> SEQUENCE: 50

```
atggcggcgc tgagtggcgg cggtggcagc agcagcggtg gcggtggcgg cggcggcggc     60

ggcggtggtg gcggcggcgg cggcggcgcc gaacagggac aggctctgtt caatggcgac    120

atggagccgg aggccggcgc tggcgccgcg gcctcttcgg ccgcggaccc ggccattcct    180

gaagaggtgt ggaatatcaa gcaaatgatt aagttgacac aggaacatat agaggcccta    240

ttggacaagt ttggtgggga gcataaccca ccgtcaatat acctggaggc ctatgaagag    300

tacaccagca agctagatgc ccttcagcag agagagcagc agctgttgga atccctggtt    360

tttcaaactc ccacagatgt atcacggaac aaccccaagt caccacagaa acctatcgtt    420

cgtgtcttcc tgcccaacaa acagaggaca gtggtgcccg caagatgtgg tgtaacggtc    480

cgagacagtc taaagaaagc actaatgatg aggggtctca tcccagagtg ctgtgctgtt    540

tacagaattc aggacggaga gaagaaacca attggctggg acactgacat ttcctggctt    600

actggagagg agctacatgt tgaagtacta gagaatgttc ctctgacaac ccacaacttc    660

gtacggaaaa ctttttttcac cttagcattt tgtgactttt gccgaaagct gcttttccag    720

ggtttccgct gtcaaacatg tggttataag tttcaccagc gttgtagtac agaggttcca    780

ctgatgtgtg ttaattatga ccaacttgat ttgctgtttg tctccaagtt ctttgagcat    840

cacccagtac cacaggagga ggccttctca gcagagacta cccttccatc tggatgctct    900

tccgcacccc cctcagactc tattgggccc caaatcctca ccagtccatc tccttcaaaa    960

tccattccaa ttccacagcc cttccggcca gcagatgaag atcatcgcaa tcagtttggg   1020

caacgagacc gctcctcctc cgctcccaat gttcatataa acacaatcga acctgtcaat   1080

attgatgaaa aattcccaga agtggaatta caggatcaaa gggatttgat tagagaccag   1140

gggtttcgtg gggatggagc ccctttgaac cagctgatgc gctgtcttcg gaaataccaa   1200

tcccggactc ccagccccct cctccattct gtccccagtg aaatagtgtt tgattttgag   1260

cctggcccag tgttcagagg gtcaaccaca ggcttgtcgg ccaccccacc tgcctcatta   1320
```

```
cctggctcac tcactaacgt gaaagcctta cagaaatctc caggacctca gcgggaaagg   1380
aagtcctcct cctcctcctc ctccacggaa gacagaagtc ggatgaaaac acttggtaga   1440
agagattcaa gtgatgattg ggagattcct gatggacaga ttacagtggg acagagaatt   1500
ggatctgggt cctttggaac tgtctacaag ggaaagtggc atggcgacgt ggcagtgaaa   1560
atgctgaatg tgacagcacc cacacctcag cagttacagg ccttcaaaaa cgaagtcgga   1620
gtactcagga aaactcgaca tgtgaacatc ctccttttca tgggctattc tacaaagcca   1680
cagctggcta ttgttacaca gtggtgtgaa ggctccagct tatatcacca tctccacatc   1740
attgagacca aatttgagat gatcaaactt atagatattg cacggcagac tgcacagggc   1800
atggattact tacacgccaa gtcaatcatc cacagagacc tcaagagtaa taatatattt   1860
cttcatgaag acctcacggt aaaaataggt gactttggtt tagccacagt gaagtcccga   1920
tggagtgggt cccatcagtt tgaacagttg tctggatcta ttttgtggat ggcacccgaa   1980
gtaatcagaa tgcaagataa aaacccatat agctttcagt cagacgtgta tgcatttggg   2040
attgttctgt atgaactgat gactggtcag ctaccttatt caaacatcaa caacagggat   2100
cagataattt ttatggtggg acgaggatac ctatctccag atctcagtaa ggtacggagt   2160
aactgtccaa aagccatgaa gagattaatg gcagagtgcc tcaaaaagaa aagagacgag   2220
agaccactct ttccccaaat tctcgcctct attgagctgc tggcccgctc attgccaaaa   2280
attcaccgca gtgcatcaga accctccttg aatcgggctg gtttccaaac agaagatttt   2340
agtctgtatg cttgtgcttc tccaaaaaca cccatccaag caggggggata tggagaattt   2400
gcagccttca agtagccact ccatcatggc agcatctact ctttatttct taagtcttgt   2460
gttcatacaa tttgttaaca tcaaaacaca gttctgttcc tcaaattttt tttaaagata   2520
caaaatttc aatgcataag ctcgtgtgga acagaatgga atttcctatt caacaaaaga   2580
gggaagaatg ttttaggaac cagaattctc tgctgcccgt gtttcttctt caacacaaat   2640
atcatgtgca tacaactctg cccattccca agaagaaaga ggagagaccc cgaattctgc   2700
ccttttggtg gtcaggcatg atggaaagaa tttgctgctg cagcttggga aaaattgcta   2760
tggaaagtct gccagtcaac tttgcccttc taaccaccag atccatttgt ggctggtcat   2820
ctgatggggc gatttcaatc accaagcatc gttcttgcct gttgtgggat tatgtcgtgg   2880
agcactttcc ctatccacca ccgttaattt ccgagggatg gagtaaatgc agcataccct   2940
ttgtgtagca cctgtccagt cctcaaccaa tgctatcaca gtgaagctct ttaaatttaa   3000
gtggtgggtg agtgttgagg agagactgcc ttgggggcag agaaaagggg atgctgcatc   3060
ttcttcctca cctccagctc tctcacctcg ggttgccttg cacactgggc tccgcctaac   3120
cactcgggct gggcagtgct ggcacacatt gccgcctttt ctcattgggt ccagcaattg   3180
agcagagggt tgggggattg tttcctccac aatgtagcaa attctcagga aaatacagtc   3240
catatcttcc tctcagctct tccagtcacc aaatacttac gtggctcctt tgtccaggac   3300
ataaaacacc gtggacaaca cctaattaaa agcctacaaa actgcttact gacagttttg   3360
aatgtgagac atttgtgtaa tttaaatgta aggtacaggt cttaatttct tctattaagt   3420
ttcttctatt tttatttaaa cgaagaaaat aattttcagg tttaattgga ataaacgaat   3480
acttcccaaa agactatata ccctgaaaat tatatttttg ttaattgtaa acaactttta   3540
aaaaatggtt attatccttt tctctaccta aaattatggg aaatcttagc ataatgacaa   3600
ttatttatac tttttaaata aatggtactt gctggatcca cactaacatc tttgctaaca   3660
```

```
ttcccattgt ttcttccaac ttcactccta cactacatcc tccatcctct ttctagtctt   3720

ttatctataa tatgcaacct aaaataaaag tggtggtgtc tccattcatt cttcttcttc   3780

ctttttttccc caagcctggt cttcaaaagg ttgggtaatt tagtagctga gttccctagg   3840

tagaaataga actattaggg acattggggt tgtaggaaag cgtgaggcct gtcaccagtt   3900

gttctt                                                             3906


<210> SEQ ID NO 51
<211> LENGTH: 804
<212> TYPE: PRT
<213> ORGANISM: Rattus norvegicus

<400> SEQUENCE: 51

Met Ala Ala Leu Ser Gly Gly Gly Gly Ser Ser Ser Gly Gly Gly Gly
1               5                   10                  15

Gly Gly Gly Gly Gly Gly Gly Gly Gly Gly Gly Gly Gly Ala Glu Gln
            20                  25                  30

Gly Gln Ala Leu Phe Asn Gly Asp Met Glu Pro Glu Ala Gly Ala Gly
        35                  40                  45

Ala Ala Ala Ser Ser Ala Ala Asp Pro Ala Ile Pro Glu Glu Val Trp
    50                  55                  60

Asn Ile Lys Gln Met Ile Lys Leu Thr Gln Glu His Ile Glu Ala Leu
65                  70                  75                  80

Leu Asp Lys Phe Gly Gly Glu His Asn Pro Pro Ser Ile Tyr Leu Glu
                85                  90                  95

Ala Tyr Glu Glu Tyr Thr Ser Lys Leu Asp Ala Leu Gln Gln Arg Glu
            100                 105                 110

Gln Gln Leu Leu Glu Ser Leu Val Phe Gln Thr Pro Thr Asp Val Ser
        115                 120                 125

Arg Asn Asn Pro Lys Ser Pro Gln Lys Pro Ile Val Arg Val Phe Leu
    130                 135                 140

Pro Asn Lys Gln Arg Thr Val Val Pro Ala Arg Cys Gly Val Thr Val
145                 150                 155                 160

Arg Asp Ser Leu Lys Lys Ala Leu Met Met Arg Gly Leu Ile Pro Glu
                165                 170                 175

Cys Cys Ala Val Tyr Arg Ile Gln Asp Gly Glu Lys Lys Pro Ile Gly
            180                 185                 190

Trp Asp Thr Asp Ile Ser Trp Leu Thr Gly Glu Glu Leu His Val Glu
        195                 200                 205

Val Leu Glu Asn Val Pro Leu Thr Thr His Asn Phe Val Arg Lys Thr
    210                 215                 220

Phe Phe Thr Leu Ala Phe Cys Asp Phe Cys Arg Lys Leu Leu Phe Gln
225                 230                 235                 240

Gly Phe Arg Cys Gln Thr Cys Gly Tyr Lys Phe His Gln Arg Cys Ser
                245                 250                 255

Thr Glu Val Pro Leu Met Cys Val Asn Tyr Asp Gln Leu Asp Leu Leu
            260                 265                 270

Phe Val Ser Lys Phe Phe Glu His His Pro Val Pro Gln Glu Glu Ala
        275                 280                 285

Phe Ser Ala Glu Thr Thr Leu Pro Ser Gly Cys Ser Ser Ala Pro Pro
    290                 295                 300

Ser Asp Ser Ile Gly Pro Gln Ile Leu Thr Ser Pro Ser Pro Ser Lys
305                 310                 315                 320

Ser Ile Pro Ile Pro Gln Pro Phe Arg Pro Ala Asp Glu Asp His Arg
```

-continued

```
                325                 330                 335

Asn Gln Phe Gly Gln Arg Asp Arg Ser Ser Ser Ala Pro Asn Val His
            340                 345                 350

Ile Asn Thr Ile Glu Pro Val Asn Ile Asp Glu Lys Phe Pro Glu Val
        355                 360                 365

Glu Leu Gln Asp Gln Arg Asp Leu Ile Arg Asp Gln Gly Phe Arg Gly
    370                 375                 380

Asp Gly Ala Pro Leu Asn Gln Leu Met Arg Cys Leu Arg Lys Tyr Gln
385                 390                 395                 400

Ser Arg Thr Pro Ser Pro Leu Leu His Ser Val Pro Ser Glu Ile Val
                405                 410                 415

Phe Asp Phe Glu Pro Gly Pro Val Phe Arg Gly Ser Thr Thr Gly Leu
            420                 425                 430

Ser Ala Thr Pro Pro Ala Ser Leu Pro Gly Ser Leu Thr Asn Val Lys
        435                 440                 445

Ala Leu Gln Lys Ser Pro Gly Pro Gln Arg Glu Arg Lys Ser Ser Ser
    450                 455                 460

Ser Ser Ser Ser Thr Glu Asp Arg Ser Arg Met Lys Thr Leu Gly Arg
465                 470                 475                 480

Arg Asp Ser Ser Asp Asp Trp Glu Ile Pro Asp Gly Gln Ile Thr Val
                485                 490                 495

Gly Gln Arg Ile Gly Ser Gly Ser Phe Gly Thr Val Tyr Lys Gly Lys
            500                 505                 510

Trp His Gly Asp Val Ala Val Lys Met Leu Asn Val Thr Ala Pro Thr
        515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750
```

```
Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800

Ala Ala Phe Lys


<210> SEQ ID NO 52
<211> LENGTH: 9728
<212> TYPE: DNA
<213> ORGANISM: Mus musculus

<400> SEQUENCE: 52

ccctcaggct cggctgcgcc ggggccgccg gcgggttcca gaggtggcct ccgccccggc      60

cgctccgccc acgccccccg cgcctccgcg cccgcctccg cccgccctgc gcctcccttc     120

cccctccccg ccccgcggcg gccgctcggc ccggctcgcg cttcgaagat ggcggcgctg     180

agtggcggcg gtggcagcag cagcggtggc ggcggcggcg gtggcggcgg cggtggcggt     240

ggcgacggcg gcggcggcgc cgagcagggc caggctctgt tcaatggcga catggagccg     300

gaggccggcg ctggcgccgc ggcctcttcg gctgcggacc cggccattcc tgaagaggta     360

tggaatatca agcaaatgat taagttgaca caggaacata tagaggccct attggacaaa     420

tttggtggag agcataaccc accatcaata tacctggagg cctatgaaga gtacaccagc     480

aagctagatg cccttcagca aagagaacag cagcttttgg aatccctggt tttcaaact     540

cccacagatg catcacggaa caaccccaag tcaccacaga aacctatcgt tagagtcttc     600

ctgcccaaca aacagaggac agtggtaccc gcaagatgtg gtgttacagt tcgagacagt     660

ctaaagaaag cactgatgat gagaggtctc atcccagaat gctgtgctgt ttacagaatt     720

caggatggag agaagaaacc aattggctgg gacacggaca tttcctggct tactggagag     780

gagttacatg ttgaagtact ggagaatgtc ccacttacaa cacacaactt tgtacggaaa     840

actttttca ccttagcatt ttgtgacttt tgccgaaagc tgcttttcca gggtttccgt     900

tgtcaaacat gtggttataa atttcaccag cgttgtagta cagaggttcc actgatgtgt     960

gtaaattatg accaacttga tttgctgttt gtctccaagt tctttgagca tcacccagta    1020

ccacaggagg aggcctcctt cccagagact gcccttccat ctggatcctc ttccgcaccc    1080

ccctcagact ctactgggcc ccaaatcctc accagtccat ctccttcaaa atccattcca    1140

attccacagc ccttccgacc agcagatgaa gatcatcgca atcagtttgg gcaacgagac    1200

cggtcctcct cagctcccaa tgttcatata aacacaattg agcctgtgaa tatcgatgaa    1260

aaattcccag aagtggaatt acaggatcaa agggatttga ttagagacca ggggtttcgt    1320

ggtgatggag ccccccttgaa ccaactgatg cgctgtcttc ggaaatacca atcccggact    1380

cccagccccc tcctccattc tgtccccagt gaaatagtgt ttgattttga gcctggccca    1440

gtgttcagag ggtcaaccac aggcttgtcc gccaccccgc ctgcctcatt acctggctca    1500

ctcactaacg tgaaagcctt acagaaatct ccaggtcctc agcgggaaag gaagtcatct    1560

tcttcctcat cctcggagga cagaagtcgg atgaaaacac ttggtagaag agattcaagt    1620

gatgactggg agattcctga tggacagatt acagtgggac agagaattgg atctgggtca    1680

tttggaactg tctacaaggg aaagtggcat ggtgatgtgg cagtgaaaat gttgaatgtg    1740

acagcaccca cacctcaaca gctacaggcc ttcaaaaatg aagtaggagt gctcaggaaa    1800
```

```
actcgacatg tgaatatcct ccttttcatg ggctattcta caaagccaca actggcaatt   1860
gttacacagt ggtgtgaggg ctccagctta tatcaccatc tccacatcat tgagaccaaa   1920
tttgagatga tcaaacttat agatattgct cggcagactg cacagggcat ggattactta   1980
cacgccaagt caatcatcca cagagacctc aagagtaata atatatttct tcatgaagac   2040
ctcacggtaa aaataggtga ctttggtcta gccacagtga aatctcggtg gagtgggtcc   2100
catcagtttg aacagttgtc tggatctatt ttgtggatgg caccagaagt aatcagaatg   2160
caagataaaa acccgtatag ctttcagtca gacgtgtatg cgtttgggat tgttctgtac   2220
gaactgatga ccggccagct accttattca aacatcaaca acagggatca gataattttt   2280
atggtgggac gaggatacct atctccagat ctcagtaagg tacggagtaa ctgtccaaaa   2340
gccatgaaga gattaatggc agagtgcctc aaaaagaaaa gagacgagag accactcttt   2400
ccccaaattc tcgcctccat tgagctgctg gcccgctcat tgccaaaaat tcaccgcagt   2460
gcatcagaac cttccttgaa tcgggctggt ttccaaacag aagattttag tctgtatgct   2520
tgtgcttctc cgaaaacacc catccaagca gggggatatg gagaatttgc agccttcaag   2580
tagccagtcc atcatggcag catctactct ttatttctta agtcttgtgt tcatacagtt   2640
tgttaacatc aaaacacagt tctgttcctc aaaaaatttt ttaaagatac aaaattttca   2700
atgcataagt tcatgtggaa cagaatggaa tttcctattc aacaaaagag ggaagaatgt   2760
tttaggaacc agaattctct gctgcccgtg tttcttcttc aacataacta tcacgtgcat   2820
acaagtctgc ccattcccaa gaagaaagag gagagaccct gaattctgcc cttttggtgg   2880
tcaggcatga tggaaagaat ttgctgctgc agcttgggaa aattgctatg gaaagtctgc   2940
cagtcgactt tgcccttcta accaccagat cagcctgtgg ctggtcatct gatggggcga   3000
tttccatcac caagcatcgt tcttgcctat tctgggatta tgttgtggag cactttccct   3060
gtccagcacc gttcatttct gagggatgga gtaaatgcag cattcccttg tgtagcgcct   3120
gttcagtcct cagcagctgc tgtcacagcg aagcttttta cagttaagtg gtgggggaga   3180
gttgaggaga gcctgcctcg ggcagagaa aagggggtgc tgcatcttct tcctcacctc   3240
cagctctctc acctcgggtt gccttgctca ctgggctccg cctaaccact caggctgctc   3300
agtgctggca cacattgcct tcttttctca ttgggtccag caattgagga gagggttggg   3360
ggattgtttc ctcctcaatg tagcaaattc tcaggaaaat acagtccata tcttcctctc   3420
agctcttcca gtcaccaaat acttacgtgg ctcctttgtc caggacataa aacaccgtgg   3480
acaacaccta attaaaagcc tacaaaactg cttactgaca gttttgaatg tgagacactt   3540
gtgtaattta aatgtaaggt acaggtttta atttctgagt ttcttctatt tttatttaaa   3600
agaagaaaat aattttcagt tttaattgga ataaatgagt acttcccaca agactatata   3660
ccctgaaaat tatatttttg ttaattgtaa acaactttta aagaataatt attatccttt   3720
tctctaccta aaaattatgg ggaatcttag cataatgaca attatttata ctttttaaat   3780
aaatggtact tgctggatcc acactaacat ctttgctaac aatcccattg tttcttccaa   3840
cttaactcct acactacatc ctacatcctc tttctagtct tttatctata atatgcaacc   3900
taaaataaac gtggtggcgt ctccattcat tctccctctt cctgttttcc ccaagcctgg   3960
tcttcaaaag gttgggtaat cggtccctga gctccctagc tggcaatgca actattaggg   4020
acattggagt tgcaggagag caggaagcct gtccccagct gttcttctag aaccctaaat   4080
cttatctttg cacagatcaa aagtatcacc tcgtcacagt tctccttagc ctttacttac   4140
```

-continued

```
aggtaatata aataaaaatc accatagtag taaagaaaac aactggatgg attgatgacc   4200
agtacctctc agagccagga atcttgaatc tccaggattt atacgtgcaa atttaaggag   4260
atgtacttag caacttcaag ccaagaactt ccaaaatact agcgaatcta aaataaaatg   4320
gaattttgag ttatttttaa agttcaaatt ataattgata ccactatgta tttaagccta   4380
ctcacagcaa gttagatgga ttttgctaaa ctcattgcca gactgtggtg gtggtggtgg   4440
tagtgtgcac ctttaatcca agcaactcag caatcagaat gaggtaaatc tctgtgaata   4500
caaggcctgc ctagtctgca gcgctagttc caggatagcc agggctacac acacaaaaac   4560
cctctctcaa aaaaaacaaa attaattagt tgataataaa aaataactaa agtatcatca   4620
aaggaaggcc tactggaagt tttatatatt cccagtaaat tgaaaaatat tctgaagtta   4680
ttaaccagtt agcaacaatg tgtttttaag tcttacataa acagagcaaa gtcttcaaat   4740
gtttcagagc tgagaagata attgtgcttg atatgaaaaa tagcctctcc atatgatgtg   4800
ccacattgaa aggcgtcatt accctttttaa atacttctta atgtggcttt gttcccttta  4860
cccaggatta gctagaaaga gctaggtagg cttcggccac agttgcacat ttcgggcctg   4920
ctgaagaatg ggagctttga aggctggcct tggtggagga gcccctcagt gctggagggt   4980
ggggcgtgta cgcagcatgg aagtggtcta gacagagtgc aaagggacag acttctttct   5040
cattttagta tagggtgatg tctcacttga aatgagaaag tagagttgat attaaacgaa   5100
gctgtgccca gaaaccaggc tcagggtatt gtgagatttt ctttttaaat agagaatata   5160
aaagatagaa ataaatattt aaaccttcct tcttattttc tatcaaatag atttttttta   5220
tcatttgcaa acaacataaa aaaaggtttc ttttgtgggg ttttctttcc ttcttttttt   5280
tttttttttt tttttaagac tgcagataat cttgttgagc tcctcggaaa atacaaggaa   5340
gtccgtgttt gtgcagagcg ctttatgagt aactgtatag acagtgtggc tgcttcactc   5400
atcccagagg gctgcagctg tcggcccatg aagtggctgc agtgcctcgt gagatctgct   5460
ttgttttgtt tggagtgaag tctttgaaag gtttgagtgc aactatatag gactgttttt   5520
aaataagtag tattcctcat gaactttctc attgttaagc tacaggaccc aaactctacc   5580
actaagatat tattaacctc aaaatgtagt ttatagaagg aatttgcaaa tagaatatcc   5640
agttcgtact tatatgcatc ttcaacaaag attctctgtg acttgttgga tttggttcct   5700
gaacagccca tttctgtatt tgaggttagg agggcataat gaggcatcct aaaagacaat   5760
ctgatataaa ctgtatgcta gatgtatgct ggtaggggag aaagcattct gtaaagacat   5820
gatttaagac ttcagctctg tcaaccagaa accttgtaaa tacttcctgt cttggtgcag   5880
ccccgcccct ttgatcacac gatgttgtct tgtgcttgtc agacactgtc agagctgctg   5940
ttcgtccctc tgcagatctc acctgtcccc actgcacacc cacctcctgc ctcttgcaga   6000
cctcagcatc tagctttagt tggaaacagt tcagggttca ggtgacttct taaaaaaaaa   6060
aaaaaaccct acctcctcag aatgaggtaa tgaatagtta tttatttaaa gtatgaagag   6120
tcaggagcgc tcgaacatga aggtgattta agatggttcc tttcgtgtgt attgtagctg   6180
agcacttgtt tttgtcctaa agggcattat acatttaagc agtgattctg tttaaagatg   6240
tttttcttta aaggtgtagc tcagagtatc tgttgttgga attggtgcca gagtctgctt   6300
aatagatttc agaatcctaa gcttaagtca gtcgcatgaa gttaagtagt tatggtaaca   6360
ctttgctagc catgatataa ttctactttt taggagtagg tttggcaaaa ctgtatgcct   6420
tcaaagtgag ttggccacag ctttgtcaca tgcacagata ctcatctgaa gagactgccc   6480
agctaagagg gcggaaggat accctttttt cctacgattc gcttctttgt ccacgttggc   6540
```

-continued

```
attgttagta ctagtttatc agcaccttga ccagcagatg tcaaccaata agctattttt   6600
aaaaccatag ccagagatgg agaggtcact gtgagtagaa acagcaggac gcttacagga   6660
gtgaaatggt gtagggaggc tctagaaaaa tatcttgaca atttgccaaa tgatcttact   6720
gtgccttcat gatgcaataa aaaagctaac attttagcag aaatcagtga tttacgaaga   6780
gagtggccag tctggtttaa ctcagctggg ataatatttt tagagtgcaa tttagactgc   6840
gaagataaat gcactaaaga gtttatagcc aattcacatt tgaaaaataa gaaaatggta   6900
aattttcagt gaaatatttt tttaaagcac ataatcccta gtgtagccag aaatatttac   6960
cacatagagc agctaggctg agatacagtc cagtgacatt tctagagaaa cctttctac    7020
tcccacgggc tcctcaaagc atggaaattt tatacaaaat gtttgacatt ttaagatact   7080
gctgtagttt agttttgaaa tagtatgtgc tgagcagcaa tcatgtacta actcagagag   7140
agaaaacaac aacaaattgt gcatctgatt tgttttcaga gaaatgctgc caacttagat   7200
actgagttct cagagcttca agtgtaaact tgcctcccaa gtcctgtttg caaatgaagt   7260
tggctagtgc tactgactgc tccagcacat gatggaaggc agggggctgt ctctgaagtg   7320
tcttctataa agggacaata gaatagtgag agacctggtc agtgtgtgtc agctggacac   7380
tccatgctat gggacttgca tcttctgtcc tcaccatccc caagacattg tgctttcctc   7440
agttgtcctc tagctgtttc actcagacac caagatgaat tactgatgcc agaaggggcc   7500
aaaatggcca gtgtgttttg gggttgtat  cagttgactg gacaataact ttaatagttt   7560
cagatcattt atttttactt ccattttgac agacatttaa atggaaattt agtcctaact   7620
tttgtcattt gaaaggaaaa attaacagtt cctataagat acttttgagg tggaatctga   7680
catcctaatt tttttcttt tcagtgggtt tgcagcgagg gtcttgtatg cactaggcaa   7740
gggttctacc actaagccac atttcccagg aaataaaatg ttaacagtta aaacatacac   7800
acaaatacac aaacacctta ttaccacttt agtaaagtga gagatgtgcg tcctttgtct   7860
cagtctccac gatttcagct gccccttgta tgaataactc agtctcgcta aactgtttac   7920
ttttatttac ctggtttgac tagttgcagc tatataacca gttgtgcatg aggacaacag   7980
ccagtgtgtt tgttttgttt ttggtttttt gtggtacatt ttttgtaaag aattctgtag   8040
attgaagtgc tctttgaaaa cagaactgag atatatttat tcttgttagc atcaaaaaac   8100
attttgtgca aatgatttgc ttttcctggc aggctgagta ccatatccag cgcccacaat   8160
tgcgggttcc catctaccat gtccacaggg gagacagacg ggaagcacat gaggggtgtg   8220
tttacagagt tgtaggagtt atgtagttct cttgttgcct tggaaatcac tgttgtttta   8280
agactgttga acccgtgtgt ttggctgggc tgtgagttac atgaagaaac tgcaaactag   8340
catatgcaga caaagctcac agactaggcg taaatggagg aaaatggacc aaaataaggc   8400
agggtgacac ataaaccttg ggcttcggag aaaactaagg gtggagatga actataatca   8460
cctgaataca atgtaagagt gcaataagtg tgcttattct aagctgtgaa cttcttttaa   8520
atcattcctt tctaatacat ttatgtatgt tccattgctg actaaaacca gctatgagaa   8580
catatgcctt tttattcatg ttaactacca gtttaagtgg ctaaccttaa tgtcttattt   8640
atcttcattt tgtattagtt tacataccag gtatgtgtgt gtgctgtact cttcttccct   8700
ttatttgaaa acacttttca ctgggtcatc tccttggcca ttccacaaca caactttggt   8760
ttggctttca atgtcacctt atttgatggc ctgtgtccca gtagcagaat ttatggtatt   8820
cccattgctg gctgctcttc cgacccttg  cttctacagc acttgtctct cctaagatag   8880
```

-continued

```
tcagaaacta actgatcagg ggatggactt caccattcat cgtgtctctt caattctatt   8940

aaatagacca ctcttgggct ttagaccagg aaaaaggaga cagctctagc catctaccaa   9000

gcctcaccct aaaaggtcac ccgtacttct tggtctgagg acaagtctcc actccagtaa   9060

gggagagggg aggaaatgct tcctgtttga aatgcagtga attcctatgg ctcctgtttc   9120

accacccgca cctatggcaa cccatataca ttcctcttgt ctgtaactgc caaaggttgg   9180

gtttatgtca cttcagttcc actcaagcat tgaaaaggtt ctcatggagt ctggggtgtg   9240

cccagtgaaa agatggggac tttttcatta tccacagacc tctctatacc tgctttgcaa   9300

aaattataat ggagtaacta tttttaaagc ttatttttca attcataaga aaaagacatt   9360

tattttcaat caaatggatg atgtctctta tcccttatcc ctcaatgttt gcttgaattt   9420

tgtttgttcc ctatacctac tccctaattc tttagttcct tcctgctcag gtcccttcat   9480

ttgtactttg gagtttttct catgtaaatt tgtataatgg aaaatattgt tcagtttgga   9540

tagaaagcat ggagaaataa ataaaaaaag atagctgaaa atcaaattga agaaatttat   9600

ttctgtgtaa agttatttaa aaactctgta ttatatttaa agaaaaaagc ccaacccccc   9660

aaaaagtgct atgtaattga tgtgaatatg cgaatactgc tataataaag attgactgca   9720

tggagaaa                                                            9728
```

<210> SEQ ID NO 53
<211> LENGTH: 804
<212> TYPE: PRT
<213> ORGANISM: Mus musculus

<400> SEQUENCE: 53

```
Met Ala Ala Leu Ser Gly Gly Gly Gly Ser Ser Ser Gly Gly Gly Gly
1               5                   10                  15

Gly Gly Gly Gly Gly Gly Gly Gly Gly Asp Gly Gly Gly Gly Ala Glu
            20                  25                  30

Gln Gly Gln Ala Leu Phe Asn Gly Asp Met Glu Pro Glu Ala Gly Ala
        35                  40                  45

Gly Ala Ala Ala Ser Ser Ala Ala Asp Pro Ala Ile Pro Glu Glu Val
    50                  55                  60

Trp Asn Ile Lys Gln Met Ile Lys Leu Thr Gln Glu His Ile Glu Ala
65                  70                  75                  80

Leu Leu Asp Lys Phe Gly Gly Glu His Asn Pro Pro Ser Ile Tyr Leu
                85                  90                  95

Glu Ala Tyr Glu Glu Tyr Thr Ser Lys Leu Asp Ala Leu Gln Gln Arg
            100                 105                 110

Glu Gln Gln Leu Leu Glu Ser Leu Val Phe Gln Thr Pro Thr Asp Ala
        115                 120                 125

Ser Arg Asn Asn Pro Lys Ser Pro Gln Lys Pro Ile Val Arg Val Phe
    130                 135                 140

Leu Pro Asn Lys Gln Arg Thr Val Val Pro Ala Arg Cys Gly Val Thr
145                 150                 155                 160

Val Arg Asp Ser Leu Lys Lys Ala Leu Met Met Arg Gly Leu Ile Pro
                165                 170                 175

Glu Cys Cys Ala Val Tyr Arg Ile Gln Asp Gly Glu Lys Lys Pro Ile
            180                 185                 190

Gly Trp Asp Thr Asp Ile Ser Trp Leu Thr Gly Glu Glu Leu His Val
        195                 200                 205

Glu Val Leu Glu Asn Val Pro Leu Thr Thr His Asn Phe Val Arg Lys
    210                 215                 220
```

-continued

```
Thr Phe Phe Thr Leu Ala Phe Cys Asp Phe Cys Arg Lys Leu Leu Phe
225                 230                 235                 240

Gln Gly Phe Arg Cys Gln Thr Cys Gly Tyr Lys Phe His Gln Arg Cys
                245                 250                 255

Ser Thr Glu Val Pro Leu Met Cys Val Asn Tyr Asp Gln Leu Asp Leu
            260                 265                 270

Leu Phe Val Ser Lys Phe Phe Glu His His Pro Val Pro Gln Glu Glu
        275                 280                 285

Ala Ser Phe Pro Glu Thr Ala Leu Pro Ser Gly Ser Ser Ser Ala Pro
    290                 295                 300

Pro Ser Asp Ser Thr Gly Pro Gln Ile Leu Thr Ser Pro Ser Pro Ser
305                 310                 315                 320

Lys Ser Ile Pro Ile Pro Gln Pro Phe Arg Pro Ala Asp Glu Asp His
                325                 330                 335

Arg Asn Gln Phe Gly Gln Arg Asp Arg Ser Ser Ser Ala Pro Asn Val
            340                 345                 350

His Ile Asn Thr Ile Glu Pro Val Asn Ile Asp Glu Lys Phe Pro Glu
        355                 360                 365

Val Glu Leu Gln Asp Gln Arg Asp Leu Ile Arg Asp Gln Gly Phe Arg
    370                 375                 380

Gly Asp Gly Ala Pro Leu Asn Gln Leu Met Arg Cys Leu Arg Lys Tyr
385                 390                 395                 400

Gln Ser Arg Thr Pro Ser Pro Leu Leu His Ser Val Pro Ser Glu Ile
                405                 410                 415

Val Phe Asp Phe Glu Pro Gly Pro Val Phe Arg Gly Ser Thr Thr Gly
            420                 425                 430

Leu Ser Ala Thr Pro Pro Ala Ser Leu Pro Gly Ser Leu Thr Asn Val
        435                 440                 445

Lys Ala Leu Gln Lys Ser Pro Gly Pro Gln Arg Glu Arg Lys Ser Ser
    450                 455                 460

Ser Ser Ser Ser Ser Glu Asp Arg Ser Arg Met Lys Thr Leu Gly Arg
465                 470                 475                 480

Arg Asp Ser Ser Asp Asp Trp Glu Ile Pro Asp Gly Gln Ile Thr Val
                485                 490                 495

Gly Gln Arg Ile Gly Ser Gly Ser Phe Gly Thr Val Tyr Lys Gly Lys
            500                 505                 510

Trp His Gly Asp Val Ala Val Lys Met Leu Asn Val Thr Ala Pro Thr
        515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640
```

-continued

```
Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800

Ala Ala Phe Lys


<210> SEQ ID NO 54
<211> LENGTH: 2232
<212> TYPE: DNA
<213> ORGANISM: Oryctolagus cuniculus

<400> SEQUENCE: 54

atggggaatg tgtggaatat caaacaaatg attaagttga cacaggagca tatagaggcc      60

ctattggaca aatttggtgg ggagcataat ccaccatcaa tatatctgga ggcctacgaa     120

gaatacacca gcaagctaga tgccctccaa caaagagaac agcagttatt ggaatcccta     180

gtttttcaaa atcccacaga tgtgtcacgg agcaacccca agtcaccaca aaaacctatt     240

gttagagtct tcctgcccaa caaacagagg acagtggtac ctgcaagatg tggagttacg     300

gttcgagaca gtctaaagaa agcgctgatg atgagaggtc tgatcccaga atgctgtgct     360

gtttacagaa ttcaggatgg agagaagaag ccaattggct gggacactga tatttcctgg     420

ctcactggag aagagctgca tgtggaagtg ttagagaatg tcccactcac cacacataac     480

tttgtacgga aaactttttt caccttagca ttttgtgact tctgtagaaa gctgcttttc     540

cagggtttcc gctgtcaaac atgtggctac aaatttcacc agcgttgtag tacggaagtt     600

ccactgatgt gtgttaatta tgaccaactt gatttgctgt ttgtctccaa gttctttgaa     660

caccacccag taccacagga ggaggcctcc ttagcagaga ctgccctcac atctgggtca     720

tcgccttccg cacctccctc agactctatt gggcaccaaa ttctcaccag tccgtcccct     780

tcaaaatcca ttccgattcc acagtccttc cgaccagcag atgaagatca tcgaaatcag     840

tttgggcaac gagaccggtc ttcatcagcg cctaatgttc acattaacac aatagaacct     900

gtcaatattg atgaaaaatt cccagaagtg gaattacagg atcaaaggga cttgattaga     960

gaccaagggt ttcgtggtga tggagcccct ttgaaccagc tgatgcgctg tcttcggaaa    1020

taccaatccc ggactcccag tcccctccta ccttctgtcc ccagtgacat agtgtttgat    1080

tttgagcctg gcccagtgtt cagaggatcg accacgggtt tgtctgccac tccccctgcc    1140

tcattacctg gctcactcac tagtgtgaaa gctgtacaga gatccccagg acctcagcga    1200
```

gagaggaagt cgtcttcctc ctcagaagac aggaatcgaa tgaaaactct tggtagacgg 1260
gattcaagtg atgattggga gattcctgat gggcagatca ccgtgggaca gagaattgga 1320
tctggatcat ttggaaccgt ctacaaggga aaatggcacg gtgatgtggc agtaaaaatg 1380
ttgaatgtga cagcacctac acctcagcag ttacaggcct tcaaaaatga agtaggagta 1440
ctcaggaaaa cacgacatgt gaatatccta cttttcatgg gctattccac aaagccacag 1500
ctggctattg ttacccagtg gtgtgagggc tccagtttat atcaccatct ccacatcatt 1560
gagaccaaat tcgagatgat caaacttata gatattgcac ggcagactgc acagggcatg 1620
gattacttac acgccaagtc aatcatccac agagacctca agagtaataa tatatttctt 1680
catgaagacc tcacagtaaa aataggtgat tttggtctag ccacagtgaa atctcgatgg 1740
agtgggtccc atcagtttga acaattgtct ggatccattt tgtggatggc accagaagta 1800
atcagaatgc aagacaaaaa cccatatagc tttcagtcag atgtatatgc atttgggatt 1860
gttctgtatg aattgatgac tggccagtta ccttactcaa acatcaacaa cagggaccag 1920
atcattttta tggtgggacg tggctacctg tctccagacc tcagtaaggt acggagtaac 1980
tgtccgaaag ccatgaagag attaatggca gagtgcctca aaaagaaaag agatgagaga 2040
ccactctttc cccaaattct cgcctccatt gagctgctgg cccgctcatt gccaaaaatc 2100
caccgcagtg catcagaacc ctccttgaat cgggctggtt tccagacaga ggattttagt 2160
ctatatgctt gtgcttctcc aaaaacaccc atccaggcag gggatatgg agaatttgca 2220 gccttcaagt ag 2232

<210> SEQ ID NO 55
<211> LENGTH: 743
<212> TYPE: PRT
<213> ORGANISM: Oryctolagus cuniculus

<400> SEQUENCE: 55

Met Gly Asn Val Trp Asn Ile Lys Gln Met Ile Lys Leu Thr Gln Glu
1 5 10 15

His Ile Glu Ala Leu Leu Asp Lys Phe Gly Gly Glu His Asn Pro Pro
20 25 30

Ser Ile Tyr Leu Glu Ala Tyr Glu Glu Tyr Thr Ser Lys Leu Asp Ala
35 40 45

Leu Gln Gln Arg Glu Gln Gln Leu Leu Glu Ser Leu Val Phe Gln Asn
50 55 60

Pro Thr Asp Val Ser Arg Ser Asn Pro Lys Ser Pro Gln Lys Pro Ile
65 70 75 80

Val Arg Val Phe Leu Pro Asn Lys Gln Arg Thr Val Val Pro Ala Arg
85 90 95

Cys Gly Val Thr Val Arg Asp Ser Leu Lys Lys Ala Leu Met Met Arg
100 105 110

Gly Leu Ile Pro Glu Cys Cys Ala Val Tyr Arg Ile Gln Asp Gly Glu
115 120 125

Lys Lys Pro Ile Gly Trp Asp Thr Asp Ile Ser Trp Leu Thr Gly Glu
130 135 140

Glu Leu His Val Glu Val Leu Glu Asn Val Pro Leu Thr Thr His Asn
145 150 155 160

Phe Val Arg Lys Thr Phe Phe Thr Leu Ala Phe Cys Asp Phe Cys Arg
165 170 175

Lys Leu Leu Phe Gln Gly Phe Arg Cys Gln Thr Cys Gly Tyr Lys Phe

-continued

```
            180                 185                 190

His Gln Arg Cys Ser Thr Glu Val Pro Leu Met Cys Val Asn Tyr Asp
        195                 200                 205

Gln Leu Asp Leu Leu Phe Val Ser Lys Phe Phe Glu His His Pro Val
    210                 215                 220

Pro Gln Glu Glu Ala Ser Leu Ala Glu Thr Ala Leu Thr Ser Gly Ser
225                 230                 235                 240

Ser Pro Ser Ala Pro Pro Ser Asp Ser Ile Gly His Gln Ile Leu Thr
                245                 250                 255

Ser Pro Ser Pro Ser Lys Ser Ile Pro Ile Pro Gln Ser Phe Arg Pro
            260                 265                 270

Ala Asp Glu Asp His Arg Asn Gln Phe Gly Gln Arg Asp Arg Ser Ser
        275                 280                 285

Ser Ala Pro Asn Val His Ile Asn Thr Ile Glu Pro Val Asn Ile Asp
    290                 295                 300

Glu Lys Phe Pro Glu Val Glu Leu Gln Asp Gln Arg Asp Leu Ile Arg
305                 310                 315                 320

Asp Gln Gly Phe Arg Gly Asp Gly Ala Pro Leu Asn Gln Leu Met Arg
                325                 330                 335

Cys Leu Arg Lys Tyr Gln Ser Arg Thr Pro Ser Pro Leu Leu Pro Ser
            340                 345                 350

Val Pro Ser Asp Ile Val Phe Asp Phe Glu Pro Gly Pro Val Phe Arg
        355                 360                 365

Gly Ser Thr Thr Gly Leu Ser Ala Thr Pro Pro Ala Ser Leu Pro Gly
    370                 375                 380

Ser Leu Thr Ser Val Lys Ala Val Gln Arg Ser Pro Gly Pro Gln Arg
385                 390                 395                 400

Glu Arg Lys Ser Ser Ser Ser Ser Glu Asp Arg Asn Arg Met Lys Thr
                405                 410                 415

Leu Gly Arg Arg Asp Ser Ser Asp Asp Trp Glu Ile Pro Asp Gly Gln
            420                 425                 430

Ile Thr Val Gly Gln Arg Ile Gly Ser Gly Ser Phe Gly Thr Val Tyr
        435                 440                 445

Lys Gly Lys Trp His Gly Asp Val Ala Val Lys Met Leu Asn Val Thr
    450                 455                 460

Ala Pro Thr Pro Gln Gln Leu Gln Ala Phe Lys Asn Glu Val Gly Val
465                 470                 475                 480

Leu Arg Lys Thr Arg His Val Asn Ile Leu Leu Phe Met Gly Tyr Ser
                485                 490                 495

Thr Lys Pro Gln Leu Ala Ile Val Thr Gln Trp Cys Glu Gly Ser Ser
            500                 505                 510

Leu Tyr His His Leu His Ile Ile Glu Thr Lys Phe Glu Met Ile Lys
        515                 520                 525

Leu Ile Asp Ile Ala Arg Gln Thr Ala Gln Gly Met Asp Tyr Leu His
    530                 535                 540

Ala Lys Ser Ile Ile His Arg Asp Leu Lys Ser Asn Asn Ile Phe Leu
545                 550                 555                 560

His Glu Asp Leu Thr Val Lys Ile Gly Asp Phe Gly Leu Ala Thr Val
                565                 570                 575

Lys Ser Arg Trp Ser Gly Ser His Gln Phe Glu Gln Leu Ser Gly Ser
            580                 585                 590

Ile Leu Trp Met Ala Pro Glu Val Ile Arg Met Gln Asp Lys Asn Pro
        595                 600                 605
```

```
Tyr Ser Phe Gln Ser Asp Val Tyr Ala Phe Gly Ile Val Leu Tyr Glu
    610                 615                 620

Leu Met Thr Gly Gln Leu Pro Tyr Ser Asn Ile Asn Asn Arg Asp Gln
625                 630                 635                 640

Ile Ile Phe Met Val Gly Arg Gly Tyr Leu Ser Pro Asp Leu Ser Lys
                645                 650                 655

Val Arg Ser Asn Cys Pro Lys Ala Met Lys Arg Leu Met Ala Glu Cys
            660                 665                 670

Leu Lys Lys Lys Arg Asp Glu Arg Pro Leu Phe Pro Gln Ile Leu Ala
        675                 680                 685

Ser Ile Glu Leu Leu Ala Arg Ser Leu Pro Lys Ile His Arg Ser Ala
    690                 695                 700

Ser Glu Pro Ser Leu Asn Arg Ala Gly Phe Gln Thr Glu Asp Phe Ser
705                 710                 715                 720

Leu Tyr Ala Cys Ala Ser Pro Lys Thr Pro Ile Gln Ala Gly Gly Tyr
                725                 730                 735

Gly Glu Phe Ala Ala Phe Lys
            740
```

<210> SEQ ID NO 56
<211> LENGTH: 2186
<212> TYPE: DNA
<213> ORGANISM: Cavia porcellus

<400> SEQUENCE: 56

```
atggcggcgc tcagcggcgg cggtggcgcg gagcagggcc aggctctgtt caacggggac      60

atggagctcg aggccggcgc cggcgccgca gcctcttcgg ctgcagaccc tgccattccc     120

gaggaggtat ggaatatcaa acaaatgatt aagttgacgc aggaacacat agaggcccta     180

ttggacaaat ttggtggaga gcataatcca ccatcaatat acctggaggc ctatgaagaa     240

tacaccagca aactagatgc cctccaacaa agagaacagc agttactgga atccctcggg     300

aatggaactg atttttctgt ttctagctct gcatcactgg acaccgttac atcttcttct     360

tcttctagcc tttcagtact accttcatct ctttcagttt ttcaaaatcc tacagatgtg     420

tcacggagca accccaaatc accacaaaaa cctattgtta gagtcttcct gcccaacaaa     480

cagaggacag tggtacctgc aaggtgtgga gttacagtcc gagacagtct gaagaaagca     540

ctcatgatga gaggtcttat cccagagtgc tgtgctgtgt acagaattca ggatggagaa     600

aagaaaccaa ttggctggga cactgacatt tcctggctta ctggggaaga attacatgta     660

gaagtattgg agaatgttcc acttacaaca cacaattttg tatgtatctt tatattttt      720

ttgctgtttg tctccaagtt ctttgaacac cacccaatac cacaggagga ggcttcctta     780

gcagagacca cccttacatc tggatcatcc ccttctgcac cccccctcaga gtccattggg     840

cccccaattc tcaccagccc atctccttca aaatccattc caattccaca gcctttccgg     900

ccaggagagg aagatcatcg aaatcaattt gggcagcgag accggtcctc atctgctccc     960

aatgtgcata taaacacaat agaacctgtc aatattgatg atttgattag agaccaaggg    1020

tttcgtagtg atggaggatc aactacaggt ttgtctgcca ccccacctgc ctcattacct    1080

ggctcactca ctaatgtgaa agccttacag aaatctccag gacctcagcg agaaaggaag    1140

tcatcttcat cctcagaaga cagaaatcga atgaaaacgc ttggtagacg ggactcaagt    1200

gatgattggg agattcctga tgggcagatt acagtgggac aaagaattgg atctgggtca    1260

tttggaacag tctacaaggg gaagtggcat ggtgacgtgg cagtgaaaat gttgaatgtg    1320
```

```
acagcaccca cacctcaaca gttacaggcc ttcaaaaatg aagtaggagt actcaggaaa   1380

acacgacatg tgaatatcct actcttcatg ggctattcca caaagccaca gctagctatt   1440

gttacccagt ggtgtgaggg ctccagctta taccaccatc tccacatcat cgagaccaaa   1500

tttgagatga tcaaacttat agatattgca cgacagactg cccagggcat ggattactta   1560

cacgccaagt caatcatcca cagagacctc aagagtaata atatatttct tcacgaagac   1620

ctcacggtta aaataggtga ttttggtcta gccacagtga aatctcgatg gagtgggtcc   1680

catcagtttg aacagttgtc tggatccatt ttgtggatgg caccagaagt aatcagaatg   1740

cgagataaaa acccatacag ttttcagtcc gatgtatatg catttgggat tgttctatat   1800

gaattgatga ctgggcagtt accctattca aatatcaaca acagggacca gataattttt   1860

atggtgggac gaggatatct atctccagat ctcagcaagg tacggagtaa ctgtccaaaa   1920

gccatgaaga ggttaatggc ggagtgcctc aaaaagaaaa gagatgagag accactcttt   1980

ccccaaattc tcgcctctat tgagctgctg gcccgctcat tgccaaaaat tcaccgcagt   2040

gcatcagaac cctccttgaa tcgggctggt ttccaaacag aggattttag tctctatgct   2100

tgtgcttctc caaaaacacc catccaggca gggggatatg gtgcgtttcc tgtccactga   2160

tgcaaattaa atgagtgaga aataaa                                          2186


<210> SEQ ID NO 57
<211> LENGTH: 719
<212> TYPE: PRT
<213> ORGANISM: Cavia porcellus

<400> SEQUENCE: 57

Met Ala Ala Leu Ser Gly Gly Gly Gly Ala Glu Gln Gly Gln Ala Leu
1               5                   10                  15

Phe Asn Gly Asp Met Glu Leu Glu Ala Gly Ala Gly Ala Ala Ala Ser
            20                  25                  30

Ser Ala Ala Asp Pro Ala Ile Pro Glu Glu Val Trp Asn Ile Lys Gln
        35                  40                  45

Met Ile Lys Leu Thr Gln Glu His Ile Glu Ala Leu Leu Asp Lys Phe
    50                  55                  60

Gly Gly Glu His Asn Pro Pro Ser Ile Tyr Leu Glu Ala Tyr Glu Glu
65                  70                  75                  80

Tyr Thr Ser Lys Leu Asp Ala Leu Gln Gln Arg Glu Gln Gln Leu Leu
                85                  90                  95

Glu Ser Leu Gly Asn Gly Thr Asp Phe Ser Val Ser Ser Ser Ala Ser
            100                 105                 110

Leu Asp Thr Val Thr Ser Ser Ser Ser Ser Ser Leu Ser Val Leu Pro
        115                 120                 125

Ser Ser Leu Ser Val Phe Gln Asn Pro Thr Asp Val Ser Arg Ser Asn
    130                 135                 140

Pro Lys Ser Pro Gln Lys Pro Ile Val Arg Val Phe Leu Pro Asn Lys
145                 150                 155                 160

Gln Arg Thr Val Val Pro Ala Arg Cys Gly Val Thr Val Arg Asp Ser
                165                 170                 175

Leu Lys Lys Ala Leu Met Met Arg Gly Leu Ile Pro Glu Cys Cys Ala
            180                 185                 190

Val Tyr Arg Ile Gln Asp Gly Glu Lys Lys Pro Ile Gly Trp Asp Thr
        195                 200                 205

Asp Ile Ser Trp Leu Thr Gly Glu Glu Leu His Val Glu Val Leu Glu
```

-continued

```
    210                 215                 220

Asn Val Pro Leu Thr Thr His Asn Phe Val Cys Ile Phe Ile Phe Phe
225                 230                 235                 240

Leu Leu Phe Val Ser Lys Phe Phe Glu His His Pro Ile Pro Gln Glu
                245                 250                 255

Glu Ala Ser Leu Ala Glu Thr Thr Leu Thr Ser Gly Ser Ser Pro Ser
            260                 265                 270

Ala Pro Pro Ser Glu Ser Ile Gly Pro Pro Ile Leu Thr Ser Pro Ser
        275                 280                 285

Pro Ser Lys Ser Ile Pro Ile Pro Gln Pro Phe Arg Pro Gly Glu Glu
    290                 295                 300

Asp His Arg Asn Gln Phe Gly Gln Arg Asp Arg Ser Ser Ser Ala Pro
305                 310                 315                 320

Asn Val His Ile Asn Thr Ile Glu Pro Val Asn Ile Asp Asp Leu Ile
                325                 330                 335

Arg Asp Gln Gly Phe Arg Ser Asp Gly Gly Ser Thr Thr Gly Leu Ser
            340                 345                 350

Ala Thr Pro Pro Ala Ser Leu Pro Gly Ser Leu Thr Asn Val Lys Ala
        355                 360                 365

Leu Gln Lys Ser Pro Gly Pro Gln Arg Glu Arg Lys Ser Ser Ser Ser
    370                 375                 380

Ser Glu Asp Arg Asn Arg Met Lys Thr Leu Gly Arg Arg Asp Ser Ser
385                 390                 395                 400

Asp Asp Trp Glu Ile Pro Asp Gly Gln Ile Thr Val Gly Gln Arg Ile
                405                 410                 415

Gly Ser Gly Ser Phe Gly Thr Val Tyr Lys Gly Lys Trp His Gly Asp
            420                 425                 430

Val Ala Val Lys Met Leu Asn Val Thr Ala Pro Thr Pro Gln Gln Leu
        435                 440                 445

Gln Ala Phe Lys Asn Glu Val Gly Val Leu Arg Lys Thr Arg His Val
    450                 455                 460

Asn Ile Leu Leu Phe Met Gly Tyr Ser Thr Lys Pro Gln Leu Ala Ile
465                 470                 475                 480

Val Thr Gln Trp Cys Glu Gly Ser Ser Leu Tyr His His Leu His Ile
                485                 490                 495

Ile Glu Thr Lys Phe Glu Met Ile Lys Leu Ile Asp Ile Ala Arg Gln
            500                 505                 510

Thr Ala Gln Gly Met Asp Tyr Leu His Ala Lys Ser Ile Ile His Arg
        515                 520                 525

Asp Leu Lys Ser Asn Asn Ile Phe Leu His Glu Asp Leu Thr Val Lys
    530                 535                 540

Ile Gly Asp Phe Gly Leu Ala Thr Val Lys Ser Arg Trp Ser Gly Ser
545                 550                 555                 560

His Gln Phe Glu Gln Leu Ser Gly Ser Ile Leu Trp Met Ala Pro Glu
                565                 570                 575

Val Ile Arg Met Arg Asp Lys Asn Pro Tyr Ser Phe Gln Ser Asp Val
            580                 585                 590

Tyr Ala Phe Gly Ile Val Leu Tyr Glu Leu Met Thr Gly Gln Leu Pro
        595                 600                 605

Tyr Ser Asn Ile Asn Asn Arg Asp Gln Ile Ile Phe Met Val Gly Arg
    610                 615                 620

Gly Tyr Leu Ser Pro Asp Leu Ser Lys Val Arg Ser Asn Cys Pro Lys
625                 630                 635                 640
```

-continued

```
Ala Met Lys Arg Leu Met Ala Glu Cys Leu Lys Lys Lys Arg Asp Glu
                645                 650                 655

Arg Pro Leu Phe Pro Gln Ile Leu Ala Ser Ile Glu Leu Leu Ala Arg
            660                 665                 670

Ser Leu Pro Lys Ile His Arg Ser Ala Ser Glu Pro Ser Leu Asn Arg
        675                 680                 685

Ala Gly Phe Gln Thr Glu Asp Phe Ser Leu Tyr Ala Cys Ala Ser Pro
    690                 695                 700

Lys Thr Pro Ile Gln Ala Gly Gly Tyr Gly Ala Phe Pro Val His
705                 710                 715


<210> SEQ ID NO 58
<211> LENGTH: 3229
<212> TYPE: DNA
<213> ORGANISM: Canis lupus familiaris

<400> SEQUENCE: 58

gtaatgctgg attttcatgg aataagtttg acctgtgctg cagtggcctc cagcaaggta      60

cccgcaagat gtggagttac agtccgggac agtctaaaga aagctctgat gatgagaggt     120

ctaatcccag agtgctgtgc tgtttacaga attcaggatg gagagaagaa accgattggc     180

tgggacactg atatttcctg gctcactgga gaggaattgc atgtagaagt gttggaaaat     240

gttccgctta ccacacacaa ctttgtacgg aaaacttttt tcaccttagc attttgtgac     300

ttttgtcgaa agctgctttt ccagggtttt cgctgtcaaa catgtggtta taaatttcac     360

cagcgttgta gtacagaggt tccactgatg tgtgttaatt atgaccaact tgatttgctg     420

tttgtctcca agttctttga acaccaccca ataccacagg aggaggcctc catagcagag     480

actgccctta cgtctggatc atccccttct gctccccccct ccgattctcc tgggccccca     540

attctgacca gtccgtctcc ttcaaaatcc attccaattc cacagccttt ccgaccagca     600

gatgaagatc atcgaaatca gtttggacaa cgagaccggt cctcatcagc tccaaatgtg     660

catataaaca caatagaacc cgtcaacatt gatgacttga ttagagacca agggtttcgt     720

agtgatggag gatcaaccac aggtttgtct gccacccccc ctgcctcatt gcctggctca     780

ctcactaatg taaaagcatt acagaaatct ccaggacctc agcgggaaag aaaatcatct     840

tcatcctcag aagataggaa tcgaatgaaa acacttggta gacgggattc aagtgatgat     900

tgggagatac ctgatgggca gatcacagtg ggacagagaa ttggatccgg gtcatttggg     960

acagtctaca agggaaagtg gcatggtgac gtggcagtga aaatgttgaa tgtgacagca    1020

cccacacctc agcagttaca ggccttcaaa aatgaagtag gagtactcag gaaaactcga    1080

catgtgaata tcctactctt tatgggctat tcaacaaagc cccaactggc tattgttacc    1140

cagtggtgtg agggctccag cttatatcac catctccaca tcattgagac caaatttgag    1200

atgataaagc ttatagatat tgcacggcag actgcacagg gcatggatta cttacacgcc    1260

aagtcaatca tccacagaga cctcaagagt aataatattt ttcttcatga agacctcaca    1320

gtaaaaatag gtgattttgg tctagccaca gtgaaatctc gatggagtgg gtcccatcag    1380

tttgaacagt tgtctggatc cattttgtgg atggcaccag aagtgatccg aatgcaagac    1440

aaaaacccat atagcttcca gtcagatgta tacgcatttg ggattgttct atatgaattg    1500

atgacagggc agttacctta ttcaaacatc aacaacaggg accagataat ttttatggtg    1560

ggacgaggat atctttctcc agatctcagt aaggtacgga gtaactgtcc aaaagccatg    1620

aagagattga tggcagagtg cctaaaaaag aaaagagatg agaggccact ctttccccaa    1680
```

```
attctcgcct ctattgagct gctggcccgc tcattgccaa aaattcaccg cagtgcatca   1740
gaaccctcct tgaatcgggc tggcttccaa acagaggatt ttagtctcta tgcttgcgct   1800
tctccaaaaa cacccatcca ggcaggggga tacggagaat ttgcagcctt caagtagcca   1860
caccatcatg gcaacaacta ctcttatttc ttaagtcttg tgttcgtaca atttgttaac   1920
atcaaaacac agttctgttc ctcaaatctt tttttaaaga tacagaattt tcaatgcata   1980
agctggtgtg gaacagaatg gaatttccca tccaacaaaa gagggaagaa tgttttagga   2040
accagaattc tctgctgcca gtgtttcttc ttcaacacaa ataccacgtg catacaagtc   2100
tgcccactcc caggaaggaa gaggagagcc tgagttctga ccttttgatg gtcaggcatg   2160
atggaaagaa actgctgcta cagcttggga gattggctgt ggagagcctg cccgtcagct   2220
ctgcccttct aaccgccaga tgagtgtgtg gctggtcacc tgacagggca gctgcaatcg   2280
ccaagcatcg ttctctttcc tgtcctggga ttttgtcgtg gagctctttc cccctagtca   2340
ccaccggttc atttctgagg gatggaacaa aaatgcagca tggcctttct gtgtggtgca   2400
tgtccggtct ttgacaaatt tttatcaagt gaagctcttg tatttaaatg gagaatgaga   2460
ggcgaggggg ggggatcacg ttttggtgta ggggcaaagg gaatgctgca tctttttcct   2520
gacccactgg gtttctggcc tttgtttcct tgctcactga gggtgtctgc ctataaccac   2580
gcaggctgga aagtgctggc acacattgcc ttctcttctc actgggtcca gcaatgaaga   2640
caagtgttgg ggattttttt ttttgccctc cacaatgtag caagttctca ggaaaataca   2700
gttaatatct tcctcctaag ctcttccagt catcaagtac ttatgtggct actttgtcca   2760
gggcacaaaa tgccatggcg gtatccaatt aaaagcctac aaaactgctt gataacagtt   2820
ttgaatgtgt gagacattta tgtaatttaa atgtaaggta caagttttaa tttctgagtt   2880
tctctattat atttttatta aaaagaaaat aattttcaga tttaattgaa ttggaataaa   2940
ataatacttc ccaccagaat tatatatcct ggaaaattgt atttttgtta tataaacaac   3000
ttttaaagaa agatcattat ccttttctct acctaaatat ggggagtctt agcataatga   3060
cagatattta taatttttaa attaatggta cttgctggat ccacactaac atctttgcta   3120
atatctcatg ttttcctcca acttactcct acactacatc ctccatcctc tttccagtct   3180
tttatctaga atatgcaacc taaaataaaa atggtggtgt ctccattca              3229
```

```
<210> SEQ ID NO 59
<211> LENGTH: 617
<212> TYPE: PRT
<213> ORGANISM: Canis lupus familiaris

<400> SEQUENCE: 59

Met Leu Asp Phe His Gly Ile Ser Leu Thr Cys Ala Ala Val Ala Ser
1               5                   10                  15

Ser Lys Val Pro Ala Arg Cys Gly Val Thr Val Arg Asp Ser Leu Lys
            20                  25                  30

Lys Ala Leu Met Met Arg Gly Leu Ile Pro Glu Cys Cys Ala Val Tyr
        35                  40                  45

Arg Ile Gln Asp Gly Glu Lys Lys Pro Ile Gly Trp Asp Thr Asp Ile
    50                  55                  60

Ser Trp Leu Thr Gly Glu Glu Leu His Val Glu Val Leu Glu Asn Val
65                  70                  75                  80

Pro Leu Thr Thr His Asn Phe Val Arg Lys Thr Phe Phe Thr Leu Ala
                85                  90                  95
```

-continued

Phe Cys Asp Phe Cys Arg Lys Leu Leu Phe Gln Gly Phe Arg Cys Gln
100 105 110

Thr Cys Gly Tyr Lys Phe His Gln Arg Cys Ser Thr Glu Val Pro Leu
115 120 125

Met Cys Val Asn Tyr Asp Gln Leu Asp Leu Leu Phe Val Ser Lys Phe
130 135 140

Phe Glu His His Pro Ile Pro Gln Glu Glu Ala Ser Ile Ala Glu Thr
145 150 155 160

Ala Leu Thr Ser Gly Ser Ser Pro Ser Ala Pro Pro Ser Asp Ser Pro
165 170 175

Gly Pro Pro Ile Leu Thr Ser Pro Ser Pro Ser Lys Ser Ile Pro Ile
180 185 190

Pro Gln Pro Phe Arg Pro Ala Asp Glu Asp His Arg Asn Gln Phe Gly
195 200 205

Gln Arg Asp Arg Ser Ser Ser Ala Pro Asn Val His Ile Asn Thr Ile
210 215 220

Glu Pro Val Asn Ile Asp Asp Leu Ile Arg Asp Gln Gly Phe Arg Ser
225 230 235 240

Asp Gly Gly Ser Thr Thr Gly Leu Ser Ala Thr Pro Pro Ala Ser Leu
245 250 255

Pro Gly Ser Leu Thr Asn Val Lys Ala Leu Gln Lys Ser Pro Gly Pro
260 265 270

Gln Arg Glu Arg Lys Ser Ser Ser Ser Ser Glu Asp Arg Asn Arg Met
275 280 285

Lys Thr Leu Gly Arg Arg Asp Ser Ser Asp Asp Trp Glu Ile Pro Asp
290 295 300

Gly Gln Ile Thr Val Gly Gln Arg Ile Gly Ser Gly Ser Phe Gly Thr
305 310 315 320

Val Tyr Lys Gly Lys Trp His Gly Asp Val Ala Val Lys Met Leu Asn
325 330 335

Val Thr Ala Pro Thr Pro Gln Gln Leu Gln Ala Phe Lys Asn Glu Val
340 345 350

Gly Val Leu Arg Lys Thr Arg His Val Asn Ile Leu Leu Phe Met Gly
355 360 365

Tyr Ser Thr Lys Pro Gln Leu Ala Ile Val Thr Gln Trp Cys Glu Gly
370 375 380

Ser Ser Leu Tyr His His Leu His Ile Ile Glu Thr Lys Phe Glu Met
385 390 395 400

Ile Lys Leu Ile Asp Ile Ala Arg Gln Thr Ala Gln Gly Met Asp Tyr
405 410 415

Leu His Ala Lys Ser Ile Ile His Arg Asp Leu Lys Ser Asn Asn Ile
420 425 430

Phe Leu His Glu Asp Leu Thr Val Lys Ile Gly Asp Phe Gly Leu Ala
435 440 445

Thr Val Lys Ser Arg Trp Ser Gly Ser His Gln Phe Glu Gln Leu Ser
450 455 460

Gly Ser Ile Leu Trp Met Ala Pro Glu Val Ile Arg Met Gln Asp Lys
465 470 475 480

Asn Pro Tyr Ser Phe Gln Ser Asp Val Tyr Ala Phe Gly Ile Val Leu
485 490 495

Tyr Glu Leu Met Thr Gly Gln Leu Pro Tyr Ser Asn Ile Asn Asn Arg
500 505 510

Asp Gln Ile Ile Phe Met Val Gly Arg Gly Tyr Leu Ser Pro Asp Leu

```
        515                 520                 525

Ser Lys Val Arg Ser Asn Cys Pro Lys Ala Met Lys Arg Leu Met Ala
    530                 535                 540

Glu Cys Leu Lys Lys Lys Arg Asp Glu Arg Pro Leu Phe Pro Gln Ile
545                 550                 555                 560

Leu Ala Ser Ile Glu Leu Leu Ala Arg Ser Leu Pro Lys Ile His Arg
                565                 570                 575

Ser Ala Ser Glu Pro Ser Leu Asn Arg Ala Gly Phe Gln Thr Glu Asp
            580                 585                 590

Phe Ser Leu Tyr Ala Cys Ala Ser Pro Lys Thr Pro Ile Gln Ala Gly
        595                 600                 605

Gly Tyr Gly Glu Phe Ala Ala Phe Lys
    610                 615


<210> SEQ ID NO 60
<211> LENGTH: 1889
<212> TYPE: DNA
<213> ORGANISM: Canis lupus familiaris

<400> SEQUENCE: 60

ggaatatcaa acaaatgatt aagttgacac aggaacatat agaagcccta ttggacaagt     60

ttggtgggga gcataatcca ccatcaatat atctggaggc ctatgaagaa tacaccagca    120

aactagatgc cctccaacag cgagaacaac agttattgga atccctgggg aatggaactg    180

atttttctgt ttctagctct gcatcaacgg acaccgttac atcttcttcc tcttctagcc    240

tttcagtgct accttcatct ctttcagttt ttcaaaatcc cacagatata tcacggagca    300

atcccaagtc accacaaaaa cctatcgtta gagtcttcct gcccaataaa cagaggacgg    360

tggtacccgc aagatgtgga gttacagtcc gggacagtct aaagaaagct ctgatgatga    420

gaggtctaat cccagagtgc tgtgctgttt acagaattca ggatggagag aagaaaccga    480

ttggctggga cactgatatt tcctggctca ctggagagga attgcatgta gaagtgttgg    540

aaaatgttcc gcttaccaca cacaactttg tacggaaaac ttttttcacc ttagcatttt    600

gtgacttttg tcgaaagctg cttttccagg gttttcgctg tcaaacatgt ggttataaat    660

ttcaccagcg ttgtagtaca gaggttccac tgatgtgtgt taattatgac caacttgatt    720

tgctgtttgt ctccaagttc tttgaacacc acccaatacc acaggaggag gcctccatag    780

cagagactgc ccttacgtct ggatcatccc cttctgctcc cccctccgat tctcctgggc    840

ccccaattct gaccagtccg tctccttcaa aatccattcc aattccacag cctttccgac    900

cagcagatga agatcatcga aatcagtttg gacaacgaga ccggtcctca tcagctccaa    960

atgtgcatat aaacacaata gaacccgtca acattgatga cttgattaga gaccaagggt   1020

ttcgtagtga tggaggatca accacaggtt tgtctgccac ccccccctgcc tcattgcctg   1080

gctcactcac taatgtaaaa gcattacaga aatctccagg acctcagcgg gaaagaaaat   1140

catcttcatc ctcagaagat aggaatcgaa tgaaaacact tggtagacgg gattcaagtg   1200

atgattggga gatacctgat gggcagatca cagtgggaca gagaattgga tccgggtcat   1260

ttgggacagt ctacaaggga aagtggcatg gtgacgtggc agtgaaaatg ttgaatgtga   1320

cagcacccac acctcagcag ttacaggcct tcaaaaatga agtaggagta ctcaggaaaa   1380

ctcgacatgt gaatatccta ctctttatgg gctattcaac aaagccccaa ctggctattg   1440

ttacccagtg gtgtgagggc tccagcttat atcaccatct ccacatcatt gagaccaaat   1500

ttgagatgat aaagcttata gatattgcac ggcagactgc acagggcatg gattacttac   1560
```

acgccaagtc aatcatccac agagacctca agagtaataa tatttttctt catgaagacc 1620
tcacagtaaa aataggtgat tttggtctag ccacagtgaa atctcgatgg agtgggtccc 1680
atcagtttga acagttgtct ggatccattt tgtggatggc accagaagtg atccgaatgc 1740
aagacaaaaa cccatatagc ttccagtcag atgtatacgc atttgggatt gttctatatg 1800
aattgatgac agggcagtta ccttattcaa acatcaacaa cagggaccag ctcagatcat 1860
gatcacggtg tcatgagatc aagccccac 1889

<210> SEQ ID NO 61
<211> LENGTH: 615
<212> TYPE: PRT
<213> ORGANISM: Canis lupus familiaris

<400> SEQUENCE: 61

Met Ile Lys Leu Thr Gln Glu His Ile Glu Ala Leu Leu Asp Lys Phe
1 5 10 15

Gly Gly Glu His Asn Pro Pro Ser Ile Tyr Leu Glu Ala Tyr Glu Glu
20 25 30

Tyr Thr Ser Lys Leu Asp Ala Leu Gln Gln Arg Glu Gln Gln Leu Leu
35 40 45

Glu Ser Leu Gly Asn Gly Thr Asp Phe Ser Val Ser Ser Ser Ala Ser
50 55 60

Thr Asp Thr Val Thr Ser Ser Ser Ser Ser Ser Leu Ser Val Leu Pro
65 70 75 80

Ser Ser Leu Ser Val Phe Gln Asn Pro Thr Asp Ile Ser Arg Ser Asn
85 90 95

Pro Lys Ser Pro Gln Lys Pro Ile Val Arg Val Phe Leu Pro Asn Lys
100 105 110

Gln Arg Thr Val Val Pro Ala Arg Cys Gly Val Thr Val Arg Asp Ser
115 120 125

Leu Lys Lys Ala Leu Met Met Arg Gly Leu Ile Pro Glu Cys Cys Ala
130 135 140

Val Tyr Arg Ile Gln Asp Gly Glu Lys Lys Pro Ile Gly Trp Asp Thr
145 150 155 160

Asp Ile Ser Trp Leu Thr Gly Glu Glu Leu His Val Glu Val Leu Glu
165 170 175

Asn Val Pro Leu Thr Thr His Asn Phe Val Arg Lys Thr Phe Phe Thr
180 185 190

Leu Ala Phe Cys Asp Phe Cys Arg Lys Leu Leu Phe Gln Gly Phe Arg
195 200 205

Cys Gln Thr Cys Gly Tyr Lys Phe His Gln Arg Cys Ser Thr Glu Val
210 215 220

Pro Leu Met Cys Val Asn Tyr Asp Gln Leu Asp Leu Leu Phe Val Ser
225 230 235 240

Lys Phe Phe Glu His His Pro Ile Pro Gln Glu Glu Ala Ser Ile Ala
245 250 255

Glu Thr Ala Leu Thr Ser Gly Ser Ser Pro Ser Ala Pro Pro Ser Asp
260 265 270

Ser Pro Gly Pro Pro Ile Leu Thr Ser Pro Ser Pro Ser Lys Ser Ile
275 280 285

Pro Ile Pro Gln Pro Phe Arg Pro Ala Asp Glu Asp His Arg Asn Gln
290 295 300

Phe Gly Gln Arg Asp Arg Ser Ser Ser Ala Pro Asn Val His Ile Asn

```
305                 310                 315                 320

Thr Ile Glu Pro Val Asn Ile Asp Asp Leu Ile Arg Asp Gln Gly Phe
                325                 330                 335

Arg Ser Asp Gly Gly Ser Thr Thr Gly Leu Ser Ala Thr Pro Pro Ala
            340                 345                 350

Ser Leu Pro Gly Ser Leu Thr Asn Val Lys Ala Leu Gln Lys Ser Pro
        355                 360                 365

Gly Pro Gln Arg Glu Arg Lys Ser Ser Ser Ser Ser Glu Asp Arg Asn
    370                 375                 380

Arg Met Lys Thr Leu Gly Arg Arg Asp Ser Ser Asp Asp Trp Glu Ile
385                 390                 395                 400

Pro Asp Gly Gln Ile Thr Val Gly Gln Arg Ile Gly Ser Gly Ser Phe
                405                 410                 415

Gly Thr Val Tyr Lys Gly Lys Trp His Gly Asp Val Ala Val Lys Met
            420                 425                 430

Leu Asn Val Thr Ala Pro Thr Pro Gln Gln Leu Gln Ala Phe Lys Asn
        435                 440                 445

Glu Val Gly Val Leu Arg Lys Thr Arg His Val Asn Ile Leu Leu Phe
    450                 455                 460

Met Gly Tyr Ser Thr Lys Pro Gln Leu Ala Ile Val Thr Gln Trp Cys
465                 470                 475                 480

Glu Gly Ser Ser Leu Tyr His His Leu His Ile Ile Glu Thr Lys Phe
                485                 490                 495

Glu Met Ile Lys Leu Ile Asp Ile Ala Arg Gln Thr Ala Gln Gly Met
            500                 505                 510

Asp Tyr Leu His Ala Lys Ser Ile Ile His Arg Asp Leu Lys Ser Asn
        515                 520                 525

Asn Ile Phe Leu His Glu Asp Leu Thr Val Lys Ile Gly Asp Phe Gly
    530                 535                 540

Leu Ala Thr Val Lys Ser Arg Trp Ser Gly Ser His Gln Phe Glu Gln
545                 550                 555                 560

Leu Ser Gly Ser Ile Leu Trp Met Ala Pro Glu Val Ile Arg Met Gln
                565                 570                 575

Asp Lys Asn Pro Tyr Ser Phe Gln Ser Asp Val Tyr Ala Phe Gly Ile
            580                 585                 590

Val Leu Tyr Glu Leu Met Thr Gly Gln Leu Pro Tyr Ser Asn Ile Asn
        595                 600                 605

Asn Arg Asp Gln Leu Arg Ser
    610                 615
```

<210> SEQ ID NO 62
<211> LENGTH: 3521
<212> TYPE: DNA
<213> ORGANISM: Felis catus
<220> FEATURE:
<221> NAME/KEY: misc_feature
<222> LOCATION: (630)..(649)
<223> OTHER INFORMATION: n is a, c, g, or t

<400> SEQUENCE: 62

```
atgcctaacc tcagtctctg ccaccacggc caatttgctc atgtgcccac tgtgtcggca      60

ctgggatatt ttgtgatttg ccttggccat tgtccactgt ccttgacatt gcctgaagga     120

gaaccactga tgctaatgtt gaaggtgacc tttgcaggct ctccactact cataccaaag     180

atgcggcccc ctgataatcc cagagccact gtctgcacat gggcaaaaca ggctacattc     240
```

-continued

```
tgtgcagact ggggagaaag gttccaagaa cacagtgcca tagttttggg cagagagttt    300
caacacagca tagtgtctat ggcagtatct ggatttggcc gggggaagtg cccaagagga    360
gacagtcagg ctgtgtccta cggccaagga cctgcactta tttttgcatg cagtggttta    420
gcacagggaa gagaacgaag taggaaatcg gagccatgga aacggcagag cggaggaaac    480
gtgcacgcgc gagggtgggc acgaaaggaa agaaccctcc ccagaagact gcgcgagggc    540
gctcctagga ttacgtcacg caccccgcga aaactgaaat gtactgtgtg tggtctttta    600
attgaactat cttccttatg tgcacttaan nnnnnnnnnn nnnnnnnnng cggcggcggc    660
ggtggcgcgg agcagggcca ggctctgttc aacggggaca tggagcccga agccggcgcc    720
gcggcctctt cggctgcgga ccctgccatt cccgaggagg tgtggaatat caaacaaatg    780
attaagttga cacaggaaca tatagaggcc ctattggaca aatttggtgg ggagcataat    840
ccaccatcaa tatatctaga ggcctatgaa gaatacacca gcaagctaga tgccctccaa    900
cagagagaac aacagttatt ggaatccctg gggaatggaa ctgatttttc tgtttctagc    960
tctgcatcaa cagacaccgt tacatcttcc tcctcttcta gcctttcagt gctaccttca   1020
tctctttcag tttttcaaaa ccccacagat gtgtcacgga gcaatcccaa gtcaccacag   1080
aaacctatcg ttagagtctt cctgcctaat aaacagagga cagtggtacc tgcaagatgt   1140
ggagttacag tccgggacag tctaaagaaa gctctgatga tgagaggtct aatccctgag   1200
tgctgtgctg tttacagaat tcaggatgga gagaagaaac caattggctg ggacactgat   1260
atctcctggc tcaccggaga ggaattgcat gtagaagtgt tggaaaatgt tccacttaca   1320
actcacaact ttgtatgtac ggaaaacgtt ttcaccttag cattttgtga cttttgtcga   1380
aagctgcttt tccaaggttt tcgctgtcaa acgtgtggtt ataaatttca ccagcgttgt   1440
agtacagagg ttccactgat gtgtgttaat tatgaccaac ttgatttgct gtttgtctcc   1500
aagttctttg aacaccaccc aataccacag gaggaggcct ccatagcaga gactgcccta   1560
acgtctggat cgtccccttc tgcccccccc tccgattcta ctgggcccca aattctcacc   1620
agtccgtctc cttcaaaatc cattccaatt ccacagcctt tccgaccagc agatgaagat   1680
catcgaaatc aatttggaca gcgagaccgg tcctcatcag ctccaaatgt gcatataaat   1740
acaatagaac ctgtcaatat tgatgacttg attagagacc aggggtttcg tagtgatgga   1800
ggatcaacca caggcttgtc tgccaccccc cctgcctcat tgccgggctc tctcactaat   1860
gtaaaagcat tacagaaatc tccagggcct cagcgggaaa ggaaatcttc ttcatcctca   1920
gaagatagga atcgaatgaa aacacttggt agaagggatt caagtgatga ttgggagatt   1980
cctgatgggc agatcacagt gggacagaga attggatccg ggtcatttgg gacagtctac   2040
aagggaaagt ggcatggtga tgtggcagtg aaaatgttga atgtgacagc acccacacct   2100
cagcagttac aggccttcaa aaatgaagta ggagtactca ggaaaactcg gcatgtgaac   2160
atcctgctct tcatgggcta ttcaacaaag ccccagctgg ctattgtcac ccagtggtgt   2220
gagggctcca gcttatacca ccatctccac atcatcgaga ccaaattcga gatgatcaag   2280
ctgatagata ttgctcggca gactgcgcag ggcatggatt acttacacgc caagtcaatc   2340
atccacagag acctcaagag taataatatt tttcttcacg aagacctcac agtaaaaata   2400
ggtgattttg gtctagccac agtgaaatct cgatggagtg ggtcccatca gtttgaacag   2460
ttgtctggat ccattttgtg gatggcacca gaagtaattc gaatgcaaga taaaaaccca   2520
tatagctttc agtcagatgt atatgcattt gggattgttc tatatgaatt gatgactgga   2580
cagttacctt attcaaacat caacaacagg gaccagataa tttttatggt gggacgagga   2640
```

```
tatctttctc cagatctcag taaggtacga agtaactgtc caaaagccat gaagagattg   2700

atggcagagt gcctaaaaaa gaaaagagat gagaggccac tgtttcccca aattcttgcc   2760

tctattgagc tgctggcccg ctcattgcca aaaattcacc gcagtgcatc agaaccctcc   2820

ttgaatcggg ctggcttcca gacagaggat tttagtctct atgcttgtgc ttctccaaaa   2880

acacccatcc aggcaggggg atatggtgcg tttcccgtcc actgagataa gttagatgag   2940

tgcgcgagtg caggggggcg gggccaagga ggtggaaatg tgcgtgcttc tgtactaagt   3000

tggatagcat cttctttttt aaaaaaagat gaaccaaaga atgtgtatgt ttttaaagac   3060

tagatataat tatttcctga tctaaaatgt atacttagct ttggattttc aatatccaag   3120

ggttttcaaa atgcacagac attgctgaac atttgcagta cctcttctgg aggctttact   3180

tcctgttaca aattggtttt gtttactggc ttatcctaat tattaaactt caattaaact   3240

tttctcctgc accttttgtt atgagctatc acatgtccct tagggactcg caagagcagt   3300

actgcccccg tgtacgggct tgcaggtaga aaggggatga cgggttttaa cacctgtgtg   3360

aggcaaggca gtccgaacag atctcattta ggaagccacg agagttgaat aagttatttt   3420

tattcttagt atttttctg taactacttt ttattataac ttggaaaata tggatgtcct    3480

ttatacacct tagcaataga ctgaatttct ttttataaat t                       3521


<210> SEQ ID NO 63
<211> LENGTH: 974
<212> TYPE: PRT
<213> ORGANISM: Felis catus
<220> FEATURE:
<221> NAME/KEY: misc_feature
<222> LOCATION: (210)..(217)
<223> OTHER INFORMATION: Xaa can be any naturally occurring amino acid

<400> SEQUENCE: 63

Met Pro Asn Leu Ser Leu Cys His His Gly Gln Phe Ala His Val Pro
1               5                   10                  15

Thr Val Ser Ala Leu Gly Tyr Phe Val Ile Cys Leu Gly His Cys Pro
            20                  25                  30

Leu Ser Leu Thr Leu Pro Glu Gly Glu Pro Leu Met Leu Met Leu Lys
        35                  40                  45

Val Thr Phe Ala Gly Ser Pro Leu Leu Ile Pro Lys Met Arg Pro Pro
    50                  55                  60

Asp Asn Pro Arg Ala Thr Val Cys Thr Trp Ala Lys Gln Ala Thr Phe
65                  70                  75                  80

Cys Ala Asp Trp Gly Glu Arg Phe Gln Glu His Ser Ala Ile Val Leu
                85                  90                  95

Gly Arg Glu Phe Gln His Ser Ile Val Ser Met Ala Val Ser Gly Phe
            100                 105                 110

Gly Arg Gly Lys Cys Pro Arg Gly Asp Ser Gln Ala Val Ser Tyr Gly
        115                 120                 125

Gln Gly Pro Ala Leu Ile Phe Ala Cys Ser Gly Leu Ala Gln Gly Arg
    130                 135                 140

Glu Arg Ser Arg Lys Ser Glu Pro Trp Lys Arg Gln Ser Gly Gly Asn
145                 150                 155                 160

Val His Ala Arg Gly Trp Ala Arg Lys Glu Arg Thr Leu Pro Arg Arg
                165                 170                 175

Leu Arg Glu Gly Ala Pro Arg Ile Thr Ser Arg Thr Pro Arg Lys Leu
            180                 185                 190
```

```
Lys Cys Thr Val Cys Gly Leu Leu Ile Glu Leu Ser Ser Leu Cys Ala
        195                 200                 205

Leu Xaa Xaa Xaa Xaa Xaa Xaa Xaa Xaa Gly Gly Gly Gly Gly Ala Glu
    210                 215                 220

Gln Gly Gln Ala Leu Phe Asn Gly Asp Met Glu Pro Glu Ala Gly Ala
225                 230                 235                 240

Ala Ala Ser Ser Ala Ala Asp Pro Ala Ile Pro Glu Glu Val Trp Asn
                245                 250                 255

Ile Lys Gln Met Ile Lys Leu Thr Gln Glu His Ile Glu Ala Leu Leu
            260                 265                 270

Asp Lys Phe Gly Gly Glu His Asn Pro Pro Ser Ile Tyr Leu Glu Ala
        275                 280                 285

Tyr Glu Glu Tyr Thr Ser Lys Leu Asp Ala Leu Gln Gln Arg Glu Gln
    290                 295                 300

Gln Leu Leu Glu Ser Leu Gly Asn Gly Thr Asp Phe Ser Val Ser Ser
305                 310                 315                 320

Ser Ala Ser Thr Asp Thr Val Thr Ser Ser Ser Ser Ser Ser Leu Ser
                325                 330                 335

Val Leu Pro Ser Ser Leu Ser Val Phe Gln Asn Pro Thr Asp Val Ser
            340                 345                 350

Arg Ser Asn Pro Lys Ser Pro Gln Lys Pro Ile Val Arg Val Phe Leu
        355                 360                 365

Pro Asn Lys Gln Arg Thr Val Val Pro Ala Arg Cys Gly Val Thr Val
    370                 375                 380

Arg Asp Ser Leu Lys Lys Ala Leu Met Met Arg Gly Leu Ile Pro Glu
385                 390                 395                 400

Cys Cys Ala Val Tyr Arg Ile Gln Asp Gly Glu Lys Lys Pro Ile Gly
                405                 410                 415

Trp Asp Thr Asp Ile Ser Trp Leu Thr Gly Glu Glu Leu His Val Glu
            420                 425                 430

Val Leu Glu Asn Val Pro Leu Thr Thr His Asn Phe Val Cys Thr Glu
        435                 440                 445

Asn Val Phe Thr Leu Ala Phe Cys Asp Phe Cys Arg Lys Leu Leu Phe
    450                 455                 460

Gln Gly Phe Arg Cys Gln Thr Cys Gly Tyr Lys Phe His Gln Arg Cys
465                 470                 475                 480

Ser Thr Glu Val Pro Leu Met Cys Val Asn Tyr Asp Gln Leu Asp Leu
                485                 490                 495

Leu Phe Val Ser Lys Phe Phe Glu His His Pro Ile Pro Gln Glu Glu
            500                 505                 510

Ala Ser Ile Ala Glu Thr Ala Leu Thr Ser Gly Ser Ser Pro Ser Ala
        515                 520                 525

Pro Pro Ser Asp Ser Thr Gly Pro Gln Ile Leu Thr Ser Pro Ser Pro
    530                 535                 540

Ser Lys Ser Ile Pro Ile Pro Gln Pro Phe Arg Pro Ala Asp Glu Asp
545                 550                 555                 560

His Arg Asn Gln Phe Gly Gln Arg Asp Arg Ser Ser Ser Ala Pro Asn
                565                 570                 575

Val His Ile Asn Thr Ile Glu Pro Val Asn Ile Asp Asp Leu Ile Arg
            580                 585                 590

Asp Gln Gly Phe Arg Ser Asp Gly Gly Ser Thr Thr Gly Leu Ser Ala
        595                 600                 605

Thr Pro Pro Ala Ser Leu Pro Gly Ser Leu Thr Asn Val Lys Ala Leu
```

```
    610                 615                 620

Gln Lys Ser Pro Gly Pro Gln Arg Glu Arg Lys Ser Ser Ser Ser Ser
625                 630                 635                 640

Glu Asp Arg Asn Arg Met Lys Thr Leu Gly Arg Arg Asp Ser Ser Asp
                645                 650                 655

Asp Trp Glu Ile Pro Asp Gly Gln Ile Thr Val Gly Gln Arg Ile Gly
            660                 665                 670

Ser Gly Ser Phe Gly Thr Val Tyr Lys Gly Lys Trp His Gly Asp Val
        675                 680                 685

Ala Val Lys Met Leu Asn Val Thr Ala Pro Thr Pro Gln Gln Leu Gln
    690                 695                 700

Ala Phe Lys Asn Glu Val Gly Val Leu Arg Lys Thr Arg His Val Asn
705                 710                 715                 720

Ile Leu Leu Phe Met Gly Tyr Ser Thr Lys Pro Gln Leu Ala Ile Val
                725                 730                 735

Thr Gln Trp Cys Glu Gly Ser Ser Leu Tyr His His Leu His Ile Ile
            740                 745                 750

Glu Thr Lys Phe Glu Met Ile Lys Leu Ile Asp Ile Ala Arg Gln Thr
        755                 760                 765

Ala Gln Gly Met Asp Tyr Leu His Ala Lys Ser Ile Ile His Arg Asp
    770                 775                 780

Leu Lys Ser Asn Asn Ile Phe Leu His Glu Asp Leu Thr Val Lys Ile
785                 790                 795                 800

Gly Asp Phe Gly Leu Ala Thr Val Lys Ser Arg Trp Ser Gly Ser His
                805                 810                 815

Gln Phe Glu Gln Leu Ser Gly Ser Ile Leu Trp Met Ala Pro Glu Val
            820                 825                 830

Ile Arg Met Gln Asp Lys Asn Pro Tyr Ser Phe Gln Ser Asp Val Tyr
        835                 840                 845

Ala Phe Gly Ile Val Leu Tyr Glu Leu Met Thr Gly Gln Leu Pro Tyr
    850                 855                 860

Ser Asn Ile Asn Asn Arg Asp Gln Ile Ile Phe Met Val Gly Arg Gly
865                 870                 875                 880

Tyr Leu Ser Pro Asp Leu Ser Lys Val Arg Ser Asn Cys Pro Lys Ala
                885                 890                 895

Met Lys Arg Leu Met Ala Glu Cys Leu Lys Lys Lys Arg Asp Glu Arg
            900                 905                 910

Pro Leu Phe Pro Gln Ile Leu Ala Ser Ile Glu Leu Leu Ala Arg Ser
        915                 920                 925

Leu Pro Lys Ile His Arg Ser Ala Ser Glu Pro Ser Leu Asn Arg Ala
    930                 935                 940

Gly Phe Gln Thr Glu Asp Phe Ser Leu Tyr Ala Cys Ala Ser Pro Lys
945                 950                 955                 960

Thr Pro Ile Gln Ala Gly Gly Tyr Gly Ala Phe Pro Val His
                965                 970
```

<210> SEQ ID NO 64
<211> LENGTH: 3853
<212> TYPE: DNA
<213> ORGANISM: Bos taurus

<400> SEQUENCE: 64

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120
```

-continued

```
ctccccccgc cctcagcctc ccttccccct ccccgcccag cagcggtcgc tcgggcccgg    180
ctctcggtta taagatggcg gcgctgagtg gcggcggcgg cggcggcggc ggtggcgcgg    240
agcagggcca ggctctgttc aacggggaca tggagcccga ggccggcgcc gcggcctctt    300
cggctgcgga ccccgccatt cccgaggagg tgtggaatat caaacaaatg attaagttga    360
cacaggagca tatagaggcc ctattggaca aatttggtgg ggagcataat ccaccatcaa    420
tatatctgga ggcctatgaa gaatacacca gcaagctaga tgccctccaa caaagagaac    480
aacagttatt ggaatccctg gggaatggaa ctgatttttc tgtttctagc tctgcatcaa    540
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aactttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac taccttcca tgtggctcat   1140
ccccttctgc acccccctcc gattctattg ggcccccaat tctcaccagt ccatctcctt   1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaaat tctcgcctct attgagctgc   2340
tggcccgctc attgccaaaa attcaccgca gtgcatcaga accctccttg aatcgggctg   2400
gcttccaaac agaggatttt agtctatatg cttgtgcttc tccaaaaaca cccattcagg   2460
```

-continued

```
caggggggata tggtacgttt cctgttcact gaaacaaacc gagtgagtga cagcatgtag   2520

gagggtaggg acaaaagaaa gtgaacaaat gtttgcttat atatttgtta aattgaatag   2580

gattttcttt ttctttaaag gtgaacaaga gaacatgtgt gtttttaaag tttggatata   2640

gttttcttcc cagtctaaaa cccatagtta gcattacatt ttcaacatcg aatttttttt   2700

taattcatag acattgctga aaatttataa tacctttcc agaggcttta cttcccattc   2760

caagtttgtt ttgtttactt ggttagtcta atcattaaac tttaaacttt ccccacctac   2820

cttttgctgt tagctatccc gcatccatta ggggctccaa gaacagcact gtctgcgtgt   2880

gtgtgttggc aggtgggaag ctgatggtaa gttaggctgt gttagtgaag gtaaactgac   2940

caggtctaat taggagtcac tagaattgaa taagcttatt tttattaata tttttctta   3000

taactatttc tttttgtaat aatttagaaa atataattgt tctttattcc cttacagcag   3060

tataaattat tggtgcaggt aaccaaagat attactgagg agtggcatgt ttgacatgag   3120

tgacatggtt taactttgga tttttagtta atatttcttt atatattaag gatgtcttac   3180

acattataga agtcaaattt actgacaaag gtattgcctc ctcttcctcc ccaaaaacac   3240

agcaaaattc tctgggaact cgtagcattg ttggttttct tttggatgac tatggttgcc   3300

aaacaaccaa gtaattgatt ttttttaaat tattattgct ttagattata ctcacctctc   3360

atgatgcctg ttagcaatca cctttatcca tgtgtcttgt aaaatatctt tcctccttat   3420

attctttgcc caacaagagt ctacttgtta tgaatgagta ctattttctt tttttgattc   3480

cccagtataa ttagtatgtt tagtgctttc taggacttcc actttcttat gttaaaaaaa   3540

aaaacaaact aatgtggcag tcagtatatt cttactgtga atcagagtct ttactgggaa   3600

tcaaagtgaa agaagcagct gttctgactt cagagtcagc ctagggacca aaaccagcct   3660

cttaaataca ccttcattta ttcagtttgg atttgtgatg attttcatta tagctgacag   3720

ttcaaggtta ttcagtggca cacagatagc atctgcataa atgcctttct tcttgaaaat   3780

aaaggagaaa attgggaaga ctttacacca atagtttagt ctttaagtac cacagataac   3840

acacaccata aat                                                        3853
```

<210> SEQ ID NO 65
<211> LENGTH: 765
<212> TYPE: PRT
<213> ORGANISM: Bos taurus

<400> SEQUENCE: 65

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125
```

-continued

```
Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540
```

-continued

```
Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
                725                 730                 735

Phe Gln Thr Glu Asp Phe Ser Leu Tyr Ala Cys Ala Ser Pro Lys Thr
            740                 745                 750

Pro Ile Gln Ala Gly Gly Tyr Gly Thr Phe Pro Val His
        755                 760                 765
```

<210> SEQ ID NO 66
<211> LENGTH: 4936
<212> TYPE: DNA
<213> ORGANISM: Bos taurus

<400> SEQUENCE: 66

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttcccccct ccccgcccag cagcggtcgc tcgggcccgg     180

ctctcggtta taagatggcg gcgctgagtg gcggcggcgg cggcggcggc ggtggcgcgg     240

agcagggcca ggctctgttc aacggggaca tggagcccga ggccggcgcc gcggcctctt     300

cggctgcgga ccccgccatt cccgaggagg tgtggaatat caaacaaatg attaagttga     360

cacaggagca tatagaggcc ctattggaca aatttggtgg ggagcataat ccaccatcaa     420

tatatctgga ggcctatgaa gaatacacca gcaagctaga tgccctccaa caaagagaac     480

aacagttatt ggaatccctg ggaatggaa ctgatttttc tgtttctagc tctgcatcaa     540

cggacaccgt tacatcttct tcctcttcta gcctttcagt gctgccttca tctctttcag     600

tttttcaaaa tcccacagat gtgtcacgga gcaaccccaa gtcaccacaa aaacctatcg     660

ttagagtctt cctgcccaat aaacagagga cagtggtacc tgcacggtgt ggagtcacag     720

tccgggacag cctgaagaag gcactgatga tgagaggtct aatcccagag tgctgtgctg     780

tttacagaat tcaggatggg gagaagaaac caattggctg ggacactgat atttcctggc     840

ttactggaga ggagttgcat gtagaagtgt tggagaatgt tccacttaca acacacaact     900
```

ttgtacggaa aactttttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc acccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaagt aggaaagact ctcctaagca 2340
agagacaaaa ttcagaagtt atcagggaaa aagataagca gattctcgcc tctattgagc 2400
tgctggcccg ctcattgcca aaaattcacc gcagtgcatc agaaccctcc ttgaatcggg 2460
ctggcttcca aacagaggat tttagtctat atgcttgtgc ttctccaaaa acacccattc 2520
aggcaggggg atatgaagca gatttggctc ttacatcaaa taaaaataga gtagaagttg 2580
ggatttagag atttcctgac atgcaagaag gaataagcaa gaaaaaaagg tttgttttcc 2640
ccaaatcata tctattgtct tttacttcta ttttttctta aattttttgt gatttcagag 2700
acatgtagag ttttattgat acctaaacta tgagttcttt tttttttttt tttttcatta 2760
ttttgatttt tttggccaag aggcatatgg gatcttagct tgagaaagca acaattttct 2820
tgatgtcatt ttgggtgagg gcacatattg ctgtgaacag tgtggtgata gccaccaggg 2880
accaaactca cacccgctgc attgaaaggt gaagtcttaa acactggacc agcagagaaa 2940
ttcctactct atgagttctt tttgtcatcc cctccccgca ccctccaccc ccaacctaaa 3000
gtctgatgat gaaatcaaca actattccat tagaagcagt agattctggt agcatgatct 3060
ttagtttgtt agtaagattt tgtgctttgt ggggttgtgt cgttttaagg ctaatattta 3120
agtttgtcaa atagaatgct gttcagattg taaaaatgag taataaacat ctgaagtttt 3180
ttttaagtta tttttaacat ggtatataca gttgagctta gagtttatca ttttctgata 3240

-continued

```
ttctcttact tagtagatga attctagcca ttttttataa agatttctgt taagcaaatc   3300

ctgttttcac atgggcttcc tttaagggat tttagattct gctggatatg gtgactgctc   3360

ataagactgt tgaaaattac ttttaagatg tattagaata cttctgaaaa aaaatagcaa   3420

ccttaaaacc ataagcaaaa gtagtaaggg tgtttataca tttctagagt ccctgtttag   3480

gtaatagcct cctatgattg tactttaaat gttttgctct ccaaggtttt agtaacttgg   3540

ctttttttct aatcagtgcc aaactccccc agttttttta actttaaata tgaggtaata   3600

aatcttttac ccttccttga tcttttgact tataatacct tggtcagttg tttcttaaaa   3660

ggaatcctta aatggaaaga gacaatatca ctgtctgcag ttctgattag tagttttatt   3720

cagaatggaa aaacagatta ttcatttttg aaaattgttc aggggtatgt tcattgttag   3780

gaccttggac tttggagtca gtgcctagct atgcattcca ggtctgccat tttctggctg   3840

tgaaattttg gacaagttac ttaaccactt taaaccccag ctttaagaag taaattaacc   3900

ccagtaaatt aagaagtaat agcagccact tcgtagagtt gttatgaggc tcagatgcag   3960

tgcaaatgtg tataaagtat tcagggagtc acctggtata ctataataga cactagaata   4020

gttgccaata ttatcagcat acaatctgag gattctgtca gccaatcatt agcaatctgt   4080

tgtttgttgg gacatgccag tgttctccag ttgaaatcag tagcaatcta aaaatggata   4140

gattattcct catttaaata gtgtgttcat ataagtgatt gcttggatcc ttatcagaag   4200

ttgctgttac tgaaaaatga taaggctgac taaattgtga tagttgtcag ttactaacca   4260

actcccagaa atgaataaga ggaacctatc tctagttcct agtagaaggt atggacaaaa   4320

tagtaggtga aaaataatgt cttgaacccc caaattaagt aagctttaaa gagtacaata   4380

cctcaaaggg tctttgcggt ttaaaatttg tatgctgaga atgatgttca ttgacatgtg   4440

cctatatgta attttttgat agtttaaaag gtgaaatgaa ctacagatgg gagaggtctg   4500

aattttcttg ccttcagtca aatgtgtaat gtggacatat tatttgacct gtgaatttta   4560

tcttttaaaa aagattaatt cctgcttctt ccttcctaat agttgcatta taataatgaa   4620

aatgagttga taatttgggg ggaaagtatt ctacaaatca accttattat tttaccattg   4680

gtttctgaga aattttgttc atttgaaccg tttatagctt gattagaatc atagcatgta   4740

aaacccaact gagggattat ctgcagactt aatgtagtat tatgtaagtt gtcttctttc   4800

atttcgacct tttttgcttt tgttgttgct agatctgtag tatgtagcta gtcacctttc   4860

agcgaggttt cagcgaggct tttctgtgtc tctaggttat ttgagataac ttttttaaaa   4920

ttagctcttg tcctcc                                                   4936
```

<210> SEQ ID NO 67
<211> LENGTH: 797
<212> TYPE: PRT
<213> ORGANISM: Bos taurus

<400> SEQUENCE: 67

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
```

-continued

```
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495
```

```
Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
                725                 730                 735

Leu Ala Arg Ser Leu Pro Lys Ile His Arg Ser Ala Ser Glu Pro Ser
            740                 745                 750

Leu Asn Arg Ala Gly Phe Gln Thr Glu Asp Phe Ser Leu Tyr Ala Cys
        755                 760                 765

Ala Ser Pro Lys Thr Pro Ile Gln Ala Gly Gly Tyr Glu Ala Asp Leu
    770                 775                 780

Ala Leu Thr Ser Asn Lys Asn Arg Val Glu Val Gly Ile
785                 790                 795


<210> SEQ ID NO 68
<211> LENGTH: 4154
<212> TYPE: DNA
<213> ORGANISM: Bos taurus

<400> SEQUENCE: 68

ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttcccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420
```

```
tatatctgga ggcctatgaa gaatacacca gcaagctaga tgccctccaa caaagagaac    480
aacagttatt ggaatccctg gggaatggaa ctgatttttc tgtttctagc tctgcatcaa    540
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aacttttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
ccccttctgc acccccctcc gattctattg ggccccccat tctcaccagt ccatctcctt   1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccccct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cggggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaagt aggaaagact ctcctaagca   2340
agagacaaaa ttcagaagtt atcagggaaa aagataagca gattctcgcc tctattgagc   2400
tgctggcccg ctcattgcca aaaattcacc gcagtgcatc agaaccctcc ttgaatcggg   2460
ctggcttcca aacagaggat tttagtctat atgcttgtgc ttctccaaaa acacccattc   2520
aggcaggggg atatggctga gcacattgtc catcacccac aagtggctgg ttctcatcgc   2580
agaatctacg tagggaatcg ggcgtgaaat tcacttaaga gatagagcag aggaagtgtt   2640
ctgtttacag gaatggagat gagagttatg agtaagttgc ttagtcagtt ggctttgttt   2700
tgaaaattat tgtgttatat ttgtgttaac ctacttgtgt tttgacagta tatgtcacat   2760
```

-continued

```
aggaagaaac ctcagactag cataataaca aagctcagac taggcacaga tgtacacaga   2820

atggaccaaa atgggatggg ggaaggtatg ggaataagtc taggggtagg gaaaaattga   2880

tgtgagggtg ggaaataaac tgtaattacc tgaaataaaa tgtaagagtg caataagtgt   2940

gctttttatt ctaagctgtg aatgggtttt ttaaaaaaag cattccttcc caatgcattt   3000

gcctatgttc catagctgat taaaaccagc tatataaaca tatgcctttt tattcatgtt   3060

aattaccaat ataaatggct aacctttacg tcttatttat cttcatgtta tgttagttta   3120

catacaggga tgtgtgtgtg tgtgtatgct ataaattttc cctccttcgt ttaaaaacgc   3180

gtttgttgga tcctctctgt ttccttaggc catgccacag ctcatagtct cagcttggcc   3240

ttcctgtcac ctgatctgaa ggactatcac agtgacgtag ctcgttcatt ggttgtacac   3300

actctaaccc ttttccttgc tcagcaatta ctgtgtcttc taaaacagga gtgtacaacc   3360

atgagattgc aattaattgt ttgacatatg tccctttgaa ttctatttat tagttatgat   3420

tgattgctct ttggtttgga ccaagaaaaa cgaaatccca cctccccacc ttttcactta   3480

tttcttactt tgaggacaat tctgtaagag agaggaaagg gaactccttc atgttttaac   3540

tgcagcaagt taatggccct ggtttacacc aaacattatg gtgattcaca ttcacattcc   3600

tctcctctct tgctgccaga ggtttgggtt ttgttcagtt ctgctcaagc actgaaaaag   3660

ttttcatgga gtctggagag tgcccagtga aaagatggtt tttaattgtc cacagacctt   3720

tctgttcctg ctttgcaaaa attacaaagg agtaactatt tttaaagctt atttttcaat   3780

tcataaaaaa gacatttatt ttcagtcaga tgatgtctcc ttgtccctta atcctcaatg   3840

tttgcttgaa tctttttttt ttttctgatt ttctcccatc cccacttctt gatacttctt   3900

gagttctctt tcctgctcag gtcctttcat ttgtactttg gagtttttttc tcatgtaaat   3960

ttgtacaatg gaaaatattg ttcagtttgg atagaacgca tggagaatta aataaaaaag   4020

atagctgaaa ttcagattga aatttatttg tgtaaagtta tttaaaaact ctgtactata   4080

taaaaggcaa aaaaagttct atgtacttga tgtgaatatg cgaatactgc tataataaag   4140

attgactgca tgga                                                      4154
```

```
<210> SEQ ID NO 69
<211> LENGTH: 781
<212> TYPE: PRT
<213> ORGANISM: Bos taurus

<400> SEQUENCE: 69

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125
```

-continued

```
Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540
```

```
Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
                725                 730                 735

Leu Ala Arg Ser Leu Pro Lys Ile His Arg Ser Ala Ser Glu Pro Ser
            740                 745                 750

Leu Asn Arg Ala Gly Phe Gln Thr Glu Asp Phe Ser Leu Tyr Ala Cys
        755                 760                 765

Ala Ser Pro Lys Thr Pro Ile Gln Ala Gly Gly Tyr Gly
    770                 775                 780


<210> SEQ ID NO 70
<211> LENGTH: 7914
<212> TYPE: DNA
<213> ORGANISM: Bos taurus

<400> SEQUENCE: 70

ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttcccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780
```

-continued

```
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aactttttc accttagcat tttgtgactt ctgtagaaag ctgcttttcc     960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
ccccttctgc acccccctcc gattctattg ggcccccaat tctcaccagt ccatctcctt   1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccctct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gatttttggtc  1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaaat tctcgcctct attgagctgc   2340
tggcccgctc attgccaaaa attcaccgca gtgcatcaga accctccttg aatcgggctg   2400
gcttccaaac agaggatttt agtctatatg cttgtgcttc tccaaaaaca cccattcagg   2460
caggggggata tggagaattt gcagccttca agtagccaca ccatcatgac agcatctact  2520
cttatttctt aagtcttgtg ttcgtacaat ttgttaacat caaaacacag ttctgttcct   2580
caactctttt taaagttaaa atttttcagt gcataagctg gtgtggaaca gaaggaaatt   2640
tcccatccaa caaaagaggg aagaatgttt taggaaccag aattctctgc tgccagtgtt   2700
tcttcttcaa cacaaatatc acaagtctgc ccactcccag gaagaaagag gagagaccct   2760
gagttctgac cttttgatgg tcaggcatga tggaaagaaa ctgctgctac agcttgggag   2820
atttgctctg ggaagtctgc cagtcaactt tgcccttcta accaccagat caatatgtgg   2880
ctgatcatct gatggggcag ttgcaatcac caagccttgt tctctttcct gttctgggat   2940
tgtgttgtgg aacccttttc cctagccacc accagttcat ttctgaggga tggaacaaaa   3000
atgcagcatg cccttcctgt gtggtgcatg ttcagtcctt gacaaatttt taccaaaatg   3060
aagctacttt atttaaaagg agggtgagag gtgaggaggt cactttgggt gtggcggaaa   3120
gggaatgctg catctttttc ctgggctgct ggggctctgg ccttggcttg ccagccggaa   3180
```

gcgctggcac gcatcgcctt cttttcccat tgggtccagc aatgaagacg agtgtttggg 3240
gttttttttt tctccaccat gtagcaagtt ctcaggaaaa tacaattgat atcttcctcc 3300
taagctcttc caatcagtca ccaagtactt atgtggttac tttgtccagg gcacaaaatg 3360
cctgtatcta attaaaagcc tacaaaactg cttgataaca gttttgaatg tgagacattt 3420
atgtaattta aatgtaaggt acaagtttta atttctgagt ttcttctatt atatttttat 3480
taaaaaaaga aaataatttt cagattgaat tggagtaaaa taatattact tcccactaga 3540
attatatatc ctggaaaatt gtatttttgt tacataagca gcttttaaag aaagatcatt 3600
acccttttct ctacataaat atatggggag tcttagccta atgacaaata tttataattt 3660
ttaaattaat ggtacttgct ggatccatac taacatcttt actaatacct cattgtttct 3720
tccaacttac tcctacacta catcctacat cttcttccta gtcttttatc tagaatatgc 3780
aacctcaaat aaaaatggtg gtgtcctcat tcattctcct ccttcctttt ttcccaagcc 3840
tgatcttcaa aaggttggtt aatttggcag ctgagttcct ccccaggcag agaatagacc 3900
aattttaggt gtattgggac tgagggagga tgtgtaaaga ttaacatcag taaagaaccg 3960
ctgtggagta attaagaact ttgttcttta taactggaga atataaccta accctaacat 4020
ccctcagcct ttactaaagt gtggcgtaaa tcacagtagt agcaaagaaa gtgactctgg 4080
atgtgttcct ggccagtacc tcccttatca tgaatgtaga ctctctcatc aagatttagg 4140
aatataaatc aaatcaaatg tgcccagcca agctatgtag taagggactt gaacaatatt 4200
aggcagaacc tataaaataa atcagggaat tagaaattat ttaaagtttt caaattgtaa 4260
attgccccgg tgtctttcag cctactgcca ttatttttgc tacaatacct acatttcaga 4320
ggagggccta ctgaaaattc catgcaagtg gaaaataatc ctcaagttat taatgagttt 4380
gaaaagcaat gagttcttaa gtctttgtga gtagagcaag atcctacaaa attcagaaat 4440
agtaaaaatg gattcatgct gatttgaaga gcatctgtgt gcataatata atgctgcatc 4500
tcttttaaaa gcagtctatt tttcttttta aatttgtccc catagatgct tttgaacatg 4560
aacatgctta tgttaccttt tccgaggttg ggaagagcca ggagctctca ggcagggccc 4620
cctccctcag ctgggcagga gctgctcagg aggagctagt tatagaggaa gcttagcgtt 4680
ggcattttca aaattcaagg tgataacgct ttcttcttcc tttctgtttt agaatagatt 4740
gctgtctgat ttgaaaaagg gaaatagatt tgatctcaaa tgaatctgtg cccagaagcc 4800
aggctcaggg tattcagaga tttgtatagt gccctcaaaa aataacaaaa ttttagcttt 4860
ccttttttct tcttttctcc atcaaattct tttttctcta gtttacaaat gacatggaaa 4920
aggaatttcc cctgagtttt gtatgccttt tttttttgg cttagactat agataggcgt 4980
gttgagctcc taagaaaata caaggaggaa ctctttgttg tgcagagcac tttatgagta 5040
gtttgtgtgg ataatatgtg actgcttccc tgacgagctt gtgaggctgt acttatgtct 5100
ttcctgtaag gcagcttcag tgccttctgt agtgtatata aggaaagatt acgccttctg 5160
aaaaatctca gagcaaccat aagattattt taaaatatgt agtatgactg atggactttt 5220
tcatcattaa attagtctag catctaaact tttaccactg aaataatatt gaccaaaaag 5280
caatttataa aaggtatttg tgaatagaaa atacaatgtg atcatttgta cttatgtgca 5340
ccttaaaaga ggaattctgt ctagctgtca aattctggtt ccttaacatc cagtccttga 5400
ttgtgattga gatctggtag gacgtgctgg ggcacgctag cagataaaat cccgtatact 5460
ttaggataga tgttacattt atgtcagtgt tggcaaagag cattgtgtag taataaagaa 5520

-continued

```
ttcaagactt cagcaatgtc aacctgaaac tttgtaaata tttcctagat tgttatttga   5580
tgcagtcaca gctctttatc acacaatgtt gtctttccct catcaggcaa ttttagaact   5640
gctgcacacc cctcctcaga tctcacctgc ccctcctgta cattcacctc tccagccttg   5700
tgcacacctc atttagcttt agtttgaaac acattgcagg gttcaggtga cctcttcaaa   5760
aactacctcc tcagaatgag gtaatgaata gttatttatt ttaaaatatg aaaagtcagg   5820
agctctagaa tatgaagatg atctaagatt ttaactttta tgtatacttg ttgagcactc   5880
tccttttgtc ctaaagggca ttatacattt aagcagtaat actgaaaaat gtagctcaga   5940
gtaactgaat gttgttgaaa gtggtgccag aatctgtttt aggggtacgt atcagaatct   6000
taatcttaaa tcggttacat gaaattaaat agttaatggt aacacttgac taacagatat   6060
aattttaatt ttcggtaggc ttttagcaag acagtaagta catcttcata atgagttagc   6120
cacagcttca tcacatgcac agattttcct gttgagagac tgcccagtta agagggtaga   6180
atgatgaacc atttttcagg attctcttct ttgtccaaac tggcattgtg agtgctagaa   6240
tatcagcact ttcaaactag tgattccaac tattaggcta ttaaaaagca aaacaaacca   6300
aacaaaccat agccagacat gggaagttta ctatgagtat aaacagcaaa tagcttacag   6360
gtcatacatt gaaatggtgt aggtaaggcg ttagaaaaat accttgacaa tttgccaaat   6420
gatcttactg tgccttcatg atgcaataaa aaaaaaaaaa atttagcata aatcagtgat   6480
ttgtgaagag agcagccacc ctggtctaac tcagctgtgt taatattttt tagcgtgcaa   6540
tttagactgc aaagataaat gcactaaaga gtttatagcc aaaatcacat ttaaaaaatg   6600
agagaaaaca caggtaaatt ttcagtgaac aaaattattt ttttaaagta cataatccct   6660
agtatagtca gatatattta tcacatagag caaataggtt gaaatcacaa ttcagtgaca   6720
tttctagaga aactttttct actcccatag gttcttcaaa gcatggaact tttatataac   6780
agaaatgtgt gacggtcatt ttaaattgct gtagtttggg gctgaagtac tgtgtgctgg   6840
gcagcaatca catgtattaa ctagtgagaa aggagaaatt aagatatagg acagaatttg   6900
attttcttgt tcccagatta ctgctgccaa cctagacact gagtttccag aggctgaaac   6960
gtaaacttgc agctcagcaa ctgttttgca aagttagtgg gactgtcctg cttatgctgt   7020
tcaaaaatgc tctgagggcc aggtggggcc tccaggggct cctctctgag gggacatcag   7080
actagctaac gacctggcgg gcggatgtga accggacaca ctccatggtg tgcttcttgt   7140
atcggtccct cgccaccctc aagaaaggct tcagcgggtt ctctagacgt ctccactaag   7200
gtgtgttact aacagccatg ggttgttgag cacccgagga gtgcaatagc atctctgcat   7260
gattgtatat tggcccgaag agaatgaagt ggccagtgta ctcatgttcc atgttgctag   7320
ctctggtaaa ctgaaaatac tggtaagatt tttgttttat cagtacacta gagagtaagc   7380
tttgttttgt tgtttttaga taatgttttc acttccattt ggaaagacat ttaaattgag   7440
tttcagtcct aaattttgcc agtcatggta attagcagtt tctatcaggt atttttaagg   7500
tagaagagga tagaaacata agttctaaaa gcttaaggta accgtggttt attttaaaat   7560
gtttaggggt ggttagtctc tacctcaaaa aaagtgagtg aatcttttat ttcagcattc   7620
acaagttcgg ctgttgtttt tgtaatacat ttttttttta accttttgac ccccctttac   7680
ctaagtgtca atgtagtttt attaattact aagtcagttt cattaaaatg tttatttagc   7740
agttttgact aattgcaatg attaatatag ccagttgtgc atgaggacac agccagtgag   7800
tatatctggg ttttttttgt gatgcttttt ttcttaagac ttctgtagat ttatgaagta   7860
ctcattgaaa acaactaaaa tacgtttatt cgtgttaata tggaaaaaaa aaaa         7914
```

<210> SEQ ID NO 71
<211> LENGTH: 766
<212> TYPE: PRT
<213> ORGANISM: Bos taurus

<400> SEQUENCE: 71

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
```

```
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
                725                 730                 735

Phe Gln Thr Glu Asp Phe Ser Leu Tyr Ala Cys Ala Ser Pro Lys Thr
            740                 745                 750

Pro Ile Gln Ala Gly Gly Tyr Gly Glu Phe Ala Ala Phe Lys
        755                 760                 765
```

<210> SEQ ID NO 72
<211> LENGTH: 4670
<212> TYPE: DNA
<213> ORGANISM: Bos taurus

<400> SEQUENCE: 72
ggtgtgtcat agtgcagcag attgaatgca gaagatatga aaattcagat gtcttctgtt 60
aaggtgtgga atatcaaaca aatgattaag ttgacacagg agcatataga ggccctattg 120
gacaaatttg gtggggagca taatccacca tcaatatatc tggaggccta tgaagaatac 180
accagcaagc tagatgccct ccaacaaaga gaacaacagt tattggaatc cctggggaat 240
ggaactgatt tttctgtttc tagctctgca tcaacggaca ccgttacatc ttcttcctct 300
tctagccttt cagtgctgcc ttcatctctt tcagtttttc aaaatcccac agatgtgtca 360
cggagcaacc ccaagtcacc acaaaaacct atcgttagag tcttcctgcc caataaacag 420
aggacagtgg tacctgcacg gtgtggagtc acagtccggg acagcctgaa gaaggcactg 480
atgatgagag gtctaatccc agagtgctgt gctgtttaca gaattcagga tggggagaag 540
aaaccaattg gctgggacac tgatatttcc tggcttactg gagaggagtt gcatgtagaa 600
gtgttggaga atgttccact tacaacacac aactttgtac ggaaaacttt tttcacctta 660
gcattttgtg acttctgtag aaagctgctt ttccagggat tccgctgtca aacatgtggt 720
tataaatttc accagcgttg tagtacagag gttccactga tgtgtgttaa ttatgaccaa 780
ctagatttgc tgtttgtctc caagttcttt gaacaccacc caataccaca ggaggaggcc 840
tccttagcag agactaccct tccatgtggc tcatcccctt ctgcaccccc ctccgattct 900
attgggcccc caattctcac cagtccatct ccttcaaaat ccattccaat tccacagcct 960
ttccgaccag cagatgaaga tcatcgaaat cagtttggac aacgagaccg gtcctcatca 1020
gctccaaatg tgcatataaa cacaatagaa cccgtcaata ttgatgactt gattagagac 1080
caagggtttc gtagtgatgg aggatcaacc acaggtttat ccgccacacc ccctgcctca 1140
ttacctggct cactctctaa tgtgaaagca ttgcagaaat ctccaggacc tcagcgagaa 1200
agaaagtcct cttcatcctc agaagacagg aatcgaatga aaacgcttgg tagacgggat 1260
tcaagtgacg attgggagat tcctgatgga cagatcacag tgggacaaag aattggatca 1320
gggtcatttg ggacagtcta caagggaaag tggcatggtg atgtggcagt gaaaatgttg 1380
aatgtgacag cacccacacc tcagcagtta caggccttca aaaatgaagt aggagtactc 1440
aggaaaacgc gacatgtgaa tatcctcctc ttcatgggtt attcaacaaa gccacaactg 1500
gctattgtta cccagtggtg tgagggctcc agtttatatc atcatctcca catcattgag 1560
accaaattcg agatgatcaa acttatagat attgcacggc agactgcaca gggcatggat 1620
tacttacacg ccaagtcaat catccacaga gacctcaaga gtaataatat ttttcttcat 1680
gaagacctca cagtaaaaat aggtgatttt ggtctagcca cagtgaaatc tcgatggagt 1740
gggtcccatc agtttgaaca gttgtctgga tccattttgt ggatggcacc agaagtaatc 1800
agaatgcaag ataaaaaccc atatagcttt cagtcagatg tatatgcatt tgggattgtt 1860
ctgtatgaat tgatgaccgg acagttacct tattcaaata tcaacaacag ggaccagata 1920
atttttatgg tgggacgagg atatctgtct ccagatctca gtaaggtacg gagtaactgt 1980
ccaaaagcca tgaagagatt aatggcagag tgcctaaaaa agaaaagaga tgaaagacca 2040
ctctttcccc aagtaggaaa gactctccta agcaagagac aaaattcaga agttatcagg 2100
gaaaaagata agcagattct cgcctctatt gagctgctgg cccgctcatt gccaaaaatt 2160
caccgcagtg catcagaacc ctccttgaat cgggctggct tccaaacaga ggattttagt 2220
ctatatgctt gtgcttctcc aaaaacaccc attcaggcag ggggatatga agcagatttg 2280

-continued

```
gctcttacat caaataaaaa tagagtagaa gttgggattt agagatttcc tgacatgcaa   2340
gaaggaataa gcaagaaaaa aaggtttgtt ttccccaaat catatctatt gtcttttact   2400
tctatttttt cttaaatttt ttgtgatttc agagacatgt agagttttat tgatacctaa   2460
actatgagtt cttttttttt ttttttttc attattttga tttttttggc caagaggcat   2520
atgggatctt agcttgagaa agcaacaatt ttcttgatgt cattttgggt gagggcacat   2580
attgctgtga acagtgtggt gatagccacc agggaccaaa ctcacacccg ctgcattgaa   2640
aggtgaagtc ttaaacactg gaccagcaga gaaattccta ctctatgagt tctttttgtc   2700
atcccctccc cgcaccctcc acccccaacc taaagtctga tgatgaaatc aacaactatt   2760
ccattagaag cagtagattc tggtagcatg atctttagtt tgttagtaag attttgtgct   2820
ttgtggggtt gtgtcgtttt aaggctaata tttaagtttg tcaaatagaa tgctgttcag   2880
attgtaaaaa tgagtaataa acatctgaag ttttttttaa gttattttta acatggtata   2940
tacagttgag cttagagttt atcattttct gatattctct tacttagtag atgaattcta   3000
gccatttttt ataaagattt ctgttaagca aatcctgttt tcacatgggc ttcctttaag   3060
ggattttaga ttctgctgga tatggtgact gctcataaga ctgttgaaaa ttacttttaa   3120
gatgtattag aatacttctg aaaaaaaata gcaaccttaa aaccataagc aaaagtagta   3180
agggtgttta tacatttcta gagtccctgt ttaggtaata gcctcctatg attgtacttt   3240
aaatgttttg ctctccaagg ttttagtaac ttggcttttt ttctaatcag tgccaaactc   3300
ccccagtttt tttaacttta aatatgaggt aataaatctt ttacccttcc ttgatctttt   3360
gacttataat accttggtca gttgtttctt aaaaggaatc cttaaatgga aagagacaat   3420
atcactgtct gcagttctga ttagtagttt tattcagaat ggaaaaacag attattcatt   3480
tttgaaaatt gttcaggggt atgttcattg ttaggacctt ggactttgga gtcagtgcct   3540
agctatgcat tccaggtctg ccatttctg gctgtgaaat tttggacaag ttacttaacc   3600
actttaaacc ccagctttaa gaagtaaatt aaccccagta aattaagaag taatagcagc   3660
cacttcgtag agttgttatg aggctcagat gcagtgcaaa tgtgtataaa gtattcaggg   3720
agtcacctgg tatactataa tagacactag aatagttgcc aatattatca gcatacaatc   3780
tgaggattct gtcagccaat cattagcaat ctgttgtttg ttgggacatg ccagtgttct   3840
ccagttgaaa tcagtagcaa tctaaaaatg gatagattat tcctcattta aatagtgtgt   3900
tcatataagt gattgcttgg atccttatca gaagttgctg ttactgaaaa atgataaggc   3960
tgactaaatt gtgatagttg tcagttacta accaactccc agaaatgaat aagaggaacc   4020
tatctctagt tcctagtaga aggtatggac aaaatagtag gtgaaaaata atgtcttgaa   4080
cccccaaatt aagtaagctt taaagagtac aatacctcaa agggtctttg cggtttaaaa   4140
tttgtatgct gagaatgatg ttcattgaca tgtgcctata tgtaattttt tgatagttta   4200
aaaggtgaaa tgaactacag atgggagagg tctgaatttt cttgccttca gtcaaatgtg   4260
taatgtggac atattatttg acctgtgaat tttatctttt aaaaaagatt aattcctgct   4320
tcttccttcc taatagttgc attataataa tgaaaatgag ttgataattt ggggggaaag   4380
tattctacaa atcaacctta ttattttacc attggtttct gagaaatttt gttcatttga   4440
accgtttata gcttgattag aatcatagca tgtaaaaccc aactgaggga ttatctgcag   4500
acttaatgta gtattatgta agttgtcttc tttcatttcg accttttttg cttttgttgt   4560
tgctagatct gtagtatgta gctagtcacc tttcagcgag gtttcagcga ggcttttctg   4620
tgtctctagg ttatttgaga taactttttt aaaattagct cttgtcctcc              4670
```

<210> SEQ ID NO 73
<211> LENGTH: 761
<212> TYPE: PRT
<213> ORGANISM: Bos taurus

<400> SEQUENCE: 73

```
Met Lys Ile Gln Met Ser Ser Val Lys Val Trp Asn Ile Lys Gln Met
1               5                   10                  15

Ile Lys Leu Thr Gln Glu His Ile Glu Ala Leu Leu Asp Lys Phe Gly
            20                  25                  30

Gly Glu His Asn Pro Pro Ser Ile Tyr Leu Glu Ala Tyr Glu Glu Tyr
        35                  40                  45

Thr Ser Lys Leu Asp Ala Leu Gln Gln Arg Glu Gln Gln Leu Leu Glu
    50                  55                  60

Ser Leu Gly Asn Gly Thr Asp Phe Ser Val Ser Ser Ser Ala Ser Thr
65                  70                  75                  80

Asp Thr Val Thr Ser Ser Ser Ser Ser Ser Leu Ser Val Leu Pro Ser
                85                  90                  95

Ser Leu Ser Val Phe Gln Asn Pro Thr Asp Val Ser Arg Ser Asn Pro
            100                 105                 110

Lys Ser Pro Gln Lys Pro Ile Val Arg Val Phe Leu Pro Asn Lys Gln
        115                 120                 125

Arg Thr Val Val Pro Ala Arg Cys Gly Val Thr Val Arg Asp Ser Leu
    130                 135                 140

Lys Lys Ala Leu Met Met Arg Gly Leu Ile Pro Glu Cys Cys Ala Val
145                 150                 155                 160

Tyr Arg Ile Gln Asp Gly Glu Lys Lys Pro Ile Gly Trp Asp Thr Asp
                165                 170                 175

Ile Ser Trp Leu Thr Gly Glu Glu Leu His Val Glu Val Leu Glu Asn
            180                 185                 190

Val Pro Leu Thr Thr His Asn Phe Val Arg Lys Thr Phe Phe Thr Leu
        195                 200                 205

Ala Phe Cys Asp Phe Cys Arg Lys Leu Leu Phe Gln Gly Phe Arg Cys
    210                 215                 220

Gln Thr Cys Gly Tyr Lys Phe His Gln Arg Cys Ser Thr Glu Val Pro
225                 230                 235                 240

Leu Met Cys Val Asn Tyr Asp Gln Leu Asp Leu Leu Phe Val Ser Lys
                245                 250                 255

Phe Phe Glu His His Pro Ile Pro Gln Glu Glu Ala Ser Leu Ala Glu
            260                 265                 270

Thr Thr Leu Pro Cys Gly Ser Ser Pro Ser Ala Pro Pro Ser Asp Ser
        275                 280                 285

Ile Gly Pro Pro Ile Leu Thr Ser Pro Ser Pro Ser Lys Ser Ile Pro
    290                 295                 300

Ile Pro Gln Pro Phe Arg Pro Ala Asp Glu Asp His Arg Asn Gln Phe
305                 310                 315                 320

Gly Gln Arg Asp Arg Ser Ser Ser Ala Pro Asn Val His Ile Asn Thr
                325                 330                 335

Ile Glu Pro Val Asn Ile Asp Asp Leu Ile Arg Asp Gln Gly Phe Arg
            340                 345                 350

Ser Asp Gly Gly Ser Thr Thr Gly Leu Ser Ala Thr Pro Pro Ala Ser
        355                 360                 365

Leu Pro Gly Ser Leu Ser Asn Val Lys Ala Leu Gln Lys Ser Pro Gly
```

```
    370                 375                 380

Pro Gln Arg Glu Arg Lys Ser Ser Ser Ser Ser Glu Asp Arg Asn Arg
385                 390                 395                 400

Met Lys Thr Leu Gly Arg Arg Asp Ser Ser Asp Asp Trp Glu Ile Pro
                405                 410                 415

Asp Gly Gln Ile Thr Val Gly Gln Arg Ile Gly Ser Gly Ser Phe Gly
            420                 425                 430

Thr Val Tyr Lys Gly Lys Trp His Gly Asp Val Ala Val Lys Met Leu
        435                 440                 445

Asn Val Thr Ala Pro Thr Pro Gln Gln Leu Gln Ala Phe Lys Asn Glu
    450                 455                 460

Val Gly Val Leu Arg Lys Thr Arg His Val Asn Ile Leu Leu Phe Met
465                 470                 475                 480

Gly Tyr Ser Thr Lys Pro Gln Leu Ala Ile Val Thr Gln Trp Cys Glu
                485                 490                 495

Gly Ser Ser Leu Tyr His His Leu His Ile Ile Glu Thr Lys Phe Glu
            500                 505                 510

Met Ile Lys Leu Ile Asp Ile Ala Arg Gln Thr Ala Gln Gly Met Asp
        515                 520                 525

Tyr Leu His Ala Lys Ser Ile Ile His Arg Asp Leu Lys Ser Asn Asn
    530                 535                 540

Ile Phe Leu His Glu Asp Leu Thr Val Lys Ile Gly Asp Phe Gly Leu
545                 550                 555                 560

Ala Thr Val Lys Ser Arg Trp Ser Gly Ser His Gln Phe Glu Gln Leu
                565                 570                 575

Ser Gly Ser Ile Leu Trp Met Ala Pro Glu Val Ile Arg Met Gln Asp
            580                 585                 590

Lys Asn Pro Tyr Ser Phe Gln Ser Asp Val Tyr Ala Phe Gly Ile Val
        595                 600                 605

Leu Tyr Glu Leu Met Thr Gly Gln Leu Pro Tyr Ser Asn Ile Asn Asn
    610                 615                 620

Arg Asp Gln Ile Ile Phe Met Val Gly Arg Gly Tyr Leu Ser Pro Asp
625                 630                 635                 640

Leu Ser Lys Val Arg Ser Asn Cys Pro Lys Ala Met Lys Arg Leu Met
                645                 650                 655

Ala Glu Cys Leu Lys Lys Lys Arg Asp Glu Arg Pro Leu Phe Pro Gln
            660                 665                 670

Val Gly Lys Thr Leu Leu Ser Lys Arg Gln Asn Ser Glu Val Ile Arg
        675                 680                 685

Glu Lys Asp Lys Gln Ile Leu Ala Ser Ile Glu Leu Leu Ala Arg Ser
    690                 695                 700

Leu Pro Lys Ile His Arg Ser Ala Ser Glu Pro Ser Leu Asn Arg Ala
705                 710                 715                 720

Gly Phe Gln Thr Glu Asp Phe Ser Leu Tyr Ala Cys Ala Ser Pro Lys
                725                 730                 735

Thr Pro Ile Gln Ala Gly Gly Tyr Glu Ala Asp Leu Ala Leu Thr Ser
            740                 745                 750

Asn Lys Asn Arg Val Glu Val Gly Ile
        755                 760
```

<210> SEQ ID NO 74
<211> LENGTH: 4816
<212> TYPE: DNA
<213> ORGANISM: Bos taurus

<400> SEQUENCE: 74
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttcccccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag agcccccaat tctcaccagt ccatctcctt 1080
caaaatccat tccaattcca cagcctttcc gaccagcaga tgaagatcat cgaaatcagt 1140
ttggacaacg agaccggtcc tcatcagctc caaatgtgca tataaacaca atagaacccg 1200
tcaatattga tgacttgatt agagaccaag ggtttcgtag tgatggagga tcaaccacag 1260
gtttatccgc cacacccct gcctcattac ctggctcact ctctaatgtg aaagcattgc 1320
agaaatctcc aggacctcag cgagaaagaa agtcctcttc atcctcagaa gacaggaatc 1380
gaatgaaaac gcttggtaga cgggattcaa gtgacgattg ggagattcct gatggacaga 1440
tcacagtggg acaaagaatt ggatcagggt catttgggac agtctacaag ggaaagtggc 1500
atggtgatgt ggcagtgaaa atgttgaatg tgacagcacc cacacctcag cagttacagg 1560
ccttcaaaaa tgaagtagga gtactcagga aaacgcgaca tgtgaatatc ctcctcttca 1620
tgggttattc aacaaagcca caactggcta ttgttaccca gtggtgtgag ggctccagtt 1680
tatatcatca tctccacatc attgagacca aattcgagat gatcaaactt atagatattg 1740
cacggcagac tgcacagggc atggattact tacacgccaa gtcaatcatc cacagagacc 1800
tcaagagtaa taatattttt cttcatgaag acctcacagt aaaaataggt gattttggtc 1860
tagccacagt gaaatctcga tggagtgggt cccatcagtt tgaacagttg tctggatcca 1920
ttttgtggat ggcaccagaa gtaatcagaa tgcaagataa aaacccatat agctttcagt 1980
cagatgtata tgcatttggg attgttctgt atgaattgat gaccggacag ttaccttatt 2040
caaatatcaa caacagggac cagataattt ttatggtggg acgaggatat ctgtctccag 2100
atctcagtaa ggtacggagt aactgtccaa aagccatgaa gagattaatg gcagagtgcc 2160
taaaaaagaa aagagatgaa agaccactct ttccccaagt aggaaagact ctcctaagca 2220
agagacaaaa ttcagaagtt atcagggaaa aagataagca gattctcgcc tctattgagc 2280

```
tgctggcccg ctcattgcca aaaattcacc gcagtgcatc agaaccctcc ttgaatcggg   2340
ctggcttcca aacagaggat tttagtctat atgcttgtgc ttctccaaaa acacccattc   2400
aggcaggggg atatgaagca gatttggctc ttacatcaaa taaaaataga gtagaagttg   2460
ggatttagag atttcctgac atgcaagaag gaataagcaa gaaaaaaagg tttgttttcc   2520
ccaaatcata tctattgtct tttacttcta ttttttctta aatttttttgt gatttcagag   2580
acatgtagag ttttattgat acctaaacta tgagttcttt tttttttttt tttttcatta   2640
ttttgatttt tttggccaag aggcatatgg gatcttagct tgagaaagca acaattttct   2700
tgatgtcatt ttgggtgagg gcacatattg ctgtgaacag tgtggtgata gccaccaggg   2760
accaaactca cacccgctgc attgaaaggt gaagtcttaa acactggacc agcagagaaa   2820
ttcctactct atgagttctt tttgtcatcc cctccccgca ccctccaccc ccaacctaaa   2880
gtctgatgat gaaatcaaca actattccat tagaagcagt agattctggt agcatgatct   2940
ttagtttgtt agtaagattt tgtgctttgt ggggttgtgt cgttttaagg ctaatattta   3000
agtttgtcaa atagaatgct gttcagattg taaaaatgag taataaacat ctgaagtttt   3060
ttttaagtta tttttaacat ggtatataca gttgagctta gagtttatca ttttctgata   3120
ttctcttact tagtagatga attctagcca ttttttataa agatttctgt taagcaaatc   3180
ctgttttcac atgggcttcc tttaagggat tttagattct gctggatatg gtgactgctc   3240
ataagactgt tgaaaattac ttttaagatg tattagaata cttctgaaaa aaaatagcaa   3300
ccttaaaacc ataagcaaaa gtagtaaggg tgtttataca tttctagagt ccctgtttag   3360
gtaatagcct cctatgattg tactttaaat gttttgctct ccaaggtttt agtaacttgg   3420
ctttttttct aatcagtgcc aaactccccc agttttttta actttaaata tgaggtaata   3480
aatcttttac ccttccttga tcttttgact tataatacct tggtcagttg tttcttaaaa   3540
ggaatcctta aatggaaaga gacaatatca ctgtctgcag ttctgattag tagttttatt   3600
cagaatggaa aaacagatta ttcatttttg aaaattgttc aggggtatgt tcattgttag   3660
gaccttggac tttggagtca gtgcctagct atgcattcca ggtctgccat tttctggctg   3720
tgaaattttg gacaagttac ttaaccactt taaaccccag ctttaagaag taaattaacc   3780
ccagtaaatt aagaagtaat agcagccact tcgtagagtt gttatgaggc tcagatgcag   3840
tgcaaatgtg tataaagtat tcagggagtc acctggtata ctataataga cactagaata   3900
gttgccaata ttatcagcat acaatctgag gattctgtca gccaatcatt agcaatctgt   3960
tgtttgttgg gacatgccag tgttctccag ttgaaatcag tagcaatcta aaaatggata   4020
gattattcct catttaaata gtgtgttcat ataagtgatt gcttggatcc ttatcagaag   4080
ttgctgttac tgaaaaatga taaggctgac taaattgtga tagttgtcag ttactaacca   4140
actcccagaa atgaataaga ggaacctatc tctagttcct agtagaaggt atggacaaaa   4200
tagtaggtga aaaataatgt cttgaacccc caaattaagt aagctttaaa gagtacaata   4260
cctcaaaggg tctttgcggt ttaaaatttg tatgctgaga atgatgttca ttgacatgtg   4320
cctatatgta attttttgat agtttaaaag gtgaaatgaa ctacagatgg gagaggtctg   4380
aattttcttg ccttcagtca aatgtgtaat gtggacatat tatttgacct gtgaatttta   4440
tcttttaaaa aagattaatt cctgcttctt ccttcctaat agttgcatta taataatgaa   4500
aatgagttga taatttgggg ggaaagtatt ctacaaatca accttattat tttaccattg   4560
gtttctgaga aattttgttc atttgaaccg tttatagctt gattagaatc atagcatgta   4620
aaacccaact gagggattat ctgcagactt aatgtagtat tatgtaagtt gtcttctttc   4680
```

```
atttcgacct tttttgcttt tgttgttgct agatctgtag tatgtagcta gtcacctttc   4740

agcgaggttt cagcgaggct tttctgtgtc tctaggttat ttgagataac ttttttaaaa   4800

ttagctcttg tcctcc                                                   4816


<210> SEQ ID NO 75
<211> LENGTH: 757
<212> TYPE: PRT
<213> ORGANISM: Bos taurus

<400> SEQUENCE: 75

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Glu Pro Pro
        275                 280                 285

Ile Leu Thr Ser Pro Ser Pro Ser Lys Ser Ile Pro Ile Pro Gln Pro
    290                 295                 300

Phe Arg Pro Ala Asp Glu Asp His Arg Asn Gln Phe Gly Gln Arg Asp
305                 310                 315                 320

Arg Ser Ser Ser Ala Pro Asn Val His Ile Asn Thr Ile Glu Pro Val
                325                 330                 335

Asn Ile Asp Asp Leu Ile Arg Asp Gln Gly Phe Arg Ser Asp Gly Gly
```

```
            340                 345                 350

Ser Thr Thr Gly Leu Ser Ala Thr Pro Pro Ala Ser Leu Pro Gly Ser
        355                 360                 365

Leu Ser Asn Val Lys Ala Leu Gln Lys Ser Pro Gly Pro Gln Arg Glu
    370                 375                 380

Arg Lys Ser Ser Ser Ser Ser Glu Asp Arg Asn Arg Met Lys Thr Leu
385                 390                 395                 400

Gly Arg Arg Asp Ser Ser Asp Asp Trp Glu Ile Pro Asp Gly Gln Ile
                405                 410                 415

Thr Val Gly Gln Arg Ile Gly Ser Gly Ser Phe Gly Thr Val Tyr Lys
            420                 425                 430

Gly Lys Trp His Gly Asp Val Ala Val Lys Met Leu Asn Val Thr Ala
        435                 440                 445

Pro Thr Pro Gln Gln Leu Gln Ala Phe Lys Asn Glu Val Gly Val Leu
    450                 455                 460

Arg Lys Thr Arg His Val Asn Ile Leu Leu Phe Met Gly Tyr Ser Thr
465                 470                 475                 480

Lys Pro Gln Leu Ala Ile Val Thr Gln Trp Cys Glu Gly Ser Ser Leu
                485                 490                 495

Tyr His His Leu His Ile Ile Glu Thr Lys Phe Glu Met Ile Lys Leu
            500                 505                 510

Ile Asp Ile Ala Arg Gln Thr Ala Gln Gly Met Asp Tyr Leu His Ala
        515                 520                 525

Lys Ser Ile Ile His Arg Asp Leu Lys Ser Asn Asn Ile Phe Leu His
    530                 535                 540

Glu Asp Leu Thr Val Lys Ile Gly Asp Phe Gly Leu Ala Thr Val Lys
545                 550                 555                 560

Ser Arg Trp Ser Gly Ser His Gln Phe Glu Gln Leu Ser Gly Ser Ile
                565                 570                 575

Leu Trp Met Ala Pro Glu Val Ile Arg Met Gln Asp Lys Asn Pro Tyr
            580                 585                 590

Ser Phe Gln Ser Asp Val Tyr Ala Phe Gly Ile Val Leu Tyr Glu Leu
        595                 600                 605

Met Thr Gly Gln Leu Pro Tyr Ser Asn Ile Asn Asn Arg Asp Gln Ile
    610                 615                 620

Ile Phe Met Val Gly Arg Gly Tyr Leu Ser Pro Asp Leu Ser Lys Val
625                 630                 635                 640

Arg Ser Asn Cys Pro Lys Ala Met Lys Arg Leu Met Ala Glu Cys Leu
                645                 650                 655

Lys Lys Lys Arg Asp Glu Arg Pro Leu Phe Pro Gln Val Gly Lys Thr
            660                 665                 670

Leu Leu Ser Lys Arg Gln Asn Ser Glu Val Ile Arg Glu Lys Asp Lys
        675                 680                 685

Gln Ile Leu Ala Ser Ile Glu Leu Leu Ala Arg Ser Leu Pro Lys Ile
    690                 695                 700

His Arg Ser Ala Ser Glu Pro Ser Leu Asn Arg Ala Gly Phe Gln Thr
705                 710                 715                 720

Glu Asp Phe Ser Leu Tyr Ala Cys Ala Ser Pro Lys Thr Pro Ile Gln
                725                 730                 735

Ala Gly Gly Tyr Glu Ala Asp Leu Ala Leu Thr Ser Asn Lys Asn Arg
            740                 745                 750

Val Glu Val Gly Ile
        755
```

<210> SEQ ID NO 76
<211> LENGTH: 2499
<212> TYPE: DNA
<213> ORGANISM: Bos taurus

<400> SEQUENCE: 76
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttccccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc acccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100

-continued cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaagt aggaaagact ctcctaagca 2340
agagacaaaa ttcagaagtt atcagggaaa aagataagca ggaaaagtat gtttctttag 2400
tacattccag gcatttggga ttacagtaaa aacaatattc tcgcctctat tgagctgctg 2460
gcccgctcat tgccaaaaat tcaccgcagt gcatcagaa 2499

<210> SEQ ID NO 77
<211> LENGTH: 744
<212> TYPE: PRT
<213> ORGANISM: Bos taurus

<400> SEQUENCE: 77

Met Ala Ala Leu Ser Gly Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln
85 90 95

Gln Leu Leu Glu Ser Leu Gly Asn Gly Thr Asp Phe Ser Val Ser Ser
100 105 110

Ser Ala Ser Thr Asp Thr Val Thr Ser Ser Ser Ser Ser Ser Leu Ser
115 120 125

Val Leu Pro Ser Ser Leu Ser Val Phe Gln Asn Pro Thr Asp Val Ser
130 135 140

Arg Ser Asn Pro Lys Ser Pro Gln Lys Pro Ile Val Arg Val Phe Leu
145 150 155 160

Pro Asn Lys Gln Arg Thr Val Val Pro Ala Arg Cys Gly Val Thr Val
165 170 175

Arg Asp Ser Leu Lys Lys Ala Leu Met Met Arg Gly Leu Ile Pro Glu
180 185 190

Cys Cys Ala Val Tyr Arg Ile Gln Asp Gly Glu Lys Lys Pro Ile Gly
195 200 205

Trp Asp Thr Asp Ile Ser Trp Leu Thr Gly Glu Glu Leu His Val Glu
210 215 220

Val Leu Glu Asn Val Pro Leu Thr Thr His Asn Phe Val Arg Lys Thr
225 230 235 240

Phe Phe Thr Leu Ala Phe Cys Asp Phe Cys Arg Lys Leu Leu Phe Gln
245 250 255

Gly Phe Arg Cys Gln Thr Cys Gly Tyr Lys Phe His Gln Arg Cys Ser
260 265 270

Thr Glu Val Pro Leu Met Cys Val Asn Tyr Asp Gln Leu Asp Leu Leu
275 280 285

Phe Val Ser Lys Phe Phe Glu His His Pro Ile Pro Gln Glu Glu Ala
290 295 300

-continued

```
Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Glu Lys Tyr Val Ser Leu Val
```

-continued 725 730 735

His Ser Arg His Leu Gly Leu Gln
740

<210> SEQ ID NO 78
<211> LENGTH: 2404
<212> TYPE: DNA
<213> ORGANISM: Bos taurus

<400> SEQUENCE: 78
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttcccccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc accccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980

-continued tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaaga tctctcttcc caccatagac 2340
acaaaaattt cagatggcta caggtttaca tgtaaaaaac agaattataa caaatgattt 2400
ttat 2404

<210> SEQ ID NO 79
<211> LENGTH: 726
<212> TYPE: PRT
<213> ORGANISM: Bos taurus

<400> SEQUENCE: 79

Met Ala Ala Leu Ser Gly Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln
85 90 95

Gln Leu Leu Glu Ser Leu Gly Asn Gly Thr Asp Phe Ser Val Ser Ser
100 105 110

Ser Ala Ser Thr Asp Thr Val Thr Ser Ser Ser Ser Ser Ser Leu Ser
115 120 125

Val Leu Pro Ser Ser Leu Ser Val Phe Gln Asn Pro Thr Asp Val Ser
130 135 140

Arg Ser Asn Pro Lys Ser Pro Gln Lys Pro Ile Val Arg Val Phe Leu
145 150 155 160

Pro Asn Lys Gln Arg Thr Val Val Pro Ala Arg Cys Gly Val Thr Val
165 170 175

Arg Asp Ser Leu Lys Lys Ala Leu Met Met Arg Gly Leu Ile Pro Glu
180 185 190

Cys Cys Ala Val Tyr Arg Ile Gln Asp Gly Glu Lys Lys Pro Ile Gly
195 200 205

Trp Asp Thr Asp Ile Ser Trp Leu Thr Gly Glu Glu Leu His Val Glu
210 215 220

Val Leu Glu Asn Val Pro Leu Thr Thr His Asn Phe Val Arg Lys Thr
225 230 235 240

Phe Phe Thr Leu Ala Phe Cys Asp Phe Cys Arg Lys Leu Leu Phe Gln
245 250 255

Gly Phe Arg Cys Gln Thr Cys Gly Tyr Lys Phe His Gln Arg Cys Ser
260 265 270

Thr Glu Val Pro Leu Met Cys Val Asn Tyr Asp Gln Leu Asp Leu Leu
275 280 285

Phe Val Ser Lys Phe Phe Glu His His Pro Ile Pro Gln Glu Glu Ala

-continued

```
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Asp Leu Ser Ser His His Arg His Lys Asn Phe Arg
705                 710                 715                 720
```

Trp Leu Gln Val Tyr Met
725

<210> SEQ ID NO 80
<211> LENGTH: 2331
<212> TYPE: DNA
<213> ORGANISM: Bos taurus

<400> SEQUENCE: 80
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttcccccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac taccccttcca tgtggctcat 1140 cccccttctgc accccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040

```
ttttgtggat ggcaccagaa gtaatcagaa tgcaagataa aaacccatat agctttcagt   2100

cagatgtata tgcatttggg attgttctgt atgaattgat gaccggacag ttaccttatt   2160

caaatatcaa caacagggac caggtgcttt gtcctccatg ggagtgtaat aaatgctgtg   2220

caagggctta cttcccatga gagaagtgag tgaccaacag aaggataatt tttatggtgg   2280

gacgaggata tctgtctcca gatctcagta aggtacggag taactgtcca a            2331


<210> SEQ ID NO 81
<211> LENGTH: 681
<212> TYPE: PRT
<213> ORGANISM: Bos taurus

<400> SEQUENCE: 81

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320
```

```
Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Val Leu Cys Pro Pro Trp Glu Cys Asn
            660                 665                 670

Lys Cys Cys Ala Arg Ala Tyr Phe Pro
        675                 680
```

<210> SEQ ID NO 82
<211> LENGTH: 2319
<212> TYPE: DNA
<213> ORGANISM: Bos taurus

<400> SEQUENCE: 82

```
ctcagctgcg ccgggtctca caagacggtt cccgaggtgg cccaggcgcc gtcccaccgc      60
```

```
cgacgccgcc cgggccgccc gggccgtccc tccccgctgc cccccgtcct ccgcctccgc    120
ctccccccgc cctcagcctc ccttcccccct ccccgcccag cagcggtcgc tcgggcccgg    180
ctctcggtta taagatggcg gcgctgagtg gcggcggcgg cggcggcggc ggtggcgcgg    240
agcagggcca ggctctgttc aacggggaca tggagcccga ggccggcgcc gcggcctctt    300
cggctgcgga ccccgccatt cccgaggagg tgtggaatat caaacaaatg attaagttga    360
cacaggagca tatagaggcc ctattggaca aatttggtgg ggagcataat ccaccatcaa    420
tatatctgga ggcctatgaa gaatacacca gcaagctaga tgccctccaa caaagagaac    480
aacagttatt ggaatccctg gggaatggaa ctgatttttc tgtttctagc tctgcatcaa    540
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aactttttc accttagcat tttgtgactt ctgtagaaag ctgcttttcc     960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac taccttcca tgtggctcat    1140
cccctttctgc accccctcc gattctattg ggcccccaat tctcaccagt ccatctcctt   1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacaccccct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac caggtgcttt gtcctccatg ggagtgtaat aaatgctgtg   2220
caagggctta cttcccatga gagaagtgag tgaccaacag aaggtctgtg caaggaaaag   2280
agacaaagcc acggatcaga agcacatggc cataactga                          2319
```

<210> SEQ ID NO 83
<211> LENGTH: 681

<212> TYPE: PRT
<213> ORGANISM: Bos taurus

<400> SEQUENCE: 83

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

-continued

```
Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Val Leu Cys Pro Pro Trp Glu Cys Asn
            660                 665                 670

Lys Cys Cys Ala Arg Ala Tyr Phe Pro
        675                 680
```

<210> SEQ ID NO 84
<211> LENGTH: 2661
<212> TYPE: DNA
<213> ORGANISM: Bos taurus

<400> SEQUENCE: 84

```
tcagctgcgc cgggtctcac aagacggttc ccgaggtggc ccaggcgccg tcccaccgcc      60

gacgccgccc gggccgcccg ggccgtccct ccccgctgcc ccccgtcctc cgcctccgcc     120

tccccccgcc ctcagcctcc cttccccctc cccgcccagc agcggtcgct cgggcccggc     180

tctcggttat aagatggcgg cgctgagtgg cggcggcggc ggcggcggcg gtggcgcgga     240

gcagggccag gctctgttca acggggacat ggagcccgag gccggcgccg cggcctcttc     300

ggctgcggac cccgccattc ccgaggaggt gtggaatatc aaacaaatga ttaagttgac     360

acaggagcat atagaggccc tattggacaa atttggtggg gagcataatc caccatcaat     420

atatctggag gcctatgaag aatacaccag caagctagat gccctccaac aaagagaaca     480
```

```
acagttattg gaatccctgg ggaatggaac tgatttttct gtttctagct ctgcatcaac    540
ggacaccgtt acatcttctt cctcttctag cctttcagtg ctgccttcat ctctttcagt    600
ttttcaaaat cccacagatg tgtcacggag caaccccaag tcaccacaaa aacctatcgt    660
tagagtcttc ctgcccaata aacagaggac agtggtacct gcacggtgtg gagtcacagt    720
ccgggacagc ctgaagaagg cactgatgat gagaggtcta atcccagagt gctgtgctgt    780
ttacagaatt caggatgggg agaagaaacc aattggctgg gacactgata tttcctggct    840
tactggagag gagttgcatg tagaagtgtt ggagaatgtt ccacttacaa cacacaactt    900
tgtacggaaa actttttca ccttagcatt ttgtgacttc tgtagaaagc tgcttttcca    960
gggattccgc tgtcaaacat gtggttataa atttcaccag cgttgtagta cagaggttcc   1020
actgatgtgt gttaattatg accaactaga tttgctgttt gtctccaagt tctttgaaca   1080
ccacccaata ccacaggagg aggcctcctt agcagagact acccttccat gtggctcatc   1140
cccttctgca cccccctccg attctattgg gcccccaatt ctcaccagtc catctccttc   1200
aaaatccatt ccaattccac agcctttccg accagcagat gaagatcatc gaaatcagtt   1260
tggacaacga gaccggtcct catcagctcc aaatgtgcat ataaacacaa tagaacccgt   1320
caatattgat gacttgatta gagaccaagg gtttcgtagt gatggaggat caaccacagg   1380
tttatccgcc acacccccctg cctcattacc tggctcactc tctaatgtga aagcattgca   1440
gaaatctcca ggacctcagc gagaaagaaa gtcctcttca tcctcagaag acaggaatcg   1500
aatgaaaacg cttggtagac gggattcaag tgacgattgg gagattcctg atggacagat   1560
cacagtggga caaagaattg gatcagggtc atttgggaca gtctacaagg gaaagtggca   1620
tggtgatgtg gcagtgaaaa tgttgaatgt gacagcaccc acacctcagc agttacaggc   1680
cttcaaaaat gaagtaggag tactcaggaa aacgcgacat gtgaatatcc tcctcttcat   1740
gggttattca acaaagccac aactggctat tgttacccag tggtgtgagg gctccagttt   1800
atatcatcat ctccacatca ttgagaccaa attcgagatg atcaaactta tagatattgc   1860
acggcagact gcacagggca tggattactt acacgccaag tcaatcatcc acagagacct   1920
caagagtaat aatatttttc ttcatgaaga cctcacagta aaaataggtg attttggtct   1980
agccacagtg aaatctcgat ggagtgggtc ccatcagttt gaacagttgt ctggatccat   2040
tttgtggatg gcaccagaag taatcagaat gcaagataaa aacccatata gctttcagtc   2100
agatgtatat gcatttggga ttgttctgta tgaattgatg accggacagt taccttattc   2160
aaatatcaac aacagggacc agtctgtgca aggaaaagag acaaagccac ggatcagaag   2220
cacatggcca taactgaaga ttttgtgaac tctcacaagg aaaaaatttg ctctttgaac   2280
aataagaagg aactcactaa aatgtaactg agaactgttc aacaggttga aagctgaaag   2340
atgccattgg aactgacaaa atgtttctta aacataaatg atgaaacagt gaaactacat   2400
aatatctcct ctggctgaaa cattcaagaa gtttaaaatg cttaagttaa aaataaaatc   2460
ctagtaaaca atggacttac tgtgcaacat agagaatatc ttacgataac ctgtaatgga   2520
aaagaatctg aaaaagaatg tatataactg aatcactttg ctgtaaacta gaatctgaca   2580
caacactgta aatcactaca cttttctgtt gcatgccaaa gattatttaa taacgtcatt   2640
aaaaaattat tttaataatt a                                             2661
```

<210> SEQ ID NO 85
<211> LENGTH: 679
<212> TYPE: PRT
<213> ORGANISM: Bos taurus

<400> SEQUENCE: 85

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln

-continued

```
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ser Val Gln Gly Lys Glu Thr Lys Pro
            660                 665                 670

Arg Ile Arg Ser Thr Trp Pro
        675


<210> SEQ ID NO 86
<211> LENGTH: 7434
<212> TYPE: DNA
<213> ORGANISM: Bos taurus

<400> SEQUENCE: 86

acaccgttac atcttcttcc tcttctagcc tttcagtgct gccttcatct ctttcagttt      60

ttcaaaatcc cacagatgtg tcacggagca accccaagtc accacaaaaa cctatcgtta     120

gagtcttcct gcccaataaa cagaggacag tggtacctgc acggtgtgga gtcacagtcc     180

gggacagcct gaagaaggca ctgatgatga gaggtctaat cccagagtgc tgtgctgttt     240

acagaattca ggatggggag aagaaaccaa ttggctggga cactgatatt tcctggctta     300

ctggagagga gttgcatgta gaagtgttgg agaatgttcc acttacaaca cacaactttg     360

tacggaaaac ttttttcacc ttagcatttt gtgacttctg tagaaagctg cttttccagg     420

gattccgctg tcaaacatgt ggttataaat ttcaccagcg ttgtagtaca gaggttccac     480

tgatgtgtgt taattatgac caactagatt tgctgtttgt ctccaagttc tttgaacacc     540
```

-continued

```
acccaatacc acaggaggag gcctccttag cagagactac ccttccatgt ggctcatccc    600
cttctgcacc cccctccgat tctattgggc ccccaattct caccagtcca tctccttcaa    660
aatccattcc aattccacag cctttccgac cagcagatga agatcatcga aatcagtttg    720
gacaacgaga ccggtcctca tcagctccaa atgtgcatat aaacacaata gaacccgtca    780
atattgatga cttgattaga gaccaagggt ttcgtagtga tggaggatca accacaggtt    840
tatccgccac accccctgcc tcattacctg gctcactctc taatgtgaaa gcattgcaga    900
aatctccagg acctcagcga gaaagaaagt cctcttcatc ctcagaagac aggaatcgaa    960
tgaaaacgct tggtagacgg gattcaagtg acgattggga gattcctgat ggacagatca   1020
cagtgggaca aagaattgga tcagggtcat ttgggacagt ctacaaggga aagtggcatg   1080
gtgatgtggc agtgaaaatg ttgaatgtga cagcacccac acctcagcag ttacaggcct   1140
tcaaaaatga agtaggagta ctcaggaaaa cgcgacatgt gaatatcctc ctcttcatgg   1200
gttattcaac aaagccacaa ctggctattg ttacccagtg gtgtgagggc tccagtttat   1260
atcatcatct ccacatcatt gagaccaaat tcgagatgat caaacttata gatattgcac   1320
ggcagactgc acagggcatg gattacttac acgccaagtc aatcatccac agagacctca   1380
agagtaataa tatttttctt catgaagacc tcacagtaaa aataggtgat tttggtctag   1440
ccacagtgaa atctcgatgg agtgggtccc atcagtttga acagttgtct ggatccattt   1500
tgtggatggc accagaagta atcagaatgc aagataaaaa cccatatagc tttcagtcag   1560
atgtatatgc atttgggatt gttctgtatg aattgatgac cggacagtta ccttattcaa   1620
atatcaacaa cagggaccag ataattttta tggtgggacg aggatatctg tctccagatc   1680
tcagtaaggt acggagtaac tgtccaaaag ccatgaagag attaatggca gagtgcctaa   1740
aaaagaaaag agatgaaaga ccactctttc cccaagtagg aaagactctc ctaagcaaga   1800
gacaaaattc agaagttatc agggaaaaag ataagcagat tctcgcctct attgagctgc   1860
tggcccgctc attgccaaaa attcaccgca gtgcatcaga accctccttg aatcgggctg   1920
gcttccaaac agaggatttt agtctatatg cttgtgcttc tccaaaaaca cccattcagg   1980
cagggggata tggagaattt gcagccttca agtagccaca ccatcatgac agcatctact   2040
cttatttctt aagtcttgtg ttcgtacaat ttgttaacat caaaacacag ttctgttcct   2100
caactctttt taaagttaaa atttttcagt gcataagctg gtgtggaaca gaaggaaatt   2160
tcccatccaa caaaagaggg aagaatgttt taggaaccag aattctctgc tgccagtgtt   2220
tcttcttcaa cacaaatatc acaagtctgc ccactcccag gaagaaagag gagagaccct   2280
gagttctgac cttttgatgg tcaggcatga tggaaagaaa ctgctgctac agcttgggag   2340
atttgctctg ggaagtctgc cagtcaactt tgcccttcta accaccagat caatatgtgg   2400
ctgatcatct gatggggcag ttgcaatcac caagccttgt tctctttcct gttctgggat   2460
tgtgttgtgg aaccctttc cctagccacc accagttcat ttctgaggga tggaacaaaa   2520
atgcagcatg cccttcctgt gtggtgcatg ttcagtcctt gacaaatttt taccaaaatg   2580
aagctacttt atttaaaagg agggtgagag gtgaggaggt cactttgggt gtggcggaaa   2640
gggaatgctg catctttttc ctgggctgct ggggctctgg ccttggcttg ccagccggaa   2700
gcgctggcac gcatcgcctt cttttcccat tgggtccagc aatgaagacg agtgtttggg   2760
gtttttttt tctccaccat gtagcaagtt ctcaggaaaa tacaattgat atcttcctcc   2820
taagctcttc caatcagtca ccaagtactt atgtggttac tttgtccagg gcacaaaatg   2880
cctgtatcta attaaaagcc tacaaaactg cttgataaca gttttgaatg tgagacattt   2940
```

```
atgtaattta aatgtaaggt acaagtttta atttctgagt ttcttctatt atatttttat   3000
taaaaaaaga aaataatttt cagattgaat tggagtaaaa taatattact tcccactaga   3060
attatatatc ctggaaaatt gtatttttgt tacataagca gcttttaaag aaagatcatt   3120
acccttttct ctacataaat atatggggag tcttagccta atgacaaata tttataattt   3180
ttaaattaat ggtacttgct ggatccatac taacatcttt actaatacct cattgtttct   3240
tccaacttac tcctacacta catcctacat cttcttccta gtcttttatc tagaatatgc   3300
aacctcaaat aaaaatggtg gtgtcctcat tcattctcct ccttcctttt ttcccaagcc   3360
tgatcttcaa aggttggtt aatttggcag ctgagttcct ccccaggcag agaatagacc   3420
aattttaggt gtattgggac tgagggagga tgtgtaaaga ttaacatcag taaagaaccg   3480
ctgtggagta attaagaact ttgttcttta taactggaga atataaccta accctaacat   3540
ccctcagcct ttactaaagt gtggcgtaaa tcacagtagt agcaaagaaa gtgactctgg   3600
atgtgttcct ggccagtacc tcccttatca tgaatgtaga ctctctcatc aagatttagg   3660
aatataaatc aaatcaaatg tgcccagcca agctatgtag taagggactt gaacaatatt   3720
aggcagaacc tataaaataa atcagggaat tagaaattat ttaaagtttt caaattgtaa   3780
attgccccgg tgtctttcag cctactgcca ttatttttgc tacaatacct acatttcaga   3840
ggagggccta ctgaaaattc catgcaagtg gaaaataatc ctcaagttat taatgagttt   3900
gaaaagcaat gagttcttaa gtctttgtga gtagagcaag atcctacaaa attcagaaat   3960
agtaaaaatg gattcatgct gatttgaaga gcatctgtgt gcataatata atgctgcatc   4020
tcttttaaaa gcagtctatt tttcttttta aatttgtccc catagatgct tttgaacatg   4080
aacatgctta tgttaccttt tccgaggttg ggaagagcca ggagctctca ggcagggccc   4140
cctccctcag ctgggcagga gctgctcagg aggagctagt tatagaggaa gcttagcgtt   4200
ggcattttca aaattcaagg tgataacgct ttcttcttcc tttctgtttt agaatagatt   4260
gctgtctgat ttgaaaaagg gaaatagatt tgatctcaaa tgaatctgtg cccagaagcc   4320
aggctcaggg tattcagaga tttgtatagt gccctcaaaa aataacaaaa ttttagcttt   4380
cctttttcct tcttttctcc atcaaattct tttttctcta gtttacaaat gacatggaaa   4440
aggaatttcc cctgagtttt gtatgccttt tttttttgg cttagactat agataggcgt   4500
gttgagctcc taagaaaata caaggaggaa ctctttgttg tgcagagcac tttatgagta   4560
gtttgtgtgg ataatatgtg actgcttccc tgacgagctt gtgaggctgt acttatgtct   4620
ttcctgtaag gcagcttcag tgccttctgt agtgtatata aggaaagatt acgccttctg   4680
aaaaatctca gagcaaccat aagattattt taaaatatgt agtatgactg atggactttt   4740
tcatcattaa attagtctag catctaaact tttaccactg aaataatatt gaccaaaaag   4800
caatttataa aaggtatttg tgaatagaaa atacaatgtg atcatttgta cttatgtgca   4860
ccttaaaaga ggaattctgt ctagctgtca aattctggtt ccttaacatc cagtccttga   4920
ttgtgattga gatctggtag gacgtgctgg ggcacgctag cagataaaat cccgtatact   4980
ttaggataga tgttacattt atgtcagtgt tggcaaagag cattgtgtag taataaagaa   5040
ttcaagactt cagcaatgtc aacctgaaac tttgtaaata tttcctagat tgttatttga   5100
tgcagtcaca gctctttatc acacaatgtt gtctttccct catcaggcaa ttttagaact   5160
gctgcacacc cctcctcaga tctcacctgc ccctcctgta cattcacctc tccagccttg   5220
tgcacacctc atttagcttt agtttgaaac acattgcagg gttcaggtga cctcttcaaa   5280
```

```
aactacctcc tcagaatgag gtaatgaata gttatttatt ttaaaatatg aaaagtcagg   5340
agctctagaa tatgaagatg atctaagatt ttaactttta tgtatacttg ttgagcactc   5400
tccttttgtc ctaaagggca ttatacattt aagcagtaat actgaaaaat gtagctcaga   5460
gtaactgaat gttgttgaaa gtggtgccag aatctgtttt aggggtacgt atcagaatct   5520
taatcttaaa tcggttacat gaaattaaat agttaatggt aacacttgac taacagatat   5580
aattttaatt ttcggtaggc ttttagcaag acagtaagta catcttcata atgagttagc   5640
cacagcttca tcacatgcac agattttcct gttgagagac tgcccagtta agagggtaga   5700
atgatgaacc atttttcagg attctcttct ttgtccaaac tggcattgtg agtgctagaa   5760
tatcagcact ttcaaactag tgattccaac tattaggcta ttaaaaagca aaacaaacca   5820
aacaaaccat agccagacat gggaagttta ctatgagtat aaacagcaaa tagcttacag   5880
gtcatacatt gaaatggtgt aggtaaggcg ttagaaaaat accttgacaa tttgccaaat   5940
gatcttactg tgccttcatg atgcaataaa aaaaaaaaaa atttagcata aatcagtgat   6000
ttgtgaagag agcagccacc ctggtctaac tcagctgtgt taatattttt tagcgtgcaa   6060
tttagactgc aaagataaat gcactaaaga gtttatagcc aaaatcacat ttaaaaaatg   6120
agagaaaaca caggtaaatt ttcagtgaac aaaattattt ttttaaagta cataatccct   6180
agtatagtca gatatattta tcacatagag caaataggtt gaaatcacaa ttcagtgaca   6240
tttctagaga aactttttct actcccatag gttcttcaaa gcatggaact tttatataac   6300
agaaatgtgt gacggtcatt ttaaattgct gtagtttggg gctgaagtac tgtgtgctgg   6360
gcagcaatca catgtattaa ctagtgagaa aggagaaatt aagatatagg acagaatttg   6420
attttcttgt tcccagatta ctgctgccaa cctagacact gagtttccag aggctgaaac   6480
gtaaacttgc agctcagcaa ctgttttgca aagttagtgg gactgtcctg cttatgctgt   6540
tcaaaaatgc tctgagggcc aggtggggcc tccaggggct cctctctgag gggacatcag   6600
actagctaac gacctggcgg gcggatgtga accggacaca ctccatggtg tgcttcttgt   6660
atcggtccct cgccaccctc aagaaaggct tcagcgggtt ctctagacgt ctccactaag   6720
gtgtgttact aacagccatg ggttgttgag cacccgagga gtgcaatagc atctctgcat   6780
gattgtatat tggcccgaag agaatgaagt ggccagtgta ctcatgttcc atgttgctag   6840
ctctggtaaa ctgaaaatac tggtaagatt tttgttttat cagtacacta gagagtaagc   6900
tttgttttgt tgtttttaga taatgttttc acttccattt ggaaagacat ttaaattgag   6960
tttcagtcct aaattttgcc agtcatggta attagcagtt tctatcaggt atttttaagg   7020
tagaagagga tagaaacata agttctaaaa gcttaaggta accgtggttt attttaaaat   7080
gtttaggggt ggttagtctc tacctcaaaa aaagtgagtg aatcttttat ttcagcattc   7140
acaagttcgg ctgttgtttt tgtaatacat ttttttttta accttttgac ccccctttac   7200
ctaagtgtca atgtagtttt attaattact aagtcagttt cattaaaatg tttatttagc   7260
agttttgact aattgcaatg attaatatag ccagttgtgc atgaggacac agccagtgag   7320
tatatctggg tttttttgt gatgcttttt ttcttaagac ttctgtagat tttatgaagta   7380
ctcattgaaa acaactaaaa tacgtttatt cgtgttaata tggaaaaaaa aaaa         7434
```

<210> SEQ ID NO 87
<211> LENGTH: 603
<212> TYPE: PRT
<213> ORGANISM: Bos taurus

<400> SEQUENCE: 87

-continued

```
Met Met Arg Gly Leu Ile Pro Glu Cys Cys Ala Val Tyr Arg Ile Gln
1               5                   10                  15

Asp Gly Glu Lys Lys Pro Ile Gly Trp Asp Thr Asp Ile Ser Trp Leu
            20                  25                  30

Thr Gly Glu Glu Leu His Val Glu Val Leu Glu Asn Val Pro Leu Thr
        35                  40                  45

Thr His Asn Phe Val Arg Lys Thr Phe Phe Thr Leu Ala Phe Cys Asp
    50                  55                  60

Phe Cys Arg Lys Leu Leu Phe Gln Gly Phe Arg Cys Gln Thr Cys Gly
65                  70                  75                  80

Tyr Lys Phe His Gln Arg Cys Ser Thr Glu Val Pro Leu Met Cys Val
                85                  90                  95

Asn Tyr Asp Gln Leu Asp Leu Leu Phe Val Ser Lys Phe Phe Glu His
            100                 105                 110

His Pro Ile Pro Gln Glu Glu Ala Ser Leu Ala Glu Thr Thr Leu Pro
        115                 120                 125

Cys Gly Ser Ser Pro Ser Ala Pro Pro Ser Asp Ser Ile Gly Pro Pro
    130                 135                 140

Ile Leu Thr Ser Pro Ser Pro Ser Lys Ser Ile Pro Ile Pro Gln Pro
145                 150                 155                 160

Phe Arg Pro Ala Asp Glu Asp His Arg Asn Gln Phe Gly Gln Arg Asp
                165                 170                 175

Arg Ser Ser Ser Ala Pro Asn Val His Ile Asn Thr Ile Glu Pro Val
            180                 185                 190

Asn Ile Asp Asp Leu Ile Arg Asp Gln Gly Phe Arg Ser Asp Gly Gly
        195                 200                 205

Ser Thr Thr Gly Leu Ser Ala Thr Pro Pro Ala Ser Leu Pro Gly Ser
    210                 215                 220

Leu Ser Asn Val Lys Ala Leu Gln Lys Ser Pro Gly Pro Gln Arg Glu
225                 230                 235                 240

Arg Lys Ser Ser Ser Ser Ser Glu Asp Arg Asn Arg Met Lys Thr Leu
                245                 250                 255

Gly Arg Arg Asp Ser Ser Asp Asp Trp Glu Ile Pro Asp Gly Gln Ile
            260                 265                 270

Thr Val Gly Gln Arg Ile Gly Ser Gly Ser Phe Gly Thr Val Tyr Lys
        275                 280                 285

Gly Lys Trp His Gly Asp Val Ala Val Lys Met Leu Asn Val Thr Ala
    290                 295                 300

Pro Thr Pro Gln Gln Leu Gln Ala Phe Lys Asn Glu Val Gly Val Leu
305                 310                 315                 320

Arg Lys Thr Arg His Val Asn Ile Leu Leu Phe Met Gly Tyr Ser Thr
                325                 330                 335

Lys Pro Gln Leu Ala Ile Val Thr Gln Trp Cys Glu Gly Ser Ser Leu
            340                 345                 350

Tyr His His Leu His Ile Ile Glu Thr Lys Phe Glu Met Ile Lys Leu
        355                 360                 365

Ile Asp Ile Ala Arg Gln Thr Ala Gln Gly Met Asp Tyr Leu His Ala
    370                 375                 380

Lys Ser Ile Ile His Arg Asp Leu Lys Ser Asn Asn Ile Phe Leu His
385                 390                 395                 400

Glu Asp Leu Thr Val Lys Ile Gly Asp Phe Gly Leu Ala Thr Val Lys
                405                 410                 415
```

-continued

```
Ser Arg Trp Ser Gly Ser His Gln Phe Glu Gln Leu Ser Gly Ser Ile
            420                 425                 430

Leu Trp Met Ala Pro Glu Val Ile Arg Met Gln Asp Lys Asn Pro Tyr
        435                 440                 445

Ser Phe Gln Ser Asp Val Tyr Ala Phe Gly Ile Val Leu Tyr Glu Leu
    450                 455                 460

Met Thr Gly Gln Leu Pro Tyr Ser Asn Ile Asn Asn Arg Asp Gln Ile
465                 470                 475                 480

Ile Phe Met Val Gly Arg Gly Tyr Leu Ser Pro Asp Leu Ser Lys Val
                485                 490                 495

Arg Ser Asn Cys Pro Lys Ala Met Lys Arg Leu Met Ala Glu Cys Leu
            500                 505                 510

Lys Lys Lys Arg Asp Glu Arg Pro Leu Phe Pro Gln Val Gly Lys Thr
        515                 520                 525

Leu Leu Ser Lys Arg Gln Asn Ser Glu Val Ile Arg Glu Lys Asp Lys
    530                 535                 540

Gln Ile Leu Ala Ser Ile Glu Leu Leu Ala Arg Ser Leu Pro Lys Ile
545                 550                 555                 560

His Arg Ser Ala Ser Glu Pro Ser Leu Asn Arg Ala Gly Phe Gln Thr
                565                 570                 575

Glu Asp Phe Ser Leu Tyr Ala Cys Ala Ser Pro Lys Thr Pro Ile Gln
            580                 585                 590

Ala Gly Gly Tyr Gly Glu Phe Ala Ala Phe Lys
        595                 600
```

```
<210> SEQ ID NO 88
<211> LENGTH: 2295
<212> TYPE: DNA
<213> ORGANISM: Equus caballus
<220> FEATURE:
<221> NAME/KEY: misc_feature
<222> LOCATION: (79)..(79)
<223> OTHER INFORMATION: n is a, c, g, or t

<400> SEQUENCE: 88

atgaagacgc tgagcggcgg cggcggcggc gcggagcagg gccaggctct gttcaacggg     60

gacatggaac ccggaggcnc cgcgccggcg cccgcggcct cgtcggccgc ggaccctgcc    120

attcccgagg aggtatggaa tatcaaacaa atgattaaat tgacacagga acatatagag    180

gccctattgg acaaatttgg tggggagcat aatccaccat caatatatct ggaggcctat    240

gaagaataca ccagcaagct agatgccctc caacaaagag aacaacagtt attggaatcc    300

ctggggaatg gaactgattt ttctgtttct agttctgcat caacggacac cgttacatct    360

tcttcctctt ctagcctttc agtgctacct tcatctcttt cagtttttca aaatcccaca    420

gatgtgtcac ggagcaaccc taagtcacca caaaaaccta tcgttagagt cttcctgccc    480

aacaaacaga ggacagtggt acctgcaagg tgtggcgtta cagtccggga cagtctaaag    540

aaagcactga tgatgagagg tctaatccca gagtgctgtg ctgtttacag aattcaggat    600

ggagagaaga aaccaattgg ctgggacact gatatttcct ggctcactgg agaggaattg    660

catgtagaag tgttggagaa tgttccactt acaacacaca actttgtacg gaaaactttt    720

ttcaccttag cattttgtga cttttgtcga aagctgcttt tccagggttt ccgctgtcaa    780

acatgtggtt ataaatttca ccagcgttgt agtacagagg ttccactgat gtgtgttaat    840

tatgaccaac ttgatttgct gtttgtctcc aagttctttg aacaccaccc agtatcacag    900

gaggaggcct ccttagcaga gactgccctt acatctggat catccccttc tgcacccccc    960
```

```
tccgattcca ttgggcccca aattctcacc agtccatctc cttcaaaatc cattccaatt   1020

ccacagcctt tccgaccagc agatgaagat catcgaaatc agtttggaca acgagaccgg   1080

tcctcatcag ctccaaatgt acatataaac acaatagaac ctgtcaatat tgatgacttg   1140

attagagacc aagggtttcg tagtgatgga ggatcaacca caggtttatc tgccaccccc   1200

cctgcctcat tacctggctc actcactaat gtgaaggcat tacagaaatc tccaggacct   1260

caacgggaaa ggaaatcatc ttcatcctca gaagacagga atcgaatgaa aactcttggt   1320

agacgggatt caagtgacga ttgggagatt cctgatgggc agatcacagt gggacaaaga   1380

attggatctg ggtcatttgg gacagtctac aagggaaagt ggcatggtga tgtggcagtg   1440

aaaatgttga atgtgacagc acccacacct cagcagttac aggccttcaa aaatgaagta   1500

ggagtactca ggaaaactcg acatgtgaat atcctactct tcatgggcta ttcaacaaag   1560

ccacaactgg ctattgttac ccagtggtgt gagggctcca gcttatatca ccatctccac   1620

atcattgaga ccaaatttga gatgatcaaa cttatagata ttgctcggca aactgcacag   1680

ggcatggatt acttacacgc caagtcaatc atccacagag acctcaagag taataatatt   1740

tttcttcatg aagacctcac agtaaaaata ggtgattttg gtctagccac agtgaaatct   1800

cgatggagtg ggtcccatca gtttgaacag ttgtctggat ccatttttgtg gatggcacca   1860

gaagtaatca gaatgcaaga taaaaacccg tatagctttc aatcagatgt atatgccttt   1920

gggattgttc tgtatgaatt gatgactgga cagttacctt attcaaacat caacaacagg   1980

gaccagataa tttttatggt gggaagagga tatctatctc cagatctcag taaggtacgg   2040

agtaactgtc caaaagccat gaagagatta atggcagagt gcctaaaaaa gaaaagagac   2100

gagagaccac tcttccccca aattctcgcc tctattgagc tgctggcccg ctcattgcca   2160

aaaattcacc gcagtgcatc agagccctcc ttgaatcggg ctggcttcca gacagaggat   2220

tttagtctat atgcttgtgc ttctccgaaa acacccatcc aggcaggggg atatggtgcg   2280

tttcctgtcc actga                                                    2295
```

```
<210> SEQ ID NO 89
<211> LENGTH: 764
<212> TYPE: PRT
<213> ORGANISM: Equus caballus
<220> FEATURE:
<221> NAME/KEY: misc_feature
<222> LOCATION: (27)..(27)
<223> OTHER INFORMATION: Xaa can be any naturally occurring amino acid

<400> SEQUENCE: 89

Met Lys Thr Leu Ser Gly Gly Gly Gly Gly Ala Glu Gln Gly Gln Ala
1               5                   10                  15

Leu Phe Asn Gly Asp Met Glu Pro Gly Gly Xaa Ala Pro Ala Pro Ala
            20                  25                  30

Ala Ser Ser Ala Ala Asp Pro Ala Ile Pro Glu Glu Val Trp Asn Ile
        35                  40                  45

Lys Gln Met Ile Lys Leu Thr Gln Glu His Ile Glu Ala Leu Leu Asp
    50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110
```

```
Ala Ser Thr Asp Thr Val Thr Ser Ser Ser Ser Ser Ser Leu Ser Val
        115                 120                 125

Leu Pro Ser Ser Leu Ser Val Phe Gln Asn Pro Thr Asp Val Ser Arg
    130                 135                 140

Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
        195                 200                 205

Asp Thr Asp Ile Ser Trp Leu Thr Gly Glu Glu Leu His Val Glu Val
    210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
            260                 265                 270

Glu Val Pro Leu Met Cys Val Asn Tyr Asp Gln Leu Asp Leu Leu Phe
        275                 280                 285

Val Ser Lys Phe Phe Glu His His Pro Val Ser Gln Glu Glu Ala Ser
    290                 295                 300

Leu Ala Glu Thr Ala Leu Thr Ser Gly Ser Ser Pro Ser Ala Pro Pro
305                 310                 315                 320

Ser Asp Ser Ile Gly Pro Gln Ile Leu Thr Ser Pro Ser Pro Ser Lys
                325                 330                 335

Ser Ile Pro Ile Pro Gln Pro Phe Arg Pro Ala Asp Glu Asp His Arg
            340                 345                 350

Asn Gln Phe Gly Gln Arg Asp Arg Ser Ser Ser Ala Pro Asn Val His
        355                 360                 365

Ile Asn Thr Ile Glu Pro Val Asn Ile Asp Asp Leu Ile Arg Asp Gln
    370                 375                 380

Gly Phe Arg Ser Asp Gly Gly Ser Thr Thr Gly Leu Ser Ala Thr Pro
385                 390                 395                 400

Pro Ala Ser Leu Pro Gly Ser Leu Thr Asn Val Lys Ala Leu Gln Lys
                405                 410                 415

Ser Pro Gly Pro Gln Arg Glu Arg Lys Ser Ser Ser Ser Ser Glu Asp
            420                 425                 430

Arg Asn Arg Met Lys Thr Leu Gly Arg Arg Asp Ser Ser Asp Asp Trp
        435                 440                 445

Glu Ile Pro Asp Gly Gln Ile Thr Val Gly Gln Arg Ile Gly Ser Gly
    450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
                485                 490                 495

Lys Asn Glu Val Gly Val Leu Arg Lys Thr Arg His Val Asn Ile Leu
            500                 505                 510

Leu Phe Met Gly Tyr Ser Thr Lys Pro Gln Leu Ala Ile Val Thr Gln
        515                 520                 525
```

-continued

```
Trp Cys Glu Gly Ser Ser Leu Tyr His His Leu His Ile Ile Glu Thr
    530                 535                 540

Lys Phe Glu Met Ile Lys Leu Ile Asp Ile Ala Arg Gln Thr Ala Gln
545                 550                 555                 560

Gly Met Asp Tyr Leu His Ala Lys Ser Ile Ile His Arg Asp Leu Lys
                565                 570                 575

Ser Asn Asn Ile Phe Leu His Glu Asp Leu Thr Val Lys Ile Gly Asp
            580                 585                 590

Phe Gly Leu Ala Thr Val Lys Ser Arg Trp Ser Gly Ser His Gln Phe
        595                 600                 605

Glu Gln Leu Ser Gly Ser Ile Leu Trp Met Ala Pro Glu Val Ile Arg
    610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685

Arg Leu Met Ala Glu Cys Leu Lys Lys Lys Arg Asp Glu Arg Pro Leu
    690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Ala Phe Pro Val His
        755                 760
```

<210> SEQ ID NO 90
<211> LENGTH: 2678
<212> TYPE: DNA
<213> ORGANISM: Gallus gallus

<400> SEQUENCE: 90

```
tccccctccc tcgccccagc gcttcgatcc aagatggcgg cgctgagcag cggcagcagc     60

gccgaggggg cctcgctctt caacggggac atggagcccg agccgccgcc gcccgtgctg    120

ggcgcctgct acgccgggag cggcggcggc gacccggcca tcccggagga ggtgtggaat    180

atcaaacaga tgattaaatt aacacaagaa catatagaag cgctgttaga caagtttgga    240

ggagagcata acccaccatc aatatattta gaggcctatg aggagtacac cagcaaacta    300

gatgctctac agcagagaga acagcagtta ttggaatcca tgggaaatgg aactgatttc    360

tctgtttcca gttcagcttc aacggacaca gttgcatcat cttcctcctc tagcctctct    420

gtagcacctt catccctttc agtttatcaa aatcctactg atatgtcgcg gaataaccct    480

aagtctccac agaagcctat tgttagagtc ttcctgccca acaagcaaag gactgtggtt    540

ccggcaagat gtggggtgac agtccgagac agcctgaaga aagctctgat gatgagaggt    600

cttattccag aatgctgtgc tgtttacaga atacaggatg gagagaagaa gccaattggc    660

tgggacactg acatttcctg gctaaccgga gaggagttac acgtggaggt cttggagaat    720

gtgccactca caacacacaa ttttgtacga aaaacattct tcacgttagc gttctgcgac    780
```

-continued

```
ttctgtcgaa agctgctttt ccagggattc cgatgccaga catgtggcta caaatttcac    840

cagcgctgta gcacagaagt gccactgatg tgtgttaact acgaccaact cgatttgctg    900

tttgtctcca agttctttga acatcacccc atatcgcagg aggagaccac cttaggagag    960

accaccccgg catcgggatc gtacccctca gtgcccccat cagattctgt tggaccacca   1020

attctcccta gtccttctcc ttcaaaatcc attccaatcc cacagccctt ccgaccagca   1080

gatgaagacc atcggaatca gtttgggcaa cgcgaccgat cctcttcagc tcccaatgtt   1140

cacatcaata caattgagcc agtcaatatt gatgacttga ttagagacca gggtgtacga   1200

ggagagggag ccccttttgaa ccagctgatg cgctgtcttc ggaaatacca atcccggact   1260

cccagtcccc tccttcattc tgtccccagt gaaatagtgt ttgattttga gcctggccca   1320

gtgttcagag gttcaactgc aggtttgtct gcaacacctc ctgcatcttt gcctgggtca   1380

cttaccaatg tgaaagcatt acagaaatca ccaggccccc aacgggaaag gaaatcatcc   1440

tcatcctcag aagacagaaa taggatgaaa acccttggtc gacgagattc aagtgatgat   1500

tgggaaatac cagatgggca gatcacagtt ggacaaagga taggatctgg atcatttgga   1560

acagtctaca aaggaaagtg gcatggtgac gtggcagtga aaatgttgaa tgttacagca   1620

cccacacctc aacagttaca ggctttcaaa aatgaagtag gagtgctcag gaaaacacgg   1680

catgtgaata tcctactttt tatgggttat tcaacaaaac ctcagttggc tattgttaca   1740

cagtggtgtg aggggtccag cttatatcac catctgcaca taattgagac caagtttgaa   1800

atgatcaaac taattgatat tgcacgacag actgcacaag gcatggatta tttgcatgcc   1860

aagtcaatca tccacagaga cctcaagagt aataatattt ttcttcatga agacctcaca   1920

gtaaaaatag gtgacttcgg tctggctaca gtgaaatcac gatggagtgg atctcatcaa   1980

tttgaacagt tatctggatc aattctatgg atggcaccgg aagtgatcag gatgcaagac   2040

aaaaacccat atagctttca gtcagatgtg tatgcattcg ggattgtgct ttatgaactg   2100

atgactggac agttaccata ctcaaacatc aacaacaggg accagataat ttttatggtg   2160

ggacgaggat atctatctcc agacctcagt aaagtaagaa gtaactgtcc aaaagctatg   2220

aagagactaa tggcagaatg cttgaaaaag aaaagagatg agagacctct tttccacag    2280

attcttgcct ccattgagct tctggcccgg tcgttgccaa aaattcaccg cagtgcatct   2340

gagccgtcac taaaccgggc tggcttccag accgaggatt tcagtctgta tgcttgtgct   2400

tctccaaaaa cgcccatcca agcaggggga tacggtgggt ttccagtaca ctgaaaagaa   2460

atgtgaaagc gtgtgcctgt ttgctcatgt gctggtgtgt tcctgtgtgt gcaacgcata   2520

cgtacgttct cagttcctac cagcgacttt ttaaggttta ctgagggaat gaagactcat   2580

ttcctaacat ggggcattga acgtcctgag cacaagtcag tgctggtaag gaatgtcttg   2640

ggaacagctg gcaagaagaa ttagaaggta cttaaagg                           2678
```

<210> SEQ ID NO 91
<211> LENGTH: 806
<212> TYPE: PRT
<213> ORGANISM: Gallus gallus

<400> SEQUENCE: 91

```
Met Ala Ala Leu Ser Ser Gly Ser Ser Ala Glu Gly Ala Ser Leu Phe
1               5                   10                  15

Asn Gly Asp Met Glu Pro Glu Pro Pro Pro Pro Val Leu Gly Ala Cys
            20                  25                  30

Tyr Ala Gly Ser Gly Gly Gly Asp Pro Ala Ile Pro Glu Glu Val Trp
```

-continued

```
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Met Gly Asn Gly Thr Asp Phe Ser Val Ser
            100                 105                 110

Ser Ser Ala Ser Thr Asp Thr Val Ala Ser Ser Ser Ser Ser Ser Leu
        115                 120                 125

Ser Val Ala Pro Ser Ser Leu Ser Val Tyr Gln Asn Pro Thr Asp Met
    130                 135                 140

Ser Arg Asn Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Ser Gln Glu Glu
    290                 295                 300

Thr Thr Leu Gly Glu Thr Thr Pro Ala Ser Gly Ser Tyr Pro Ser Val
305                 310                 315                 320

Pro Pro Ser Asp Ser Val Gly Pro Pro Ile Leu Pro Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Val Arg Gly Glu Gly Ala Pro Leu Asn Gln Leu Met Arg
385                 390                 395                 400

Cys Leu Arg Lys Tyr Gln Ser Arg Thr Pro Ser Pro Leu Leu His Ser
                405                 410                 415

Val Pro Ser Glu Ile Val Phe Asp Phe Glu Pro Gly Pro Val Phe Arg
            420                 425                 430

Gly Ser Thr Ala Gly Leu Ser Ala Thr Pro Pro Ala Ser Leu Pro Gly
        435                 440                 445

Ser Leu Thr Asn Val Lys Ala Leu Gln Lys Ser Pro Gly Pro Gln Arg
    450                 455                 460
```

-continued

```
Glu Arg Lys Ser Ser Ser Ser Ser Glu Asp Arg Asn Arg Met Lys Thr
465                 470                 475                 480

Leu Gly Arg Arg Asp Ser Ser Asp Asp Trp Glu Ile Pro Asp Gly Gln
                485                 490                 495

Ile Thr Val Gly Gln Arg Ile Gly Ser Gly Ser Phe Gly Thr Val Tyr
            500                 505                 510

Lys Gly Lys Trp His Gly Asp Val Ala Val Lys Met Leu Asn Val Thr
        515                 520                 525

Ala Pro Thr Pro Gln Gln Leu Gln Ala Phe Lys Asn Glu Val Gly Val
    530                 535                 540

Leu Arg Lys Thr Arg His Val Asn Ile Leu Leu Phe Met Gly Tyr Ser
545                 550                 555                 560

Thr Lys Pro Gln Leu Ala Ile Val Thr Gln Trp Cys Glu Gly Ser Ser
                565                 570                 575

Leu Tyr His His Leu His Ile Ile Glu Thr Lys Phe Glu Met Ile Lys
            580                 585                 590

Leu Ile Asp Ile Ala Arg Gln Thr Ala Gln Gly Met Asp Tyr Leu His
        595                 600                 605

Ala Lys Ser Ile Ile His Arg Asp Leu Lys Ser Asn Asn Ile Phe Leu
    610                 615                 620

His Glu Asp Leu Thr Val Lys Ile Gly Asp Phe Gly Leu Ala Thr Val
625                 630                 635                 640

Lys Ser Arg Trp Ser Gly Ser His Gln Phe Glu Gln Leu Ser Gly Ser
                645                 650                 655

Ile Leu Trp Met Ala Pro Glu Val Ile Arg Met Gln Asp Lys Asn Pro
            660                 665                 670

Tyr Ser Phe Gln Ser Asp Val Tyr Ala Phe Gly Ile Val Leu Tyr Glu
        675                 680                 685

Leu Met Thr Gly Gln Leu Pro Tyr Ser Asn Ile Asn Asn Arg Asp Gln
    690                 695                 700

Ile Ile Phe Met Val Gly Arg Gly Tyr Leu Ser Pro Asp Leu Ser Lys
705                 710                 715                 720

Val Arg Ser Asn Cys Pro Lys Ala Met Lys Arg Leu Met Ala Glu Cys
                725                 730                 735

Leu Lys Lys Lys Arg Asp Glu Arg Pro Leu Phe Pro Gln Ile Leu Ala
            740                 745                 750

Ser Ile Glu Leu Leu Ala Arg Ser Leu Pro Lys Ile His Arg Ser Ala
        755                 760                 765

Ser Glu Pro Ser Leu Asn Arg Ala Gly Phe Gln Thr Glu Asp Phe Ser
    770                 775                 780

Leu Tyr Ala Cys Ala Ser Pro Lys Thr Pro Ile Gln Ala Gly Gly Tyr
785                 790                 795                 800

Gly Gly Phe Pro Val His
                805
```